(12) United States Patent
Molino et al.

(10) Patent No.: US 9,499,531 B2
(45) Date of Patent: Nov. 22, 2016

(54) ARYL- AND HETEROARYL-SUBSTITUTED TETRAHYDROISOQUINOLINES AND USE THEREOF TO BLOCK REUPTAKE OF NOREPINEPHRINE, DOPAMINE, AND SEROTONIN

(71) Applicants: Albany Molecular Research, Inc., Albany, NY (US); Bristol-Myers Squibb Company, Princeton, NJ (US)

(72) Inventors: Bruce F. Molino, Slingerlands, NY (US); Shuang Liu, Schenectady, NY (US); Peter R. Guzzo, Niskayuna, NY (US); James P. Beck, Zionsville, IN (US)

(73) Assignee: Albany Molecular Research, Inc., Albany, NY (US)

( * ) Notice: Subject to any disclaimer, the term of this patent is extended or adjusted under 35 U.S.C. 154(b) by 0 days.

(21) Appl. No.: 14/737,897

(22) Filed: Jun. 12, 2015

(65) Prior Publication Data
US 2015/0274713 A1 Oct. 1, 2015

Related U.S. Application Data

(60) Continuation of application No. 14/268,753, filed on May 2, 2014, now Pat. No. 9,085,531, which is a division of application No. 13/540,446, filed on Jul. 2, 2012, now Pat. No. 8,741,901, which is a division of application No. 12/252,823, filed on Oct. 16, 2008, now Pat. No. 8,227,486, which is a continuation of application No. 11/183,066, filed on Jul. 15, 2005, now Pat. No. 7,541,357.

(60) Provisional application No. 60/588,448, filed on Jul. 15, 2004.

(51) Int. Cl.
C07D 417/04 (2006.01)
A61K 31/4709 (2006.01)
(Continued)

(52) U.S. Cl.
CPC ......... *C07D 417/04* (2013.01); *A61K 31/4709* (2013.01); *A61K 31/4741* (2013.01); *A61K 31/4743* (2013.01); *A61K 31/502* (2013.01); *A61K 31/517* (2013.01); *A61K 31/53* (2013.01); *C07D 217/00* (2013.01); *C07D 217/04* (2013.01); *C07D 217/08* (2013.01); *C07D 217/12* (2013.01); *C07D 217/14* (2013.01); *C07D 217/16* (2013.01); *C07D 217/20* (2013.01); *C07D 401/04* (2013.01); *C07D 401/12* (2013.01); *C07D 401/14* (2013.01); *C07D 403/04* (2013.01); *C07D 403/12* (2013.01); *C07D 405/04* (2013.01); *C07D 405/12* (2013.01); *C07D 405/14* (2013.01); *C07D 407/04* (2013.01);
(Continued)

(58) Field of Classification Search
CPC .................................................. C07D 403/04
See application file for complete search history.

(56) References Cited

U.S. PATENT DOCUMENTS 3,666,763 A 5/1972 Grethe et al.
3,947,456 A 3/1976 Rheiner
(Continued)

FOREIGN PATENT DOCUMENTS

CA 2015114 10/1990
CH 538 477 8/1973
(Continued)

OTHER PUBLICATIONS

Aihara et al., "Increasing 5-Lipoxygenase Inhibitory Activities by Oxidative Conversion of o-Methoxyphenols to Catechols Using a $Cu^{2+}$-Ascorbic Acid-$O_2$ System," *Chem. Pharm. Bull.* 38(3):842-844 (1990).
(Continued)

*Primary Examiner* — Paul V Ward
(74) *Attorney, Agent, or Firm* — LeClairRyan, a Professional Corporation

(57) ABSTRACT

The compounds of the present invention are represented by the chemical structure found in Formula (I):

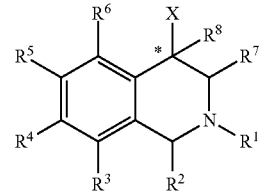

Formula I wherein:
the carbon atom designated * is in the R or S configuration; and
X is a fused bicyclic carbocycle or heterocycle selected from the group consisting of benzofuranyl, benzo[b]thiophenyl, benzoisothiazolyl, benzoisoxazolyl, indazolyl, indolyl, isoindolyl, indolizinyl, benzoimidazolyl, benzooxazolyl, benzothiazolyl, benzotriazolyl, imidazo[1,2-a]pyridinyl, pyrazolo[1,5-a]pyridinyl, [1,2,4]triazolo[4,3-a]pyridinyl, thieno[2,3-b]pyridinyl, thieno[3,2-b]pyridinyl, 1H-pyrrolo[2,3-b]pyridinyl, indenyl, indanyl, dihydrobenzocycloheptenyl, tetrahydrobenzocycloheptenyl, dihydrobenzothiophenyl, dihydrobenzofuranyl, indolinyl, naphthyl, tetrahydronaphthyl, quinolinyl, isoquinolinyl, 4H-quinolizinyl, 9aH-quinolizinyl, quinazolinyl, cinnolinyl, phthalazinyl, quinoxalinyl, benzo[1,2,3]triazinyl, benzo[1,2,4]triazinyl, 2H-chromenyl, 4H-chromenyl, and a fused bicyclic carbocycle or fused bicyclic heterocycle optionally substituted with substituents (1 to 4 in number) as defined in $R^{14}$;
with $R^1$, $R^2$, $R^3$, $R^4$, $R^5$, $R^6$, $R^7$, $R^8$, and $R^{14}$ defined herein.

6 Claims, No Drawings

(51) Int. Cl.

| | |
|---|---|
| *A61K 31/4741* | (2006.01) |
| *A61K 31/4743* | (2006.01) |
| *A61K 31/502* | (2006.01) |
| *A61K 31/517* | (2006.01) |
| *A61K 31/53* | (2006.01) |
| *C07D 217/04* | (2006.01) |
| *C07D 217/08* | (2006.01) |
| *C07D 217/12* | (2006.01) |
| *C07D 217/14* | (2006.01) |
| *C07D 217/16* | (2006.01) |
| *C07D 401/04* | (2006.01) |
| *C07D 401/12* | (2006.01) |
| *C07D 401/14* | (2006.01) |
| *C07D 403/04* | (2006.01) |
| *C07D 403/12* | (2006.01) |
| *C07D 405/04* | (2006.01) |
| *C07D 405/12* | (2006.01) |
| *C07D 405/14* | (2006.01) |
| *C07D 409/04* | (2006.01) |
| *C07D 409/12* | (2006.01) |
| *C07D 409/14* | (2006.01) |
| *C07D 413/04* | (2006.01) |
| *C07D 413/12* | (2006.01) |
| *C07D 413/14* | (2006.01) |
| *C07D 417/12* | (2006.01) |
| *C07D 417/14* | (2006.01) |
| *C07D 471/04* | (2006.01) |
| *C07D 487/04* | (2006.01) |
| *C07D 495/04* | (2006.01) |
| *C07D 217/00* | (2006.01) |
| *C07D 217/20* | (2006.01) |
| *C07D 407/04* | (2006.01) |

(52) U.S. Cl.
CPC ......... *C07D 409/04* (2013.01); *C07D 409/12* (2013.01); *C07D 409/14* (2013.01); *C07D 413/04* (2013.01); *C07D 413/12* (2013.01); *C07D 413/14* (2013.01); *C07D 417/12* (2013.01); *C07D 417/14* (2013.01); *C07D 471/04* (2013.01); *C07D 487/04* (2013.01); *C07D 495/04* (2013.01)

(56) References Cited

U.S. PATENT DOCUMENTS

| | | | |
|---|---|---|---|
| 4,113,869 A | 9/1978 | Gardner | |
| 4,340,600 A | 7/1982 | Brenner et al. | |
| 4,564,613 A | 1/1986 | Boltze et al. | |
| 4,843,071 A | 6/1989 | Hohenwarter | |
| 4,902,710 A | 2/1990 | Foster et al. | |
| 5,212,185 A | 5/1993 | Hanson | |
| 5,241,065 A | 8/1993 | Berger et al. | |
| 5,444,070 A | 8/1995 | Moldt et al. | |
| 5,447,947 A | 9/1995 | Campbell | |
| 5,532,244 A | 7/1996 | Wong et al. | |
| 5,587,380 A | 12/1996 | Miller et al. | |
| 5,595,872 A | 1/1997 | Wetterau, II | |
| 5,654,296 A | 8/1997 | Kato et al. | |
| 5,654,316 A | 8/1997 | Carruthers et al. | |
| 5,656,642 A | 8/1997 | Fujioka et al. | |
| 5,789,449 A | 8/1998 | Norden | |
| 5,817,832 A | 10/1998 | Wallquist et al. | |
| 5,827,875 A | 10/1998 | Dickson, Jr. et al. | |
| 5,843,967 A | 12/1998 | Riedl et al. | |
| 5,885,983 A | 3/1999 | Biller et al. | |
| 6,043,253 A | 3/2000 | Brockunier et al. | |
| 6,121,261 A | 9/2000 | Glatt et al. | |
| 6,136,803 A | 10/2000 | Freedman et al. | |
| 6,162,809 A | 12/2000 | Kohl et al. | |
| 6,211,170 B1 | 4/2001 | Yaokim et al. | |
| 6,218,404 B1 | 4/2001 | Bigge et al. | |
| 6,239,125 B1 | 5/2001 | Melenfant et al. | |
| 6,262,074 B1 | 7/2001 | Otten et al. | |
| 6,340,681 B1 | 1/2002 | Ito | |
| 6,358,993 B1 | 3/2002 | Reddy et al. | |
| 6,441,244 B1 | 8/2002 | Avar et al. | |
| 6,479,436 B1 | 11/2002 | Otten et al. | |
| 6,506,772 B1 | 1/2003 | Brodbeck et al. | |
| 6,506,773 B2 | 1/2003 | Hannah et al. | |
| 6,562,836 B1 | 5/2003 | Szarck et al. | |
| 6,579,885 B2 | 6/2003 | Beck et al. | |
| 6,586,447 B1 | 7/2003 | Lyssikatos et al. | |
| 6,642,228 B1 | 11/2003 | Hayashi et al. | |
| 6,664,256 B1 | 12/2003 | Ohkuchi et al. | |
| 6,664,293 B2 | 12/2003 | Yamada et al. | |
| 6,703,405 B2 | 3/2004 | Hofmeister et al. | |
| 6,900,220 B2 | 5/2005 | Becker et al. | |
| 6,911,453 B2 | 6/2005 | Hofmeister et al. | |
| 6,919,376 B2 | 7/2005 | Llompart et al. | |
| 6,943,159 B1 | 9/2005 | Gouliaev et al. | |
| 6,974,803 B2 | 12/2005 | Yeadon | |
| 6,977,261 B2 | 12/2005 | Bunker et al. | |
| 7,041,702 B1 | 5/2006 | Durant et al. | |
| 7,084,152 B2 | 8/2006 | Beck et al. | |
| 7,163,949 B1 | 1/2007 | Beck et al. | |
| 7,211,584 B2 | 5/2007 | Jover et al. | |
| 7,211,585 B2 | 5/2007 | Jover et al. | |
| 7,241,774 B2 | 7/2007 | Miller et al. | |
| 7,241,775 B2 | 7/2007 | Hofmeister et al. | |
| 7,256,201 B2 | 8/2007 | Barlaam et al. | |
| 7,265,116 B2 | 9/2007 | Beck et al. | |
| 7,268,142 B2 | 9/2007 | Allen et al. | |
| 7,309,789 B2 | 12/2007 | Beck et al. | |
| 7,321,064 B1 | 1/2008 | Cabaj et al. | |
| 7,345,057 B2 | 3/2008 | Torrens Jover et al. | |
| 7,388,019 B2 | 6/2008 | Ashton et al. | |
| 7,419,985 B2 | 9/2008 | Beck et al. | |
| 7,425,633 B2 | 9/2008 | Jiaang et al. | |
| 7,459,460 B2 | 12/2008 | Yang et al. | |
| 7,491,794 B2 | 2/2009 | Blatt et al. | |
| 7,501,538 B2 | 3/2009 | Mjalli et al. | |
| 7,541,357 B2 * | 6/2009 | Molino | A61K 31/4709 514/235.2 |
| 7,544,497 B2 | 6/2009 | Sinclair et al. | |
| 7,582,803 B2 | 9/2009 | Akerman et al. | |
| 7,612,090 B2 | 11/2009 | Beck et al. | |
| 7,790,742 B2 | 9/2010 | Lang et al. | |
| 7,846,930 B2 | 12/2010 | Keith | |
| 7,872,138 B2 | 1/2011 | Villani et al. | |
| 7,956,050 B2 | 6/2011 | Molino et al. | |
| 7,973,057 B2 | 7/2011 | Greig et al. | |
| 8,178,545 B2 | 5/2012 | Brown | |
| 8,227,486 B2 | 7/2012 | Molino et al. | |
| 8,236,796 B2 | 8/2012 | Molino et al. | |
| 8,420,811 B2 | 4/2013 | Loben et al. | |
| 8,445,494 B2 | 5/2013 | Qui et al. | |
| 9,156,812 B2 | 10/2015 | Qiu et al. | |
| 2003/0203920 A1 | 10/2003 | Beck et al. | |
| 2004/0044000 A1 | 3/2004 | Bunker et al. | |
| 2004/0248932 A1 | 12/2004 | Friail et al. | |
| 2004/0248933 A1 | 12/2004 | Frail et al. | |
| 2005/0020597 A1 | 1/2005 | Beck et al. | |
| 2005/0113283 A1 | 5/2005 | Solow-Cordero et al. | |
| 2005/0171027 A1 | 8/2005 | Sinclair et al. | |
| 2005/0256318 A1 | 11/2005 | Michel | |
| 2005/0261298 A1 | 11/2005 | Solow-Cordero et al. | |
| 2006/0014705 A1 | 1/2006 | Howitz et al. | |
| 2006/0052378 A1 | 3/2006 | Molino et al. | |
| 2006/0063766 A1 | 3/2006 | Molino et al. | |
| 2006/0084135 A1 | 4/2006 | Howitz et al. | |
| 2006/0111385 A1 | 5/2006 | Molino et al. | |
| 2006/0111386 A1 | 5/2006 | Molino et al. | |
| 2006/0111393 A1 | 5/2006 | Molino et al. | |
| 2006/0111394 A1 | 5/2006 | Molino et al. | |
| 2006/0111395 A1 | 5/2006 | Molino et al. | |
| 2006/0111396 A1 | 5/2006 | Molino et al. | |
| 2006/0194837 A1 | 8/2006 | Carruthers et al. | |
| 2006/0217409 A1 | 9/2006 | Beck et al. | |

(56) References Cited

U.S. PATENT DOCUMENTS

| | | |
|---|---|---|
| 2006/0229265 A1 | 10/2006 | Milburn et al. |
| 2006/0276416 A1 | 12/2006 | Sinclair et al. |
| 2007/0015737 A1 | 1/2007 | Clark et al. |
| 2007/0048728 A1 | 3/2007 | Ratcliffe et al. |
| 2007/0060589 A1 | 3/2007 | Purandare et al. |
| 2007/0082907 A1 | 4/2007 | Canada et al. |
| 2007/0105838 A1 | 5/2007 | Best et al. |
| 2007/0112012 A1 | 5/2007 | Boehringer et al. |
| 2008/0004336 A1 | 1/2008 | Gougoutas et al. |
| 2008/0207595 A9 | 8/2008 | Molino et al. |
| 2008/0318997 A1 | 12/2008 | Beck et al. |
| 2009/0048443 A1 | 2/2009 | Molino et al. |
| 2009/0069374 A1 | 3/2009 | Skolnick et al. |
| 2009/0099158 A1 | 4/2009 | Grice et al. |
| 2009/0253906 A1 | 10/2009 | Molino et al. |
| 2010/0137287 A1 | 6/2010 | Guzzo et al. |
| 2010/0210624 A1 | 8/2010 | Liu et al. |
| 2010/0292242 A1 | 11/2010 | Liu et al. |
| 2010/0292243 A1 | 11/2010 | Liu et al. |
| 2010/0292250 A1 | 11/2010 | Wei et al. |
| 2011/0003850 A1 | 1/2011 | Vernier et al. |
| 2011/0281842 A1 | 11/2011 | Michaelides et al. |
| 2012/0046271 A1 | 2/2012 | Guzzo et al. |
| 2016/0022675 A1 | 1/2016 | Gonzalez-Bobes et al. |

FOREIGN PATENT DOCUMENTS

| | | |
|---|---|---|
| DE | 2 062 001 | 7/1971 |
| DE | 102005025625 | 12/2006 |
| EP | 0 140 070 A1 | 5/1985 |
| EP | 0 360 390 A1 | 3/1990 |
| EP | 0380223 | 8/1990 |
| EP | 0 394 989 B1 | 10/1990 |
| EP | 0 400 319 A1 | 12/1990 |
| EP | 0421436 | 4/1991 |
| EP | 0 428 434 A2 | 5/1991 |
| EP | 0 429 366 B1 | 5/1991 |
| EP | 0 430 771 B1 | 6/1991 |
| EP | 0 436 334 B1 | 7/1991 |
| EP | 0 443 132 B1 | 8/1991 |
| EP | 0 482 539 B1 | 4/1992 |
| EP | 0 498 069 B1 | 8/1992 |
| EP | 0 499 313 B1 | 8/1992 |
| EP | 0 512 901 B1 | 11/1992 |
| EP | 0 512 902 A1 | 11/1992 |
| EP | 0 514 273 A1 | 11/1992 |
| EP | 0 514 274 A1 | 11/1992 |
| EP | 0 514 275 A1 | 11/1992 |
| EP | 0 514 276 A1 | 11/1992 |
| EP | 0 515 681 A1 | 12/1992 |
| EP | 0 517 589 B1 | 12/1992 |
| EP | 0 520 555 A1 | 12/1992 |
| EP | 0 522 808 A2 | 1/1993 |
| EP | 0 528 495 A1 | 2/1993 |
| EP | 0 532 456 B1 | 3/1993 |
| EP | 0 533 280 B1 | 3/1993 |
| EP | 0 536 817 A1 | 4/1993 |
| EP | 0 545 478 A1 | 6/1993 |
| EP | 0 558 156 A2 | 9/1993 |
| EP | 0 577 394 B1 | 1/1994 |
| EP | 0 585 913 B1 | 3/1994 |
| EP | 0 599 338 A2 | 6/1994 |
| EP | 0 599 538 A1 | 6/1994 |
| EP | 0 610 793 A1 | 8/1994 |
| EP | 0 634 402 A1 | 1/1995 |
| EP | 0 686 629 A2 | 12/1995 |
| EP | 0 693 489 A1 | 1/1996 |
| EP | 0 694 535 A1 | 1/1996 |
| EP | 0694543 A1 | 1/1996 |
| EP | 0 699 674 A1 | 3/1996 |
| EP | 0 707 006 B1 | 4/1996 |
| EP | 0 708 101 B1 | 4/1996 |
| EP | 0 709 375 A2 | 5/1996 |
| EP | 0 709 376 A2 | 5/1996 |
| EP | 0 714 891 A1 | 6/1996 |
| EP | 0 723 959 A1 | 7/1996 |
| EP | 0 733 632 A1 | 9/1996 |
| EP | 0 776 893 A1 | 6/1997 |
| EP | 0 699 655 B1 | 9/1997 |
| EP | 0 520 555 B1 | 9/1999 |
| GB | 2 266 529 A | 11/1993 |
| GB | 2 268 931 A | 1/1994 |
| GB | 2 269 170 A | 2/1994 |
| GB | 2 269 590 A | 2/1994 |
| GB | 2 271 566 A | 4/1994 |
| GB | 2 271 774 A | 4/1994 |
| GB | 2 292 144 A | 2/1996 |
| GB | 2 293 168 A | 3/1996 |
| GB | 2 293 169 A | 3/1996 |
| GB | 2 302 689 A | 1/1997 |
| HU | 9903186 | 2/2000 |
| JP | 52-23083 | 2/1977 |
| JP | 02-281203 | 11/1990 |
| JP | 04193867 | 7/1992 |
| JP | 10-292008 | 11/1998 |
| JP | 200186110 | 7/2000 |
| JP | 2001026580 | 1/2001 |
| JP | 2003513074 | 4/2003 |
| JP | 2004501860 | 1/2004 |
| WO | WO 90/05525 | 5/1990 |
| WO | WO 90/05729 | 5/1990 |
| WO | WO 91/09844 | 7/1991 |
| WO | WO 91/18899 | 12/1991 |
| WO | WO 92/01688 | 2/1992 |
| WO | WO 92/06079 | 4/1992 |
| WO | WO 92/12151 | 7/1992 |
| WO | WO 92/15585 | 9/1992 |
| WO | WO 92/17449 | 10/1992 |
| WO | WO 92/20661 | 11/1992 |
| WO | WO 92/20676 | 11/1992 |
| WO | WO 92/21677 | 12/1992 |
| WO | WO 92/22569 | 12/1992 |
| WO | WO 93/00330 | 1/1993 |
| WO | WO 93/00331 | 1/1993 |
| WO | WO 93/01159 | 1/1993 |
| WO | WO 93/01165 | 1/1993 |
| WO | WO 93/01169 | 1/1993 |
| WO | WO 93/01170 | 1/1993 |
| WO | WO 93/06099 | 4/1993 |
| WO | WO 93/09116 | 5/1993 |
| WO | WO 93/10073 | 5/1993 |
| WO | WO 93/14084 | 7/1993 |
| WO | WO 93/14113 | 7/1993 |
| WO | WO 93/18023 | 9/1993 |
| WO | WO 93/19064 | 9/1993 |
| WO | WO 93/21155 | 10/1993 |
| WO | WO 93/21181 | 10/1993 |
| WO | WO 93/23380 | 11/1993 |
| WO | WO 93/24465 | 12/1993 |
| WO | WO 94/00440 | 1/1994 |
| WO | WO 94/01402 | 1/1994 |
| WO | WO 94/02461 | 2/1994 |
| WO | WO 94/02595 | 2/1994 |
| WO | WO 94/03429 | 2/1994 |
| WO | WO 94/03445 | 2/1994 |
| WO | WO 94/04494 | 3/1994 |
| WO | WO 94/04496 | 3/1994 |
| WO | WO 94/05625 | 3/1994 |
| WO | WO 94/07843 | 4/1994 |
| WO | WO 94/08997 | 4/1994 |
| WO | WO 94/10165 | 5/1994 |
| WO | WO 94/10167 | 5/1994 |
| WO | WO 94/10168 | 5/1994 |
| WO | WO 94/10170 | 5/1994 |
| WO | WO 94/11368 | 5/1994 |
| WO | WO 94/13639 | 6/1994 |
| WO | WO 94/13663 | 6/1994 |
| WO | WO 94/14767 | 7/1994 |
| WO | WO 94/15903 | 7/1994 |
| WO | WO 94/19320 | 9/1994 |
| WO | WO 94/19323 | 9/1994 |
| WO | WO 94/20500 | 9/1994 |
| WO | WO 94/26735 | 11/1994 |
| WO | WO 94/26740 | 11/1994 |

(56) References Cited

FOREIGN PATENT DOCUMENTS

| WO | WO 94/29309 | 12/1994 |
|---|---|---|
| WO | WO 95/02595 | 1/1995 |
| WO | WO 95/04040 | 2/1995 |
| WO | WO 95/04042 | 2/1995 |
| WO | WO 95/06645 | 3/1995 |
| WO | WO 95/07886 | 3/1995 |
| WO | WO 95/07908 | 3/1995 |
| WO | WO 95/08549 | 3/1995 |
| WO | WO 95/11880 | 5/1995 |
| WO | WO 95/14017 | 5/1995 |
| WO | WO 95/15311 | 6/1995 |
| WO | WO 95/16679 | 6/1995 |
| WO | WO 95/17382 | 6/1995 |
| WO | WO 95/18124 | 7/1995 |
| WO | WO 95/18129 | 7/1995 |
| WO | WO 95/20575 | 8/1995 |
| WO | WO 95/21819 | 8/1995 |
| WO | WO 95/22525 | 8/1995 |
| WO | WO 95/23798 | 9/1995 |
| WO | WO 95/26338 | 10/1995 |
| WO | WO 95/28418 | 10/1995 |
| WO | WO 95/30674 | 11/1995 |
| WO | WO 95/30687 | 11/1995 |
| WO | WO 95/33744 | 12/1995 |
| WO | WO 96/05181 | 2/1996 |
| WO | WO 96/05193 | 2/1996 |
| WO | WO 96/05203 | 2/1996 |
| WO | WO 96/06094 | 2/1996 |
| WO | WO 96/07649 | 3/1996 |
| WO | WO 96/10562 | 4/1996 |
| WO | WO 96/16939 | 6/1996 |
| WO | WO 96/18643 | 6/1996 |
| WO | WO 96/20197 | 7/1996 |
| WO | WO 96/21661 | 7/1996 |
| WO | WO 96/29304 | 9/1996 |
| WO | WO 96/29317 | 9/1996 |
| WO | WO 96/29326 | 9/1996 |
| WO | WO 96/29328 | 9/1996 |
| WO | WO 96/31214 | 10/1996 |
| WO | WO 96/32385 | 10/1996 |
| WO | WO 96/37489 | 11/1996 |
| WO | WO 97/01553 | 1/1997 |
| WO | WO 97/01554 | 1/1997 |
| WO | WO 97/03066 | 1/1997 |
| WO | WO 97/08144 | 3/1997 |
| WO | WO 97/14671 | 4/1997 |
| WO | WO 97/17362 | 5/1997 |
| WO | WO 97/18206 | 5/1997 |
| WO | WO 97/19084 | 5/1997 |
| WO | WO 97/19942 | 6/1997 |
| WO | WO 97/21702 | 6/1997 |
| WO | WO 97/23458 | 7/1997 |
| WO | WO 97/36876 | 10/1997 |
| WO | WO 9743255 | 11/1997 |
| WO | WO 9743257 | 11/1997 |
| WO | WO 97/49710 | 12/1997 |
| WO | WO 9835939 | 8/1998 |
| WO | WO 98/40358 | 9/1998 |
| WO | WO 00/14076 | 3/2000 |
| WO | WO 01/32624 A1 | 5/2001 |
| WO | WO 01/32625 | 5/2001 |
| WO | 01/51919 A2 | 7/2001 |
| WO | WO 0170728 | 9/2001 |
| WO | WO 02/04455 A3 | 1/2002 |
| WO | WO 0377874 | 9/2003 |
| WO | WO 2004067514 | 8/2004 |
| WO | WO 2004096774 | 11/2004 |
| WO | WO 2005035503 | 4/2005 |
| WO | WO 2005087235 | 9/2005 |
| WO | WO 2005095403 | 10/2005 |
| WO | WO 2006020049 | 2/2006 |
| WO | WO 2006020145 | 2/2006 |
| WO | WO 2006/057955 | 6/2006 |
| WO | WO 2006087309 | 8/2006 |
| WO | WO 2007038459 | 4/2007 |
| WO | WO 2007048788 | 5/2007 |
| WO | WO 2007098608 | 9/2007 |
| WO | WO 2007117982 | 10/2007 |
| WO | 2008003665 A1 | 1/2008 |
| WO | 2008005368 A2 | 1/2008 |
| WO | WO 2008024398 | 2/2008 |
| WO | WO 2008037482 | 4/2008 |
| WO | 2008058126 A2 | 5/2008 |
| WO | 2009149258 A2 | 12/2009 |
| WO | WO 2009/155565 | 12/2009 |
| WO | WO 2010/027500 | 3/2010 |
| WO | WO 2010132437 | 11/2010 |
| WO | WO 2010132442 | 11/2010 |
| WO | WO 2010132487 | 11/2010 |

OTHER PUBLICATIONS

Banerji et al., "Studies on Single-Electron Transfer Reagents. Part IV Reaction of Nitrogen Heterocycles with Sodium Naphthalenide," *Tetrahedron* 50(30):9079-9096 (1994).

Beilstein No. 4048047 (CAS 17074-38-3, 17074-39-4), Beilstein Data, Elsevier Information Systems Gmbh, 2 pages (Mar. 19, 1991).

Beilstein No. 4102323 (CAS 53885-34-0), Beilstein Data, Elsevier Information Systems Gmbh, 3 pages (Mar. 19, 1991).

Beilstein No. 4341479 (CAS 134021-24-2), Beilstein Data, Elsevier Information Systems Gmbh, 5 pages (Jul. 20, 1992).

Beilstein No. 4494373 (CAS 82416-61-3), Beilstein Data, Elsevier Information Systems Gmbh, 3 pages (Dec. 2, 1991).

Beilstein No. 455853 (CAS 71730-66-0), Beilstein Data, Elsevier Information Systems Gmbh, 2 pages (Nov. 28, 1988).

Beilstein No. 4774688 (CAS 133160-36-8), Beilstein Data, Elsevier Information Systems Gmbh, 2 pages (Jul. 20, 1992).

Beilstein No. 4787749 (CAS 133043-12-6, 133160-34-6, 133160-35-7), Beilstein Data, Elsevier Information Systems Gmbh, 5 pages (Jul. 20, 1992).

Beilstein No. 4787750 (CAS 133043-12-6, 133160-34-6, 133160-35-7), Beilstein Data, Elsevier Information Systems Gmbh, 5 pages (Jul. 20, 1992).

Beilstein No. 4787836 (CAS 133043-20-6, 133043-31-9), Beilstein Data, Elsevier Information Systems Gmbh, 4 pages (Jul. 20, 1992).

Beilstein No. 4787837 (CAS 133043-20-6, 133043-31-9), Beilstein Data, Elsevier Information Systems Gmbh, 4 pages (Jul. 20, 1992).

Beilstein No. 4788234 (CAS 133043-19-3, 133043-30-8), Beilstein Data, Elsevier Information Systems Gmbh, 4 pages (Jul. 20, 1992).

Beilstein No. 4788235 (CAS 133043-19-3, 133043-30-8), Beilstein Data, Elsevier Information Systems Gmbh, 4 pages (Jul. 20, 1992).

Beilstein No. 4789758 (CAS 133043-21-7, 133043-22-8), Bcilstcin Data, Elsevier Information Systems Gmbh, 5 pages (Jul. 20, 1992).

Beilstein No. 594629 (CAS 53885-32-8), Beilstein Data, Elsevier Information Systems Gmbh, 2 pages (Nov. 28, 1988).

Berge et al., "Pharmaceutical Salts," *J. Pharm. Sci.* 66(1):1-19 (1977).

Blomberg et al., "The Barbier Reaction—A One Step Alternative for Syntheses via Organomagnesium Compounds," *Synthesis* pp. 18-30 (1977).

Bobowski & Gottlieb, "4-Substituted 1,2,3,4-tetrahydro-3,3-dimethylisoquinolines. II.," *J. Heterocyclic Chem.* 19(1):21-27 (1982).

Brown & Dyke, "1,2-Dihydroisoquinolines. II. Berbine Synthesis," *Tetrahedron* 22(8):2429-35 (1966).

Brown & Dyke, "1,2-Dihydroisoquinolines. III. Dimerization," *Tetrahedron* 22(8):2437-2443 (1966).

Bundgaard, "Means to Enhance Penetration," *Adv. Drug Delivery Rev.* 8:1-38 (1992).

Burrows et al., "Antidepressant Efficacy and Tolerability of the Selective Norepinephrine Reuptake Inhibitor Reboxetine: A Review," *J. Clin. Psychiatry* 59(Suppl. 14):4-7 (1998) (98819-76-2 Registry (Reboxetine)).

Bundgaard, *Design of Prodrugs*, Amsterdam, The Netherlands: Elsevier Science Publishers B.V. (1985) (Table of Contents only).

CAS No. 53885-23-7, ACS on STN, 1 page (Nov. 16, 1984).

CAS No. 53885-32-8, ACS on STN, 1 page (Nov. 16, 1984).

(56) References Cited

OTHER PUBLICATIONS

Chandrasekhar et al., "Highly Efficient Synthesis of 3-alkyl/aryl-4-aryl-1,2,3,4-tetrahydroisoquinolines from N,N-dibenzylaminols," *Tetrahedron Lett.* 43(10):1885-1888 (2002).
Cherpillod et al., "A Controlled Trial with Diclofensine, A New Psychoactive Drug, in the Treatment of Depression," *J. Int. Med. Res.* 9(5):324-329 (1981).
Cliffe et al., "(S)-N-tert-Butyl-3-(4-(2-methoxyphenyl)-piperazin-1-yl)-2-phenylpropanamide [(S)-WAY- 100135]: A Selective Antagonist at Presynaptic and Postsynaptic-5 -$HT_{1A}$ Receptors," *J. Med. Chem.* 36:1509-10 (1993).
Dandridge et al., "Synthesis, Resolution, Absolute Stereochemistry, and Enantioselectivity of 3', 4'- Dihydroxynomifensine," *J. Med. Chem.* 27:28-35 (1984).
Desai et al., "Relationship Between in Vivo Occupancy at the Dopamine Transporter and Behavioral Effects of Cocaine, GBR 12909 [1- {2-[Bis-(4-fluorophenyl)methoxy]ethyl} -4-(3-phenylpropyl)piperazine], and Benztropine Analogs," *J. Pharmacol. Exp. Ther.* 315(1):397-404 (2005).
Dudley et al., "The Actions of Xylamine on Central Noradrenergic Neurons," *J. Pharm. Exp. Ther.* 217(3):834-840 (1981).
Euerby et al., "Methylthio Activiating Groups in the Synthesis of Tetrahydroisoquinolines and Tetrahydro-2-benzazepines from N-Allyl- and N-Cinnamyl-benzylamines," *J. Chem. Research* pp. 40-41 (1987).
Gao et al., "Asymmetric Hetero Diels-Alder Reaction Catalyzed by Stable and Easily Prepared CAB Catalysts," *Tetrahedron* 50(4):979-988 (1994).
Georgiadis et al., "Synthesis and Complexation Properties of a Water-Soluble Optically Active Cyclophane Incorporating a 4-Naphthyl-1,2,3,4-tetrahydroisoquinoline Unit as a Chiral Spacer," *J. Org. Chem.* 56(10):3362-3369 (1991).
Greene et al., *Protective Groups in Organic Synthesis*, 2d. Ed., New York, New York: John Wiley & Sons, Inc. (1991) (Table of Contents only).
Hudlicky, "Fluorination with Diethylaminosulfur Trifluoride and Related Amino fluoro sul furane s," *Organic Reactions* 35:513-637 (1985).
Iiyttel, "Pharmacological Characterization of Selective Serotonin Reuptake Inhibitors (SSRIs)," *Int. Clin. Psychopharmacol.* 9(Suppl. 1):19-26 (1994) (61869-08-7 Registry (Paroxetine); 59729-32-7 Registry (Citalopram); 79559-97-0 Registry (Sertraline); 54910-89-3 Registry (Fluoxetine); 54739-18-3 Registry (Fluvoxamine)).
Ishikura et al., "The Synthesis of 4-Substituted Isoquinoline Derivatives from Diethyl (4-Isoquinolyl) Borane," *Heterocycles* 26:1603-1610 (1987).
Jacob et al., "Dopamine Agonist Properties of N-Alkyl-4-(3,4-dihydroxyphenyl)-1,2,3,4-tetrahydroisoquinolines," *J. Med. Chem.* 24:1013-1015 (1981).
Jorgenson, "Preparation of Ketones from the Reaction of Organolithium Reagents with Carboxylic Acids," Dauben et al., eds., *Organic Reactions*, vol. 18, New York, New York: John Wiley & Sons, Inc., Chapter 1 (1970) (Table of Contents only).
Kakeya et al., "Studies on Prodrugs of Cephalosporins. I. Synthesis and Biological Properties of Glycyloxybenzoyloxymethyl and Glycylaminobenzoyloxymethyl Esters of 7β[2-(2-Aminothiazol-4-yl)-(Z)-2-Methoxyiminoacetamido]-3-Methyl-3-Cephem- 4-Carboxylic Acid," *Chem. Pharm. Bull.* 32(2):692-698 (1984).
Kametani et al., "Studies on the Synthesis of Heterocyclic Compounds," *Tetrahedron* 31:235-238 (1975).
Kihara et al., "A Convenient Synthesis of 4-Substituted 1,2,3,4-Tetrahydroisoquinolin- 4-OLS by a Novel Intramolecular Barbier Reaction and by an Insertion Reaction: Reaction Scope and Limitations," *Tetrahedron* 48(1):67-78 (1992).
Kihara et al., "Synthesis and Enantioselectivity of Optically Active 1- and 3-Substituted 4-Phenyl-1,2,3,4- Tetrahydroisoquinolin-4-ols and Related Compounds As Norepinephrine Potentiators," *Chem. Pharm. Bull.* 43(9):1543-1546 (1995).
Kihara et al., "Synthesis and Pharmacological Evaluation of Phenolic 2-Methyl-4- Phenyl-1,2,3,4,- Tetrahydroisoquinolin-4-ols As New Norepinephrine Potentiator," *Drug Design Dis.* 11(3):175-183 (1994).
Knabe & Herbort, "Dehydrogenation of Tertiary Amines with Aercury (II) Acetate in the Presence of EDTA. XIII. Oxidative Dimerization of 6,7-dimetlioxy-2-methyl-1,1-diethyl-1,2,3,4-tetrahydroisoquinoline," *Archiv. der Pharmazie. und Berichte der Deutschen Pharmazeutischen Gesellschaft* 300(9):774-783 (1967).
Knabe & Renz, "Synthesis of 3,4'-Biisoquinolines," *Archiv. der Pharmazie.* (Weinheim, Germany) 307(8):612-622 (1974).
Krogsgaard-Larsen et al., eds., *A Textbook of Drug Design and Development*, Chur, Switzerland: Harwood Academic Publishers GmbH (1991) (portion of Table of Contents only).
Larock, *Comprehensive Organic Transformations: A Guide to Functional Group Preparation*, New York, New York: VCH Publishers, Inc. (1989) (Table of Contents only).
Maryanoff et al., "Pyrroloisoquinoline Antidepressants. 2. In-Depth Exploration of Structure-Activity Relationships," *J. Med. Chem.* 30(8):1433-1454 (1987).
McOmie, ed., *Protective Groups in Organic Chemistry*, London: Plenum Press (1973) (Table of Contents only).
Middlemiss et al., "Centrally Active 5-HT Receptor Agonists and Antagonists," *Neurosci. Biobehavioral Rev.* 16:75-82 (1992).
Miller et al., "An Efficient Synthesis of 4-Aryl-1,2,3,4-Tetrahydroisoquinolines," *Synthetic Com.* 24(8):1187-1193 (1994).
Mondeshka et al., "Synthesis, Antiulcer and Antidepressive Activity of 4-(4-Halophenyl)-2-Phenyl-1,2,3,4-Tetrahydroisoquinolines," *Il Farmaco* 49:475-480 (1994).
Müller, "Current St. John's Wort Research from Mode of Action to Clinical Efficacy," *Pharmacological Research* 47:101-109 (2003).
Nielsen et al., "Glycolamide Esters as Biolabile Prodrugs of Carboxylic Acid Agents: Synthesis, Stability, Bioconversion, and Physicochemical Properties," *J. Pharm. Sci.* 77(4):285-298 (1988).
Salama et al., "Antigenic Determinants Responsible for the Reactions of Drug-Dependent Antibodies with Blood Cells," *Br. J. Haematol.* 78:535-539 (1991).
Seebach et al., "Alkylation of Amino Acids without Loss of the Optical Activity: Preparation of α-Substituted Proline Derivatives. A Case of Self-Reproduction of Chirality," *J. American Chem. Soc.* 105(16):5390-5398 (1983).
Stille, "Zur pharmakologischen Prating von Antidepressiva am Beispiel eines Dibenzodiazepins," *Arzneimittel-Forschung* 14:534-537 (1964) (English summary included).
Sugiura & Hamada, "Studies on Nitrogen-Containing Heterocyclic Compounds. XXXV. Syntheses and Reduction of 4-Amino-2-cyano-1,3-dimethoxy-1,2,3,4-tetrahydroisoquinolines," *Yakugaku Zasshi* 99(6):556-563 (1979).
Sugiura et al., "Synthesis and Stereochemistry of 3,7-Diazatricyclo[4.2.2.2$^{2,5}$]dodeca-9,11-dienes Derived by [4+4] Cyclodimerization of 2,3-Dihydroisoquinoline Derivatives," *Chem. Pharm. Bull.* 46(12):1862-1865 (1998).
Tirelli et al., "Differential Effects of Direct and Indirect Dopamine Agonists on the Induction of Gnawing in C57B1/6J Mice," *J. Pharm. Exp. Therapy* 273(1):7-15 (1995).
Trepanier et al., "3,4-Dihydroisocarbostyril and 1,2,3,4-Tetrahydroisoquinoline Derivatives of Ephedrine," *J. Med. Chem.* 16(4):342-347 (1973).
Uno & Okada, "A Novel Method for the Synthesis of 4-Isoquinolinols," *J. Heterocyclic Chem.* 28(2):341-346 (1991).
Venkov et al., "A New Synthesis of 1,2,3,4-Tetrahydro-2-Methyl-4-Phenylisoquinolines," *Synthesis* 253-255 (1990).
Zára-Kaczián et al., "8-Amino-4-Aryl-2Methyl-1,2,3,4-Tetrahydroisoquinlines. Reactions of the Amino Group Via the Diazonium Salts," *Acta Chimica Hungarica*, 12(4):573-584 (1989).
Office Action dated Jun. 16, 2011 for JP 2007-521686.
Office Action dated Aug. 20, 2010 for AU 2005274927.
Office Action dated Sep. 18, 2009 for CH 200580030990.2.
Supplemental Search Report dated Jul. 9, 2010 for EP 05793999.3.
Knabe et al., "Synthese von 3,4'-Biisochinolinen," *Archiv de Pharmazie* 307(8):612-622 (1974) (abstract in English).
Office Action dated Oct. 18, 2010 for IL 180349.
Office Action dated Mar. 18, 2011 for SI 200904617-8.

(56) References Cited

OTHER PUBLICATIONS

Office Action dated Mar. 5, 2009 for RU 2007105596.
Office Action dated Aug. 24, 2009 for RU 2007105596.
Office Action dated Apr. 10, 2008 for SI 2007001670.
Office Action dated Oct. 25, 2011 for Singapore Patent Application No. 200904617-8.
Office Action dated Dec. 16, 2011 for China Patent Application No. 200580030990.2.
Office Action dated Oct. 28, 2011 for U.S. Appl. No. 12/417,598.
International Search Report and Written Opinion for PCT/US2005/025193 (mailed Aug. 3, 2006).
Office Action dated Jan. 25, 2012 for U.S. Appl. No. 12/252,823.
Translation of Office Action for Colombia Patent Application No. 07 014.254 (received Mar. 20, 2012).
Office Action dated Feb. 14, 2012 for EP 05793999.3.
Office Action dated Sep. 19, 2012 for EP 05793999.3.
Office Action dated Jul. 27, 2012 for India Patent Application No. 660/CHENP/2007.
Translation of Office Action dated Jun. 21, 2012 for Korea Patent Application No. 10-2007-7003549.
Translation of Office Action dated Jul. 27, 2012 for China Patent Application No. 200580030990.2.
European Search Report dated Nov. 2, 2012, for EP Application Serial No. 10775394.9.
European Search Report dated Dec. 7, 2012, for EP Application Serial No. 10775398.0.
European Search Report dated Jan. 2, 2013, for EP Application Serial No. 10775425.1.
Office Action dated Jan. 4, 2013 for China Patent Application No. 200580030990.2.
Substantive Examination Report and Search Report dated Apr. 15, 2011 for Malaysian Patent Application No. PI 20070018.
Opposition dated Jan. 22, 2013 for Chilean Patent Application No. 2810-2011 (redacted).
Office Action dated Nov. 13, 2012, for U.S. Appl. No. 12/777,840.
Office Action dated Nov. 9, 2012, for U.S. Appl. No. 12/777,776.
Search Report and Written Opinion dated Jan. 11, 2013, for Singapore Patent Application Serial No. 201108011-6.
Mondeshka et al., "Resolution, Absolute Sterochemistry and Enantiospecificity of 4-(4-bromophenyl)-2-methyl-1,2,3,4-tetrahydroisoquinoline. The Crystal and Molecular Structures of the Racemic and 4R-Enantiomeric Hydrochloride Salt Forms," *Acta. Chemica. Scandinavica* 48:689-698 (1994).
West, Solid State Chemistry and its Applications, Wiley, New York, pp. 358-365 (1988).
International Search Report and Written Opinion for International Application No. PCT/US10/34373 dated on Jun. 18, 2010.
International Search Report and Written Opinion for International Application No. PCT/US10/34379 dated on Jun. 21, 2010.
International Search Report and Written Opinion for International Application No. PCT/US10/34428 dated on Jun. 21, 2010.
Office Action dated May 31, 2012 for U.S. Appl. No. 12/777,728.
Office Action dated Mar. 5, 2013 for China Patent Application No. 201080031666.3.
Office Action dated Mar. 26, 2013 for Canadian Patent Application No. 2,573,271.
Translation of Office Action for Korean Patent Application No. 10-2013-7001614 (May 16, 2013).
Examination Report for European Patent Application No. 05793999.3 (Apr. 15, 2013).
Examination Report for New Zealand Patent Application No. 596104 (Sep. 13, 2012).
Translation of Office Action for Chinese Patent Application No. 201080031616.5 (May 2, 2013).
Translation of Office Action for Chinese Patent Application No. 200580030990.2 (Jul. 1, 2013).
Hearing Notice in Reference of India Patent Application No. 660/CHENP/2007 dated Jul. 9, 2013.
Translation of Office Action for Eurasian Patent Application No. 201171393 (Mar. 20, 2013).

Office Action dated Jun. 5, 2013 for China Patent Application No. 201080031617.X.
Translation of Office Action for Thai Patent Application No. 1101003072 (Sep. 18, 2013)(redacted).
Translation of Office Action for Mexico Patent Application No. MX/a/2011/011900 (Sep. 17, 2013)(redacted).
Examination report for European Patent Application No. 10775398.0 (Aug. 13, 2013).
Office Action dated Aug. 29, 2013 for Korean Patent Application No. 10-2007-7003549(redacted).
Translation of Official Action for Mexican Patent Application No. MX/a/2009/012414 (Oct. 16, 2013)(redacted).
Translation of Notice of Reasons for Rejection for Japanese Patent Application No. 2012-086151 (Oct. 11, 2013).
Written Opinion for Singapore Application No. 201108011-6 (mailed Aug. 9, 2013).
Translation of Official Action for Mexican Patent Application No. MX/a/2011/011901 (Sep. 19, 2013)(redacted).
Examination report for European Patent Application No. 05793999.3 (Oct. 16, 2013).
Examination report for Philippines Patent Application No. 1/2010/501539 (Oct. 8, 2013) (redacted).
Office Action dated Jun. 23, 2008 for U.S. Appl. No. 11/183,066.
Translation of Office Action dated Oct. 23, 2013 for Eurasian Patent Application No. 201171393 (redacted).
Translation of Office Action for Chinese Patent Application No. 201080031666.3 (Jan. 15, 2014).
Translation of Office Action for Mexican patent Application No. MX/a/2009/012414 (Feb. 5, 2014)(redacted).
Office Action dated Feb. 24, 2015 for U.S. Appl. No. 14/466,009.
Translation of Decision on Rejection for Chinese Patent Application No. 201080031666.3 (received Nov. 19, 2014) (redacted).
Patent Examination Report dated Sep. 24, 2014 for Australian Application No. 2010247849.
Translation of Office Action for Chinese Patent Application No. 201080031616.5 (Sep. 29, 2014).
Examination report for European Patent Application No. 10775398.0 (Sep. 23, 2014).
Examination Report for Singapore Patent Application Serial No. 2011080116 (Sep. 16, 2014).
Translation of Notice of Reasons for Rejection for Japanese Patent Application No. 2012-510930 dated Jun. 25, 2014.
Translation of Office Action for Chinese Patent Application No. 201080031617.X dated Apr. 24, 2014.
Translation of Notice of Reasons for Rejection for Japanese Patent Application No. 2012-510933 dated Jun. 25, 2014.
Office Action for Peruvian Patent Application No. 1937-2011 dated May 15, 2014.
Translation of Office Action dated Mar. 31, 2014 for Chile Patent Application No. 2810-2011 (redacted).
Examination report for Australia Patent Application No. 2010247735 dated Jun. 6, 2014.
Translation of Notice of Reason for Rejection for Japanese Patent Application No. 2012-510952 dated Jul. 7, 2014.
Office Action dated Mar. 25, 2014 for Canadian Patent Application No. 2,573,271.
Translation of Notice of Defects dated Apr. 2, 2014 for Israel Patent Application No. 216049 (redacted).
Translation of Office Action dated Mar. 18, 2014 for Mexican Patent Application No. MX/a/2011/011900 (redacted).
Translation of Office Action dated Mar. 12, 2014 for Taiwan Patent Application No. 099115160.
Translation of Office Action dated Mar. 11, 2014 for China Patent Application No. 201080031616.5.
Translation of Office Action for Mexican Patent Application No. MX/a/2011/011907 (Aug. 12, 2014)(redacted).
Banker et al., "Modern Pharmaceutics," 3rd Ed., p. 451, 596 (1996).
Vippagunta et al., "Crystalline Solids," Adv. Drug Del. Rev. 48:3-26 (2001).
Wolff, M.E., "Burger's Medicinal Chemistry and Drug Discovery," 5th Ed., pp. 975-977 (1997).
Office Action dated Sep. 17, 2013 for U.S. Appl. No. 13/540,446.

(56) References Cited

OTHER PUBLICATIONS

Raeder et al., "Obesity, Dyslipidemia, and Diabetes with Selective Serotoni Hordaland Health Study," J. Clin. Psychiatry 67(12):1974-82 (2006).
Lee et al., "A Review of SSRIs and SNRIs in Neuropathic Pain," Expert Opin. Pharmacother. 11(17):2813-25 (2010).
Mandal, A., "Antidepressants May Increase Stroke Risk in Men: Study," retrieved from http://www.news-medical.net/news/20110403/Antipressants (Apr. 3, 2011).
Brambilla et al., "GABAergic Dysfunction in Mood Disorders," Molecular Psychiatry 8:721-37 (2003).
Wikipedia, "Selective Serotonin Reuptake Inhibitor," retrieved from http://en.wikipedia.org/wiki/Ssri pp. 1-40 (Nov. 25, 2011).
Cohen, J.S., "The Underlying Cause of Suicides and Homicides with SSRI Antidepressants: Is it the Drugs, the Doctors, or the Drug Companies?," retrieved at http://medicationsense.com/articles/april_june_04/underlying_cause.html pp. 1-8 (Nov. 30, 2011).
Office Action for U.S. Appl. No. 14/593,750 (Feb. 4, 2016).
Examination report for European Application No. EP10775398.0 (Feb. 5, 2016).
Translation of Notice of Preliminary Rejection and Request for Consultation for Korean Patent Application No. 10-2011-7029425 (Apr. 25, 2016).
International Preliminary Report on Patentability for International Application PCT/US2009/046256 dated Dec. 6, 2010.
International Preliminary Report on Patentability and Written Opinion for PCT/US2014/023938 dated Sep. 15, 2015.
Translation of Office Action for Mexican Patent Application No. MX/a/2011/011907 (Oct. 1, 2015) (redacted).
Examination Report for Australian National Patent Application No. 2010247763 (Oct. 21, 2014).
Translation of Reexamination Notice for Chinese Patent Application No. 201080031666.3 (Aug. 14, 2015).
Office Action dated Jul. 2, 2015 for U.S. Appl. No. 14/661,063.
First examination report for European National Patent Application No. 09759417.0 (Sep. 15, 2015).
International Search Report and Written Opinion for International Application PCT/US2009/046256 dated Dec. 9, 2009.
Office Action dated Dec. 19, 2014 for U.S. Appl. No. 13/664,546.
PCT International Search Report corresponding to PCT/US2014/023938, filed Mar. 12, 2014 (mailed Sep. 29, 2014).
International Search Report and Written Opinion for International Application PCT/US2009/046259 dated Mar. 1, 2010.
International Preliminary Report on Patentability for International Application PCT/US2009/046259 dated Dec. 6, 2010.
Ahn et al., "A Facile One-Pot Preparation of Organoselanyltrifluoroborates from Dihalobenzenes and Their Cross-Coupling Reaction," Org. Lett. 11(2):361-364 (2009).
Liang et al., "Antidepressant-Like Pharmacological Profile of a Novel Triple Reuptake Inhibitor, (1S,2S)-3-(Methylamino)-2-(naphthalen-2-yl)-1-phenylpropan-1-ol (PRC200-SS)," J. Pharmacology and Experimental Therapeutics 327(2):573-583 (2008).
Tran, "Efficacy and Tolerability of the Novel Triple Reuptake Inhibitor Amitifadine in the Treatment of Patients with Major Depressive Disorder: A Randomized, Double-Blind, Placebo-Controlled trial" J. Phychiatric Research 46:64-71 (2012).
Bennett et al., "Heteronuclear Decoupling in Rotating Solids," J. Chem. Phys., 103(16):6951-6958 (1995).
Bodkin et al., "Combining Serotonin Reuptake Inhibitors and Bupropion in Partial Responders to Antidepressant Monotherapy," J. Clin. Psychiatry, 58(4):137-145 (1997).
Chou et al., "Quantitative Analysis of Dose-Effect Relationships: The Combined Effects of Multiple Drugs or Enzyme Inhibitors," Adv. Enzyme Regul., 22:27-55 (1984).
Dunlop et al., "The Role of Dopamine in the Pathophysiology of Depression," Arch. Gen. Psychiatry, 64:327-337 (2007).
Earl et al., "Measurement of 13C Chemical Shifts in Solids," Journal of Magnetic Resonance, 48:35-54 (1982).
Garlow et al., Chapter 31: "The Neurochemistry of Depressive Disorders: Clinical Studies," Charney et al., eds. Neurobiology of Mental Illness, Second Edition, pp. 440-460, Oxford University Press, publ. (2004).
Gennaro, A.R., ed., Remington's Pharmaceutical Sciences, 18th Edition, p. 1445, Mack Publishing Company, publ. (1990).
Gennaro, A.R., ed., Remington's Pharmaceutical Sciences, 18th Edition, pp. xv-xvi, Mack Publishing Company, publ. (1990) (table of contents).
Gennaro, A.R., ed., Remington: The Science and Practice of Pharmacy, 19th Edition, pp. vii-viii, Mack Publishing Company, publ. (1995) (table of contents).
Hirschfeld et al., "Partial Response and Nonresponse to Antidepressant Therapy: Current Approaches and Treatment Options," J. Clin. Psychiatry, 63(9):826-837 (2002).
Kessler et al., "Prevalence, Severity, and Comorbidity of 12-Month DSM-IV Disorders in the National Comorbidity Survey Replication," Arch Gen. Psychiatry, 62:617-627 (2005).
Lavretsky et al., "Combined Treatment with Methylphenidate and Citalopram for Accelerated Response in the Elderly: An Open Trial," J. Clin. Psychiatry, 64(12):1410-1414 (2003).
Marshall et al., "Paroxetine/Bupropion Combination Treatment for Refractory Depression," J. Clin. Psychopharmacol., 16(1):80-81 (1996).
Metz et al., "Ramped-Amplitude Cross Polarization in Magic-Angle-Spinning NMR," Journal of Magnet Resonance, Series A, 110:219-227 (1994).
Mullin et al, "Programmed Cooling of Batch Crystalizers," Chemical Engineering Science, 26:369-377 (1971).
Papakostas et al., "A Metaanalysis of Clinical Trials Comparing Moclobemide with Selective Serotonin Reuptake Inhibitors for the Treatment of Major Depressive Disorder," Can J. Psychiatry, 51(12):783-790 (2006).
Stout et al., Chapter 3: "Symmetry Operations and Space Groups," X-ray Structure Determination: A Practical Guide, pp. 38-61, The Macmillan Company, publ. (1968).
Trivedi et al., "Medication Augmentation after the Failure of SSRIs for Depression," The New England Journal of Medicine, 354(12):1243-1252 (2006).
Üstün et al., "Global Burden of Depressive Disorders in the Year 2000," British Journal of Psychiatry, 184:386-392 (2004).
Yin et al., "Simulated PXRD Patterns in Studies of the Phase Composition and Thermal Behavior of Bulk Crystalline Solids," American Pharmaceutical Review, 6(2):80-85 (2003).
Hu et al., "Synthesis and Herbicidal Activity of 3-Arylalkylamino-6-chloropyridazines," Chinese Journal of Organic Chemistry, 26(6):808-812 (2006) (English Abstract only).
Translation of Substantive Examination dated Feb. 15, 2016 for Mexican Patent Application No. PI 20070018.
Translation of Office Action dated Feb. 16, 2015 for Mexican Patent Application No. MX/a/2011/011907 (redacted).
Byrn et al., "Solid-State Chemistry of Drugs," Second Edition, pp. ix-xvii, SSCI, Inc., publ. (1999) (table of contents).
Translation of Notice of Reasons for Rejection for Japanese Patent Application No. 2012-510930 dated Jun. 1, 2015.
Examination report for European Patent Application No. 10775398.0 (Aug. 20, 2015).
Office Action dated Jul. 24, 2015 for U.S. Appl. No. 14/593,750.
Translation of Decision on Rejection dated Jun. 3, 2015 for Chinese Patent Application No. 201410074721.7.
Completion of Final Requirements dated Jul. 9, 2015 for Philippine Application No. 1-2011-502550.
Office Action for U.S. Appl. No. 12/777,728 (Apr. 7, 2014).
Substantive Examination Report for Philippines Patent Application No. 1/2011/502550 (Apr. 10, 2015).
CAS Registry No. 944788-71-0, ACS on STN, 2 pages (Aug. 16, 2007).
Rollins "A Framework for Creating Customized Multi-Model Interfaces for XML Documents," Multimedia and Expo, (2000).
Office Action dated Jul. 2, 2014 for U.S. Appl. No. 13/664,546.
Translation of Office Action for Thailand Patent Application No. 0901002469 (Mar. 3, 2011) (redacted).

(56) References Cited

OTHER PUBLICATIONS

Translation of Notice of Reason for Refusal for Japanese Patent Application No. 2011-512645 (Nov. 12, 2013).
Translation of Notice of Decision of Refusal for Japanese Patent Application No. 2011-512645 (Oct. 28, 2014).
Translation of Office Action for Chinese Patent Application No. 200980130762.0 (Nov. 1, 2012).
Translation of Office Action for Chinese Patent Application No. 200980130762.0 (Sep. 18, 2013).
Translation of Office Action for Argentina Patent Application No. P090101990 (Jun. 27, 2012) (redacted).
Translation of Office Action for Argentina Patent Application No. P090101990 (Aug. 6, 2014) (redacted).
Translation of Office Action for Argentina Patent Application No. P090101990 (Dec. 30, 2014) (redacted).
Translation of Office Action for Taiwan Patent Application No. 098118594 (Jan. 17, 2014).
Translation of Office Action for Taiwan Patent Application No. 098118594 (Nov. 24, 2014).
Office Action for U.S. Appl. No. 12/995,771 (Dec. 20, 2011).
Office Action for U.S. Appl. No. 12/995,771 (May 9, 2012).
Office Action for U.S. Appl. No. 12/995,771 (Sep. 7, 2012).
Chen et al., "Triple Uptake Inhibitors: Therapeutic Potential in Depression and Beyond," Expert Opin. Investig. Drugs 6(9):1365-1377 (2007).

\* cited by examiner

ARYL- AND HETEROARYL-SUBSTITUTED TETRAHYDROISOQUINOLINES AND USE THEREOF TO BLOCK REUPTAKE OF NOREPINEPHRINE, DOPAMINE, AND SEROTONIN

This application is a continuation of U.S. patent application Ser. No. 14/268,753, filed May 2, 2014, which is a division of U.S. patent application Ser. No. 13/540,446, filed Jul. 2, 2012, now U.S. Pat. No. 8,741,901, issued on Jun. 3, 2014, which is a division of U.S. patent application Ser. No. 12/252,823, filed Oct. 16, 2008, now U.S. Pat. No. 8,227,486, issued on Jul. 24, 2012. which is a continuation of U.S. patent application Ser. No. 11/183,066, filed Jul. 15, 2005, now U.S. Pat. No. 7,541,357, issued on Jun. 2, 2009, which claims the benefit of U.S. Provisional Patent Application Ser. No. 60/588,448, filed Jul. 15, 2004, each of which is hereby incorporated by reference in its entirety.

FIELD OF THE INVENTION

The present invention relates to novel 4-bicyclic carbocycle- and heterocycle-substituted tetrahydroisoquinoline derivative compounds, pharmaceutical compositions comprising such compounds, methods of using such compounds for the treatment of various neurological and psychological disorders and for combination therapy.

BACKGROUND OF THE INVENTION

It is well known that the neurotransmitters, dopamine (DA), norepinephrine (NE), and serotonin (5-HT), regulate a number of biological processes and that decreased levels of DA, NE, and 5-HT are associated with a number of neurological disorders and their physical manifestations. Significant effort has been expended on devising methods for adjusting the levels of these neurotransmitters in order to produce a desired pharmacological effect. Preventing the reuptake of these neurotransmitters in any combination of one, two, or all three of them is likely to be effective in treating these disorders. Targeting the dopamine transporter (DAT), norepinephrine transporter (NET), and the serotonin transporter (SERT) proteins has proven to be an effective way of increasing the levels of the respective monoamines.

Methylphenidate, which is currently used for the treatment of attention deficit hyperactivity disorder (ADHD), is known to be selective for inhibition of the DAT. U.S. Pat. No. 5,444,070 discloses selective inhibitors of dopamine reuptake as treatments for Parkinson's disease and drug addiction or abuse including cocaine and amphetamines.

Selective norepinephrine reuptake inhibitors (NARI) have also been disclosed. For example, U.S. Pat. No. 6,352,986 describes methods of treating ADHD, addictive disorders, and psychoactive substance use disorders with Reboxetine. In addition, Atomoxetine (Strattera®) is currently marketed as a selective NET reuptake inhibitor for ADHD.

The use of selective serotonin reuptake inhibitors (SSRI) has also been shown to be effective in treating depressive disorders. Sertraline, Citalopram, and Paroxetine are well-known examples of SSRIs used to treat disorders such as depression, obsessive compulsive disorder, and panic attacks. There are several known difficulties with the SSRI class of therapeutics, including the slow onset of action, unwanted side effects, and the existence of a significant subset of the population that is not responsive to SSRI therapy.

Selective inhibitors of DAT, NET, and SERT reuptake may also be co-administered with each other or with other drugs. U.S. Pat. No. 5,532,244 discloses the use of serotonin reuptake inhibitors in combination with a serotonin 1A antagonist for the treatment of obsessive-compulsive disorder, depression, and obesity. The use of a serotonin or norepinephrine reuptake inhibitor in combination with a neurokinin-1 receptor antagonist has been disclosed in U.S. Pat. No. 6,121,261 for the treatment of ADHD. U.S. Pat. No. 4,843,071 discloses the use of a norepinephrine reuptake inhibitor in combination with a norepinephrine precursor in the treatment of obesity, drug abuse, or narcolepsy. U.S. Pat. No. 6,596,741 discloses the use of a NE, DA, or 5-HT inhibitor with either a neurokinin-1 receptor antagonist or a serotonin-1A antagonist for the treatment of a wide variety of conditions.

Also advantageous is the use of compounds that inhibit one or more of the neurotransmitters at the same time. The antidepressant qualities of the dual NET and SERT reuptake inhibitor duloxetine is disclosed in European Patent No. 273658. Venlafaxine is disclosed in U.S. Pat. No. 4,535,186 as a reuptake inhibitor of both NE and 5-HT for the treatment of depressive disorders. U.S. Pat. No. 6,635,675 discloses the use of the dual NE and 5-HT reuptake inhibitor milnacipran for the treatment of chronic fatigue syndrome and fibromyalgia syndrome. In addition, dual NE and 5-HT reuptake inhibitors are disclosed in U.S. Pat. No. 6,136,083 for the treatment of depression. It is also recognized that compounds which inhibit the reuptake of NE, DA, and 5-HT in varying ratios not specifically mentioned here would also be advantageous.

Treating illnesses by inhibiting the reuptake of all three of the monoamines, either through combination therapy or "triple inhibitors," may have clinical benefit as well. PCT International Publication Nos. WO 03/101453 and WO 97/30997 disclose a class of compounds which are active against all three monoamine transporters. The rationale for the inclusion of a dopamine-enhancing component in anti-depressant therapy includes observed deficits in dopaminergic function, the success of combination therapy with dopamine agonists and traditional antidepressants, and an increased sensitivity in dopamine receptors due to chronic antidepressant administration (Skolnick et al., *Life Sciences* 73:3175-3179 (2003)). As such, inhibitory activity against DA reuptake, in addition to NE and 5-HT reuptake, is expected to provide a more rapid onset of antidepressant effect, compared to other mixed inhibitors which are selective for NET and SERT over DAT. In addition, PCT International Publication No. WO 03/049736 discloses a series of 4-substituted piperidines, each of which displays similar activity against DA, NE and 5-HT transporters. Bicyclo [2.2.1]heptanes (Axford et al., *Bioorg Med Chem Lett* 13:3277-3280 (2003)) and azabicyclo[3.1.0]hexanes (Skolnick et al., *Eur J Pharm,* 461:99-104 (2003)) are also described as triple inhibitors of the three monoamine transporters.

U.S. Pat. No. 3,947,456 discloses tetrahydroisoquinolines which are said to have utility as antidepressants. U.S. Pat. No. 3,666,763 describes the use of phenyl tetrahydroisoquinoline derivatives as antidepressants and antihypotensives. Canadian Patent Application No. 2,015,114 discloses the use of phenyl tetrahydroisoquinoline derivatives as antidepressants; the compounds described therein are apparently non-selective as to norepinephrine, serotonin, and dopamine uptake. United Kingdom Patent Application No. 2,271,566 discloses the use of phenyl tetrahydroisoquinoline derivatives as anti-HIV agents. PCT International Publication No.

WO 98/40358 discloses the use of phenyl tetrahydroisoquinoline derivatives to be useful in the treatment of disorders of glucose metabolic pathways. PCT International Publication No. WO 97/36876 discloses the use of phenyl tetrahydroisoquinoline derivatives as anticancer agents. PCT International Publication No. WO 97/23458 also describes 4-phenyl-substituted tetrahydroisoquinolines as NMDA receptor ligands useful for conditions associated with neuronal loss. Phenyl-substituted tetrahydroisoquinolines are also described in Mondeshka et al., *Il Farmaco* 49:475-481 (1994).

U.S. Pat. No. 6,579,885 discloses the use of 7-aryl-substituted tetrahydroisoquinolines as being useful for the treatment of disorders involving decreased availability of serotonin, norepinephrine, or dopamine. Tupper et al., *J Heterocyclic Chem* 33:1123-1129 (1996) describes the synthesis of tetrahydroisoquinolines substituted with a 2- or 3-thienyl group in the 4 position as possible dopamine $D_1$ and $D_2$ antagonists. Prat et al., *J Heterocyclic Chem* 37:767-771 (2000) describes the synthesis of N-methyl-4-pyridyl-1,2,3,4-tetrahydroisoquinolines, as well as the 2-pyridyl and 3-pyridyl analogs, which were designed as potential serotonin analogs, but no activity was reported. Chandrasekhar et al., *Tetrahedron Lett* 43:1885-1888 (2002) described the synthesis of trans-4-benzo[1,3]dioxol-5-yl-2-benzyl-3-methyl-1,2,3,4-tetrahydroisoquinoline; however, neither usage nor activity was reported. Lopez et al., *Tetrahedron* 50:9097-9106 (1994) described the synthesis of 2-(1,2,3,4-tetrahydroisoquinolin-4-yl)-quinolin-3-ol; however, neither usage nor activity was reported. Uno et al., *J Heterocyclic Chem* 38:341-346 (1991) described the synthesis of 1-ethyl-1'-pentafluoroethyl-1,2,3,4-tetrahydro-[4,4']bis(isoquinoline); however, neither usage nor activity was reported.

Nomifensine®, which is a 4-phenyl-substituted tetrahydroisoquinoline derivative, is known to inhibit the neuronal uptake of dopamine and other catecholamines and has shown clinical efficacy for ADHD. However, long term administration of Nomifensine® resulted in fatal immune hemolytic anemia in a very small number of patients causing the manufacturer to discontinue this drug from the market. Thus, there continues to remain a need to develop novel compounds which treat ADHD but do not have the serious side effects associated with Nomifensine® or the currently prescribed psychostimulants.

The present invention is directed to achieving these objectives.

SUMMARY OF THE INVENTION

The compounds of the present invention are represented by the chemical structure found in Formula (I):

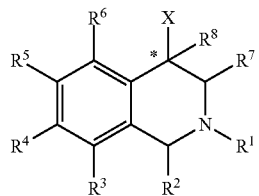

Formula I wherein:
the carbon atom designated * is in the R or S configuration;
X is a fused bicyclic carbocycle or heterocycle selected from the group consisting of benzofuranyl, benzo[b]thiophenyl, benzoisothiazolyl, benzoisoxazolyl, indazolyl, indolyl, isoindolyl, indolizinyl, benzoimidazolyl, benzooxazolyl, benzothiazolyl, benzotriazolyl, imidazo[1,2-a]pyridinyl, pyrazolo[1,5-a]pyridinyl, [1,2,4]triazolo[4,3-a]pyridinyl, thieno[2,3-b]pyridinyl, thieno[3,2-b]pyridinyl, 1H-pyrrolo[2,3-b]pyridinyl, indenyl, indanyl, dihydrobenzocycloheptenyl, tetrahydrobenzocycloheptenyl, dihydrobenzothiophenyl, dihydrobenzofuranyl, indolinyl, naphthyl, tetrahydronaphthyl, quinolinyl, isoquinolinyl, 4H-quinolizinyl, 9aH-quinolizinyl, quinazolinyl, cinnolinyl, phthalazinyl, quinoxalinyl, benzo[1,2,3]triazinyl, benzo[1,2,4]triazinyl, 2H-chromenyl, 4H-chromenyl, and a fused bicyclic carbocycle or fused bicyclic heterocycle optionally substituted with substituents (1 to 4 in number) as defined below in $R^{14}$;

$R^1$ is H, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, each of which is optionally substituted with from 1 to 3 substituents independently selected at each occurrence thereof from the group consisting of: $C_1$-$C_3$ alkyl, halogen, aryl, —CN, —$OR^9$, and —$NR^9R^{10}$;

$R^2$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, or $C_1$-$C_6$ haloalkyl, each of which is optionally substituted with from 1 to 3 substituents independently selected at each occurrence thereof from the group consisting of: $C_1$-$C_3$ alkyl, halogen, aryl, —CN, —$OR^9$, and —$NR^9R^{10}$; or
$R^2$ is gem-dimethyl;

$R^3$ is H, halogen, —$OR^{11}$, —$S(O)_nR^{12}$, —CN, —$C(O)R^{12}$, —$C(O)NR^{11}R^{12}$, —$NR^9R^{10}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with from 1 to 3 substituents independently selected at each occurrence thereof from the group consisting of: $C_1$-$C_3$ alkyl, halogen, —CN, —$OR^9$, —$NR^9R^{10}$, and phenyl, which is optionally substituted 1 to 3 times with a substituent selected from the group consisting of: halogen, cyano, $C_1$-$C_4$ alkyl, $C_1$-$C_4$ haloalkyl, $C_1$-$C_4$ alkoxy, —CN, and —$OR^9$;

$R^4$ is H, halogen, —$OR^{11}$, —$S(O)_nR^{12}$, —CN, —$C(O)R^{12}$, —$C(O)NR^{11}R^{12}$, —$NR^9R^{10}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, wherein each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with from 1 to 3 substituents independently selected at each occurrence thereof from the group consisting of: $C_1$-$C_3$ alkyl, halogen, —CN, —$OR^9$, —$NR^9R^{10}$, and phenyl, which is optionally substituted 1 to 3 times with a substituent selected from the group consisting of: halogen, cyano, $C_1$-$C_4$ alkyl, $C_1$-$C_4$ haloalkyl, $C_1$-$C_4$ alkoxy, —CN, and —$OR^9$; or $R^4$ is phenyl, naphthyl, indenyl, pyridyl, pyrimidinyl, pyridazinyl, pyrazinyl, [1,2,4]triazinyl, [1,3,5]triazinyl, triazolyl, furanyl, thiophenyl, pyranyl, indazolyl, benzimidazolyl, quinolinyl, quinazolinyl, quinoxalinyl, phthalazinyl, cinnolinyl, isoquinolinyl, thienyl, imidazolyl, thiazolyl, benzthiazolyl, purinyl, isothiazolyl, indolyl, pyrrolyl, oxazolyl, benzofuranyl, benzothienyl, benzthiazolyl, isoxazolyl, pyrazolyl, oxadiazolyl, thiadiazolyl, 3-oxo-[1,2,4]triazolo[4,3-a]pyridinyl, imidazo[1,2-a]pyridinyl, pyrazolo[1,5-a]pyridinyl, [1,2,4]triazolo[4,3-a]pyridinyl, thieno[2,3-b]pyridinyl, thieno[3,2-b]pyridinyl, 1H-pyrrolo[2,3-b]pyridinyl, or other heterocycles optionally substituted with substituents (1 to 4 in number) as defined below in $R^{14}$;

R⁵ and R⁶ are each independently selected from the group consisting of: H, halogen, —OR¹¹, —S(O)ₙR¹², —CN, —C(O)R¹², —C(O)NR¹¹R¹², —NR⁹R¹⁰, C₁-C₆ alkyl, C₂-C₆ alkenyl, C₂-C₆ alkynyl, C₃-C₆ cycloalkyl, and C₄-C₇ cycloalkylalkyl, wherein each of C₁-C₆ alkyl, C₂-C₆ alkenyl, C₂-C₆ alkynyl, C₃-C₆ cycloalkyl, C₄-C₇ cycloalkylalkyl, and phenyl is optionally substituted with from 1 to 3 substituents independently selected at each occurrence thereof from the group consisting of: C₁-C₃ alkyl, halogen, —CN, —OR⁹, —NR⁹R¹⁰, and phenyl, which is optionally substituted 1 to 3 times with a substituent selected from the group consisting of: halogen, C₁-C₄ alkyl, C₁-C₄ haloalkyl, C₁-C₄ alkoxy, —CN, and —OR⁹;

R⁷ is H, C₁-C₆ alkyl, C₂-C₆ alkenyl, C₂-C₆ alkynyl, C₃-C₆ cycloalkyl, or C₄-C₇ cycloalkylalkyl, wherein each of C₁-C₆ alkyl, C₂-C₆ alkenyl, C₂-C₆ alkynyl, C₃-C₆ cycloalkyl, and C₄-C₇ cycloalkylalkyl is optionally substituted with from 1 to 3 substituents independently selected at each occurrence thereof from the group consisting of: C₁-C₃ alkyl, halogen, —CN, —OR⁹, —NR⁹R¹⁰, and phenyl which is optionally substituted 1 to 3 times with a substituent selected from the group consisting of: halogen, C₁-C₄ alkyl, C₁-C₄ haloalkyl, C₁-C₄ alkoxy, —CN, and —OR⁹; or R⁷ is gem-dimethyl;

R⁸ is H, halogen, —OR⁹, —SR⁹, C₁-C₆ alkyl, —CN, or —NR⁹R¹⁰;

R⁹ and R¹⁰ are each independently selected from the group consisting of: H, C₁-C₄ alkyl, C₁-C₄ haloalkyl, C₁-C₄ alkoxyalkyl, C₃-C₆ cycloalkyl, C₄-C₇ cycloalkylalkyl, —C(O)R¹³, phenyl, and benzyl, where phenyl or benzyl is optionally substituted from 1 to 3 times with a substituent selected independently at each occurrence thereof from the group consisting of: halogen, cyano, C₁-C₄ alkyl, C₁-C₄ haloalkyl, and C₁-C₄ alkoxy; or R⁹ and R¹⁰ are taken together with the nitrogen to which they are attached to form a piperidine, pyrrolidine, piperazine, N-methylpiperazine, morpholine, thiomorpholine, [1,2] oxazinane, isoxazolidine, or 2-oxo-2H-pyridine, which is optionally substituted from 1 to 3 times with a substituent selected independently at each occurrence thereof from the group consisting of: halogen, cyano, C₁-C₄ alkyl, C₁-C₄ haloalkyl, and C₁-C₄ alkoxy;

R¹¹ is H, C₁-C₄ alkyl, C₁-C₄ haloalkyl, C₁-C₄ alkoxyalkyl, C₃-C₆ cycloalkyl, C₄-C₇ cycloalkylalkyl, —C(O)R¹³, phenyl, or benzyl, where phenyl or benzyl is optionally substituted 1 to 3 times with halogen, cyano, C₁-C₄ alkyl, C₁-C₄ haloalkyl, or C₁-C₄ alkoxy;

R¹² is H, C₁-C₄ alkyl, C₁-C₄ haloalkyl, C₁-C₄ alkoxyalkyl, C₃-C₆ cycloalkyl, C₄-C₇ cycloalkylalkyl, phenyl, or benzyl, where phenyl or benzyl is optionally substituted 1 to 3 times with halogen, cyano, C₁-C₄ alkyl, C₁-C₄ haloalkyl, or C₁-C₄ alkoxy; or R¹¹ and R¹² are taken together with the nitrogen to which they are attached to form a piperidine, pyrrolidine, piperazine, N-methylpiperazine, morpholine, or thiomorpholine ring, with the proviso that only one of R⁹ and R¹⁰ or R¹¹ and R¹² are taken together with the nitrogen to which they are attached to form a piperidine, pyrrolidine, piperazine, N-methylpiperazine, morpholine, or thiomorpholine ring;

R¹³ is C₁-C₄ alkyl, C₁-C₄ haloalkyl, or phenyl;

n is 0, 1, or 2; and

R¹⁴ is independently selected at each occurrence from a substituent selected from the group consisting of: halogen, —NO₂, —OR¹¹, —NR¹¹R¹², —NR¹¹C(O)R¹², —NR¹¹C(O)₂R¹², —NR¹¹C(O)NR¹²R¹³, —S(O)ₙR¹², —CN, —C(O)R¹², —C(O)NR¹¹R¹², C₁-C₆ alkyl, C₂-C₆ alkenyl, C₂-C₆ alkynyl, C₃-C₆ cycloalkyl, and C₄-C₇ cycloalkylalkyl, where C₁-C₆ alkyl, C₂-C₆ alkenyl, C₂-C₆ alkynyl, C₃-C₆ cycloalkyl, and C₄-C₇ cycloalkylalkyl are optionally substituted with 1 to 3 substituents independently selected at each occurrence from the group consisting of: C₁-C₃ alkyl, halogen, aryl, —CN, —OR⁹, and —NR⁹R¹⁰;

or an oxide thereof or a pharmaceutically acceptable salt thereof.

The compounds of the present invention are also represented by the chemical structure found in Formula (I):

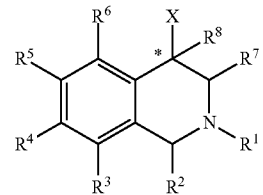

Formula I wherein:

the carbon atom designated * is in the R or S configuration;

X is a fused aromatic bicyclic carbocycle or heterocycle optionally substituted with substituents (1 to 4 in number) as defined below in R¹⁴, with the proviso that X≠isoquinolinyl, naphthyl, or phthalimidyl;

R¹ is H, C₁-C₆ alkyl, C₂-C₆ alkenyl, C₂-C₆ alkynyl, C₃-C₆ cycloalkyl, or C₄-C₇ cycloalkylalkyl, each of which is optionally substituted with from 1 to 3 substituents independently selected at each occurrence thereof from the group consisting of: C₁-C₃ alkyl, halogen, aryl, —CN, —OR⁹, and —NR⁹R¹⁰;

R² is H, C₁-C₆ alkyl, C₂-C₆ alkenyl, C₂-C₆ alkynyl, C₃-C₆ cycloalkyl, C₄-C₇ cycloalkylalkyl, or C₁-C₆ haloalkyl, each of which is optionally substituted with from 1 to 3 substituents independently selected at each occurrence thereof from the group consisting of: C₁-C₃ alkyl, halogen, aryl, —CN, —OR⁹, and —NR⁹R¹⁰; or R² is gem-dimethyl;

R³ is H, halogen, —OR¹¹, —S(O)ₙR¹², —CN, —C(O)R¹², —C(O)NR¹¹R¹², —NR⁹R¹⁰, C₁-C₆ alkyl, C₂-C₆ alkenyl, C₂-C₆ alkynyl, C₃-C₆ cycloalkyl, or C₄-C₇ cycloalkylalkyl, wherein each of C₁-C₆ alkyl, C₂-C₆ alkenyl, C₂-C₆ alkynyl, C₃-C₆ cycloalkyl, and C₄-C₇ cycloalkylalkyl is optionally substituted with from 1 to 3 substituents independently selected at each occurrence thereof from the group consisting of: C₁-C₃ alkyl, halogen, —CN, —OR⁹, —NR⁹R¹⁰, and phenyl, which is optionally substituted 1 to 3 times with a substituent selected from the group consisting of: halogen, cyano, C₁-C₄ alkyl, C₁-C₄ haloalkyl, C₁-C₄ alkoxy, —CN, and —OR⁹;

R⁴ is H, halogen, —OR¹¹, —S(O)ₙR¹², —CN, —C(O)R¹², —C(O)NR¹¹R¹², —NR⁹R¹⁰, C₁-C₆ alkyl, C₂-C₆ alkenyl, C₂-C₆ alkynyl, C₃-C₆ cycloalkyl, or C₄-C₇ cycloalkylalkyl, wherein each of the C₁-C₆ alkyl, C₂-C₆ alkenyl, C₂-C₆ alkynyl, C₃-C₆ cycloalkyl, and C₄-C₇ cycloalkylalkyl is optionally substituted with from 1 to 3 substituents independently selected at each occurrence thereof from the group consisting of: C₁-C₃ alkyl, halogen, —CN, —OR⁹, —NR⁹R¹⁰, and phenyl, which is optionally substituted 1 to 3 times with a substituent selected from the group consisting of: halogen, cyano, $C_1$-$C_4$ alkyl, $C_1$-$C_4$ haloalkyl, $C_1$-$C_4$ alkoxy, —CN, and —$OR^9$; or $R^4$ is phenyl, naphthyl, indenyl, pyridyl, pyrimidinyl, pyridazinyl, pyrazinyl, [1,2,4]triazinyl, [1,3,5]triazinyl, triazolyl, furanyl, thiophenyl, pyranyl, indazolyl, benzimidazolyl, quinolinyl, quinazolinyl, quinoxalinyl, phthalazinyl, cinnolinyl, isoquinolinyl, thienyl, imidazolyl, thiazolyl, benzthiazolyl, purinyl, isothiazolyl, indolyl, pyrrolyl, oxazolyl, benzofuranyl, benzothienyl, benzthiazolyl, isoxazolyl, pyrazolyl, oxadiazolyl, thiadiazolyl, 3-oxo-[1,2,4]triazolo[4,3-a]pyridinyl, imidazo[1,2-a]pyridinyl, pyrazolo[1,5-a]pyridinyl, [1,2,4]triazolo[4,3-a]pyridinyl, thieno[2,3-b]pyridinyl, thieno[3,2-b]pyridinyl, 1H-pyrrolo[2,3-b]pyridinyl, or other heterocycles optionally substituted with substituents (1 to 4 in number) as defined below in $R^{14}$;

$R^5$ and $R^6$ are each independently selected from the group consisting of: H, halogen, —$OR^{11}$, —$S(O)_nR^{12}$, —CN, —$C(O)R^{12}$, —$C(O)NR^{11}R^{12}$, —$NR^9R^{10}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and phenyl is optionally substituted with from 1 to 3 substituents independently selected at each occurrence thereof from the group consisting of: $C_1$-$C_3$ alkyl, halogen, —CN, —$OR^9$, —$NR^9R^{10}$, and phenyl, which is optionally substituted 1 to 3 times with a substituent selected from the group consisting of: halogen, $C_1$-$C_4$ alkyl, $C_1$-$C_4$ haloalkyl, $C_1$-$C_4$ alkoxy, —CN, and —$OR^9$;

$R^7$ is H, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with from 1 to 3 substituents independently selected at each occurrence thereof from the group consisting of: $C_1$-$C_3$ alkyl, halogen, —CN, —$OR^9$, —$NR^9R^{10}$, and phenyl which is optionally substituted 1 to 3 times with a substituent selected from the group consisting of: halogen, $C_1$-$C_4$ alkyl, $C_1$-$C_4$ haloalkyl, $C_1$-$C_4$ alkoxy, —CN, and —$OR^9$; or $R^7$ is gem-dimethyl;

$R^8$ is H, halogen, —$OR^9$, —$SR^9$, $C_1$-$C_6$ alkyl, —CN, or —$NR^9R^{10}$;

$R^9$ and $R^{10}$ are each independently selected from the group consisting of: H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —$C(O)R^{13}$, phenyl, and benzyl, where phenyl or benzyl is optionally substituted from 1 to 3 times with a substituent selected independently at each occurrence thereof from the group consisting of: halogen, cyano, $C_1$-$C_4$ alkyl, $C_1$-$C_4$ haloalkyl, and $C_1$-$C_4$ alkoxy; or $R^9$ and $R^{10}$ are taken together with the nitrogen to which they are attached to form a piperidine, pyrrolidine, piperazine, N-methylpiperazine, morpholine, thiomorpholine, [1,2]oxazinane, isoxazolidine, or 2-oxo-2H-pyridine, which is optionally substituted from 1 to 3 times with a substituent selected independently at each occurrence thereof from the group consisting of, halogen, cyano, $C_1$-$C_4$ alkyl, $C_1$-$C_4$ haloalkyl, and $C_1$-$C_4$ alkoxy;

$R^{11}$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —$C(O)R^{13}$, phenyl, or benzyl, where phenyl or benzyl is optionally substituted 1 to 3 times with halogen, cyano, $C_1$-$C_4$ alkyl, $C_1$-$C_4$ haloalkyl, or $C_1$-$C_4$ alkoxy;

$R^{12}$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, phenyl, or benzyl, where phenyl or benzyl is optionally substituted 1 to 3 times with halogen, cyano, $C_1$-$C_4$ alkyl, $C_1$-$C_4$ haloalkyl, or $C_1$-$C_4$ alkoxy; or $R^{11}$ and $R^{12}$ are taken together with the nitrogen to which they are attached to form a piperidine, pyrrolidine, piperazine, N-methylpiperazine, morpholine, or thiomorpholine ring, with the proviso that only one of $R^9$ and $R^{10}$ or $R^{11}$ and $R^{12}$ are taken together with the nitrogen to which they are attached to form a piperidine, pyrrolidine, piperazine, N-methylpiperazine, morpholine, or thiomorpholine ring;

$R^{13}$ is $C_1$-$C_4$ alkyl, $C_1$-$C_4$ haloalkyl, or phenyl;

n is 0, 1, or 2; and $R^{14}$ is independently selected at each occurrence from a substituent selected from the group consisting of: halogen, —$NO_2$, —$OR^{11}$, —$NR^{11}R^{12}$, —$NR^{11}C(O)R^{12}$, —$NR^{11}C(O)_2R^{12}$, —$NR^{11}C(O)NR^{12}R^{13}$, —$S(O)_nR^{12}$, —CN, —$C(O)R^{12}$, —$C(O)NR^{11}R^{12}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl are optionally substituted with 1 to 3 substituents independently selected at each occurrence from the group consisting of: $C_1$-$C_3$ alkyl, halogen, aryl, —CN, —$OR^9$, and —$NR^9R^{10}$;

or an oxide thereof or a pharmaceutically acceptable salt thereof.

In addition, the compounds of the present invention are represented by the chemical structure found in Formula (I):

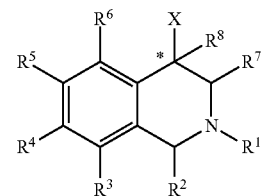

Formula I wherein:

the carbon atom designated * is in the R or S configuration;

X is a fused bicyclic carbocycle or heterocycle selected from the group consisting of benzofuranyl, benzo[b]thiophenyl, benzoisothiazolyl, benzoisoxazolyl, indazolyl, indolyl, isoindolyl, indolizinyl, benzoimidazolyl, benzooxazolyl, benzothiazolyl, benzotriazolyl, imidazo[1,2-a]pyridinyl, pyrazolo[1,5-a]pyridinyl, [1,2,4]triazolo[4,3-a]pyridinyl, thieno[2,3-b]pyridinyl, thieno[3,2-b]pyridinyl, 1H-pyrrolo[2,3-b]pyridinyl, indenyl, indanyl, dihydrobenzocycloheptenyl, tetrahydrobenzocycloheptenyl, dihydrobenzothiophenyl, dihydrobenzofuranyl, indolinyl, naphthyl, tetrahydronaphthyl, quinolinyl, isoquinolinyl, 4H-quinolizinyl, 9aH-quinolizinyl, quinazolinyl, cinnolinyl, phthalazinyl, quinoxalinyl, benzo[1,2,3]triazinyl, benzo[1,2,4]triazinyl, 2H-chromenyl, 4H-chromenyl, and a fused bicyclic carbocycle or fused bicyclic heterocycle optionally substituted with substituents (1 to 4 in number) as defined below in $R^{14}$, with the provisos that (1) where X=naphthyl and $R^4$ is $NH_2$ or $OR^{11}$, $R^5$ cannot be H, and (2) where X=naphthyl and $R^5$=$OR^{11}$, $R^4$ cannot be H;

$R^1$ is H, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, each of which is optionally substituted with from 1 to 3 substituents independently selected at each occurrence thereof from the group consisting of: $C_1$-$C_3$ alkyl, halogen, aryl, —CN, —$OR^9$, and —$NR^9R^{10}$;

$R^2$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, or $C_1$-$C_6$ haloalkyl, each of which is optionally substituted with from 1 to 3 substituents independently selected at each occurrence thereof from the group consisting of: $C_1$-$C_3$ alkyl, halogen, aryl, —CN, —$OR^9$, and —$NR^9R^{10}$; or $R^2$ is gem-dimethyl;

$R^3$ is H, halogen, —$OR^{11}$, —$S(O)_nR^{12}$, —CN, —$C(O)R^{12}$, —$C(O)NR^{11}R^{12}$, —$NR^9R^{10}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with from 1 to 3 substituents independently selected at each occurrence thereof from the group consisting of: $C_1$-$C_3$ alkyl, halogen, —CN, —$OR^9$, —$NR^9R^{10}$, and phenyl, which is optionally substituted 1 to 3 times with a substituent selected from the group consisting of: halogen, cyano, $C_1$-$C_4$ alkyl, $C_1$-$C_4$ haloalkyl, $C_1$-$C_4$ alkoxy, —CN, and —$OR^9$;

$R^4$ is H, halogen, —$OR^{11}$, —$S(O)_nR^{12}$, —CN, —$C(O)R^{12}$, —$C(O)NR^{11}R^{12}$, —$NR^9R^{10}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, wherein each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with from 1 to 3 substituents independently selected at each occurrence thereof from the group consisting of: $C_1$-$C_3$ alkyl, halogen, —CN, —$OR^9$, —$NR^9R^{10}$, and phenyl, which is optionally substituted 1 to 3 times with a substituent selected from the group consisting of: halogen, cyano, $C_1$-$C_4$ alkyl, $C_1$-$C_4$ haloalkyl, $C_1$-$C_4$ alkoxy, —CN, and —$OR^9$; or $R^4$ is phenyl, naphthyl, indenyl, pyridyl, pyrimidinyl, pyridazinyl, pyrazinyl, [1,2,4]triazinyl, [1,3,5]triazinyl, triazolyl, furanyl, thiophenyl, pyranyl, indazolyl, benzimidazolyl, quinolinyl, quinazolinyl, quinoxalinyl, phthalazinyl, cinnolinyl, isoquinolinyl, thienyl, imidazolyl, thiazolyl, benzthiazolyl, purinyl, isothiazolyl, indolyl, pyrrolyl, oxazolyl, benzofuranyl, benzothienyl, benzthiazolyl, isoxazolyl, pyrazolyl, oxadiazolyl, thiadiazolyl, 3-oxo-[1,2,4]triazolo[4,3-a]pyridinyl, imidazo[1,2-a]pyridinyl, pyrazolo[1,5-a]pyridinyl, [1,2,4]triazolo[4,3-a]pyridinyl, thieno[2,3-b]pyridinyl, thieno[3,2-b]pyridinyl, 1H-pyrrolo[2,3-b]pyridinyl, or other heterocycles optionally substituted with substituents (1 to 4 in number) as defined below in $R^{14}$;

$R^5$ and $R^6$ are each independently selected from the group consisting of: H, halogen, —$OR^{11}$, —$S(O)_nR^{12}$, —CN, —$C(O)R^{12}$, —$C(O)NR^{11}R^{12}$, —$NR^9R^{10}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and phenyl is optionally substituted with from 1 to 3 substituents independently selected at each occurrence thereof from the group consisting of: $C_1$-$C_3$ alkyl, halogen, —CN, —$OR^9$, —$NR^9R^{10}$, and phenyl, which is optionally substituted 1 to 3 times with a substituent selected from the group consisting of: halogen, $C_1$-$C_4$ alkyl, $C_1$-$C_4$ haloalkyl, $C_1$-$C_4$ alkoxy, —CN, and —$OR^9$;

$R^7$ is H, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with from 1 to 3 substituents independently selected at each occurrence thereof from the group consisting of: $C_1$-$C_3$ alkyl, halogen, —CN, —$OR^9$, —$NR^9R^{10}$, and phenyl which is optionally substituted 1 to 3 times with a substituent selected from the group consisting of: halogen, $C_1$-$C_4$ alkyl, $C_1$-$C_4$ haloalkyl, $C_1$-$C_4$ alkoxy, —CN, and —$OR^9$; or $R^7$ is gem-dimethyl;

$R^8$ is H, halogen, —$OR^9$, —$SR^9$, $C_1$-$C_6$ alkyl, —CN, or —$NR^9R^{10}$;

$R^9$ and $R^{10}$ are each independently selected from the group consisting of: H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —$C(O)R^{13}$, phenyl, and benzyl, where phenyl or benzyl is optionally substituted from 1 to 3 times with a substituent selected independently at each occurrence thereof from the group consisting of: halogen, cyano, $C_1$-$C_4$ alkyl, $C_1$-$C_4$ haloalkyl, and $C_1$-$C_4$ alkoxy; or $R^9$ and $R^{10}$ are taken together with the nitrogen to which they are attached to form a piperidine, pyrrolidine, piperazine, N-methylpiperazine, morpholine, thiomorpholine, [1,2]oxazinane, isoxazolidine, or 2-oxo-2H-pyridine, which is optionally substituted from 1 to 3 times with a substituent selected independently at each occurrence thereof from the group consisting of, halogen, cyano, $C_1$-$C_4$ alkyl, $C_1$-$C_4$ haloalkyl, and $C_1$-$C_4$ alkoxy;

$R^{11}$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —$C(O)R^{13}$, phenyl, or benzyl, where phenyl or benzyl is optionally substituted 1 to 3 times with halogen, cyano, $C_1$-$C_4$ alkyl, $C_1$-$C_4$ haloalkyl, or $C_1$-$C_4$ alkoxy;

$R^{12}$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, phenyl, or benzyl, where phenyl or benzyl is optionally substituted 1 to 3 times with halogen, cyano, $C_1$-$C_4$ alkyl, $C_1$-$C_4$ haloalkyl, or $C_1$-$C_4$ alkoxy; or $R^{11}$ and $R^{12}$ are taken together with the nitrogen to which they are attached to form a piperidine, pyrrolidine, piperazine, N-methylpiperazine, morpholine, or thiomorpholine ring, with the proviso that only one of $R^9$ and $R^{10}$ or $R^{11}$ and $R^{12}$ are taken together with the nitrogen to which they are attached to form a piperidine, pyrrolidine, piperazine, N-methylpiperazine, morpholine, or thiomorpholine ring;

$R^{13}$ is $C_1$-$C_4$ alkyl, $C_1$-$C_4$ haloalkyl, or phenyl;

n is 0, 1, or 2; and $R^{14}$ is independently selected at each occurrence from a substituent selected from the group consisting of: halogen, —$NO_2$, —$OR^{11}$, —$NR^{11}R^{12}$, —$NR^{11}C(O)R^{12}$, —$NR^{11}C(O)_2R^{12}$, —$NR^{11}C(O)NR^{12}R^{13}$, —$S(O)_nR^{12}$, —CN, —$C(O)R^{12}$, —$C(O)NR^{11}R^{12}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl are optionally substituted with 1 to 3 substituents independently selected at each occurrence from the group consisting of: $C_1$-$C_3$ alkyl, halogen, aryl, —CN, —$OR^9$, and —$NR^9R^{10}$;

or an oxide thereof or a pharmaceutically acceptable salt thereof.

Another aspect of the present invention relates to a process for preparation of a product compound of Formula (I):

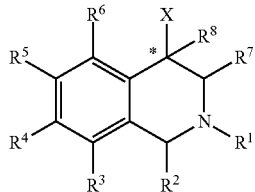

Formula (I)

wherein:
the carbon atom designated * is in the R or S configuration;
X is a fused bicyclic carbocycle or heterocycle selected from the group consisting of benzofuranyl, benzo[b]thiophenyl, benzoisothiazolyl, benzoisoxazolyl, indazolyl, indolyl, isoindolyl, indolizinyl, benzoimidazolyl, benzooxazolyl, benzothiazolyl, benzotriazolyl, imidazo[1,2-a]pyridinyl, pyrazolo[1,5-a]pyridinyl, [1,2,4]triazolo[4,3-a]pyridinyl, thieno[2,3-b]pyridinyl, thieno[3,2-b]pyridinyl, 1H-pyrrolo[2,3-b]pyridinyl, indenyl, indanyl, dihydrobenzocycloheptenyl, tetrahydrobenzocycloheptenyl, dihydrobenzothiophenyl, dihydrobenzofuranyl, indolinyl, naphthyl, tetrahydronaphthyl, quinolinyl, isoquinolinyl, 4H-quinolizinyl, 9aH-quinolizinyl, quinazolinyl, cinnolinyl, phthalazinyl, quinoxalinyl, benzo[1,2,3]triazinyl, benzo[1,2,4]triazinyl, 2H-chromenyl, 4H-chromenyl, and a fused bicyclic carbocycle or fused bicyclic heterocycle optionally substituted with substituents (1 to 4 in number) as defined below in $R^{14}$;

$R^1$ is H, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, each of which is optionally substituted with from 1 to 3 substituents independently selected at each occurrence thereof from the group consisting of: $C_1$-$C_3$ alkyl, halogen, aryl, —CN, —$OR^9$, and —$NR^9R^{10}$;

$R^2$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, or $C_1$-$C_6$ haloalkyl, each of which is optionally substituted with from 1 to 3 substituents independently selected at each occurrence thereof from the group consisting of: $C_1$-$C_3$ alkyl, halogen, aryl, —CN, —$OR^9$, and —$NR^9R^{10}$; or $R^2$ is gem-dimethyl;

$R^3$ is H, halogen, —$OR^{11}$, —$S(O)_nR^{12}$, —CN, —$C(O)R^{12}$, —$C(O)NR^{11}R^{12}$, —$NR^9R^{10}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with from 1 to 3 substituents independently selected at each occurrence thereof from the group consisting of: $C_1$-$C_3$ alkyl, halogen, —CN, —$OR^9$, —$NR^9R^{10}$, and phenyl, which is optionally substituted 1 to 3 times with a substituent selected from the group consisting of: halogen, cyano, $C_1$-$C_4$ alkyl, $C_1$-$C_4$ haloalkyl, $C_1$-$C_4$ alkoxy, —CN, and —$OR^9$;

$R^4$ is H, halogen, —$OR^{11}$, —$S(O)_nR^{12}$, —CN, —$C(O)R^{12}$, —$C(O)NR^{11}R^{12}$, —$NR^9R^{10}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, wherein each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with from 1 to 3 substituents independently selected at each occurrence thereof from the group consisting of: $C_1$-$C_3$ alkyl, halogen, —CN, —$OR^9$, —$NR^9R^{10}$, and phenyl, which is optionally substituted 1 to 3 times with a substituent selected from the group consisting of: halogen, cyano, $C_1$-$C_4$ alkyl, $C_1$-$C_4$ haloalkyl, $C_1$-$C_4$ alkoxy, —CN, and —$OR^9$; or $R^4$ is phenyl, naphthyl, indenyl, pyridyl, pyrimidinyl, pyridazinyl, pyrazinyl, [1,2,4]triazinyl, [1,3,5]triazinyl, triazolyl, furanyl, thiophenyl, pyranyl, indazolyl, benzimidazolyl, quinolinyl, quinazolinyl, quinoxalinyl, phthalazinyl, cinnolinyl, isoquinolinyl, thienyl, imidazolyl, thiazolyl, benzthiazolyl, purinyl, isothiazolyl, indolyl, pyrrolyl, oxazolyl, benzofuranyl, benzothienyl, benzthiazolyl, isoxazolyl, pyrazolyl, oxadiazolyl, thiadiazolyl, 3-oxo-[1,2,4]triazolo[4,3-a]pyridinyl, imidazo[1,2-a]pyridinyl, pyrazolo[1,5-a]pyridinyl, [1,2,4]triazolo[4,3-a]pyridinyl, thieno[2,3-b]pyridinyl, thieno[3,2-b]pyridinyl, 1H-pyrrolo[2,3-b]pyridinyl, or other heterocycles optionally substituted with substituents (1 to 4 in number) as defined below in $R^{14}$;

$R^5$ and $R^6$ are each independently selected from the group consisting of: H, halogen, —$OR^{11}$, —$S(O)_nR^{12}$, —CN, —$C(O)R^{12}$, —$C(O)NR^{11}R^{12}$, —$NR^9R^{10}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and phenyl is optionally substituted with from 1 to 3 substituents independently selected at each occurrence thereof from the group consisting of: $C_1$-$C_3$ alkyl, halogen, —CN, —$OR^9$, —$NR^9R^{10}$, and phenyl, which is optionally substituted 1 to 3 times with a substituent selected from the group consisting of: halogen, $C_1$-$C_4$ alkyl, $C_1$-$C_4$ haloalkyl, $C_1$-$C_4$ alkoxy, —CN, and —$OR^9$;

$R^7$ is H;

$R^8$ is H, halogen, —$OR^9$, —$SR^9$, $C_1$-$C_6$ alkyl, —CN, or —$NR^9R^{10}$;

$R^9$ and $R^{10}$ are each independently selected from the group consisting of: H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —$C(O)R^{13}$, phenyl, and benzyl, where phenyl or benzyl is optionally substituted from 1 to 3 times with a substituent selected independently at each occurrence thereof from the group consisting of: halogen, cyano, $C_1$-$C_4$ alkyl, $C_1$-$C_4$ haloalkyl, and $C_1$-$C_4$ alkoxy; or $R^9$ and $R^{10}$ are taken together with the nitrogen to which they are attached to form a piperidine, pyrrolidine, piperazine, N-methylpiperazine, morpholine, thiomorpholine, [1,2]oxazinane, isoxazolidine, or 2-oxo-2H-pyridine, which is optionally substituted from 1 to 3 times with a substituent selected independently at each occurrence thereof from the group consisting of, halogen, cyano, $C_1$-$C_4$ alkyl, $C_1$-$C_4$ haloalkyl, and $C_1$-$C_4$ alkoxy;

$R^{11}$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —$C(O)R^{13}$, phenyl, or benzyl, where phenyl or benzyl is optionally substituted 1 to 3 times with halogen, cyano, $C_1$-$C_4$ alkyl, $C_1$-$C_4$ haloalkyl, or $C_1$-$C_4$ alkoxy;

$R^{12}$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, phenyl, or benzyl, where phenyl or benzyl is optionally substituted 1 to 3 times with halogen, cyano, $C_1$-$C_4$ alkyl, $C_1$-$C_4$ haloalkyl, or $C_1$-$C_4$ alkoxy; or $R^{11}$ and $R^{12}$ are taken together with the nitrogen to which they are attached to form a piperidine, pyrrolidine, piperazine, N-methylpiperazine, morpholine, or thiomorpholine ring, with the proviso that only one of $R^9$ and $R^{10}$ or $R^{11}$ and $R^{12}$ are taken together with the nitrogen to which they are attached to form a piperidine, pyrrolidine, piperazine, N-methylpiperazine, morpholine, or thiomorpholine ring;

$R^{13}$ is $C_1$-$C_4$ alkyl, $C_1$-$C_4$ haloalkyl, or phenyl;

n is 0, 1, or 2; and $R^{14}$ is independently selected at each occurrence from a substituent selected from the group consisting of: halogen, —$NO_2$, —$OR^{11}$, —$NR^{11}R^{12}$, —$NR^{11}C(O)R^{12}$, —$NR^{11}C(O)_2R^{12}$, —$NR^{11}C(O)NR^{12}R^{13}$, —$S(O)_nR^{12}$, —CN, —$C(O)R^{12}$, —$C(O)NR^{11}R^{12}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl are optionally substituted with 1 to 3 substituents independently selected at each occurrence from the group consisting of: $C_1$-$C_3$ alkyl, halogen, aryl, —CN, —$OR^9$, and —$NR^9R^{10}$. The process involves treating a first intermediate compound of Formula (XVIII):

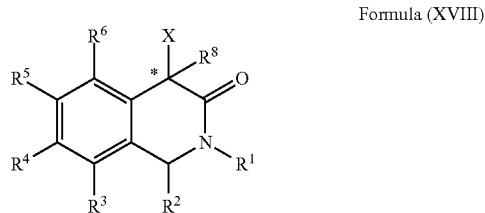

Formula (XVIII)

with a reducing agent, under conditions effective to produce the product compound.

Results of recent clinical investigations with drugs, such as duloxetine, venlafaxine, atomoxetine, and others that work mechanistically through transporter reuptake inhibition, provide evidence that the potency and selectivity are important factors in leading to drugs with an improved efficacy, improved therapeutic index, and utility for treatment of new clinical indications. Duloxetine, a dual action transporter reuptake inhibitor, is a selective inhibitor for serotonin transporter protein ("SERT") and norepinephrine transporter protein ("NET") reuptake (Sorbera et al., *Drugs of the Future*, 25(9):907-916 (2000), which is hereby incorporated by reference in its entirety) and is in clinical development for the treatment of depression and stress urinary incontinence. In clinical studies, researchers attribute the effect of the medication on a broad spectrum of depression symptoms, which include emotional and painful physical symptoms as well as anxiety, to its dual reuptake inhibition of both serotonin and norepinephrine. Venlafaxine, which is also reported to be a selective serotonin and norepinephrine reuptake inhibitor (SNRI class), has been reported to exhibit a more rapid onset of action. This has been a drawback with the first generation antidepressants, i.e., the single action serotonin selective reuptake inhibitors (SSRI class). Prozac®, the prototype drug in this class, can take four weeks or longer for full anti-depressive activity to take effect.

Atomoxetine (Strattera®) was recently approved for the treatment of attention deficit hyperactivity disorder (ADHD). Atomoxetine is a norepinephrine selective transporter reuptake inhibitor. Unlike Ritalin®, one of the most frequently used drugs for treatment of ADHD, atomoxetine has little or no activity at the dopamine transporter. As a result, atomoxetine has the advantage that it is not scheduled as a controlled substance because it has minimal potential for substance abuse.

In a manner similar to the newer clinical agents like atomoxetine, duloxetine and venlafaxine, the compounds of the present invention may exhibit improved efficacy towards broader symptoms of depression. The compounds of the present invention may also exhibit more rapid onset of action in the treatment of CNS diseases like depression. In addition to providing improved efficacy, the compounds of the present invention may also exhibit fewer undesirable side effects. Finally, because the compounds of the present invention possess a diverse transporter reuptake inhibition profile, they are expected to be useful for a wider variety of CNS disorders.

DETAILED DESCRIPTION OF THE INVENTION

The compounds of the present invention are represented by the chemical structure found in Formula (I):

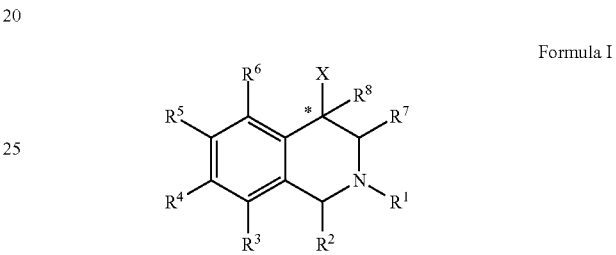

Formula I wherein:

the carbon atom designated * is in the R or S configuration;

X is a fused bicyclic carbocycle or heterocycle selected from the group consisting of benzofuranyl, benzo[b]thiophenyl, benzoisothiazolyl, benzoisoxazolyl, indazolyl, indolyl, isoindolyl, indolizinyl, benzoimidazolyl, benzooxazolyl, benzothiazolyl, benzotriazolyl, imidazo[1,2-a]pyridinyl, pyrazolo[1,5-a]pyridinyl, [1,2,4]triazolo[4,3-a]pyridinyl, thieno[2,3-b]pyridinyl, thieno[3,2-b]pyridinyl, 1H-pyrrolo[2,3-b]pyridinyl, indenyl, indanyl, dihydrobenzocycloheptenyl, tetrahydrobenzocycloheptenyl, dihydrobenzothiophenyl, dihydrobenzofuranyl, indolinyl, naphthyl, tetrahydronaphthyl, quinolinyl, isoquinolinyl, 4H-quinolizinyl, 9aH-quinolizinyl, quinazolinyl, cinnolinyl, phthalazinyl, quinoxalinyl, benzo[1,2,3]triazinyl, benzo[1,2,4]triazinyl, 2H-chromenyl, 4H-chromenyl, and a fused bicyclic carbocycle or fused bicyclic heterocycle optionally substituted with substituents (1 to 4 in number) as defined below in $R^{14}$;

$R^1$ is H, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, each of which is optionally substituted with from 1 to 3 substituents independently selected at each occurrence thereof from the group consisting of: $C_1$-$C_3$ alkyl, halogen, aryl, —CN, —$OR^9$, and —$NR^9R^{10}$;

$R^2$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, or $C_1$-$C_6$ haloalkyl, each of which is optionally substituted with from 1 to 3 substituents independently selected at each occurrence thereof from the group consisting of: $C_1$-$C_3$ alkyl, halogen, aryl, —CN, —$OR^9$, and —$NR^9R^{10}$; or $R^2$ is gem-dimethyl;

$R^3$ is H, halogen, —$OR^{11}$, —$S(O)_nR^{12}$, —CN, —$C(O)R^{12}$, —$C(O)NR^{11}R^{12}$, —$NR^9R^{10}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with from 1 to 3 substituents independently selected at each occurrence thereof from the group consisting of: $C_1$-$C_3$ alkyl, halogen, —CN, —$OR^9$, —$NR^9R^{10}$, and phenyl, which is optionally substituted 1 to 3 times with a substituent selected from the group consisting of: halogen, cyano, $C_1$-$C_4$ alkyl, $C_1$-$C_4$ haloalkyl, $C_1$-$C_4$ alkoxy, —CN, and —$OR^9$;

$R^4$ is H, halogen, —$OR^{11}$, —$S(O)_nR^{12}$, —CN, —$C(O)R^{12}$, —$C(O)NR^{11}R^{12}$, —$NR^9R^{10}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, wherein each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with from 1 to 3 substituents independently selected at each occurrence thereof from the group consisting of: $C_1$-$C_3$ alkyl, halogen, —CN, —$OR^9$, —$NR^9R^{10}$, and phenyl, which is optionally substituted 1 to 3 times with a substituent selected from the group consisting of: halogen, cyano, $C_1$-$C_4$ alkyl, $C_1$-$C_4$ haloalkyl, $C_1$-$C_4$ alkoxy, —CN, and —$OR^9$; or $R^4$ is phenyl, naphthyl, indenyl, pyridyl, pyrimidinyl, pyridazinyl, pyrazinyl, [1,2,4]triazinyl, [1,3,5]triazinyl, triazolyl, furanyl, thiophenyl, pyranyl, indazolyl, benzimidazolyl, quinolinyl, quinazolinyl, quinoxalinyl, phthalazinyl, cinnolinyl, isoquinolinyl, thienyl, imidazolyl, thiazolyl, benzthiazolyl, purinyl, isothiazolyl, indolyl, pyrrolyl, oxazolyl, benzofuranyl, benzothienyl, benzthiazolyl, isoxazolyl, pyrazolyl, oxadiazolyl, thiadiazolyl, 3-oxo-[1,2,4]triazolo[4,3-a]pyridinyl, imidazo[1,2-a]pyridinyl, pyrazolo[1,5-a]pyridinyl, [1,2,4]triazolo[4,3-a]pyridinyl, thieno[2,3-b]pyridinyl, thieno[3,2-b]pyridinyl, 1H-pyrrolo[2,3-b]pyridinyl, or other heterocycles optionally substituted with substituents (1 to 4 in number) as defined below in $R^{14}$;

$R^5$ and $R^6$ are each independently selected from the group consisting of: H, halogen, —$OR^{11}$, —$S(O)_nR^{12}$, —CN, —$C(O)R^{12}$, —$C(O)NR^{11}R^{12}$, —$NR^9R^{10}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and phenyl is optionally substituted with from 1 to 3 substituents independently selected at each occurrence thereof from the group consisting of: $C_1$-$C_3$ alkyl, halogen, —CN, —$OR^9$, —$NR^9R^{10}$, and phenyl, which is optionally substituted 1 to 3 times with a substituent selected from the group consisting of: halogen, $C_1$-$C_4$ alkyl, $C_1$-$C_4$ haloalkyl, $C_1$-$C_4$ alkoxy, —CN, and —$OR^9$;

$R^7$ is H, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with from 1 to 3 substituents independently selected at each occurrence thereof from the group consisting of: $C_1$-$C_3$ alkyl, halogen, —CN, —$OR^9$, —$NR^9R^{10}$, and phenyl which is optionally substituted 1 to 3 times with a substituent selected from the group consisting of: halogen, $C_1$-$C_4$ alkyl, $C_1$-$C_4$ haloalkyl, $C_1$-$C_4$ alkoxy, —CN, and —$OR^9$; or $R^7$ is gem-dimethyl;

$R^8$ is H, halogen, —$OR^9$, —$SR^9$, $C_1$-$C_6$ alkyl, —CN, or —$NR^9R^{10}$;

$R^9$ and $R^{10}$ are each independently selected from the group consisting of: H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —$C(O)R^{13}$, phenyl, and benzyl, where phenyl or benzyl is optionally substituted from 1 to 3 times with a substituent selected independently at each occurrence thereof from the group consisting of: halogen, cyano, $C_1$-$C_4$ alkyl, $C_1$-$C_4$ haloalkyl, and $C_1$-$C_4$ alkoxy; or $R^9$ and $R^{10}$ are taken together with the nitrogen to which they are attached to form a piperidine, pyrrolidine, piperazine, N-methylpiperazine, morpholine, thiomorpholine, [1,2]oxazinane, isoxazolidine, or 2-oxo-2H-pyridine, which is optionally substituted from 1 to 3 times with a substituent selected independently at each occurrence thereof from the group consisting of, halogen, cyano, $C_1$-$C_4$ alkyl, $C_1$-$C_4$ haloalkyl, and $C_1$-$C_4$ alkoxy;

$R^{11}$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —$C(O)R^{13}$, phenyl, or benzyl, where phenyl or benzyl is optionally substituted 1 to 3 times with halogen, cyano, $C_1$-$C_4$ alkyl, $C_1$-$C_4$ haloalkyl, or $C_1$-$C_4$ alkoxy;

$R^{12}$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, phenyl, or benzyl, where phenyl or benzyl is optionally substituted 1 to 3 times with halogen, cyano, $C_1$-$C_4$ alkyl, $C_1$-$C_4$ haloalkyl, or $C_1$-$C_4$ alkoxy; or $R^{11}$ and $R^{12}$ are taken together with the nitrogen to which they are attached to form a piperidine, pyrrolidine, piperazine, N-methylpiperazine, morpholine, or thiomorpholine ring, with the proviso that only one of $R^9$ and $R^{10}$ or $R^{11}$ and $R^{12}$ are taken together with the nitrogen to which they are attached to form a piperidine, pyrrolidine, piperazine, N-methylpiperazine, morpholine, or thiomorpholine ring;

$R^{13}$ is $C_1$-$C_4$ alkyl, $C_1$-$C_4$ haloalkyl, or phenyl;

n is 0, 1, or 2; and $R^{14}$ is independently selected at each occurrence from a substituent selected from the group consisting of: halogen, —$NO_2$, —$OR^{11}$, —$NR^{11}R^{12}$, —$NR^{11}C(O)R^{12}$, —$NR^{11}C(O)_2R^{12}$, —$NR^{11}C(O)NR^{12}R^{13}$, —$S(O)_nR^{12}$, —CN, —$C(O)R^{12}$, —$C(O)NR^{11}R^{12}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl are optionally substituted with 1 to 3 substituents independently selected at each occurrence from the group consisting of: $C_1$-$C_3$ alkyl, halogen, aryl, —CN, —$OR^9$, and —$NR^9R^{10}$;

or an oxide thereof or a pharmaceutically acceptable salt thereof.

As used above, and throughout the description of the invention, the following terms, unless otherwise indicated, shall be understood to have the following meanings.

The term "fused bicyclic carbocycle" means a bicyclic ring system consisting of about 8 to 11 ring carbon atoms, preferably 9 or 10. One or both of the rings is/are aromatic. Representative fused bicyclic carbocycles include indenyl, indanyl, naphthyl (or naphthalenyl), dihydronaphthyl, tetrahydronapthyl, benzocycloheptenyl, dihydrobenzocycloheptenyl, tetrahydrobenzocyloheptenyl, and the like.

The term "fused bicyclic heterocycle" means a bicyclic ring system consisting of about 8 to 11 ring atoms, preferably 9 or 10, in which one or more of the atoms in the ring system is/are element(s) other than carbon, for example, nitrogen, oxygen, or sulfur. The prefix aza, oxa, or thia before heterocycle means that at least a nitrogen, oxygen, or sulfur atom, respectively, is present as a ring atom. A nitrogen atom of a heteroaryl is optionally oxidized to the corresponding N-oxide. Representative fused bicyclic heterocycles include benzofuranyl, benzo[b]thiophenyl, benzoisothiazolyl, benzoisoxazolyl, indazolyl, indolyl, isoindolyl, indolizinyl, benzoimidazolyl, benzooxazolyl, benzothiazolyl, benzotriazolyl, imidazo[1,2-a]pyridinyl, pyrazolo[1,5- a]pyridinyl, [1,2,4]triazolo[4,3-a]pyridinyl, thieno[2,3-b]pyridinyl, thieno[3,2-b]pyridinyl, 1H-pyrrolo[2,3-b]pyridinyl, chromenyl, dihydrobenzothiophenyl, dihydrobenzofuranyl, indolinyl, quinolinyl, isoquinolinyl, 4H-quinolizinyl, 9aH-quinolizinyl, quinazolinyl, cinnolinyl, quinoxalinyl, benzo[1,2,3]triazinyl, benzo[1,2,4]triazinyl, and the like.

The term "alkyl" means an aliphatic hydrocarbon group which may be straight or branched having about 1 to about 6 carbon atoms in the chain. "Branched" means that one or more lower alkyl groups, such as methyl, ethyl, or propyl, are attached to a linear alkyl chain. Exemplary alkyl groups include methyl, ethyl, n-propyl, i-propyl, n-butyl, t-butyl, n-pentyl, and 3-pentyl.

The term "alkenyl" means an aliphatic hydrocarbon group containing a carbon-carbon double bond and which may be straight or branched having about 2 to about 6 carbon atoms in the chain. Preferred alkenyl groups have 2 to about 4 carbon atoms in the chain. "Branched" means that one or more lower alkyl groups, such as methyl, ethyl, or propyl, are attached to a linear alkenyl chain. Exemplary alkenyl groups include ethenyl, propenyl, n-butenyl, and i-butenyl.

The term "alkynyl" means an aliphatic hydrocarbon group containing a carbon-carbon triple bond and which may be straight or branched having about 2 to about 6 carbon atoms in the chain. Preferred alkynyl groups have 2 to about 4 carbon atoms in the chain. "Branched" means that one or more lower alkyl groups, such as methyl, ethyl, or propyl, are attached to a linear alkynyl chain. Exemplary alkynyl groups include ethynyl, propynyl, n-butynyl, 2-butynyl, 3-methylbutynyl, and n-pentynyl.

The term "aryl" means an aromatic monocyclic or multicyclic ring system of 6 to about 14 carbon atoms, preferably of 6 to about 10 carbon atoms. Representative aryl groups include phenyl and naphthyl. The terms "naphthyl" and "naphthalenyl" are used interchangeably.

The term "alkoxy" means an alkyl-O-group wherein the alkyl group is as herein described. Exemplary alkoxy groups include methoxy, ethoxy, n-propoxy, i-propoxy, n-butoxy, and heptoxy.

The term "compounds of the invention", and equivalent expressions are meant to embrace compounds of general Formula (I) as hereinbefore described, which expression includes the prodrugs, the pharmaceutically acceptable salts, and the solvates, e.g., hydrates, where the context so permits. Similarly, reference to intermediates, whether or not they themselves are claimed, is meant to embrace their salts and solvates, where the context so permits. For the sake of clarity, particular instances, when the context so permits, are sometimes indicated in the text, but these instances are purely illustrative and it is not intended to exclude other instances when the context so permits.

The term "cycloalkyl" means a non-aromatic monocyclic or multicyclic ring system of about 3 to about 7 carbon atoms, preferably of about 5 to about 7 carbon atoms. Exemplary monocyclic cycloalkyl groups include cyclopentyl, cyclohexyl, cycloheptyl, and the like.

The term "cycloalkylalkyl" means a cycloalkyl-alkyl-group in which the cycloalkyl and alkyl are as defined herein. Exemplary cycloalkylalkyl groups include cyclopropylmethyl and cyclopentylmethyl.

The term "halo" or "halogen" means fluoro, chloro, bromo, or iodo.

The term "haloalkyl" means both branched and straight-chain alkyl substituted with one or more halogen, wherein the alkyl group is as herein described.

The term "haloalkoxy" means a $C_{1-4}$ alkoxy group substituted by at least one halogen atom, wherein the alkoxy group is as herein described.

The term "substituted" or "substitution" of an atom means that one or more hydrogen on the designated atom is replaced with a selection from the indicated group, provided that the designated atom's normal valency is not exceeded. "Unsubstituted" atoms bear all of the hydrogen atoms dictated by their valency. When a substituent is keto (i.e., =O), then 2 hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The term "pharmaceutically acceptable salts" means the relatively non-toxic, inorganic and organic acid addition salts, and base addition salts of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulphamates, malonates, salicylates, propionates, methylene-bis-b-hydroxynaphthoates, gentisates, isothionates, di-p-toluoyltartrates, methanesulphonates, ethanesulphonates, benzenesulphonates, p-toluenesulphonates, cyclohexylsulphamates and quinateslaurylsulphonate salts, and the like. (See, for example Berge et al., "Pharmaceutical Salts," *J Pharm Sci,* 66:1-sup. 19 (1977) and *Remington's Pharmaceutical Sciences,* 17th ed, Easton, Pa., Mack Publishing Company, p. 1418 (1985), which are hereby incorporated by reference in their entirety.) Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, and zinc hydroxide. Suitable amine base addition salts are prepared from amines which have sufficient basicity to form a stable salt and preferably include those amines which are frequently used in medicinal chemistry because of their low toxicity and acceptability for medical use. Examples of such amines include ammonia, ethylenediamine, N-methyl-glucamine, lysine, arginine, omithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids such as lysine and arginine, dicyclohexylamine, and the like.

The term "pharmaceutically acceptable prodrugs" as used herein means those prodrugs of the compounds useful according to the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" means compounds that are rapidly transformed in vivo to yield the parent compound of the above formula, for example by hydrolysis in blood. Functional groups which may be rapidly transformed, by metabolic cleavage in vivo, form a class of groups reactive with the carboxyl group of the compounds of the present invention. They include, but are not limited to, such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: Bundgaard, ed., *Design of Prodrugs*, Elsevier (1985); Widder et al., Methods in Enzymology, ed., Academic Press, 42:309-396 (1985); "Design and Applications of Prodrugs," Krogsgaard-Larsen, ed., *A Textbook of Drug Design and Development*, Chapter 5:113-191 (1991); Bundgaard, "*Advanced Drug Delivery Reviews*," 8:1-38 (1992); Bundgaard et al., *Journal of Pharmaceutical Sciences*, 77:285 (1988); Nakeya et al., *Chem Pharm Bull*, 32:692 (1984); Higuchi, "Pro-drugs as Novel Delivery Systems" Roche, ed., *A.C.S. Symposium Series*, Vol. 14, and "Bioreversible Carriers in Drug Design" American Pharmaceutical Association and Pergamon Press (1987), which are hereby incorporated by reference in their entirety. Examples of prodrugs include, but are not limited to, acetate, formate, and benzoate derivatives of alcohol and amine functional groups in the compounds of the invention.

The term "therapeutically effective amounts" is meant to describe an amount of compound of the present invention effective in increasing the levels of serotonin, norepinephrine, or dopamine at the synapse and, thus, producing the desired therapeutic effect. Such amounts generally vary according to a number of factors well within the purview of ordinarily skilled artisans given the description provided herein to determine and account for. These include, without limitation: the particular subject, as well as its age, weight, height, general physical condition and medical history, the particular compound used, as well as the carrier in which it is formulated and the route of administration selected for it, and the nature and severity of the condition being treated.

The term "pharmaceutical composition" means a composition comprising a compound of Formula (I) and at least one component selected from pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged absorption of the injectable pharmaceutical form can be brought about by the use of agents delaying absorption, for example, aluminum monosterate and gelatin. Examples of suitable carriers, diluents, solvents or vehicles include water, ethanol, polyols, suitable mixtures thereof, vegetable oils (such as olive oil), and injectable organic esters, such as ethyl oleate. Examples of excipients include lactose, milk sugar, sodium citrate, calcium carbonate, dicalcium phosphate phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgment, suitable for use in contact with the cells of humans and lower animals without undue toxicity, irritation, allergic response and the like, and are commensurate with a reasonable benefit/risk ratio.

The term "pharmaceutically acceptable dosage forms" means dosage forms of the compound of the invention, and includes, for example, tablets, dragees, powders, elixirs, syrups, liquid preparations, including suspensions, sprays, inhalants tablets, lozenges, emulsions, solutions, granules, capsules and suppositories, as well as liquid preparations for injections, including liposome preparations. Techniques and formulations generally may be found in Remington's Pharmaceutical Sciences, 17th ed, Easton, Pa., Mack Publishing Company (1985), which is hereby incorporated by reference in its entirety.

One embodiment of the present invention relates to the compound of the Formula (I) where:

X is selected from the group consisting of benzofuranyl, benzo[b]thiophenyl, benzoisothiazolyl, benzoisoxazolyl, indazolyl, indolyl, isoindolyl, indolizinyl, benzoimidazolyl, benzooxazolyl, benzothiazolyl, benzotriazolyl, imidazo[1,2-a]pyridinyl, pyrazolo[1,5-a]pyridinyl, [1,2,4]triazolo[4,3-a]pyridinyl, thieno[2,3-b]pyridinyl, thieno[3,2-b]pyridinyl, 1H-pyrrolo[2,3-b]pyridinyl, indenyl, indanyl, dihydrobenzocycloheptenyl, tetrahydrobenzocycloheptenyl, dihydrobenzothiophenyl, dihydrobenzofuranyl, indolinyl, naphthyl, tetrahydronaphthyl, quinolinyl, isoquinolinyl, 4H-quinolizinyl, 9aH-quinolizinyl, quinazolinyl, cinnolinyl, phthalazinyl, quinoxalinyl, benzo[1,2,3]triazinyl, benzo[1,2,4]triazinyl, 2H-chromenyl, 4H-chromenyl, and a fused bicyclic carbocycle or fused bicyclic heterocycle optionally substituted with substituents (1 to 4 in number) as defined below in $R^{14}$;

$R^1$ is H or $C_1$-$C_6$ alkyl;

$R^2$ is H, $C_1$-$C_6$ alkyl, or $C_1$-$C_6$ haloalkyl;

$R^3$ is H, halogen, —$OR^{11}$, —$S(O)_nR^{12}$, —CN, —$C(O)R^{12}$, —$C(O)NR^{11}R^{12}$, —$NR^9R^{10}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with from 1 to 3 substituents independently selected at each occurrence thereof from the group consisting of: $C_1$-$C_3$ alkyl, halogen, —CN, —$OR^9$, —$NR^9R^{10}$, and phenyl, which is optionally substituted from 1 to 3 times with a substituent selected from the group consisting of: halogen, cyano, $C_1$-$C_4$ alkyl, $C_1$-$C_4$ haloalkyl, or $C_1$-$C_4$ alkoxy, —CN, and —$OR^9$;

$R^4$ is H, halogen, —$OR^{11}$, —$S(O)_nR^{12}$, —CN, —$C(O)R^{12}$, —$C(O)NR^{11}R^{12}$, —$NR^9R^{10}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, wherein each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with from 1 to 3 substituents independently selected at each occurrence thereof from the group consisting of: $C_1$-$C_3$ alkyl, halogen, —CN, —$OR^9$, —$NR^9R^{10}$, and phenyl, which is optionally substituted from 1 to 3 times with a substituent selected from the group consisting of: halogen, $C_1$-$C_4$ alkyl, $C_1$-$C_4$ haloalkyl, $C_1$-$C_4$ alkoxy, —CN, and —$OR^9$; or $R^4$ is phenyl, naphthyl, indenyl, pyridyl, pyrimidinyl, pyridazinyl, pyrazinyl, [1,2,4]triazinyl, [1,3,5]triazinyl, triazolyl, furanyl, thiophenyl, pyranyl, indazolyl, benzimidazolyl, quinolinyl, quinazolinyl, quinoxalinyl, phthalazinyl, cinnolinyl, isoquinolinyl, thienyl, imidazolyl, thiazolyl, benzthiazolyl, purinyl, isothiazolyl, indolyl, pyrrolyl, oxazolyl, benzofuranyl, benzothienyl, benzthiazolyl, isoxazolyl, pyrazolyl, oxadiazolyl, thiadiazolyl, 3-oxo-[1,2,4]triazolo[4,3-a]pyridinyl, imidazo[1,2-a]pyridinyl, pyrazolo[1,5-a]pyridinyl, [1,2,4]triazolo[4,3-a]pyridinyl, thieno[2,3-b]pyridinyl, thieno[3,2-b]pyridinyl, 1H-pyrrolo[2,3-b]pyridinyl, or other heterocycles optionally substituted with substituents (1 to 4 in number) as defined below in $R^{14}$;

$R^5$ and $R^6$ are each independently selected from H, halogen, $C_1$-$C_6$ alkyl, or $C_1$-$C_4$ alkoxyalkyl;

$R^7$ is H or $C_1$-$C_6$ alkyl;

$R^8$ is H, halogen, —$OR^9$, —$SR^9$ —CN, $C_1$-$C_6$ alkyl, —CN, or —$NR^9R^{10}$;

$R^{14}$ is independently selected at each occurrence from a substituent selected from the group consisting of: halogen, —$NO_2$, —$OR^{11}$, —$NR^{11}R^{12}$, —$NR^{11}C(O)R^{12}$, —$NR^{11}C(O)_2R^{12}$, —$NR^{11}C(O)NR^{12}R^{13}$, —$S(O)_nR^{12}$, —CN, —$C(O)R^{12}$, —$C(O)NR^{11}R^{12}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl are optionally substituted with 1 to 3 substituents independently selected at each occurrence from the group consisting of: $C_1$-$C_3$ alkyl, halogen, aryl, —CN, —$OR^9$, and —$NR^9R^{10}$.

Another embodiment of the present invention relates to the compound of Formula (I) where:

X is benzofuran-2-yl, 5-chloro-benzofuran-2-yl, 4-fluoro-benzofuran-2-yl, 5-fluoro-benzofuran-2-yl, 5-methoxy-benzofuran-2-yl, 6-fluoro-benzofuran-2-yl, 7-fluoro-benzofuran-2-yl, 7-methoxy-benzofuran-2-yl benzofuran-3-yl, benzofuran-4-yl, benzofuran-5-yl, benzofuran-6-yl, benzofuran-7-yl, 2,3-dihydro-benzofuran-5-yl, benzo[b]thiophen-2-yl, 4-chloro-benzo[b]thiophen-2-yl, 4-fluoro-benzo[b]thiophen-2-yl, 4-methoxy-benzo[b]thiophen-2-yl, 5-chloro-benzo[b]thiophen-2-yl, 5-fluoro-benzo[b]thiophen-2-yl, 6-chloro-benzo[b]thiophen-2-yl, 6-fluoro-benzo[b]thiophen-2-yl, 7-chloro-benzo[b]thiophen-2-yl, 7-fluoro-benzo[b]thiophen-2-yl, 1,1-dioxo-1H-1$\lambda^6$-benzo[b]thiophen-2-yl, benzo[b]thiophen-3-yl, benzo[b]thiophen-4-yl, benzo[b]thiophen-5-yl, 2-methylbenzo[b]thiophen-5-yl, 2-chloro-benzo[b]thiophen-5-yl, 3-trifluoromethyl-benzo[b]thiophen-5-yl, 4-cyano-benzo[b]thiophen-5-yl, 4-methoxy-benzo[b]thiophen-5-yl, 4-hydroxy-benzo[b]thiophen-5-yl, 4-methyl-benzo[b]thiophen-5-yl, 1,1-dioxo-1H-1$\lambda^6$-benzo[b]thiophen-5-yl, benzo[b]thiophen-6-yl, 2-chloro-benzo[b]thiophen-6-yl, 3-trifluoromethyl-benzo[b]thiophen-6-yl, 7-methoxy-benzo[b]thiophen-6-yl, 7-hydroxy-benzo[b]thiophen-6-yl, 7-methyl-benzo[b]thiophen-6-yl, 1,1-dioxo-1H-1$\lambda^6$-benzo[b]thiophen-6-yl, benzo[b]thiophen-7-yl, 1H-indazol-1-yl, 1H-indazol-3-yl, 1H-indazol-4-yl, 1H-indazol-5-yl, 1-methyl-indazol-5-yl, 6-methoxy-1H-indazol-5-yl, 7-methoxy-1H-indazol-5-yl, 7-fluoro-1H-indazol-5-yl, 7-chloro-1H-indazol-5-yl, 7-methoxy-1H-indazol-5-yl, 1H-indazol-6-yl, 1-methyl-indazol-6-yl, 7-fluoro-1H-indazol-6-yl, 1H-indazol-7-yl, indol-1-yl, 1-methyl-indol-2-yl, 1H-indol-2-yl, 7-fluoro-1H-indol-2-yl, 1H-indol-3-yl, 1H-indol-4-yl, 1H-indol-5-yl, 1-methyl-indol-5-yl, 7-fluoro-1H-indol-5-yl, 1H-indol-6-yl, 1-methyl-indol-6-yl, 7-fluoro-1H-indol-6-yl, 2H-isoindol-1-yl, 2H-isoindol-2-yl, 2H-isoindol-4-yl, 2H-isoindol-5-yl, indolizin-1-yl, indolizin-2-yl, indolizin-3-yl, indolizin-5-yl, indolizin-6-yl, indolizin-7-yl, indolizin-8-yl, benzooxazol-2-yl, benzooxazol-4-yl, benzooxazol-5-yl, 2-methyl-benzooxazol-5-yl, benzooxazol-6-yl, 2-methyl-benzooxazol-6-yl, benzooxazol-7-yl, benzothiazol-2-yl, benzothiazol-4-yl, benzothiazol-5-yl, 2-methylbenzothiazol-5-yl, benzothiazol-6-yl, 2-methylbenzothiazol-6-yl, benzothiazol-7-yl, benzoisothiazol-4-yl, benzoisothiazol-5-yl, benzoisothiazol-6-yl, benzoisothiazol-7-yl, benzoisoxazolyl-4-yl, benzoisoxazolyl-5-yl, benzoisoxazolyl-6-yl, benzoisoxazolyl-7-yl, imidazo[1,2-a]pyridine-2-yl, imidazo[1,2-a]pyridin-6-yl, imidazo[1,2-a]pyridine-7-yl, pyrazolo[1,5-a]pyridine-2-yl, pyrazolo[1,5-a]pyridin-5-yl, pyrazolo[1,5-a]pyridin-6-yl, [1,2,4]triazolo[4,3-a]pyridin-6-yl, thieno[2,3-b]pyridin-2-yl, [1,2,4]triazolo[4,3-a]pyridin-7-yl, thieno[2,3-b]pyridin-6-yl, thieno[2,3-b]pyridin-5-yl, thieno[3,2-b]pyridin-2-yl, thieno[3,2-b]pyridin-5-yl, thieno[3,2-b]pyridin-6-yl, 1H-pyrrolo[2,3-b]pyridin-2-yl, 1H-pyrrolo[2,3-b]pyridin-5-yl, 1H-pyrrolo[2,3-b]pyridin-6-yl, 3H-inden-5-yl, indan-5-yl, naphthalen-1-yl, 4-methyl-naphthalen-1-yl, naphthalen-2-yl, 1-fluoro-naphthalen-2-yl, 1-chloro-naphthalen-2-yl, 1-methoxy-naphthalen-2-yl, 1-methyl-naphthalen-2-yl, 3-fluoro-naphthalen-2-yl, 3-chloro-naphthalen-2-yl, 3-methoxy-naphthalen-2-yl, 3-cyano-naphthalen-2-yl, 4-fluoro-naphthalen-2-yl, 4-chloro-naphthalen-2-yl, 4-methyl-naphthalen-2-yl, 4-methyl-naphthalen-1-yl, 5-fluoro-naphthalen-2-yl, 5-chloro-naphthalen-2-yl, 5-cyano-naphthalen-2-yl, 5-methyl-naphthalen-2-yl, 6-methoxy-naphthalen-2-yl, 6-chloro-naphthalen-2-yl, 6-fluoro-naphthalen-2-yl, 6-cyano-naphthalen-2-yl, 6-methanesulfonyl-naphthalen-2-yl, 7-methoxy-naphthalen-2-yl, 7-chloro-naphthalen-2-yl, 7-fluoro-naphthalen-2-yl, 7-cyano-naphthalen-2-yl, 8-methoxy-naphthalen-2-yl, 8-chloro-naphthalen-2-yl, 8-fluoro-naphthalen-2-yl, 8-cyano-naphthalen-2-yl, 5,6,7,8-tetrahydro-naphthalen-2-yl, 2-quinolinyl, 3-quinolinyl, 6-quinolinyl, 7-quinolinyl, 1-isoquinolinyl, 3-isoquinolinyl, 6-isoquinolinyl, 7-isoquinolinyl, 2-quinoxalinyl, 6-quinoxalinyl, 2-quinazolinyl, 2-quinazolinyl, 6-quinazolinyl, 7-quinazolinyl, 3-cinnolinyl, 6-cinnolinyl, 7-cinnolinyl, 6-phthalazinyl, 2H-chromen-3-yl, or 8,9-dihydro-7H-benzocyclohepten-6-yl;

$R^1$ is H, methyl, ethyl, or isopropyl;

$R^2$ is H, methyl, or gem-dimethyl;

$R^3$ is H, methyl, hydroxy, methoxy, fluoro, chloro, or CN;

$R^4$ is H, $C_1$-$C_6$ alkyl, fluoro, chloro, —$OR^{11}$, morpholin-4-yl, 2,6-dimethyl-morpholin-4-yl, piperazin-1-yl, 4-methyl-piperazin-1-yl, piperidin-1-yl, pyrrolidin-1-yl, morpholin-4-ylmethyl, 1-methyl-1-morpholin-4-ylethyl, 1-morpholin-4-yl-cyclopropyl, piperidin-1-ylmethyl, pyrrolidin-1-ylmethyl, dimethylaminomethyl, 1-dimethylamino-1-methylethyl, 1-dimethylamino-cyclopropanyl, methylaminomethyl, 1-methyl-1-methylaminoethyl, 1-methylamino-cyclopropyl, aminomethyl, 1-amino-1-methylethyl, 1-aminocyclopropyl, methanesulfonyl or —CN; or $R^4$ is phenyl, 2-chlorophenyl, 3-chlorophenyl, 4-chlorophenyl, 2-cyanophenyl, 3-cyanophenyl, 4-cyanophenyl, 2-fluorophenyl, 3-fluorophenyl, 4-fluorophenyl, 2,5-difluorophenyl, 3,5-difluorophenyl, 2,4-difluorophenyl, 2,6-difluorophenyl, 2-methoxyphenyl, 3-methoxyphenyl, 4-methoxyphenyl, 4-dimethylaminophenyl, 2-methylsufonylphenyl, 3-methylsufonylphenyl, 4-methylsufonylphenyl, 2-trifuoromethylphenyl, 3-trifuoromethylphenyl, 4-trifuoromethylphenyl, furan-2-yl, 4-methyl-furan-2-yl, 5-methyl-furan-2-yl, furan-3-yl, thiophen-2-yl, thiophen-3-yl, 3,5-dimethyl-isoxazol-4-yl, pyridin-2-yl, 3-methoxy-pyridin-2-yl, 4-methoxy-pyridin-2-yl, 3-methyl-pyridin-2-yl, 4-methyl-pyridin-2-yl, 6-methyoxy-pyridin-2-yl, pyridin-3-yl, 2-methoxy-pyridin-3-yl, 6-methoxy-pyridin-3-yl, pyridin-4-yl, pyrimidin-4-yl, pyrimidin-2-yl, pyrimidin-5-yl, pyrazin-2-yl, 3-methyl-pyrazin-2-yl, 5-methyl-pyrazin-2-yl, 6-methyl-pyrazin-2-yl, 3-methoxy-pyrazin-2-yl, 5-methoxy-pyrazin-2-yl, 6-methoxy-pyrazin-2-yl, 6-ethyl-pyrazin-2-yl, 6-trifluoromethyl-pyrazin-2-yl, pyridazin-3-yl, 5-methylpyridazin-3-yl, 6-methylpyridazin-3-yl, 6-dimethylamino-pyridazin-3-yl, 6-methylamino-pyridazin-3-yl, 6-amino-pyridazin-3-yl, 6-morpholin-4-yl-pyridazin-3-yl, 6-trifluoromethyl-pyridazin-3-yl, 6-cyano-pyridazin-3-yl, pyridazin-4-yl, 2-quinolinyl, 3-quinolinyl, 6-quinolinyl, 7-quinolinyl, 1-isoquinolinyl, 3-isoquinolinyl, 6-isoquinolinyl, 7-isoquinolinyl, [1,3,5]triazin-2-yl, [1,2,4]triazin-3-yl, [1,2,4]triazin-5-yl, [1,2,4]triazin-6-yl, cinnolin-3-yl, phthalazin-1-yl, phthalazin-7-yl, quinoxalin-2-yl, quinoxalin-6-yl, quinazolin-2-yl, quinazolin-4-yl, quinazolin-6-yl, quinazolin-7-yl, 3-oxo-[1,2,4]triazolo[4,3-a]pyridin-2-yl, or 2-oxo-2H-pyridin-1-yl;

$R^5$ is H, fluoro, chloro, methyl, —OH, or methoxy;
$R^6$ is H; fluoro, chloro, methyl, —OH, or methoxy;
$R^7$ is H; and
$R^8$ is H, fluoro, chloro, —OH, —CN, methyl, or ethyl.

Another embodiment of the present invention relates to the compound of Formula (I) where the carbon atom designated * is in the R configuration.

Another embodiment of the present invention relates to the compound of Formula (I) where the carbon atom designated * is in the S configuration.

Another embodiment of the present invention relates to a mixture of stereoisomeric compounds of Formula (I) where the carbon atom designated * is in the S or R configuration.

Within these embodiments, the selection of a particular preferred substituent at any one of $R^1$-$R^8$ does not affect the selection of a substituent at any of the others of $R^1$-$R^8$. That is, the specific compounds provided herein have any of the specific substituents at any of the positions. For example, as described hereinabove, $R^1$ is preferably $C_1$-$C_6$ alkyl; the selection of $R^1$ as any one of $C_1$, $C_2$, $C_3$, $C_4$, $C_5$ or $C_6$ alkyl, does not limit the choice of $R^2$ in particular to any one of H, $C_1$-$C_6$ alkyl, or $C_1$-$C_6$ haloalkyl. Rather, for $R^1$ as any of $C_1$, $C_2$, $C_3$, $C_4$, $C_5$ or $C_6$ alkyl, $R^2$ is any of H, $C_1$, $C_2$, $C_3$, $C_4$, $C_5$ or $C_6$ alkyl or $C_1$, $C_2$, $C_3$, $C_4$, $C_5$ or $C_6$ haloalkyl. Similarly, the selection of $R^2$ as any of H, $C_1$, $C_2$, $C_3$, $C_4$, $C_5$ or $C_6$ alkyl or $C_1$, $C_2$, $C_3$, $C_4$, $C_5$ or $C_6$ haloalkyl does not limit the selection of $R^3$ in particular to any one of H, halogen, —$OR^{11}$, —$S(O)_nR^{12}$, —CN, —$C(O)R^{12}$, $C_1$-$C_6$ alkyl, $C_3$-$C_6$ cycloalkyl, $C_4$-$C_7$ cycloalkylalkyl, or substituted $C_4$-$C_7$ cycloalkylalkyl.

Other specific compounds of the invention are those with the following substituents:

TABLE A

| X | $R^1$ | $R^2$ | $R^3$ | $R^4$ | $R^5$ | $R^6$ | $R^7$ | $R^8$ |
|---|---|---|---|---|---|---|---|---|
| benzo[b]thiophen-2-yl | H | H | H | H | H | H | H | H |
| benzo[b]thiophen-2-yl | H | Me | H | H | H | H | H | H |
| benzo[b]thiophen-2-yl | Me | H | H | H | H | H | H | H |
| benzo[b]thiophen-2-yl | Et | H | H | H | H | H | H | H |
| benzo[b]thiophen-2-yl | Me | Me | H | H | H | H | H | H |
| 4-fluoro-benzo[b]thiophen-2-yl | Me | H | H | H | H | H | H | H |
| 5-fluoro-benzo[b]thiophen-2-yl | Me | H | H | H | H | H | H | H |
| 6-fluoro-benzo[b]thiophen-2-yl | Me | H | H | H | H | H | H | H |
| 7-fluoro-benzo[b]thiophen-2-yl | Me | H | H | H | H | H | H | H |
| 4-chloro-benzo[b]thiophen-2-yl | Me | H | H | H | H | H | H | H |
| 5-chloro-benzo[b]thiophen-2-yl | Me | H | H | H | H | H | H | H |
| 6-chloro-benzo[b]thiophen-2-yl | Me | H | H | H | H | H | H | H |
| 7-chloro-benzo[b]thiophen-2-yl | Me | H | H | H | H | H | H | H |
| 4-methoxy- | Me | H | H | H | H | H | H | H |

TABLE A-continued

| X | R¹ | R² | R³ | R⁴ | R⁵ | R⁶ | R⁷ | R⁸ |
|---|---|---|---|---|---|---|---|---|
| benzo[b]thiophen-2-yl | | | | | | | | |
| 5-methoxy-benzo[b]thiophen-2-yl | Me | H | H | H | H | H | H | H |
| 6-methoxy-benzo[b]thiophen-2-yl | Me | H | H | H | H | H | H | H |
| 7-methoxy-benzo[b]thiophen-2-yl | Me | H | H | H | H | H | H | H |
| 1,1-dioxo-1H-1λ⁶-benzo[b]thiophen-2-yl | Me | H | H | H | H | H | H | H |
| benzo[b]thiophen-2-yl | Me | H | H | H | H | H | H | OH |
| benzo[b]thiophen-2-yl | Me | H | H | H | H | H | H | OMe |
| benzo[b]thiophen-2-yl | Me | H | H | H | H | H | H | Me |
| benzo[b]thiophen-2-yl | Me | H | H | H | H | H | H | CN |
| benzo[b]thiophen-2-yl | Me | H | H | H | H | H | H | F |
| benzo[b]thiophen-2-yl | Me | H | H | H | H | H | H | Cl |
| benzo[b]thiophen-2-yl | Me | H | H | H | H | Me | H | H |
| benzo[b]thiophen-2-yl | Me | H | H | OH | H | H | H | H |
| benzo[b]thiophen-2-yl | Me | H | H | OMe | H | H | H | H |
| benzo[b]thiophen-2-yl | Me | H | H | Me | H | H | H | H |
| benzo[b]thiophen-2-yl | Me | H | H | F | H | H | H | H |
| benzo[b]thiophen-2-yl | Me | H | H | pyridazin-3-yl | H | H | H | H |
| 4-fluoro-benzo[b]thiophen-2-yl | Me | H | H | pyridazin-3-yl | H | H | H | H |
| 5-fluoro-benzo[b]thiophen-2-yl | Me | H | H | pyridazin-3-yl | H | H | H | H |
| 6-fluoro-benzo[b]thiophen-2-yl | Me | H | H | pyridazin-3-yl | H | H | H | H |
| 7-fluoro-benzo[b]thiophen-2-yl | Me | H | H | pyridazin-3-yl | H | H | H | H |
| benzo[b]thiophen-2-yl | Et | H | H | pyridazin-3-yl | H | H | H | H |
| benzo[b]thiophen-2-yl | Me | H | H | 6-methylpyridazin-3-yl | H | H | H | H |
| benzo[b]thiophen-2-yl | Me | H | H | 6-dimethylamino-pyridazin-3-yl | H | H | H | H |
| benzo[b]thiophen-2-yl | Me | H | H | 6-methylamino-pyridazin-3-yl | H | H | H | H |
| benzo[b]thiophen-2-yl | Me | H | H | 6-amino-pyridazin-3-yl | H | H | H | H |
| benzo[b]thiophen-2-yl | Me | H | H | 6-morpholin-4-yl-pyridazin-3-yl | H | H | H | H |
| benzo[b]thiophen-2-yl | Me | H | H | 6-trifluoromethyl-pyridazin-3-yl | H | H | H | H |
| benzo[b]thiophen-2-yl | Me | H | H | 6-cyano-pyridazin-3-yl | H | H | H | H |
| benzo[b]thiophen-2-yl | Me | H | F | pyridazin-3-yl | H | H | H | H |
| benzo[b]thiophen-2-yl | Me | H | OMe | pyridazin-3-yl | H | H | H | H |
| benzo[b]thiophen-2-yl | Me | H | OH | pyridazin-3-yl | H | H | H | H |
| benzo[b]thiophen-2-yl | Me | H | Me | pyridazin-3-yl | H | H | H | H |
| benzo[b]thiophen-2-yl | Et | H | F | pyridazin-3-yl | H | H | H | H |
| benzo[b]thiophen-2-yl | Me | H | H | pyridazin-3-yl | F | H | H | H |
| benzo[b]thiophen-2-yl | Me | H | H | pyridazin-3-yl | H | F | H | H |
| benzo[b]thiophen-2-yl | Me | H | H | pyridazin-3-yl | H | H | H | OH |
| benzo[b]thiophen-2-yl | Me | H | H | pyridazin-3-yl | H | H | H | Me |
| benzo[b]thiophen-2-yl | Me | H | H | pyridazin-4-yl | H | H | H | H |
| benzo[b]thiophen-2-yl | Me | H | F | pyridazin-4-yl | H | H | H | H |
| benzo[b]thiophen-2-yl | Me | H | H | pyrazin-2-yl | H | H | H | H |
| benzo[b]thiophen-2-yl | Me | H | H | 3-methyl-pyrazin-2-yl | H | H | H | H |
| benzo[b]thiophen-2-yl | Me | H | H | 3-methoxy-pyrazin-2-yl | H | H | H | H |
| benzo[b]thiophen-2-yl | Me | H | H | 6-methyl-pyrazin-2-yl | H | H | H | H |
| benzo[b]thiophen-2-yl | Me | H | H | 6-methoxy-pyrazin-2-yl | H | H | H | H |
| benzo[b]thiophen-2-yl | Me | H | F | pyrazin-2-yl | H | H | H | H |
| benzo[b]thiophen-2-yl | Me | H | H | pyrimidin-2-yl | H | H | H | H |
| benzo[b]thiophen-2-yl | Me | H | F | pyrimidin-2-yl | H | H | H | H |
| benzo[b]thiophen-2-yl | Me | H | H | pyrimidin-4-yl | H | H | H | H |

TABLE A-continued

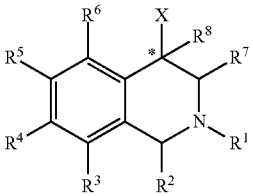

| X | R¹ | R² | R³ | R⁴ | R⁵ | R⁶ | R⁷ | R⁸ |
|---|---|---|---|---|---|---|---|---|
| benzo[b]thiophen-2-yl | Me | H | F | pyrimidin-4-yl | H | H | H | H |
| benzo[b]thiophen-2-yl | Me | H | H | pyrimidin-5-yl | H | H | H | H |
| benzo[b]thiophen-2-yl | Me | H | H | pyrimidin-5-yl | H | F | H | H |
| benzo[b]thiophen-2-yl | Me | H | H | 3,5-dimethyl-isoxazol-4-yl | H | H | H | H |
| benzo[b]thiophen-2-yl | Me | H | H | thiazol-2-yl | H | H | H | H |
| benzo[b]thiophen-2-yl | Me | H | H | 5-methyl-thiazol-2-yl | H | H | H | H |
| benzo[b]thiophen-2-yl | Me | H | H | [1,3,5]triazin-2-yl | H | H | H | H |
| benzo[b]thiophen-2-yl | Me | H | H | [1,2,4]triazon-3-yl | H | H | H | H |
| benzo[b]thiophen-2-yl | Me | H | H | [1,2,4]triazin-5-yl | H | H | H | H |
| benzo[b]thiophen-2-yl | Me | H | H | [1,2,4]triazin-6-yl | H | H | H | H |
| benzo[b]thiophen-2-yl | Me | H | H | cinnolin-3-yl | H | H | H | H |
| benzo[b]thiophen-2-yl | Me | H | H | phthalazin-1-yl | H | H | H | H |
| benzo[b]thiophen-2-yl | Me | H | H | quinoxalin-2-yl | H | H | H | H |
| benzo[b]thiophen-2-yl | Me | H | H | quinazolin-2-yl | H | H | H | H |
| benzo[b]thiophen-2-yl | Me | H | H | quinazolin-6-yl | H | H | H | H |
| benzo[b]thiophen-2-yl | Me | H | H | quinazolin-7-yl | H | H | H | H |
| benzo[b]thiophen-2-yl | Me | H | H | 3-oxo-[1,2,4]triazolo[4,3-a]pyridin-2-yl | H | H | H | H |
| benzo[b]thiophen-2-yl | Me | H | H | morpholin-4-yl | H | H | H | H |
| 4-fluoro-benzo[b]thiophen-2-yl | Me | H | H | morpholin-4-yl | H | H | H | H |
| 5-fluoro-benzo[b]thiophen-2-yl | Me | H | H | morpholin-4-yl | H | H | H | H |
| 6-fluoro-benzo[b]thiophen-2-yl | Me | H | H | morpholin-4-yl | H | H | H | H |
| 7-fluoro-benzo[b]thiophen-2-yl | Me | H | H | morpholin-4-yl | H | H | H | H |
| benzo[b]thiophen-2-yl | Me | H | H | 2,6-dimethyl-morpholin-4-yl | H | H | H | H |
| benzo[b]thiophen-2-yl | Et | H | H | morpholin-4-yl | H | H | H | H |
| benzo[b]thiophen-2-yl | Me | H | F | morpholin-4-yl | H | H | H | H |
| benzo[b]thiophen-2-yl | Me | H | OMe | morpholin-4-yl | H | H | H | H |
| benzo[b]thiophen-2-yl | Me | H | OH | morpholin-4-yl | H | H | H | H |
| benzo[b]thiophen-2-yl | Me | H | Me | morpholin-4-yl | H | H | H | H |
| benzo[b]thiophen-2-yl | Et | H | F | morpholin-4-yl | H | H | H | H |
| benzo[b]thiophen-2-yl | Me | H | H | morpholin-4-yl | F | H | H | H |
| benzo[b]thiophen-2-yl | Me | H | H | morpholin-4-yl | H | F | H | H |
| benzo[b]thiophen-2-yl | Me | H | H | morpholin-4-yl | H | H | H | OH |
| benzo[b]thiophen-2-yl | Me | H | H | morpholin-4-yl | H | H | H | Me |
| benzo[b]thiophen-2-yl | Me | H | H | piperazin-1-yl | H | H | H | H |
| benzo[b]thiophen-2-yl | Me | H | H | 4-methyl-piperazin-1-yl | H | H | H | H |
| benzo[b]thiophen-2-yl | Me | H | H | piperidin-1-yl | H | H | H | H |
| benzo[b]thiophen-2-yl | Me | H | H | pyrrolidin-1-yl | H | H | H | H |
| benzo[b]thiophen-2-yl | Me | H | H | morpholin-4-ylmethyl | H | H | H | H |
| benzo[b]thiophen-2-yl | Me | H | H | 1-methyl-1-morpholin-4-yl-ethyl | H | H | H | H |
| benzo[b]thiophen-2-yl | Me | H | H | 1-morpholin-4-yl-cyclopropyl | H | H | H | H |
| benzo[b]thiophen-2-yl | Me | H | H | piperidin-4-ylmethyl | H | H | H | H |
| benzo[b]thiophen-2-yl | Me | H | H | pyrrolidin-1-ylmethyl | H | H | H | H |
| benzo[b]thiophen-2-yl | Me | H | H | $CH_2NMe_2$ | H | H | H | H |
| benzo[b]thiophen-2-yl | Me | H | H | 1-dimethylamino-1-methylethyl | H | H | H | H |
| benzo[b]thiophen-2-yl | Me | H | H | 1-dimethylamino-cyclopropyl | H | H | H | H |
| benzo[b]thiophen-2-yl | Me | H | H | $CH_2NHMe$ | H | H | H | H |
| benzo[b]thiophen-2-yl | Me | H | H | 1-methyl-1-methylaminoethyl | H | H | H | H |
| benzo[b]thiophen-2-yl | Me | H | H | 1-methylamino-cyclopropyl | H | H | H | H |

TABLE A-continued

| X | R¹ | R² | R³ | R⁴ | R⁵ | R⁶ | R⁷ | R⁸ |
|---|---|---|---|---|---|---|---|---|
| benzo[b]thiophen-2-yl | Me | H | H | $CH_2NH_2$ | H | H | H | H |
| benzo[b]thiophen-2-yl | Me | H | H | 1-amino-1-methylethyl | H | H | H | H |
| benzo[b]thiophen-2-yl | Me | H | H | 1-amino-cyclopropyl | H | H | H | H |
| benzo[b]thiophen-2-yl | Me | H | H | 2-oxo-2H-pyridin-1-yl | H | H | H | H |
| benzo[b]thiophen-2-yl | Me | H | H | $SO_2CH_3$ | H | H | H | H |
| benzo[b]thiophen-2-yl | Me | H | H | CN | H | H | H | H |
| benzo[b]thiophen-2-yl | Me | H | Me | H | H | H | H | H |
| benzo[b]thiophen-3-yl | Me | H | H | H | H | H | H | H |
| benzo[b]thiophen-3-yl | Me | H | H | morpholin-4-yl | H | H | H | H |
| benzo[b]thiophen-3-yl | Me | H | H | pyridazin-3-yl | H | H | H | H |
| benzo[b]thiophen-4-yl | Me | H | H | H | H | H | H | H |
| benzo[b]thiophen-4-yl | Me | H | H | morpholin-4-yl | H | H | H | H |
| benzo[b]thiophen-4-yl | Me | H | H | pyridazin-3-yl | H | H | H | H |
| benzo[b]thiophen-5-yl | H | H | H | H | H | H | H | H |
| benzo[b]thiophen-5-yl | H | Me | H | H | H | H | H | H |
| benzo[b]thiophen-5-yl | Me | H | H | H | H | H | H | H |
| benzo[b]thiophen-5-yl | Me | H | F | H | H | H | H | H |
| benzo[b]thiophen-5-yl | Me | H | OMe | H | H | H | H | H |
| benzo[b]thiophen-5-yl | Et | H | H | H | H | H | H | H |
| benzo[b]thiophen-5-yl | Me | Me | H | H | H | H | H | H |
| 2-methyl-benzo[b]thiophen-5-yl | Me | H | H | H | H | H | H | H |
| 2-chlorobenzo[b]thiophen-5-yl | Me | H | H | pyridazin-3-yl | H | H | H | H |
| 2-chlorobenzo[b]thiophen-5-yl | Me | H | H | pyrimidin-2-yl | H | H | H | H |
| 2-chlorobenzo[b]thiophen-5-yl | Me | H | H | pyrimidin-4-yl | H | H | H | H |
| 2-chlorobenzo[b]thiophen-5-yl | Me | H | H | pyrimidin-5-yl | H | H | H | H |
| 2-chlorobenzo[b]thiophen-5-yl | Me | H | H | pyrazin-2-yl | H | H | H | H |
| 2-chlorobenzo[b]thiophen-5-yl | Me | H | H | morpholin-4-yl | H | H | H | H |
| 3-trifluoromethyl-benzo[b]thiophen-5-yl | Me | H | H | pyridazin-3-yl | H | H | H | H |
| 3-trifluoromethyl-benzo[b]thiophen-5-yl | Me | H | H | pyrimidin-2-yl | H | H | H | H |
| 3-trifluoromethyl-benzo[b]thiophen-5-yl | Me | H | H | pyrimidin-4-yl | H | H | H | H |
| 3-trifluoromethyl-benzo[b]thiophen-5-yl | Me | H | H | pyrimidin-5-yl | H | H | H | H |
| 3-trifluoromethyl-benzo[b]thiophen-5-yl | Me | H | H | pyrazin-2-yl | H | H | H | H |
| 3-trifluoromethyl-benzo[b]thiophen-5-yl | Me | H | H | morpholin-4-yl | H | H | H | H |
| 4-cyanobenzo[b]thiophen-5-yl | Me | H | H | H | H | H | H | H |
| 4-methoxybenzo[b]thiophen-5-yl | Me | H | H | H | H | H | H | H |
| 4-methoxybenzo[b]thiophen-5-yl | Me | H | H | pyridazin-3-yl | H | H | H | H |
| 4-methoxybenzo[b]thiophen-5-yl | Et | H | H | pyridazin-3-yl | H | H | H | H |
| 4-methoxybenzo[b]thiophen-5-yl | Me | H | F | pyridazin-3-yl | H | H | H | H |
| 4-methoxybenzo[b]thiophen-5-yl | Et | H | F | pyridazin-3-yl | H | H | H | H |

TABLE A-continued

| X | R¹ | R² | R³ | R⁴ | R⁵ | R⁶ | R⁷ | R⁸ |
|---|---|---|---|---|---|---|---|---|
| 4-methoxybenzo[b]thiophen-5-yl | Me | H | H | 6-methylpyridazin-3-yl | H | H | H | H |
| 4-methoxybenzo[b]thiophen-5-yl | Me | H | H | pyrimidin-2-yl | H | H | H | H |
| 4-methoxybenzo[b]thiophen-5-yl | Me | H | H | pyrimidin-4-yl | H | H | H | H |
| 4-methoxybenzo[b]thiophen-5-yl | Me | H | H | pyrimidin-5-yl | H | H | H | H |
| 4-methoxybenzo[b]thiophen-5-yl | Me | H | H | pyrazin-2-yl | H | H | H | H |
| 4-methoxybenzo[b]thiophen-5-yl | Me | H | H | morpholin-4-yl | H | H | H | H |
| 4-methoxybenzo[b]thiophen-5-yl | Me | H | H | H | H | OH | H | H |
| 4-methoxybenzo[b]thiophen-5-yl | Me | H | H | OH | H | H | H | H |
| 4-methoxybenzo[b]thiophen-5-yl | Me | H | H | H | H | H | H | H |
| 4-methoxybenzo[b]thiophen-5-yl | Et | H | H | H | H | H | H | H |
| 4-methoxybenzo[b]thiophen-5-yl | Et | H | H | H | H | H | H | H |
| 1,1-dioxo-1H-1λ⁶-benzo[b]thiophen-5-yl | Me | H | H | H | H | H | H | H |
| benzo[b]thiophen-5-yl | Me | H | H | H | H | H | H | OH |
| benzo[b]thiophen-5-yl | Me | H | OMe | H | H | H | H | OH |
| benzo[b]thiophen-5-yl | Me | H | H | F | H | H | H | OH |
| benzo[b]thiophen-5-yl | Me | H | H | H | H | H | H | OMe |
| benzo[b]thiophen-5-yl | Me | H | H | H | H | H | H | Me |
| benzo[b]thiophen-5-yl | Me | H | H | H | H | H | H | CN |
| benzo[b]thiophen-5-yl | Me | H | H | H | H | H | H | F |
| benzo[b]thiophen-5-yl | Me | H | H | H | H | H | H | Cl |
| benzo[b]thiophen-5-yl | Me | H | H | OH | H | H | H | H |
| benzo[b]thiophen-5-yl | Me | H | H | OMe | H | H | H | H |
| benzo[b]thiophen-5-yl | Me | H | H | Me | H | H | H | H |
| benzo[b]thiophen-5-yl | Me | H | H | F | H | H | H | H |
| benzo[b]thiophen-5-yl | Me | H | H | pyridazin-3-yl | H | H | H | H |
| benzo[b]thiophen-5-yl | Et | H | H | pyridazin-3-yl | H | H | H | H |
| benzo[b]thiophen-5-yl | Me | H | H | 6-methylpyridazin-3-yl | H | H | H | H |
| benzo[b]thiophen-5-yl | Me | H | H | 6-dimethylamino-pyridazin-3-yl | H | H | H | H |
| benzo[b]thiophen-5-yl | Me | H | H | 6-methylamino-pyridazin-3-yl | H | H | H | H |
| benzo[b]thiophen-5-yl | Me | H | H | 6-amino-pyridazin-3-yl | H | H | H | H |
| benzo[b]thiophen-5-yl | Me | H | H | 6-morpholin-4-yl-pyridazin-3-yl | H | H | H | H |
| benzo[b]thiophen-5-yl | Me | H | H | 6-trifluoromethyl-pyridazin-3-yl | H | H | H | H |
| benzo[b]thiophen-5-yl | Me | H | H | 6-cyano-pyridazin-3-yl | H | H | H | H |
| benzo[b]thiophen-5-yl | Me | H | F | pyridazin-3-yl | H | H | H | H |
| benzo[b]thiophen-5-yl | Me | H | OMe | pyridazin-3-yl | H | H | H | H |
| benzo[b]thiophen-5-yl | Me | H | OH | pyridazin-3-yl | H | H | H | H |
| benzo[b]thiophen-5-yl | Me | H | Me | pyridazin-3-yl | H | H | H | H |
| benzo[b]thiophen-5-yl | Et | H | F | pyridazin-3-yl | H | H | H | H |

TABLE A-continued

| X | $R^1$ | $R^2$ | $R^3$ | $R^4$ | $R^5$ | $R^6$ | $R^7$ | $R^8$ |
|---|---|---|---|---|---|---|---|---|
| benzo[b]thiophen-5-yl | Me | H | H | pyridazin-3-yl | F | H | H | H |
| benzo[b]thiophen-5-yl | Me | H | H | pyridazin-3-yl | H | F | H | H |
| benzo[b]thiophen-5-yl | Me | H | H | pyridazin-3-yl | H | H | H | OH |
| benzo[b]thiophen-5-yl | Me | H | H | pyridazin-3-yl | H | H | H | Me |
| benzo[b]thiophen-5-yl | Me | H | H | pyridazin-4-yl | H | H | H | H |
| benzo[b]thiophen-5-yl | Me | H | F | pyridazin-4-yl | H | H | H | H |
| benzo[b]thiophen-5-yl | Me | H | H | pyrazin-2-yl | H | H | H | H |
| benzo[b]thiophen-5-yl | Me | H | H | 3-methyl-pyrazin-2-yl | H | H | H | H |
| benzo[b]thiophen-5-yl | Me | H | H | 3-methoxy-pyrazin-2-yl | H | H | H | H |
| benzo[b]thiophen-5-yl | Me | H | H | 6-methyl-pyrazin-2-yl | H | H | H | H |
| benzo[b]thiophen-5-yl | Me | H | H | 6-methoxy-pyrazin-2-yl | H | H | H | H |
| benzo[b]thiophen-5-yl | Me | H | F | pyrazin-2-yl | H | H | H | H |
| benzo[b]thiophen-5-yl | Me | H | OMe | pyrazin-2-yl | H | H | H | H |
| benzo[b]thiophen-5-yl | Me | H | OH | pyrazin-2-yl | H | H | H | H |
| benzo[b]thiophen-5-yl | Me | H | Me | pyrazin-2-yl | H | H | H | H |
| benzo[b]thiophen-5-yl | Me | H | H | pyrimidin-2-yl | H | H | H | H |
| benzo[b]thiophen-5-yl | Me | H | F | pyrimidin-2-yl | H | H | H | H |
| benzo[b]thiophen-5-yl | Me | H | OMe | pyrimidin-2-yl | H | H | H | H |
| benzo[b]thiophen-5-yl | Me | H | OH | pyrimidin-2-yl | H | H | H | H |
| benzo[b]thiophen-5-yl | Me | H | Me | pyrimidin-2-yl | H | H | H | H |
| benzo[b]thiophen-5-yl | Me | H | H | pyrimidin-4-yl | H | H | H | H |
| benzo[b]thiophen-5-yl | Me | H | F | pyrimidin-4-yl | H | H | H | H |
| benzo[b]thiophen-5-yl | Me | H | OMe | pyrimidin-4-yl | H | H | H | H |
| benzo[b]thiophen-5-yl | Me | H | OH | pyrimidin-4-yl | H | H | H | H |
| benzo[b]thiophen-5-yl | Me | H | Me | pyrimidin-4-yl | H | H | H | H |
| benzo[b]thiophen-5-yl | Me | H | H | pyrimidin-5-yl | H | H | H | H |
| benzo[b]thiophen-5-yl | Me | H | F | pyrimidin-5-yl | H | H | H | H |
| benzo[b]thiophen-5-yl | Me | H | OMe | pyrimidin-5-yl | H | H | H | H |
| benzo[b]thiophen-5-yl | Me | H | OH | pyrimidin-5-yl | H | H | H | H |
| benzo[b]thiophen-5-yl | Me | H | Me | pyrimidin-5-yl | H | H | H | H |
| benzo[b]thiophen-5-yl | Me | H | H | 3,5-dimethyl-isoxazol-4-yl | H | H | H | H |
| benzo[b]thiophen-5-yl | Me | H | H | thiazol-2-yl | H | H | H | H |
| benzo[b]thiophen-5-yl | Me | H | H | 5-methyl-thiazol-2-yl | H | H | H | H |
| benzo[b]thiophen-5-yl | Me | H | H | [1,3,5]triazin-2-yl | H | H | H | H |
| benzo[b]thiophen-5-yl | Me | H | H | [1,2,4]triazin-3-yl | H | H | H | H |
| benzo[b]thiophen-5-yl | Me | H | H | [1,2,4]triazin-5-yl | H | H | H | H |
| benzo[b]thiophen-5-yl | Me | H | H | [1,2,4]triazin-6-yl | H | H | H | H |
| benzo[b]thiophen-5-yl | Me | H | H | cinnolin-3-yl | H | H | H | H |
| benzo[b]thiophen-5-yl | Me | H | H | phthalazin-1-yl | H | H | H | H |
| benzo[b]thiophen-5-yl | Me | H | H | quinoxalin-2-yl | H | H | H | H |
| benzo[b]thiophen-5-yl | Me | H | H | quinazolin-2-yl | H | H | H | H |
| benzo[b]thiophen-5-yl | Me | H | H | quinazolin-6-yl | H | H | H | H |
| benzo[b]thiophen-5-yl | Me | H | H | quinazolin-7-yl | H | H | H | H |
| benzo[b]thiophen-5-yl | Me | H | H | 3-oxo-[1,2,4]triazolo[4,3-a]pyridin-2-yl | H | H | H | H |
| benzo[b]thiophen-5-yl | Me | H | H | morpholin-4-yl | H | H | H | H |
| benzo[b]thiophen-5-yl | Me | H | H | 2,6-dimethyl-morpholin-4-yl | H | H | H | H |
| benzo[b]thiophen-5-yl | Et | H | H | morpholin-4-yl | H | H | H | H |
| benzo[b]thiophen-5-yl | Me | H | F | morpholin-4-yl | H | H | H | H |
| benzo[b]thiophen-5-yl | Me | H | OMe | morpholin-4-yl | H | H | H | H |
| benzo[b]thiophen-5-yl | Me | H | OH | morpholin-4-yl | H | H | H | H |
| benzo[b]thiophen-5-yl | Me | H | Me | morpholin-4-yl | H | H | H | H |
| benzo[b]thiophen-5-yl | Et | H | F | morpholin-4-yl | H | H | H | H |
| benzo[b]thiophen-5-yl | Me | H | H | morpholin-4-yl | F | H | H | H |
| benzo[b]thiophen-5-yl | Me | H | H | morpholin-4-yl | H | F | H | H |
| benzo[b]thiophen-5-yl | Me | H | H | morpholin-4-yl | H | H | H | OH |
| benzo[b]thiophen-5-yl | Me | H | H | morpholin-4-yl | H | H | H | Me |
| benzo[b]thiophen-5-yl | Me | H | H | piperazin-1-yl | H | H | H | H |
| benzo[b]thiophen-5-yl | Me | H | H | 4-methyl-piperazin-1-yl | H | H | H | H |

TABLE A-continued

| X | R¹ | R² | R³ | R⁴ | R⁵ | R⁶ | R⁷ | R⁸ |
|---|---|---|---|---|---|---|---|---|
| benzo[b]thiophen-5-yl | Me | H | H | piperidin-1-yl | H | H | H | H |
| benzo[b]thiophen-5-yl | Me | H | H | pyrrolidin-1-yl | H | H | H | H |
| benzo[b]thiophen-5-yl | Me | H | H | morpholin-4-ylmethyl | H | H | H | H |
| benzo[b]thiophen-5-yl | Me | H | H | 1-methyl-1-morpholin-4-yl-ethyl | H | H | H | H |
| benzo[b]thiophen-5-yl | Me | H | H | 1-morpholin-4-yl-cyclopropyl | H | H | H | H |
| benzo[b]thiophen-5-yl | Me | H | H | piperidin-1-ylmethyl | H | H | H | H |
| benzo[b]thiophen-5-yl | Me | H | H | pyrrolidin-1-ylmethyl | H | H | H | H |
| benzo[b]thiophen-5-yl | Me | H | H | $CH_2NMe_2$ | H | H | H | H |
| benzo[b]thiophen-5-yl | Me | H | H | 1-dimethylamino-1-methylethyl | H | H | H | H |
| benzo[b]thiophen-5-yl | Me | H | H | 1-dimethylamino-cyclopropyl | H | H | H | H |
| benzo[b]thiophen-5-yl | Me | H | H | $CH_2NHMe$ | H | H | H | H |
| benzo[b]thiophen-5-yl | Me | H | H | 1-methyl-1-methylaminoethyl | H | H | H | H |
| benzo[b]thiophen-5-yl | Me | H | H | 1-methylamino-cyclopropyl | H | H | H | H |
| benzo[b]thiophen-5-yl | Me | H | H | $CH_2NH_2$ | H | H | H | H |
| benzo[b]thiophen-5-yl | Me | H | H | 1-methyl-1-methylaminoethyl | H | H | H | H |
| benzo[b]thiophen-5-yl | Me | H | H | 1-methylamino-cyclopropyl | H | H | H | H |
| benzo[b]thiophen-5-yl | Me | H | H | 2-oxo-2H-pyridin-1-yl | H | H | H | H |
| benzo[b]thiophen-5-yl | Me | H | H | $SO_2CH_3$ | H | H | H | H |
| benzo[b]thiophen-5-yl | Me | H | H | CN | H | H | H | H |
| benzo[b]thiophen-5-yl | Me | H | F | CN | H | H | H | H |
| benzo[b]thiophen-5-yl | Me | H | Me | H | H | H | H | H |
| benzo[b]thiophen-6-yl | H | H | H | H | H | H | H | H |
| benzo[b]thiophen-6-yl | H | Me | H | H | H | H | H | H |
| benzo[b]thiophen-6-yl | Me | H | H | H | H | H | H | H |
| benzo[b]thiophen-6-yl | Me | H | F | H | H | H | H | H |
| benzo[b]thiophen-6-yl | Et | H | H | H | H | H | H | H |
| benzo[b]thiophen-6-yl | Me | Me | H | H | H | H | H | H |
| 2-methyl benzo[b]thiophen-6-yl | Me | H | H | H | H | H | H | H |
| 1,1-dioxo-1H-1λ⁶-benzo[b]thiophen-6-yl | Me | H | H | H | H | H | H | H |
| benzo[b]thiophen-6-yl | Me | H | H | H | H | H | H | OH |
| benzo[b]thiophen-6-yl | Me | H | H | H | H | H | H | OMe |
| benzo[b]thiophen-6-yl | Me | H | H | H | H | H | H | Me |
| benzo[b]thiophen-6-yl | Me | H | H | H | H | H | H | CN |
| benzo[b]thiophen-6-yl | Me | H | H | H | H | H | H | F |
| benzo[b]thiophen-6-yl | Me | H | H | H | H | H | H | Cl |
| 2-chlorobenzo[b]thiophen-6-yl | Me | H | H | pyridazin-3-yl | H | H | H | H |
| 2-chlorobenzo[b]thiophen-6-yl | Me | H | H | pyrimidin-2-yl | H | H | H | H |
| 2-chlorobenzo[b]thiophen-6-yl | Me | H | H | pyrimidin-4-yl | H | H | H | H |
| 2-chlorobenzo[b]thiophen-6-yl | Me | H | H | pyrimidin-5-yl | H | H | H | H |
| 2-chlorobenzo[b]thiophen-6-yl | Me | H | H | pyrazin-2-yl | H | H | H | H |
| 2-chlorobenzo[b]thiophen-6-yl | Me | H | H | morpholin-4-yl | H | H | H | H |
| 3-trifluoromethyl-benzo[b]thiophen-6-yl | Me | H | H | pyridazin-3-yl | H | H | H | H |
| 3-trifluoromethyl-benzo[b]thiophen-6-yl | Me | H | H | pyrimidin-2-yl | H | H | H | H |
| 3-trifluoromethyl-benzo[b]thiophen-6-yl | Me | H | H | pyrimidin-4-yl | H | H | H | H |

TABLE A-continued

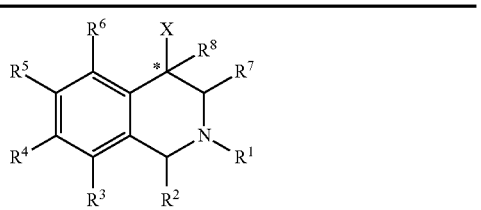

| X | R¹ | R² | R³ | R⁴ | R⁵ | R⁶ | R⁷ | R⁸ |
|---|---|---|---|---|---|---|---|---|
| 3-trifluoromethyl-benzo[b]thiophen-6-yl | Me | H | H | pyrimidin-5-yl | H | H | H | H |
| 3-trifluoromethyl-benzo[b]thiophen-6-yl | Me | H | H | pyrazin-2-yl | H | H | H | H |
| 3-trifluoromethyl-benzo[b]thiophen-6-yl | Me | H | H | morpholin-4-yl | H | H | H | H |
| 7-methoxybenzo[b]thiophen-6-yl | Me | H | H | H | H | H | H | H |
| 7-methoxybenzo[b]thiophen-6-yl | Me | H | H | pyridazin-3-yl | H | H | H | H |
| 7-methoxybenzo[b]thiophen-6-yl | Et | H | H | pyridazin-3-yl | H | H | H | H |
| 7-methoxybenzo[b]thiophen-6-yl | Me | H | F | pyridazin-3-yl | H | H | H | H |
| 7-methoxybenzo[b]thiophen-6-yl | Et | H | F | pyridazin-3-yl | H | H | H | H |
| 7-methoxybenzo[b]thiophen-6-yl | Me | H | H | 6-methylpyridazin-3-yl | H | H | H | H |
| 7-methoxybenzo[b]thiophen-6-yl | Me | H | H | pyrimidin-2-yl | H | H | H | H |
| 7-methoxybenzo[b]thiophen-6-yl | Me | H | H | pyrimidin-4-yl | H | H | H | H |
| 7-methoxybenzo[b]thiophen-6-yl | Me | H | H | pyrimidin-5-yl | H | H | H | H |
| 7-methoxybenzo[b]thiophen-6-yl | Me | H | H | pyrazin-2-yl | H | H | H | H |
| 7-methoxybenzo[b]thiophen-6-yl | Me | H | H | morpholin-4-yl | H | H | H | H |
| 7-methoxybenzo[b]thiophen-6-yl | Me | H | H | OH | H | H | H | H |
| benzo[b]thiophen-6-yl | Me | H | H | OH | H | H | H | H |
| benzo[b]thiophen-6-yl | Me | H | H | OMe | H | H | H | H |
| benzo[b]thiophen-6-yl | Me | H | H | Me | H | H | H | H |
| benzo[b]thiophen-6-yl | Me | H | H | F | H | H | H | H |
| benzo[b]thiophen-6-yl | Me | H | H | pyridazin-3-yl | H | H | H | H |
| benzo[b]thiophen-6-yl | Et | H | H | pyridazin-3-yl | H | H | H | H |
| benzo[b]thiophen-6-yl | Me | H | H | 6-methylpyridazin-3-yl | H | H | H | H |
| benzo[b]thiophen-6-yl | Me | H | H | 6-dimethylamino-pyridazine-3-yl | H | H | H | H |
| benzo[b]thiophen-6-yl | Me | H | H | 6-methylamino-pyridazine-3-yl | H | H | H | H |
| benzo[b]thiophen-6-yl | Me | H | H | 6-amino-pyridazine-3-yl | H | H | H | H |
| benzo[b]thiophen-6-yl | Me | H | H | 6-morpholin-4-yl-pyridazine-3-yl | H | H | H | H |
| benzo[b]thiophen-6-yl | Me | H | H | 6-trifluoromethyl-pyridazine-3-yl | H | H | H | H |
| benzo[b]thiophen-6-yl | Me | H | H | 6-cyano-pyridazine-3-yl | H | H | H | H |
| benzo[b]thiophen-6-yl | Me | H | F | pyridazin-3-yl | H | H | H | H |
| benzo[b]thiophen-6-yl | Me | H | OMe | pyridazin-3-yl | H | H | H | H |
| benzo[b]thiophen-6-yl | Me | H | OH | pyridazin-3-yl | H | H | H | H |
| benzo[b]thiophen-6-yl | Me | H | Me | pyridazin-3-yl | H | H | H | H |
| benzo[b]thiophen-6-yl | Et | H | F | pyridazin-3-yl | H | H | H | H |
| benzo[b]thiophen-6-yl | Me | H | H | pyridazin-3-yl | F | H | H | H |

TABLE A-continued

[Structure diagram of a tetrahydroisoquinoline with substituents R¹–R⁸ and X]

| X | R¹ | R² | R³ | R⁴ | R⁵ | R⁶ | R⁷ | R⁸ |
|---|----|----|----|----|----|----|----|----|
| benzo[b]thiophen-6-yl | Me | H | H | pyridazin-3-yl | H | F | H | H |
| benzo[b]thiophen-6-yl | Me | H | H | pyridazin-3-yl | H | H | H | OH |
| benzo[b]thiophen-6-yl | Me | H | H | pyridazin-3-yl | H | H | H | Me |
| benzo[b]thiophen-6-yl | Me | H | H | pyridazin-3-yl | H | H | H | H |
| benzo[b]thiophen-6-yl | Me | H | F | pyridazin-4-yl | H | H | H | H |
| benzo[b]thiophen-6-yl | Me | H | H | pyridazin-4-yl | H | H | H | H |
| benzo[b]thiophen-6-yl | Me | H | H | pyrazin-2-yl | H | H | H | H |
| benzo[b]thiophen-6-yl | Me | H | H | 3-methyl-pyrazin-2-yl | H | H | H | H |
| benzo[b]thiophen-6-yl | Me | H | H | 3-methoxy-pyrazin-2-yl | H | H | H | H |
| benzo[b]thiophen-6-yl | Me | H | H | 6-methyl-pyrazin-2-yl | H | H | H | H |
| benzo[b]thiophen-6-yl | Me | H | H | 6-methoxy-pyrazin-2-yl | H | H | H | H |
| benzo[b]thiophen-6-yl | Me | H | F | pyrazin-2-yl | H | H | H | H |
| benzo[b]thiophen-6-yl | Me | H | OMe | pyrazin-2-yl | H | H | H | H |
| benzo[b]thiophen-6-yl | Me | H | OH | pyrazin-2-yl | H | H | H | H |
| benzo[b]thiophen-6-yl | Me | H | Me | pyrazin-2-yl | H | H | H | H |
| benzo[b]thiophen-6-yl | Me | H | H | pyrimidin-2-yl | H | H | H | H |
| benzo[b]thiophen-6-yl | Me | H | F | pyrimidin-2-yl | H | H | H | H |
| benzo[b]thiophen-6-yl | Me | H | OMe | pyrimidin-2-yl | H | H | H | H |
| benzo[b]thiophen-6-yl | Me | H | OH | pyrimidin-2-yl | H | H | H | H |
| benzo[b]thiophen-6-yl | Me | H | Me | pyrimidin-2-yl | H | H | H | H |
| benzo[b]thiophen-6-yl | Me | H | H | pyrimidin-4-yl | H | H | H | H |
| benzo[b]thiophen-6-yl | Me | H | F | pyrimidin-4-yl | H | H | H | H |
| benzo[b]thiophen-6-yl | Me | H | OMe | pyrimidin-4-yl | H | H | H | H |
| benzo[b]thiophen-6-yl | Me | H | OH | pyrimidin-4-yl | H | H | H | H |
| benzo[b]thiophen-6-yl | Me | H | Me | pyrimidin-4-yl | H | H | H | H |
| benzo[b]thiophen-6-yl | Me | H | H | pyrimidin-5-yl | H | H | H | H |
| benzo[b]thiophen-6-yl | Me | H | F | pyrimidin-5-yl | H | H | H | H |
| benzo[b]thiophen-6-yl | Me | H | OMe | pyrimidin-5-yl | H | H | H | H |
| benzo[b]thiophen-6-yl | Me | H | OH | pyrimidin-5-yl | H | H | H | H |
| benzo[b]thiophen-6-yl | Me | H | Me | pyrimidin-5-yl | H | H | H | H |
| benzo[b]thiophen-6-yl | Me | H | H | 3,5-dimethyl-isoxazol-4-yl | H | H | H | H |
| benzo[b]thiophen-6-yl | Me | H | H | thiazol-2-yl | H | H | H | H |
| benzo[b]thiophen-6-yl | Me | H | H | 5-methyl-thiazol-2-yl | H | H | H | H |
| benzo[b]thiophen-6-yl | Me | H | H | [1,3,5]triazin-2-yl | H | H | H | H |
| benzo[b]thiophen-6-yl | Me | H | H | [1,2,4]triazin-3-yl | H | H | H | H |
| benzo[b]thiophen-6-yl | Me | H | H | [1,2,4]triazin-5-yl | H | H | H | H |
| benzo[b]thiophen-6-yl | Me | H | H | [1,2,4]triazin-6-yl | H | H | H | H |
| benzo[b]thiophen-6-yl | Me | H | H | cinnolin-3-yl | H | H | H | H |
| benzo[b]thiophen-6-yl | Me | H | H | phthalazin-1-yl | H | H | H | H |
| benzo[b]thiophen-6-yl | Me | H | H | quinoxalin-2-yl | H | H | H | H |
| benzo[b]thiophen-6-yl | Me | H | H | quinazolin-2-yl | H | H | H | H |
| benzo[b]thiophen-6-yl | Me | H | H | quinazolin-6-yl | H | H | H | H |
| benzo[b]thiophen-6-yl | Me | H | H | quinazolin-7-yl | H | H | H | H |
| benzo[b]thiophen-6-yl | Me | H | H | 3-oxo-[1,2,4]triazolo[4,3-a]pyridin-2-yl | H | H | H | H |
| benzo[b]thiophen-6-yl | Me | H | H | morpholin-4-yl | H | H | H | H |
| benzo[b]thiophen-6-yl | Me | H | H | 2,6-dimethyl-morpholin-4-yl | H | H | H | H |
| benzo[b]thiophen-6-yl | Et | H | H | morpholin-4-yl | H | H | H | H |
| benzo[b]thiophen-6-yl | Me | H | F | morpholin-4-yl | H | H | H | H |
| benzo[b]thiophen-6-yl | Me | H | OMe | morpholin-4-yl | H | H | H | H |
| benzo[b]thiophen-6-yl | Me | H | OH | morpholin-4-yl | H | H | H | H |
| benzo[b]thiophen-6-yl | Me | H | Me | morpholin-4-yl | H | H | H | H |
| benzo[b]thiophen-6-yl | Et | H | F | morpholin-4-yl | H | H | H | H |
| benzo[b]thiophen-6-yl | Me | H | H | morpholin-4-yl | F | H | H | H |
| benzo[b]thiophen-6-yl | Me | H | H | morpholin-4-yl | H | F | H | H |
| benzo[b]thiophen-6-yl | Me | H | H | morpholin-4-yl | H | H | H | OH |
| benzo[b]thiophen-6-yl | Me | H | H | morpholin-4-yl | H | H | H | Me |
| benzo[b]thiophen-6-yl | Me | H | H | morpholin-4-yl | H | H | H | H |
| benzo[b]thiophen-6-yl | Me | H | H | 4-methyl-piperazin-1-yl | H | H | H | H |

TABLE A-continued

| X | R¹ | R² | R³ | R⁴ | R⁵ | R⁶ | R⁷ | R⁸ |
|---|---|---|---|---|---|---|---|---|
| benzo[b]thiophen-6-yl | Me | H | H | piperidin-1-yl | H | H | H | H |
| benzo[b]thiophen-6-yl | Me | H | H | pyrrolidin-1-yl | H | H | H | H |
| benzo[b]thiophen-6-yl | Me | H | H | morpholin-4-ylmethyl | H | H | H | H |
| benzo[b]thiophen-6-yl | Me | H | H | 1-methyl-1-morpholin-4-yl-ethyl | H | H | H | H |
| benzo[b]thiophen-6-yl | Me | H | H | 1-morpholin-4-yl-cyclopropyl | H | H | H | H |
| benzo[b]thiophen-6-yl | Me | H | H | piperidin-1-ylmethyl | H | H | H | H |
| benzo[b]thiophen-6-yl | Me | H | H | pyrrolidin-1-ylmethyl | H | H | H | H |
| benzo[b]thiophen-6-yl | Me | H | H | $CH_2NMe_2$ | H | H | H | H |
| benzo[b]thiophen-6-yl | Me | H | H | 1-dimethylamino-1-methylethyl | H | H | H | H |
| benzo[b]thiophen-6-yl | Me | H | H | 1-dimethylamino-cyclopropyl | H | H | H | H |
| benzo[b]thiophen-6-yl | Me | H | H | $CH_2NHMe$ | H | H | H | H |
| benzo[b]thiophen-6-yl | Me | H | H | 1-methyl-1-methylaminoethyl | H | H | H | H |
| benzo[b]thiophen-6-yl | Me | H | H | 1-methylamino-cyclopropyl | H | H | H | H |
| benzo[b]thiophen-6-yl | Me | H | H | $CH_2NH_2$ | H | H | H | H |
| benzo[b]thiophen-6-yl | Me | H | H | 1-methyl-1-methylaminoethyl | H | H | H | H |
| benzo[b]thiophen-6-yl | Me | H | H | 1-methylamino-cyclopropyl | H | H | H | H |
| benzo[b]thiophen-6-yl | Me | H | H | 2-oxo-2H-pyridin-1-yl | H | H | H | H |
| benzo[b]thiophen-6-yl | Me | H | H | $SO_2CH_3$ | H | H | H | H |
| benzo[b]thiophen-6-yl | Me | H | H | CN | H | H | H | H |
| benzo[b]thiophen-6-yl | Me | H | F | CN | H | H | H | H |
| benzo[b]thiophen-6-yl | Me | H | Me | H | H | H | H | H |
| benzo[b]thiophen-7-yl | Me | H | H | H | H | H | H | H |
| benzo[b]thiophen-7-yl | Et | H | H | H | H | H | H | H |
| benzo[b]thiophen-7-yl | Me | H | F | H | H | H | H | H |
| benzo[b]thiophen-7-yl | Et | H | F | H | H | H | H | H |
| benzo[b]thiophen-7-yl | Me | H | H | pyridazin-3-yl | H | H | H | H |
| benzo[b]thiophen-7-yl | Me | H | H | morpholin-4-yl | H | H | H | H |
| benzo[b]thiophen-5-yl | S1$^a$ | H | H | H | H | H | H | H |
| benzo[b]thiophen-5-yl | S2$^a$ | H | H | H | H | H | H | H |
| benzo[b]thiophen-5-yl | S3$^a$ | H | H | H | H | H | H | H |
| benzo[b]thiophen-5-yl | S4$^a$ | H | H | H | H | H | H | H |
| benzo[b]thiophen-5-yl | S5$^a$ | H | H | H | H | H | H | H |
| benzo[b]thiophen-5-yl | Me | H | H | H | H | H | H | S6$^a$ |

$^a$:
S1 = cyclopropyl
S2 = cyanomethyl
S3 = 2-dimethylaminoethyl
S4 = 2-hydroxyethyl
S5 = isopropyl
S6 = morpholin-4-yl
wherein the carbon atom designated * is in the R or S configuration.

That is, the specific compounds herein include:
4-(benzo[b]thiophen-2-yl)-1,2,3,4-tetrahydroisoquinoline;
4-(benzo[b]thiophen-2-yl)-1-methyl-1,2,3,4-tetrahydroisoquinoline;
4-(benzo[b]thiophen-2-yl)-2-methyl-1,2,3,4-tetrahydroisoquinoline;
4-(benzo[b]thiophen-2-yl)-2-ethyl-1,2,3,4-tetrahydroisoquinoline;
4-(benzo[b]thiophen-2-yl)-1,2-dimethyl-1,2,3,4-tetrahydroisoquinoline;
4-(4-fluoro-benzo[b]thiophen-2-yl)-2-methyl-1,2,3,4-tetrahydroisoquinoline;
4-(5-fluoro-benzo[b]thiophen-2-yl)-2-methyl-1,2,3,4-tetrahydroisoquinoline;
4-(6-fluoro-benzo[b]thiophen-2-yl)-2-methyl-1,2,3,4-tetrahydroisoquinoline;
4-(7-fluoro-benzo[b]thiophen-2-yl)-2-methyl-1,2,3,4-tetrahydroisoquinoline;
4-(4-chloro-benzo[b]thiophen-2-yl)-2-methyl-1,2,3,4-tetrahydroisoquinoline;

4-(5-chloro-benzo[b]thiophen-2-yl)-2-methyl-1,2,3,4-tetrahydroisoquinoline;
4-(6-chloro-benzo[b]thiophen-2-yl)-2-methyl-1,2,3,4-tetrahydroisoquinoline;
4-(7-chloro-benzo[b]thiophen-2-yl)-2-methyl-1,2,3,4-tetrahydroisoquinoline;
4-(4-methoxy-benzo[b]thiophen-2-yl)-2-methyl-1,2,3,4-tetrahydroisoquinoline;
4-(5-methoxy-benzo[b]thiophen-2-yl)-2-methyl-1,2,3,4-tetrahydroisoquinoline;
4-(6-methoxy-benzo[b]thiophen-2-yl)-2-methyl-1,2,3,4-tetrahydroisoquinoline;
4-(7-methoxy-benzo[b]thiophen-2-yl)-2-methyl-1,2,3,4-tetrahydroisoquinoline;
4-(1,1-dioxo-1H-1$\lambda^6$-benzo[b]thiophen-2-yl)-2-methyl-1,2,3,4-tetrahydroisoquinoline;
4-(benzo[b]thiophen-2-yl)-2-methyl-1,2,3,4-tetrahydroisoquinoline-4-ol;
4-(benzo[b]thiophen-2-yl)-4-methoxy-2-methyl-1,2,3,4-tetrahydroisoquinoline;
4-(benzo[b]thiophen-2-yl)-2,4-dimethyl-1,2,3,4-tetrahydroisoquinoline;
4-(benzo[b]thiophen-2-yl)-2-methyl-1,2,3,4-tetrahydroisoquinoline-4-carbonitrile;
4-(benzo[b]thiophen-2-yl)-4-fluoro-2-methyl-1,2,3,4-tetrahydroisoquinoline;
4-(benzo[b]thiophen-2-yl)-4-chloro-2-methyl-1,2,3,4-tetrahydroisoquinoline;
4-(benzo[b]thiophen-2-yl)-2,5-dimethyl-1,2,3,4-tetrahydroisoquinoline;
4-(benzo[b]thiophen-2-yl)-2-methyl-1,2,3,4-tetrahydroisoquinolin-7-ol;
4-(benzo[b]thiophen-2-yl)-7-methoxy-2-methyl-1,2,3,4-tetrahydroisoquinoline;
4-(benzo[b]thiophen-2-yl)-2,7-dimethyl-1,2,3,4-tetrahydroisoquinoline;
4-(benzo[b]thiophen-2-yl)-7-fluoro-2-methyl-1,2,3,4-tetrahydroisoquinoline;
4-(benzo[b]thiophen-2-yl)-2-methyl-7-(pyridazin-3-yl)-1,2,3,4-tetrahydroisoquinoline;
4-(4-fluoro-benzo[b]thiophen-2-yl)-2-methyl-7-(pyridazin-3-yl)-1,2,3,4-tetrahydroisoquinoline;
4-(5-fluoro-benzo[b]thiophen-2-yl)-2-methyl-7-(pyridazin-3-yl)-1,2,3,4-tetrahydroisoquinoline;
4-(6-fluoro-benzo[b]thiophen-2-yl)-2-methyl-7-(pyridazin-3-yl)-1,2,3,4-tetrahydroisoquinoline;
4-(7-fluoro-benzo[b]thiophen-2-yl)-2-methyl-7-(pyridazin-3-yl)-1,2,3,4-tetrahydroisoquinoline;
4-(benzo[b]thiophen-2-yl)-2-ethyl-7-pyridazin-3-yl-1,2,3,4-tetrahydroisoquinoline;
4-benzo[b]thiophen-2-yl-2-methyl-7-(6-methylpyridazin-3-yl)-1,2,3,4-tetrahydroisoquinoline;
[6-(4-benzo[b]thiophen-2-yl-2-methyl-1,2,3,4-tetrahydroisoquinolin-7-yl)-pyridazin-3-yl]-dimethylamine;
[6-(4-benzo[b]thiophen-2-yl-2-methyl-1,2,3,4-tetrahydroisoquinolin-7-yl)-pyridazin-3-yl]-methylamine;
6-(4-benzo[b]thiophen-2-yl-2-methyl-1,2,3,4-tetrahydroisoquinolin-7-yl)-pyridazin-3-ylamine;
4-benzo[b]thiophen-2-yl-2-methyl-7-(6-morpholin-4-yl-pyridazin-3-yl)-1,2,3,4-tetrahydroisoquinoline;
4-benzo[b]thiophen-2-yl-2-methyl-7-(6-trifluoromethyl-pyridazin-3-yl)-1,2,3,4-tetrahydroisoquinoline;
6-(4-benzo[b]thiophen-2-yl-2-methyl-1,2,3,4-tetrahydroisoquinolin-7-yl)-pyridazin-3-yl-carbonitrile;
4-benzo[b]thiophen-2-yl-8-fluoro-2-methyl-7-pyridazin-3-yl-1,2,3,4-tetrahydroisoquinoline;
4-benzo[b]thiophen-2-yl-8-methoxy-2-methyl-7-pyridazin-3-yl-1,2,3,4-tetrahydroisoquinoline;
4-benzo[b]thiophen-2-yl-2-methyl-7-pyridazin-3-yl-1,2,3,4-tetrahydroisoquinolin-8-ol;
4-benzo[b]thiophen-2-yl-2,8-dimethyl-7-pyridazin-3-yl-1,2,3,4-tetrahydroisoquinoline;
4-benzo[b]thiophen-2-yl-2-ethyl-8-fluoro-7-pyridazin-3-yl-1,2,3,4-tetrahydroisoquinoline;
4-benzo[b]thiophen-2-yl-6-fluoro-2-methyl-7-pyridazin-3-yl-1,2,3,4-tetrahydroisoquinoline;
4-benzo[b]thiophen-2-yl-5-fluoro-2-methyl-7-pyridazin-3-yl-1,2,3,4-tetrahydroisoquinoline;
4-benzo[b]thiophen-2-yl-2-methyl-7-pyridazin-3-yl-1,2,3,4-tetrahydroisoquinolin-4-ol;
4-benzo[b]thiophen-2-yl-2,4-dimethyl-7-pyridazin-3-yl-1,2,3,4-tetrahydroisoquinoline;
4-(benzo[b]thiophen-2-yl)-2-methyl-7-(pyridazin-4-yl)-1,2,3,4-tetrahydroisoquinoline;
4-(benzo[b]thiophen-2-yl)-8-fluoro-2-methyl-7-(pyridazin-4-yl)-1,2,3,4-tetrahydroisoquinoline;
4-(benzo[b]thiophen-2-yl)-2-methyl-7-(pyrazin-2-yl)-1,2,3,4-tetrahydroisoquinoline;
4-benzo[b]thiophen-2-yl-2-methyl-7-(3-methyl-pyrazin-2-yl)-1,2,3,4-tetrahydroisoquinoline;
4-benzo[b]thiophen-2-yl-7-(3-methoxy-pyrazin-2-yl)-2-methyl-1,2,3,4-tetrahydroisoquinoline;
4-benzo[b]thiophen-2-yl-2-methyl-7-(6-methyl-pyrazin-2-yl)-1,2,3,4-tetrahydroisoquinoline;
4-benzo[b]thiophen-2-yl-7-(6-methoxy-pyrazin-2-yl)-2-methyl-1,2,3,4-tetrahydroisoquinoline;
4-benzo[b]thiophen-2-yl-8-fluoro-2-methyl-7-pyrazin-2-yl-1,2,3,4-tetrahydroisoquinoline;
4-(benzo[b]thiophen-2-yl)-2-methyl-7-(pyrimidin-2-yl)-1,2,3,4-tetrahydroisoquinoline;
4-benzo[b]thiophen-2-yl-8-fluoro-2-methyl-7-pyrimidin-2-yl-1,2,3,4-tetrahydroisoquinoline;
4-(benzo[b]thiophen-2-yl)-2-methyl-7-(pyrimidin-4-yl)-1,2,3,4-tetrahydroisoquinoline;
4-benzo[b]thiophen-2-yl-8-fluoro-2-methyl-7-pyrimidin-4-yl-1,2,3,4-tetrahydroisoquinoline;
4-(benzo[b]thiophen-2-yl)-2-methyl-7-(pyrimidin-5-yl)-1,2,3,4-tetrahydroisoquinoline;
4-benzo[b]thiophen-2-yl-8-fluoro-2-methyl-7-pyrimidin-5-yl-1,2,3,4-tetrahydroisoquinoline;
4-(benzo[b]thiophen-2-yl)-7-(3,5-dimethyl-isoxazol-4-yl)-2-methyl-1,2,3,4-tetrahydroisoquinoline;
4-(benzo[b]thiophen-2-yl)-2-methyl-7-(thiazol-2-yl)-1,2,3,4-tetrahydroisoquinoline;
4-(benzo[b]thiophen-2-yl)-2-methyl-7-(5-methyl-thiazol-2-yl)-1,2,3,4-tetrahydroisoquinoline;
4-benzo[b]thiophen-2-yl-2-methyl-7-[1,3,5]triazin-2-yl-1,2,3,4-tetrahydroisoquinoline;
4-benzo[b]thiophen-2-yl-2-methyl-7-[1,2,4]triazin-3-yl-1,2,3,4-tetrahydroisoquinoline;
4-benzo[b]thiophen-2-yl-2-methyl-7-[1,2,4]triazin-5-yl-1,2,3,4-tetrahydroisoquinoline;
4-benzo[b]thiophen-2-yl-2-methyl-7-[1,2,4]triazin-6-yl-1,2,3,4-tetrahydroisoquinoline;
3-(4-benzo[b]thiophen-2-yl-2-methyl-1,2,3,4-tetrahydroisoquinolin-7-yl)-cinnoline;
1-(4-benzo[b]thiophen-2-yl-2-methyl-1,2,3,4-tetrahydroisoquinolin-7-yl)-phthalazine;
2-(4-benzo[b]thiophen-2-yl-2-methyl-1,2,3,4-tetrahydroisoquinolin-7-yl)-quinoxaline;
2-(4-benzo[b]thiophen-2-yl-2-methyl-1,2,3,4-tetrahydroisoquinolin-7-yl)-quinazoline;

6-(4-benzo[b]thiophen-2-yl-2-methyl-1,2,3,4-tetrahydroisoquinolin-7-yl)-quinazoline;
7-(4-benzo[b]thiophen-2-yl-2-methyl-1,2,3,4-tetrahydroisoquinolin-7-yl)-quinazoline;
2-(4-benzo[b]thiophen-2-yl-2-methyl-1,2,3,4-tetrahydroisoquinolin-7-yl)-2H-[1,2,4]triazolo[4,3-a]pyridin-3-one;
4-(benzo[b]thiophen-2-yl)-2-methyl-7-(morpholin-4-yl)-1,2,3,4-tetrahydroisoquinoline;
4-(4-fluoro-benzo[b]thiophen-2-yl)-2-methyl-7-morpholin-4-yl-1,2,3,4-tetrahydroisoquinoline;
4-(5-fluoro-benzo[b]thiophen-2-yl)-2-methyl-7-morpholin-4-yl-1,2,3,4-tetrahydroisoquinoline;
4-(6-fluoro-benzo[b]thiophen-2-yl)-2-methyl-7-morpholin-4-yl-1,2,3,4-tetrahydroisoquinoline;
4-(7-fluoro-benzo[b]thiophen-2-yl)-2-methyl-7-morpholin-4-yl-1,2,3,4-tetrahydroisoquinoline;
4-benzo[b]thiophen-2-yl-7-(2,6-dimethyl-morpholin-4-yl)-2-methyl-1,2,3,4-tetrahydroisoquinoline;
4-benzo[b]thiophen-2-yl-2-ethyl-7-morpholin-4-yl-1,2,3,4-tetrahydroisoquinoline;
4-benzo[b]thiophen-2-yl-8-fluoro-2-methyl-7-morpholin-4-yl-1,2,3,4-tetrahydroisoquinoline;
4-benzo[b]thiophen-2-yl-8-methoxy-2-methyl-7-morpholin-4-yl-1,2,3,4-tetrahydroisoquinoline;
4-benzo[b]thiophen-2-yl-2-methyl-7-morpholin-4-yl-1,2,3,4-tetrahydroisoquinolin-8-ol;
4-benzo[b]thiophen-2-yl-2,8-dimethyl-7-morpholin-4-yl-1,2,3,4-tetrahydroisoquinoline;
4-benzo[b]thiophen-2-yl-2-ethyl-8-fluoro-7-morpholin-4-yl-1,2,3,4-tetrahydroisoquinoline;
4-benzo[b]thiophen-2-yl-6-fluoro-2-methyl-7-morpholin-4-yl-1,2,3,4-tetrahydroisoquinoline;
4-benzo[b]thiophen-2-yl-5-fluoro-2-methyl-7-morpholin-4-yl-1,2,3,4-tetrahydroisoquinoline;
4-benzo[b]thiophen-2-yl-2-methyl-7-morpholin-4-yl-1,2,3,4-tetrahydroisoquinolin-4-ol;
4-benzo[b]thiophen-2-yl-2,4-dimethyl-7-morpholin-4-yl-1,2,3,4-tetrahydroisoquinoline;
4-benzo[b]thiophen-2-yl-2-methyl-7-piperazin-1-yl-1,2,3,4-tetrahydroisoquinoline;
4-benzo[b]thiophen-2-yl-2-methyl-7-(4-methyl-piperazin-1-yl)-1,2,3,4-tetrahydroisoquinoline;
4-(benzo[b]thiophen-2-yl)-2-methyl-7-(piperidin-1-yl)-1,2,3,4-tetrahydroisoquinoline;
4-(benzo[b]thiophen-2-yl)-2-methyl-7-(pyrrolidin-1-yl)-1,2,3,4-tetrahydroisoquinoline;
4-benzo[b]thiophen-2-yl-2-methyl-7-morpholin-4-ylmethyl-1,2,3,4-tetrahydroisoquinoline;
4-benzo[b]thiophen-2-yl-2-methyl-7-(1-methyl-1-morpholin-4-yl-ethyl)-1,2,3,4-tetrahydroisoquinoline
4-benzo[b]thiophen-2-yl-2-methyl-7-(1-morpholin-4-yl-cyclopropyl)-1,2,3,4-tetrahydroisoquinoline;
4-benzo[b]thiophen-2-yl-2-methyl-7-piperidin-1-ylmethyl-1,2,3,4-tetrahydroisoquinoline;
4-(benzo[b]thiophen-2-yl)-2-methyl-7-pyrrolidin-1-ylmethyl-1,2,3,4-tetrahydroisoquinoline;
(4-benzo[b]thiophen-2-yl-2-methyl-1,2,3,4-tetrahydroisoquinolin-7-ylmethyl)-dimethylamine;
[1-(4-benzo[b]thiophen-2-yl-2-methyl-1,2,3,4-tetrahydroisoquinolin-7-yl)-1-methylethyl]-dimethylamine;
[1-(4-benzo[b]thiophen-2-yl-2-methyl-1,2,3,4-tetrahydroisoquinolin-7-yl)-cyclopropyl]-dimethylamine;
(4-benzo[b]thiophen-2-yl-2-methyl-1,2,3,4-tetrahydroisoquinolin-7-ylmethyl)-methylamine;
[1-(4-benzo[b]thiophen-2-yl-2-methyl-1,2,3,4-tetrahydroisoquinolin-7-yl)-1-methylethyl]-methylamine;
[1-(4-benzo[b]thiophen-2-yl-2-methyl-1,2,3,4-tetrahydroisoquinolin-7-yl)-cyclopropyl]-methylamine;
C-(4-benzo[b]thiophen-2-yl-2-methyl-1,2,3,4-tetrahydroisoquinolin-7-yl)-methylamine;
1-(4-benzo[b]thiophen-2-yl-2-methyl-1,2,3,4-tetrahydroisoquinolin-7-yl)-1-methyl-ethylamine;
1-(4-benzo[b]thiophen-2-yl-2-methyl-1,2,3,4-tetrahydroisoquinolin-7-yl)-cyclopropylamine;
1-(4-benzo[b]thiophen-2-yl-2-methyl-1,2,3,4-tetrahydroisoquinolin-7-yl)-1H-pyridin-2-one;
4-(benzo[b]thiophen-2-yl)-7-methanesulfonyl-2-methyl-1,2,3,4-tetrahydroisoquinoline;
4-benzo[b]thiophen-2-yl-2-methyl-1,2,3,4-tetrahydroisoquinoline-7-carbonitrile;
4-(benzo[b]thiophen-2-yl)-2,8-dimethyl-1,2,3,4-tetrahydroisoquinoline;
4-(benzo[b]thiophen-3-yl)-2-methyl-1,2,3,4-tetrahydroisoquinoline;
4-(benzo[b]thiophen-3-yl)-2-methyl-7-(morpholin-4-yl)-1,2,3,4-tetrahydroisoquinoline;
4-(benzo[b]thiophen-3-yl)-2-methyl-7-(pyridazin-3-yl)-1,2,3,4-tetrahydroisoquinoline;
4-(benzo[b]thiophen-4-yl)-2-methyl-1,2,3,4-tetrahydroisoquinoline;
4-(benzo[b]thiophen-4-yl)-2-methyl-7-(morpholin-4-yl)-1,2,3,4-tetrahydroisoquinoline;
4-(benzo[b]thiophen-4-yl)-2-methyl-7-(pyridazin-3-yl)-1,2,3,4-tetrahydroisoquinoline;
4-(benzo[b]thiophen-5-yl)-1,2,3,4-tetrahydroisoquinoline;
4-(benzo[b]thiophen-5-yl)-1-methyl-1,2,3,4-tetrahydroisoquinoline;
4-(benzo[b]thiophen-5-yl)-2-methyl-1,2,3,4-tetrahydroisoquinoline;
4-benzo[b]thiophen-5-yl-8-fluoro-2-methyl-1,2,3,4-tetrahydroisoquinoline;
4-benzo[b]thiophen-5-yl-8-methoxy-2-methyl-1,2,3,4-tetrahydroisoquinoline;
4-(benzo[b]thiophen-5-yl)-2-ethyl-1,2,3,4-tetrahydroisoquinoline;
4-(benzo[b]thiophen-5-yl)-1,2-dimethyl-1,2,3,4-tetrahydroisoquinoline;
4-(2-methyl-benzo[b]thiophen-5-yl)-2-methyl-1,2,3,4-tetrahydroisoquinoline;
4-(2-chlorobenzo[b]thiophen-5-yl)-2-methyl-7-(pyridazin-3-yl)-1,2,3,4-tetrahydroisoquinoline;
4-(2-chlorobenzo[b]thiophen-5-yl)-2-methyl-7-(pyrimidin-2-yl)-1,2,3,4-tetrahydroisoquinoline;
4-(2-chlorobenzo[b]thiophen-5-yl)-2-methyl-7-(pyrimidin-4-yl)-1,2,3,4-tetrahydroisoquinoline;
4-(2-chlorobenzo[b]thiophen-5-yl)-2-methyl-7-(pyrimidin-5-yl)-1,2,3,4-tetrahydroisoquinoline;
4-(2-chlorobenzo[b]thiophen-5-yl)-2-methyl-7-(pyrazin-2-yl)-1,2,3,4-tetrahydroisoquinoline;
4-(2-chlorobenzo[b]thiophen-5-yl)-2-methyl-7-(morpholin-4-yl)-1,2,3,4-tetrahydroisoquinoline;
2-methyl-7-pyridazin-3-yl-4-(3-trifluoromethyl-benzo[b]thiophen-5-yl)-1,2,3,4-tetrahydroisoquinoline;
2-methyl-7-pyrimidin-2-yl-4-(3-trifluoromethyl-benzo[b]thiophen-5-yl)-1,2,3,4-tetrahydroisoquinoline;
2-methyl-7-pyrimidin-4-yl-4-(3-trifluoromethyl-benzo[b]thiophen-5-yl)-1,2,3,4-tetrahydroisoquinoline;
2-methyl-7-pyrimidin-5-yl-4-(3-trifluoromethyl-benzo[b]thiophen-5-yl)-1,2,3,4-tetrahydroisoquinoline;
2-methyl-7-pyrazin-2-yl-4-(3-trifluoromethyl-benzo[b]thiophen-5-yl)-1,2,3,4-tetrahydroisoquinoline;
2-methyl-7-morpholin-4-yl-4-(3-trifluoromethyl-benzo[b]thiophen-5-yl)-1,2,3,4-tetrahydroisoquinoline;

5-(2-methyl-1,2,3,4-tetrahydroisoquinolin-4-yl)-benzo[b]thiophene-4-carbonitrile;
4-(4-methoxybenzo[b]thiophen-5-yl)-2-methyl-1,2,3,4-tetrahydroisoquinoline;
4-(4-methoxybenzo[b]thiophen-5-yl)-2-methyl-7-(pyridazin-3-yl)-1,2,3,4-tetrahydroisoquinoline;
2-ethyl-4-(4-methoxybenzo[b]thiophen-5-yl)-7-(pyridazin-3-yl)-1,2,3,4-tetrahydroisoquinoline;
8-fluoro-4-(4-methoxybenzo[b]thiophen-5-yl)-2-methyl-7-(pyridazin-3-yl)-1,2,3,4-tetrahydroisoquinoline;
2-ethyl-8-fluoro-4-(4-methoxybenzo[b]thiophen-5-yl)-7-(pyridazin-3-yl)-1,2,3,4-tetrahydroisoquinoline;
4-(4-methoxybenzo[b]thiophen-5-yl)-2-methyl-7-(6-methyl-pyridazin-3-yl)-1,2,3,4-tetrahydroisoquinoline;
4-(4-methoxybenzo[b]thiophen-5-yl)-2-methyl-7-(pyrimidin-2-yl)-1,2,3,4-tetrahydroisoquinoline;
4-(4-methoxybenzo[b]thiophen-5-yl)-2-methyl-7-(pyrimidin-4-yl)-1,2,3,4-tetrahydroisoquinoline;
4-(4-methoxybenzo[b]thiophen-5-yl)-2-methyl-7-(pyrimidin-5-yl)-1,2,3,4-tetrahydroisoquinoline;
4-(4-methoxybenzo[b]thiophen-5-yl)-2-methyl-7-(pyrazin-2-yl)-1,2,3,4-tetrahydroisoquinoline;
4-(4-methoxybenzo[b]thiophen-5-yl)-2-methyl-7-(morpholin-4-yl)-1,2,3,4-tetrahydroisoquinoline;
4-(4-methoxy-benzo[b]thiophen-5-yl)-2-methyl-1,2,3,4-tetrahydroisoquinolin-5-ol;
4-(4-methoxy-benzo[b]thiophen-5-yl)-2-methyl-1,2,3,4-tetrahydroisoquinolin-7-ol;
5-(2-methyl-1,2,3,4-tetrahydroisoquinolin-4-yl)-benzo[b]thiophen-4-ol;
5-(2-ethyl-1,2,3,4-tetrahydroisoquinolin-4-yl)-benzo[b]thiophen-4-ol;
2-ethyl-4-(4-methoxy-benzo[b]thiophen-5-yl)-1,2,3,4-tetrahydroisoquinoline;
4-(1,1-dioxo-1H-1$\lambda^6$-benzo[b]thiophen-5-yl)-2-methyl-1,2,3,4-tetrahydroisoquinoline;
4-benzo[b]thiophen-5-yl-2-methyl-1,2,3,4-tetrahydroisoquinolin-4-ol;
4-benzo[b]thiophen-5-yl-8-methoxy-2-methyl-1,2,3,4-tetrahydroisoquinolin-4-ol;
4-benzo[b]thiophen-5-yl-7-fluoro-2-methyl-1,2,3,4-tetrahydroisoquinolin-4-ol;
4-(benzo[b]thiophen-5-yl)-4-methoxy-2-methyl-1,2,3,4-tetrahydroisoquinoline;
4-(benzo[b]thiophen-5-yl)-2,4-dimethyl-1,2,3,4-tetrahydroisoquinoline;
4-benzo[b]thiophen-5-yl-2-methyl-1,2,3,4-tetrahydroisoquinoline-4-carbonitrile;
4-(benzo[b]thiophen-5-yl)-4-fluoro-2-methyl-1,2,3,4-tetrahydroisoquinoline;
4-(benzo[b]thiophen-5-yl)-4-chloro-2-methyl-1,2,3,4-tetrahydroisoquinoline;
4-benzo[b]thiophen-5-yl-2-methyl-1,2,3,4-tetrahydroisoquinolin-7-ol;
4-(benzo[b]thiophen-5-yl)-7-methoxy-2-methyl-1,2,3,4-tetrahydroisoquinoline;
4-(benzo[b]thiophen-5-yl)-2,7-dimethyl-1,2,3,4-tetrahydroisoquinoline;
4-(benzo[b]thiophen-5-yl)-7-fluoro-2-methyl-1,2,3,4-tetrahydroisoquinoline;
4-(benzo[b]thiophen-5-yl)-2-methyl-7-(pyridazin-3-yl)-1,2,3,4-tetrahydroisoquinoline;
4-benzo[b]thiophen-5-yl-2-ethyl-7-pyridazin-3-yl-1,2,3,4-tetrahydroisoquinoline;
4-benzo[b]thiophen-5-yl-2-methyl-7-(6-methyl-pyridazin-3-yl)-1,2,3,4-tetrahydroisoquinoline;
[6-(4-benzo[b]thiophen-5-yl-2-methyl-1,2,3,4-tetrahydroisoquinolin-7-yl)-pyridazin-3-yl]-dimethylamine;
[6-(4-benzo[b]thiophen-5-yl-2-methyl-1,2,3,4-tetrahydroisoquinolin-7-yl)-pyridazin-3-yl]-methylamine;
6-(4-benzo[b]thiophen-5-yl-2-methyl-1,2,3,4-tetrahydroisoquinolin-7-yl)-pyridazin-3-ylamine;
4-benzo[b]thiophen-5-yl-2-methyl-7-(6-morpholin-4-yl-pyridazin-3-yl)-1,2,3,4-tetrahydroisoquinoline;
4-benzo[b]thiophen-5-yl-2-methyl-7-(6-trifluoromethyl-pyridazin-3-yl)-1,2,3,4-tetrahydroisoquinoline;
6-(4-benzo[b]thiophen-5-yl-2-methyl-1,2,3,4-tetrahydroisoquinolin-7-yl)-pyridazine-3-carbonitrile;
4-benzo[b]thiophen-5-yl-8-fluoro-2-methyl-7-pyridazin-3-yl-1,2,3,4-tetrahydroisoquinoline;
4-benzo[b]thiophen-5-yl-8-methoxy-2-methyl-7-pyridazin-3-yl-1,2,3,4-tetrahydroisoquinoline;
4-benzo[b]thiophen-5-yl-2-methyl-7-pyridazin-3-yl-1,2,3,4-tetrahydroisoquinolin-8-ol;
4-benzo[b]thiophen-5-yl-2,8-dimethyl-7-pyridazin-3-yl-1,2,3,4-tetrahydroisoquinoline;
4-benzo[b]thiophen-5-yl-2-ethyl-8-fluoro-7-pyridazin-3-yl-1,2,3,4-tetrahydroisoquinoline;
4-benzo[b]thiophen-5-yl-6-fluoro-2-methyl-7-pyridazin-3-yl-1,2,3,4-tetrahydroisoquinoline;
4-benzo[b]thiophen-5-yl-5-fluoro-2-methyl-7-pyridazin-3-yl-1,2,3,4-tetrahydroisoquinoline;
4-benzo[b]thiophen-5-yl-2-methyl-7-pyridazin-3-yl-1,2,3,4-tetrahydroisoquinolin-4-ol;
4-benzo[b]thiophen-5-yl-2,4-dimethyl-7-pyridazin-3-yl-1,2,3,4-tetrahydroisoquinoline;
4-(benzo[b]thiophen-5-yl)-2-methyl-7-(pyridazin-4-yl)-1,2,3,4-tetrahydroisoquinoline;
4-(benzo[b]thiophen-5-yl)-8-fluoro-2-methyl-7-(pyridazin-4-yl)-1,2,3,4-tetrahydroisoquinoline;
4-(benzo[b]thiophen-5-yl)-2-methyl-7-(pyrazin-2-yl)-1,2,3,4-tetrahydroisoquinoline;
4-benzo[b]thiophen-5-yl-2-methyl-7-(3-methyl-pyrazin-2-yl)-1,2,3,4-tetrahydroisoquinoline;
4-benzo[b]thiophen-5-yl-7-(3-methoxy-pyrazin-2-yl)-2-methyl-1,2,3,4-tetrahydroisoquinoline;
4-benzo[b]thiophen-5-yl-2-methyl-7-(6-methyl-pyrazin-2-yl)-1,2,3,4-tetrahydroisoquinoline;
4-benzo[b]thiophen-5-yl-7-(6-methoxy-pyrazin-2-yl)-2-methyl-1,2,3,4-tetrahydroisoquinoline;
4-benzo[b]thiophen-5-yl-8-fluoro-2-methyl-7-pyrazin-2-yl-1,2,3,4-tetrahydroisoquinoline;
4-benzo[b]thiophen-5-yl-8-methoxy-2-methyl-7-pyrazin-2-yl-1,2,3,4-tetrahydroisoquinoline;
4-benzo[b]thiophen-5-yl-2-methyl-7-pyrazin-2-yl-1,2,3,4-tetrahydroisoquinolin-8-ol;
4-benzo[b]thiophen-5-yl-2,8-dimethyl-7-pyrazin-2-yl-1,2,3,4-tetrahydroisoquinoline;
4-(benzo[b]thiophen-5-yl)-2-methyl-7-(pyrimidin-2-yl)-1,2,3,4-tetrahydroisoquinoline;
4-benzo[b]thiophen-5-yl-8-fluoro-2-methyl-7-pyrimidin-2-yl-1,2,3,4-tetrahydroisoquinoline;
4-benzo[b]thiophen-5-yl-8-methoxy-2-methyl-7-pyrimidin-2-yl-1,2,3,4-tetrahydroisoquinoline;
4-benzo[b]thiophen-5-yl-2-methyl-7-pyrimidin-2-yl-1,2,3,4-tetrahydroisoquinolin-8-ol;
4-benzo[b]thiophen-5-yl-2,8-dimethyl-7-pyrimidin-2-yl-1,2,3,4-tetrahydroisoquinoline;
4-(benzo[b]thiophen-5-yl)-2-methyl-7-(pyrimidin-4-yl)-1,2,3,4-tetrahydroisoquinoline;
4-(benzo[b]thiophen-5-yl)-8-fluoro-2-methyl-7-(pyrimidin-4-yl)-1,2,3,4-tetrahydroisoquinoline;

4-(benzo[b]thiophen-5-yl)-8-methoxy-2-methyl-7-(pyrimidin-4-yl)-1,2,3,4-tetrahydroisoquinoline;
4-benzo[b]thiophen-5-yl-2-methyl-7-(pyrimidin-4-yl)-1,2,3,4-tetrahydroisoquinolin-8-ol;
4-(benzo[b]thiophen-5-yl)-2,8-dimethyl-7-(pyrimidin-4-yl)-1,2,3,4-tetrahydroisoquinoline;
4-(benzo[b]thiophen-5-yl)-2-methyl-7-(pyrimidin-5-yl)-1,2,3,4-tetrahydroisoquinoline;
4-(benzo[b]thiophen-5-yl)-8-fluoro-2-methyl-7-(pyrimidin-5-yl)-1,2,3,4-tetrahydroisoquinoline;
4-(benzo[b]thiophen-5-yl)-8-methoxy-2-methyl-7-(pyrimidin-5-yl)-1,2,3,4-tetrahydroisoquinoline;
4-benzo[b]thiophen-5-yl-2-methyl-7-(pyrimidin-5-yl)-1,2,3,4-tetrahydroisoquinolin-8-ol;
4-(benzo[b]thiophen-5-yl)-2,8-dimethyl-7-(pyrimidin-5-yl)-1,2,3,4-tetrahydroisoquinoline;
4-(benzo[b]thiophen-5-yl)-7-(3,5-dimethyl-isoxazol-4-yl)-2-methyl-1,2,3,4-tetrahydroisoquinoline;
4-(benzo[b]thiophen-5-yl)-2-methyl-7-(thiazol-2-yl)-1,2,3,4-tetrahydroisoquinoline;
4-(benzo[b]thiophen-5-yl)-2-methyl-7-(5-methyl-thiazol-2-yl)-1,2,3,4-tetrahydroisoquinoline;
4-benzo[b]thiophen-5-yl-2-methyl-7-[1,3,5]triazin-2-yl-1,2,3,4-tetrahydroisoquinoline;
4-benzo[b]thiophen-5-yl-2-methyl-7-[1,2,4]triazin-3-yl-1,2,3,4-tetrahydroisoquinoline;
4-benzo[b]thiophen-5-yl-2-methyl-7-[1,2,4]triazin-5-yl-1,2,3,4-tetrahydroisoquinoline;
4-benzo[b]thiophen-5-yl-2-methyl-7-[1,2,4]triazin-6-yl-1,2,3,4-tetrahydroisoquinoline;
3-(4-benzo[b]thiophen-5-yl-2-methyl-1,2,3,4-tetrahydroisoquinolin-7-yl)-cinnoline;
1-(4-benzo[b]thiophen-5-yl-2-methyl-1,2,3,4-tetrahydroisoquinolin-7-yl)-phthalazine;
2-(4-benzo[b]thiophen-5-yl-2-methyl-1,2,3,4-tetrahydroisoquinolin-7-yl)-quinoxaline;
2-(4-benzo[b]thiophen-5-yl-2-methyl-1,2,3,4-tetrahydroisoquinolin-7-yl)-quinazoline;
6-(4-benzo[b]thiophen-5-yl-2-methyl-1,2,3,4-tetrahydroisoquinolin-7-yl)-quinazoline;
7-(4-benzo[b]thiophen-5-yl-2-methyl-1,2,3,4-tetrahydroisoquinolin-7-yl)-quinazoline;
2-(4-benzo[b]thiophen-5-yl-2-methyl-1,2,3,4-tetrahydroisoquinolin-7-yl)-2H-[1,2,4]triazolo[4,3-a]pyridin-3-one;
4-(benzo[b]thiophen-5-yl)-2-methyl-7-(morpholin-4-yl)-1,2,3,4-tetrahydroisoquinoline;
4-benzo[b]thiophen-5-yl-7-(2,6-dimethyl-morpholin-4-yl)-2-methyl-1,2,3,4-tetrahydroisoquinoline;
4-benzo[b]thiophen-5-yl-2-ethyl-7-morpholin-4-yl-1,2,3,4-tetrahydroisoquinoline;
4-benzo[b]thiophen-5-yl-8-fluoro-2-methyl-7-morpholin-4-yl-1,2,3,4-tetrahydroisoquinoline;
4-benzo[b]thiophen-5-yl-8-methoxy-2-methyl-7-morpholin-4-yl-1,2,3,4-tetrahydroisoquinoline;
4-benzo[b]thiophen-5-yl-2-methyl-7-morpholin-4-yl-1,2,3,4-tetrahydroisoquinolin-8-ol;
4-benzo[b]thiophen-5-yl-2,8-dimethyl-7-morpholin-4-yl-1,2,3,4-tetrahydroisoquinoline;
4-benzo[b]thiophen-5-yl-2-ethyl-8-fluoro-7-morpholin-4-yl-1,2,3,4-tetrahydroisoquinoline;
4-benzo[b]thiophen-5-yl-6-fluoro-2-methyl-7-morpholin-4-yl-1,2,3,4-tetrahydroisoquinoline;
4-benzo[b]thiophen-5-yl-5-fluoro-2-methyl-7-morpholin-4-yl-1,2,3,4-tetrahydroisoquinoline;
4-benzo[b]thiophen-5-yl-2-methyl-7-morpholin-4-yl-1,2,3,4-tetrahydroisoquinolin-4-ol;
4-benzo[b]thiophen-5-yl-2,4-dimethyl-7-morpholin-4-yl-1,2,3,4-tetrahydroisoquinoline;
4-benzo[b]thiophen-5-yl-2-methyl-7-piperazin-1-yl-1,2,3,4-tetrahydroisoquinoline;
4-benzo[b]thiophen-5-yl-2-methyl-7-(4-methyl-piperazin-1-yl)-1,2,3,4-tetrahydroisoquinoline;
4-(benzo[b]thiophen-5-yl)-2-methyl-7-(piperidin-1-yl)-1,2,3,4-tetrahydroisoquinoline;
4-(benzo[b]thiophen-5-yl)-2-methyl-7-(pyrrolidin-1-yl)-1,2,3,4-tetrahydroisoquinoline;
4-(benzo[b]thiophen-5-yl)-2-methyl-7-(morpholin-4-yl)methyl-1,2,3,4-tetrahydroisoquinoline;
4-benzo[b]thiophen-5-yl-2-methyl-7-(1-methyl-1-morpholin-4-yl-ethyl)-1,2,3,4-tetrahydroisoquinoline;
4-benzo[b]thiophen-5-yl-2-methyl-7-(1-morpholin-4-yl-cyclopropyl)-1,2,3,4-tetrahydroisoquinoline;
4-(benzo[b]thiophen-5-yl)-2-methyl-7-(piperidin-1-yl)methyl-1,2,3,4-tetrahydroisoquinoline;
4-(benzo[b]thiophen-5-yl)-2-methyl-7-(pyrrolidin-1-yl)methyl-1,2,3,4-tetrahydroisoquinoline;
(4-benzo[b]thiophen-5-yl-2-methyl-1,2,3,4-tetrahydroisoquinolin-7-ylmethyl)-dimethylamine;
[1-(4-benzo[b]thiophen-5-yl-2-methyl-1,2,3,4-tetrahydroisoquinolin-7-yl)-1-methyl-ethyl]-dimethylamine;
[1-(4-benzo[b]thiophen-5-yl-2-methyl-1,2,3,4-tetrahydroisoquinolin-7-yl)-cyclopropyl]-dimethylamine;
(4-benzo[b]thiophen-5-yl-2-methyl-1,2,3,4-tetrahydroisoquinolin-7-ylmethyl)-methylamine;
[1-(4-benzo[b]thiophen-5-yl-2-methyl-1,2,3,4-tetrahydroisoquinolin-7-yl)-1-methyl-ethyl]-methylamine;
[1-(4-benzo[b]thiophen-5-yl-2-methyl-1,2,3,4-tetrahydroisoquinolin-7-yl)-cyclopropyl]-methylamine;
C-(4-benzo[b]thiophen-5-yl-2-methyl-1,2,3,4-tetrahydroisoquinolin-7-yl)methylamine;
1-(4-benzo[b]thiophen-5-yl-2-methyl-1,2,3,4-tetrahydroisoquinolin-7-yl)-1-methyl-ethylamine;
1-(4-benzo[b]thiophen-5-yl-2-methyl-1,2,3,4-tetrahydroisoquinolin-7-yl)-cyclopropylamine;
1-(4-benzo[b]thiophen-5-yl-2-methyl-1,2,3,4-tetrahydroisoquinolin-7-yl)-1H-pyridin-2-one;
4-(benzo[b]thiophen-5-yl)-7-methanesulfonyl-2-methyl-1,2,3,4-tetrahydroisoquinoline;
4-benzo[b]thiophen-5-yl-2-methyl-1,2,3,4-tetrahydroisoquinoline-7-carbonitrile;
4-benzo[b]thiophen-5-yl-8-fluoro-2-methyl-1,2,3,4-tetrahydroisoquinoline-7-carbonitrile;
4-(benzo[b]thiophen-5-yl)-2,8-dimethyl-1,2,3,4-tetrahydroisoquinoline;
4-(benzo[b]thiophen-6-yl)-1,2,3,4-tetrahydroisoquinoline;
4-(benzo[b]thiophen-6-yl)-1-methyl-1,2,3,4-tetrahydroisoquinoline;
4-(benzo[b]thiophen-6-yl)-2-methyl-1,2,3,4-tetrahydroisoquinoline;
4-(benzo[b]thiophen-6-yl)-8-fluoro-2-methyl-1,2,3,4-tetrahydroisoquinoline;
4-(benzo[b]thiophen-6-yl)-2-ethyl-1,2,3,4-tetrahydroisoquinoline;
4-(benzo[b]thiophen-6-yl)-1,2-dimethyl-1,2,3,4-tetrahydroisoquinoline;
2-methyl-4-(2-methyl-benzo[b]thiophen-6-yl)-1,2,3,4-tetrahydroisoquinoline;
4-(1,1-dioxo-1H-1$\lambda^6$-benzo[b]thiophen-6-yl)-2-methyl-1,2,3,4-tetrahydroisoquinoline;
4-benzo[b]thiophen-6-yl-2-methyl-1,2,3,4-tetrahydroisoquinolin-4-ol;
4-(benzo[b]thiophen-6-yl)-4-methoxy-2-methyl-1,2,3,4-tetrahydroisoquinoline;

4-(benzo[b]thiophen-6-yl)-2,4-dimethyl-1,2,3,4-tetrahydroisoquinoline;
4-benzo[b]thiophen-6-yl-2-methyl-1,2,3,4-tetrahydroisoquinoline-4-carbonitrile;
4-(benzo[b]thiophen-6-yl)-4-fluoro-2-methyl-1,2,3,4-tetrahydroisoquinoline;
4-benzo[b]thiophen-6-yl-4-chloro-2-methyl-1,2,3,4-tetrahydroisoquinoline;
4-(2-chloro-benzo[b]thiophen-6-yl)-2-methyl-7-(pyridazin-3-yl)-1,2,3,4-tetrahydroisoquinoline;
4-(2-chloro-benzo[b]thiophen-6-yl)-2-methyl-7-(pyrimidin-2-yl)-1,2,3,4-tetrahydroisoquinoline;
4-(2-chloro-benzo[b]thiophen-6-yl)-2-methyl-7-(pyrimidin-4-yl)-1,2,3,4-tetrahydroisoquinoline;
4-(2-chloro-benzo[b]thiophen-6-yl)-2-methyl-7-(pyrimidin-5-yl)-1,2,3,4-tetrahydroisoquinoline;
4-(2-chloro-benzo[b]thiophen-6-yl)-2-methyl-7-(pyrazin-2-yl)-1,2,3,4-tetrahydroisoquinoline;
4-(2-chloro-benzo[b]thiophen-6-yl)-2-methyl-7-(morpholin-4-yl)-1,2,3,4-tetrahydroisoquinoline;
2-methyl-7-pyridazin-3-yl-4-(3-trifluoromethyl-benzo[b]thiophen-6-yl)-1,2,3,4-tetrahydroisoquinoline;
2-methyl-7-pyrimidin-2-yl-4-(3-trifluoromethyl-benzo[b]thiophen-6-yl)-1,2,3,4-tetrahydroisoquinoline;
2-methyl-7-pyrimidin-4-yl-4-(3-trifluoromethyl-benzo[b]thiophen-6-yl)-1,2,3,4-tetrahydroisoquinoline;
2-methyl-7-pyrimidin-5-yl-4-(3-trifluoromethyl-benzo[b]thiophen-6-yl)-1,2,3,4-tetrahydroisoquinoline;
2-methyl-7-pyrazin-2-yl-4-(3-trifluoromethyl-benzo[b]thiophen-6-yl)-1,2,3,4-tetrahydroisoquinoline;
2-methyl-7-morpholin-4-yl-4-(3-trifluoromethyl-benzo[b]thiophen-6-yl)-1,2,3,4-tetrahydroisoquinoline;
4-(7-methoxybenzo[b]thiophen-6-yl)-2-methyl-1,2,3,4-tetrahydroisoquinoline;
4-(7-methoxybenzo[b]thiophen-6-yl)-2-methyl-7-(pyridazin-3-yl)-1,2,3,4-tetrahydroisoquinoline;
2-ethyl-4-(7-methoxybenzo[b]thiophen-6-yl)-7-(pyridazin-3-yl)-1,2,3,4-tetrahydroisoquinoline;
8-fluoro-4-(7-methoxybenzo[b]thiophen-6-yl)-2-methyl-7-(pyridazin-3-yl)-1,2,3,4-tetrahydroisoquinoline;
2-ethyl-8-fluoro-4-(7-methoxybenzo[b]thiophen-6-yl)-7-(pyridazin-3-yl)-1,2,3,4-tetrahydroisoquinoline;
4-(7-methoxybenzo[b]thiophen-6-yl)-2-methyl-7-(6-methyl-pyridazin-3-yl)-1,2,3,4-tetrahydroisoquinoline;
4-(7-methoxybenzo[b]thiophen-6-yl)-2-methyl-7-(pyrimidin-2-yl)-1,2,3,4-tetrahydroisoquinoline;
4-(7-methoxybenzo[b]thiophen-6-yl)-2-methyl-7-(pyrimidin-4-yl)-1,2,3,4-tetrahydroisoquinoline;
4-(7-methoxybenzo[b]thiophen-6-yl)-2-methyl-7-(pyrimidin-5-yl)-1,2,3,4-tetrahydroisoquinoline;
4-(7-methoxybenzo[b]thiophen-6-yl)-2-methyl-7-(pyrazin-2-yl)-1,2,3,4-tetrahydroisoquinoline;
4-(7-methoxybenzo[b]thiophen-6-yl)-2-methyl-7-(morpholin-4-yl)-1,2,3,4-tetrahydroisoquinoline;
4-(7-methoxy-benzo[b]thiophen-6-yl)-2-methyl-1,2,3,4-tetrahydroisoquinoline-7-ol;
4-benzo[b]thiophen-6-yl-2-methyl-1,2,3,4-tetrahydroisoquinolin-7-ol;
(benzo[b]thiophen-6-yl)-7-methoxy-2-methyl-1,2,3,4-tetrahydroisoquinoline;
4-(benzo[b]thiophen-6-yl)-2,7-dimethyl-1,2,3,4-tetrahydroisoquinoline;
4-(benzo[b]thiophen-6-yl)-7-fluoro-2-methyl-1,2,3,4-tetrahydroisoquinoline;
4-(benzo[b]thiophen-6-yl)-2-methyl-7-(pyridazin-3-yl)-1,2,3,4-tetrahydroisoquinoline;
4-benzo[b]thiophen-6-yl-2-ethyl-7-pyridazin-3-yl-1,2,3,4-tetrahydroisoquinoline;
4-benzo[b]thiophen-6-yl-2-methyl-7-(6-methyl-pyridazin-3-yl)-1,2,3,4-tetrahydroisoquinoline;
[6-(4-benzo[b]thiophen-6-yl-2-methyl-1,2,3,4-tetrahydroisoquinolin-7-yl)-pyridazin-3-yl]-dimethylamine;
[6-(4-benzo[b]thiophen-6-yl-2-methyl-1,2,3,4-tetrahydroisoquinolin-7-yl)-pyridazin-3-yl]-methylamine;
6-(4-benzo[b]thiophen-6-yl-2-methyl-1,2,3,4-tetrahydroisoquinolin-7-yl)-pyridazin-3-ylamine;
4-benzo[b]thiophen-6-yl-2-methyl-7-(6-morpholin-4-yl-pyridazin-3-yl)-1,2,3,4-tetrahydroisoquinoline;
4-benzo[b]thiophen-6-yl-2-methyl-7-(6-trifluoromethyl-pyridazin-3-yl)-1,2,3,4-tetrahydroisoquinoline;
6-(4-benzo[b]thiophen-6-yl-2-methyl-1,2,3,4-tetrahydroisoquinolin-7-yl)-pyridazine-3-carbonitrile;
4-benzo[b]thiophen-6-yl-8-fluoro-2-methyl-7-pyridazin-3-yl-1,2,3,4-tetrahydroisoquinoline;
4-benzo[b]thiophen-6-yl-8-methoxy-2-methyl-7-pyridazin-3-yl-1,2,3,4-tetrahydroisoquinoline;
4-benzo[b]thiophen-6-yl-2-methyl-7-pyridazin-3-yl-1,2,3,4-tetrahydroisoquinolin-8-ol;
4-benzo[b]thiophen-6-yl-2,8-dimethyl-7-pyridazin-3-yl-1,2,3,4-tetrahydroisoquinoline;
4-benzo[b]thiophen-6-yl-2-ethyl-8-fluoro-7-pyridazin-3-yl-1,2,3,4-tetrahydroisoquinoline;
4-benzo[b]thiophen-6-yl-6-fluoro-2-methyl-7-pyridazin-3-yl-1,2,3,4-tetrahydroisoquinoline;
4-benzo[b]thiophen-6-yl-5-fluoro-2-methyl-7-pyridazin-3-yl-1,2,3,4-tetrahydroisoquinoline;
4-benzo[b]thiophen-6-yl-2-methyl-7-pyridazin-3-yl-1,2,3,4-tetrahydroisoquinolin-4-ol;
4-benzo[b]thiophen-6-yl-2,4-dimethyl-7-pyridazin-3-yl-1,2,3,4-tetrahydroisoquinoline;
4-(benzo[b]thiophen-6-yl)-2-methyl-7-(pyridazin-4-yl)-1,2,3,4-tetrahydroisoquinoline;
4-(benzo[b]thiophen-6-yl)-8-fluoro-2-methyl-7-(pyridazin-4-yl)-1,2,3,4-tetrahydroisoquinoline;
4-(benzo[b]thiophen-6-yl)-2-methyl-7-(pyrazin-2-yl)-1,2,3,4-tetrahydroisoquinoline;
4-benzo[b]thiophen-6-yl-2-methyl-7-(3-methyl-pyrazin-2-yl)-1,2,3,4-tetrahydroisoquinoline;
4-benzo[b]thiophen-6-yl-7-(3-methoxy-pyrazin-2-yl)-2-methyl-1,2,3,4-tetrahydroisoquinoline;
4-benzo[b]thiophen-6-yl-2-methyl-7-(6-methyl-pyrazin-2-yl)-1,2,3,4-tetrahydroisoquinoline;
4-benzo[b]thiophen-6-yl-7-(6-methoxy-pyrazin-2-yl)-2-methyl-1,2,3,4-tetrahydroisoquinoline;
4-benzo[b]thiophen-6-yl-8-fluoro-2-methyl-7-pyrazin-2-yl-1,2,3,4-tetrahydroisoquinoline;
4-Benzo[b]thiophen-6-yl-8-methoxy-2-methyl-7-pyrazin-2-yl-1,2,3,4-tetrahydroisoquinoline;
4-benzo[b]thiophen-6-yl-2-methyl-7-pyrazin-2-yl-1,2,3,4-tetrahydroisoquinolin-8-ol;
4-benzo[b]thiophen-6-yl-2,8-dimethyl-7-pyrazin-2-yl-1,2,3,4-tetrahydroisoquinoline;
4-(benzo[b]thiophen-6-yl)-2-methyl-7-(pyrimidin-2-yl)-1,2,3,4-tetrahydroisoquinoline;
4-benzo[b]thiophen-6-yl-8-fluoro-2-methyl-7-pyrimidin-2-yl-1,2,3,4-tetrahydroisoquinoline;
4-benzo[b]thiophen-6-yl-8-methoxy-2-methyl-7-pyrimidin-2-yl-1,2,3,4-tetrahydroisoquinoline;
4-benzo[b]thiophen-6-yl-2-methyl-7-pyrimidin-2-yl-1,2,3,4-tetrahydroisoquinolin-8-ol;
4-benzo[b]thiophen-6-yl-2,8-dimethyl-7-pyrimidin-2-yl-1,2,3,4-tetrahydroisoquinoline;

4-(benzo[b]thiophen-6-yl)-2-methyl-7-(pyrimidin-4-yl)-1,2,3,4-tetrahydroisoquinoline;
4-(benzo[b]thiophen-6-yl)-8-fluoro-2-methyl-7-(pyrimidin-4-yl)-1,2,3,4-tetrahydroisoquinoline;
4-(benzo[b]thiophen-6-yl)-8-methoxy-2-methyl-7-(pyrimidin-4-yl)-1,2,3,4-tetrahydroisoquinoline;
4-benzo[b]thiophen-6-yl-2-methyl-7-(pyrimidin-4-yl)-1,2,3,4-tetrahydroisoquinolin-8-ol;
4-(benzo[b]thiophen-6-yl)-2,8-dimethyl-7-(pyrimidin-4-yl)-1,2,3,4-tetrahydroisoquinoline;
4-(benzo[b]thiophen-6-yl)-2-methyl-7-(pyrimidin-5-yl)-1,2,3,4-tetrahydroisoquinoline;
4-(benzo[b]thiophen-6-yl)-8-fluoro-2-methyl-7-(pyrimidin-5-yl)-1,2,3,4-tetrahydroisoquinoline;
4-(benzo[b]thiophen-6-yl)-8-methoxy-2-methyl-7-(pyrimidin-5-yl)-1,2,3,4-tetrahydroisoquinoline;
4-benzo[b]thiophen-6-yl-2-methyl-7-(pyrimidin-5-yl)-1,2,3,4-tetrahydroisoquinolin-8-ol;
4-(benzo[b]thiophen-6-yl)-2,8-dimethyl-7-(pyrimidin-5-yl)-1,2,3,4-tetrahydroisoquinoline;
4-(benzo[b]thiophen-6-yl)-7-(3,5-dimethyl-isoxazol-4-yl)-2-methyl-1,2,3,4-tetrahydroisoquinoline;
4-(benzo[b]thiophen-6-yl)-2-methyl-7-(thiazol-2-yl)-1,2,3,4-tetrahydroisoquinoline;
4-(benzo[b]thiophen-6-yl)-2-methyl-7-(5-methyl-thiazol-2-yl)-1,2,3,4-tetrahydroisoquinoline;
4-benzo[b]thiophen-6-yl-2-methyl-7-[1,3,5]triazin-2-yl-1,2,3,4-tetrahydroisoquinoline;
4-benzo[b]thiophen-6-yl-2-methyl-7-[1,2,4]triazin-3-yl-1,2,3,4-tetrahydroisoquinoline;
4-benzo[b]thiophen-6-yl-2-methyl-7-[1,2,4]triazin-5-yl-1,2,3,4-tetrahydroisoquinoline;
4-benzo[b]thiophen-6-yl-2-methyl-7-[1,2,4]triazin-6-yl-1,2,3,4-tetrahydroisoquinoline;
3-(4-benzo[b]thiophen-6-yl-2-methyl-1,2,3,4-tetrahydroisoquinolin-7-yl)-cinnoline;
1-(4-benzo[b]thiophen-6-yl-2-methyl-1,2,3,4-tetrahydroisoquinolin-7-yl)-phthalazine;
2-(4-benzo[b]thiophen-6-yl-2-methyl-1,2,3,4-tetrahydroisoquinolin-7-yl)-quinoxaline;
2-(4-benzo[b]thiophen-6-yl-2-methyl-1,2,3,4-tetrahydroisoquinolin-7-yl)-quinazoline;
6-(4-benzo[b]thiophen-6-yl-2-methyl-1,2,3,4-tetrahydroisoquinolin-7-yl)-quinazoline;
7-(4-benzo[b]thiophen-6-yl-2-methyl-1,2,3,4-tetrahydroisoquinolin-7-yl)-quinazoline;
2-(4-benzo[b]thiophen-6-yl-2-methyl-1,2,3,4-tetrahydroisoquinolin-7-yl)-2H-[1,2,4]triazolo[4,3-a]pyridin-3-one;
4-(benzo[b]thiophen-6-yl)-2-methyl-7-(morpholin-4-yl)-1,2,3,4-tetrahydroisoquinoline;
4-benzo[b]thiophen-6-yl-7-(2,6-dimethyl-morpholin-4-yl)-2-methyl-1,2,3,4-tetrahydroisoquinoline;
4-benzo[b]thiophen-6-yl-2-ethyl-7-morpholin-4-yl-1,2,3,4-tetrahydroisoquinoline;
4-benzo[b]thiophen-6-yl-8-fluoro-2-methyl-7-morpholin-4-yl-1,2,3,4-tetrahydroisoquinoline;
4-benzo[b]thiophen-6-yl-8-methoxy-2-methyl-7-morpholin-4-yl-1,2,3,4-tetrahydroisoquinoline;
4-benzo[b]thiophen-6-yl-2-methyl-7-morpholin-4-yl-1,2,3,4-tetrahydroisoquinolin-8-ol;
4-benzo[b]thiophen-6-yl-2,8-dimethyl-7-morpholin-4-yl-1,2,3,4-tetrahydroisoquinoline;
4-benzo[b]thiophen-6-yl-2-ethyl-8-fluoro-7-morpholin-4-yl-1,2,3,4-tetrahydroisoquinoline;
4-benzo[b]thiophen-6-yl-6-fluoro-2-methyl-7-morpholin-4-yl-1,2,3,4-tetrahydroisoquinoline;
4-benzo[b]thiophen-6-yl-5-fluoro-2-methyl-7-morpholin-4-yl-1,2,3,4-tetrahydroisoquinoline;
4-benzo[b]thiophen-6-yl-2-methyl-7-morpholin-4-yl-1,2,3,4-tetrahydroisoquinolin-4-ol;
4-benzo[b]thiophen-6-yl-2,4-dimethyl-7-morpholin-4-yl-1,2,3,4-tetrahydroisoquinoline;
4-benzo[b]thiophen-6-yl-2-methyl-7-piperazin-1-yl-1,2,3,4-tetrahydroisoquinoline;
4-benzo[b]thiophen-6-yl-2-methyl-7-(4-methyl-piperazin-1-yl)-1,2,3,4-tetrahydroisoquinoline;
4-(benzo[b]thiophen-6-yl)-2-methyl-7-(piperidin-1-yl)-1,2,3,4-tetrahydroisoquinoline;
4-(benzo[b]thiophen-6-yl)-2-methyl-7-(pyrrolidin-1-yl)-1,2,3,4-tetrahydroisoquinoline;
4-(benzo[b]thiophen-6-yl)-2-methyl-7-(morpholin-4-yl)methyl-1,2,3,4-tetrahydroisoquinoline;
4-benzo[b]thiophen-6-yl-2-methyl-7-(1-methyl-1-morpholin-4-yl-ethyl)-1,2,3,4-tetrahydroisoquinoline;
4-benzo[b]thiophen-6-yl-2-methyl-7-(1-morpholin-4-yl-cyclopropyl)-1,2,3,4-tetrahydroisoquinoline;
4-(benzo[b]thiophen-6-yl)-2-methyl-7-(piperidin-1-yl)methyl-1,2,3,4-tetrahydroisoquinoline;
4-(benzo[b]thiophen-6-yl)-2-methyl-7-(pyrrolidin-1-yl)methyl-1,2,3,4-tetrahydroisoquinoline;
(4-benzo[b]thiophen-6-yl-2-methyl-1,2,3,4-tetrahydroisoquinolin-7-ylmethyl)-dimethylamine;
[1-(4-benzo[b]thiophen-6-yl-2-methyl-1,2,3,4-tetrahydroisoquinolin-7-yl)-1-methylethyl]-dimethylamine;
[1-(4-benzo[b]thiophen-6-yl-2-methyl-1,2,3,4-tetrahydroisoquinolin-7-yl)-cyclopropyl]-dimethylamine;
(4-benzo[b]thiophen-6-yl-2-methyl-1,2,3,4-tetrahydroisoquinolin-7-ylmethyl)-methylamine;
[1-(4-benzo[b]thiophen-6-yl-2-methyl-1,2,3,4-tetrahydroisoquinolin-7-yl)-1-methylethyl]-methylamine;
[1-(4-benzo[b]thiophen-6-yl-2-methyl-1,2,3,4-tetrahydroisoquinolin-7-yl)-cyclopropyl]-methylamine;
C-(4-benzo[b]thiophen-6-yl-2-methyl-1,2,3,4-tetrahydroisoquinolin-7-yl)-methylamine;
1-(4-benzo[b]thiophen-6-yl-2-methyl-1,2,3,4-tetrahydroisoquinolin-7-yl)-1-methyl-ethylamine;
1-(4-benzo[b]thiophen-6-yl-2-methyl-1,2,3,4-tetrahydroisoquinolin-7-yl)-cyclopropylamine;
1-(4-benzo[b]thiophen-6-yl-2-methyl-1,2,3,4-tetrahydroisoquinolin-7-yl)-1H-pyridin-2-one;
4-(benzo[b]thiophen-6-yl)-7-methanesulfonyl-2-methyl-1,2,3,4-tetrahydroisoquinoline;
4-(benzo[b]thiophen-6-yl)-2-methyl-1,2,3,4-tetrahydroisoquinoline-7-carbonitrile;
4-benzo[b]thiophen-6-yl-8-fluoro-2-methyl-1,2,3,4-tetrahydroisoquinoline-7-carbonitrile;
4-(benzo[b]thiophen-6-yl)-2,8-dimethyl-1,2,3,4-tetrahydroisoquinoline;
4-(benzo[b]thiophen-7-yl)-2-methyl-1,2,3,4-tetrahydroisoquinoline;
4-(benzo[b]thiophen-7-yl)-2-ethyl-1,2,3,4-tetrahydroisoquinoline;
4-(benzo[b]thiophen-7-yl)-8-fluoro-2-methyl-1,2,3,4-tetrahydroisoquinoline;
4-(benzo[b]thiophen-7-yl)-2-ethyl-8-fluoro-1,2,3,4-tetrahydroisoquinoline;
4-(benzo[b]thiophen-7-yl)-2-methyl-7-(pyridazin-3-yl)-1,2,3,4-tetrahydroisoquinoline;

4-(benzo[b]thiophen-7-yl)-2-methyl-7-(morpholin-4-yl)-1,2,3,4-tetrahydroisoquinoline;
4-benzo[b]thiophen-5-yl-2-cyclopropyl-1,2,3,4-tetrahydroisoquinoline;
(4-benzo[b]thiophen-5-yl-3,4-dihydro-1H-isoquinolin-2-yl)-acetonitrile;
[2-(4-benzo[b]thiophen-5-yl-3,4-dihydro-1H-isoquinolin-2-yl)-ethyl]-dimethylamine;
2-(4-benzo[b]thiophen-5-yl-3,4-dihydro-1H-isoquinolin-2-yl)-ethanol;
4-benzo[b]thiophen-5-yl-2-isopropyl-1,2,3,4-tetrahydroisoquinoline;
4-benzo[b]thiophen-5-yl-2-methyl-8-morpholin-4-yl-1,2,3,4-tetrahydroisoquinoline;

or an oxide thereof, a pharmaceutically acceptable salt thereof, a solvate thereof, or a prodrug thereof.

In addition, other specific compounds of the present invention are those with the following substituents:

TABLE B

| X | R¹ | R² | R³ | R⁴ | R⁵ | R⁶ | R⁷ | R⁸ |
|---|----|----|----|----|----|----|----|----|
| benzofuran-2-yl | H | H | H | H | H | H | H | H |
| benzofuran-2-yl | H | Me | H | H | H | H | H | H |
| benzofuran-2-yl | Me | H | H | H | H | H | H | H |
| benzofuran-2-yl | Et | H | H | H | H | H | H | H |
| benzofuran-2-yl | Me | Me | H | H | H | H | H | H |
| 5-chloro-benzofuran-2-yl | Me | H | H | H | H | H | H | H |
| 5-fluoro-benzofuran-2-yl | Me | H | H | H | H | H | H | H |
| 7-fluoro-benzofuran-2-yl | Me | H | H | H | H | H | H | H |
| 5-methoxy-benzofuran-2-yl | Me | H | H | H | H | H | H | H |
| 7-methoxy-benzofuran-2-yl | Me | H | H | H | H | H | H | H |
| 7-methoxy-benzofuran-2-yl | Me | H | H | pyridazin-3-yl | H | H | H | H |
| 7-methoxy-benzofuran-2-yl | Me | H | F | pyridazin-3-yl | H | H | H | H |
| 7-methoxy-benzofuran-2-yl | Me | H | H | morpholin-4-yl | H | H | H | H |
| 7-methoxy-benzofuran-2-yl | Me | H | F | morpholin-4-yl | H | H | H | H |
| benzofuran-2-yl | Me | H | H | H | H | H | H | OH |
| benzofuran-2-yl | Me | H | H | H | H | H | H | OMe |
| benzofuran-2-yl | Me | H | H | H | H | H | H | Me |
| benzofuran-2-yl | Me | H | H | H | H | H | H | CN |
| benzofuran-2-yl | Me | H | H | H | H | H | H | F |
| benzofuran-2-yl | Me | H | H | H | H | H | H | Cl |
| benzofuran-2-yl | Me | H | H | H | H | Me | H | H |
| benzofuran-2-yl | Me | H | H | OH | H | H | H | H |
| benzofuran-2-yl | Me | H | H | OMe | H | H | H | H |
| benzofuran-2-yl | Me | H | H | Me | H | H | H | H |
| benzofuran-2-yl | Me | H | H | F | H | H | H | H |
| benzofuran-2-yl | Me | H | H | pyridazin-3-yl | H | H | H | H |
| 4-fluoro-benzofuran-2-yl | Me | H | H | pyridazin-3-yl | H | H | H | H |
| 5-fluoro-benzofuran-2-yl | Me | H | H | pyridazin-3-yl | H | H | H | H |
| 6-fluoro-benzofuran-2-yl | Me | H | H | pyridazin-3-yl | H | H | H | H |
| 7-fluoro-benzofuran-2-yl | Me | H | H | pyridazin-3-yl | H | H | H | H |
| benzofuran-2-yl | Et | H | H | pyridazin-3-yl | H | H | H | H |
| benzofuran-2-yl | Me | H | H | 6-methylpyridazin-3-yl | H | H | H | H |
| benzofuran-2-yl | Me | H | H | 6-dimethylamino-pyridazin-3-yl | H | H | H | H |
| benzofuran-2-yl | Me | H | H | 6-methylamino-pyridazin-3-yl | H | H | H | H |
| benzofuran-2-yl | Me | H | H | 6-amino-pyridazin-3-yl | H | H | H | H |
| benzofuran-2-yl | Me | H | H | 6-morpholin-4-yl-pyridazin-3-yl | H | H | H | H |
| benzofuran-2-yl | Me | H | H | 6-trifluoromethyl-pyridazin-3-yl | H | H | H | H |
| benzofuran-2-yl | Me | H | H | 6-cyano-pyridazin-3-yl | H | H | H | H |
| benzofuran-2-yl | Me | H | F | pyridazin-3-yl | H | H | H | H |
| benzofuran-2-yl | Me | H | OMe | pyridazin-3-yl | H | H | H | H |
| benzofuran-2-yl | Me | H | OH | pyridazin-3-yl | H | H | H | H |
| benzofuran-2-yl | Me | H | Me | pyridazin-3-yl | H | H | H | H |
| benzofuran-2-yl | Et | H | F | pyridazin-3-yl | H | H | H | H |
| benzofuran-2-yl | Me | H | H | pyridazin-3-yl | F | H | H | H |
| benzofuran-2-yl | Me | H | H | pyridazin-3-yl | H | F | H | H |
| benzofuran-2-yl | Me | H | H | pyridazin-3-yl | H | H | H | OH |
| benzofuran-2-yl | Me | H | H | pyridazin-3-yl | H | H | H | Me |

TABLE B-continued

| X | R$^1$ | R$^2$ | R$^3$ | R$^4$ | R$^5$ | R$^6$ | R$^7$ | R$^8$ |
|---|---|---|---|---|---|---|---|---|
| benzofuran-2-yl | Me | H | H | pyridazin-4-yl | H | H | H | H |
| benzofuran-2-yl | Me | H | F | pyridazin-4-yl | H | H | H | H |
| benzofuran-2-yl | Me | H | H | pyrazin-2-yl | H | H | H | H |
| benzofuran-2-yl | Me | H | H | 3-methyl-pyrazin-2-yl | H | H | H | H |
| benzofuran-2-yl | Me | H | H | 3-methoxy-pyrazin-2-yl | H | H | H | H |
| benzofuran-2-yl | Me | H | H | 6-methyl-pyrazin-2-yl | H | H | H | H |
| benzofuran-2-yl | Me | H | H | 6-methoxy-pyrazin-2-yl | H | H | H | H |
| benzofuran-2-yl | Me | H | F | pyrazin-2-yl | H | H | H | H |
| benzofuran-2-yl | Me | H | H | pyrimidin-2-yl | H | H | H | H |
| benzofuran-2-yl | Me | H | F | pyrimidin-2-yl | H | H | H | H |
| benzofuran-2-yl | Me | H | H | pyrimidin-4-yl | H | H | H | H |
| benzofuran-2-yl | Me | H | F | pyrimidin-4-yl | H | H | H | H |
| benzofuran-2-yl | Me | H | H | pyrimidin-5-yl | H | H | H | H |
| benzofuran-2-yl | Me | H | F | pyrimidin-5-yl | H | H | H | H |
| benzofuran-2-yl | Me | H | H | 3,5-dimethyl-isoxazol-4-yl | H | H | H | H |
| benzofuran-2-yl | Me | H | H | thiazol-2-yl | H | H | H | H |
| benzofuran-2-yl | Me | H | H | 5-methyl-thiazol-2-yl | H | H | H | H |
| benzofuran-2-yl | Me | H | H | [1,3,5]triazin-2-yl | H | H | H | H |
| benzofuran-2-yl | Me | H | H | [1,2,4]triazin-3-yl | H | H | H | H |
| benzofuran-2-yl | Me | H | H | [1,2,4]triazin-5-yl | H | H | H | H |
| benzofuran-2-yl | Me | H | H | [1,2,4]triazin-6-yl | H | H | H | H |
| benzofuran-2-yl | Me | H | H | cinnolin-3-yl | H | H | H | H |
| benzofuran-2-yl | Me | H | H | phthalazin-1-yl | H | H | H | H |
| benzofuran-2-yl | Me | H | H | quinoxalin-2-yl | H | H | H | H |
| benzofuran-2-yl | Me | H | H | quinazolin-2-yl | H | H | H | H |
| benzofuran-2-yl | Me | H | H | quinazolin-6-yl | H | H | H | H |
| benzofuran-2-yl | Me | H | H | quinazolin-7-yl | H | H | H | H |
| benzofuran-2-yl | Me | H | H | 3-oxo-[1,2,4]triazolo[4,3-c]pyridin-2-yl | H | H | H | H |
| benzofuran-2-yl | Me | H | H | morpholin-4-yl | H | H | H | H |
| 4-fluoro-benzofuran-2-yl | Me | H | H | morpholin-4-yl | H | H | H | H |
| 5-fluoro-benzofuran-2-yl | Me | H | H | morpholin-4-yl | H | H | H | H |
| 6-fluoro-benzofuran-2-yl | Me | H | H | morpholin-4-yl | H | H | H | H |
| 7-fluoro-benzofuran-2-yl | Me | H | H | morpholin-4-yl | H | H | H | H |
| benzofuran-2-yl | Me | H | H | 2,6-dimethyl-morpholin-4-yl | H | H | H | H |
| benzofuran-2-yl | Et | H | H | morpholin-4-yl | H | H | H | H |
| benzofuran-2-yl | Me | H | F | morpholin-4-yl | H | H | H | H |
| benzofuran-2-yl | Et | H | F | morpholin-4-yl | H | H | H | H |
| benzofuran-2-yl | Me | H | H | morpholin-4-yl | F | H | H | H |
| benzofuran-2-yl | Me | H | H | morpholin-4-yl | H | F | H | H |
| benzofuran-2-yl | Me | H | OMe | morpholin-4-yl | H | H | H | H |
| benzofuran-2-yl | Me | H | OH | morpholin-4-yl | H | H | H | H |
| benzofuran-2-yl | Me | H | Me | morpholin-4-yl | H | H | H | H |
| benzofuran-2-yl | Me | H | H | morpholin-4-yl | H | H | H | OH |
| benzofuran-2-yl | Me | H | H | morpholin-4-yl | H | H | H | Me |
| benzofuran-2-yl | Me | H | H | piperazin-1-yl | H | H | H | H |
| benzofuran-2-yl | Me | H | H | 4-methyl-piperazin-1-yl | H | H | H | H |
| benzofuran-2-yl | Me | H | H | piperidin-1-yl | H | H | H | H |
| benzofuran-2-yl | Me | H | H | pyrrolidin-1-yl | H | H | H | H |
| benzofuran-2-yl | Me | H | H | morpholin-4-ylmethyl | H | H | H | H |
| benzofuran-2-yl | Me | H | H | 1-methyl-1-morpholin-4-yl-ethyl | H | H | H | H |
| benzofuran-2-yl | Me | H | H | 1-morpholin-4-yl-cyclopropyl | H | H | H | H |
| benzofuran-2-yl | Me | H | H | piperidin-1-ylmethyl | H | H | H | H |

TABLE B-continued

| X | R$^1$ | R$^2$ | R$^3$ | R$^4$ | R$^5$ | R$^6$ | R$^7$ | R$^8$ |
|---|---|---|---|---|---|---|---|---|
| benzofuran-2-yl | Me | H | H | pyrrolidin-1-ylmethyl | H | H | H | H |
| benzofuran-2-yl | Me | H | H | CH$_2$NMe$_2$ | H | H | H | H |
| benzofuran-2-yl | Me | H | H | 1-dimethylamino-1-methylethyl | H | H | H | H |
| benzofuran-2-yl | Me | H | H | 1-dimethylamino-cyclopropyl | H | H | H | H |
| benzofuran-2-yl | Me | H | H | CH$_2$NHMe | H | H | H | H |
| benzofuran-2-yl | Me | H | H | 1-methyl-1-methylaminoethyl | H | H | H | H |
| benzofuran-2-yl | Me | H | H | 1-methylamino-cyclopropyl | H | H | H | H |
| benzofuran-2-yl | Me | H | H | CH$_2$NH$_2$ | H | H | H | H |
| benzofuran-2-yl | Me | H | H | 1-amino-1-methylethyl | H | H | H | H |
| benzofuran-2-yl | Me | H | H | 1-amino-cyclopropyl | H | H | H | H |
| benzofuran-2-yl | Me | H | H | 2-oxo-2H-pyridin-1-yl | H | H | H | H |
| benzofuran-2-yl | Me | H | H | SO$_2$CH$_3$ | H | H | H | H |
| benzofuran-2-yl | Me | H | H | CN | H | H | H | H |
| benzofuran-2-yl | Me | H | Me | H | H | H | H | H |
| benzofuran-3-yl | Me | H | H | H | H | H | H | H |
| benzofuran-3-yl | Me | H | H | morpholin-4-yl | H | H | H | H |
| benzofuran-3-yl | Me | H | H | pyridazin-3-yl | H | H | H | H |
| benzofuran-4-yl | Me | H | H | H | H | H | H | H |
| benzofuran-4-yl | Me | H | H | morpholin-4-yl | H | H | H | H |
| benzofuran-4-yl | Me | H | H | pyridazin-3-yl | H | H | H | H |
| benzofuran-5-yl | H | H | H | H | H | H | H | H |
| benzofuran-5-yl | H | Me | H | H | H | H | H | H |
| benzofuran-5-yl | Me | H | H | H | H | H | H | H |
| benzofuran-5-yl | Me | H | F | H | H | H | H | H |
| benzofuran-5-yl | Et | H | H | H | H | H | H | H |
| benzofuran-5-yl | Me | Me | H | H | H | H | H | H |
| 3-methyl-benzofuran-5-yl | Me | H | H | H | H | H | H | H |
| benzofuran-5-yl | Me | H | H | H | H | H | H | OH |
| benzofuran-5-yl | Me | H | H | H | H | H | H | OMe |
| benzofuran-5-yl | Me | H | H | H | H | H | H | Me |
| benzofuran-5-yl | Me | H | H | H | H | H | H | CN |
| benzofuran-5-yl | Me | H | H | H | H | H | H | F |
| benzofuran-5-yl | Me | H | H | H | H | H | H | Cl |
| benzofuran-5-yl | Me | H | H | OH | H | H | H | H |
| benzofuran-5-yl | Me | H | H | OMe | H | H | H | H |
| benzofuran-5-yl | Me | H | H | Me | H | H | H | H |
| benzofuran-5-yl | Me | H | H | F | H | H | H | H |
| benzofuran-5-yl | Me | H | H | pyridazin-3-yl | H | H | H | H |
| benzofuran-5-yl | Et | H | H | pyridazin-3-yl | H | H | H | H |
| benzofuran-5-yl | Me | H | H | 6-methylpyridazin-3-yl | H | H | H | H |
| benzofuran-5-yl | Me | H | H | 6-dimethylamino-pyridazin-3-yl | H | H | H | H |
| benzofuran-5-yl | Me | H | H | 6-methylamino-pyridazin-3-yl | H | H | H | H |
| benzofuran-5-yl | Me | H | H | 6-amino-pyridazin-3-yl | H | H | H | H |
| benzofuran-5-yl | Me | H | H | 6-morpholin-4-yl-pyridazin-3-yl | H | H | H | H |
| benzofuran-5-yl | Me | H | H | 6-trifluoromethyl-pyridazin-3-yl | H | H | H | H |
| benzofuran-5-yl | Me | H | H | 6-cyano-pyridazin-3-yl | H | H | H | H |
| benzofuran-5-yl | Me | H | F | pyridazin-3-yl | H | H | H | H |
| benzofuran-5-yl | Me | H | OMe | pyridazin-3-yl | H | H | H | H |
| benzofuran-5-yl | Me | H | OH | pyridazin-3-yl | H | H | H | H |
| benzofuran-5-yl | Me | H | Me | pyridazin-3-yl | H | H | H | H |
| benzofuran-5-yl | Et | H | F | pyridazin-3-yl | H | H | H | H |
| benzofuran-5-yl | Me | H | H | pyridazin-3-yl | F | H | H | H |

TABLE B-continued

| X | R¹ | R² | R³ | R⁴ | R⁵ | R⁶ | R⁷ | R⁸ |
|---|---|---|---|---|---|---|---|---|
| benzofuran-5-yl | Me | H | H | pyridazin-3-yl | H | F | H | H |
| benzofuran-5-yl | Me | H | H | pyridazin-3-yl | H | H | H | OH |
| benzofuran-5-yl | Me | H | H | pyridazin-3-yl | H | H | H | Me |
| benzofuran-5-yl | Me | H | H | pyridazin-4-yl | H | H | H | H |
| benzofuran-5-yl | Me | H | F | pyridazin-4-yl | H | H | H | H |
| benzofuran-5-yl | Me | H | H | pyrazin-2-yl | H | H | H | H |
| benzofuran-5-yl | Me | H | H | 3-methyl-pyrazin-2-yl | H | H | H | H |
| benzofuran-5-yl | Me | H | H | 3-methoxy-pyrazin-2-yl | H | H | H | H |
| benzofuran-5-yl | Me | H | H | 6-methyl-pyrazin-2-yl | H | H | H | H |
| benzofuran-5-yl | Me | H | H | 6-methoxy-pyrazin-2-yl | H | H | H | H |
| benzofuran-5-yl | Me | H | F | pyrazin-2-yl | H | H | H | H |
| benzofuran-5-yl | Me | H | OMe | pyrazin-2-yl | H | H | H | H |
| benzofuran-5-yl | Me | H | OH | pyrazin-2-yl | H | H | H | H |
| benzofuran-5-yl | Me | H | Me | pyrazin-2-yl | H | H | H | H |
| benzofuran-5-yl | Me | H | H | pyrimidin-2-yl | H | H | H | H |
| benzofuran-5-yl | Me | H | F | pyrimidin-2-yl | H | H | H | H |
| benzofuran-5-yl | Me | H | OMe | pyrimidin-2-yl | H | H | H | H |
| benzofuran-5-yl | Me | H | OH | pyrimidin-2-yl | H | H | H | H |
| benzofuran-5-yl | Me | H | Me | pyrimidin-2-yl | H | H | H | H |
| benzofuran-5-yl | Me | H | H | pyrimidin-4-yl | H | H | H | H |
| benzofuran-5-yl | Me | H | F | pyrimidin-4-yl | H | H | H | H |
| benzofuran-5-yl | Me | H | OMe | pyrimidin-4-yl | H | H | H | H |
| benzofuran-5-yl | Me | H | OH | pyrimidin-4-yl | H | H | H | H |
| benzofuran-5-yl | Me | H | Me | pyrimidin-4-yl | H | H | H | H |
| benzofuran-5-yl | Me | H | H | pyrimidin-5-yl | H | H | H | H |
| benzofuran-5-yl | Me | H | F | pyrimidin-5-yl | H | H | H | H |
| benzofuran-5-yl | Me | H | OMe | pyrimidin-5-yl | H | H | H | H |
| benzofuran-5-yl | Me | H | OH | pyrimidin-5-yl | H | H | H | H |
| benzofuran-5-yl | Me | H | Me | pyrimidin-5-yl | H | H | H | H |
| benzofuran-5-yl | Me | H | H | 3,5-dimethyl-isoxazol-4-yl | H | H | H | H |
| benzofuran-5-yl | Me | H | H | thiazol-2-yl | H | H | H | H |
| benzofuran-5-yl | Me | H | H | 5-methyl-thiazol-2-yl | H | H | H | H |
| benzofuran-5-yl | Me | H | H | [1,3,5]triazin-2-yl | H | H | H | H |
| benzofuran-5-yl | Me | H | H | [1,2,4]triazin-3-yl | H | H | H | H |
| benzofuran-5-yl | Me | H | H | [1,2,4]triazin-5-yl | H | H | H | H |
| benzofuran-5-yl | Me | H | H | [1,2,4]triazin-6-yl | H | H | H | H |
| benzofuran-5-yl | Me | H | H | cinnolin-3-yl | H | H | H | H |
| benzofuran-5-yl | Me | H | H | phthalazin-1-yl | H | H | H | H |
| benzofuran-5-yl | Me | H | H | quinoxalin-2-yl | H | H | H | H |
| benzofuran-5-yl | Me | H | H | quinazolin-2-yl | H | H | H | H |
| benzofuran-5-yl | Me | H | H | quinazolin-6-yl | H | H | H | H |
| benzofuran-5-yl | Me | H | H | quinazolin-7-yl | H | H | H | H |
| benzofuran-5-yl | Me | H | H | 3-oxo-[1,2,4]triazolo[4,3-a]pyridin-2-yl | H | H | H | H |
| benzofuran-5-yl | Me | H | H | morpholin-4-yl | H | H | H | H |
| benzofuran-5-yl | Me | H | H | 2,6-dimethyl-morpholin-4-yl | H | H | H | H |
| benzofuran-5-yl | Et | H | H | morpholin-4-yl | H | H | H | H |
| benzofuran-5-yl | Me | H | F | morpholin-4-yl | H | H | H | H |
| benzofuran-5-yl | Me | H | OMe | morpholin-4-yl | H | H | H | H |
| benzofuran-5-yl | Me | H | OH | morpholin-4-yl | H | H | H | H |
| benzofuran-5-yl | Me | H | Me | morpholin-4-yl | H | H | H | H |
| benzofuran-5-yl | Et | H | F | morpholin-4-yl | H | H | H | H |
| benzofuran-5-yl | Me | H | H | morpholin-4-yl | F | H | H | H |
| benzofuran-5-yl | Me | H | H | morpholin-4-yl | H | F | H | H |
| benzofuran-5-yl | Me | H | H | morpholin-4-yl | H | H | H | OH |
| benzofuran-5-yl | Me | H | H | morpholin-4-yl | H | H | H | Me |
| benzofuran-5-yl | Me | H | H | piperidin-1-yl | H | H | H | H |
| benzofuran-5-yl | Me | H | H | pyrrolidin-1-yl | H | H | H | H |
| benzofuran-5-yl | Me | H | H | morpholin-4-ylmethyl | H | H | H | H |

TABLE B-continued

| X | R¹ | R² | R³ | R⁴ | R⁵ | R⁶ | R⁷ | R⁸ |
|---|---|---|---|---|---|---|---|---|
| benzofuran-5-yl | Me | H | H | 1-methyl-1-morpholin-4-yl-ethyl | H | H | H | H |
| benzofuran-5-yl | Me | H | H | 1-morpholin-4-yl-cyclopropyl | H | H | H | H |
| benzofuran-5-yl | Me | H | H | piperidin-1-ylmethyl | H | H | H | H |
| benzofuran-5-yl | Me | H | H | pyrrolidin-1-ylmethyl | H | H | H | H |
| benzofuran-5-yl | Me | H | H | CH₂NMe₂ | H | H | H | H |
| benzofuran-5-yl | Me | H | H | 1-dimethylamino-1-methylethyl | H | H | H | H |
| benzofuran-5-yl | Me | H | H | 1-dimethylamino-cyclopropyl | H | H | H | H |
| benzofuran-5-yl | Me | H | H | CH₂NHMe | H | H | H | H |
| benzofuran-5-yl | Me | H | H | 1-methyl-1-methylaminoethyl | H | H | H | H |
| benzofuran-5-yl | Me | H | H | 1-methylamino-cyclopropyl | H | H | H | H |
| benzofuran-5-yl | Me | H | H | CH₂NH₂ | H | H | H | H |
| benzofuran-5-yl | Me | H | H | 1-methyl-1-methylaminoethyl | H | H | H | H |
| benzofuran-5-yl | Me | H | H | 1-methylamino-cyclopropyl | H | H | H | H |
| benzofuran-5-yl | Me | H | H | 2-oxo-2H-pyridin-1-yl | H | H | H | H |
| benzofuran-5-yl | Me | H | H | SO₂CH₃ | H | H | H | H |
| benzofuran-5-yl | Me | H | H | CN | H | H | H | H |
| benzofuran-5-yl | Me | H | F | CN | H | H | H | H |
| benzofuran-5-yl | Me | H | Me | H | H | H | H | H |
| 2,3-dihydrobenzofuran-5-yl | Me | H | H | H | H | H | H | H |
| benzofuran-6-yl | H | H | H | H | H | H | H | H |
| benzofuran-6-yl | H | Me | H | H | H | H | H | H |
| benzofuran-6-yl | Me | H | H | H | H | H | H | H |
| benzofuran-6-yl | Et | H | H | H | H | H | H | H |
| benzofuran-6-yl | Me | Me | H | H | H | H | H | H |
| benzofuran-6-yl | Me | H | H | H | H | H | H | OH |
| benzofuran-6-yl | Me | H | H | H | H | H | H | OMe |
| benzofuran-6-yl | Me | H | H | H | H | H | H | Me |
| benzofuran-6-yl | Me | H | H | H | H | H | H | CN |
| benzofuran-6-yl | Me | H | H | H | H | H | H | F |
| benzofuran-6-yl | Me | H | H | H | H | H | H | Cl |
| benzofuran-6-yl | Me | H | H | OH | H | H | H | H |
| benzofuran-6-yl | Me | H | H | OMe | H | H | H | H |
| benzofuran-6-yl | Me | H | H | Me | H | H | H | H |
| benzofuran-6-yl | Me | H | H | F | H | H | H | H |
| benzofuran-6-yl | Me | H | H | pyridazin-3-yl | H | H | H | H |
| benzofuran-6-yl | Et | H | H | pyridazin-3-yl | H | H | H | H |
| benzofuran-6-yl | Me | H | H | 6-methylpyridazin-3-yl | H | H | H | H |
| benzofuran-6-yl | Me | H | H | 6-dimethylamino-pyridazin-3-yl | H | H | H | H |
| benzofuran-6-yl | Me | H | H | 6-methylamino-pyridazin-3-yl | H | H | H | H |
| benzofuran-6-yl | Me | H | H | 6-amino-pyridazin-3-yl | H | H | H | H |
| benzofuran-6-yl | Me | H | H | 6-morpholin-4-yl-pyridazin-3-yl | H | H | H | H |
| benzofuran-6-yl | Me | H | H | 6-trifluoromethyl-pyridazin-3-yl | H | H | H | H |
| benzofuran-6-yl | Me | H | H | 6-cyano-pyridazin-3-yl | H | H | H | H |
| benzofuran-6-yl | Me | H | F | pyridazin-3-yl | H | H | H | H |
| benzofuran-6-yl | Me | H | OMe | pyridazin-3-yl | H | H | H | H |
| benzofuran-6-yl | Me | H | OH | pyridazin-3-yl | H | H | H | H |
| benzofuran-6-yl | Me | H | Me | pyridazin-3-yl | H | H | H | H |
| benzofuran-6-yl | Et | H | F | pyridazin-3-yl | H | H | H | H |

TABLE B-continued

| X | R¹ | R² | R³ | R⁴ | R⁵ | R⁶ | R⁷ | R⁸ |
|---|----|----|----|----|----|----|----|----|
| benzofuran-6-yl | Me | H | H | pyridazin-3-yl | F | H | H | H |
| benzofuran-6-yl | Me | H | H | pyridazin-3-yl | H | F | H | H |
| benzofuran-6-yl | Me | H | H | pyridazin-4-yl | H | H | H | H |
| benzofuran-6-yl | Me | H | F | pyridazin-4-yl | H | H | H | H |
| benzofuran-6-yl | Me | H | H | pyrazin-2-yl | H | H | H | H |
| benzofuran-6-yl | Me | H | H | 3-methyl-pyrazin-2-yl | H | H | H | H |
| benzofuran-6-yl | Me | H | H | 3-methoxy-pyrazin-2-yl | H | H | H | H |
| benzofuran-6-yl | Me | H | H | 6-methyl-pyrazin-2-yl | H | H | H | H |
| benzofuran-6-yl | Me | H | H | 6-methoxy-pyrazin-2-yl | H | H | H | H |
| benzofuran-6-yl | Me | H | F | pyrazin-2-yl | H | H | H | H |
| benzofuran-6-yl | Me | H | OMe | pyrazin-2-yl | H | H | H | H |
| benzofuran-6-yl | Me | H | OH | pyrazin-2-yl | H | H | H | H |
| benzofuran-6-yl | Me | H | Me | pyrazin-2-yl | H | H | H | H |
| benzofuran-6-yl | Me | H | H | pyrimidin-2-yl | H | H | H | H |
| benzofuran-6-yl | Me | H | F | pyrimidin-2-yl | H | H | H | H |
| benzofuran-6-yl | Me | H | OMe | pyrimidin-2-yl | H | H | H | H |
| benzofuran-6-yl | Me | H | OH | pyrimidin-2-yl | H | H | H | H |
| benzofuran-6-yl | Me | H | Me | pyrimidin-2-yl | H | H | H | H |
| benzofuran-6-yl | Me | H | H | pyrimidin-4-yl | H | H | H | H |
| benzofuran-6-yl | Me | H | F | pyrimidin-4-yl | H | H | H | H |
| benzofuran-6-yl | Me | H | OMe | pyrimidin-4-yl | H | H | H | H |
| benzofuran-6-yl | Me | H | OH | pyrimidin-4-yl | H | H | H | H |
| benzofuran-6-yl | Me | H | Me | pyrimidin-4-yl | H | H | H | H |
| benzofuran-6-yl | Me | H | H | pyrimidin-5-yl | H | H | H | H |
| benzofuran-6-yl | Me | H | F | pyrimidin-5-yl | H | H | H | H |
| benzofuran-6-yl | Me | H | OMe | pyrimidin-5-yl | H | H | H | H |
| benzofuran-6-yl | Me | H | OH | pyrimidin-5-yl | H | H | H | H |
| benzofuran-6-yl | Me | H | Me | pyrimidin-5-yl | H | H | H | H |
| benzofuran-6-yl | Me | H | H | 3,5-dimethyl-isoxazol-4-yl | H | H | H | H |
| benzofuran-6-yl | Me | H | H | thiazol-2-yl | H | H | H | H |
| benzofuran-6-yl | Me | H | H | 5-methyl-thiazol-2-yl | H | H | H | H |
| benzofuran-6-yl | Me | H | H | [1,3,5]triazin-2-yl | H | H | H | H |
| benzofuran-6-yl | Me | H | H | [1,2,4]triazin-3-yl | H | H | H | H |
| benzofuran-6-yl | Me | H | H | [1,2,4]triazin-5-yl | H | H | H | H |
| benzofuran-6-yl | Me | H | H | [1,2,4]triazin-6-yl | H | H | H | H |
| benzofuran-6-yl | Me | H | H | cinnolin-3-yl | H | H | H | H |
| benzofuran-6-yl | Me | H | H | phthalazin-1-yl | H | H | H | H |
| benzofuran-6-yl | Me | H | H | quinoxalin-2-yl | H | H | H | H |
| benzofuran-6-yl | Me | H | H | quinazolin-2-yl | H | H | H | H |
| benzofuran-6-yl | Me | H | H | quinazolin-6-yl | H | H | H | H |
| benzofuran-6-yl | Me | H | H | quinazolin-7-yl | H | H | H | H |
| benzofuran-6-yl | Me | H | H | 3-oxo-[1,2,4]triazolo[4,3-a]pyridin-2-yl | H | H | H | H |
| benzofuran-6-yl | Me | H | H | morpholin-4-yl | H | H | H | H |
| benzofuran-6-yl | Me | H | H | 2,6-dimethyl-morpholin-4-yl | H | H | H | H |
| benzofuran-6-yl | Et | H | H | morpholin-4-yl | H | H | H | H |
| benzofuran-6-yl | Me | H | F | morpholin-4-yl | H | H | H | H |
| benzofuran-6-yl | Me | H | OMe | morpholin-4-yl | H | H | H | H |
| benzofuran-6-yl | Me | H | OH | morpholin-4-yl | H | H | H | H |
| benzofuran-6-yl | Me | H | Me | morpholin-4-yl | H | H | H | H |
| benzofuran-6-yl | Et | H | F | morpholin-4-yl | H | H | H | H |
| benzofuran-6-yl | Me | H | H | morpholin-4-yl | F | H | H | H |
| benzofuran-6-yl | Me | H | H | morpholin-4-yl | H | F | H | H |
| benzofuran-6-yl | Me | H | H | morpholin-4-yl | H | H | H | OH |
| benzofuran-6-yl | Me | H | H | morpholin-4-yl | H | H | H | Me |
| benzofuran-6-yl | Me | H | H | piperidin-1-yl | H | H | H | H |
| benzofuran-6-yl | Me | H | H | pyrrolidin-1-yl | H | H | H | H |
| benzofuran-6-yl | Me | H | H | morpholin-4-ylmethyl | H | H | H | H |

TABLE B-continued

| X | R¹ | R² | R³ | R⁴ | R⁵ | R⁶ | R⁷ | R⁸ |
|---|---|---|---|---|---|---|---|---|
| benzofuran-6-yl | Me | H | H | 1-methyl-1-morpholin-4-yl-ethyl | H | H | H | H |
| benzofuran-6-yl | Me | H | H | 1-morpholin-4-yl-cyclopropyl | H | H | H | H |
| benzofuran-6-yl | Me | H | H | piperidin-1-ylmethyl | H | H | H | H |
| benzofuran-6-yl | Me | H | H | pyrrolidin-1-ylmethyl | H | H | H | H |
| benzofuran-6-yl | Me | H | H | $CH_2NMe_2$ | H | H | H | H |
| benzofuran-6-yl | Me | H | H | 1-dimethylamino-1-methylethyl | H | H | H | H |
| benzofuran-6-yl | Me | H | H | 1-dimethylamino-cyclopropyl | H | H | H | H |
| benzofuran-6-yl | Me | H | H | $CH_2NHMe$ | H | H | H | H |
| benzofuran-6-yl | Me | H | H | 1-methyl-1-methylaminoethyl | H | H | H | H |
| benzofuran-6-yl | Me | H | H | 1-methylamino-cyclopropyl | H | H | H | H |
| benzofuran-6-yl | Me | H | H | $CH_2NH_2$ | H | H | H | H |
| benzofuran-6-yl | Me | H | H | 1-methyl-1-methylaminoethyl | H | H | H | H |
| benzofuran-6-yl | Me | H | H | 1-methylamino-cyclopropyl | H | H | H | H |
| benzofuran-6-yl | Me | H | H | 2-oxo-2H-pyridin-1-yl | H | H | H | H |
| benzofuran-6-yl | Me | H | H | $SO_2CH_3$ | H | H | H | H |
| benzofuran-6-yl | Me | H | H | CN | H | H | H | H |
| benzofuran-6-yl | Me | H | F | CN | H | H | H | H |
| benzofuran-6-yl | Me | H | Me | H | H | H | H | H |
| benzofuran-7-yl | Me | H | H | H | H | H | H | H |
| benzofuran-7-yl | Et | H | H | H | H | H | H | H |
| benzofuran-7-yl | Me | H | F | H | H | H | H | H |
| benzofuran-7-yl | Et | H | F | H | H | H | H | H |
| benzofuran-7-yl | Me | H | H | pyridazin-3-yl | H | H | H | H |
| benzofuran-7-yl | Me | H | H | morpholin-4-yl | H | H | H | H | wherein the carbon atom designated * is in the R or S configuration.

That is, the specific compounds herein include:
4-(benzofuran-2-yl)-1,2,3,4-tetrahydroisoquinoline;
4-(benzofuran-2-yl)-1-methyl-1,2,3,4-tetrahydroisoquinoline;
4-(benzofuran-2-yl)-2-methyl-1,2,3,4-tetrahydroisoquinoline;
4-(benzofuran-2-yl)-2-ethyl-1,2,3,4-tetrahydroisoquinoline;
4-(benzofuran-2-yl)-1,2-dimethyl-1,2,3,4-tetrahydroisoquinoline;
4-(5-chloro-benzofuran-2-yl)-2-methyl-1,2,3,4-tetrahydroisoquinoline;
4-(5-fluoro-benzofuran-2-yl)-2-methyl-1,2,3,4-tetrahydroisoquinoline;
4-(7-fluoro-benzofuran-2-yl)-2-methyl-1,2,3,4-tetrahydroisoquinoline;
4-(5-methoxy-benzofuran-2-yl)-2-methyl-1,2,3,4-tetrahydroisoquinoline;
4-(7-methoxy-benzofuran-2-yl)-2-methyl-1,2,3,4-tetrahydroisoquinoline;
4-(7-methoxy-benzofuran-2-yl)-2-methyl-7-(pyridazin-3-yl)-1,2,3,4-tetrahydroisoquinoline;
4-(7-methoxy-benzofuran-2-yl)-8-fluoro-2-methyl-7-(pyridazin-3-yl)-1,2,3,4-tetrahydroisoquinoline;
4-(7-methoxy-benzofuran-2-yl)-2-methyl-7-(morpholin-4-yl)-1,2,3,4-tetrahydroisoquinoline;
4-(7-methoxy-benzofuran-2-yl)-8-fluoro-2-methyl-7-(morpholin-4-yl)-1,2,3,4-tetrahydroisoquinoline;
4-benzofuran-2-yl-2-methyl-1,2,3,4-tetrahydroisoquinolin-4-ol;
4-benzofuran-2-yl-4-methoxy-2-methyl-1,2,3,4-tetrahydroisoquinoline;
4-(benzofuran-2-yl)-2,4-dimethyl-1,2,3,4-tetrahydroisoquinoline;
4-benzofuran-2-yl-2-methyl-1,2,3,4-tetrahydroisoquinoline-4-carbonitrile;
4-(benzofuran-2-yl)-4-fluoro-2-methyl-1,2,3,4-tetrahydroisoquinoline;
4-(benzofuran-2-yl)-4-chloro-2-methyl-1,2,3,4-tetrahydroisoquinoline;
4-(benzofuran-2-yl)-2,5-dimethyl-1,2,3,4-tetrahydroisoquinoline;
4-(benzofuran-2-yl)-7-fluoro-2-methyl-1,2,3,4-tetrahydroisoquinoline;
4-(benzofuran-2-yl)-7-hydroxy-2-methyl-1,2,3,4-tetrahydroisoquinoline;
4-(benzofuran-2-yl)-7-methoxy-2-methyl-1,2,3,4-tetrahydroisoquinoline;

4-(benzofuran-2-yl)-2,7-dimethyl-1,2,3,4-tetrahydroisoquinoline;
4-(benzofuran-2-yl)-2-methyl-7-(pyridazin-3-yl)-1,2,3,4-tetrahydroisoquinoline;
4-(4-fluoro-benzofuran-2-yl)-2-methyl-7-(pyridazin-3-yl)-1,2,3,4-tetrahydroisoquinoline;
4-(5-fluoro-benzofuran-2-yl)-2-methyl-7-(pyridazin-3-yl)-1,2,3,4-tetrahydroisoquinoline;
4-(6-fluoro-benzofuran-2-yl)-2-methyl-7-(pyridazin-3-yl)-1,2,3,4-tetrahydroisoquinoline;
4-(7-fluoro-benzofuran-2-yl)-2-methyl-7-(pyridazin-3-yl)-1,2,3,4-tetrahydroisoquinoline;
4-(benzofuran-2-yl)-2-ethyl-7-(pyridazin-3-yl)-1,2,3,4-tetrahydroisoquinoline;
4-(benzofuran-2-yl)-2-methyl-7-(6-methyl-pyridazin-3-yl)-1,2,3,4-tetrahydroisoquinoline;
[6-(4-(benzofuran-2-yl)-2-methyl-1,2,3,4-tetrahydroisoquinolin-7-yl)-pyridazin-3-yl]-dimethylamine;
[6-(4-(benzofuran-2-yl)-2-methyl-1,2,3,4-tetrahydroisoquinolin-7-yl)-pyridazin-3-yl]-methylamine;
6-(4-(benzofuran-2-yl)-2-methyl-1,2,3,4-tetrahydroisoquinolin-7-yl)-pyridazin-3-ylamine;
4-(benzofuran-2-yl)-2-methyl-7-(6-morpholin-4-yl-pyridazin-3-yl)-1,2,3,4-tetrahydroisoquinoline;
4-(benzofuran-2-yl)-2-methyl-7-(6-trifluoromethyl-pyridazin-3-yl)-1,2,3,4-tetrahydroisoquinoline;
6-(4-(benzofuran-2-yl)-2-methyl-1,2,3,4-tetrahydroisoquinolin-7-yl)-pyridazine-3-carbonitrile;
4-(benzofuran-2-yl)-8-fluoro-2-methyl-7-pyridazin-3-yl-1,2,3,4-tetrahydroisoquinoline;
4-(benzofuran-2-yl)-8-methoxy-2-methyl-7-pyridazin-3-yl-1,2,3,4-tetrahydroisoquinoline;
4-(benzofuran-2-yl)-2-methyl-7-pyridazin-3-yl-1,2,3,4-tetrahydroisoquinolin-8-ol;
4-(benzofuran-2-yl)-2,8-dimethyl-7-pyridazin-3-yl-1,2,3,4-tetrahydroisoquinoline;
4-(benzofuran-2-yl)-2-ethyl-8-fluoro-7-pyridazin-3-yl-1,2,3,4-tetrahydroisoquinoline;
4-(benzofuran-2-yl)-6-fluoro-2-methyl-7-pyridazin-3-yl-1,2,3,4-tetrahydroisoquinoline;
4-(benzofuran-2-yl)-5-fluoro-2-methyl-7-pyridazin-3-yl-1,2,3,4-tetrahydroisoquinoline;
4-(benzofuran-2-yl)-2-methyl-7-pyridazin-3-yl-1,2,3,4-tetrahydroisoquinolin-4-ol;
4-(benzofuran-2-yl)-2,4-dimethyl-7-pyridazin-3-yl-1,2,3,4-tetrahydroisoquinoline;
4-(benzofuran-2-yl)-2-methyl-7-(pyridazin-4-yl)-1,2,3,4-tetrahydroisoquinoline;
4-(benzofuran-2-yl)-8-fluoro-2-methyl-7-(pyridazin-4-yl)-1,2,3,4-tetrahydroisoquinoline;
4-(benzofuran-2-yl)-2-methyl-7-(pyrazin-2-yl)-1,2,3,4-tetrahydroisoquinoline;
4-(benzofuran-2-yl)-2-methyl-7-(3-methyl-pyrazin-2-yl)-1,2,3,4-tetrahydroisoquinoline;
4-(benzofuran-2-yl)-7-(3-methoxy-pyrazin-2-yl)-2-methyl-1,2,3,4-tetrahydroisoquinoline;
4-(benzofuran-2-yl)-2-methyl-7-(6-methyl-pyrazin-2-yl)-1,2,3,4-tetrahydroisoquinoline;
4-(benzofuran-2-yl)-7-(6-methoxy-pyrazin-2-yl)-2-methyl-1,2,3,4-tetrahydroisoquinoline;
4-(benzofuran-2-yl)-2-methyl-8-fluoro-7-(pyrazin-2-yl)-1,2,3,4-tetrahydroisoquinoline;
4-(benzofuran-2-yl)-2-methyl-7-(pyrimidin-2-yl)-1,2,3,4-tetrahydroisoquinoline;
4-(benzofuran-2-yl)-2-methyl-8-fluoro-7-(pyrimidin-2-yl)-1,2,3,4-tetrahydroisoquinoline;
4-(benzofuran-2-yl)-2-methyl-7-(pyrimidin-4-yl)-1,2,3,4-tetrahydroisoquinoline;
4-(benzofuran-2-yl)-2-methyl-8-fluoro-7-(pyrimidin-4-yl)-1,2,3,4-tetrahydroisoquinoline;
4-(benzofuran-2-yl)-2-methyl-7-(pyrimidin-5-yl)-1,2,3,4-tetrahydroisoquinoline;
4-(benzofuran-2-yl)-2-methyl-8-fluoro-7-(pyrimidin-5-yl)-1,2,3,4-tetrahydroisoquinoline;
4-(benzofuran-2-yl)-7-(3,5-dimethyl-isoxazol-4-yl)-2-methyl-1,2,3,4-tetrahydroisoquinoline;
4-(benzofuran-2-yl)-2-methyl-7-(thiazol-2-yl)-1,2,3,4-tetrahydroisoquinoline;
4-(benzofuran-2-yl)-2-methyl-7-(5-methyl-thiazol-2-yl)-1,2,3,4-tetrahydroisoquinoline;
4-(benzofuran-2-yl)-2-methyl-7-[1,3,5]triazin-2-yl-1,2,3,4-tetrahydroisoquinoline;
4-(benzofuran-2-yl)-2-methyl-7-[1,2,4]triazin-3-yl-1,2,3,4-tetrahydroisoquinoline;
4-(benzofuran-2-yl)-2-methyl-7-[1,2,4]triazin-5-yl-1,2,3,4-tetrahydroisoquinoline;
4-(benzofuran-2-yl)-2-methyl-7-[1,2,4]triazin-6-yl-1,2,3,4-tetrahydroisoquinoline;
3-(4-(benzofuran-2-yl)-2-methyl-1,2,3,4-tetrahydroisoquinolin-7-yl)-cinnoline;
1-(4-(benzofuran-2-yl)-2-methyl-1,2,3,4-tetrahydroisoquinolin-7-yl)-phthalazine;
2-(4-(benzofuran-2-yl)-2-methyl-1,2,3,4-tetrahydroisoquinolin-7-yl)-quinoxaline;
2-(4-(benzofuran-2-yl)-2-methyl-1,2,3,4-tetrahydroisoquinolin-7-yl)-quinazoline;
6-(4-(benzofuran-2-yl)-2-methyl-1,2,3,4-tetrahydroisoquinolin-7-yl)-quinazoline;
7-(4-(benzofuran-2-yl)-2-methyl-1,2,3,4-tetrahydroisoquinolin-7-yl)-quinazoline;
2-(4-(benzofuran-2-yl)-2-methyl-1,2,3,4-tetrahydroisoquinolin-7-yl)-2H-[1,2,4]triazolo[4,3-a]pyridin-3-one;
4-(benzofuran-2-yl)-2-methyl-7-(morpholin-4-yl)-1,2,3,4-tetrahydroisoquinoline;
4-(4-fluoro-benzofuran-2-yl)-2-methyl-7-(morpholin-4-yl)-1,2,3,4-tetrahydroisoquinoline;
4-(5-fluoro-benzofuran-2-yl)-2-methyl-7-(morpholin-4-yl)-1,2,3,4-tetrahydroisoquinoline;
4-(6-fluoro-benzofuran-2-yl)-2-methyl-7-(morpholin-4-yl)-1,2,3,4-tetrahydroisoquinoline;
4-(7-fluoro-benzofuran-2-yl)-2-methyl-7-(morpholin-4-yl)-1,2,3,4-tetrahydroisoquinoline;
4-(benzofuran-2-yl)-7-(2,6-dimethyl-morpholin-4-yl)-2-methyl-1,2,3,4-tetrahydroisoquinoline;
4-(benzofuran-2-yl)-2-ethyl-7-morpholin-4-yl-1,2,3,4-tetrahydroisoquinoline;
4-(benzofuran-2-yl)-8-fluoro-2-methyl-7-morpholin-4-yl-1,2,3,4-tetrahydroisoquinoline;
4-(benzofuran-2-yl)-8-methoxy-2-methyl-7-morpholin-4-yl-1,2,3,4-tetrahydroisoquinoline;
4-(benzofuran-2-yl)-2-methyl-7-morpholin-4-yl-1,2,3,4-tetrahydroisoquinolin-8-ol;
4-(benzofuran-2-yl)-2,8-dimethyl-7-morpholin-4-yl-1,2,3,4-tetrahydroisoquinoline;
4-(benzofuran-2-yl)-2-ethyl-8-fluoro-7-morpholin-4-yl-1,2,3,4-tetrahydroisoquinoline;
4-(benzofuran-2-yl)-6-fluoro-2-methyl-7-morpholin-4-yl-1,2,3,4-tetrahydroisoquinoline;
4-(benzofuran-2-yl)-5-fluoro-2-methyl-7-morpholin-4-yl-1,2,3,4-tetrahydroisoquinoline;
4-(benzofuran-2-yl)-2-methyl-7-morpholin-4-yl-1,2,3,4-tetrahydroisoquinolin-4-ol;

4-(benzofuran-2-yl)-2,4-dimethyl-7-morpholin-4-yl-1,2,3,4-tetrahydroisoquinoline;
4-benzofuran-2-yl-2-methyl-7-piperazin-1-yl-1,2,3,4-tetrahydroisoquinoline;
4-benzofuran-2-yl-2-methyl-7-(4-methyl-piperazin-1-yl)-1,2,3,4-tetrahydroisoquinoline;
4-(benzofuran-2-yl)-2-methyl-7-(piperidin-1-yl)-1,2,3,4-tetrahydroisoquinoline;
4-(benzofuran-2-yl)-2-methyl-7-(pyrrolidin-1-yl)-1,2,3,4-tetrahydroisoquinoline;
4-(benzofuran-2-yl)-2-methyl-7-(morpholin-4-yl)methyl-1,2,3,4-tetrahydroisoquinoline;
4-(benzofuran-2-yl)-2-methyl-7-(1-methyl-1-morpholin-4-yl-ethyl)-1,2,3,4-tetrahydroisoquinoline;
4-(benzofuran-2-yl)-2-methyl-7-(1-morpholin-4-yl-cyclopropyl)-1,2,3,4-tetrahydroisoquinoline;
4-(benzofuran-2-yl)-2-methyl-7-(piperidin-1-yl)methyl-1,2,3,4-tetrahydroisoquinoline;
4-(benzofuran-2-yl)-2-methyl-7-(pyrrolidin-1-yl)methyl-1,2,3,4-tetrahydroisoquinoline;
4-(benzofuran-2-yl)-2-methyl-1,2,3,4-tetrahydroisoquinolin-7-ylmethyl)-dimethylamine;
[1-4-(benzofuran-2-yl)-2-methyl-1,2,3,4-tetrahydroisoquinolin-7-yl)-1-methylethyl]-dimethylamine;
[1-4-(benzofuran-2-yl)-2-methyl-1,2,3,4-tetrahydroisoquinolin-7-yl)-cyclopropyl]-dimethylamine;
(4-(benzofuran-2-yl)-2-methyl-1,2,3,4-tetrahydroisoquinolin-7-ylmethyl)-methylamine;
[1-4-(benzofuran-2-yl)-2-methyl-1,2,3,4-tetrahydroisoquinolin-7-yl)-1-methylethyl]-methylamine;
[1-4-(benzofuran-2-yl)-2-methyl-1,2,3,4-tetrahydroisoquinolin-7-yl)-cyclopropyl]-methylamine;
C-4-(benzofuran-2-yl)-2-methyl-1,2,3,4-tetrahydroisoquinolin-7-yl)-methylamine;
1-4-(benzofuran-2-yl)-2-methyl-1,2,3,4-tetrahydroisoquinolin-7-yl)-1-methyl-ethylamine;
1-4-(benzofuran-2-yl)-2-methyl-1,2,3,4-tetrahydroisoquinolin-7-yl)-cyclopropylamine;
1-(4-benzofuran-2-yl-2-methyl-1,2,3,4-tetrahydroisoquinolin-7-yl)-1H-pyridin-2-one;
4-(benzofuran-2-yl)-7-methanesulfonyl-2-methyl-1,2,3,4-tetrahydroisoquinoline;
4-(benzofuran-2-yl)-2-methyl-1,2,3,4-tetrahydroisoquinoline-7-carbonitrile;
4-(benzofuran-2-yl)-2,8-dimethyl-1,2,3,4-tetrahydroisoquinoline;
4-(benzofuran-3-yl)-2-methyl-1,2,3,4-tetrahydroisoquinoline;
4-(benzofuran-3-yl)-2-methyl-7-(pyridazin-3-yl)-1,2,3,4-tetrahydroisoquinoline;
4-(benzofuran-3-yl)-2-methyl-7-(morpholin-4-yl)-1,2,3,4-tetrahydroisoquinoline;
4-(benzofuran-4-yl)-2-methyl-1,2,3,4-tetrahydroisoquinoline;
4-(benzofuran-4-yl)-2-methyl-7-(pyridazin-3-yl)-1,2,3,4-tetrahydroisoquinoline;
4-(benzofuran-4-yl)-2-methyl-7-(morpholin-4-yl)-1,2,3,4-tetrahydroisoquinoline;
4-(benzofuran-5-yl)-1,2,3,4-tetrahydroisoquinoline;
4-(benzofuran-5-yl)-1-methyl-1,2,3,4-tetrahydroisoquinoline;
4-(benzofuran-5-yl)-2-methyl-1,2,3,4-tetrahydroisoquinoline;
4-(benzofuran-5-yl)-8-fluoro-2-methyl-1,2,3,4-tetrahydroisoquinoline;
4-(benzofuran-5-yl)-2-ethyl-1,2,3,4-tetrahydroisoquinoline;
4-(benzofuran-5-yl)-1,2-dimethyl-1,2,3,4-tetrahydroisoquinoline;
4-(3-methyl-benzofuran-5-yl)-2-methyl-1,2,3,4-tetrahydroisoquinoline;
4-benzofuran-5-yl-2-methyl-1,2,3,4-tetrahydroisoquinolin-4-ol;
4-(benzofuran-5-yl)-4-methoxy-2-methyl-1,2,3,4-tetrahydroisoquinoline;
4-(benzofuran-5-yl)-2,4-dimethyl-1,2,3,4-tetrahydroisoquinoline;
4-(benzofuran-5-yl)-2-methyl-1,2,3,4-tetrahydroisoquinoline-4-carbonitrile;
4-(benzofuran-5-yl)-4-fluoro-2-methyl-1,2,3,4-tetrahydroisoquinoline;
4-(benzofuran-5-yl)-4-chloro-2-methyl-1,2,3,4-tetrahydroisoquinoline;
4-(benzofuran-5-yl)-2-methyl-1,2,3,4-tetrahydroisoquinolin-7-ol;
4-(benzofuran-5-yl)-7-methoxy-2-methyl-1,2,3,4-tetrahydroisoquinoline;
4-(benzofuran-5-yl)-2,7-dimethyl-1,2,3,4-tetrahydroisoquinoline;
4-(benzofuran-5-yl)-7-fluoro-2-methyl-1,2,3,4-tetrahydroisoquinoline;
4-(benzofuran-5-yl)-2-methyl-7-(pyridazin-3-yl)-1,2,3,4-tetrahydroisoquinoline;
4-(benzofuran-5-yl)-2-ethyl-7-pyridazin-3-yl-1,2,3,4-tetrahydroisoquinoline;
4-(benzofuran-5-yl)-2-methyl-7-(6-methyl-pyridazin-3-yl)-1,2,3,4-tetrahydroisoquinoline;
[6-4-(benzofuran-5-yl)-2-methyl-1,2,3,4-tetrahydroisoquinolin-7-yl)-pyridazin-3-yl]-dimethylamine;
[6-4-(benzofuran-5-yl)-2-methyl-1,2,3,4-tetrahydroisoquinolin-7-yl)-pyridazin-3-yl]-methylamine;
6-4-(benzofuran-5-yl)-2-methyl-1,2,3,4-tetrahydroisoquinolin-7-yl)-pyridazin-3-ylamine;
6-4-(benzofuran-5-yl)-2-methyl-7-(6-morpholin-4-yl-pyridazin-3-yl)-1,2,3,4-tetrahydroisoquinoline;
6-4-(benzofuran-5-yl)-2-methyl-7-(6-trifluoromethyl-pyridazin-3-yl)-1,2,3,4-tetrahydroisoquinoline;
6-(4-(benzofuran-5-yl)-2-methyl-1,2,3,4-tetrahydroisoquinolin-7-yl)-pyridazine-3-carbonitrile;
4-(benzofuran-5-yl)-8-fluoro-2-methyl-7-pyridazin-3-yl-1,2,3,4-tetrahydroisoquinoline;
4-(benzofuran-5-yl)-8-methoxy-2-methyl-7-pyridazin-3-yl-1,2,3,4-tetrahydroisoquinoline;
4-(benzofuran-5-yl)-2-methyl-7-pyridazin-3-yl-1,2,3,4-tetrahydroisoquinolin-8-ol;
4-(benzofuran-5-yl)-2,8-dimethyl-7-pyridazin-3-yl-1,2,3,4-tetrahydroisoquinoline;
4-(benzofuran-5-yl)-2-ethyl-8-fluoro-7-pyridazin-3-yl-1,2,3,4-tetrahydroisoquinoline;
4-(benzofuran-5-yl)-6-fluoro-2-methyl-7-pyridazin-3-yl-1,2,3,4-tetrahydroisoquinoline;
4-(benzofuran-5-yl)-5-fluoro-2-methyl-7-pyridazin-3-yl-1,2,3,4-tetrahydroisoquinoline;
4-(benzofuran-5-yl)-2-methyl-7-pyridazin-3-yl-1,2,3,4-tetrahydroisoquinolin-4-ol;
4-(benzofuran-5-yl)-2,4-dimethyl-7-pyridazin-3-yl-1,2,3,4-tetrahydroisoquinoline;
4-(benzofuran-5-yl)-2-methyl-7-(pyridazin-4-yl)-1,2,3,4-tetrahydroisoquinoline;
4-(benzofuran-5-yl)-8-fluoro-2-methyl-7-(pyridazin-4-yl)-1,2,3,4-tetrahydroisoquinoline;
4-(benzofuran-5-yl)-2-methyl-7-(pyrazin-2-yl)-1,2,3,4-tetrahydroisoquinoline;

4-(benzofuran-5-yl)-2-methyl-7-(3-methyl-pyrazin-2-yl)-1,2,3,4-tetrahydroisoquinoline;
4-(benzofuran-5-yl)-7-(3-methoxy-pyrazin-2-yl)-2-methyl-1,2,3,4-tetrahydroisoquinoline;
4-(benzofuran-5-yl)-2-methyl-7-(6-methyl-pyrazin-2-yl)-1,2,3,4-tetrahydroisoquinoline;
4-(benzofuran-5-yl)-7-(6-methoxy-pyrazin-2-yl)-2-methyl-1,2,3,4-tetrahydroisoquinoline;
4-(benzofuran-5-yl)-8-fluoro-2-methyl-7-pyrazin-2-yl-1,2,3,4-tetrahydroisoquinoline;
4-(benzofuran-5-yl)-8-methoxy-2-methyl-7-pyrazin-2-yl-1,2,3,4-tetrahydroisoquinoline
4-(benzofuran-5-yl)-2-methyl-7-pyrazin-2-yl-1,2,3,4-tetrahydroisoquinolin-8-ol;
4-(benzofuran-5-yl)-2,8-dimethyl-7-pyrazin-2-yl-1,2,3,4-tetrahydroisoquinoline;
4-((benzofuran-5-yl)-2-methyl-7-(pyrimidin-2-yl)-1,2,3,4-tetrahydroisoquinoline;
4-(benzofuran-5-yl)-8-fluoro-2-methyl-7-pyrimidin-2-yl-1,2,3,4-tetrahydroisoquinoline;
4-(benzofuran-5-yl)-8-methoxy-2-methyl-7-pyrimidin-2-yl-1,2,3,4-tetrahydroisoquinoline;
4-(benzofuran-5-yl)-2-methyl-7-pyrimidin-2-yl-1,2,3,4-tetrahydroisoquinolin-8-ol;
4-(benzofuran-5-yl)-2,8-dimethyl-7-pyrimidin-2-yl-1,2,3,4-tetrahydroisoquinoline;
4-((benzofuran-5-yl)-2-methyl-7-(pyrimidin-4-yl)-1,2,3,4-tetrahydroisoquinoline;
4-(benzofuran-5-yl)-8-fluoro-2-methyl-7-(pyrimidin-4-yl)-1,2,3,4-tetrahydroisoquinoline;
4-(benzofuran-5-yl)-8-methoxy-2-methyl-7-(pyrimidin-4-yl)-1,2,3,4-tetrahydroisoquinoline;
4-(benzofuran-5-yl)-2-methyl-7-(pyrimidin-4-yl)-1,2,3,4-tetrahydroisoquinolin-8-ol;
4-(benzofuran-5-yl)-2,8-dimethyl-7-(pyrimidin-4-yl)-1,2,3,4-tetrahydroisoquinoline;
4-(benzofuran-5-yl)-yl)-2-methyl-7-(pyrimidin-5-yl)-1,2,3,4-tetrahydroisoquinoline;
4-(benzofuran-5-yl)-8-fluoro-2-methyl-7-(pyrimidin-5-yl)-1,2,3,4-tetrahydroisoquinoline;
4-(benzofuran-5-yl)-8-methoxy-2-methyl-7-(pyrimidin-5-yl)-1,2,3,4-tetrahydroisoquinoline;
4-(benzofuran-5-yl)-2-methyl-7-(pyrimidin-5-yl)-1,2,3,4-tetrahydroisoquinolin-8-ol;
4-(benzofuran-5-yl)-2,8-dimethyl-7-(pyrimidin-5-yl)-1,2,3,4-tetrahydroisoquinoline;
4-(benzofuran-5-yl)-7-(3,5-dimethyl-isoxazol-4-yl)-2-methyl-1,2,3,4-tetrahydroisoquinoline;
4-(benzofuran-5-yl)-2-methyl-7-(thiazol-2-yl)-1,2,3,4-tetrahydroisoquinoline;
4-(benzofuran-5-yl)-2-methyl-7-(5-methyl-thiazol-2-yl)-1,2,3,4-tetrahydroisoquinoline;
4-(benzofuran-5-yl)-2-methyl-7-[1,3,5]triazin-2-yl-1,2,3,4-tetrahydroisoquinoline;
4-(benzofuran-5-yl)-2-methyl-7-[1,2,4]triazin-3-yl-1,2,3,4-tetrahydroisoquinoline;
4-(benzofuran-5-yl)-2-methyl-7-[1,2,4]triazin-5-yl-1,2,3,4-tetrahydroisoquinoline;
4-(benzofuran-5-yl)-2-methyl-7-[1,2,4]triazin-6-yl-1,2,3,4-tetrahydroisoquinoline;
3-(4-(benzofuran-5-yl)-2-methyl-1,2,3,4-tetrahydroisoquinolin-7-yl)-cinnoline;
1-(4-(benzofuran-5-yl)-2-methyl-1,2,3,4-tetrahydroisoquinolin-7-yl)-phthalazine;
2-(4-(benzofuran-5-yl)-2-methyl-1,2,3,4-tetrahydroisoquinolin-7-yl)-quinoxaline;
2-(4-(benzofuran-5-yl)-2-methyl-1,2,3,4-tetrahydroisoquinolin-7-yl)-quinazoline;
6-(4-(benzofuran-5-yl)-2-methyl-1,2,3,4-tetrahydroisoquinolin-7-yl)-quinazoline;
7-(4-(benzofuran-5-yl)-2-methyl-1,2,3,4-tetrahydroisoquinolin-7-yl)-quinazoline;
2-(4-(benzofuran-5-yl)-2-methyl-1,2,3,4-tetrahydroisoquinolin-7-yl)-2H-[1,2,4]triazolo[4,3-a]pyridin-3-one;
4-(benzofuran-5-yl)-2-methyl-7-(morpholin-4-yl)-1,2,3,4-tetrahydroisoquinoline;
4-(benzofuran-5-yl)-7-(2,6-dimethyl-morpholin-4-yl)-2-methyl-1,2,3,4-tetrahydroisoquinoline;
4-(benzofuran-5-yl)-2-ethyl-7-morpholin-4-yl-1,2,3,4-tetrahydroisoquinoline;
4-(benzofuran-5-yl)-8-fluoro-2-methyl-7-morpholin-4-yl-1,2,3,4-tetrahydroisoquinoline;
4-(benzofuran-5-yl)-8-methoxy-2-methyl-7-morpholin-4-yl-1,2,3,4-tetrahydroisoquinoline;
4-(benzofuran-5-yl)-2-methyl-7-morpholin-4-yl-1,2,3,4-tetrahydroisoquinolin-8-ol;
4-(benzofuran-5-yl)-2,8-dimethyl-7-morpholin-4-yl-1,2,3,4-tetrahydroisoquinoline;
4-(benzofuran-5-yl)-2-ethyl-8-fluoro-7-morpholin-4-yl-1,2,3,4-tetrahydroisoquinoline;
4-(benzofuran-5-yl)-6-fluoro-2-methyl-7-morpholin-4-yl-1,2,3,4-tetrahydroisoquinoline;
4-(benzofuran-5-yl)-5-fluoro-2-methyl-7-morpholin-4-yl-1,2,3,4-tetrahydroisoquinoline;
4-(benzofuran-5-yl)-2-methyl-7-morpholin-4-yl-1,2,3,4-tetrahydroisoquinolin-4-ol;
4-(benzofuran-5-yl)-2,4-dimethyl-7-morpholin-4-yl-1,2,3,4-tetrahydroisoquinoline;
4-(benzofuran-5-yl)-2-methyl-7-(piperidin-1-yl)-1,2,3,4-tetrahydroisoquinoline;
4-(benzofuran-5-yl)-2-methyl-7-(pyrrolidin-1-yl)-1,2,3,4-tetrahydroisoquinoline;
4-(benzofuran-5-yl)-2-methyl-7-(morpholin-4-yl)methyl-1,2,3,4-tetrahydroisoquinoline;
4-(benzofuran-5-yl)-2-methyl-7-(1-methyl-1-morpholin-4-yl-ethyl)-1,2,3,4-tetrahydroisoquinoline;
4-(benzofuran-5-yl)-2-methyl-7-(1-morpholin-4-yl-cyclopropyl)-1,2,3,4-tetrahydroisoquinoline;
4-(benzofuran-5-yl)-2-methyl-7-(piperidin-1-yl)methyl-1,2,3,4-tetrahydroisoquinoline;
4-(benzofuran-5-yl)-2-methyl-7-(pyrrolidin-1-yl)methyl-1,2,3,4-tetrahydroisoquinoline;
(4-(benzofuran-5-yl)-2-methyl-1,2,3,4-tetrahydroisoquinolin-7-ylmethyl)-dimethylamine;
[1-(4-(benzofuran-5-yl)-2-methyl-1,2,3,4-tetrahydroisoquinolin-7-yl)-1-methylethyl]-dimethylamine;
[1-(4-(benzofuran-5-yl)-2-methyl-1,2,3,4-tetrahydroisoquinolin-7-yl)-cyclopropyl]-dimethylamine;
(4-(benzofuran-5-yl)-2-methyl-1,2,3,4-tetrahydroisoquinolin-7-ylmethyl)-methylamine;
[1-(4-(benzofuran-5-yl)-2-methyl-1,2,3,4-tetrahydroisoquinolin-7-yl)-1-methylethyl]-methylamine;
[1-(4-(benzofuran-5-yl)-2-methyl-1,2,3,4-tetrahydroisoquinolin-7-yl)-cyclopropyl]-methylamine;
C-(4-(benzofuran-5-yl)-2-methyl-1,2,3,4-tetrahydroisoquinolin-7-yl)-methylamine;
1-(4-(benzofuran-5-yl)-2-methyl-1,2,3,4-tetrahydroisoquinolin-7-yl)-1-methyl-ethylamine;
1-(4-(benzofuran-5-yl)-2-methyl-1,2,3,4-tetrahydroisoquinolin-7-yl)-cyclopropylamine;
1-(4-(benzofuran-5-yl)-2-methyl-1,2,3,4-tetrahydroisoquinolin-7-yl)-1H-pyridin-2-one;

4-(benzofuran-5-yl)-7-methanesulfonyl-2-methyl-1,2,3,4-tetrahydroisoquinoline;
4-(benzofuran-5-yl)-2-methyl-1,2,3,4-tetrahydroisoquinoline-7-carbonitrile;
4-(benzofuran-5-yl)-8-fluoro-2-methyl-1,2,3,4-tetrahydroisoquinoline-7-carbonitrile;
4-(benzofuran-5-yl)-2,8-dimethyl-1,2,3,4-tetrahydroisoquinoline;
4-(2,3-dihydrobenzofuran-5-yl)-2-methyl-1,2,3,4-tetrahydroisoquinoline;
4-(benzofuran-6-yl)-1,2,3,4-tetrahydroisoquinoline;
4-(benzofuran-6-yl)-1-methyl-1,2,3,4-tetrahydroisoquinoline;
4-(benzofuran-6-yl)-2-methyl-1,2,3,4-tetrahydroisoquinoline;
4-(benzofuran-6-yl)-2-ethyl-1,2,3,4-tetrahydroisoquinoline;
4-(benzofuran-6-yl)-1,2-dimethyl-1,2,3,4-tetrahydroisoquinoline;
4-benzofuran-6-yl-2-methyl-1,2,3,4-tetrahydroisoquinolin-4-ol;
4-(benzofuran-6-yl)-4-methoxy-2-methyl-1,2,3,4-tetrahydroisoquinoline;
4-(benzofuran-6-yl)-2,4-dimethyl-1,2,3,4-tetrahydroisoquinoline;
4-(benzofuran-6-yl)-2-methyl-1,2,3,4-tetrahydroisoquinoline-4-carbonitrile;
4-(benzofuran-6-yl)-4-fluoro-2-methyl-1,2,3,4-tetrahydroisoquinoline;
4-(benzofuran-6-yl)-4-chloro-2-methyl-1,2,3,4-tetrahydroisoquinoline;
4-(benzofuran-6-yl)-2-methyl-1,2,3,4-tetrahydroisoquinolin-7-ol;
4-(benzofuran-6-yl)-7-methoxy-2-methyl-1,2,3,4-tetrahydroisoquinoline;
4-(benzofuran-6-yl)-2,7-dimethyl-1,2,3,4-tetrahydroisoquinoline;
4-(benzofuran-6-yl)-7-fluoro-2-methyl-1,2,3,4-tetrahydroisoquinoline;
4-(benzofuran-6-yl)-2-methyl-7-(pyridazin-3-yl)-1,2,3,4-tetrahydroisoquinoline;
4-(benzofuran-6-yl)-2-ethyl-7-pyridazin-3-yl-1,2,3,4-tetrahydroisoquinoline;
4-(benzofuran-6-yl)-2-methyl-7-(6-methyl-pyridazin-3-yl)-1,2,3,4-tetrahydroisoquinoline;
[6-(4-benzofuran-6-yl)-2-methyl-1,2,3,4-tetrahydroisoquinolin-7-yl)-pyridazin-3-yl]-dimethylamine;
[6-(4-benzofuran-6-yl)-2-methyl-1,2,3,4-tetrahydroisoquinolin-7-yl)-pyridazin-3-yl]-methylamine;
6-(4-benzofuran-6-yl)-2-methyl-1,2,3,4-tetrahydroisoquinolin-7-yl)-pyridazin-3-ylamine;
4-(benzofuran-6-yl)-2-methyl-7-(6-morpholin-4-yl-pyridazin-3-yl)-1,2,3,4-tetrahydroisoquinoline;
4-(benzofuran-6-yl)-2-methyl-7-(6-trifluoromethyl-pyridazin-3-yl)-1,2,3,4-tetrahydroisoquinoline;
4-(benzofuran-6-yl)-2-methyl-1,2,3,4-tetrahydroisoquinolin-7-yl)-pyridazine-3-carbonitrile;
4-(benzofuran-6-yl)-8-fluoro-2-methyl-7-pyridazin-3-yl-1,2,3,4-tetrahydroisoquinoline;
4-(benzofuran-6-yl)-8-methoxy-2-methyl-7-pyridazin-3-yl-1,2,3,4-tetrahydroisoquinoline;
4-(benzofuran-6-yl)-2-methyl-7-pyridazin-3-yl-1,2,3,4-tetrahydroisoquinolin-8-ol;
4-(benzofuran-6-yl)-2,8-dimethyl-7-pyridazin-3-yl-1,2,3,4-tetrahydroisoquinoline;
4-(benzofuran-6-yl)-2-ethyl-8-fluoro-7-pyridazin-3-yl-1,2,3,4-tetrahydroisoquinoline;
4-(benzofuran-6-yl)-6-fluoro-2-methyl-7-pyridazin-3-yl-1,2,3,4-tetrahydroisoquinoline;
4-(benzofuran-6-yl)-5-fluoro-2-methyl-7-pyridazin-3-yl-1,2,3,4-tetrahydroisoquinoline;
4-(benzofuran-6-yl-)-2-methyl-7-(pyridazin-4-yl)-1,2,3,4-tetrahydroisoquinoline;
4-(benzofuran-6-yl-)-8-fluoro-2-methyl-7-(pyridazin-4-yl)-1,2,3,4-tetrahydroisoquinoline;
4-(benzofuran-6-yl-)-2-methyl-7-(pyrazin-2-yl)-1,2,3,4-tetrahydroisoquinoline;
4-(benzofuran-6-yl)-2-methyl-7-(3-methyl-pyrazin-2-yl)-1,2,3,4-tetrahydroisoquinoline;
4-(benzofuran-6-yl)-7-(3-methoxy-pyrazin-2-yl)-2-methyl-1,2,3,4-tetrahydroisoquinoline;
4-(benzofuran-6-yl)-2-methyl-7-(6-methyl-pyrazin-2-yl)-1,2,3,4-tetrahydroisoquinoline;
4-(benzofuran-6-yl)-7-(6-methoxy-pyrazin-2-yl)-2-methyl-1,2,3,4-tetrahydroisoquinoline;
4-(benzofuran-6-yl)-8-fluoro-2-methyl-7-pyrazin-2-yl-1,2,3,4-tetrahydroisoquinoline;
4-(benzofuran-6-yl)-8-methoxy-2-methyl-7-pyrazin-2-yl-1,2,3,4-tetrahydroisoquinoline
4-(benzofuran-6-yl)-2-methyl-7-pyrazin-2-yl-1,2,3,4-tetrahydroisoquinolin-8-ol;
4-(benzofuran-6-yl)-2,8-dimethyl-7-pyrazin-2-yl-1,2,3,4-tetrahydroisoquinoline;
4-(benzofuran-6-yl-)-2-methyl-7-(pyrimidin-2-yl)-1,2,3,4-tetrahydroisoquinoline;
4-(benzofuran-6-yl)-8-fluoro-2-methyl-7-pyrimidin-2-yl-1,2,3,4-tetrahydroisoquinoline;
4-(benzofuran-6-yl)-8-methoxy-2-methyl-7-pyrimidin-2-yl-1,2,3,4-tetrahydroisoquinoline;
4-(benzofuran-6-yl)-2-methyl-7-pyrimidin-2-yl-1,2,3,4-tetrahydroisoquinolin-8-ol;
4-(benzofuran-6-yl)-2,8-dimethyl-7-pyrimidin-2-yl-1,2,3,4-tetrahydroisoquinoline;
4-(benzofuran-6-yl-)-2-methyl-7-(pyrimidin-4-yl)-1,2,3,4-tetrahydroisoquinoline;
4-(benzofuran-6-yl-)-8-fluoro-2-methyl-7-(pyrimidin-4-yl)-1,2,3,4-tetrahydroisoquinoline;
4-(benzofuran-6-yl-)-8-methoxy-2-methyl-7-(pyrimidin-4-yl)-1,2,3,4-tetrahydroisoquinoline;
4-(benzofuran-6-yl)-2-methyl-7-(pyrimidin-4-yl)-1,2,3,4-tetrahydroisoquinolin-8-ol;
4-(benzofuran-6-yl-)-2,8-dimethyl-7-(pyrimidin-4-yl)-1,2,3,4-tetrahydroisoquinoline;
4-(benzofuran-6-yl-)-2-methyl-7-(pyrimidin-5-yl)-1,2,3,4-tetrahydroisoquinoline;
4-(benzofuran-6-yl-)-8-fluoro-2-methyl-7-(pyrimidin-5-yl)-1,2,3,4-tetrahydroisoquinoline;
4-(benzofuran-6-yl-)-8-methoxy-2-methyl-7-(pyrimidin-5-yl)-1,2,3,4-tetrahydroisoquinoline;
4-(benzofuran-6-yl)-2-methyl-7-(pyrimidin-5-yl)-1,2,3,4-tetrahydroisoquinolin-8-ol;
4-(benzofuran-6-yl-)-2,8-dimethyl-7-(pyrimidin-5-yl)-1,2,3,4-tetrahydroisoquinoline;
4-(benzofuran-6-yl-)-7-(3,5-dimethyl-isoxazol-4-yl)-2-methyl-1,2,3,4-tetrahydroisoquinoline;
4-(benzofuran-6-yl-)-2-methyl-7-(thiazol-2-yl)-1,2,3,4-tetrahydroisoquinoline;
4-(benzofuran-6-yl-)-2-methyl-7-(5-methyl-thiazol-2-yl)-1,2,3,4-tetrahydroisoquinoline;
4-(benzofuran-6-yl)-2-methyl-7-[1,3,5]triazin-2-yl-1,2,3,4-tetrahydroisoquinoline;
4-(benzofuran-6-yl)-2-methyl-7-[1,2,4]triazin-3-yl-1,2,3,4-tetrahydroisoquinoline;

4-(benzofuran-6-yl)-2-methyl-7-[1,2,4]triazin-5-yl-1,2,3,4-tetrahydroisoquinoline;
4-(benzofuran-6-yl)-2-methyl-7-[1,2,4]triazin-6-yl-1,2,3,4-tetrahydroisoquinoline;
3-(4-(benzofuran-6-yl)-2-methyl-1,2,3,4-tetrahydroisoquinolin-7-yl)-cinnoline;
1-(4-(benzofuran-6-yl)-2-methyl-1,2,3,4-tetrahydroisoquinolin-7-yl)-phthalazine;
2-(4-(benzofuran-6-yl)-2-methyl-1,2,3,4-tetrahydroisoquinolin-7-yl)-quinoxaline;
2-(4-(benzofuran-6-yl)-2-methyl-1,2,3,4-tetrahydroisoquinolin-7-yl)-quinazoline;
6-(4-(benzofuran-6-yl)-2-methyl-1,2,3,4-tetrahydroisoquinolin-7-yl)-quinazoline;
7-(4-(benzofuran-6-yl)-2-methyl-1,2,3,4-tetrahydroisoquinolin-7-yl)-quinazoline;
2-(4-(benzofuran-6-yl)-2-methyl-1,2,3,4-tetrahydroisoquinolin-7-yl)-2H-[1,2,4]triazolo[4,3-a]pyridin-3-one;
4-(benzofuran-6-yl-)-2-methyl-7-(morpholin-4-yl)-1,2,3,4-tetrahydroisoquinoline;
4-(benzofuran-6-yl)-7-(2,6-dimethyl-morpholin-4-yl)-2-methyl-1,2,3,4-tetrahydroisoquinoline;
4-(benzofuran-6-yl)-2-ethyl-7-morpholin-4-yl-1,2,3,4-tetrahydroisoquinoline;
4-(benzofuran-6-yl)-8-fluoro-2-methyl-7-morpholin-4-yl-1,2,3,4-tetrahydroisoquinoline;
4-(benzofuran-6-yl)-8-methoxy-2-methyl-7-morpholin-4-yl-1,2,3,4-tetrahydroisoquinoline;
4-(benzofuran-6-yl)-2-methyl-7-morpholin-4-yl-1,2,3,4-tetrahydroisoquinolin-8-ol;
4-(benzofuran-6-yl)-2,8-dimethyl-7-morpholin-4-yl-1,2,3,4-tetrahydroisoquinoline;
4-(benzofuran-6-yl)-2-ethyl-8-fluoro-7-morpholin-4-yl-1,2,3,4-tetrahydroisoquinoline;
4-(benzofuran-6-yl)-6-fluoro-2-methyl-7-morpholin-4-yl-1,2,3,4-tetrahydroisoquinoline;
4-(benzofuran-6-yl)-5-fluoro-2-methyl-7-morpholin-4-yl-1,2,3,4-tetrahydroisoquinoline;
4-(benzofuran-6-yl)-2-methyl-7-morpholin-4-yl-1,2,3,4-tetrahydroisoquinolin-4-ol;
4-(benzofuran-6-yl)-2,4-dimethyl-7-morpholin-4-yl-1,2,3,4-tetrahydroisoquinoline;
4-(benzofuran-6-yl-)-2-methyl-7-(piperidin-1-yl)-1,2,3,4-tetrahydroisoquinoline;
4-(benzofuran-6-yl-)-2-methyl-7-(pyrrolidin-1-yl)-1,2,3,4-tetrahydroisoquinoline;
4-(benzofuran-6-yl-)-2-methyl-7-(morpholin-4-yl)methyl-1,2,3,4-tetrahydroisoquinoline;
4-(benzofuran-6-yl)-2-methyl-7-(1-methyl-1-morpholin-4-yl-ethyl)-1,2,3,4-tetrahydroisoquinoline;
4-(benzofuran-6-yl)-2-methyl-7-(1-morpholin-4-yl-cyclopropyl)-1,2,3,4-tetrahydroisoquinoline;
4-(benzofuran-6-yl-)-2-methyl-7-(piperidin-1-yl)methyl-1,2,3,4-tetrahydroisoquinoline;
4-(benzofuran-6-yl-)-2-methyl-7-(pyrrolidin-1-yl)methyl-1,2,3,4-tetrahydroisoquinoline;
(4-(benzofuran-6-yl)-2-methyl-1,2,3,4-tetrahydroisoquinolin-7-ylmethyl)-dimethylamine;
[1-(4-(benzofuran-6-yl)-2-methyl-1,2,3,4-tetrahydroisoquinolin-7-yl)-1-methylethyl]-dimethylamine;
[1-(4-(benzofuran-6-yl)-2-methyl-1,2,3,4-tetrahydroisoquinolin-7-yl)-cyclopropyl]-dimethylamine;
(4-(benzofuran-6-yl)-2-methyl-1,2,3,4-tetrahydroisoquinolin-7-ylmethyl)-methylamine;
[1-(4-(benzofuran-6-yl)-2-methyl-1,2,3,4-tetrahydroisoquinolin-7-yl)-1-methylethyl]-methylamine;
[1-(4-(benzofuran-6-yl)-2-methyl-1,2,3,4-tetrahydroisoquinolin-7-yl)-cyclopropyl]-methylamine;
C-(4-(benzofuran-6-yl)-2-methyl-1,2,3,4-tetrahydroisoquinolin-7-yl)-methylamine;
1-(4-(benzofuran-6-yl)-2-methyl-1,2,3,4-tetrahydroisoquinolin-7-yl)-1-methyl-ethylamine;
1-(4-(benzofuran-6-yl)-2-methyl-1,2,3,4-tetrahydroisoquinolin-7-yl)-cyclopropylamine;
1-(4-(benzofuran-6-yl)-2-methyl-1,2,3,4-tetrahydroisoquinolin-7-yl)-1H-pyridin-2-one;
4-(benzofuran-6-yl-)-7-methanesulfonyl-2-methyl-1,2,3,4-tetrahydroisoquinoline;
4-(benzofuran-6-yl-)-2-methyl-1,2,3,4-tetrahydroisoquinoline-7-carbonitrile;
4-(benzofuran-6-yl)-8-fluoro-2-methyl-1,2,3,4-tetrahydroisoquinoline-7-carbonitrile;
4-(benzofuran-6-yl)-2,8-dimethyl-1,2,3,4-tetrahydroisoquinoline;
4-(benzofuran-7-yl)-2-methyl-1,2,3,4-tetrahydroisoquinoline;
4-(benzofuran-7-yl)-2-ethyl-1,2,3,4-tetrahydroisoquinoline;
4-(benzofuran-7-yl)-8-fluoro-2-methyl-1,2,3,4-tetrahydroisoquinoline;
4-(benzofuran-7-yl)-2-ethyl-8-fluoro-1,2,3,4-tetrahydroisoquinoline;
4-(benzofuran-7-yl)-2-methyl-7-(pyridazin-3-yl)-1,2,3,4-tetrahydroisoquinoline;
4-(benzofuran-7-yl)-2-methyl-7-(morpholin-4-yl)-1,2,3,4-tetrahydroisoquinoline;

or an oxide thereof, a pharmaceutically acceptable salt thereof, a solvate thereof, or a prodrug thereof.

In addition, other specific compounds of the present invention are those with the following substituents:

TABLE C

| X | $R^1$ | $R^2$ | $R^3$ | $R^4$ | $R^5$ | $R^6$ | $R^7$ | $R^8$ |
|---|---|---|---|---|---|---|---|---|
| indol-1-yl | Me | H | H | H | H | H | H | H |
| 1H-indol-2-yl | H | H | H | H | H | H | H | H |
| 1H-indol-2-yl | H | Me | H | H | H | H | H | H |
| 1H-indol-2-yl | Me | H | H | H | H | H | H | H |
| 1H-indol-2-yl | Et | H | H | H | H | H | H | H |
| 1H-indol-2-yl | Me | Me | H | H | H | H | H | H |
| 5-methoxy-1H-indol-2-yl | Me | H | H | H | H | H | H | H |
| 1H-indol-2-yl | Me | H | H | H | H | H | H | OH |
| 1H-indol-2-yl | Me | H | H | H | H | H | H | OMe |
| 1H-indol-2-yl | Me | H | H | H | H | H | H | Me |
| 1H-indol-2-yl | Me | H | H | H | H | H | H | CN |
| 1H-indol-2-yl | Me | H | H | H | H | H | H | F |
| 1H-indol-2-yl | Me | H | H | H | H | H | H | Cl |
| 1H-indol-2-yl | Me | H | H | OH | H | H | H | H |
| 1H-indol-2-yl | Me | H | H | OMe | H | H | H | H |
| 1H-indol-2-yl | Me | H | H | Me | H | H | H | H |
| 1H-indol-2-yl | Me | H | H | F | H | H | H | H |
| 1H-indol-2-yl | Me | H | H | pyridazin-3-yl | H | H | H | H |
| 1-methyl-1H-indol-2-yl | Me | H | H | pyridazin-3-yl | H | H | H | H |
| 7-fluoro-1H-indol-2-yl | Me | H | H | pyridazin-3-yl | H | H | H | H |

TABLE C-continued

| X | R¹ | R² | R³ | R⁴ | R⁵ | R⁶ | R⁷ | R⁸ |
|---|---|---|---|---|---|---|---|---|
| 1H-indol-2-yl | Et | H | H | pyridazin-3-yl | H | H | H | H |
| 1H-indol-2-yl | Me | H | H | 6-methyl-pyridazin-3-yl | H | H | H | H |
| 1H-indol-2-yl | Me | H | H | 6-dimethyl-amino-pyridazin-3-yl | H | H | H | H |
| 1H-indol-2-yl | Me | H | H | 6-methylamino-pyridazin-3-yl | H | H | H | H |
| 1H-indol-2-yl | Me | H | H | 6-amino-pyridazin-3-yl | H | H | H | H |
| 1H-indol-2-yl | Me | H | H | 6-morpholin-4-yl-pyridazin-3-yl | H | H | H | H |
| 1H-indol-2-yl | Me | H | H | 6-trifluoromethyl-pyridazin-3-yl | H | H | H | H |
| 1H-indol-2-yl | Me | H | H | 6-cyano-pyridazin-3-yl | H | H | H | H |
| 1H-indol-2-yl | Me | H | F | pyridazin-3-yl | H | H | H | H |
| 1H-indol-2-yl | Et | H | F | pyridazin-3-yl | H | H | H | H |
| 1H-indol-2-yl | Me | H | H | pyridazin-3-yl | F | H | H | H |
| 1H-indol-2-yl | Me | H | H | pyridazin-3-yl | H | F | H | H |
| 1H-indol-2-yl | Me | H | OMe | pyridazin-3-yl | H | H | H | H |
| 1H-indol-2-yl | Me | H | OH | pyridazin-3-yl | H | H | H | H |
| 1H-indol-2-yl | Me | H | Me | pyridazin-3-yl | H | H | H | H |
| 1H-indol-2-yl | Me | H | H | pyridazin-3-yl | H | H | H | OH |
| 1H-indol-2-yl | Me | H | H | pyridazin-3-yl | H | H | H | Me |
| 1H-indol-2-yl | Me | H | H | pyridazin-4-yl | H | H | H | H |
| 1H-indol-2-yl | Me | H | F | pyridazin-4-yl | H | H | H | H |
| 1H-indol-2-yl | Me | H | H | pyrazin-2-yl | H | H | H | H |
| 1H-indol-2-yl | Me | H | H | 3-methyl-pyrazin-2-yl | H | H | H | H |
| 1H-indol-2-yl | Me | H | H | 3-methoxy-pyrazin-2-yl | H | H | H | H |
| 1H-indol-2-yl | Me | H | H | 6-methyl-pyrazin-2-yl | H | H | H | H |
| 1H-indol-2-yl | Me | H | H | 6-methoxy-pyrazin-2-yl | H | H | H | H |
| 1H-indol-2-yl | Me | H | F | pyrazin-2-yl | H | H | H | H |
| 1H-indol-2-yl | Me | H | H | pyrimidin-2-yl | H | H | H | H |
| 1H-indol-2-yl | Me | H | F | pyrimidin-2-yl | H | H | H | H |
| 1H-indol-2-yl | Me | H | H | pyrimidin-4-yl | H | H | H | H |
| 1H-indol-2-yl | Me | H | F | pyrimidin-4-yl | H | H | H | H |
| 1H-indol-2-yl | Me | H | H | pyrimidin-5-yl | H | H | H | H |
| 1H-indol-2-yl | Me | H | F | pyrimidin-5-yl | H | H | H | H |
| 1H-indol-2-yl | Me | H | H | 3,5-dimethyl-isoxazol-4-yl | H | H | H | H |
| 1H-indol-2-yl | Me | H | H | thiazol-2-yl | H | H | H | H |
| 1H-indol-2-yl | Me | H | H | 5-methyl-thiazol-2-yl | H | H | H | H |
| 1H-indol-2-yl | Me | H | H | cinnolin-3-yl | H | H | H | H |
| 1H-indol-2-yl | Me | H | H | phthalazin-1-yl | H | H | H | H |
| 1H-indol-2-yl | Me | H | H | quinoxalin-2-yl | H | H | H | H |
| 1H-indol-2-yl | Me | H | H | quinazolin-2-yl | H | H | H | H |
| 1H-indol-2-yl | Me | H | H | quinazolin-6-yl | H | H | H | H |
| 1H-indol-2-yl | Me | H | H | quinazolin-7-yl | H | H | H | H |
| 1H-indol-2-yl | Me | H | H | 3-oxo-[1,2,4]triazolo[4,3-a]pyridin-2-yl | H | H | H | H |
| 1H-indol-2-yl | Me | H | H | morpholin-4-yl | H | H | H | H |
| 1-methyl-indol-2-yl | Me | H | H | morpholin-4-yl | H | H | H | H |
| 7-fluoro-1H-indol-2-yl | Me | H | H | morpholin-4-yl | H | H | H | H |
| 1H-indol-2-yl | Me | H | H | 2,6-dimethyl-morpholin-4-yl | H | H | H | H |
| 1H-indol-2-yl | Et | H | H | morpholin-4-yl | H | H | H | H |
| 1H-indol-2-yl | Me | H | F | morpholin-4-yl | H | H | H | H |
| 1H-indol-2-yl | Et | H | F | morpholin-4-yl | H | H | H | H |
| 1H-indol-2-yl | Me | H | H | morpholin-4-yl | F | H | H | H |
| 1H-indol-2-yl | Me | H | H | morpholin-4-yl | H | F | H | H |
| 1H-indol-2-yl | Me | H | OMe | morpholin-4-yl | H | H | H | H |
| 1H-indol-2-yl | Me | H | OH | morpholin-4-yl | H | H | H | H |
| 1H-indol-2-yl | Me | Me | H | morpholin-4-yl | H | H | H | H |
| 1H-indol-2-yl | Me | H | H | morpholin-4-yl | H | H | H | OH |
| 1H-indol-2-yl | Me | H | H | morpholin-4-yl | H | H | H | Me |
| 1H-indol-2-yl | Me | H | H | piperidin-1-yl | H | H | H | H |
| 1H-indol-2-yl | Me | H | H | pyrrolidin-1-yl | H | H | H | H |
| 1H-indol-2-yl | Me | H | H | morpholin-4-ylmethyl | H | H | H | H |
| 1H-indol-2-yl | Me | H | H | 1-methyl-1-morpholin-4-yl-ethyl | H | H | H | H |
| 1H-indol-2-yl | Me | H | H | 1-morpholin-4-yl-cyclopropyl | H | H | H | H |
| 1H-indol-2-yl | Me | H | H | piperidin-1-ylmethyl | H | H | H | H |
| 1H-indol-2-yl | Me | H | H | pyrrolidin-1-ylmethyl | H | H | H | H |
| 1H-indol-2-yl | Me | H | H | $CH_2NMe_2$ | H | H | H | H |
| 1H-indol-2-yl | Me | H | H | 1-dimethyl-amino-1-methylethyl | H | H | H | H |
| 1H-indol-2-yl | Me | H | H | 1-dimethyl-aminocyclopropyl | H | H | H | H |
| 1H-indol-2-yl | Me | H | H | $CH_2NHMe$ | H | H | H | H |
| 1H-indol-2-yl | Me | H | H | 1-methyl-1-methylaminoethyl | H | H | H | H |
| 1H-indol-2-yl | Me | H | H | 1-methylamino-cyclopropyl | H | H | H | H |
| 1H-indol-2-yl | Me | H | H | $CH_2NH_2$ | H | H | H | H |
| 1H-indol-2-yl | Me | H | H | 1-amino-1-methylethyl | H | H | H | H |
| 1H-indol-2-yl | Me | H | H | 1-amino-cyclopropyl | H | H | H | H |
| 1H-indol-2-yl | Me | H | H | 2-oxo-2H-pyridin-1-yl | H | H | H | H |
| 1H-indol-2-yl | Me | H | H | $SO_2CH_3$ | H | H | H | H |
| 1H-indol-2-yl | Me | H | H | CN | H | H | H | H |
| 1H-indol-2-yl | Me | H | Me | H | H | H | H | H |
| 1H-indol-3-yl | Me | H | H | H | H | H | H | H |
| 1H-indol-4-yl | Me | H | H | H | H | H | H | H |
| 1H-indol-5-yl | H | H | H | H | H | H | H | H |
| 1H-indol-5-yl | H | Me | H | H | H | H | H | H |
| 1H-indol-5-yl | Et | H | H | H | H | H | H | H |
| 1H-indol-5-yl | Me | Me | H | H | H | H | H | H |
| 1H-indol-5-yl | Me | H | H | H | H | H | H | OH |
| 1H-indol-5-yl | Me | H | H | H | H | H | H | OMe |
| 1H-indol-5-yl | Me | H | H | H | H | H | H | Me |
| 1H-indol-5-yl | Me | H | H | H | H | H | H | CN |
| 1H-indol-5-yl | Me | H | H | H | H | H | H | F |
| 1H-indol-5-yl | Me | H | H | H | H | H | H | Cl |
| 1H-indol-5-yl | Me | H | H | OH | H | H | H | H |
| 1H-indol-5-yl | Me | H | H | OMe | H | H | H | H |
| 1H-indol-5-yl | Me | H | H | Me | H | H | H | H |
| 1H-indol-5-yl | Me | H | H | F | H | H | H | H |
| 1H-indol-5-yl | Me | H | H | pyridazin-3-yl | H | H | H | H |
| 1-methyl-indol-5-yl | Me | H | H | pyridazin-3-yl | H | H | H | H |
| 7-fluoro-1H-indol-5-yl | Me | H | H | pyridazin-3-yl | H | H | H | H |
| 1H-indol-5-yl | Et | H | H | pyridazin-3-yl | H | H | H | H |
| 1H-indol-5-yl | Me | H | H | 6-methyl-pyridazin-3-yl | H | H | H | H |

TABLE C-continued

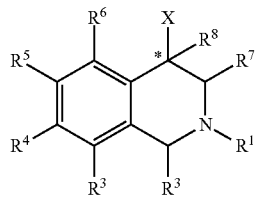

| X | R¹ | R² | R³ | R⁴ | R⁵ | R⁶ | R⁷ | R⁸ |
|---|---|---|---|---|---|---|---|---|
| 1H-indol-5-yl | Me | H | H | 6-dimethylamino-pyridazin-3-yl | H | H | H | H |
| 1H-indol-5-yl | Me | H | H | 6-methylamino-pyridazin-3-yl | H | H | H | H |
| 1H-indol-5-yl | Me | H | H | 6-amino-pyridazin-3-yl | H | H | H | H |
| 1H-indol-5-yl | Me | H | H | 6-morpholin-4-yl-pyridazin-3-yl | H | H | H | H |
| 1H-indol-5-yl | Me | H | H | 6-trifluoromethyl-pyridazin-3-yl | H | H | H | H |
| 1H-indol-5-yl | Me | H | H | 6-cyano-pyridazin-3-yl | H | H | H | H |
| 1H-indol-5-yl | Me | H | F | pyridazin-3-yl | H | H | H | H |
| 1H-indol-5-yl | Et | H | F | pyridazin-3-yl | H | H | H | H |
| 1H-indol-5-yl | Me | H | H | pyridazin-3-yl | F | H | H | H |
| 1H-indol-5-yl | Me | H | H | pyridazin-3-yl | H | F | H | H |
| 1H-indol-5-yl | Me | H | OMe | pyridazin-3-yl | H | H | H | H |
| 1H-indol-5-yl | Me | H | OH | pyridazin-3-yl | H | H | H | H |
| 1H-indol-5-yl | Me | H | Me | pyridazin-3-yl | H | H | H | H |
| 1H-indol-5-yl | Me | H | H | pyridazin-3-yl | H | H | H | OH |
| 1H-indol-5-yl | Me | H | H | pyridazin-3-yl | H | H | H | Me |
| 1H-indol-5-yl | Me | H | H | pyridazin-4-yl | H | H | H | H |
| 1H-indol-5-yl | Me | H | F | pyridazin-4-yl | H | H | H | H |
| 1H-indol-5-yl | Me | H | H | pyrazin-2-yl | H | H | H | H |
| 1H-indol-5-yl | Me | H | H | 3-methyl-pyrazin-2-yl | H | H | H | H |
| 1H-indol-5-yl | Me | H | H | 3-methoxy-pyrazin-2-yl | H | H | H | H |
| 1H-indol-5-yl | Me | H | H | 6-methyl-pyrazin-2-yl | H | H | H | H |
| 1H-indol-5-yl | Me | H | H | 6-methoxy-pyrazin-2-yl | H | H | H | H |
| 1H-indol-5-yl | Me | H | H | pyrazin-2-yl | H | F | H | H |
| 1H-indol-5-yl | Me | H | H | pyrimidin-2-yl | H | H | H | H |
| 1H-indol-5-yl | Me | H | F | pyrimidin-2-yl | H | H | H | H |
| 1H-indol-5-yl | Me | H | H | pyrimidin-4-yl | H | H | H | H |
| 1H-indol-5-yl | Me | H | F | pyrimidin-4-yl | H | H | H | H |
| 1H-indol-5-yl | Me | H | H | pyrimidin-5-yl | H | H | H | H |
| 1H-indol-5-yl | Me | H | F | pyrimidin-5-yl | H | H | H | H |
| 1H-indol-5-yl | Me | H | H | 3,5-dimethyl-isoxazol-4-yl | H | H | H | H |
| 1H-indol-5-yl | Me | H | H | thiazol-2-yl | H | H | H | H |
| 1H-indol-5-yl | Me | H | H | 5-methyl-thiazol-2-yl | H | H | H | H |
| 1H-indol-5-yl | Me | H | H | cinnolin-3-yl | H | H | H | H |
| 1H-indol-5-yl | Me | H | H | phthalazin-1-yl | H | H | H | H |
| 1H-indol-5-yl | Me | H | H | quinoxalin-2-yl | H | H | H | H |
| 1H-indol-5-yl | Me | H | H | quinazolin-2-yl | H | H | H | H |
| 1H-indol-5-yl | Me | H | H | quinazolin-6-yl | H | H | H | H |
| 1H-indol-5-yl | Me | H | H | quinazolin-7-yl | H | H | H | H |
| 1H-indol-5-yl | Me | H | H | 3-oxo-[1,2,4]triazolo[4,3-a]pyridin-2-yl | H | H | H | H |
| 1H-indol-5-yl | Me | H | H | morpholin-4-yl | H | H | H | H |
| 1-methyl-indol-5-yl | Me | H | H | morpholin-4-yl | H | H | H | H |
| 7-fluoro-1H-indol-5-yl | Me | H | H | morpholin-4-yl | H | H | H | H |
| 1H-indol-5-yl | Me | H | H | 2,6-dimethyl-morpholin-4-yl | H | H | H | H |
| 1H-indol-5-yl | Et | H | H | morpholin-4-yl | H | H | H | H |
| 1H-indol-5-yl | Me | H | F | morpholin-4-yl | H | H | H | H |
| 1H-indol-5-yl | Et | H | F | morpholin-4-yl | H | H | H | H |
| 1H-indol-5-yl | Me | H | H | morpholin-4-yl | F | H | H | H |
| 1H-indol-5-yl | Me | H | H | morpholin-4-yl | H | F | H | H |
| 1H-indol-5-yl | Me | H | OMe | morpholin-4-yl | H | H | H | H |
| 1H-indol-5-yl | Me | H | OH | morpholin-4-yl | H | H | H | H |

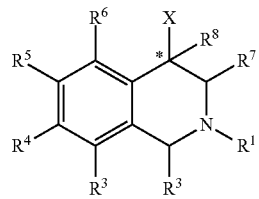

| X | R¹ | R² | R³ | R⁴ | R⁵ | R⁶ | R⁷ | R⁸ |
|---|---|---|---|---|---|---|---|---|
| 1H-indol-5-yl | Me | H | Me | morpholin-4-yl | H | H | H | H |
| 1H-indol-5-yl | Me | H | H | morpholin-4-yl | H | H | H | OH |
| 1H-indol-5-yl | Me | H | H | morpholin-4-yl | H | H | H | Me |
| 1H-indol-5-yl | Me | H | H | piperidin-1-yl | H | H | H | H |
| 1H-indol-5-yl | Me | H | H | pyrrolidin-1-yl | H | H | H | H |
| 1H-indol-5-yl | Me | H | H | morpholin-4-ylmethyl | H | H | H | H |
| 1H-indol-5-yl | Me | H | H | 1-methyl-1-morpholin-4-yl-ethyl | H | H | H | H |
| 1H-indol-5-yl | Me | H | H | 1-morpholin-4-yl-cyclopropyl | H | H | H | H |
| 1H-indol-5-yl | Me | H | H | piperidin-1-ylmethyl | H | H | H | H |
| 1H-indol-5-yl | Me | H | H | pyrrolidin-1-ylmethyl | H | H | H | H |
| 1H-indol-5-yl | Me | H | H | CH₂NMe₂ | H | H | H | H |
| 1H-indol-5-yl | Me | H | H | 1-dimethyl-amino-1-methylethyl | H | H | H | H |
| 1H-indol-5-yl | Me | H | H | 1-dimethyl-amino-cyclopropyl | H | H | H | H |
| 1H-indol-5-yl | Me | H | H | CH₂NHMe | H | H | H | H |
| 1H-indol-5-yl | Me | H | H | 1-methyl-1-methylaminoethyl | H | H | H | H |
| 1H-indol-5-yl | Me | H | H | 1-methylamino-cyclopropyl | H | H | H | H |
| 1H-indol-5-yl | Me | H | H | CH₂NH₂ | H | H | H | H |
| 1H-indol-5-yl | Me | H | H | 1-amino-1-methylethyl | H | H | H | H |
| 1H-indol-5-yl | Me | H | H | 1-amino-cyclopropyl | H | H | H | H |
| 1H-indol-5-yl | Me | H | H | 2-oxo-2H-pyridin-1-yl | H | H | H | H |
| 1H-indol-5-yl | Me | H | H | SO₂CH₃ | H | H | H | H |
| 1H-indol-5-yl | Me | H | H | CN | H | H | H | H |
| 1H-indol-5-yl | Me | H | Me | H | H | H | H | H |
| 1-benzyl-1H-indol-5-yl | Me | H | H | H | H | H | H | H |
| 1H-indol-6-yl | H | H | H | H | H | H | H | H |
| 1H-indol-6-yl | H | Me | H | H | H | H | H | H |
| 1H-indol-6-yl | Me | H | H | H | H | H | H | H |
| 3-chloro-1H-indol-6-yl | Me | H | H | H | H | H | H | H |
| 1H-indol-6-yl | Et | H | H | H | H | H | H | H |
| 1H-indol-6-yl | Me | Me | H | H | H | H | H | H |
| 1H-indol-6-yl | Me | H | H | H | H | H | H | OH |
| 1H-indol-6-yl | Me | H | H | H | H | H | H | OMe |
| 1H-indol-6-yl | Me | H | H | H | H | H | H | Me |
| 1H-indol-6-yl | Me | H | H | H | H | H | H | CN |
| 1H-indol-6-yl | Me | H | H | H | H | H | H | F |
| 1H-indol-6-yl | Me | H | H | H | H | H | H | Cl |
| 1H-indol-6-yl | Me | H | H | OH | H | H | H | H |
| 1H-indol-6-yl | Me | H | H | OMe | H | H | H | H |
| 1H-indol-6-yl | Me | H | H | Me | H | H | H | H |
| 1H-indol-6-yl | Me | H | H | F | H | H | H | H |
| 1H-indol-6-yl | Me | H | H | pyridazin-3-yl | H | H | H | H |
| 1-methyl-indol-6-yl | Me | H | H | pyridazin-3-yl | H | H | H | H |
| 7-fluoro-1H-indol-6-yl | Me | H | H | pyridazin-3-yl | H | H | H | H |
| 1H-indol-6-yl | Et | H | H | pyridazin-3-yl | H | H | H | H |
| 1H-indol-6-yl | Me | H | H | 6-methyl-pyridazin-3-yl | H | H | H | H |
| 1H-indol-6-yl | Me | H | H | 6-dimethyl-amino-pyridazin-3-yl | H | H | H | H |

TABLE C-continued

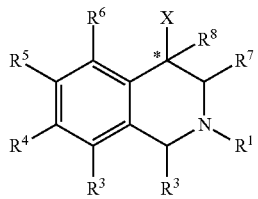

| X | R¹ | R² | R³ | R⁴ | R⁵ | R⁶ | R⁷ | R⁸ |
|---|---|---|---|---|---|---|---|---|
| 1H-indol-6-yl | Me | H | H | 6-methylamino-pyridazin-3-yl | H | H | H | H |
| 1H-indol-6-yl | Me | H | H | 6-amino-pyridazin-3-yl | H | H | H | H |
| 1H-indol-6-yl | Me | H | H | 6-morpholin-4-yl-pyridazin-3-yl | H | H | H | H |
| 1H-indol-6-yl | Me | H | H | 6-trifluoromethyl-pyridazin-3-yl | H | H | H | H |
| 1H-indol-6-yl | Me | H | H | 6-cyano-pyridazin-3-yl | H | H | H | H |
| 1H-indol-6-yl | Me | H | F | pyridazin-3-yl | H | H | H | H |
| 1H-indol-6-yl | Et | H | F | pyridazin-3-yl | H | H | H | H |
| 1H-indol-6-yl | Me | H | H | pyridazin-3-yl | F | H | H | H |
| 1H-indol-6-yl | Me | H | H | pyridazin-3-yl | H | F | H | H |
| 1H-indol-6-yl | Me | H | OMe | pyridazin-3-yl | H | H | H | H |
| 1H-indol-6-yl | Me | H | OH | pyridazin-3-yl | H | H | H | H |
| 1H-indol-6-yl | Me | H | Me | pyridazin-3-yl | H | H | H | H |
| 1H-indol-6-yl | Me | H | H | pyridazin-3-yl | H | H | H | OH |
| 1H-indol-6-yl | Me | H | H | pyridazin-3-yl | H | H | H | Me |
| 1H-indol-6-yl | Me | H | H | pyridazin-4-yl | H | H | H | H |
| 1H-indol-6-yl | Me | H | F | pyridazin-4-yl | H | H | H | H |
| 1H-indol-6-yl | Me | H | H | pyrazin-2-yl | H | H | H | H |
| 1H-indol-6-yl | Me | H | H | 3-methyl-pyrazin-2-yl | H | H | H | H |
| 1H-indol-6-yl | Me | H | H | 3-methoxy-pyrazin-2-yl | H | H | H | H |
| 1H-indol-6-yl | Me | H | H | 6-methyl-pyrazin-2-yl | H | H | H | H |
| 1H-indol-6-yl | Me | H | H | 6-methoxy-pyrazin-2-yl | H | H | H | H |
| 1H-indol-6-yl | Me | H | F | pyrazin-2-yl | H | H | H | H |
| 1H-indol-6-yl | Me | H | H | pyrimidin-2-yl | H | H | H | H |
| 1H-indol-6-yl | Me | H | F | pyrimidin-2-yl | H | H | H | H |
| 1H-indol-6-yl | Me | H | H | pyrimidin-4-yl | H | H | H | H |
| 1H-indol-6-yl | Me | H | F | pyrimidin-4-yl | H | H | H | H |
| 1H-indol-6-yl | Me | H | H | pyrimidin-5-yl | H | H | H | H |
| 1H-indol-6-yl | Me | H | F | pyrimidin-5-yl | H | H | H | H |
| 1H-indol-6-yl | Me | H | H | 3,5-dimethyl-isoxazol-4-yl | H | H | H | H |
| 1H-indol-6-yl | Me | H | H | thiazol-2-yl | H | H | H | H |
| 1H-indol-6-yl | Me | H | H | 5-methyl-thiazol-2-yl | H | H | H | H |
| 1H-indol-6-yl | Me | H | H | cinnolin-3-yl | H | H | H | H |
| 1H-indol-6-yl | Me | H | H | phthalazin-1-yl | H | H | H | H |
| 1H-indol-6-yl | Me | H | H | quinoxalin-2-yl | H | H | H | H |
| 1H-indol-6-yl | Me | H | H | quinazolin-2-yl | H | H | H | H |
| 1H-indol-6-yl | Me | H | H | quinazolin-6-yl | H | H | H | H |
| 1H-indol-6-yl | Me | H | H | quinazolin-7-yl | H | H | H | H |
| 1H-indol-6-yl | Me | H | H | 3-oxo-[1,2,4]triazolo[4,3-a]pyridin-2-yl | H | H | H | H |
| 1H-indol-6-yl | Me | H | H | morpholin-4-yl | H | H | H | H |
| 1-methyl-indol-6-yl | Me | H | H | morpholin-4-yl | H | H | H | H |
| 7-fluoro-1H-indol-6-yl | Me | H | H | morpholin-4-yl | H | H | H | H |
| 1H-indol-6-yl | Me | H | H | 2,6-dimethyl-morpholin-4-yl | H | H | H | H |
| 1H-indol-6-yl | Et | H | H | morpholin-4-yl | H | H | H | H |
| 1H-indol-6-yl | Me | H | F | morpholin-4-yl | H | H | H | H |
| 1H-indol-6-yl | Et | H | F | morpholin-4-yl | H | H | H | H |
| 1H-indol-6-yl | Me | H | H | morpholin-4-yl | F | H | H | H |
| 1H-indol-6-yl | Me | H | H | morpholin-4-yl | H | F | H | H |
| 1H-indol-6-yl | Me | H | OMe | morpholin-4-yl | H | H | H | H |
| 1H-indol-6-yl | Me | H | OH | morpholin-4-yl | H | H | H | H |
| 1H-indol-6-yl | Me | H | Me | morpholin-4-yl | H | H | H | H |
| 1H-indol-6-yl | Me | H | H | morpholin-4-yl | H | H | H | OH |
| 1H-indol-6-yl | Me | H | H | morpholin-4-yl | H | H | H | Me |
| 1H-indol-6-yl | Me | H | H | piperidin-1-yl | H | H | H | H |
| 1H-indol-6-yl | Me | H | H | pyrrolidin-1-yl | H | H | H | H |
| 1H-indol-6-yl | Me | H | H | morpholin-4-ylmethyl | H | H | H | H |
| 1H-indol-6-yl | Me | H | H | 1-methyl-1-morpholin-4-yl-ethyl | H | H | H | H |
| 1H-indol-6-yl | Me | H | H | 1-morpholin-4-yl-cyclopropyl | H | H | H | H |
| 1H-indol-6-yl | Me | H | H | piperidin-1-ylmethyl | H | H | H | H |
| 1H-indol-6-yl | Me | H | H | pyrrolidin-1-ylmethyl | H | H | H | H |
| 1H-indol-6-yl | Me | H | H | CH₂NMe₂ | H | H | H | H |
| 1H-indol-6-yl | Me | H | H | 1-dimethylamino-1-methylethyl | H | H | H | H |
| 1H-indol-6-yl | Me | H | H | 1-dimethylamino-cyclopropyl | H | H | H | H |
| 1H-indol-6-yl | Me | H | H | CH₂NHMe | H | H | H | H |
| 1H-indol-6-yl | Me | H | H | 1-methyl-1-methylaminoethyl | H | H | H | H |
| 1H-indol-6-yl | Me | H | H | 1-methylamino-cyclopropyl | H | H | H | H |
| 1H-indol-6-yl | Me | H | H | CH₂NH₂ | H | H | H | H |
| 1H-indol-6-yl | Me | H | H | 1-amino-1-methylethyl | H | H | H | H |
| 1H-indol-6-yl | Me | H | H | 1-amino-cyclopropyl | H | H | H | H |
| 1H-indol-6-yl | Me | H | H | 2-oxo-2H-pyridin-1-yl | H | H | H | H |
| 1H-indol-6-yl | Me | H | H | SO₂CH₃ | H | H | H | H |
| 1H-indol-6-yl | Me | H | H | CN | H | H | H | H |
| 1H-indol-6-yl | Me | H | Me | H | H | H | H | H |
| 1-methyl-1H-indol-5-yl | Me | H | H | H | H | H | H | H |
| 1-methyl-1H-indol-5-yl | Me | H | F | H | H | H | H | H |
| 1-methyl-1H-indol-5-yl | Et | H | F | H | H | H | H | H |
| 1-benzyl-1H-indol-5-yl | Me | H | H | H | H | H | H | H |
| (3-cyano-benzyl)-1H-indol-5-yl | Me | H | H | H | H | H | H | H |
| (2-cyano-benzyl)-1H-indol-5-yl | Me | H | H | H | H | H | H | H |
| 1-methyl-1H-indol-6-yl | Me | H | H | H | H | H | H | H |
| 1-methyl-1H-indol-6-yl | Me | H | F | H | H | H | H | H |
| 1-methyl-1H-indol-6-yl | Et | H | F | H | H | H | H | H |
| 1-benzyl-1H-indol-6-yl | Me | H | H | H | H | H | H | H |
| (3-cyano-benzyl)-1H-indol-6-yl | Me | H | H | H | H | H | H | H |
| (2-cyano-benzyl)-1H-indol-6-yl | Me | H | H | H | H | H | H | H | wherein the carbon atom designated * is the R or S configuration.

That is, the specific compounds herein include:
- 4-(1H-indol-1-yl)-2-methyl-1,2,3,4-tetrahydroisoquinoline;
- 4-(1H-indol-2-yl)-1,2,3,4-tetrahydroisoquinoline;
- 4-(1H-indol-2-yl)-1-methyl-1,2,3,4-tetrahydroisoquinoline;
- 4-(1H-indol-2-yl)-2-methyl-1,2,3,4-tetrahydroisoquinoline;
- 2-ethyl-4-(1H-indol-2-yl)-1,2,3,4-tetrahydroisoquinoline;
- 1,2-dimethyl-4-(1H-indol-2-yl)-1,2,3,4-tetrahydroisoquinoline;
- 4-(5-methoxy-1H-indol-2-yl)-2-methyl-1,2,3,4-tetrahydroisoquinoline;
- 4-(1H-indol-2-yl)-2-methyl-1,2,3,4-tetrahydroisoquinolin-4-ol;
- 4-(1H-indol-2-yl)-4-methoxy-2-methyl-1,2,3,4-tetrahydroisoquinoline;
- 4-(1H-indol-2-yl)-2,4-dimethyl-1,2,3,4-tetrahydroisoquinoline;
- 4-(1H-indol-2-yl)-2-methyl-1,2,3,4-tetrahydroisoquinoline-4-carbonitrile;
- 4-fluoro-4-(1H-indol-2-yl)-2-methyl-1,2,3,4-tetrahydroisoquinoline;
- 4-chloro-4-(1H-indol-2-yl)-2-methyl-1,2,3,4-tetrahydroisoquinoline;
- 4-(1H-indol-2-yl)-2-methyl-1,2,3,4-tetrahydroisoquinolin-7-ol;
- 4-(1H-indol-2-yl)-7-methoxy-2-methyl-1,2,3,4-tetrahydroisoquinoline;
- 2,7-dimethyl-4-(1H-indol-2-yl)-1,2,3,4-tetrahydroisoquinoline;
- 7-fluoro-4-(1H-indol-2-yl)-2-methyl-1,2,3,4-tetrahydroisoquinoline;
- 4-(1H-indol-2-yl)-2-methyl-7-(pyridazin-3-yl)-1,2,3,4-tetrahydroisoquinoline;
- 4-(1-methyl-1H-indol-2-yl)-2-methyl-7-(pyridazin-3-yl)-1,2,3,4-tetrahydroisoquinoline;
- 4-(7-fluoro-1H-indol-2-yl)-2-methyl-7-(pyridazin-3-yl)-1,2,3,4-tetrahydroisoquinoline;
- 2-ethyl-4-(1H-indol-2-yl)-7-pyridazin-3-yl-1,2,3,4-tetrahydroisoquinoline;
- 4-(1H-indol-2-yl)-2-methyl-7-(6-methylpyridazin-3-yl)-1,2,3,4-tetrahydroisoquinoline;
- [6-(4-(1H-indol-2-yl)-2-methyl-1,2,3,4-tetrahydroisoquinolin-7-yl)-pyridazin-3-yl]-dimethylamine;
- [6-(4-(1H-indol-2-yl)-2-methyl-1,2,3,4-tetrahydroisoquinolin-7-yl)-pyridazin-3-yl]-methylamine;
- 6-(4-(1H-indol-2-yl)-2-methyl-1,2,3,4-tetrahydroisoquinolin-7-yl)-pyridazin-3-ylamine;
- 4-(1H-indol-2-yl)-2-methyl-7-(6-morpholin-4-yl-pyridazin-3-yl)-1,2,3,4-tetrahydroisoquinoline;
- 4-(1H-indol-2-yl)-2-methyl-7-(6-trifluoromethyl-pyridazin-3-yl)-1,2,3,4-tetrahydroisoquinoline;
- 6-(4-(1H-indol-2-yl)-2-methyl-1,2,3,4-tetrahydroisoquinolin-7-yl)-pyridazine-3-carbonitrile;
- 8-fluoro-4-(1H-indol-2-yl)-2-methyl-7-pyridazin-3-yl-1,2,3,4-tetrahydroisoquinoline;
- 2-ethyl-8-fluoro-4-(1H-indol-2-yl)-7-pyridazin-3-yl-1,2,3,4-tetrahydroisoquinoline;
- 6-fluoro-4-(1H-indol-2-yl)-2-methyl-7-pyridazin-3-yl-1,2,3,4-tetrahydroisoquinoline;
- 5-fluoro-4-(1H-indol-2-yl)-2-methyl-7-pyridazin-3-yl-1,2,3,4-tetrahydroisoquinoline;
- 4-(1H-indol-2-yl)-8-methoxy-2-methyl-7-pyridazin-3-yl-1,2,3,4-tetrahydroisoquinoline;
- 4-(1H-indol-2-yl)-2-methyl-7-pyridazin-3-yl-1,2,3,4-tetrahydroisoquinolin-8-ol;
- 2,8-dimethyl-4-(1H-indol-2-yl)-7-pyridazin-3-yl-1,2,3,4-tetrahydroisoquinoline;
- 4-(1H-indol-2-yl)-2-methyl-7-pyridazin-3-yl-1,2,3,4-tetrahydroisoquinolin-4-ol;
- 2,4-dimethyl-4-(1H-indol-2-yl)-7-pyridazin-3-yl-1,2,3,4-tetrahydroisoquinoline;
- 4-(1H-indol-2-yl)-2-methyl-7-(pyridazin-4-yl)-1,2,3,4-tetrahydroisoquinoline;
- 8-fluoro-4-(1H-indol-2-yl)-2-methyl-7-(pyridazin-4-yl)-1,2,3,4-tetrahydroisoquinoline;
- 4-(1H-indol-2-yl)-2-methyl-7-(pyrazin-2-yl)-1,2,3,4-tetrahydroisoquinoline;
- 4-(1H-indol-2-yl)-2-methyl-7-(3-methyl-pyrazin-2-yl)-1,2,3,4-tetrahydroisoquinoline;
- 4-(1H-indol-2-yl)-7-(3-methoxy-pyrazin-2-yl)-2-methyl-1,2,3,4-tetrahydroisoquinoline;
- 4-(1H-indol-2-yl)-2-methyl-7-(6-methyl-pyrazin-2-yl)-1,2,3,4-tetrahydroisoquinoline;
- 4-(1H-indol-2-yl)-7-(6-methoxy-pyrazin-2-yl)-2-methyl-1,2,3,4-tetrahydroisoquinoline;
- 4-(1H-indol-2-yl)-8-fluoro-2-methyl-7-pyrazin-2-yl-1,2,3,4-tetrahydroisoquinoline;
- 4-(1H-indol-2-yl)-2-methyl-7-(pyrimidin-2-yl)-1,2,3,4-tetrahydroisoquinoline;
- 8-fluoro-4-(1H-indol-2-yl)-2-methyl-7-pyrimidin-2-yl-1,2,3,4-tetrahydroisoquinoline;
- 4-(1H-indol-2-yl)-2-methyl-7-(pyrimidin-4-yl)-1,2,3,4-tetrahydroisoquinoline;
- 8-fluoro-4-(1H-indol-2-yl)-2-methyl-7-pyrimidin-4-yl-1,2,3,4-tetrahydroisoquinoline;
- 4-(1H-indol-2-yl)-2-methyl-7-(pyrimidin-5-yl)-1,2,3,4-tetrahydroisoquinoline;
- 8-fluoro-4-(1H-indol-2-yl)-2-methyl-7-pyrimidin-5-yl-1,2,3,4-tetrahydroisoquinoline;
- 4-(1H-indol-2-yl)-7-(3,5-dimethyl-isoxazol-4-yl)-2-methyl-1,2,3,4-tetrahydroisoquinoline;
- 4-(1H-indol-2-yl)-2-methyl-7-(thiazol-2-yl)-1,2,3,4-tetrahydroisoquinoline;
- 4-(1H-indol-2-yl)-2-methyl-7-(5-methyl-thiazol-2-yl)-1,2,3,4-tetrahydroisoquinoline;
- 3-(4-(1H-indol-2-yl)-2-methyl-1,2,3,4-tetrahydroisoquinolin-7-yl)-cinnoline;
- 1-(4-(1H-indol-2-yl)-2-methyl-1,2,3,4-tetrahydroisoquinolin-7-yl)-phthalazine;
- 2-(4-(1H-indol-2-yl)-2-methyl-1,2,3,4-tetrahydroisoquinolin-7-yl)-quinoxaline;
- 2-(4-(1H-indol-2-yl)-2-methyl-1,2,3,4-tetrahydroisoquinolin-7-yl)-quinazoline;
- 6-(4-(1H-indol-2-yl)-2-methyl-1,2,3,4-tetrahydroisoquinolin-7-yl)-quinazoline;
- 7-(4-(1H-indol-2-yl)-2-methyl-1,2,3,4-tetrahydroisoquinolin-7-yl)-quinazoline;
- 2-(4-(1H-indol-2-yl)-2-methyl-1,2,3,4-tetrahydroisoquinolin-7-yl)-2H-[1,2,4]triazolo[4,3-a]pyridin-3-one;
- 4-(1H-indol-2-yl)-2-methyl-7-(morpholin-4-yl)-1,2,3,4-tetrahydroisoquinoline;
- 4-(1-methyl-1H-indol-2-yl)-2-methyl-7-morpholin-4-yl-1,2,3,4-tetrahydroisoquinoline;
- 4-(7-fluoro-1H-indol-2-yl)-2-methyl-7-morpholin-4-yl-1,2,3,4-tetrahydroisoquinoline;
- 7-(2,6-dimethyl-morpholin-4-yl)-4-(1H-indol-2-yl)-2-methyl-1,2,3,4-tetrahydroisoquinoline;
- 2-ethyl-4-(1H-indol-2-yl)-7-morpholin-4-yl-1,2,3,4-tetrahydroisoquinoline;
- 8-fluoro-4-(1H-indol-2-yl)-2-methyl-7-morpholin-4-yl-1,2,3,4-tetrahydroisoquinoline;
- 2-ethyl-8-fluoro-4-(1H-indol-2-yl)-7-morpholin-4-yl-1,2,3,4-tetrahydroisoquinoline;

6-fluoro-4-(1H-indol-2-yl)-2-methyl-7-morpholin-4-yl-1,2,3,4-tetrahydroisoquinoline;
5-fluoro-4-(1H-indol-2-yl)-2-methyl-7-morpholin-4-yl-1,2,3,4-tetrahydroisoquinoline;
4-(1H-indol-2-yl)-8-methoxy-2-methyl-7-morpholin-4-yl-1,2,3,4-tetrahydroisoquinoline;
4-(1H-indol-2-yl)-2-methyl-7-morpholin-4-yl-1,2,3,4-tetrahydroisoquinolin-8-ol;
4-(1H-indol-2-yl)-2,8-dimethyl-7-morpholin-4-yl-1,2,3,4-tetrahydroisoquinoline;
4-(1H-indol-2-yl)-2-methyl-7-morpholin-4-yl-1,2,3,4-tetrahydroisoquinolin-4-ol;
4-(1H-indol-2-yl)-2,4-dimethyl-7-morpholin-4-yl-1,2,3,4-tetrahydroisoquinoline;
4-(1H-indol-2-yl)-2-methyl-7-(piperidin-1-yl)-1,2,3,4-tetrahydroisoquinoline;
4-(1H-indol-2-yl)-2-methyl-7-(pyrrolidin-1-yl)-1,2,3,4-tetrahydroisoquinoline;
4-(1H-indol-2-yl)-2-methyl-7-(morpholin-4-yl)methyl-1,2,3,4-tetrahydroisoquinoline;
4-(1H-indol-2-yl)-2-methyl-7-(1-methyl-1-morpholin-4-yl-ethyl)-1,2,3,4-tetrahydroisoquinoline;
4-(1H-indol-2-yl)-2-methyl-7-(1-morpholin-4-yl-cyclopropyl)-1,2,3,4-tetrahydroisoquinoline;
4-(1H-indol-2-yl)-2-methyl-7-(piperidin-1-yl)methyl-1,2,3,4-tetrahydroisoquinoline;
4-(1H-indol-2-yl)-2-methyl-7-(pyrrolidin-1-yl)methyl-1,2,3,4-tetrahydroisoquinoline;
(4-(1H-indol-2-yl)-2-methyl-1,2,3,4-tetrahydroisoquinolin-7-ylmethyl)-dimethylamine;
[1-(4-(1H-indol-2-yl)-2-methyl-1,2,3,4-tetrahydroisoquinolin-7-yl)-1-methylethyl]-dimethylamine;
[1-(4-(1H-indol-2-yl)-2-methyl-1,2,3,4-tetrahydroisoquinolin-7-yl)-cyclopropyl]-dimethylamine;
(4-(1H-indol-2-yl)-2-methyl-1,2,3,4-tetrahydroisoquinolin-7-ylmethyl)-methylamine;
[1-(4-(1H-indol-2-yl)-2-methyl-1,2,3,4-tetrahydroisoquinolin-7-yl)-1-methylethyl]-methylamine;
[1-(4-(1H-indol-2-yl)-2-methyl-1,2,3,4-tetrahydroisoquinolin-7-yl)-cyclopropyl]-methylamine;
C-(4-(1H-indol-2-yl)-2-methyl-1,2,3,4-tetrahydroisoquinolin-7-yl)-methylamine;
1-(4-(1H-indol-2-yl)-2-methyl-1,2,3,4-tetrahydroisoquinolin-7-yl)-1-methyl-ethylamine;
1-(4-(1H-indol-2-yl)-2-methyl-1,2,3,4-tetrahydroisoquinolin-7-yl)-cyclopropylamine;
1-(4-(1H-indol-2-yl)-2-methyl-1,2,3,4-tetrahydroisoquinolin-7-yl)-1H-pyridin-2-one;
4-(1H-indol-2-yl)-7-methanesulfonyl-2-methyl-1,2,3,4-tetrahydroisoquinoline;
4-(1H-indol-2-yl)-2-methyl-1,2,3,4-tetrahydroisoquinoline-7-carbonitrile;
2,8-dimethyl-4-(1H-indol-2-yl)-1,2,3,4-tetrahydroisoquinoline;
4-(1H-indol-3-yl)-2-methyl-1,2,3,4-tetrahydroisoquinoline;
4-(1H-indol-4-yl)-2-methyl-1,2,3,4-tetrahydroisoquinoline;
4-(1H-indol-5-yl)-1,2,3,4-tetrahydroisoquinoline;
4-(1H-indol-5-yl)-1-methyl-1,2,3,4-tetrahydroisoquinoline;
4-(1H-indol-5-yl)-2-methyl-1,2,3,4-tetrahydroisoquinoline;
2-ethyl-4-(1H-indol-5-yl)-1,2,3,4-tetrahydroisoquinoline;
1,2-dimethyl-4-(1H-indol-5-yl)-1,2,3,4-tetrahydroisoquinoline;
4-(1H-indol-5-yl)-2-methyl-1,2,3,4-tetrahydroisoquinolin-4-ol;
4-(1H-indol-5-yl)-4-methoxy-2-methyl-1,2,3,4-tetrahydroisoquinoline;
4-(1H-indol-5-yl)-2,4-dimethyl-1,2,3,4-tetrahydroisoquinoline;
4-(1H-indol-5-yl)-2-methyl-1,2,3,4-tetrahydroisoquinoline-4-carbonitrile;
4-fluoro-4-(1H-indol-5-yl)-2-methyl-1,2,3,4-tetrahydroisoquinoline;
4-chloro-4-(1H-indol-5-yl)-2-methyl-1,2,3,4-tetrahydroisoquinoline;
4-(1H-indol-5-yl)-2-methyl-1,2,3,4-tetrahydroisoquinolin-7-ol;
4-(1H-indol-5-yl)-7-methoxy-2-methyl-1,2,3,4-tetrahydroisoquinoline;
2,7-dimethyl-4-(1H-indol-5-yl)-1,2,3,4-tetrahydroisoquinoline;
7-fluoro-4-(1H-indol-5-yl)-2-methyl-1,2,3,4-tetrahydroisoquinoline;
4-(1H-indol-5-yl)-2-methyl-7-(pyridazin-3-yl)-1,2,3,4-tetrahydroisoquinoline;
4-(1-methyl-indol-5-yl)-2-methyl-7-(pyridazin-3-yl)-1,2,3,4-tetrahydroisoquinoline;
4-(7-fluoro-1H-indol-5-yl)-2-methyl-7-(pyridazin-3-yl)-1,2,3,4-tetrahydroisoquinoline;
2-ethyl-4-(1H-indol-5-yl)-7-pyridazin-3-yl-1,2,3,4-tetrahydroisoquinoline;
4-(1H-indol-5-yl)-2-methyl-7-(6-methylpyridazin-3-yl)-1,2,3,4-tetrahydroisoquinoline;
[6-(4-(1H-indol-5-yl)-2-methyl-1,2,3,4-tetrahydroisoquinolin-7-yl)-pyridazin-3-yl]-dimethylamine;
[6-(4-(1H-indol-5-yl)-2-methyl-1,2,3,4-tetrahydroisoquinolin-7-yl)-pyridazin-3-yl]-methylamine;
6-(4-(1H-indol-5-yl)-2-methyl-1,2,3,4-tetrahydroisoquinolin-7-yl)-pyridazin-3-ylamine;
4-(1H-indol-5-yl)-2-methyl-7-(6-morpholin-4-yl-pyridazin-3-yl)-1,2,3,4-tetrahydroisoquinoline;
4-(1H-indol-5-yl)-2-methyl-7-(6-trifluoromethyl-pyridazin-3-yl)-1,2,3,4-tetrahydroisoquinoline;
6-(4-(1H-indol-5-yl)-2-methyl-1,2,3,4-tetrahydroisoquinolin-7-yl)-pyridazine-3-carbonitrile;
8-fluoro-4-(1H-indol-5-yl)-2-methyl-7-pyridazin-3-yl-1,2,3,4-tetrahydroisoquinoline;
2-ethyl-8-fluoro-4-(1H-indol-5-yl)-7-pyridazin-3-yl-1,2,3,4-tetrahydroisoquinoline;
6-fluoro-4-(1H-indol-5-yl)-2-methyl-7-pyridazin-3-yl-1,2,3,4-tetrahydroisoquinoline;
5-fluoro-4-(1H-indol-5-yl)-2-methyl-7-pyridazin-3-yl-1,2,3,4-tetrahydroisoquinoline;
4-(1H-indol-5-yl)-8-methoxy-2-methyl-7-pyridazin-3-yl-1,2,3,4-tetrahydroisoquinoline;
4-(1H-indol-5-yl)-2-methyl-7-pyridazin-3-yl-1,2,3,4-tetrahydroisoquinolin-8-ol;
2,8-dimethyl-4-(1H-indol-5-yl)-7-pyridazin-3-yl-1,2,3,4-tetrahydroisoquinoline;
4-(1H-indol-5-yl)-2-methyl-7-pyridazin-3-yl-1,2,3,4-tetrahydroisoquinolin-4-ol;
2,4-dimethyl-4-(1H-indol-5-yl)-7-pyridazin-3-yl-1,2,3,4-tetrahydroisoquinoline;
4-(1H-indol-5-yl)-2-methyl-7-(pyridazin-4-yl)-1,2,3,4-tetrahydroisoquinoline;
8-fluoro-4-(1H-indol-5-yl)-2-methyl-7-(pyridazin-4-yl)-1,2,3,4-tetrahydroisoquinoline;
4-(1H-indol-5-yl)-2-methyl-7-(pyrazin-2-yl)-1,2,3,4-tetrahydroisoquinoline;
4-(1H-indol-5-yl)-2-methyl-7-(3-methyl-pyrazin-2-yl)-1,2,3,4-tetrahydroisoquinoline;
4-(1H-indol-5-yl)-7-(3-methoxy-pyrazin-2-yl)-2-methyl-1,2,3,4-tetrahydroisoquinoline;

4-(1H-indol-5-yl)-2-methyl-7-(6-methyl-pyrazin-2-yl)-1,2,3,4-tetrahydroisoquinoline;
4-(1H-indol-5-yl)-7-(6-methoxy-pyrazin-2-yl)-2-methyl-1,2,3,4-tetrahydroisoquinoline;
4-(1H-indol-5-yl)-8-fluoro-2-methyl-7-pyrazin-2-yl-1,2,3,4-tetrahydroisoquinoline;
4-(1H-indol-5-yl)-2-methyl-7-(pyrimidin-2-yl)-1,2,3,4-tetrahydroisoquinoline;
8-fluoro-4-(1H-indol-5-yl)-2-methyl-7-pyrimidin-2-yl-1,2,3,4-tetrahydroisoquinoline;
4-(1H-indol-5-yl)-2-methyl-7-(pyrimidin-4-yl)-1,2,3,4-tetrahydroisoquinoline;
8-fluoro-4-(1H-indol-5-yl)-2-methyl-7-pyrimidin-4-yl-1,2,3,4-tetrahydroisoquinoline;
4-(1H-indol-5-yl)-2-methyl-7-(pyrimidin-5-yl)-1,2,3,4-tetrahydroisoquinoline;
8-fluoro-4-(1H-indol-5-yl)-2-methyl-7-pyrimidin-5-yl-1,2,3,4-tetrahydroisoquinoline;
4-(1H-indol-5-yl)-7-(3,5-dimethyl-isoxazol-4-yl)-2-methyl-1,2,3,4-tetrahydroisoquinoline;
4-(1H-indol-5-yl)-2-methyl-7-(thiazol-2-yl)-1,2,3,4-tetrahydroisoquinoline;
4-(1H-indol-5-yl)-2-methyl-7-(5-methyl-thiazol-2-yl)-1,2,3,4-tetrahydroisoquinoline;
3-(4-(1H-indol-5-yl)-2-methyl-1,2,3,4-tetrahydroisoquinolin-7-yl)-cinnoline;
1-(4-(1H-indol-5-yl)-2-methyl-1,2,3,4-tetrahydroisoquinolin-7-yl)-phthalazine;
2-(4-(1H-indol-5-yl)-2-methyl-1,2,3,4-tetrahydroisoquinolin-7-yl)-quinoxaline;
2-(4-(1H-indol-5-yl)-2-methyl-1,2,3,4-tetrahydroisoquinolin-7-yl)-quinazoline;
6-(4-(1H-indol-5-yl)-2-methyl-1,2,3,4-tetrahydroisoquinolin-7-yl)-quinazoline;
7-(4-(1H-indol-5-yl)-2-methyl-1,2,3,4-tetrahydroisoquinolin-7-yl)-quinazoline;
2-(4-(1H-indol-5-yl)-2-methyl-1,2,3,4-tetrahydroisoquinolin-7-yl)-2H-[1,2,4]triazolo[4,3-a]pyridin-3-one;
4-(1H-indol-5-yl)-2-methyl-7-(morpholin-4-yl)-1,2,3,4-tetrahydroisoquinoline;
4-(1-methyl-1H-indol-5-yl)-2-methyl-7-morpholin-4-yl-1,2,3,4-tetrahydroisoquinoline;
4-(7-fluoro-1H-indol-5-yl)-2-methyl-7-morpholin-4-yl-1,2,3,4-tetrahydroisoquinoline;
7-(2,6-dimethyl-morpholin-4-yl)-4-(1H-indol-5-yl)-2-methyl-1,2,3,4-tetrahydroisoquinoline;
2-ethyl-4-(1H-indol-5-yl)-7-morpholin-4-yl-1,2,3,4-tetrahydroisoquinoline;
8-fluoro-4-(1H-indol-5-yl)-2-methyl-7-morpholin-4-yl-1,2,3,4-tetrahydroisoquinoline;
2-ethyl-8-fluoro-4-(1H-indol-5-yl)-7-morpholin-4-yl-1,2,3,4-tetrahydroisoquinoline;
6-fluoro-4-(1H-indol-5-yl)-2-methyl-7-morpholin-4-yl-1,2,3,4-tetrahydroisoquinoline;
5-fluoro-4-(1H-indol-5-yl)-2-methyl-7-morpholin-4-yl-1,2,3,4-tetrahydroisoquinoline;
4-(1H-indol-5-yl)-8-methoxy-2-methyl-7-morpholin-4-yl-1,2,3,4-tetrahydroisoquinoline;
4-(1H-indol-5-yl)-2-methyl-7-morpholin-4-yl-1,2,3,4-tetrahydroisoquinolin-8-ol;
2,8-dimethyl-4-(1H-indol-5-yl)-7-morpholin-4-yl-1,2,3,4-tetrahydroisoquinoline;
4-(1H-indol-5-yl)-2-methyl-7-morpholin-4-yl-1,2,3,4-tetrahydroisoquinolin-4-ol;
2,4-dimethyl-4-(1H-indol-5-yl)-7-morpholin-4-yl-1,2,3,4-tetrahydroisoquinoline;
4-(1H-indol-5-yl)-2-methyl-7-(piperidin-1-yl)-1,2,3,4-tetrahydroisoquinoline;
4-(1H-indol-5-yl)-2-methyl-7-(pyrrolidin-1-yl)-1,2,3,4-tetrahydroisoquinoline;
4-(1H-indol-5-yl)-2-methyl-7-(morpholin-4-yl)methyl-1,2,3,4-tetrahydroisoquinoline;
4-(1H-indol-5-yl)-2-methyl-7-(1-methyl-1-morpholin-4-yl-ethyl)-1,2,3,4-tetrahydroisoquinoline;
4-(1H-indol-5-yl)-2-methyl-7-(1-morpholin-4-yl-cyclopropyl)-1,2,3,4-tetrahydroisoquinoline;
4-(1H-indol-5-yl)-2-methyl-7-(piperidin-1-yl)methyl-1,2,3,4-tetrahydroisoquinoline;
4-(1H-indol-5-yl)-2-methyl-7-(pyrrolidin-1-yl)methyl-1,2,3,4-tetrahydroisoquinoline;
(4-(1H-indol-5-yl)-2-methyl-1,2,3,4-tetrahydroisoquinolin-7-ylmethyl)-dimethylamine;
[1-(4-(1H-indol-5-yl)-2-methyl-1,2,3,4-tetrahydroisoquinolin-7-yl)-1-methylethyl]-dimethylamine;
[1-(4-(1H-indol-5-yl)-2-methyl-1,2,3,4-tetrahydroisoquinolin-7-yl)-cyclopropyl]-dimethylamine;
(4-(1H-indol-5-yl)-2-methyl-1,2,3,4-tetrahydroisoquinolin-7-ylmethyl)-methylamine;
[1-(4-(1H-indol-5-yl)-2-methyl-1,2,3,4-tetrahydroisoquinolin-7-yl)-1-methylethyl]-methylamine;
[1-(4-(1H-indol-5-yl)-2-methyl-1,2,3,4-tetrahydroisoquinolin-7-yl)-cyclopropyl]-methylamine;
C-(4-(1H-indol-5-yl)-2-methyl-1,2,3,4-tetrahydroisoquinolin-7-yl)-methylamine;
1-(4-(1H-indol-5-yl)-2-methyl-1,2,3,4-tetrahydroisoquinolin-7-yl)-1-methyl-ethylamine;
1-(4-(1H-indol-5-yl)-2-methyl-1,2,3,4-tetrahydroisoquinolin-7-yl)-cyclopropylamine;
1-(4-(1H-indol-5-yl)-2-methyl-1,2,3,4-tetrahydroisoquinolin-7-yl)-1H-pyridin-2-one;
4-(1H-indol-5-yl)-7-methanesulfonyl-2-methyl-1,2,3,4-tetrahydroisoquinoline;
4-(1H-indol-5-yl)-2-methyl-1,2,3,4-tetrahydroisoquinoline-7-carbonitrile;
4-(1H-indol-5-yl)-2,8-dimethyl-1,2,3,4-tetrahydroisoquinoline;
4-(1-benzyl-1H-indol-5-yl)-2-methyl-1,2,3,4-tetrahydroisoquinoline;
4-(1H-indol-6-yl)-1,2,3,4-tetrahydroisoquinoline;
4-(1H-indol-6-yl)-1-methyl-1,2,3,4-tetrahydroisoquinoline;
4-(1H-indol-6-yl)-2-methyl-1,2,3,4-tetrahydroisoquinoline;
4-(3-chloro-1H-indol-6-yl)-2-methyl-1,2,3,4-tetrahydroisoquinoline;
2-ethyl-4-(1H-indol-6-yl)-1,2,3,4-tetrahydroisoquinoline;
1,2-dimethyl-4-(1H-indol-6-yl)-1,2,3,4-tetrahydroisoquinoline;
4-(1H-indol-6-yl)-2-methyl-1,2,3,4-tetrahydroisoquinolin-4-ol;
4-(1H-indol-6-yl)-4-methoxy-2-methyl-1,2,3,4-tetrahydroisoquinoline;
2,4-dimethyl-4-(1H-indol-6-yl)-1,2,3,4-tetrahydroisoquinoline;
4-(1H-indol-6-yl)-2-methyl-1,2,3,4-tetrahydroisoquinoline-4-carbonitrile;
4-fluoro-4-(1H-indol-6-yl)-2-methyl-1,2,3,4-tetrahydroisoquinoline;
4-chloro-4-(1H-indol-6-yl)-2-methyl-1,2,3,4-tetrahydroisoquinoline;
4-(1H-indol-6-yl)-2-methyl-1,2,3,4-tetrahydroisoquinolin-7-ol;
4-(1H-indol-6-yl)-7-methoxy-2-methyl-1,2,3,4-tetrahydroisoquinoline;

2,7-dimethyl-4-(1H-indol-6-yl)-1,2,3,4-tetrahydroisoquinoline;
7-fluoro-4-(1H-indol-6-yl)-2-methyl-1,2,3,4-tetrahydroisoquinoline;
4-(1H-indol-6-yl)-2-methyl-7-(pyridazin-3-yl)-1,2,3,4-tetrahydroisoquinoline;
4-(1-methyl-indol-6-yl)-2-methyl-7-(pyridazin-3-yl)-1,2,3,4-tetrahydroisoquinoline;
4-(7-fluoro-1H-indol-6-yl)-2-methyl-7-(pyridazin-3-yl)-1,2,3,4-tetrahydroisoquinoline;
2-ethyl-4-(1H-indol-6-yl)-7-pyridazin-3-yl-1,2,3,4-tetrahydroisoquinoline;
4-(1H-indol-6-yl)-2-methyl-7-(6-methyl-pyridazin-3-yl)-1,2,3,4-tetrahydroisoquinoline;
[6-(4-(1H-indol-6-yl)-2-methyl-1,2,3,4-tetrahydroisoquinolin-7-yl)-pyridazin-3-yl]-dimethylamine;
[6-(4-(1H-indol-6-yl)-2-methyl-1,2,3,4-tetrahydroisoquinolin-7-yl)-pyridazin-3-yl]-methylamine;
6-(4-(1H-indol-6-yl)-2-methyl-1,2,3,4-tetrahydroisoquinolin-7-yl)-pyridazin-3-ylamine;
4-(1H-indol-6-yl)-2-methyl-7-(6-morpholin-4-yl-pyridazin-3-yl)-1,2,3,4-tetrahydroisoquinoline;
4-(1H-indol-6-yl)-2-methyl-7-(6-trifluoromethyl-pyridazin-3-yl)-1,2,3,4-tetrahydroisoquinoline;
6-(4-(1H-indol-6-yl)-2-methyl-1,2,3,4-tetrahydroisoquinolin-7-yl)-pyridazine-3-carbonitrile;
8-fluoro-4-(1H-indol-6-yl)-2-methyl-7-pyridazin-3-yl-1,2,3,4-tetrahydroisoquinoline;
2-ethyl-8-fluoro-4-(1H-indol-6-yl)-7-pyridazin-3-yl-1,2,3,4-tetrahydroisoquinoline;
6-fluoro-4-(1H-indol-6-yl)-2-methyl-7-pyridazin-3-yl-1,2,3,4-tetrahydroisoquinoline;
5-fluoro-4-(1H-indol-6-yl)-2-methyl-7-pyridazin-3-yl-1,2,3,4-tetrahydroisoquinoline;
4-(1H-indol-6-yl)-8-methoxy-2-methyl-7-pyridazin-3-yl-1,2,3,4-tetrahydroisoquinoline;
4-(1H-indol-6-yl)-2-methyl-7-pyridazin-3-yl-1,2,3,4-tetrahydroisoquinolin-8-ol;
2,8-dimethyl-4-(1H-indol-6-yl)-7-pyridazin-3-yl-1,2,3,4-tetrahydroisoquinoline;
4-(1H-indol-6-yl)-2-methyl-7-pyridazin-3-yl-1,2,3,4-tetrahydroisoquinolin-4-ol;
2,4-dimethyl-4-(1H-indol-6-yl)-7-pyridazin-3-yl-1,2,3,4-tetrahydroisoquinoline;
4-(1H-indol-6-yl)-2-methyl-7-(pyridazin-4-yl)-1,2,3,4-tetrahydroisoquinoline;
8-fluoro-4-(1H-indol-6-yl)-2-methyl-7-(pyridazin-4-yl)-1,2,3,4-tetrahydroisoquinoline;
4-(1H-indol-6-yl)-2-methyl-7-(pyrazin-2-yl)-1,2,3,4-tetrahydroisoquinoline;
4-(1H-indol-6-yl)-2-methyl-7-(3-methyl-pyrazin-2-yl)-1,2,3,4-tetrahydroisoquinoline;
4-(1H-indol-6-yl)-7-(3-methoxy-pyrazin-2-yl)-2-methyl-1,2,3,4-tetrahydroisoquinoline;
4-(1H-indol-6-yl)-2-methyl-7-(6-methyl-pyrazin-2-yl)-1,2,3,4-tetrahydroisoquinoline;
4-(1H-indol-6-yl)-7-(6-methoxy-pyrazin-2-yl)-2-methyl-1,2,3,4-tetrahydroisoquinoline;
8-fluoro-4-(1H-indol-6-yl)-2-methyl-7-pyrazin-2-yl-1,2,3,4-tetrahydroisoquinoline;
4-(1H-indol-6-yl)-2-methyl-7-(pyrimidin-2-yl)-1,2,3,4-tetrahydroisoquinoline;
8-fluoro-4-(1H-indol-6-yl)-2-methyl-7-pyrimidin-2-yl-1,2,3,4-tetrahydroisoquinoline;
4-(1H-indol-6-yl)-2-methyl-7-(pyrimidin-4-yl)-1,2,3,4-tetrahydroisoquinoline;
8-fluoro-4-(1H-indol-6-yl)-2-methyl-7-pyrimidin-4-yl-1,2,3,4-tetrahydroisoquinoline;
4-(1H-indol-6-yl)-2-methyl-7-(pyrimidin-5-yl)-1,2,3,4-tetrahydroisoquinoline;
8-fluoro-4-(1H-indol-6-yl)-2-methyl-7-pyrimidin-5-yl-1,2,3,4-tetrahydroisoquinoline;
4-(1H-indol-6-yl)-7-(3,5-dimethyl-isoxazol-4-yl)-2-methyl-1,2,3,4-tetrahydroisoquinoline;
4-(1H-indol-6-yl)-2-methyl-7-(thiazol-2-yl)-1,2,3,4-tetrahydroisoquinoline;
4-(1H-indol-6-yl)-2-methyl-7-(5-methyl-thiazol-2-yl)-1,2,3,4-tetrahydroisoquinoline;
3-(4-(1H-indol-6-yl)-2-methyl-1,2,3,4-tetrahydroisoquinolin-7-yl)-cinnoline;
1-(4-(1H-indol-6-yl)-2-methyl-1,2,3,4-tetrahydroisoquinolin-7-yl)-phthalazine;
2-(4-(1H-indol-6-yl)-2-methyl-1,2,3,4-tetrahydroisoquinolin-7-yl)-quinoxaline;
2-(4-(1H-indol-6-yl)-2-methyl-1,2,3,4-tetrahydroisoquinolin-7-yl)-quinazoline;
6-(4-(1H-indol-6-yl)-2-methyl-1,2,3,4-tetrahydroisoquinolin-7-yl)-quinazoline;
7-(4-(1H-indol-6-yl)-2-methyl-1,2,3,4-tetrahydroisoquinolin-7-yl)-quinazoline;
2-(4-(1H-indol-6-yl)-2-methyl-1,2,3,4-tetrahydroisoquinolin-7-yl)-2H-[1,2,4]triazolo[4,3-a]pyridin-3-one;
4-(1H-indol-6-yl)-2-methyl-7-(morpholin-4-yl)-1,2,3,4-tetrahydroisoquinoline;
4-(1-methyl-1H-indol-6-yl)-2-methyl-7-morpholin-4-yl-1,2,3,4-tetrahydroisoquinoline;
4-(7-fluoro-1H-indol-6-yl)-2-methyl-7-morpholin-4-yl-1,2,3,4-tetrahydroisoquinoline;
7-(2,6-dimethyl-morpholin-4-yl)-4-(1H-indol-6-yl)-2-methyl-1,2,3,4-tetrahydroisoquinoline;
2-ethyl-4-(1H-indol-6-yl)-7-morpholin-4-yl-1,2,3,4-tetrahydroisoquinoline;
8-fluoro-4-(1H-indol-6-yl)-2-methyl-7-morpholin-4-yl-1,2,3,4-tetrahydroisoquinoline;
2-ethyl-8-fluoro-4-(1H-indol-6-yl)-7-morpholin-4-yl-1,2,3,4-tetrahydroisoquinoline;
6-fluoro-4-(1H-indol-6-yl)-2-methyl-7-morpholin-4-yl-1,2,3,4-tetrahydroisoquinoline;
5-fluoro-4-(1H-indol-6-yl)-2-methyl-7-morpholin-4-yl-1,2,3,4-tetrahydroisoquinoline;
4-(1H-indol-6-yl)-8-methoxy-2-methyl-7-morpholin-4-yl-1,2,3,4-tetrahydroisoquinoline;
4-(1H-indol-6-yl)-2-methyl-7-morpholin-4-yl-1,2,3,4-tetrahydroisoquinolin-8-ol;
2,8-dimethyl-4-(1H-indol-6-yl)-7-morpholin-4-yl-1,2,3,4-tetrahydroisoquinoline;
4-(1H-indol-6-yl)-2-methyl-7-morpholin-4-yl-1,2,3,4-tetrahydroisoquinolin-4-ol;
2,4-dimethyl-4-(1H-indol-6-yl)-7-morpholin-4-yl-1,2,3,4-tetrahydroisoquinoline;
4-(1H-indol-6-yl)-2-methyl-7-(piperidin-1-yl)-1,2,3,4-tetrahydroisoquinoline;
4-(1H-indol-6-yl)-2-methyl-7-(pyrrolidin-1-yl)-1,2,3,4-tetrahydroisoquinoline;
4-(1H-indol-6-yl)-2-methyl-7-(morpholin-4-yl)methyl-1,2,3,4-tetrahydroisoquinoline;
4-(1H-indol-6-yl)-2-methyl-7-(1-methyl-1-morpholin-4-yl-ethyl)-1,2,3,4-tetrahydroisoquinoline;
4-(1H-indol-6-yl)-2-methyl-7-(1-morpholin-4-yl-cyclopropyl)-1,2,3,4-tetrahydroisoquinoline;
4-(1H-indol-6-yl)-2-methyl-7-(piperidin-1-yl)methyl-1,2,3,4-tetrahydroisoquinoline;

4-(1H-indol-6-yl)-2-methyl-7-(pyrrolidin-1-yl)methyl-1,2, 3,4-tetrahydroisoquinoline;

(4-(1H-indol-6-yl)-2-methyl-1,2,3,4-tetrahydroisoquinolin-7-ylmethyl)-dimethylamine;

[1-(4-(1H-indol-6-yl)-2-methyl-1,2,3,4-tetrahydroisoquinolin-7-yl)-1-methylethyl]-dimethylamine;

[1-(4-(1H-indol-6-yl)-2-methyl-1,2,3,4-tetrahydroisoquinolin-7-yl)-cyclopropyl]-dimethylamine;

(4-(1H-indol-6-yl)-2-methyl-1,2,3,4-tetrahydroisoquinolin-7-ylmethyl)-methylamine;

[1-(4-(1H-indol-6-yl)-2-methyl-1,2,3,4-tetrahydroisoquinolin-7-yl)-1-methylethyl]-methylamine;

[1-(4-(1H-indol-6-yl)-2-methyl-1,2,3,4-tetrahydroisoquinolin-7-yl)-cyclopropyl]-methylamine;

C-(4-(1H-indol-6-yl)-2-methyl-1,2,3,4-tetrahydroisoquinolin-7-yl)-methylamine;

1-(4-(1H-indol-6-yl)-2-methyl-1,2,3,4-tetrahydroisoquinolin-7-yl)-1-methyl-ethylamine;

1-(4-(1H-indol-6-yl)-2-methyl-1,2,3,4-tetrahydroisoquinolin-7-yl)-cyclopropylamine;

1-(4-(1H-indol-6-yl)-2-methyl-1,2,3,4-tetrahydroisoquinolin-7-yl)-1H-pyridin-2-one;

4-(1H-indol-6-yl)-7-methanesulfonyl-2-methyl-1,2,3,4-tetrahydroisoquinoline;

4-(1H-indol-6-yl)-2-methyl-1,2,3,4-tetrahydroisoquinoline-7-carbonitrile;

2,8-dimethyl-4-(1H-indol-6-yl)-1,2,3,4-tetrahydroisoquinoline;

2-methyl-4-(1-methyl-1H-indol-5-yl)-1,2,3,4-tetrahydroisoquinoline;

8-fluoro-2-methyl-4-(1-methyl-1H-indol-5-yl)-1,2,3,4-tetrahydroisoquinoline;

2-ethyl-8-fluoro-4-(1-methyl-1H-indol-5-yl)-1,2,3,4-tetrahydroisoquinoline;

4-(1-benzyl-1H-indol-5-yl)-2-methyl-1,2,3,4-tetrahydroisoquinoline;

3-[5-(2-methyl-1,2,3,4-tetrahydroisoquinolin-4-yl)-indol-1-ylmethyl]-benzonitrile;

2-[5-(2-methyl-1,2,3,4-tetrahydroisoquinolin-4-yl)-indol-1-ylmethyl]-benzonitrile;

2-methyl-4-(1-methyl-1H-indol-6-yl)-1,2,3,4-tetrahydroisoquinoline;

8-fluoro-2-methyl-4-(1-methyl-1H-indol-6-yl)-1,2,3,4-tetrahydroisoquinoline;

2-ethyl-8-fluoro-4-(1-methyl-1H-indol-6-yl)-1,2,3,4-tetrahydroisoquinoline;

4-(1-benzyl-1H-indol-6-yl)-2-methyl-1,2,3,4-tetrahydroisoquinoline;

3-[6-(2-methyl-1,2,3,4-tetrahydroisoquinolin-4-yl)-indol-1-ylmethyl]-benzonitrile;

2-[6-(2-methyl-1,2,3,4-tetrahydroisoquinolin-4-yl)-indol-1-ylmethyl]-benzonitrile;

or an oxide thereof, a pharmaceutically acceptable salt thereof, a solvate thereof, or a prodrug thereof.

Other specific compounds of the present invention are those with the following substituents:

TABLE D

| X | $R^1$ | $R^2$ | $R^3$ | $R^4$ | $R^5$ | $R^6$ | $R^7$ | $R^8$ |
|---|---|---|---|---|---|---|---|---|
| indazol-1-yl | Me | H | H | H | H | H | H | H |
| 1H-indazol-3-yl | Me | H | H | H | H | H | H | H |
| 1H-indazol-4-yl | Me | H | H | H | H | H | H | H |
| 1H-indazol-5-yl | H | H | H | H | H | H | H | H |
| 1H-indazol-5-yl | H | Me | H | H | H | H | H | H |
| 1H-indazol-5-yl | Me | H | H | H | H | H | H | H |
| 1-methyl-1H-indazol-5-yl | Me | H | H | H | H | H | H | H |
| 6-methoxy-1H-indazol-5-yl | Me | H | H | H | H | H | H | H |
| 7-methoxy-1H-indazol-5-yl | Me | H | H | H | H | H | H | H |
| 7-fluoro-1H-indazol-5-yl | Me | H | H | H | H | H | H | H |
| 7-chloro-1H-indazol-5-yl | Me | H | H | H | H | H | H | H |
| 7-methyl-1H-indazol-5-yl | Me | H | H | H | H | H | H | H |
| 1H-indazol-5-yl | Me | H | F | H | H | H | H | H |
| 1H-indazol-5-yl | Et | H | H | H | H | H | H | H |
| 1H-indazol-5-yl | Et | H | F | H | H | H | H | H |
| 1H-indazol-5-yl | Me | Me | H | H | H | H | H | H |
| 1H-indazol-5-yl | Me | H | H | H | H | H | H | OH |
| 1H-indazol-5-yl | Me | H | H | H | H | H | H | OMe |
| 1H-indazol-5-yl | Me | H | H | H | H | H | H | Me |
| 1H-indazol-5-yl | Me | H | H | H | H | H | H | CN |
| 1H-indazol-5-yl | Me | H | H | H | H | H | H | F |
| 1H-indazol-5-yl | Me | H | H | H | H | H | H | Cl |
| 1H-indazol-5-yl | Me | H | H | OH | H | H | H | H |
| 1H-indazol-5-yl | Me | H | H | OMe | H | H | H | H |
| 1H-indazol-5-yl | Me | H | H | Me | H | H | H | H |
| 1H-indazol-5-yl | Me | H | H | F | H | H | H | H |
| 1H-indazol-5-yl | Me | H | H | pyridazin-3-yl | H | H | H | H |
| 1-methyl-indazol-5-yl | Me | H | H | pyridazin-3-yl | H | H | H | H |
| 7-fluoro-1H-indazol-5-yl | Me | H | H | pyridazin-3-yl | H | H | H | H |
| 1H-indazol-5-yl | Et | H | H | pyridazin-3-yl | H | H | H | H |
| 1H-indazol-5-yl | Me | H | H | 6-methylpyridazin-3-yl | H | H | H | H |
| 1H-indazol-5-yl | Me | H | H | 6-dimethylamino-pyridazin-3-yl | H | H | H | H |
| 1H-indazol-5-yl | Me | H | H | 6-methylamino-pyridazin-3-yl | H | H | H | H |
| 1H-indazol-5-yl | Me | H | H | 6-amino-pyridazin-3-yl | H | H | H | H |
| 1H-indazol-5-yl | Me | H | H | 6-morpholin-4-yl-pyridazin-3-yl | H | H | H | H |
| 1H-indazol-5-yl | Me | H | H | 6-trifluoromethyl-pyridazin-3-yl | H | H | H | H |
| 1H-indazol-5-yl | Me | H | H | pyridazin-4-yl | H | H | H | H |
| 1H-indazol-5-yl | Me | H | H | pyrazin-2-yl | H | H | H | H |
| 1H-indazol-5-yl | Me | H | H | pyrimidin-2-yl | H | H | H | H |
| 1H-indazol-5-yl | Me | H | H | pyrimidin-4-yl | H | H | H | H |
| 1H-indazol-5-yl | Me | H | H | pyrimidin-5-yl | H | H | H | H |
| 1H-indazol-5-yl | Me | H | H | 3,5-dimethyl-isoxazol-4-yl | H | H | H | H |
| 1H-indazol-5-yl | Me | H | H | thiazol-2-yl | H | H | H | H |
| 1H-indazol-5-yl | Me | H | H | 5-methyl-thiazol-2-yl | H | H | H | H |
| 1H-indazol-5-yl | Me | H | H | cinnolin-3-yl | H | H | H | H |
| 1H-indazol-5-yl | Me | H | H | phthalazin-1-yl | H | H | H | H |
| 1H-indazol-5-yl | Me | H | H | quinoxalin-2-yl | H | H | H | H |

TABLE D-continued

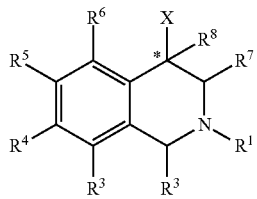

| X | R¹ | R² | R³ | R⁴ | R⁵ | R⁶ | R⁷ | R⁸ |
|---|---|---|---|---|---|---|---|---|
| 1H-indazol-5-yl | Me | H | H | quinazolin-2-yl | H | H | H | H |
| 1H-indazol-5-yl | Me | H | H | quinazolin-6-yl | H | H | H | H |
| 1H-indazol-5-yl | Me | H | H | quinazolin-7-yl | H | H | H | H |
| 1H-indazol-5-yl | Me | H | H | 3-oxo-[1,2,4]triazolo[4,3-a]pyridin-2-yl | H | H | H | H |
| 1H-indazol-5-yl | Me | H | H | morpholin-4-yl | H | H | H | H |
| 1-methyl-1H-indazol-5-yl | Me | H | H | morpholin-4-yl | H | H | H | H |
| 7-fluoro-1H-indazol-5-yl | Me | H | H | morpholin-4-yl | H | H | H | H |
| 1H-indazol-5-yl | Me | H | H | 2,6-dimethyl-morpholin-4-yl | H | H | H | H |
| 1H-indazol-5-yl | Et | H | H | morpholin-4-yl | H | H | H | H |
| 1H-indazol-5-yl | Me | H | F | morpholin-4-yl | H | H | H | H |
| 1H-indazol-5-yl | Et | H | F | morpholin-4-yl | H | H | H | H |
| 1H-indazol-5-yl | Me | H | H | morpholin-4-yl | F | H | H | H |
| 1H-indazol-5-yl | Me | H | H | morpholin-4-yl | H | F | H | H |
| 1H-indazol-5-yl | Me | H | OMe | morpholin-4-yl | H | H | H | H |
| 1H-indazol-5-yl | Me | H | OH | morpholin-4-yl | H | H | H | H |
| 1H-indazol-5-yl | Me | H | Me | morpholin-4-yl | H | H | H | H |
| 1H-indazol-5-yl | Me | H | H | morpholin-4-yl | H | H | H | OH |
| 1H-indazol-5-yl | Me | H | H | morpholin-4-yl | H | H | H | Me |
| 1H-indazol-5-yl | Me | H | H | piperidin-1-yl | H | H | H | H |
| 1H-indazol-5-yl | Me | H | H | pyrrolidin-1-yl | H | H | H | H |
| 1H-indazol-5-yl | Me | H | H | morpholin-4-ylmethyl | H | H | H | H |
| 1H-indazol-5-yl | Me | H | H | 1-methyl-1-morpholin-4-yl-ethyl | H | H | H | H |
| 1H-indazol-5-yl | Me | H | H | 1-morpholin-4-yl-cyclopropyl | H | H | H | H |
| 1H-indazol-5-yl | Me | H | H | piperidin-1-ylmethyl | H | H | H | H |
| 1H-indazol-5-yl | Me | H | H | pyrrolidin-1-ylmethyl | H | H | H | H |
| 1H-indazol-5-yl | Me | H | H | CH₂NMe₂ | H | H | H | H |
| 1H-indazol-5-yl | Me | H | H | CH₂NHMe | H | H | H | H |
| 1H-indazol-5-yl | Me | H | H | 2-oxo-2H-pyridin-1-yl | H | H | H | H |
| 1H-indazol-5-yl | Me | H | H | SO₂CH₃ | H | H | H | H |
| 1H-indazol-5-yl | Me | H | H | CN | H | H | H | H |
| 1H-indazol-5-yl | Me | H | Me | H | H | H | H | H |
| 1-methyl-1H-indazol-5-yl | Me | H | F | H | H | H | H | H |
| 1-methyl-1H-indazol-5-yl | Et | H | F | H | H | H | H | H |
| 1-benzyl-1H-indazol-5-yl | Me | H | H | H | H | H | H | H |
| (3-cyano-benzyl)-1H-indazol-5-yl | Me | H | H | H | H | H | H | H |
| (2-cyano-benzyl)-1H-indazol-5-yl | Me | H | H | H | H | H | H | H |
| 1H-indazol-6-yl | H | H | H | H | H | H | H | H |
| 1H-indazol-6-yl | H | Me | H | H | H | H | H | H |
| 1H-indazol-6-yl | Me | H | H | H | H | H | H | H |
| 1-methyl-indazol-6-yl | Me | H | H | H | H | H | H | H |
| 7-fluoro-1H-indazol-6-yl | Me | H | H | H | H | H | H | H |
| 1H-indazol-6-yl | Et | H | H | H | H | H | H | H |
| 1H-indazol-6-yl | Me | Me | H | H | H | H | H | H |
| 1H-indazol-6-yl | Me | H | H | H | H | H | H | OH |
| 1H-indazol-6-yl | Me | H | H | H | H | H | H | OMe |
| 1H-indazol-6-yl | Me | H | H | H | H | H | H | Me |
| 1H-indazol-6-yl | Me | H | H | H | H | H | H | CN |
| 1H-indazol-6-yl | Me | H | H | H | H | H | H | F |
| 1H-indazol-6-yl | Me | H | H | H | H | H | H | Cl |

TABLE D-continued

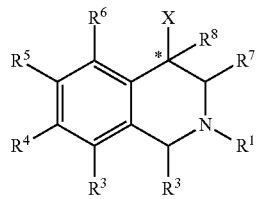

| X | R¹ | R² | R³ | R⁴ | R⁵ | R⁶ | R⁷ | R⁸ |
|---|---|---|---|---|---|---|---|---|
| 1H-indazol-6-yl | Me | H | H | OH | H | H | H | H |
| 1H-indazol-6-yl | Me | H | H | OMe | H | H | H | H |
| 1H-indazol-6-yl | Me | H | H | Me | H | H | H | H |
| 1H-indazol-6-yl | Me | H | H | F | H | H | H | H |
| 1H-indazol-6-yl | Me | H | H | pyridazin-3-yl | H | H | H | H |
| 1-methyl-indazol-6-yl | Me | H | H | pyridazin-3-yl | H | H | H | H |
| 7-fluoro-1H-indazol-6-yl | Me | H | H | pyridazin-3-yl | H | H | H | H |
| 1H-indazol-6-yl | Et | H | H | pyridazin-3-yl | H | H | H | H |
| 1H-indazol-6-yl | Me | H | H | 6-methylpyridazin-3-yl | H | H | H | H |
| 1H-indazol-6-yl | Me | H | H | 6-dimethylamino-pyridazin-3-yl | H | H | H | H |
| 1H-indazol-6-yl | Me | H | H | 6-methylamino-pyridazin-3-yl | H | H | H | H |
| 1H-indazol-6-yl | Me | H | H | 6-amino-pyridazin-3-yl | H | H | H | H |
| 1H-indazol-6-yl | Me | H | H | 6-morpholin-4-yl-pyridazin-3-yl | H | H | H | H |
| 1H-indazol-6-yl | Me | H | H | 6-trifluoromethyl-pyridazin-3-yl | H | H | H | H |
| 1H-indazol-6-yl | Me | H | H | pyridazin-4-yl | H | H | H | H |
| 1H-indazol-6-yl | Me | H | H | pyrazin-2-yl | H | H | H | H |
| 1H-indazol-6-yl | Me | H | H | pyrimidin-2-yl | H | H | H | H |
| 1H-indazol-6-yl | Me | H | H | pyrimidin-4-yl | H | H | H | H |
| 1H-indazol-6-yl | Me | H | H | pyrimidin-5-yl | H | H | H | H |
| 1H-indazol-6-yl | Me | H | H | 3,5-dimethyl-isoxazol-4-yl | H | H | H | H |
| 1H-indazol-6-yl | Me | H | H | thiazol-2-yl | H | H | H | H |
| 1H-indazol-6-yl | Me | H | H | 5-methyl-thiazol-2-yl | H | H | H | H |
| 1H-indazol-6-yl | Me | H | H | cinnolin-3-yl | H | H | H | H |
| 1H-indazol-6-yl | Me | H | H | phthalazin-1-yl | H | H | H | H |
| 1H-indazol-6-yl | Me | H | H | quinoxalin-2-yl | H | H | H | H |
| 1H-indazol-6-yl | Me | H | H | quinazolin-2-yl | H | H | H | H |
| 1H-indazol-6-yl | Me | H | H | quinazolin-6-yl | H | H | H | H |
| 1H-indazol-6-yl | Me | H | H | quinazolin-7-yl | H | H | H | H |
| 1H-indazol-6-yl | Me | H | H | 3-oxo-[1,2,4]triazolo[4,3-a]pyridin-2-yl | H | H | H | H |
| 1H-indazol-6-yl | Me | H | H | morpholin-4-yl | H | H | H | H |
| 1-methyl-1H-indazol-6-yl | Me | H | H | morpholin-4-yl | H | H | H | H |
| 7-fluoro-1H-indazol-6-yl | Me | H | H | morpholin-4-yl | H | H | H | H |
| 1H-indazol-6-yl | Me | H | H | 2,6-dimethyl-morpholin-4-yl | H | H | H | H |
| 1H-indazol-6-yl | Et | H | H | morpholin-4-yl | H | H | H | H |
| 1H-indazol-6-yl | Me | H | F | morpholin-4-yl | H | H | H | H |
| 1H-indazol-6-yl | Et | H | F | morpholin-4-yl | H | H | H | H |
| 1H-indazol-6-yl | Me | H | H | morpholin-4-yl | F | H | H | H |
| 1H-indazol-6-yl | Me | H | H | morpholin-4-yl | H | F | H | H |
| 1H-indazol-6-yl | Me | H | OMe | morpholin-4-yl | H | H | H | H |
| 1H-indazol-6-yl | Me | H | OH | morpholin-4-yl | H | H | H | H |
| 1H-indazol-6-yl | Me | H | Me | morpholin-4-yl | H | H | H | H |
| 1H-indazol-6-yl | Me | H | H | morpholin-4-yl | H | H | H | OH |
| 1H-indazol-6-yl | Me | H | H | morpholin-4-yl | H | H | H | Me |
| 1H-indazol-6-yl | Me | H | H | piperidin-1-yl | H | H | H | H |
| 1H-indazol-6-yl | Me | H | H | pyrrolidin-1-yl | H | H | H | H |
| 1H-indazol-6-yl | Me | H | H | morpholin-4-ylmethyl | H | H | H | H |
| 1H-indazol-6-yl | Me | H | H | 1-methyl-1-morpholin-4-yl-ethyl | H | H | H | H |
| 1H-indazol-6-yl | Me | H | H | 1-morpholin-4-yl-cyclopropyl | H | H | H | H |

TABLE D-continued

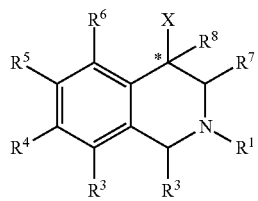

| X | R¹ | R² | R³ | R⁴ | R⁵ | R⁶ | R⁷ | R⁸ |
|---|---|---|---|---|---|---|---|---|
| 1H-indazol-6-yl | Me | H | H | piperidin-1-ylmethyl | H | H | H | H |
| 1H-indazol-6-yl | Me | H | H | pyrrolidin-1-ylmethyl | H | H | H | H |
| 1H-indazol-6-yl | Me | H | H | CH₂NMe₂ | H | H | H | H |
| 1H-indazol-6-yl | Me | H | H | CH₂NHMe | H | H | H | H |
| 1H-indazol-6-yl | Me | H | H | 2-oxo-2H-pyridin-1-yl | H | H | H | H |
| 1H-indazol-6-yl | Me | H | H | SO₂CH₃ | H | H | H | H |
| 1H-indazol-6-yl | Me | H | H | CN | H | H | H | H |
| 1H-indazol-6-yl | Me | H | Me | H | H | H | H | H |
| 1-methyl-1H-indazol-6-yl | Me | H | F | H | H | H | H | H |
| 1-methyl-1H-indazol-6-yl | Et | H | F | H | H | H | H | H |
| 1-benzyl-1H-indazol-6-yl | Me | H | H | H | H | H | H | H |
| (3-cyano-benzyl)-1H-indazol-6-yl | Me | H | H | H | H | H | H | H |
| (2-cyano-benzyl)-1H-indazol-6-yl | Me | H | H | H | H | H | H | H |
| 1H-indazol-7-yl | Me | H | H | H | H | H | H | H | wherein the carbon atom designated * is in the R or S configuration.

That is, the specific compounds herein include:
4-(indazol-1-yl)-2-methyl-1,2,3,4-tetrahydroisoquinoline;
4-(1H-indazol-3-yl)-2-methyl-1,2,3,4-tetrahydroisoquinoline;
4-(1H-indazol-4-yl)-2-methyl-1,2,3,4-tetrahydroisoquinoline;
4-(1H-indazol-5-yl)-1,2,3,4-tetrahydroisoquinoline;
4-(1H-indazol-5-yl)-1-methyl-1,2,3,4-tetrahydroisoquinoline;
4-(1H-indazol-5-yl)-2-methyl-1,2,3,4-tetrahydroisoquinoline;
2-methyl-4-(1-methyl-1H-indazol-5-yl)-1,2,3,4-tetrahydroisoquinoline;
4-(6-methoxy-indazol-5-yl)-2-methyl-1,2,3,4-tetrahydroisoquinoline;
4-(7-methoxy-indazol-5-yl)-2-methyl-1,2,3,4-tetrahydroisoquinoline;
4-(7-fluoro-indazol-5-yl)-2-methyl-1,2,3,4-tetrahydroisoquinoline;
4-(7-chloro-indazol-5-yl)-2-methyl-1,2,3,4-tetrahydroisoquinoline;
4-(7-methyl-indazol-5-yl)-2-methyl-1,2,3,4-tetrahydroisoquinoline;
8-fluoro-4-(1H-indazol-5-yl)-2-methyl-1,2,3,4-tetrahydroisoquinoline;
2-ethyl-4-(1H-indazol-5-yl)-1,2,3,4-tetrahydroisoquinoline;
2-ethyl-8-fluoro-4-(1H-indazol-5-yl)-1,2,3,4-tetrahydroisoquinoline;
1,2-dimethyl-4-(1H-indazol-5-yl)-1,2,3,4-tetrahydroisoquinoline;
4-(1H-indazol-5-yl)-2-methyl-1,2,3,4-tetrahydroisoquinolin-4-ol;
4-(1H-indazol-5-yl)-4-methoxy-2-methyl-1,2,3,4-tetrahydroisoquinoline;
2,4-dimethyl-4-(1H-indazol-5-yl)-1,2,3,4-tetrahydroisoquinoline;
4-(1H-indazol-5-yl)-2-methyl-1,2,3,4-tetrahydroisoquinoline-4-carbonitrile;
4-fluoro-4-(1H-indazol-5-yl)-2-methyl-1,2,3,4-tetrahydroisoquinoline;
4-chloro-4-(1H-indazol-5-yl)-2-methyl-1,2,3,4-tetrahydroisoquinoline;
4-(1H-indazol-5-yl)-2-methyl-1,2,3,4-tetrahydroisoquinolin-7-ol;
4-(1H-indazol-5-yl)-7-methoxy-2-methyl-1,2,3,4-tetrahydroisoquinoline;
2,7-dimethyl-4-(1H-indazol-5-yl)-1,2,3,4-tetrahydroisoquinoline;
7-fluoro-2-methyl-4-(1H-indazol-5-yl)-1,2,3,4-tetrahydroisoquinoline;
4-(1H-indazol-5-yl)-2-methyl-7-(pyridazin-3-yl)-1,2,3,4-tetrahydroisoquinoline;
4-(1-methyl-1H-indazol-5-yl)-2-methyl-7-(pyridazin-3-yl)-1,2,3,4-tetrahydroisoquinoline;
4-(7-fluoro-1H-indazol-5-yl)-2-methyl-7-(pyridazin-3-yl)-1,2,3,4-tetrahydroisoquinoline;
2-ethyl-4-(1H-indazol-5-yl)-7-(pyridazin-3-yl)-1,2,3,4-tetrahydroisoquinoline;
4-(1H-indazol-5-yl)-2-methyl-7-(6-methyl-pyridazin-3-yl)-1,2,3,4-tetrahydroisoquinoline;
[6-(4-(1H-indazol-5-yl)-2-methyl-1,2,3,4-tetrahydroisoquinolin-7-yl)-pyridazin-3-yl]-dimethylamine;
[6-(4-(1H-indazol-5-yl)-2-methyl-1,2,3,4-tetrahydroisoquinolin-7-yl)-pyridazin-3-yl]-methylamine;
6-(4-(1H-indazol-5-yl)-2-methyl-1,2,3,4-tetrahydroisoquinolin-7-yl)-pyridazin-3-ylamine;
4-(1H-indazol-5-yl)-2-methyl-7-(6-morpholin-4-yl-pyridazin-3-yl)-1,2,3,4-tetrahydroisoquinoline;
4-(1H-indazol-5-yl)-2-methyl-7-(6-trifluoromethyl-pyridazin-3-yl)-1,2,3,4-tetrahydroisoquinoline;
4-(1H-indazol-5-yl)-2-methyl-7-(pyridazin-4-yl)-1,2,3,4-tetrahydroisoquinoline;
4-(1H-indazol-5-yl)-2-methyl-7-(pyrazin-2-yl)-1,2,3,4-tetrahydroisoquinoline;
4-(1H-indazol-5-yl)-2-methyl-7-(pyrimidin-2-yl)-1,2,3,4-tetrahydroisoquinoline;
4-(1H-indazol-5-yl)-2-methyl-7-(pyrimidin-4-yl)-1,2,3,4-tetrahydroisoquinoline;
4-(1H-indazol-5-yl)-2-methyl-7-(pyrimidin-5-yl)-1,2,3,4-tetrahydroisoquinoline;
4-(1H-indazol-5-yl)-7-(3,5-dimethyl-isoxazol-4-yl)-2-methyl-1,2,3,4-tetrahydroisoquinoline;
4-(1H-indazol-5-yl)-2-methyl-7-(thiazol-2-yl)-1,2,3,4-tetrahydroisoquinoline;
4-(1H-indazol-5-yl)-2-methyl-7-(5-methyl-thiazol-2-yl)-1,2,3,4-tetrahydroisoquinoline;
3-(4-(1H-indazol-5-yl)-2-methyl-1,2,3,4-tetrahydroisoquinolin-7-yl)-cinnoline;
1-(4-(1H-indazol-5-yl)-2-methyl-1,2,3,4-tetrahydroisoquinolin-7-yl)-phthalazine;
2-(4-(1H-indazol-5-yl)-2-methyl-1,2,3,4-tetrahydroisoquinolin-7-yl)-quinoxaline;
2-(4-(1H-indazol-5-yl)-2-methyl-1,2,3,4-tetrahydroisoquinolin-7-yl)-quinazoline;
6-(4-(1H-indazol-5-yl)-2-methyl-1,2,3,4-tetrahydroisoquinolin-7-yl)-quinazoline;
7-(4-(1H-indazol-5-yl)-2-methyl-1,2,3,4-tetrahydroisoquinolin-7-yl)-quinazoline;
2-(4-(1H-indazol-5-yl)-2-methyl-1,2,3,4-tetrahydroisoquinolin-7-yl)-2H-[1,2,4]triazolo[4,3-a]pyridin-3-one;

4-(1H-indazol-5-yl)-2-methyl-7-(morpholin-4-yl)-1,2,3,4-tetrahydroisoquinoline;
4-(1-methyl-1H-indazol-5-yl)-2-methyl-7-morpholin-4-yl-1,2,3,4-tetrahydroisoquinoline;
4-(7-fluoro-1H-indazol-5-yl)-2-methyl-7-morpholin-4-yl-1,2,3,4-tetrahydroisoquinoline;
7-(2,6-dimethyl-morpholin-4-yl)-4-(1H-indazol-5-yl)-2-methyl-1,2,3,4-tetrahydroisoquinoline;
2-ethyl-4-(1H-indazol-5-yl)-7-morpholin-4-yl-1,2,3,4-tetrahydroisoquinoline;
8-fluoro-4-(1H-indazol-5-yl)-2-methyl-7-morpholin-4-yl-1,2,3,4-tetrahydroisoquinoline;
2-ethyl-8-fluoro-4-(1H-indazol-5-yl)-7-morpholin-4-yl-1,2,3,4-tetrahydroisoquinoline;
6-fluoro-4-(1H-indazol-5-yl)-2-methyl-7-morpholin-4-yl-1,2,3,4-tetrahydroisoquinoline;
5-fluoro-4-(1H-indazol-5-yl)-2-methyl-7-morpholin-4-yl-1,2,3,4-tetrahydroisoquinoline;
4-(1H-indazol-5-yl)-8-methoxy-2-methyl-7-morpholin-4-yl-1,2,3,4-tetrahydroisoquinoline;
4-(1H-indazol-5-yl)-2-methyl-7-morpholin-4-yl-1,2,3,4-tetrahydroisoquinolin-8-ol;
2,8-dimethyl-4-(1H-indazol-5-yl)-7-morpholin-4-yl-1,2,3,4-tetrahydroisoquinoline;
4-(1H-indazol-5-yl)-2-methyl-7-morpholin-4-yl-1,2,3,4-tetrahydroisoquinolin-4-ol;
2,4-dimethyl-4-(1H-indazol-5-yl)-7-morpholin-4-yl-1,2,3,4-tetrahydroisoquinoline;
4-(1H-indazol-5-yl)-2-methyl-7-(piperidin-1-yl)-1,2,3,4-tetrahydroisoquinoline;
4-(1H-indazol-5-yl)-2-methyl-7-(pyrrolidin-1-yl)-1,2,3,4-tetrahydroisoquinoline;
4-(1H-indazol-5-yl)-2-methyl-7-((morpholin-4-yl)methyl)-1,2,3,4-tetrahydroisoquinoline;
4-(1H-indazol-5-yl)-2-methyl-7-(1-methyl-1-morpholin-4-yl-ethyl)-1,2,3,4-tetrahydroisoquinoline;
4-(1H-indazol-5-yl)-2-methyl-7-(1-morpholin-4-yl-cyclopropyl)-1,2,3,4-tetrahydroisoquinoline;
4-(1H-indazol-5-yl)-2-methyl-7-piperidin-1-ylmethyl-1,2,3,4-tetrahydroisoquinoline;
4-(1H-indazol-5-yl)-2-methyl-7-pyrrolidin-1-ylmethyl-1,2,3,4-tetrahydroisoquinoline;
[4-(1H-indazol-5-yl)-2-methyl-1,2,3,4-tetrahydroisoquinolin-7-ylmethyl]-dimethylamine;
[4-(1H-indazol-5-yl)-2-methyl-1,2,3,4-tetrahydroisoquinolin-7-ylmethyl]-methylamine;
1-(4-(1H-indazol-5-yl)-2-methyl-1,2,3,4-tetrahydroisoquinolin-7-yl)-1H-pyridin-2-one;
4-(1H-indazol-5-yl)-7-methanesulfonyl-2-methyl-1,2,3,4-tetrahydroisoquinoline;
4-(1H-indazol-5-yl)-2-methyl-1,2,3,4-tetrahydroisoquinoline-7-carbonitrile;
4-(1H-indazol-5-yl)-2,8-dimethyl-1,2,3,4-tetrahydroisoquinoline;
7-fluoro-2-methyl-4-(1-methyl-1H-indazol-5-yl)-1,2,3,4-tetrahydroisoquinoline;
2-ethyl-7-fluoro-4-(1-methyl-1H-indazol-5-yl)-1,2,3,4-tetrahydroisoquinoline;
4-(1-benzyl-1H-indazol-5-yl)-2-methyl-1,2,3,4-tetrahydroisoquinoline;
3-[5-(2-methyl-1,2,3,4-tetrahydroisoquinolin-4-yl)-indazol-1-ylmethyl]-benzonitrile;
2-[5-(2-methyl-1,2,3,4-tetrahydroisoquinolin-4-yl)-indazol-1-ylmethyl]-benzonitrile;
4-(1H-indazol-6-yl)-1,2,3,4-tetrahydroisoquinoline;
4-(1H-indazol-6-yl)-1-methyl-1,2,3,4-tetrahydroisoquinoline;
4-(1H-indazol-6-yl)-2-methyl-1,2,3,4-tetrahydroisoquinoline;
2-methyl-4-(1-methyl-indazol-6-yl)-1,2,3,4-tetrahydroisoquinoline;
4-(7-fluoro-1H-indazol-6-yl)-2-methyl-1,2,3,4-tetrahydroisoquinoline;
2-ethyl-4-(1H-indazol-6-yl)-1,2,3,4-tetrahydroisoquinoline;
1,2-dimethyl-4-(1H-indazol-6-yl)-1,2,3,4-tetrahydroisoquinoline;
4-(1H-indazol-6-yl)-4-methyl-1,2,3,4-tetrahydroisoquinoline-4-ol;
4-(1H-indazol-6-yl)-4-methoxy-2-methyl-1,2,3,4-tetrahydroisoquinoline;
2,4-dimethyl-4-(1H-indazol-6-yl)-1,2,3,4-tetrahydroisoquinoline;
4-(1H-indazol-6-yl)-2-methyl-1,2,3,4-tetrahydroisoquinoline-4-carbonitrile;
4-fluoro-4-(1H-indazol-6-yl)-2-methyl-1,2,3,4-tetrahydroisoquinoline;
4-chloro-4-(1H-indazol-6-yl)-2-methyl-1,2,3,4-tetrahydroisoquinoline;
4-(1H-indazol-6-yl)-2-methyl-1,2,3,4-tetrahydroisoquinolin-7-ol;
4-(1H-indazol-6-yl)-7-methoxy-2-methyl-1,2,3,4-tetrahydroisoquinoline;
2,7-dimethyl-4-(1H-indazol-6-yl)-1,2,3,4-tetrahydroisoquinoline;
7-fluoro-2-methyl-4-(1H-indazol-6-yl)-1,2,3,4-tetrahydroisoquinoline;
4-(1H-indazol-6-yl)-2-methyl-7-(pyridazin-3-yl)-1,2,3,4-tetrahydroisoquinoline;
2-methyl-4-(1-methyl-1H-indazol-6-yl)-7-(pyridazin-3-yl)-1,2,3,4-tetrahydroisoquinoline;
4-(7-fluoro-1H-indazol-6-yl)-2-methyl-7-(pyridazin-3-yl)-1,2,3,4-tetrahydroisoquinoline;
2-ethyl-4-(1H-indazol-6-yl)-7-(pyridazin-3-yl)-1,2,3,4-tetrahydroisoquinoline;
4-(1H-indazol-6-yl)-2-methyl-7-(6-methyl-pyridazin-3-yl)-1,2,3,4-tetrahydroisoquinoline;
[6-(4-(1H-indazol-6-yl)-2-methyl-1,2,3,4-tetrahydroisoquinolin-7-yl)-pyridazin-3-yl]dimethylamine;
[6-(4-(1H-indazol-6-yl)-2-methyl-1,2,3,4-tetrahydroisoquinolin-7-yl)-pyridazin-3-yl]methylamine;
6-(4-(1H-indazol-6-yl)-2-methyl-1,2,3,4-tetrahydroisoquinolin-7-yl)-pyridazin-3-ylamine;
4-(1H-indazol-6-yl)-2-methyl-7-(6-morpholin-4-yl-pyridazin-3-yl)-1,2,3,4-tetrahydroisoquinoline;
4-(1H-indazol-6-yl)-2-methyl-7-(6-trifluoromethyl-pyridazin-3-yl)-1,2,3,4-tetrahydroisoquinoline;
4-(1H-indazol-6-yl)-2-methyl-7-(pyridazin-4-yl)-1,2,3,4-tetrahydroisoquinoline;
4-(1H-indazol-6-yl)-2-methyl-7-(pyrazin-2-yl)-1,2,3,4-tetrahydroisoquinoline;
4-(1H-indazol-6-yl)-2-methyl-7-(pyrimidin-2-yl)-1,2,3,4-tetrahydroisoquinoline;
4-(1H-indazol-6-yl)-2-methyl-7-(pyrimidin-4-yl)-1,2,3,4-tetrahydroisoquinoline;
4-(1H-indazol-6-yl)-2-methyl-7-(pyrimidin-5-yl)-1,2,3,4-tetrahydroisoquinoline;
4-(1H-indazol-6-yl)-7-(3,5-dimethyl-isoxazol-4-yl)-2-methyl-1,2,3,4-tetrahydroisoquinoline;
4-(1H-indazol-6-yl)-2-methyl-7-(thiazol-2-yl)-1,2,3,4-tetrahydroisoquinoline;
4-(1H-indazol-6-yl)-2-methyl-7-(5-methyl-thiazol-2-yl)-1,2,3,4-tetrahydroisoquinoline;
3-(4-(1H-indazol-6-yl)-2-methyl-1,2,3,4-tetrahydroisoquinolin-7-yl)-cinnoline;

1-(4-(1H-indazol-6-yl)-2-methyl-1,2,3,4-tetrahydroisoquinolin-7-yl)-phthalazine;
2-(4-(1H-indazol-6-yl)-2-methyl-1,2,3,4-tetrahydroisoquinolin-7-yl)-quinoxaline;
2-(4-(1H-indazol-6-yl)-2-methyl-1,2,3,4-tetrahydroisoquinolin-7-yl)-quinazoline;
6-(4-(1H-indazol-6-yl)-2-methyl-1,2,3,4-tetrahydroisoquinolin-7-yl)-quinazoline;
7-(4-(1H-indazol-6-yl)-2-methyl-1,2,3,4-tetrahydroisoquinolin-7-yl)-quinazoline;
2-(4-(1H-indazol-6-yl)-2-methyl-1,2,3,4-tetrahydroisoquinolin-7-yl)-2H-[1,2,4]triazolo[4,3-a]pyridin-3-one;
4-(1H-indazol-6-yl)-2-methyl-7-(morpholin-4-yl)-1,2,3,4-tetrahydroisoquinoline;
2-methyl-4-(1-methyl-1H-indazol-6-yl)-7-morpholin-4-yl-1,2,3,4-tetrahydroisoquinoline;
4-(7-fluoro-1H-indazol-6-yl)-2-methyl-7-morpholin-4-yl-1,2,3,4-tetrahydroisoquinoline;
7-(2,6-dimethyl-morpholin-4-yl)-4-(1H-indazol-6-yl)-2-methyl-1,2,3,4-tetrahydroisoquinoline;
2-ethyl-4-(1H-indazol-6-yl)-7-morpholin-4-yl-1,2,3,4-tetrahydroisoquinoline;
8-fluoro-4-(1H-indazol-6-yl)-2-methyl-7-morpholin-4-yl-1,2,3,4-tetrahydroisoquinoline;
2-ethyl-8-fluoro-4-(1H-indazol-6-yl)-7-morpholin-4-yl-1,2,3,4-tetrahydroisoquinoline;
6-fluoro-4-(1H-indazol-6-yl)-2-methyl-7-morpholin-4-yl-1,2,3,4-tetrahydroisoquinoline;
5-fluoro-4-(1H-indazol-6-yl)-2-methyl-7-morpholin-4-yl-1,2,3,4-tetrahydroisoquinoline;
4-(1H-indazol-6-yl)-8-methoxy-2-methyl-7-morpholin-4-yl-1,2,3,4-tetrahydroisoquinoline;
4-(1H-indazol-6-yl)-2-methyl-7-morpholin-4-yl-1,2,3,4-tetrahydroisoquinolin-8-ol;
2,8-dimethyl-4-(1H-indazol-6-yl)-7-morpholin-4-yl-1,2,3,4-tetrahydroisoquinoline;
4-(1H-indazol-6-yl)-2-methyl-7-morpholin-4-yl-1,2,3,4-tetrahydroisoquinolin-4-ol;
2,4-dimethyl-4-(1H-indazol-6-yl)-7-morpholin-4-yl-1,2,3,4-tetrahydroisoquinoline;
4-(1H-indazol-6-yl)-2-methyl-7-(piperidin-1-yl)-1,2,3,4-tetrahydroisoquinoline;
4-(1H-indazol-6-yl)-2-methyl-7-(pyrrolidin-1-yl)-1,2,3,4-tetrahydroisoquinoline;
4-(1H-indazol-6-yl)-2-methyl-7-morpholin-4-ylmethyl-1,2,3,4-tetrahydroisoquinoline;
4-(1H-indazol-6-yl)-2-methyl-7-(1-methyl-1-morpholin-4-yl-ethyl)-1,2,3,4-tetrahydroisoquinoline;
4-(1H-indazol-6-yl)-2-methyl-7-(1-morpholin-4-yl-cyclopropyl)-1,2,3,4-tetrahydroisoquinoline;
4-(1H-indazol-6-yl)-2-methyl-7-piperidin-1-ylmethyl-1,2,3,4-tetrahydroisoquinoline;
4-(1H-indazol-6-yl)-2-methyl-7-pyrrolidin-1-ylmethyl-1,2,3,4-tetrahydroisoquinoline;
[4-(1H-indazol-6-yl)-2-methyl-1,2,3,4-tetrahydroisoquinolin-7-ylmethyl]-dimethylamine;
[4-(1H-indazol-6-yl)-2-methyl-1,2,3,4-tetrahydroisoquinolin-7-ylmethyl]-methylamine;
1-(4-(1H-indazol-6-yl)-2-methyl-1,2,3,4-tetrahydroisoquinolin-7-yl)-1H-pyridin-2-one;
4-(1H-indazol-6-yl)-7-methanesulfonyl-2-methyl-1,2,3,4-tetrahydroisoquinoline;
4-(1H-indazol-6-yl)-2-methyl-1,2,3,4-tetrahydroisoquinoline-7-carbonitrile;
2,8-dimethyl-4-(1H-indazol-6-yl)-1,2,3,4-tetrahydroisoquinoline;
7-fluoro-2-methyl-4-(1-methyl-1H-indazol-6-yl)-1,2,3,4-tetrahydroisoquinoline;
2-ethyl-7-fluoro-4-(1-methyl-1H-indazol-6-yl)-1,2,3,4-tetrahydroisoquinoline;
4-(1-benzyl-1H-indazol-6-yl)-2-methyl-1,2,3,4-tetrahydroisoquinoline;
3-[6-(2-methyl-1,2,3,4-tetrahydroisoquinolin-4-yl)-indazol-1-ylmethyl]-benzonitrile;
2-[6-(2-methyl-1,2,3,4-tetrahydroisoquinolin-4-yl)-indazol-1-ylmethyl]-benzonitrile;
4-(1H-indazol-7-yl)-2-methyl-1,2,3,4-tetrahydroisoquinoline;

or an oxide thereof, a pharmaceutically acceptable salt thereof, a solvate thereof, or a prodrug thereof.

In addition, other specific compounds of the present invention are those with the following substituents:

TABLE E

| X | $R^1$ | $R^2$ | $R^3$ | $R^4$ | $R^5$ | $R^6$ | $R^7$ | $R^8$ |
|---|---|---|---|---|---|---|---|---|
| benzooxazol-2-yl | Me | H | H | H | H | H | H | H |
| benzooxazol-2-yl | Me | H | H | morpholin-4-yl | H | H | H | H |
| benzooxazol-2-yl | Me | H | H | piperidin-1-yl | H | H | H | H |
| benzooxazol-2-yl | Me | H | H | pyrrolidin-1-yl | H | H | H | H |
| benzooxazol-4-yl | Me | H | H | H | H | H | H | H |
| benzooxazol-5-yl | Me | H | H | H | H | H | H | H |
| benzooxazol-5-yl | Me | H | H | morpholin-4-yl | H | H | H | H |
| benzooxazol-5-yl | Me | H | H | piperidin-1-yl | H | H | H | H |
| benzooxazol-5-yl | Me | H | H | pyrrolidin-1-yl | H | H | H | H |
| 2-methyl-benzooxazol-5-yl | Me | H | H | H | H | H | H | H |
| benzooxazol-6-yl | Me | H | H | H | H | H | H | H |
| benzooxazol-6-yl | Me | H | H | morpholin-4-yl | H | H | H | H |
| benzooxazol-6-yl | Me | H | H | piperidin-1-yl | H | H | H | H |
| benzooxazol-6-yl | Me | H | H | pyrrolidin-1-yl | H | H | H | H |
| 2-methyl-benzooxazol-6-yl | Me | H | H | H | H | H | H | H |
| benzooxazol-7-yl | Me | H | H | H | H | H | H | H |
| benzothiazol-2-yl | Me | H | H | H | H | H | H | H |
| benzothiazol-2-yl | Me | H | H | morpholin-4-yl | H | H | H | H |
| benzothiazol-2-yl | Me | H | H | piperidin-1-yl | H | H | H | H |
| benzothiazol-2-yl | Me | H | H | pyrrolidin-1-yl | H | H | H | H |
| benzothiazol-4-yl | Me | H | H | H | H | H | H | H |
| benzothiazol-5-yl | Me | H | H | H | H | H | H | H |
| benzothiazol-5-yl | Me | H | H | morpholin-4-yl | H | H | H | H |
| benzothiazol-5-yl | Me | H | H | piperidin-1-yl | H | H | H | H |
| benzothiazol-5-yl | Me | H | H | pyrrolidin-1-yl | H | H | H | H |
| 2-methyl-benzothiazol-5-yl | Me | H | H | H | H | H | H | H |
| benzothiazol-6-yl | Me | H | H | H | H | H | H | H |
| benzothiazol-6-yl | Me | H | H | morpholin-4-yl | H | H | H | H |
| benzothiazol-6-yl | Me | H | H | piperidin-1-yl | H | H | H | H |
| benzothiazol-6-yl | Me | H | H | pyrrolidin-1-yl | H | H | H | H |
| 2-methyl-benzothiazol-6-yl | Me | H | H | H | H | H | H | H |
| benzothiazol-7-yl | Me | H | H | H | H | H | H | H |
| benzo[d]isothiazol-5-yl | Me | H | H | H | H | H | H | H |
| benzo[d]isothiazol-5-yl | Me | H | H | morpholin-4-yl | H | H | H | H |
| benzo[d]isothiazol-5-yl | Me | H | H | piperidin-1-yl | H | H | H | H |
| benzo[d]isothiazol-5-yl | Me | H | H | pyrrolidin-1-yl | H | H | H | H |
| benzo[d]isothiazol-6-yl | Me | H | H | H | H | H | H | H |
| benzo[d]isothiazol-6-yl | Me | H | H | morpholin-4-yl | H | H | H | H |
| benzo[d]isothiazol-6-yl | Me | H | H | piperidin-1-yl | H | H | H | H |
| benzo[d]isothiazol-6-yl | Me | H | H | pyrrolidin-1-yl | H | H | H | H |
| benzo[d]isothiazol-7-yl | Me | H | H | H | H | H | H | H |

TABLE E-continued

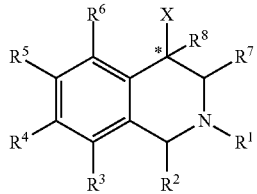

| X | R¹ | R² | R³ | R⁴ | R⁵ | R⁶ | R⁷ | R⁸ |
|---|---|---|---|---|---|---|---|---|
| benzo[d]isoxazol-4-yl | Me | H | H | H | H | H | H | H |
| benzo[d]isoxazol-5-yl | Me | H | H | H | H | H | H | H |
| benzo[d]isoxazol-6-yl | Me | H | H | H | H | H | H | H |
| benzo[d]isoxazol-7-yl | Me | H | H | H | H | H | H | H |
| imidazo[1,2-a]pyridin-6-yl | Me | H | H | H | H | H | H | H |
| imidazo[1,2-a]pyridin-6-yl | Me | H | H | morpholin-4-yl | H | H | H | H |
| imidazo[1,2-a]pyridin-6-yl | Me | H | H | piperidin-1-yl | H | H | H | H |
| imidazo[1,2-a]pyridin-6-yl | Me | H | H | pyrrolidin-1-yl | H | H | H | H |
| imidazo[1,2-a]pyridin-7-yl | Me | H | H | H | H | H | H | H |
| imidazo[1,2-a]pyridin-7-yl | Me | H | H | morpholin-4-yl | H | H | H | H |
| imidazo[1,2-a]pyridin-7-yl | Me | H | H | piperidin-1-yl | H | H | H | H |
| imidazo[1,2-a]pyridin-7-yl | Me | H | H | pyrrolidin-1-yl | H | H | H | H |
| pyrazolo[1,5-a]pyridin-5-yl | Me | H | H | H | H | H | H | H |
| pyrazolo[1,5-a]pyridin-5-yl | Me | H | H | morpholin-4-yl | H | H | H | H |
| pyrazolo[1,5-a]pyridin-5-yl | Me | H | H | piperidin-1-yl | H | H | H | H |
| pyrazolo[1,5-a]pyridin-5-yl | Me | H | H | pyrrolidin-1-yl | H | H | H | H |
| pyrazolo[1,5-a]pyridin-6-yl | Me | H | H | H | H | H | H | H |
| pyrazolo[1,5-a]pyridin-6-yl | Me | H | H | morpholin-4-yl | H | H | H | H |
| pyrazolo[1,5-a]pyridin-6-yl | Me | H | H | piperidin-1-yl | H | H | H | H |
| pyrazolo[1,5-a]pyridin-6-yl | Me | H | H | pyrrolidin-1-yl | H | H | H | H |
| [1,2,4]triazolo[4,3-a]pyridin-6-yl | Me | H | H | H | H | H | H | H |
| [1,2,4]triazolo[4,3-a]pyridin-6-yl | Me | H | H | morpholin-4-yl | H | H | H | H |
| [1,2,4]triazolo[4,3-a]pyridin-6-yl | Me | H | H | piperidin-1-yl | H | H | H | H |
| [1,2,4]triazolo[4,3-a]pyridin-6-yl | Me | H | H | pyrrolidin-1-yl | H | H | H | H |
| [1,2,4]triazolo[4,3-a]pyridin-7-yl | Me | H | H | H | H | H | H | H |
| [1,2,4]triazolo[4,3-a]pyridin-7-yl | Me | H | H | morpholin-4-yl | H | H | H | H |
| [1,2,4]triazolo[4,3-a]pyridin-7-yl | Me | H | H | piperidin-1-yl | H | H | H | H |
| [1,2,4]triazolo[4,3-a]pyridin-7-yl | Me | H | H | pyrrolidin-1-yl | H | H | H | H |
| thieno[2,3-b]pyridin-2-yl | Me | H | H | H | H | H | H | H |
| thieno[2,3-b]pyridin-2-yl | Me | H | H | morpholin-4-yl | H | H | H | H |
| thieno[2,3-b]pyridin-2-yl | Me | H | H | piperidin-1-yl | H | H | H | H |
| thieno[2,3-b]pyridin-2-yl | Me | H | H | pyrrolidin-1-yl | H | H | H | H |
| thieno[2,3-b]pyridin-5-yl | Me | H | H | H | H | H | H | H |
| thieno[2,3-b]pyridin-5-yl | Me | H | H | morpholin-4-yl | H | H | H | H |
| thieno[2,3-b]pyridin-5-yl | Me | H | H | piperidin-1-yl | H | H | H | H |
| thieno[2,3-b]pyridin-5-yl | Me | H | H | pyrrolidin-1-yl | H | H | H | H |
| thieno[2,3-b]pyridin-6-yl | Me | H | H | H | H | H | H | H |
| thieno[2,3-b]pyridin-6-yl | Me | H | H | morpholin-4-yl | H | H | H | H |
| thieno[2,3-b]pyridin-6-yl | Me | H | H | piperidin-1-yl | H | H | H | H |
| thieno[2,3-b]pyridin-6-yl | Me | H | H | pyrrolidin-1-yl | H | H | H | H |
| thieno[3,2-b]pyridin-2-yl | Me | H | H | H | H | H | H | H |
| thieno[3,2-b]pyridin-2-yl | Me | H | H | morpholin-4-yl | H | H | H | H |
| thieno[3,2-b]pyridin-2-yl | Me | H | H | piperidin-1-yl | H | H | H | H |
| thieno[3,2-b]pyridin-2-yl | Me | H | H | pyrrolidin-1-yl | H | H | H | H |
| thieno[3,2-b]pyridin-5-yl | Me | H | H | H | H | H | H | H |
| thieno[3,2-b]pyridin-5-yl | Me | H | H | morpholin-4-yl | H | H | H | H |
| thieno[3,2-b]pyridin-5-yl | Me | H | H | piperidin-1-yl | H | H | H | H |
| thieno[3,2-b]pyridin-5-yl | Me | H | H | pyrrolidin-1-yl | H | H | H | H |
| thieno[3,2-b]pyridin-6-yl | Me | H | H | H | H | H | H | H |
| thieno[3,2-b]pyridin-6-yl | Me | H | H | morpholin-4-yl | H | H | H | H |
| thieno[3,2-b]pyridin-6-yl | Me | H | H | piperidin-1-yl | H | H | H | H |
| thieno[3,2-b]pyridin-6-yl | Me | H | H | pyrrolidin-1-yl | H | H | H | H |
| indolizin-2-yl | Me | H | H | H | H | H | H | H |
| indolizin-2-yl | Me | H | H | pyidazin-3-yl | H | H | H | H |
| indolizin-2-yl | Me | H | H | pyrimidin-2-yl | H | H | H | H |
| indolizin-2-yl | Me | H | H | pyrimidin-4-yl | H | H | H | H |
| indolizin-2-yl | Me | H | H | pyrimidin-5-yl | H | H | H | H |
| indolizin-2-yl | Me | H | H | morpholin-4-yl | H | H | H | H |
| indolizin-6-yl | Me | H | H | H | H | H | H | H |
| indolizin-6-yl | Me | H | H | pyridazin-3-yl | H | H | H | H |
| indolizin-6-yl | Me | H | H | pyrimidin-2-yl | H | H | H | H |
| indolizin-6-yl | Me | H | H | pyrimidin-4-yl | H | H | H | H |
| indolizin-6-yl | Me | H | H | pyrimidin-5-yl | H | H | H | H |
| indolizin-6-yl | Me | H | H | morpholin-4-yl | H | H | H | H |
| indolizin-7-yl | Me | H | H | H | H | H | H | H |
| indolizin-7-yl | Me | H | H | pyridazin-3-yl | H | H | H | H |
| indolizin-7-yl | Me | H | H | pyrimidin-2-yl | H | H | H | H |
| indolizin-7-yl | Me | H | H | pyrimidin-4-yl | H | H | H | H |
| indolizin-7-yl | Me | H | H | pyrimidin-5-yl | H | H | H | H |
| indolizin-7-yl | Me | H | H | morpholin-4-yl | H | H | H | H |
| 1H-inden-2-yl | Me | H | H | H | H | H | H | H |
| indan-5-yl | Me | H | H | H | H | H | H | H | wherein the carbon atom designated * is in the R or S configuration.

That is, the specific compounds herein include:
4-(benzooxazol-2-yl)-2-methyl-1,2,3,4-tetrahydroisoquinoline;
4-(benzooxazol-2-yl)-2-methyl-(morpholin-4-yl)-1,2,3,4-tetrahydroisoquinoline;
4-(benzooxazol-2-yl)-2-methyl-(piperidin-1-yl)-1,2,3,4-tetrahydroisoquinoline;
4-(benzooxazol-2-yl)-2-methyl-(pyrrolidin-1-yl)-1,2,3,4-tetrahydroisoquinoline;
4-(benzooxazol-4-yl)-2-methyl-1,2,3,4-tetrahydroisoquinoline;

4-(benzooxazol-5-yl)-2-methyl-1,2,3,4-tetrahydroisoquinoline;
4-(benzooxazol-5-yl)-2-methyl-(morpholin-4-yl)-1,2,3,4-tetrahydroisoquinoline;
4-(benzooxazol-5-yl)-2-methyl-(piperidin-1-yl)-1,2,3,4-tetrahydroisoquinoline;
4-(benzooxazol-5-yl)-2-methyl-(pyrrolidin-1-yl)-1,2,3,4-tetrahydroisoquinoline;
2-methyl-4-(2-methyl-benzooxazol-5-yl)-1,2,3,4-tetrahydroisoquinoline;
4-(benzooxazol-6-yl)-2-methyl-1,2,3,4-tetrahydroisoquinoline;
4-(benzooxazol-6-yl)-2-methyl-(morpholin-4-yl)-1,2,3,4-tetrahydroisoquinoline;
4-(benzooxazol-6-yl)-2-methyl-(piperidin-1-yl)-1,2,3,4-tetrahydroisoquinoline;
4-(benzooxazol-6-yl)-2-methyl-(pyrrolidin-1-yl)-1,2,3,4-tetrahydroisoquinoline;
2-methyl-4-(2-methyl-benzooxazol-6-yl)-1,2,3,4-tetrahydroisoquinoline;
4-(benzooxazol-7-yl)-2-methyl-1,2,3,4-tetrahydroisoquinoline;
4-(benzothiazol-2-yl)-2-methyl-1,2,3,4-tetrahydroisoquinoline;
4-(benzothiazol-2-yl)-2-methyl-(morpholin-4-yl)-1,2,3,4-tetrahydroisoquinoline;
4-(benzothiazol-2-yl)-2-methyl-(piperidin-1-yl)-1,2,3,4-tetrahydroisoquinoline;
4-(benzothiazol-2-yl)-2-methyl-(pyrrolidin-1-yl)-1,2,3,4-tetrahydroisoquinoline;
4-(benzothiazol-4-yl)-2-methyl-1,2,3,4-tetrahydroisoquinoline;
4-(benzothiazol-5-yl)-2-methyl-1,2,3,4-tetrahydroisoquinoline;
4-(benzothiazol-5-yl)-2-methyl-(morpholin-4-yl)-1,2,3,4-tetrahydroisoquinoline;
4-(benzothiazol-5-yl)-2-methyl-(piperidin-1-yl)-1,2,3,4-tetrahydroisoquinoline;
4-(benzothiazol-5-yl)-2-methyl-(pyrrolidin-1-yl)-1,2,3,4-tetrahydroisoquinoline;
2-methyl-4-(2-methyl-benzothiazol-5-yl)-1,2,3,4-tetrahydroisoquinoline;
4-(benzothiazol-6-yl)-2-methyl-1,2,3,4-tetrahydroisoquinoline;
4-(benzothiazol-6-yl)-2-methyl-(morpholin-4-yl)-1,2,3,4-tetrahydroisoquinoline;
4-(benzothiazol-6-yl)-2-methyl-(piperidin-1-yl)-1,2,3,4-tetrahydroisoquinoline;
4-(benzothiazol-6-yl)-2-methyl-(pyrrolidin-1-yl)-1,2,3,4-tetrahydroisoquinoline;
2-methyl-4-(2-methyl-benzothiazol-6-yl)-1,2,3,4-tetrahydroisoquinoline;
4-(benzothiazol-7-yl)-2-methyl-1,2,3,4-tetrahydroisoquinoline;
4-(benzo[d]isothiazol-4-yl)-2-methyl-1,2,3,4-tetrahydroisoquinoline;
4-(benzo[d]isothiazol-5-yl)-2-methyl-1,2,3,4-tetrahydroisoquinoline;
4-(benzo[d]isothiazol-5-yl)-2-methyl-(morpholin-4-yl)-1,2,3,4-tetrahydroisoquinoline;
4-(benzo[d]isothiazol-5-yl)-2-methyl-(piperidin-1-yl)-1,2,3,4-tetrahydroisoquinoline;
4-(benzo[d]isothiazol-5-yl)-2-methyl-(pyrrolidin-1-yl)-1,2,3,4-tetrahydroisoquinoline;
4-(benzo[d]isothiazol-6-yl)-2-methyl-1,2,3,4-tetrahydroisoquinoline;
4-(benzo[d]isothiazol-6-yl)-2-methyl-(morpholin-4-yl)-1,2,3,4-tetrahydroisoquinoline;
4-(benzo[d]isothiazol-6-yl)-2-methyl-(piperidin-1-yl)-1,2,3,4-tetrahydroisoquinoline;
4-(benzo[d]isothiazol-6-yl)-2-methyl-(pyrrolidin-1-yl)-1,2,3,4-tetrahydroisoquinoline;
4-(benzo[d]isothiazol-7-yl)-2-methyl-1,2,3,4-tetrahydroisoquinoline;
4-(benzo[d]isoxazol-4-yl)-2-methyl-1,2,3,4-tetrahydroisoquinoline;
4-(benzo[d]isoxazol-5-yl)-2-methyl-1,2,3,4-tetrahydroisoquinoline;
4-(benzo[d]isoxazol-6-yl)-2-methyl-1,2,3,4-tetrahydroisoquinoline;
4-(benzo[d]isoxazol-7-yl)-2-methyl-1,2,3,4-tetrahydroisoquinoline;
4-imidazo[1,2-a]pyridin-6-yl-2-methyl-1,2,3,4-tetrahydroisoquinoline;
4-imidazo[1,2-a]pyridin-6-yl-2-methyl-(morpholin-4-yl)-1,2,3,4-tetrahydroisoquinoline;
4-imidazo[1,2-a]pyridin-6-yl-2-methyl-(piperidin-1-yl)-1,2,3,4-tetrahydroisoquinoline;
4-imidazo[1,2-a]pyridin-6-yl-2-methyl-(pyrrolidin-1-yl)-1,2,3,4-tetrahydroisoquinoline;
4-imidazo[1,2-a]pyridin-7-yl-2-methyl-1,2,3,4-tetrahydroisoquinoline;
4-imidazo[1,2-a]pyridin-7-yl-2-methyl-7-(morpholin-4-yl)-1,2,3,4-tetrahydroisoquinoline;
4-imidazo[1,2-a]pyridin-7-yl-2-methyl-7-(piperidin-1-yl)-1,2,3,4-tetrahydroisoquinoline;
4-imidazo[1,2-a]pyridin-7-yl-2-methyl-7-(pyrrolidin-1-yl)-1,2,3,4-tetrahydroisoquinoline;
2-methyl-4-pyrazolo[1,5-a]pyridin-5-yl-1,2,3,4-tetrahydroisoquinoline;
2-methyl-7-(morpholin-4-yl)-4-pyrazolo[1,5-a]pyridin-5-yl-1,2,3,4-tetrahydroisoquinoline;
2-methyl-7-(piperidin-1-yl)-4-pyrazolo[1,5-a]pyridin-5-yl-1,2,3,4-tetrahydroisoquinoline;
2-methyl-4-pyrazolo[1,5-a]pyridin-5-yl-7-(pyrrolidin-1-yl)-1,2,3,4-tetrahydroisoquinoline;
2-methyl-4-pyrazolo[1,5-a]pyridin-6-yl-1,2,3,4-tetrahydroisoquinoline;
2-methyl-7-(morpholin-4-yl)-4-pyrazolo[1,5-a]pyridin-6-yl-1,2,3,4-tetrahydroisoquinoline;
2-methyl-7-(piperidin-1-yl)-4-pyrazolo[1,5-a]pyridin-6-yl-1,2,3,4-tetrahydroisoquinoline;
2-methyl-4-pyrazolo[1,5-a]pyridin-6-yl-7-(pyrrolidin-1-yl)-1,2,3,4-tetrahydroisoquinoline;
2-methyl-4-[1,2,4]triazolo[4,3-a]pyridin-6-yl-1,2,3,4-tetrahydroisoquinoline;
2-methyl-7-(morpholin-4-yl)-4-[1,2,4]triazolo[4,3-a]pyridin-6-yl-1,2,3,4-tetrahydroisoquinoline;
2-methyl-7-(piperidin-1-yl)-4-[1,2,4]triazolo[4,3-a]pyridin-6-yl-1,2,3,4-tetrahydroisoquinoline;
2-methyl-7-(pyrrolidin-1-yl)-4-[1,2,4]triazolo[4,3-a]pyridin-6-yl-1,2,3,4-tetrahydroisoquinoline;
2-methyl-4-[1,2,4]triazolo[4,3-a]pyridin-7-yl-1,2,3,4-tetrahydroisoquinoline;
2-methyl-7-(morpholin-4-yl)-4-[1,2,4]triazolo[4,3-a]pyridin-7-yl-1,2,3,4-tetrahydroisoquinoline;
2-methyl-7-(piperidin-1-yl)-4-[1,2,4]triazolo[4,3-a]pyridin-7-yl-1,2,3,4-tetrahydroisoquinoline;
2-methyl-7-(pyrrolidin-1-yl)-4-[1,2,4]triazolo[4,3-a]pyridin-7-yl-1,2,3,4-tetrahydroisoquinoline;
2-methyl-4-thieno[2,3-b]pyridin-2-yl-1,2,3,4-tetrahydroisoquinoline;

2-methyl-7-(morpholin-4-yl)-4-thieno[2,3-b]pyridin-2-yl-1,2,3,4-tetrahydroisoquinoline;
2-methyl-7-(piperidin-1-yl)-4-thieno[2,3-b]pyridin-2-yl-1,2,3,4-tetrahydroisoquinoline;
2-methyl-7-(pyrrolidin-1-yl)-4-thieno[2,3-b]pyridin-2-yl-1,2,3,4-tetrahydroisoquinoline;
2-methyl-4-thieno[2,3-b]pyridin-5-yl-1,2,3,4-tetrahydroisoquinoline;
2-methyl-7-(morpholin-4-yl)-4-thieno[2,3-b]pyridin-5-yl-1,2,3,4-tetrahydroisoquinoline;
2-methyl-7-(piperidin-1-yl)-4-thieno[2,3-b]pyridin-5-yl-1,2,3,4-tetrahydroisoquinoline;
2-methyl-7-(pyrrolidin-1-yl)-4-thieno[2,3-b]pyridin-5-yl-1,2,3,4-tetrahydroisoquinoline;
2-methyl-4-thieno[2,3-b]pyridin-6-yl-1,2,3,4-tetrahydroisoquinoline;
2-methyl-7-(morpholin-4-yl)-4-thieno[2,3-b]pyridin-6-yl-1,2,3,4-tetrahydroisoquinoline;
2-methyl-7-(piperidin-1-yl)-4-thieno[2,3-b]pyridin-6-yl-1,2,3,4-tetrahydroisoquinoline;
2-methyl-7-(pyrrolidin-1-yl)-4-thieno[2,3-b]pyridin-6-yl-1,2,3,4-tetrahydroisoquinoline;
2-methyl-4-thieno[3,2-b]pyridin-2-yl-1,2,3,4-tetrahydroisoquinoline;
2-methyl-7-(morpholin-4-yl)-4-thieno[3,2-b]pyridin-2-yl-1,2,3,4-tetrahydroisoquinoline;
2-methyl-7-(piperidin-1-yl)-4-thieno[3,2-b]pyridin-2-yl-1,2,3,4-tetrahydroisoquinoline;
2-methyl-7-(pyrrolidin-1-yl)-4-thieno[3,2-b]pyridin-2-yl-1,2,3,4-tetrahydroisoquinoline;
2-methyl-4-thieno[3,2-b]pyridin-5-yl-1,2,3,4-tetrahydroisoquinoline;
2-methyl-7-(morpholin-4-yl)-4-thieno[3,2-b]pyridin-5-yl-1,2,3,4-tetrahydroisoquinoline;
2-methyl-7-(piperidin-1-yl)-4-thieno[3,2-b]pyridin-5-yl-1,2,3,4-tetrahydroisoquinoline;
2-methyl-7-(pyrrolidin-1-yl)-4-thieno[3,2-b]pyridin-5-yl-1,2,3,4-tetrahydroisoquinoline;
2-methyl-4-thieno[3,2-b]pyridin-6-yl-1,2,3,4-tetrahydroisoquinoline;
2-methyl-7-(morpholin-4-yl)-4-thieno[3,2-b]pyridin-6-yl-1,2,3,4-tetrahydroisoquinoline;
2-methyl-7-(piperidin-1-yl)-4-thieno[3,2-b]pyridin-6-yl-1,2,3,4-tetrahydroisoquinoline;
2-methyl-7-(pyrrolidin-1-yl)-4-thieno[3,2-b]pyridin-6-yl-1,2,3,4-tetrahydroisoquinoline;
4-indolizin-2-yl-2-methyl-1,2,3,4-tetrahydroisoquinoline;
4-indolizin-2-yl-2-methyl-7-pyridazin-3-yl-1,2,3,4-tetrahydroisoquinoline;
4-indolizin-2-yl-2-methyl-7-pyrimidin-2-yl-1,2,3,4-tetrahydroisoquinoline;
4-indolizin-2-yl-2-methyl-7-pyrimidin-4-yl-1,2,3,4-tetrahydroisoquinoline;
4-indolizin-2-yl-2-methyl-7-pyrimidin-5-yl-1,2,3,4-tetrahydroisoquinoline;
4-indolizin-2-yl-2-methyl-7-morpholin-4-yl-1,2,3,4-tetrahydroisoquinoline;
4-indolizin-6-yl-2-methyl-1,2,3,4-tetrahydroisoquinoline;
4-indolizin-6-yl-2-methyl-7-pyridazin-3-yl-1,2,3,4-tetrahydroisoquinoline;
4-indolizin-6-yl-2-methyl-7-pyrimidin-2-yl-1,2,3,4-tetrahydroisoquinoline;
4-indolizin-6-yl-2-methyl-7-pyrimidin-4-yl-1,2,3,4-tetrahydroisoquinoline;
4-indolizin-6-yl-2-methyl-7-pyrimidin-5-yl-1,2,3,4-tetrahydroisoquinoline;
4-indolizin-6-yl-2-methyl-7-morpholin-4-yl-1,2,3,4-tetrahydroisoquinoline;
4-indolizin-7-yl-2-methyl-1,2,3,4-tetrahydroisoquinoline;
4-indolizin-7-yl-2-methyl-7-pyridazin-3-yl-1,2,3,4-tetrahydroisoquinoline;
4-indolizin-7-yl-2-methyl-7-pyrimidin-2-yl-1,2,3,4-tetrahydroisoquinoline;
4-indolizin-7-yl-2-methyl-7-pyrimidin-4-yl-1,2,3,4-tetrahydroisoquinoline;
4-indolizin-7-yl-2-methyl-7-pyrimidin-5-yl-1,2,3,4-tetrahydroisoquinoline;
4-indolizin-7-yl-2-methyl-7-morpholin-4-yl-1,2,3,4-tetrahydroisoquinoline;
4-(1H-inden-2-yl)-2-methyl-1,2,3,4-tetrahydroisoquinoline;
4-(indan-5-yl)-2-methyl-1,2,3,4-tetrahydroisoquinoline;
or an oxide thereof, a pharmaceutically acceptable salt thereof, a solvate thereof, or a prodrug thereof.

In addition, other specific compounds of the present invention are those with the following substituents:

TABLE F

| X | $R^1$ | $R^2$ | $R^3$ | $R^4$ | $R^5$ | $R^6$ | $R^7$ | $R^8$ |
|---|---|---|---|---|---|---|---|---|
| naphthalen-1-yl | Me | H | H | H | H | H | H | H |
| 4-methyl-naphthalen-1-yl | Me | H | H | H | H | H | H | H |
| naphthalen-2-yl | H | H | H | H | H | H | H | H |
| naphthalen-2-yl | H | Me | H | H | H | H | H | H |
| naphthalen-2-yl | Me | H | H | H | H | H | H | H |
| naphthalen-2-yl | Et | H | H | H | H | H | H | H |
| naphthalen-2-yl | Me | Me | H | H | H | H | H | H |
| naphthalen-2-yl | Me | H | H | H | H | Me | H | H |
| naphthalen-2-yl | Me | H | H | H | H | H | H | OH |
| naphthalen-2-yl | Me | H | H | H | H | H | H | OMe |
| naphthalen-2-yl | Me | H | H | H | H | H | H | Me |
| naphthalen-2-yl | Me | H | H | H | H | H | H | CN |
| naphthalen-2-yl | Me | H | H | H | H | H | H | F |
| naphthalen-2-yl | Me | H | H | H | H | H | H | Cl |
| 6-methoxy-naphthalen-2-yl | Me | H | H | H | H | H | H | H |
| 7-methoxy-naphthalen-2-yl | Me | H | H | H | H | H | H | H |
| 8-methoxy-naphthalen-2-yl | Me | H | H | H | H | H | H | H |
| 8-methoxy-naphthalen-2-yl | Me | H | H | H | H | H | H | OH |
| 8-methoxy-naphthalen-2-yl | Me | H | H | OH | H | H | H | H |
| 8-chloro-naphthalen-2-yl | Me | H | H | H | H | H | H | H |
| 8-chloro-naphthalen-2-yl | Me | H | H | H | H | H | H | OH |
| 8-chloro-naphthalen-2-yl | Me | H | H | OH | H | H | H | H |
| 8-fluoro-naphthalen-2-yl | Me | H | H | H | H | H | H | H |
| naphthalen-2-yl | Me | H | H | OH | H | H | H | H |
| naphthalen-2-yl | Me | H | H | OMe | H | H | H | H |
| naphthalen-2-yl | Me | H | H | Me | H | H | H | H |
| naphthalen-2-yl | Me | H | H | F | H | H | H | H |
| naphthalen-2-yl | Me | H | H | pyridazin-3-yl | H | H | H | H |
| 1-fluoro-naphthalen-2-yl | Me | H | H | pyridazin-3-yl | H | H | H | H |
| 1-chloro-naphthalen-2-yl | Me | H | H | pyridazin-3-yl | H | H | H | H |

TABLE F-continued

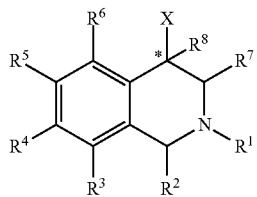

| X | R¹ | R² | R³ | R⁴ | R⁵ | R⁶ | R⁷ | R⁸ |
|---|---|---|---|---|---|---|---|---|
| 1-methoxy-naphthalen-2-yl | Me | H | H | pyridazin-3-yl | H | H | H | H |
| 1-methyl-naphthalen-2-yl | Me | H | H | pyridazin-3-yl | H | H | H | H |
| 3-fluoro-naphthalen-2-yl | Me | H | H | pyridazin-3-yl | H | H | H | H |
| 3-chloro-naphthalen-2-yl | Me | H | H | pyridazin-3-yl | H | H | H | H |
| 3-methoxy-naphthalen-2-yl | Me | H | H | pyridazin-3-yl | H | H | H | H |
| 3-cyano-naphthalen-2-yl | Me | H | H | pyridazin-3-yl | H | H | H | H |
| 4-fluoro-naphthalen-2-yl | Me | H | H | pyridazin-3-yl | H | H | H | H |
| 4-chloro-naphthalen-2-yl | Me | H | H | pyridazin-3-yl | H | H | H | H |
| 5-fluoro-naphthalen-2-yl | Me | H | H | pyridazin-3-yl | H | H | H | H |
| 5-chloro-naphthalen-2-yl | Me | H | H | pyridazin-3-yl | H | H | H | H |
| 5-cyano-naphthalen-2-yl | Me | H | H | pyridazin-3-yl | H | H | H | H |
| 5-methyl-naphthalen-2-yl | Me | H | H | pyridazin-3-yl | H | H | H | H |
| 6-methoxy-naphthalen-2-yl | Me | H | H | pyridazin-3-yl | H | H | H | H |
| 6-chloro-naphthalen-2-yl | Me | H | H | pyridazin-3-yl | H | H | H | H |
| 6-fluoro-naphthalen-2-yl | Me | H | H | pyridazin-3-yl | H | H | H | H |
| 6-cyano-naphthalen-2-yl | Me | H | H | pyridazin-3-yl | H | H | H | H |
| 6-methanesulfonyl-naphthalen-2-yl | Me | H | H | pyridazin-3-yl | H | H | H | H |
| 7-methoxy-naphthalen-2-yl | Me | H | H | pyridazin-3-yl | H | H | H | H |
| 7-chloro-naphthalen-2-yl | Me | H | H | pyridazin-3-yl | H | H | H | H |
| 7-fluoro-naphthalen-2-yl | Me | H | H | pyridazin-3-yl | H | H | H | H |
| 7-cyano-naphthalen-2-yl | Me | H | H | pyridazin-3-yl | H | H | H | H |
| 8-methoxy-naphthalen-2-yl | Me | H | H | pyridazin-3-yl | H | H | H | H |
| 8-chloro-naphthalen-2-yl | Me | H | H | pyridazin-3-yl | H | H | H | H |
| 8-fluoro-naphthalen-2-yl | Me | H | H | pyridazin-3-yl | H | H | H | H |
| 8-cyano-naphthalen-2-yl | Me | H | H | pyridazin-3-yl | H | H | H | H |
| naphthalen-2-yl | Et | H | H | pyridazin-3-yl | H | H | H | H |
| naphthalen-2-yl | Me | H | H | 6-methyl-pyridazin-3-yl | H | H | H | H |
| naphthalen-2-yl | Me | H | H | 6-dimethylamino-pyridazin-3-yl | H | H | H | H |
| naphthalen-2-yl | Me | H | H | 6-methylamino-pyridazin-3-yl | H | H | H | H |
| naphthalen-2-yl | Me | H | H | 6-amino-pyridazin-3-yl | H | H | H | H |
| naphthalen-2-yl | Me | H | H | 6-morpholin-4-yl-pyridazin-3-yl | H | H | H | H |
| naphthalen-2-yl | Me | H | H | 6-trifluoromethylpyridazin-3-yl | H | H | H | H |
| naphthalen-2-yl | Me | H | H | 6-cyano-pyridazin-3-yl | H | H | H | H |
| naphthalen-2-yl | Me | H | F | pyridazin-3-yl | H | H | H | H |
| naphthalen-2-yl | Me | H | OMe | pyridazin-3-yl | H | H | H | H |
| naphthalen-2-yl | Me | H | OH | pyridazin-3-yl | H | H | H | H |
| naphthalen-2-yl | Me | H | Me | pyridazin-3-yl | H | H | H | H |
| naphthalen-2-yl | Et | H | F | pyridazin-3-yl | H | H | H | H |
| naphthalen-2-yl | Me | H | H | pyridazin-3-yl | F | H | H | H |
| naphthalen-2-yl | Me | H | H | pyridazin-3-yl | H | F | H | H |
| naphthalen-2-yl | Me | H | H | pyridazin-4-yl | H | H | H | H |
| naphthalen-2-yl | Me | H | F | pyridazin-4-yl | H | H | H | H |
| naphthalen-2-yl | Me | H | H | pyrazin-2-yl | H | H | H | H |
| naphthalen-2-yl | Me | H | H | 3-methyl-pyrazin-2-yl | H | H | H | H |
| naphthalen-2-yl | Me | H | H | 3-methoxy-pyrazin-2-yl | H | H | H | H |
| naphthalen-2-yl | Me | H | H | 6-methyl-pyrazin-2-yl | H | H | H | H |
| naphthalen-2-yl | Me | H | H | 6-methoxy-pyrazin-2-yl | H | H | H | H |
| naphthalen-2-yl | Me | H | F | pyrazin-2-yl | H | H | H | H |
| naphthalen-2-yl | Me | H | OMe | pyrazin-2-yl | H | H | H | H |
| naphthalen-2-yl | Me | H | OH | pyrazin-2-yl | H | H | H | H |
| naphthalen-2-yl | Me | H | Me | pyrazin-2-yl | H | H | H | H |
| naphthalen-2-yl | Me | H | H | pyrimidin-2-yl | H | H | H | H |
| naphthalen-2-yl | Me | H | F | pyrimidin-2-yl | H | H | H | H |
| naphthalen-2-yl | Me | H | OMe | pyrimidin-2-yl | H | H | H | H |
| naphthalen-2-yl | Me | H | OH | pyrimidin-2-yl | H | H | H | H |
| naphthalen-2-yl | Me | H | Me | pyrimidin-2-yl | H | H | H | H |
| naphthalen-2-yl | Me | H | H | pyrimidin-4-yl | H | H | H | H |
| naphthalen-2-yl | Me | H | F | pyrimidin-4-yl | H | H | H | H |
| naphthalen-2-yl | Me | H | OMe | pyrimidin-4-yl | H | H | H | H |
| naphthalen-2-yl | Me | H | OH | pyrimidin-4-yl | H | H | H | H |
| naphthalen-2-yl | Me | H | Me | pyrimidin-4-yl | H | H | H | H |
| naphthalen-2-yl | Me | H | H | pyrimidin-5-yl | H | H | H | H |
| naphthalen-2-yl | Me | H | F | pyrimidin-5-yl | H | H | H | H |
| naphthalen-2-yl | Me | H | OMe | pyrimidin-5-yl | H | H | H | H |
| naphthalen-2-yl | Me | H | OH | pyrimidin-5-yl | H | H | H | H |
| naphthalen-2-yl | Me | H | Me | pyrimidin-5-yl | H | H | H | H |
| naphthalen-2-yl | Me | H | H | 3,5-dimethyl-isoxazol-4-yl | H | H | H | H |
| naphthalen-2-yl | Me | H | H | thiazol-2-yl | H | H | H | H |
| naphthalen-2-yl | Me | H | H | 5-methyl-thiazol-2-yl | H | H | H | H |
| naphthalen-2-yl | Me | H | H | [1,3,5]triazin-2-yl | H | H | H | H |
| naphthalen-2-yl | Me | H | H | [1,2,4]triazin-3-yl | H | H | H | H |
| naphthalen-2-yl | Me | H | H | [1,2,4]triazin-5-yl | H | H | H | H |
| naphthalen-2-yl | Me | H | H | [1,2,4]triazin-6-yl | H | H | H | H |
| naphthalen-2-yl | Me | H | H | cinnolin-3-yl | H | H | H | H |
| naphthalen-2-yl | Me | H | H | phthalazin-1-yl | H | H | H | H |
| naphthalen-2-yl | Me | H | H | quinoxalin-2-yl | H | H | H | H |
| naphthalen-2-yl | Me | H | H | quinazolin-2-yl | H | H | H | H |
| naphthalen-2-yl | Me | H | H | quinazolin-6-yl | H | H | H | H |
| naphthalen-2-yl | Me | H | H | quinazolin-7-yl | H | H | H | H |
| naphthalen-2-yl | Me | H | H | 3-oxo-[1,2,4]triazolo[4,3-a]pyridin-2-yl | H | H | H | H |
| naphthalen-2-yl | Me | H | H | morpholin-4-yl | H | H | H | H |
| 1-fluoro-naphthalen-2-yl | Me | H | H | morpholin-4-yl | H | H | H | H |
| 1-chloro-naphthalen-2-yl | Me | H | H | morpholin-4-yl | H | H | H | H |
| 1-methoxy-naphthalen-2-yl | Me | H | H | morpholin-4-yl | H | H | H | H |
| 1-methyl-naphthalen-2-yl | Me | H | H | morpholin-4-yl | H | H | H | H |
| 3-fluoro-naphthalen-2-yl | Me | H | H | morpholin-4-yl | H | H | H | H |

TABLE F-continued

| X | R¹ | R² | R³ | R⁴ | R⁵ | R⁶ | R⁷ | R⁸ |
|---|---|---|---|---|---|---|---|---|
| 3-chloro-naphthalen-2-yl | Me | H | H | morpholin-4-yl | H | H | H | H |
| 3-methoxy-naphthalen-2-yl | Me | H | H | morpholin-4-yl | H | H | H | H |
| 3-cyano-naphthalen-2-yl | Me | H | H | morpholin-4-yl | H | H | H | H |
| 4-fluoro-naphthalen-2-yl | Me | H | H | morpholin-4-yl | H | H | H | H |
| 4-chloro-naphthalen-2-yl | Me | H | H | morpholin-4-yl | H | H | H | H |
| 5-fluoro-naphthalen-2-yl | Me | H | H | morpholin-4-yl | H | H | H | H |
| 5-chloro-naphthalen-2-yl | Me | H | H | morpholin-4-yl | H | H | H | H |
| 5-cyano-naphthalen-2-yl | Me | H | H | morpholin-4-yl | H | H | H | H |
| 5-methyl-naphthalen-2-yl | Me | H | H | morpholin-4-yl | H | H | H | H |
| 6-methoxy-naphthalen-2-yl | Me | H | H | morpholin-4-yl | H | H | H | H |
| 6-chloro-naphthalen-2-yl | Me | H | H | morpholin-4-yl | H | H | H | H |
| 6-fluoro-naphthalen-2-yl | Me | H | H | morpholin-4-yl | H | H | H | H |
| 6-cyano-naphthalen-2-yl | Me | H | H | morpholin-4-yl | H | H | H | H |
| 6-methanesulfonyl-naphthalen-2-yl | Me | H | H | morpholin-4-yl | H | H | H | H |
| 7-methoxy-naphthalen-2-yl | Me | H | H | morpholin-4-yl | H | H | H | H |
| 7-chloro-naphthalen-2-yl | Me | H | H | morpholin-4-yl | H | H | H | H |
| 7-fluoro-naphthalen-2-yl | Me | H | H | morpholin-4-yl | H | H | H | H |
| 7-cyano-naphthalen-2-yl | Me | H | H | morpholin-4-yl | H | H | H | H |
| 8-methoxy-naphthalen-2-yl | Me | H | H | morpholin-4-yl | H | H | H | H |
| 8-chloro-naphthalen-2-yl | Me | H | H | morpholin-4-yl | H | H | H | H |
| 8-fluoro-naphthalen-2-yl | Me | H | H | morpholin-4-yl | H | H | H | H |
| 8-cyano-naphthalen-2-yl | Me | H | H | morpholin-4-yl | H | H | H | H |
| naphthalen-2-yl | Me | H | H | 2,6-dimethyl-morpholin-4-yl | H | H | H | H |
| naphthalen-2-yl | Et | H | H | morpholin-4-yl | H | H | H | H |
| naphthalen-2-yl | Me | H | F | morpholin-4-yl | H | H | H | H |
| naphthalen-2-yl | Me | H | OMe | morpholin-4-yl | H | H | H | H |
| naphthalen-2-yl | Me | H | OH | morpholin-4-yl | H | H | H | H |
| naphthalen-2-yl | Me | H | Me | morpholin-4-yl | H | H | H | H |
| naphthalen-2-yl | Et | H | F | morpholin-4-yl | H | H | H | H |
| naphthalen-2-yl | Me | H | H | morpholin-4-yl | F | H | H | H |
| naphthalen-2-yl | Me | H | H | morpholin-4-yl | H | F | H | H |
| naphthalen-2-yl | Me | H | H | morpholin-4-yl | H | H | OH | H |
| naphthalen-2-yl | Me | H | H | morpholin-4-yl | H | H | H | Me |
| naphthalen-2-yl | Me | H | H | piperazin-1-yl | H | H | H | H |
| naphthalene-2-yl | Me | H | H | 4-methyl-piperazin-1-yl | H | H | H | H |
| naphthalen-2-yl | Me | H | H | piperidin-1-yl | H | H | H | H |
| naphthalen-2-yl | Me | H | H | pyrrolidin-1-yl | H | H | H | H |
| naphthalen-2-yl | Me | H | H | morpholin-4-ylmethyl | H | H | H | H |
| naphthalen-2-yl | Me | H | H | 1-methyl-1-morpholin-4-yl-ethyl | H | H | H | H |
| naphthalen-2-yl | Me | H | H | 1-morpholin-4-yl-cyclopropyl | H | H | H | H |
| naphthalen-2-yl | Me | H | H | piperidin-1-ylmethyl | H | H | H | H |
| naphthalen-2-yl | Me | H | H | pyrrolidin-1-ylmethyl | H | H | H | H |
| naphthalen-2-yl | Me | H | H | CH₂NMe₂ | H | H | H | H |
| naphthalen-2-yl | Me | H | H | 1-dimethyl-amino-1-methylethyl | H | H | H | H |
| naphthalen-2-yl | Me | H | H | 1-dimethyl-amino-cyclopropyl | H | H | H | H |
| naphthalen-2-yl | Me | H | H | CH₂NHMe | H | H | H | H |
| naphthalen-2-yl | Me | H | H | 1-methyl-1-methylamino-ethyl | H | H | H | H |
| naphthalen-2-yl | Me | H | H | 1-methylamino-cyclopropyl | H | H | H | H |
| naphthalen-2-yl | Me | H | H | CH₂NH₂ | H | H | H | H |
| naphthalen-2-yl | Me | H | H | 1-methyl-1-methylamino-ethyl | H | H | H | H |
| naphthalen-2-yl | Me | H | H | 1-methylamino-cyclopropyl | H | H | H | H |
| naphthalen-2-yl | Me | H | H | 2-oxo-2H-pyridin-1-yl | H | H | H | H |
| naphthalen-2-yl | Me | H | H | SO₂CH₃ | H | H | H | H |
| naphthalen-2-yl | Me | H | F | CN | H | H | H | H |
| naphthalen-2-yl | Me | H | Me | H | H | H | H | H |
| 5,6,7,8-tetrahydro-naphthalen-2-yl | Me | H | H | H | H | H | H | H | wherein the carbon atom designated * is in the R or S configuration.

That is, the specific compounds herein include:
2-methyl-4-(naphthalen-1-yl)-1,2,3,4-tetrahydroisoquinoline;
2-methyl-4-(4-methylnaphthalen-1-yl)-1,2,3,4-tetrahydroisoquinoline;
4-(naphthalen-2-yl)-1,2,3,4-tetrahydroisoquinoline;
1-methyl-4-(naphthalen-2-yl)-1,2,3,4-tetrahydroisoquinoline;
2-methyl-4-(naphthalen-2-yl)-1,2,3,4-tetrahydroisoquinoline;
2-ethyl-4-(naphthalen-2-yl)-1,2,3,4-tetrahydroisoquinoline;
1,2-dimethyl-4-(naphthalen-2-yl)-1,2,3,4-tetrahydroisoquinoline;
2,5-dimethyl-4-(naphthalen-2-yl)-1,2,3,4-tetrahydroisoquinoline;
2-methyl-4-(naphthalen-2-yl)-1,2,3,4-tetrahydroisoquinoline-4-ol;
4-methoxy-2-methyl-4-(naphthalen-2-yl)-1,2,3,4-tetrahydroisoquinoline;
2,4-dimethyl-4-(naphthalen-2-yl)-1,2,3,4-tetrahydroisoquinoline;
2-methyl-4-naphthalen-2-yl-1,2,3,4-tetrahydroisoquinoline-4-carbonitrile;
4-fluoro-2-methyl-4-(naphthalen-2-yl)-1,2,3,4-tetrahydroisoquinoline;
4-chloro-2-methyl-4-(naphthalen-2-yl)-1,2,3,4-tetrahydroisoquinoline;

4-(6-methoxy-naphthalen-2-yl)-2-methyl-1,2,3,4-tetrahydroisoquinoline;
4-(7-methoxy-naphthalen-2-yl)-2-methyl-1,2,3,4-tetrahydroisoquinoline;
4-(8-methoxy-naphthalen-2-yl)-2-methyl-1,2,3,4-tetrahydroisoquinoline;
4-(8-methoxy-naphthalen-2-yl)-2-methyl-1,2,3,4-tetrahydroisoquinolin-4-ol;
4-(8-methoxy-naphthalen-2-yl)-2-methyl-1,2,3,4-tetrahydroisoquinolin-7-ol;
4-(8-chloro-naphthalen-2-yl)-2-methyl-1,2,3,4-tetrahydroisoquinoline;
4-(8-chloro-naphthalen-2-yl)-2-methyl-1,2,3,4-tetrahydroisoquinolin-4-ol;
4-(8-chloro-naphthalen-2-yl)-2-methyl-1,2,3,4-tetrahydroisoquinolin-7-ol;
4-(8-fluoro-naphthalen-2-yl)-2-methyl-1,2,3,4-tetrahydroisoquinoline;
2-methyl-4-(naphthalen-2-yl)-1,2,3,4-tetrahydroisoquinoline-7-ol;
7-methoxy-4-(naphthalen-2-yl)-2-methyl-1,2,3,4-tetrahydroisoquinoline;
2,7-dimethyl-4-(naphthalen-2-yl)-1,2,3,4-tetrahydroisoquinoline;
7-fluoro-2-methyl-4-(naphthalen-2-yl)-1,2,3,4-tetrahydroisoquinoline;
2-methyl-4-(naphthalen-2-yl)-7-(pyridazin-3-yl)-1,2,3,4-tetrahydroisoquinoline;
4-(1-fluoro-naphthalen-2-yl)-2-methyl-7-(pyridazin-3-yl)-1,2,3,4-tetrahydroisoquinoline;
4-(1-chloro-naphthalen-2-yl)-2-methyl-7-(pyridazin-3-yl)-1,2,3,4-tetrahydroisoquinoline;
4-(1-methoxy-naphthalen-2-yl)-2-methyl-7-(pyridazin-3-yl)-1,2,3,4-tetrahydroisoquinoline;
4-(1-methyl-naphthalen-2-yl)-2-methyl-7-(pyridazin-3-yl)-1,2,3,4-tetrahydroisoquinoline;
4-(3-fluoro-naphthalen-2-yl)-2-methyl-7-(pyridazin-3-yl)-1,2,3,4-tetrahydroisoquinoline;
4-(3-chloro-naphthalen-2-yl)-2-methyl-7-(pyridazin-3-yl)-1,2,3,4-tetrahydroisoquinoline;
4-(3-methoxy-naphthalen-2-yl)-2-methyl-7-(pyridazin-3-yl)-1,2,3,4-tetrahydroisoquinoline;
3-(2-methyl-7-pyridazin-3-yl-1,2,3,4-tetrahydroisoquinolin-4-yl)-naphthalene-2-carbonitrile;
4-(4-fluoro-naphthalen-2-yl)-2-methyl-7-(pyridazin-3-yl)-1,2,3,4-tetrahydroisoquinoline;
4-(4-chloro-naphthalen-2-yl)-2-methyl-7-(pyridazin-3-yl)-1,2,3,4-tetrahydroisoquinoline;
4-(5-fluoro-naphthalen-2-yl)-2-methyl-7-(pyridazin-3-yl)-1,2,3,4-tetrahydroisoquinoline;
4-(5-chloro-naphthalen-2-yl)-2-methyl-7-(pyridazin-3-yl)-1,2,3,4-tetrahydroisoquinoline;
6-(2-methyl-7-pyridazin-3-yl-1,2,3,4-tetrahydroisoquinolin-4-yl)-naphthalene-1-carbonitrile;
4-(5-methyl-naphthalen-2-yl)-2-methyl-7-(pyridazin-3-yl)-1,2,3,4-tetrahydroisoquinoline;
4-(6-methoxy-naphthalen-2-yl)-2-methyl-7-(pyridazin-3-yl)-1,2,3,4-tetrahydroisoquinoline;
4-(6-chloro-naphthalen-2-yl)-2-methyl-7-(pyridazin-3-yl)-1,2,3,4-tetrahydroisoquinoline;
4-(6-fluoro-naphthalen-2-yl)-2-methyl-7-(pyridazin-3-yl)-1,2,3,4-tetrahydroisoquinoline;
6-(2-methyl-7-pyridazin-3-yl-1,2,3,4-tetrahydroisoquinolin-4-yl)-naphthalene-2-carbonitrile;
4-(6-methanesulfonyl-naphthalen-2-yl)-2-methyl-7-pyridazin-3-yl-1,2,3,4-tetrahydroisoquinoline;
4-(7-methoxy-naphthalen-2-yl)-2-methyl-7-(pyridazin-3-yl)-1,2,3,4-tetrahydroisoquinoline;
4-(7-chloro-naphthalen-2-yl)-2-methyl-7-(pyridazin-3-yl)-1,2,3,4-tetrahydroisoquinoline;
4-(7-fluoro-naphthalen-2-yl)-2-methyl-7-(pyridazin-3-yl)-1,2,3,4-tetrahydroisoquinoline;
7-(2-methyl-7-pyridazin-3-yl-1,2,3,4-tetrahydroisoquinolin-4-yl)-naphthalene-2-carbonitrile;
4-(8-methoxy-naphthalen-2-yl)-2-methyl-7-(pyridazin-3-yl)-1,2,3,4-tetrahydroisoquinoline;
4-(8-chloro-naphthalen-2-yl)-2-methyl-7-(pyridazin-3-yl)-1,2,3,4-tetrahydroisoquinoline;
4-(8-fluoro-naphthalen-2-yl)-2-methyl-7-(pyridazin-3-yl)-1,2,3,4-tetrahydroisoquinoline;
8-(2-methyl-7-pyridazin-3-yl-1,2,3,4-tetrahydroisoquinolin-4-yl)-naphthalene-1-carbonitrile;
2-ethyl-4-(naphthalen-2-yl)-7-(pyridazin-3-yl)-1,2,3,4-tetrahydroisoquinoline;
2-methyl-7-(6-methyl-pyridazin-3-yl)-4-naphthalen-2-yl-1,2,3,4-tetrahydroisoquinoline;
dimethyl-[6-(2-methyl-4-naphthalene-2-yl-1,2,3,4-tetrahydroisoquinolin-7-yl)-pyridazin-3-yl]-amine;
methyl-[6-(2-methyl-4-naphthalene-2-yl-1,2,3,4-tetrahydroisoquinolin-7-yl)-pyridazin-3-yl]-amine;
6-(2-methyl-4-naphthalene-2-yl-1,2,3,4-tetrahydroisoquinolin-7-yl)-pyridazin-3-ylamine;
2-methyl-7-(6-morpholin-4-yl-pyridazin-3-yl)-4-naphthalen-2-yl-1,2,3,4-tetrahydroisoquinoline;
2-methyl-4-naphthalene-2-yl-7-(6-trifluoromethyl-pyridazin-3yl)-1,2,3,4-tetrahdyro-isoquinoline;
6-(2-methyl-4-naphthalene-2-yl-1,2,3,4-tetrahydroisoquinolin-7-yl)-pyridazin-3-yl-carbonitrile;
8-fluoro-2-methyl-4-(naphthalen-2-yl)-7-(pyridazin-3-yl)-1,2,3,4-tetrahydroisoquinoline;
8-methoxy-2-methyl-4-(naphthalen-2-yl)-7-(pyridazin-3-yl)-1,2,3,4-tetrahydroisoquinoline;
2-methyl-4-(naphthalen-2-yl)-7-(pyridazin-3-yl)-1,2,3,4-tetrahydroisoquinolin-8-ol;
2,8-dimethyl-4-(naphthalen-2-yl)-7-(pyridazin-3-yl))-1,2,3,4-tetrahydroisoquinoline;
2-ethyl-8-fluoro-4-(naphthalen-2-yl)-7-(pyridazin-3-yl)-1,2,3,4-tetrahydroisoquinoline;
6-fluoro-2-methyl-4-(naphthalen-2-yl)-7-(pyridazin-3-yl)-1,2,3,4-tetrahydroisoquinoline;
5-fluoro-2-methyl-4-(naphthalen-2-yl)-7-(pyridazin-3-yl)-1,2,3,4-tetrahydroisoquinoline;
2-methyl-4-(naphthalen-2-yl)-7-(pyridazin-4-yl)-1,2,3,4-tetrahydroisoquinoline;
8-fluoro-2-methyl-4-(naphthalen-2-yl)-7-(pyridazin-4-yl)-1,2,3,4-tetrahydroisoquinoline;
2-methyl-4-(naphthalen-2-yl)-7-(pyrazin-2-yl)-1,2,3,4-tetrahydroisoquinoline;
2-methyl-7-(3-methyl-pyrazin-2-yl)-4-(naphthalene-2-yl)-1,2,3,4-tetrahydroisoquinoline;
7-(3-methoxy-pyrazin-2yl)-2-methyl-4-(naphthalene-2-yl)-1,2,3,4-tetrahydroisoquinoline;
2-methyl-7-(6-methyl-pyrazin-2-yl)-4-(naphthalene-2-yl)-1,2,3,4-tetrahydroisoquinoline;
7-(6-methoxy-pyrazin-2yl)-2-methyl-4-(naphthalene-2-yl)-1,2,3,4-tetrahydroisoquinoline;
8-fluoro-2-methyl-4-(naphthalen-2-yl)-7-(pyrazin-2-yl)-1,2,3,4-tetrahydroisoquinoline;
8-methoxy-2-methyl-4-(naphthalen-2-yl)-7-(pyrazin-2-yl)-1,2,3,4-tetrahydroisoquinoline;
2-methyl-4-(naphthalene-2-yl)-7-(pyrazin-2-yl)-1,2,3,4-tetrahydroisoquinolin-8-ol;

2,8-dimethyl-4-(naphthalen-2-yl)-7-(pyrazin-2-yl)-1,2,3,4-tetrahydroisoquinoline;
2-methyl-4-(naphthalen-2-yl)-7-(pyrimidin-2-yl)-1,2,3,4-tetrahydroisoquinoline;
8-fluoro-2-methyl-4-(naphthalen-2-yl)-7-(pyrimidin-2-yl)-1,2,3,4-tetrahydroisoquinoline;
8-methoxy-2-methyl-4-(naphthalen-2-yl)-7-(pyrimidin-2-yl)-1,2,3,4-tetrahydroisoquinoline;
2-methyl-4-(naphthalen-2-yl)-7-(pyrimidin-2-yl)-1,2,3,4-tetrahydroisoquinolin-8-ol;
2,8-dimethyl-4-(naphthalen-2-yl)-7-(pyrimidin-2-yl)-1,2,3,4-tetrahydroisoquinoline;
2-methyl-4-(naphthalen-2-yl)-7-(pyrimidin-4-yl)-1,2,3,4-tetrahydroisoquinoline;
8-fluoro-2-methyl-4-(naphthalen-2-yl)-7-(pyrimidin-4-yl)-1,2,3,4-tetrahydroisoquinoline;
8-methoxy-2-methyl-4-(naphthalen-2-yl)-7-(pyrimidin-4-yl)-1,2,3,4-tetrahydroisoquinoline;
2-methyl-4-(naphthalen-2-yl)-7-(pyrimidin-4-yl)-1,2,3,4-tetrahydroisoquinolin-8-ol;
2,8-dimethyl-4-(naphthalen-2-yl)-7-(pyrimidin-4-yl)-1,2,3,4-tetrahydroisoquinoline;
2-methyl-4-(naphthalen-2-yl)-7-(pyrimidin-5-yl)-1,2,3,4-tetrahydroisoquinoline;
8-fluoro-2-methyl-4-(naphthalen-2-yl)-7-(pyrimidin-5-yl)-1,2,3,4-tetrahydroisoquinoline;
8-methoxy-2-methyl-4-(naphthalen-2-yl)-7-(pyrimidin-5-yl)-1,2,3,4-tetrahydroisoquinoline;
2-methyl-4-(naphthalen-2-yl)-7-(pyrimidin-5-yl)-1,2,3,4-tetrahydroisoquinolin-8-ol;
2,8-dimethyl-4-(naphthalen-2-yl)-7-(pyrimidin-5-yl)-1,2,3,4-tetrahydroisoquinoline;
7-(3,5-dimethyl-isoxazol-4-yl)-2-methyl-4-(naphthalen-2-yl)-1,2,3,4-tetrahydroisoquinoline;
2-methyl-4-(naphthalen-2-yl)-7-(thiazol-2-yl)-1,2,3,4-tetrahydroisoquinoline;
2-methyl-4-(naphthalen-2-yl)-7-(5-methyl-thiazol-2-yl)-1,2,3,4-tetrahydroisoquinoline;
2-methyl-4-naphthalen-2-yl-7-[1,3,5]triazin-2-yl-1,2,3,4-tetrahydroisoquinoline;
2-methyl-4-naphthalen-2-yl-7-[1,2,4]triazin-3-yl-1,2,3,4-tetrahydroisoquinoline;
2-methyl-4-naphthalen-2-yl-7-[1,2,4]triazin-5-yl-1,2,3,4-tetrahydroisoquinoline;
2-methyl-4-naphthalen-2-yl-7-[1,2,4]triazin-6-yl-1,2,3,4-tetrahydroisoquinoline;
3-(2-methyl-4-naphthalen-2-yl-1,2,3,4-tetrahydroisoquinolin-7-yl)-cinnoline;
1-(2-methyl-4-naphthalen-2-yl-1,2,3,4-tetrahydroisoquinolin-7-yl)-phthalazine;
2-(2-methyl-4-naphthalen-2-yl-1,2,3,4-tetrahydroisoquinolin-7-yl)-quinoxaline;
2-(2-methyl-4-naphthalen-2-yl-1,2,3,4-tetrahydroisoquinolin-7-yl)-quinazoline;
6-(2-methyl-4-naphthalen-2-yl-2-1,2,3,4-tetrahydroisoquinolin-7-yl)-quinazoline;
7-(2-methyl-4-naphthalen-2-yl-1,2,3,4-tetrahydroisoquinolin-7-yl)-quinazoline;
2-(2-methyl-4-naphthalen-2-yl-1,2,3,4-tetrahydroisoquinolin-7-yl)-2H-[1,2,4]triazolo[4,3-a]pyridin-3-one;
2-methyl-7-(morpholin-4-yl)-4-(naphthalen-2-yl)-1,2,3,4-tetrahydroisoquinoline;
4-(1-fluoro-naphthalen-2-yl)-2-methyl-7-(morpholin-4-yl)-1,2,3,4-tetrahydroisoquinoline;
4-(1-chloro-naphthalen-2-yl)-2-methyl-7-(morpholin-4-yl)-1,2,3,4-tetrahydroisoquinoline;
4-(1-methoxy-naphthalen-2-yl)-2-methyl-7-(morpholin-4-yl)-1,2,3,4-tetrahydroisoquinoline;
4-(1-methyl-naphthalen-2-yl)-2-methyl-7-(morpholin-4-yl)-1,2,3,4-tetrahydroisoquinoline;
4-(3-fluoro-naphthalen-2-yl)-2-methyl-7-(morpholin-4-yl)-1,2,3,4-tetrahydroisoquinoline;
4-(3-chloro-naphthalen-2-yl)-2-methyl-7-(morpholin-4-yl)-1,2,3,4-tetrahydroisoquinoline;
4-(3-methoxy-naphthalen-2-yl)-2-methyl-7-(morpholin-4-yl)-1,2,3,4-tetrahydroisoquinoline;
3-(2-methyl-7-morpholin-4-yl-1,2,3,4-tetrahydroisoquinol-4-yl)-naphthalene-2-carbonitrile;
4-(4-fluoro-naphthalen-2-yl)-2-methyl-7-(morpholin-4-yl)-1,2,3,4-tetrahydroisoquinoline;
4-(4-chloro-naphthalen-2-yl)-2-methyl-7-(morpholin-4-yl)-1,2,3,4-tetrahydroisoquinoline;
4-(5-fluoro-naphthalen-2-yl)-2-methyl-7-(morpholin-4-yl)-1,2,3,4-tetrahydroisoquinoline;
4-(5-chloro-naphthalen-2-yl)-2-methyl-7-(morpholin-4-yl)-1,2,3,4-tetrahydroisoquinoline;
6-(2-methyl-7-morpholin-4-yl-1,2,3,4-tetrahydroisoquinol-4-yl)-naphthalene-1-carbonitrile;
2-methyl-4-(5-methyl-naphthalen-2-yl)-7-(morpholin-4-yl)-1,2,3,4-tetrahydroisoquinoline;
4-(6-methoxy-naphthalen-2-yl)-2-methyl-7-(morpholin-4-yl)-1,2,3,4-tetrahydroisoquinoline;
4-(6-chloro-naphthalen-2-yl)-2-methyl-7-(morpholin-4-yl)-1,2,3,4-tetrahydroisoquinoline;
4-(6-fluoro-naphthalen-2-yl)-2-methyl-7-(morpholin-4-yl)-1,2,3,4-tetrahydroisoquinoline;
6-(2-methyl-7-morpholin-4-yl-1,2,3,4-tetrahydroisoquinol-4-yl)-naphthalene-2-carbonitrile;
4-(6-methanesulfonyl-naphthalen-2-yl)-2-methyl-7-(morpholin-4-yl)-1,2,3,4-tetrahydroisoquinoline;
4-(7-methoxy-naphthalen-2-yl)-2-methyl-7-(morpholin-4-yl)-1,2,3,4-tetrahydroisoquinoline;
4-(7-chloro-naphthalen-2-yl)-2-methyl-7-(morpholin-4-yl)-1,2,3,4-tetrahydroisoquinoline;
4-(7-fluoro-naphthalen-2-yl)-2-methyl-7-(morpholin-4-yl)-1,2,3,4-tetrahydroisoquinoline;
7-(2-methyl-7-morpholin-4-yl-1,2,3,4-tetrahydroisoquinol-4-yl)-naphthalene-2-carbonitrile;
4-(8-methoxy-naphthalen-2-yl)-2-methyl-7-(morpholin-4-yl)-1,2,3,4-tetrahydroisoquinoline;
4-(8-chloro-naphthalen-2-yl)-2-methyl-7-(morpholin-4-yl)-1,2,3,4-tetrahydroisoquinoline;
4-(8-fluoro-naphthalene-2-yl)-2-methyl-7-(morpholin-4-yl)-1,2,3,4-tetrahydroisoquinoline;
8-(2-methyl-7-morpholin-4-yl-1,2,3,4-tetrahydroisoquinol-4-yl)-naphthalene-1-carbonitrile;
7-(2,6-dimethyl-morpholin-4-yl)-2-methyl-4-naphthalen-2-yl-1,2,3,4-tetrahydroisoquinoline;
2-ethyl-7-(morpholin-4-yl)-4-naphthalen-2-yl-1,2,3,4-tetrahydroisoquinoline;
8-fluoro-2-methyl-7-(morpholin-4-yl)-(4-naphthalen-2-yl)-1,2,3,4-tetrahydroisoquinoline;
8-methoxy-2-methyl-7-(morpholin-4-yl)-(4-naphthalen-2-yl)-1,2,3,4-tetrahydroisoquinoline;
2-methyl-7-morpholin-4-yl-4-naphthalen-2-yl-1,2,3,4-tetrahydroisoquinolin-8-ol;
2,8-dimethyl-7-(morpholin-4-yl)-(4-naphthalen-2-yl)-1,2,3,4-tetrahydroisoquinoline;
2-ethyl-8-fluoro-7-(morpholin-4-yl)-(4-naphthalen-2-yl)-1,2,3,4-tetrahydroisoquinoline;
6-fluoro-2-methyl-7-(morpholin-4-yl)-(4-naphthalen-2-yl)-1,2,3,4-tetrahydroisoquinoline;

5-fluoro-2-methyl-7-(morpholin-4-yl)-(4-naphthalen-2-yl)-1,2,3,4-tetrahydroisoquinoline;

2-methyl-7-(morpholin-4-yl)-(4-naphthalen-2-yl)-1,2,3,4-tetrahydroisoquinolin-4-ol;

2,4-dimethyl-7-(morpholin-4-yl)-(4-naphthalen-2-yl)-1,2,3,4-tetrahydroisoquinoline;

2-methyl-4-naphthalen-2-yl-7-piperazin-1-yl-1,2,3,4-tetrahydroisoquinoline;

2-methyl-7-(4-methyl-piperazin-1-yl)-4-naphthalen-2-yl-1,2,3,4-tetrahydroisoquinoline;

2-methyl-4-(naphthalen-2-yl)-7-(piperidin-1-yl)-1,2,3,4-tetrahydroisoquinoline;

2-methyl-4-(naphthalen-2-yl)-7-(pyrrolidin-1-yl)-1,2,3,4-tetrahydroisoquinoline;

2-methyl-7-(morpholin-4-yl)methyl-4-(naphthalen-2-yl)-1,2,3,4-tetrahydroisoquinoline;

2-methyl-4-(naphthalen-2-yl)-7-(1-methyl-1-morpholin-4-yl-ethyl)-1,2,3,4-tetrahydroisoquinoline;

2-methyl-4-(naphthalen-2-yl)-7-(1-morpholin-4-yl-cyclopropyl)-1,2,3,4-tetrahydroisoquinoline;

2-methyl-4-(naphthalen-2-yl)-7-(piperidin-1-yl)methyl-1,2,3,4-tetrahydroisoquinoline;

2-methyl-4-(naphthalen-2-yl)-7-(pyrrolidin-1-yl)methyl-1,2,3,4-tetrahydroisoquinoline;

dimethyl-(2-methyl-4-naphthalen-2-yl-1,2,3,4-tetrahydroisoquinolin-7-ylmethyl)-amine;

2-methyl-[1-(4-naphthalen-2-yl-1,2,3,4-tetrahydroisoquinolin-7-yl)-1-methylethyl]-dimethylamine;

2-methyl-[1-(4-naphthalen-2-yl-1,2,3,4-tetrahydroisoquinolin-7-yl)-cyclopropyl]-dimethylamine;

methyl-(2-methyl-4-naphthalen-2-yl-1,2,3,4-tetrahydroisoquinolin-7-ylmethyl)-amine;

[2-methyl-[1-(4-naphthalen-2-yl-1,2,3,4-tetrahydroisoquinolin-7-yl)-1-methylethyl]-methylamine;

[2-methyl-[1-(4-naphthalen-2-yl-1,2,3,4-tetrahydroisoquinolin-7-yl)-cyclopropyl]-methylamine;

C-(2-methyl-[1-(4-naphthalen-2-yl-1,2,3,4-tetrahydroisoquinolin-7-yl)-methylamine;

1-(2-methyl-[1-(4-naphthalen-2-yl-1,2,3,4-tetrahydroisoquinolin-7-yl)-1-methyl-ethylamine;

1-(2-methyl-[1-(4-naphthalen-2-yl-1,2,3,4-tetrahydroisoquinolin-7-yl)-cyclopropylamine;

1-(2-methyl-4-naphthalen-2-yl-1,2,3,4-tetrahydroisoquinolin-7-yl)-1H-pyridin-2-one;

7-methanesulfonyl-2-methyl-4-(naphthalen-2-yl)-1,2,3,4-tetrahydroisoquinoline;

2-methyl-4-(naphthalen-2-yl)-1,2,3,4-tetrahydroisoquinoline-7-carbonitrile;

8-fluoro-2-methyl-4-(naphthalene-2-yl)-1,2,3,4-tetrahydroisoquinoline-7-carbonitrile;

2,8-dimethyl-4-(naphthalen-2-yl)-1,2,3,4-tetrahydroisoquinoline;

2-methyl-4-(5,6,7,8-tetrahydro-naphthalen-2-yl)-1,2,3,4-tetrahydroisoquinoline;

or an oxide thereof, a pharmaceutically acceptable salt thereof, a solvate thereof, or a prodrug thereof.

In addition, other specific compounds of the present invention are those with the following substituents:

TABLE G

| X | R¹ | R² | R³ | R⁴ | R⁵ | R⁶ | R⁷ | R⁸ |
|---|----|----|----|----|----|----|----|----|
| 2H-chromen-3-yl | Me | H | H | H | H | H | H | H |
| quinolin-2-yl | Me | H | H | H | H | H | H | H |
| quinolin-3-yl | Me | H | H | H | H | H | H | H |
| quinolin-6-yl | Me | H | H | OMe | H | H | H | OH |
| quinolin-6-yl | Me | H | H | OMe | H | H | H | H |
| quinolin-6-yl | Me | H | H | H | H | H | H | OH |
| quinolin-6-yl | Me | H | H | H | H | H | H | H |
| quinolin-6-yl | Me | H | H | pyridazin-3-yl | H | H | H | H |
| quinolin-6-yl | Me | H | H | morpholin-4-yl | H | H | H | H |
| quinolin-7-yl | Me | H | H | H | H | H | H | H |
| quinolin-7-yl | Me | H | H | pyridazin-3-yl | H | H | H | H |
| quinolin-7-yl | Me | H | H | morpholin-4-yl | H | H | H | H |
| isoquinolin-3-yl | Me | H | H | H | H | H | H | H |
| isoquinolin-6-yl | Me | H | H | H | H | H | H | H |
| isoquinolin-6-yl | Me | H | H | pyridazin-3-yl | H | H | H | H |
| isoquinolin-6-yl | Me | H | H | morpholin-4-yl | H | H | H | H |
| isoquinolin-7-yl | Me | H | H | H | H | H | H | H |
| isoquinolin-7-yl | Me | H | H | pyridazin-3-yl | H | H | H | H |
| isoquinolin-7-yl | Me | H | H | morpholin-4-yl | H | H | H | H |
| quinoxalin-2-yl | Me | H | H | H | H | H | H | H |
| quinoxalin-6-yl | Me | H | H | H | H | H | H | H |
| quinoxalin-6-yl | Me | H | H | morpholin-4-yl | H | H | H | H |
| quinoxalin-6-yl | Me | H | H | piperidin-1-yl | H | H | H | H |
| quinoxalin-6-yl | Me | H | H | pyrrolidin-1-yl | H | H | H | H |
| quinazolin-2-yl | Me | H | H | H | H | H | H | H |
| quinazolin-6-yl | Me | H | H | H | H | H | H | H |
| quinazolin-6-yl | Me | H | H | morpholin-4-yl | H | H | H | H |
| quinazolin-6-yl | Me | H | H | piperidin-1-yl | H | H | H | H |
| quinazolin-6-yl | Me | H | H | pyrrolidin-1-yl | H | H | H | H |
| quinazolin-7-yl | Me | H | H | H | H | H | H | H |
| quinazolin-7-yl | Me | H | H | morpholin-4-yl | H | H | H | H |
| quinazolin-7-yl | Me | H | H | piperidin-1-yl | H | H | H | H |
| quinazolin-7-yl | Me | H | H | pyrrolidin-1-yl | H | H | H | H |
| phthalazin-6-yl | Me | H | H | H | H | H | H | H |
| phthalazin-6-yl | Me | H | H | morpholin-4-yl | H | H | H | H |
| phthalazin-6-yl | Me | H | H | piperidin-1-yl | H | H | H | H |
| phthalazin-6-yl | Me | H | H | pyrrolidin-1-yl | H | H | H | H |
| cinnolin-3-yl | Me | H | H | H | H | H | H | H |
| cinnolin-6-yl | Me | H | H | H | H | H | H | H |
| cinnolin-6-yl | Me | H | H | morpholin-4-yl | H | H | H | H |
| cinnolin-6-yl | Me | H | H | piperidin-1-yl | H | H | H | H |
| cinnolin-6-yl | Me | H | H | pyrrolidin-1-yl | H | H | H | H |
| cinnolin-7-yl | Me | H | H | H | H | H | H | H |
| cinnolin-7-yl | Me | H | H | morpholin-4-yl | H | H | H | H |
| cinnolin-7-yl | Me | H | H | piperidin-1-yl | H | H | H | H |
| cinnolin-7-yl | Me | H | H | pyrrolidin-1-yl | H | H | H | H |
| 8,9-dihydro-7H-benzocyclohepten-6-yl | Me | H | H | H | H | H | H | H | wherein the carbon atom designated * is in the R or S configuration.

That is, the specific compounds herein include:

4-(2H-chromen-3-yl)-2-methyl-1,2,3,4-tetrahydroisoquinoline;

2-(2-methyl-1,2,3,4-tetrahydroisoquinolin-4-yl)-quinoline;

3-(2-methyl-1,2,3,4-tetrahydroisoquinolin-4-yl)-quinoline;

7-methoxy-2-methyl-4-quinolin-6-yl-1,2,3,4-tetrahydroisoquinolin-4-ol;

6-(7-methoxy-2-methyl-1,2,3,4-tetrahydroisoquinolin-4-yl)-quinoline;

2-methyl-4-quinolin-6-yl-1,2,3,4-tetrahydroisoquinolin-4-ol;

6-(2-methyl-1,2,3,4-tetrahydroisoquinolin-4-yl)-quinoline;

6-(2-methyl-7-pyridazin-3-yl-1,2,3,4-tetrahydroisoquinolin-4-yl)-quinoline;

6-(2-methyl-7-morpholin-4-yl-1,2,3,4-tetrahydroisoquinolin-4-yl)-quinoline;
7-(2-methyl-1,2,3,4-tetrahydroisoquinolin-4-yl)-quinoline;
7-(2-methyl-7-pyridazin-3-yl-1,2,3,4-tetrahydroisoquinolin-4-yl)-quinoline;
7-(2-methyl-7-morpholin-4-yl-1,2,3,4-tetrahydroisoquinolin-4-yl)-quinoline;
2'-methyl-1',2',3',4'-tetrahydro-[3,4']biisoquinolinyl;
2-methyl-1,2,3,4-tetrahydro-[4,6']biisoquinolinyl;
2-methyl-7-pyridazin-3-yl-1,2,3,4-tetrahydro-[4,6']biisoquinolinyl;
2-methyl-7-morpholin-4-yl-1,2,3,4-tetrahydro-[4,6']biisoquinolinyl
2-methyl-1,2,3,4-tetrahydro-[4,7']biisoquinolinyl;
2-methyl-7-pyridazin-3-yl-1,2,3,4-tetrahydro-[4,7']biisoquinolinyl;
2-methyl-7-morpholin-4-yl-1,2,3,4-tetrahydro-[4,7']biisoquinolinyl;
2-(2-methyl-1,2,3,4-tetrahydroisoquinolin-4-yl)-quinoxaline;
6-(2-methyl-1,2,3,4-tetrahydroisoquinolin-4-yl)-quinoxaline;
6-(2-methyl-7-morpholin-4-yl-1,2,3,4-tetrahydroisoquinolin-4-yl)-quinoxaline;
6-(2-methyl-7-piperidin-1-yl-1,2,3,4-tetrahydroisoquinolin-4-yl)-quinoxaline;
6-(2-methyl-7-pyrrolidin-1-yl-1,2,3,4-tetrahydroisoquinolin-4-yl)-quinoxaline;
2-(2-methyl-1,2,3,4-tetrahydroisoquinolin-4-yl)-quinazoline;
6-(2-methyl-1,2,3,4-tetrahydroisoquinolin-4-yl)-quinazoline;
6-(2-methyl-7-morpholin-4-yl-1,2,3,4-tetrahydroisoquinolin-4-yl)-quinazoline;
6-(2-methyl-7-piperidin-1-yl-1,2,3,4-tetrahydroisoquinolin-4-yl)-quinazoline;
6-(2-methyl-7-pyrrolidin-1-yl-1,2,3,4-tetrahydroisoquinolin-4-yl)-quinazoline;
7-(2-methyl-1,2,3,4-tetrahydroisoquinolin-4-yl)-quinazoline;
7-(2-methyl-7-morpholin-4-yl-1,2,3,4-tetrahydroisoquinolin-4-yl)-quinazoline;
7-(2-methyl-7-piperidin-1-yl-1,2,3,4-tetrahydroisoquinolin-4-yl)-quinazoline;
7-(2-methyl-7-pyrrolidin-1-yl-1,2,3,4-tetrahydroisoquinolin-4-yl)-quinazoline;
6-(2-methyl-1,2,3,4-tetrahydroisoquinolin-4-yl)-phthalazine;
6-(2-methyl-7-morpholin-4-yl-1,2,3,4-tetrahydroisoquinolin-4-yl)-phthalazine;
6-(2-methyl-7-piperidin-1-yl-1,2,3,4-tetrahydroisoquinolin-4-yl)-phthalazine;
6-(2-methyl-7-pyrrolidin-1-yl-1,2,3,4-tetrahydroisoquinolin-4-yl)-phthalazine;
3-(2-methyl-1,2,3,4-tetrahydroisoquinolin-4-yl)-cinnoline;
6-(2-methyl-1,2,3,4-tetrahydroisoquinolin-4-yl)-cinnoline;
6-(2-methyl-7-morpholin-4-yl-1,2,3,4-tetrahydroisoquinolin-4-yl)-cinnoline;
6-(2-methyl-7-piperidin-1-yl-1,2,3,4-tetrahydroisoquinolin-4-yl)-cinnoline;
6-(2-methyl-7-pyrrolidin-1-yl-1,2,3,4-tetrahydroisoquinolin-4-yl)-cinnoline;
7-(2-methyl-1,2,3,4-tetrahydroisoquinolin-4-yl)-cinnoline;
7-(2-methyl-7-morpholin-4-yl-1,2,3,4-tetrahydroisoquinolin-4-yl)-cinnoline;
7-(2-methyl-7-piperidin-1-yl-1,2,3,4-tetrahydroisoquinolin-4-yl)-cinnoline;
7-(2-methyl-7-pyrrolidin-1-yl-1,2,3,4-tetrahydroisoquinolin-4-yl)-cinnoline;
4-(8,9-dihydro-7H-benzocyclohepten-6-yl)-2-methyl-1,2,3,4-tetrahydroisoquinoline;
or an oxide thereof, a pharmaceutically acceptable salt thereof, a solvate thereof, or a prodrug thereof.

Table H exemplifies several of the optically pure compounds prepared in this invention.

TABLE H

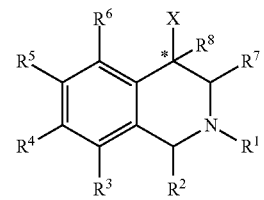

| X | Example number | R$^1$ | R$^2$ | R$^3$ | R$^4$ | R$^5$ | R$^6$ | R$^7$ | R$^8$ | $[\alpha]_D^{25}$ (c 1.0, MeOH) |
|---|---|---|---|---|---|---|---|---|---|---|
| 7-methoxy-benzofuran-2-yl | 11 | Me | H | H | H | H | H | H | H | +5.3° |
| 7-methoxy-benzofuran-2-yl | 11 | Me | H | H | H | H | H | H | H | −10.4° |
| benzo[b]thiophen-2-yl | 21 | Me | H | H | H | H | H | H | H | +114° (c 0.35) |
| benzo[b]thiophen-2-yl | 21 | Me | H | H | H | H | H | H | H | −116° (c 0.35) |
| benzo[b]thiophen-5-yl | 40 | Me | H | H | H | H | H | H | H | +60.0° |
| benzo[b]thiophen-5-yl | 40 | Me | H | H | H | H | H | H | H | −60.0° |
| benzo[b]thiophen-5-yl | 20 | H | H | H | H | H | H | H | H | +6.0° (c 0.15) |
| benzo[b]thiophen-5-yl | 20 | H | H | H | H | H | H | H | H | −30.7° (c 0.15) |
| benzo[b]thiophen-5-yl | 24 | Et | H | H | H | H | H | H | H | +83.3° (c 0.05) |

TABLE H-continued

| X | Example number | R¹ | R² | R³ | R⁴ | R⁵ | R⁶ | R⁷ | R⁸ | $[\alpha]_D^{25}$ (c 1.0, MeOH) |
|---|---|---|---|---|---|---|---|---|---|---|
| benzo[b]thiophen-5-yl | 24 | Et | H | H | H | H | H | H | H | −33.8° (c 0.07) |
| benzofuran-2-yl | 6 | Me | H | H | Me | H | H | H | H | +20° |
| benzofuran-2-yl | 6 | Me | H | H | Me | H | H | H | H | −17° |
| benzofuran-5-yl | 14 | Me | H | H | H | H | H | H | H | +37° |
| benzofuran-5-yl | 14 | Me | H | H | H | H | H | H | H | −37° |
| 1H-indazol-5-yl | 122 | Me | H | H | H | H | H | H | H | +34.0° (c 0.05) |
| 1H-indazol-5-yl | 122 | Me | H | H | H | H | H | H | H | −53.0° (c 0.11) |
| 4-methoxy-benzo[b]thiophen-5-yl | 84 | Me | H | H | 6-methyl-pyridazin-3-yl | H | H | H | H | −87.3° (c 0.11) |
| 4-methoxy-benzo[b]thiophen-5-yl | 84 | Me | H | H | 6-methyl-pyridazin-3-yl | H | H | H | H | +81.0° (c 0.10) |
| benzo[b]thiophen-6-yl | 115 | Me | H | H | pyridazin-3-yl | H | H | H | H | −32.7° (c 0.10) * |
| benzo[b]thiophen-6-yl | 115 | Me | H | H | pyridazin-3-yl | H | H | H | H | +32.5° (c 0.10) * |
| benzo[b]thiophen-5-yl | 92 | Me | H | H | H | H | H | H | OH | +71.3° (c 0.05) |
| benzo[b]thiophen-5-yl | 92 | Me | H | H | H | H | H | H | OH | −83.3° (c 0.05) |
| benzo[b]thiophen-5-yl | 108 | Me | H | H | F | H | H | H | OH | +32.4° (c 0.05) ** |
| benzo[b]thiophen-5-yl | 108 | Me | H | H | F | H | H | H | OH | −30.9° (c 0.09) ** |
| benzo[b]thiophen-7-yl | 116 | Me | H | H | H | H | H | H | H | +42.2° (c 0.60) |
| benzo[b]thiophen-7-yl | 116 | Me | H | H | H | H | H | H | H | −42.4° (c 0.85) |
| benzo[d]isothiazol-6-yl | 134 | Me | H | H | H | H | H | H | H | +36.0° (c 0.08) ** |
| benzo[d]isothiazol-6-yl | 134 | Me | H | H | H | H | H | H | H | −37.5° (c 0.06) ** |
| 1-methoxy-naphthalen-2-yl | 138 | Me | H | H | pyridazin-3-yl | H | H | H | H | +195.3° (c 0.10) |
| 1-methoxy-naphthalen-2-yl | 138 | Me | H | H | pyridazin-3-yl | H | H | H | H | −191.2° (c 0.11) |
| naphthalen-2-yl | 143 | Me | H | H | morpholino-4-yl | H | H | H | H | +47.8° (c 0.06) |
| naphthalen-2-yl | 143 | Me | H | H | morpholino-4-yl | H | H | H | H | −38.8° (c 0.16) |

\* optical rotation measured using maleate salt
\*\* optical rotation measured using fumarate salt Another embodiment of the present invention relates to a mixture of compounds of Formula (I) where the compound of Formula (I) is radiolabeled, i.e., wherein one or more of the atoms described are replaced by a radioactive isotope of that atom (e.g., C replaced by $^{14}C$ and H replaced by $^{3}H$). Such compounds have a variety of potential uses, e.g., as standards and reagents in determining the ability of a potential pharmaceutical to bind to neurotransmitter transporter proteins.

The compounds of the present invention are also represented by the chemical structure found in Formula (I):

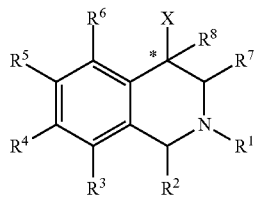

Formula I wherein:
the carbon atom designated * is in the R or S configuration;
X is a fused aromatic bicyclic carbocycle or heterocycle optionally substituted with substituents (1 to 4 in number) as defined below in $R^{14}$, with the proviso that X≠isoquinolinyl, naphthyl, or phthalimidyl;

$R^1$ is H, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, each of which is optionally substituted with from 1 to 3 substituents independently selected at each occurrence thereof from the group consisting of: $C_1$-$C_3$ alkyl, halogen, aryl, —CN, —$OR^9$, and —$NR^9R^{10}$;

$R^2$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, or $C_1$-$C_6$ haloalkyl, each of which is optionally substituted with from 1 to 3 substituents independently selected at each occurrence thereof from the group consisting of: $C_1$-$C_3$ alkyl, halogen, aryl, —CN, —$OR^9$, and —$NR^9R^{10}$; or $R^2$ is gem-dimethyl;

$R^3$ is H, halogen, —$OR^{11}$, —$S(O)_nR^{12}$, —CN, —$C(O)R^{12}$, —$C(O)NR^{11}R^{12}$, —$NR^9R^{10}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with from 1 to 3 substituents independently selected at each occurrence thereof from the group consisting of: $C_1$-$C_3$ alkyl, halogen, —CN, —$OR^9$, —$NR^9R^{10}$, and phenyl, which is optionally substituted 1 to 3 times with a substituent selected from the group consisting of: halogen, cyano, $C_1$-$C_4$ alkyl, $C_1$-$C_4$ haloalkyl, $C_1$-$C_4$ alkoxy, —CN, and —$OR^9$;

$R^4$ is H, halogen, —$OR^{11}$, —$S(O)_nR^{12}$, —CN, —$C(O)R^{12}$, —$C(O)NR^{11}R^{12}$, —$NR^9R^{10}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, wherein each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with from 1 to 3 substituents independently selected at each occurrence thereof from the group consisting of: $C_1$-$C_3$ alkyl, halogen, —CN, —$OR^9$, —$NR^9R^{10}$, and phenyl, which is optionally substituted 1 to 3 times with a substituent selected from the group consisting of: halogen, cyano, $C_1$-$C_4$ alkyl, $C_1$-$C_4$ haloalkyl, $C_1$-$C_4$ alkoxy, —CN, and —$OR^9$; or $R^4$ is phenyl, naphthyl, indenyl, pyridyl, pyrimidinyl, pyridazinyl, pyrazinyl, [1,2,4]triazinyl, [1,3,5]triazinyl, triazolyl, furanyl, thiophenyl, pyranyl, indazolyl, benzimidazolyl, quinolinyl, quinazolinyl, quinoxalinyl, phthalazinyl, cinnolinyl, isoquinolinyl, thienyl, imidazolyl, thiazolyl, benzthiazolyl, purinyl, isothiazolyl, indolyl, pyrrolyl, oxazolyl, benzofuranyl, benzothienyl, benzthiazolyl, isoxazolyl, pyrazolyl, oxadiazolyl, thiadiazolyl, 3-oxo-[1,2,4]triazolo[4,3-a]pyridinyl, imidazo[1,2-a]pyridinyl, pyrazolo[1,5-a]pyridinyl, [1,2,4]triazolo[4,3-a]pyridinyl, thieno[2,3-b]pyridinyl, thieno[3,2-b]pyridinyl, 1H-pyrrolo[2,3-b]pyridinyl, or other heterocycles optionally substituted with substituents (1 to 4 in number) as defined below in $R^{14}$;

$R^5$ and $R^6$ are each independently selected from the group consisting of: H, halogen, —$OR^{11}$, —$S(O)_nR^{12}$, —CN, —$C(O)R^{12}$, —$C(O)NR^{11}R^{12}$, —$NR^9R^{10}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and phenyl is optionally substituted with from 1 to 3 substituents independently selected at each occurrence thereof from the group consisting of: $C_1$-$C_3$ alkyl, halogen, —CN, —$OR^9$, —$NR^9R^{10}$, and phenyl, which is optionally substituted 1 to 3 times with a substituent selected from the group consisting of: halogen, $C_1$-$C_4$ alkyl, $C_1$-$C_4$ haloalkyl, $C_1$-$C_4$ alkoxy, —CN, and —$OR^9$;

$R^7$ is H, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with from 1 to 3 substituents independently selected at each occurrence thereof from the group consisting of: $C_1$-$C_3$ alkyl, halogen, —CN, —$OR^9$, —$NR^9R^{10}$, and phenyl which is optionally substituted 1 to 3 times with a substituent selected from the group consisting of: halogen, $C_1$-$C_4$ alkyl, $C_1$-$C_4$ haloalkyl, $C_1$-$C_4$ alkoxy, —CN, and —$OR^9$; or $R^7$ is gem-dimethyl;

$R^8$ is H, halogen, —$OR^9$, —$SR^9$, $C_1$-$C_6$ alkyl, —CN, or —$NR^9R^{10}$;

$R^9$ and $R^{10}$ are each independently selected from the group consisting of: H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —$C(O)R^{13}$, phenyl, and benzyl, where phenyl or benzyl is optionally substituted from 1 to 3 times with a substituent selected independently at each occurrence thereof from the group consisting of: halogen, cyano, $C_1$-$C_4$ alkyl, $C_1$-$C_4$ haloalkyl, and $C_1$-$C_4$ alkoxy; or $R^9$ and $R^{10}$ are taken together with the nitrogen to which they are attached to form a piperidine, pyrrolidine, piperazine, N-methylpiperazine, morpholine, thiomorpholine, [1,2]oxazinane, isoxazolidine, or 2-oxo-2H-pyridine, which is optionally substituted from 1 to 3 times with a substituent selected independently at each occurrence thereof from the group consisting of, halogen, cyano, $C_1$-$C_4$ alkyl, $C_1$-$C_4$ haloalkyl, and $C_1$-$C_4$ alkoxy;

$R^{11}$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —$C(O)R^{13}$, phenyl, or benzyl, where phenyl or benzyl is optionally substituted 1 to 3 times with halogen, cyano, $C_1$-$C_4$ alkyl, $C_1$-$C_4$ haloalkyl, or $C_1$-$C_4$ alkoxy;

$R^{12}$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, phenyl, or benzyl, where phenyl or benzyl is optionally substituted 1 to 3 times with halogen, cyano, $C_1$-$C_4$ alkyl, $C_1$-$C_4$ haloalkyl, or $C_1$-$C_4$ alkoxy; or $R^{11}$ and $R^{12}$ are taken together with the nitrogen to which they are attached to form a piperidine, pyrrolidine, piperazine, N-methylpiperazine, morpholine, or thiomorpholine ring, with the proviso that only one of $R^9$ and $R^{10}$ or $R^{11}$ and $R^{12}$ are taken together with the nitrogen to which they are attached to form a piperidine, pyrrolidine, piperazine, N-methylpiperazine, morpholine, or thiomorpholine ring;

$R^{13}$ is $C_1$-$C_4$ alkyl, $C_1$-$C_4$ haloalkyl, or phenyl;

n is 0, 1, or 2; and $R^{14}$ is independently selected at each occurrence from a substituent selected from the group consisting of: halogen, —$NO_2$, —$OR^{11}$, —$NR^{11}R^{12}$, —$NR^{11}C(O)R^{12}$, —$NR^{11}C(O)_2R^{12}$, —$NR^{11}C(O)NR^{12}R^{13}$, —$S(O)_nR^{12}$, —CN, —$C(O)R^{12}$, —$C(O)NR^{11}R^{12}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl are optionally substituted with 1 to 3 substituents independently selected at each occurrence from the group consisting of: $C_1$-$C_3$ alkyl, halogen, aryl, —CN, —$OR^9$, and —$NR^9R^{10}$;

or an oxide thereof or a pharmaceutically acceptable salt thereof.

In addition, the compounds of the present invention are represented by the chemical structure found in Formula (I):

Formula I

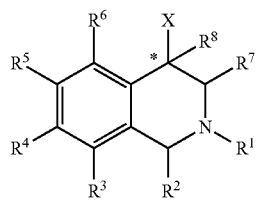

wherein:

the carbon atom designated * is in the R or S configuration;

X is a fused bicyclic carbocycle or heterocycle selected from the group consisting of benzofuranyl, benzo[b]thiophenyl, benzoisothiazolyl, benzoisoxazolyl, indazolyl, indolyl, isoindolyl, indolizinyl, benzoimidazolyl, benzooxazolyl, benzothiazolyl, benzotriazolyl, imidazo[1,2-a]pyridinyl, pyrazolo[1,5-a]pyridinyl, [1,2,4]triazolo[4,3-a]pyridinyl, thieno[2,3-b]pyridinyl, thieno[3,2-b]pyridinyl, 1H-pyrrolo[2,3-b]pyridinyl, indenyl, indanyl, dihydrobenzocycloheptenyl, tetrahydrobenzocycloheptenyl, dihydrobenzothiophenyl, dihydrobenzofuranyl, indolinyl, naphthyl, tetrahydronaphthyl, quinolinyl, isoquinolinyl, 4H-quinolizinyl, 9aH-quinolizinyl, quinazolinyl, cinnolinyl, phthalazinyl, quinoxalinyl, benzo[1,2,3]triazinyl, benzo[1,2,4]triazinyl, 2H-chromenyl, 4H-chromenyl, and a fused bicyclic carbocycle or fused bicyclic heterocycle optionally substituted with substituents (1 to 4 in number) as defined below in $R^{14}$, with the provisos that (1) where X=naphthyl and $R^4$ is $NH_2$ or $OR^{11}$, $R^5$ cannot be H, and (2) where X=naphthyl and $R^5=OR^{11}$, $R^4$ cannot be H;

$R^1$ is H, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, each of which is optionally substituted with from 1 to 3 substituents independently selected at each occurrence thereof from the group consisting of: $C_1$-$C_3$ alkyl, halogen, aryl, —CN, —$OR^9$, and —$NR^9R^{10}$;

$R^2$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, or $C_1$-$C_6$ haloalkyl, each of which is optionally substituted with from 1 to 3 substituents independently selected at each occurrence thereof from the group consisting of: $C_1$-$C_3$ alkyl, halogen, aryl, —CN, —$OR^9$, and —$NR^9R^{10}$; or $R^2$ is gem-dimethyl;

$R^3$ is H, halogen, —$OR^{11}$, —$S(O)_nR^{12}$, —CN, —$C(O)R^{12}$, —$C(O)NR^{11}R^{12}$, —$NR^9R^{10}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with from 1 to 3 substituents independently selected at each occurrence thereof from the group consisting of: $C_1$-$C_3$ alkyl, halogen, —CN, —$OR^9$, —$NR^9R^{10}$, and phenyl, which is optionally substituted 1 to 3 times with a substituent selected from the group consisting of: halogen, cyano, $C_1$-$C_4$ alkyl, $C_1$-$C_4$ haloalkyl, $C_1$-$C_4$ alkoxy, —CN, and —$OR^9$;

$R^4$ is H, halogen, —$OR^{11}$, —$S(O)_nR^{12}$, —CN, —$C(O)R^{12}$, —$C(O)NR^{11}R^{12}$, —$NR^9R^{10}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, wherein each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with from 1 to 3 substituents independently selected at each occurrence thereof from the group consisting of: $C_1$-$C_3$ alkyl, halogen, —CN, —$OR^9$, —$NR^9R^{10}$, and phenyl, which is optionally substituted 1 to 3 times with a substituent selected from the group consisting of: halogen, cyano, $C_1$-$C_4$ alkyl, $C_1$-$C_4$ haloalkyl, $C_1$-$C_4$ alkoxy, —CN, and —$OR^9$; or $R^4$ is phenyl, naphthyl, indenyl, pyridyl, pyrimidinyl, pyridazinyl, pyrazinyl, [1,2,4]triazinyl, [1,3,5]triazinyl, triazolyl, furanyl, thiophenyl, pyranyl, indazolyl, benzimidazolyl, quinolinyl, quinazolinyl, quinoxalinyl, phthalazinyl, cinnolinyl, isoquinolinyl, thienyl, imidazolyl, thiazolyl, benzthiazolyl, purinyl, isothiazolyl, indolyl, pyrrolyl, oxazolyl, benzofuranyl, benzothienyl, benzthiazolyl, isoxazolyl, pyrazolyl, oxadiazolyl, thiadiazolyl, 3-oxo-[1,2,4]triazolo[4,3-a]pyridinyl, imidazo[1,2-a]pyridinyl, pyrazolo[1,5-a]pyridinyl, [1,2,4]triazolo[4,3-a]pyridinyl, thieno[2,3-b]pyridinyl, thieno[3,2-b]pyridinyl, 1H-pyrrolo[2,3-b]pyridinyl, or other heterocycles optionally substituted with substituents (1 to 4 in number) as defined below in $R^{14}$;

$R^5$ and $R^6$ are each independently selected from the group consisting of: H, halogen, —$OR^{11}$, —$S(O)_nR^{12}$, —CN, —$C(O)R^{12}$, —$C(O)NR^{11}R^{12}$, —$NR^9R^{10}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and phenyl is optionally substituted with from 1 to 3 substituents independently selected at each occurrence thereof from the group consisting of: $C_1$-$C_3$ alkyl, halogen, —CN, —$OR^9$, —$NR^9R^{10}$, and phenyl, which is optionally substituted 1 to 3 times with a substituent selected from the group consisting of: halogen, $C_1$-$C_4$ alkyl, $C_1$-$C_4$ haloalkyl, $C_1$-$C_4$ alkoxy, —CN, and —$OR^9$;

$R^7$ is H, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with from 1 to 3 substituents independently selected at each occurrence thereof from the group consisting of: $C_1$-$C_3$ alkyl, halogen, —CN, —$OR^9$, —$NR^9R^{10}$, and phenyl which is optionally substituted 1 to 3 times with a substituent selected from the group consisting of: halogen, $C_1$-$C_4$ alkyl, $C_1$-$C_4$ haloalkyl, $C_1$-$C_4$ alkoxy, —CN, and —$OR^9$; or $R^7$ is gem-dimethyl;

$R^8$ is H, halogen, —$OR^9$, —$SR^9$, $C_1$-$C_6$ alkyl, —CN, or —$NR^9R^{10}$;

$R^9$ and $R^{10}$ are each independently selected from the group consisting of: H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —$C(O)R^{13}$, phenyl, and benzyl, where phenyl or benzyl is optionally substituted from 1 to 3 times with a substituent selected independently at each occurrence thereof from the group consisting of: halogen, cyano, $C_1$-$C_4$ alkyl, $C_1$-$C_4$ haloalkyl, and $C_1$-$C_4$ alkoxy; or $R^9$ and $R^{10}$ are taken together with the nitrogen to which they are attached to form a piperidine, pyrrolidine, piperazine, N-methylpiperazine, morpholine, thiomorpholine, [1,2]oxazinane, isoxazolidine, or 2-oxo-2H-pyridine, which is optionally substituted from 1 to 3 times with a substituent selected independently at each occurrence thereof from the group consisting of, halogen, cyano, $C_1$-$C_4$ alkyl, $C_1$-$C_4$ haloalkyl, and $C_1$-$C_4$ alkoxy;

$R^{11}$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —$C(O)R^{13}$, phenyl, or benzyl, where phenyl or benzyl is optionally substituted 1 to 3 times with halogen, cyano, $C_1$-$C_4$ alkyl, $C_1$-$C_4$ haloalkyl, or $C_1$-$C_4$ alkoxy;

$R^{12}$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, phenyl, or benzyl, where phenyl or benzyl is optionally substituted 1 to 3 times with halogen, cyano, $C_1$-$C_4$ alkyl, $C_1$-$C_4$ haloalkyl, or $C_1$-$C_4$ alkoxy; or $R^{11}$ and $R^{12}$ are taken together with the nitrogen to which they are attached to form a piperidine, pyrrolidine, piperazine, N-methylpiperazine, morpholine, or thiomorpholine ring, with the proviso that only one of $R^9$ and $R^{10}$ or $R^{11}$ and $R^{12}$ are taken together with the nitrogen to which they are attached to form a piperidine, pyrrolidine, piperazine, N-methylpiperazine, morpholine, or thiomorpholine ring;

$R^{13}$ is $C_1$-$C_4$ alkyl, $C_1$-$C_4$ haloalkyl, or phenyl;

n is 0, 1, or 2; and $R^{14}$ is independently selected at each occurrence from a substituent selected from the group consisting of: halogen, $-NO_2$, $-OR^{11}$, $-NR^{11}R^{12}$, $-NR^{11}C(O)R^{12}$, $-NR^{11}C(O)_2R^{12}$, $-NR^{11}C(O)NR^{12}R^{13}$, $-S(O)_nR^{12}$, $-CN$, $-C(O)R^{12}$, $-C(O)NR^{11}R^{12}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl are optionally substituted with 1 to 3 substituents independently selected at each occurrence from the group consisting of: $C_1$-$C_3$ alkyl, halogen, aryl, $-CN$, $-OR^9$, and $-NR^9R^{10}$;

or an oxide thereof or a pharmaceutically acceptable salt thereof.

Another embodiment of the present invention relates to a pharmaceutical composition containing a therapeutically effective amount of the compound of Formula (I) and a pharmaceutically acceptable carrier.

Another aspect of the present invention relates to a method of treating a disorder which is created by or is dependent upon decreased availability of serotonin, norepinephrine, or dopamine. The method involves administering to a patient in need of such treatment a therapeutically effective amount of a compound of Formula (I) or a pharmaceutically acceptable salt thereof.

In another embodiment, the method of the present invention further involves administering a therapeutically effective amount of a serotonin 1A receptor antagonist or a pharmaceutically acceptable salt thereof.

The serotonin 1A receptor antagonist can be WAY 100135 or spiperone. WAY 100135 (N-(t-butyl)-3-[α-(2-methoxyphenyl)piperazin-1-yl]-2 phenylpropanamide) is disclosed in U.S. Pat. No. 4,988,814 to Abou-Gharbia et al., which is hereby incorporated by reference in its entirety, as having an affinity for the 5-$HT_{1A}$ receptor. Also, Cliffe et al., *J Med Chem* 36:1509-10 (1993), which is hereby incorporated by reference in its entirety, showed that the compound is a 5-$HT_{1A}$ antagonist. Spiperone (8-[4-(4-fluorophenyl)-4-oxobutyl]-1-phenyl-1,3,8-triazaspiro[4,5]decan-4-one) is a well-known compound, and is disclosed in U.S. Pat. Nos. 3,155,669 and 3,155,670, which are hereby incorporated by reference in their entirety. The activity of spiperone as a 5-$HT_{1A}$ antagonist is shown in Middlemiss et al., *Neurosc and Biobehav Rev.* 16:75-82 (1992), which is hereby incorporated by reference in its entirety.

In another embodiment, the method of the present invention further involves administering a therapeutically effective amount of a selective neurokinin-1 receptor antagonist or a pharmaceutically acceptable salt thereof.

Neurokinin-1 receptor antagonists that can be used in combination with the compound of Formula (I) in the present invention are fully described, for example, in U.S. Pat. Nos. 5,373,003, 5,387,595, 5,459,270, 5,494,926, 5,162,339, 5,232,929, 5,242,930, 5,496,833, and 5,637,699; PCT International Patent Publication Nos. WO 90/05525, 90/05729, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942, 97/21702, and 97/49710; U.K. Patent Application Nos. 2 266 529, 2 268 931, 2 269 170, 2 269 590, 2 271 774, 2 292 144, 2 293168, 2 293 169, and 2 302 689; and European Patent Publication Nos. EP 0 360 390, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 699 674, 0 707 006, 0 708 101, 0 709 375, 0 709 376, 0 714 891, 0 723 959, 0733 632 and 0 776 893, which are hereby incorporated by reference in their entirety. The preparations of such compounds are fully described in the aforementioned patents and publications.

In another embodiment, the method of the present invention further involves administering a therapeutically effective amount of a norepinephrine precursor or pharmaceutically acceptable salt thereof.

The norepinephrine precursor can be L-tyrosine or L-phenylalanine.

Another aspect of the present invention relates to a method of inhibiting synaptic norepinephrine uptake in a patient in need thereof comprising administering a therapeutically effective inhibitory amount of the compound of Formula (I).

Another aspect of the present invention relates to a method of inhibiting synaptic serotonin uptake in a patient in need thereof comprising administering a therapeutically effective inhibitory amount of the compound of Formula (I).

Another aspect of the present invention relates to a method of inhibiting synaptic dopamine uptake in a patient in need thereof comprising administering a therapeutically effective inhibitory amount of the compound of Formula (I).

Another aspect of the present invention relates to a therapeutic method described herein wherein the (+)-stereoisomer of the compound of Formula (I) is employed.

Another aspect of the present invention relates to a therapeutic method described herein wherein the (−)-stereoisomer of the compound of Formula (I) is employed.

Another aspect of the present invention relates to a kit comprising the compound of Formula (I) and at least one compound selected from the group consisting of: a serotonin 1A receptor antagonist compound, a selective neurokinin-1 receptor antagonist compound, and a norepinephrine precursor compound.

Another aspect of the present invention relates to a method of treating a disorder referred to in the above-mentioned embodiments in a patient in need thereof comprising inhibiting synaptic serotonin and norepinephrine uptake by administering a therapeutically effective inhibitory amount of the compound of Formula (I) which functions as both a dual acting serotonin and norepinephrine uptake inhibitor.

Another aspect of the present invention relates to a method of treating a disorder referred to in the above-mentioned embodiments in a patient in need thereof comprising inhibiting synaptic serotonin and dopamine uptake by administering a therapeutically effective inhibitory amount of the compound of Formula (I) which functions as both a dual acting serotonin and dopamine uptake inhibitor.

Another aspect of the present invention relates to a method of treating a disorder referred to in the above-mentioned embodiments in a patient in need thereof comprising inhibiting synaptic dopamine and norepinephrine uptake by administering a therapeutically effective inhibitory amount of the compound of Formula (I) which functions as both a dual acting dopamine and norepinephrine uptake inhibitor.

Another aspect of the present invention relates to a method of treating a disorder referred to in the above-mentioned embodiments in a patient in need thereof comprising inhibiting synaptic norepinephrine, dopamine and serotonin uptake by administering a therapeutically effective inhibitory amount of the compound of Formula (I) which functions as a triple acting norepinephrine, dopamine and serotonin uptake inhibitor.

Another aspect of the present invention relates to a method for inhibiting serotonin uptake in mammals which comprises administering to a mammal requiring increased neurotransmission of serotonin a pharmaceutically effective amount of the compound of Formula (I).

Another aspect of the present invention relates to a method for inhibiting dopamine uptake in humans which comprises administering to a human requiring increased neurotransmission of dopamine a pharmaceutically effective amount of the compound of Formula (I).

Another aspect of the present invention relates to a method for inhibiting norepinephrine uptake in humans which comprises administering to a human requiring increased neurotransmission of norepinephrine a pharmaceutically effective amount of the compound of Formula (I).

Another aspect of the present invention relates to a method of suppressing the desire of humans to smoke comprising administering to a human in need of such suppression an effective dose, to relieve the desire to smoke, of the compound of Formula (I).

Another aspect of the present invention relates to a method of suppressing the desire of humans to consume alcohol comprising administering to a human in need of such suppression an effective dose, to relieve the desire to consume alcohol, of the compound of Formula (I).

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

Compounds according to the invention, for example, starting materials, intermediates or products, are prepared as described herein or by the application or adaptation of known methods, by which is meant methods used heretofore or described in the literature.

Compounds useful according to the invention may be prepared by the application or adaptation of known methods, by which is meant methods used heretofore or described in the literature, for example, those described by Larock, *Comprehensive Organic Transformations*, VCH publishers (1989), which is hereby incorporated by reference in its entirety.

A compound of Formula (I) including a group containing one or more nitrogen ring atoms, may be converted to the corresponding compound wherein one or more nitrogen ring atom of the group is oxidized to an N-oxide, preferably by reacting with a peracid, for example peracetic acid in acetic acid or m-chloroperoxybenzoic acid in an inert solvent, such as dichloromethane, at a temperature from about room temperature to reflux, preferably at elevated temperature.

In the reactions described hereinafter, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice; for examples, see Green, *Protective Groups in Organic Chemistry*, John Wiley and Sons (1991), and McOmie, *Protective Groups in Organic Chemistry*, Plenum Press (1973), which are hereby incorporated by reference in their entirety.

The novel tetrahydroisoquinoline reuptake inhibitors of Formula (I) of this invention can be prepared by the general scheme outlined below (Scheme 1). The $R^1$-substituted N-benzyl amines of Formula (III) may be purchased from commercial sources, or alternatively, obtained from a simple reductive amination protocol. Thus, carbonyl containing compounds of Formula (II) may be treated with $H_2N-R^1$ in lower alkyl alcoholic solvents (preferably methanol or ethanol) at temperatures at or below room temperature. The resulting imine may be reduced most commonly with alkaline earth borohydrides (preferably sodium borohydride) to provide the desired amine intermediates.

Scheme 1

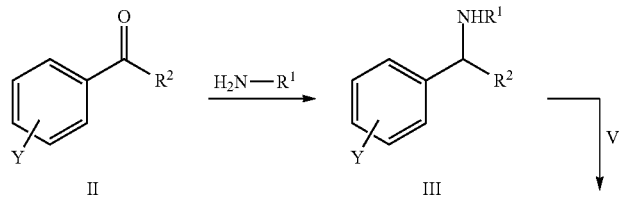

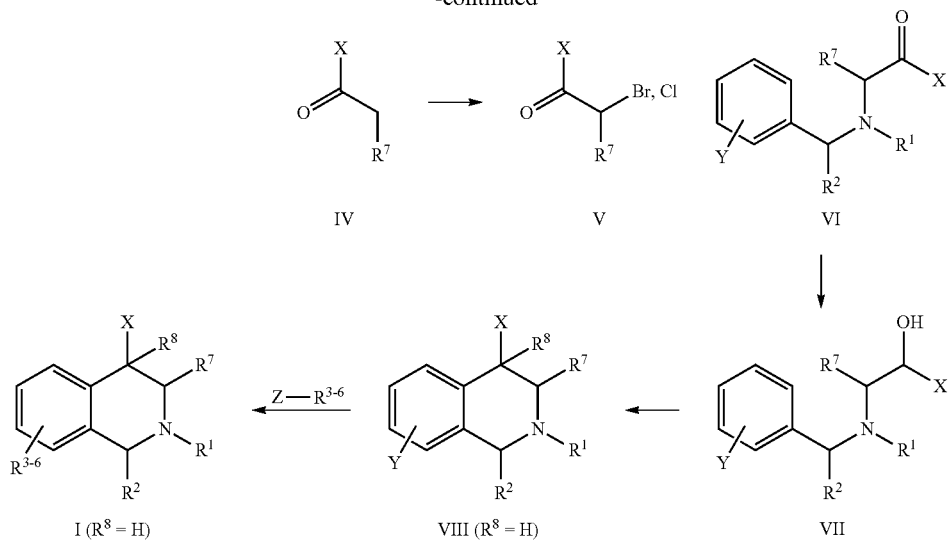

Treatment of intermediates of Formula (III) with intermediates of Formula (V) cleanly generates the alkylation products of Formula (VI). The alkylation reactions may be run under a wide variety of conditions familiar to one skilled in the art of organic synthesis. Typical solvents include acetonitrile, toluene, diethyl ether, tetrahydrofuran, dimethylsulfoxide, dimethylformamide, methylene chloride, and lower alkyl alcohols including ethanol. The reactions may be successfully run at temperatures ranging from 0° C. up to the boiling point of the solvent employed. Reaction progress is conventionally monitored by standard chromatographic and spectroscopic methods. The alkylation reaction is optionally run with the addition of a non-nucleophilic organic base such as, but not limited to, pyridine, triethylamine and diisopropyl ethylamine.

The aforementioned intermediate of Formula (V) may be purchased from commercial sources or prepared via treatment of an optionally substituted ketone of Formula (IV) with common brominating agents such as, but not limited to, bromine, NBS, or tetrabutylammonium tribromide which readily affords the desired bromoacetophenones of Formula (V). These reactions are optimally conducted in acetic acid or methylene chloride with methanol used as a co-solvent for the tribromide reagent with reaction temperatures at or below room temperature. Another embodiment of this methodology would include the use of chloroacetophenone compounds of Formula (V).

The ketones of Formula (IV) are also available from commercial sources or are conveniently obtained via several well known methods, including the treatment of the corresponding aromatic or heteroaromatic carboxylic acid intermediates with two stoichiometric equivalents of methyllithium (see, e.g., Jorgenson, *Organic Reactions*, 18:1 (1970), which is hereby incorporated by reference in its entirety.). Alternatively, one may treat the corresponding aromatic or heteroaromatic aldehydes with an alkyl-Grignard (for example, MeMgBr) or alkyl-lithium (for example, MeLi) nucleophile followed by routine oxidation to the ketone (see, e.g., Larock, *Comprehensive Organic Transformations*, VCH Publishers, New York, p. 604 (1989), which is hereby incorporated by reference in its entirety).

Reductions of compounds of Formula (VI) to the secondary alcohols of Formula (VII) proceeds with many reducing agents including, for example, sodium borohydride, lithium borohydride, borane, diisobutylaluminum hydride, and lithium aluminum hydride. The reductions are carried out for a period of time between 1 hour to 3 days at room temperature or elevated temperature up to the reflux point of the solvent employed. If borane is used, it may be employed as a complex for example, but not limited to, borane-methyl sulfide complex, borane-piperidine complex, or borane-tetrahydrofuran complex. One skilled in the art will understand the optimal combination of reducing agents and reaction conditions needed or may seek guidance from the text of Larock, R. C., *Comprehensive Organic Transformations*, VCH Publishers, New York, p. 604 (1989), which is hereby incorporated by reference in its entirety.

Compounds of Formula (VII) may be cyclized to the tetrahydroisoquinoline compounds of Formula (VIII) of this invention by brief treatment with a strong acid. Suitable acids include, but are not limited to, concentrated sulfuric acid, polyphosphoric acid, methanesulfonic acid and trifluoroacetic acid. The reactions are run neat or in the optional presence of a co-solvent such as, for example, methylene chloride or 1,2-dichloroethane. The cyclizations may be conducted at temperatures ranging from 0° C. up to the reflux point of the solvent employed. One skilled in the art of heterocyclic chemistry will readily understand these conditions or may consult the teachings of Mondeshka, *Il Farmaco*, 49:475-480 (1994) and Venkov, *Synthesis*, 253-255 (1990), which are hereby incorporated by reference in their entirety. Cyclizations may also be effected by treatment of compounds of Formula (VII) with strong Lewis acids, such as aluminum trichloride typically in halogenated solvents such as methylene chloride. One skilled in the art will be familiar with the precedent taught by Kaiser, *J Med Chem* 27:28-35 (1984) and Wyrick, *J Med Chem* 24:1013-1015 (1981), which are hereby incorporated by reference in their entirety.

Finally, the target compounds of Formula (I) of this invention may be prepared by treatment of compounds of Formula (VIII; Y=Br, I, $OSO_2CF_3$) with an aryl or heteroaryl boronic acids or aryl or heteroaryl boronic acid esters where Z is equivalent to $B(OH)_2$ or $B(OR^a)(OR^b)$ (where $R^a$ and $R^b$ are lower alkyl, ie. $C_1$-$C_6$, or taken together, $R^a$ and $R^b$ are lower alkylene, ie. $C_2$-$C_{12}$) in the presence of a metal catalyst with or without a base in an inert solvent to give isoquinoline compounds of Formula (XIII). Metal catalysts include, but are not limited to, salts or phosphine complexes of Cu, Pd, or Ni (e.g., Cu(OAc)$_2$, PdCl$_2$ (PPh$_3$)$_2$, and NiCl$_2$ (PPh$_3$)$_2$). Bases may include, but are not limited to, alkaline earth metal carbonates, alkaline earth metal bicarbonates, alkaline earth metal hydroxides, alkali metal carbonates, alkali metal bicarbonates, alkali metal hydroxides, alkali metal hydrides (preferably sodium hydride), alkali metal alkoxides (preferably sodium methoxide or sodium ethoxide), alkaline earth metal hydrides, alkali metal dialkylamides (preferably lithium diisopropylamide), alkali metal bis(trialkylsilyl)amides (preferably sodium bis (trimethylsilyl)amide), trialkyl amines (preferably diisopropylethylamine or triethylamine) or aromatic amines (preferably pyridine). Inert solvents may include, but are not limited to acetonitrile, dialkyl ethers (preferably diethyl ether), cyclic ethers (preferably tetrahydrofuran or 1,4-dioxane), N,N-dialkylacetamides (preferably dimethylacetamide), N,N-dialkylformamides (preferably dimethylformamide), dialkylsulfoxides (preferably dimethylsulfoxide), aromatic hydrocarbons (preferably benzene or toluene) or haloalkanes (preferably methylene chloride). Preferred reaction temperatures range from room temperature up to the boiling point of the solvent employed. The reactions may be run in conventional glassware or in one of many commercially available parallel synthesizer units. Non-commercially available boronic acids or boronic acid esters may be obtained from the corresponding optionally substituted aryl halide as described by Gao, Tetrahedron, 50:979-988 (1994), which is hereby incorporated by reference in its entirety. It will also be appreciated by one skilled in the art that compounds of Formula (VIII) may be converted to the boronic acid or boronate ester and subsequently treated with the desired optionally substituted aryl or heteroaryl halide in discreet steps or in tandem as taught by Baudoin, J Org Chem 67:1199-1207 (2002), which is hereby incorporated in its entirety.

Compounds of Formula (VI) may be treated with a C$_1$-C$_4$ alkyl lithium reagent or a C$_1$-C$_4$ alkyl Grignard reagent. The resulting tertiary alcohols may then be converted to compounds of Formula (VIII), wherein R$^8$ is the corresponding C$_1$-C$_4$ alkyl, then to compounds of Formula (I), wherein R$^8$ is the corresponding C$_1$-C$_4$ alkyl, using the aforementioned methods.

Compounds of Formula (I) may also be prepared according to the scheme outlined below (Scheme 2). The 4-substituted isoquinolines of Formula (IX) may be purchased from commercial sources. Treatment of compounds of Formula IX (typically Y=Br) with a bicyclic carbocycle or bicyclic heterocycle boronic acid or bicyclic carbocycle or bicyclic heterocycle boronate ester where Z is equivalent to B(OH)$_2$ or B(OR$^a$)(OR$^b$) (where R$^a$ and R$^b$ are lower alkyl, ie. C$_1$-C$_6$, or taken together, R$^a$ and R$^b$ are lower alkylene, ie. C$_2$-C$_{12}$) in the presence of a metal catalyst with or without a base in an inert solvent to give isoquinoline compounds of Formula (X). Metal catalysts include, but are not limited to, salts or phosphine complexes of Cu, Pd, or Ni (eg. Cu(OAc)$_2$, PdCl$_2$ (PPh$_3$)$_2$, NiCl$_2$ (PPh$_3$)$_2$). Bases may include, but are not limited to, alkaline earth metal carbonates, alkaline earth metal bicarbonates, alkaline earth metal hydroxides, alkali metal carbonates, alkali metal bicarbonates, alkali metal hydroxides, alkali metal hydrides (preferably sodium hydride), alkali metal alkoxides (preferably sodium methoxide or sodium ethoxide), alkaline earth metal hydrides, alkali metal dialkylamides (preferably lithium diisopropylamide), alkali metal bis(trialkylsilyl)amides (preferably sodium bis(trimethylsilyl)amide), trialkyl amines (preferably diisopropylethylamine or triethylamine) or aromatic amines (preferably pyridine). Inert solvents may include, but are not limited to acetonitrile, dialkyl ethers (preferably diethyl ether), cyclic ethers (preferably tetrahydrofuran or 1,4-dioxane), N,N-dialkylacetamides (preferably dimethylacetamide), N,N-dialkylformamides (preferably dimethylformamide), dialkylsulfoxides (preferably dimethylsulfoxide), aromatic hydrocarbons (preferably benzene or toluene) or haloalkanes (preferably methylene chloride). Preferred reaction temperatures range from room temperature up to the boiling point of the solvent employed. The reactions may be run in conventional glassware or in one of many commercially available parallel synthesizer units. Non-commercially available boronic acids or boronic acid esters may be obtained from the corresponding optionally substituted aryl halide as described by Gao, Tetrahedron 50:979-988 (1994), which is hereby incorporated by reference in its entirety. It will also be appreciated by one skilled in the art that compounds of Formula (IX) may be converted to the corresponding boronic acid and boronate ester and subsequently treated with the desired optionally substituted aryl or heteroaryl halide in discrete steps or in tandem as taught by Baudoin, J Org Chem 67:1199-1207 (2002), which is hereby incorporated by reference in its entirety, to give the desired isoquinolines of Formula (X).

Treatment of intermediates of Formula (X) with a suitable alkylating reagent R$^1$—W where W may be equivalent but not limited to I, Br, —OSO$_2$CF$_3$ (preferably —OSO$_2$CF$_3$) provides the isoquinoliniums of Formula (XI). Suitable solvents include, but are not limited to, methylene chloride, dichloroethane, toluene, diethyl ether, and tetrahydrofuran. The reactions may be successfully run at temperatures at or below room temperature. The reactions may be run in conventional glassware or in one of many commercially available parallel synthesizer units.

Scheme 2

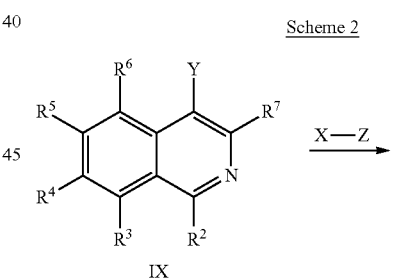

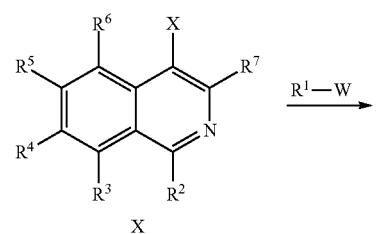

-continued

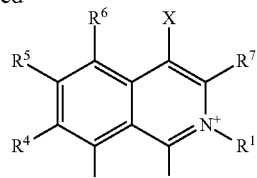
XI

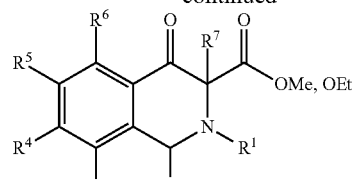
XIII

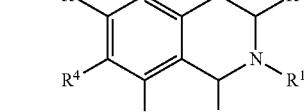
XIV

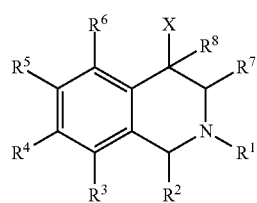
I
(R⁸ = H)

I
R⁸ = OH

I
R⁸ = Cl, F, CN or OR¹¹

Compounds of Formula (XI) may be reduced to the tetrahydroisoquinoline, most commonly with sodium cyanoborohydride, to provide the compounds of Formula (I). Suitable solvents for this reaction include, but are not limited to, lower alcohols including methanol and ethanol. The reactions may be run at temperatures ranging from 0° C. to the boiling point of the solvent employed.

Compounds of Formula (I) wherein R⁸=OH, of this invention can be prepared by the general scheme outlined below (Scheme 3). The R¹ substituted ketone of Formula (XIV) can be prepared using the methodology taught by Hanna, *J Med Chem* 17(9):1020-1023 (1974), which is hereby incorporated by reference in its entirety. Thus, the bis-esters of Formula (XII) are conveniently obtained from commercially available, optionally substituted ortho-methyl benzoic acids or, ortho-methyl/ethyl benzoate, via several well known methods, such as, but not limited to, esterification, bromination, N-alkylation, Claisen type condensation and decarboxylation. Compounds of Formula (XIV) may be conveniently converted to the compounds of Formula (I), wherein R⁸=OH, by the treatment of a Grignard reagent with the formula of X—MgBr or a lithium reagent with the formula of X—Li by one skilled in the art.

Scheme 3

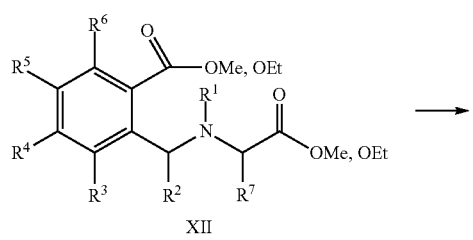
XII

Additionally, compounds of Formula (I) wherein R⁸=OH, may be readily alkylated (see above) to afford compounds formula (I) wherein R⁸=OR¹¹ Treatment of compounds of Formula (I) wherein R⁸=OH, with a fluorinating reagent such as, but not limited to, diethylaminosulfur trifluoride (DAST), readily provides compounds of Formula (I) wherein R⁸=F.

Treatment of compounds of Formula (I) wherein R⁸=OH, with a chlorinating reagent such as, but not limited to, thionyl chloride or phosphorus trichloride may provide compounds of Formula (I) wherein R⁸=Cl. Further reference may be gained from the review of Hudlicky, *Organic Reactions* 35:513-637 (1985), which is hereby incorporated by reference in its entirety. Treatment of compounds of Formula (I) wherein R⁸=OH, with a cyanation reagent, such as, but not limited to, sodium cyanide or trimethlysilyl cyanide may provide compounds of Formula (I) wherein R⁸=CN.

Compounds of Formula (I) wherein R⁸=OH, of this invention may also be prepared according to the teaching of Kihara, *Tetrahedron* 48:67-78 (1992) and Blomberg, *Synthesis*, p. 18-30, (1977), which are hereby incorporated by reference in their entirety. Thus, ketone compounds of Formula (VI) which possess an ortho-iodide may be treated with strong bases, such as, but not limited to, lower alkyl (C₁₋₆) lithium bases (preferably t-BuLi or n-BuLi) to afford the anticipated halogen-metal exchange followed by intramolecular Barbier cyclization to generate compounds of Formula (I) wherein $R^8$=OH. Inert solvents such as dialkyl ethers (preferably diethyl ether), cyclic ethers (preferably tetrahydrofuran or 1,4-dioxane) are necessary, and reaction temperatures are kept low (—78° C. to −25° C.) to avoid by-products. Alternatively, halogen-metal exchange may also be effected in the presence of zerovalent nickel, in which case N,N-dialkylformamides (preferably dimethylformamide) serve as ideal solvents.

Compounds of Formula (I) wherein $R^8$=OH is conveniently converted to compounds of Formula (I) wherein $R^8$=H via dehydration followed by reduction with a reducing agent such as, but not limited to, sodium cyanoborohydride.

In another embodiment of the present invention, compounds of Formula (I) wherein $R^7$=H may be prepared from compounds of Formula (XV) as outlined below (Scheme 4). Compounds of Formula (XV) are obtained from commercial sources or may be conveniently obtained via well known methods. The conversion of the phenylacetic acids of Formula (XV) to the corresponding acyl chlorides may be achieved by using common reagents such as, but not limited to, thionyl chloride or oxalyl chloride in solvents such as, but not limited to, toluene. The so formed acyl chloride may be readily transformed to, without separation from the reaction mixture, the amides of Formula (XVI) upon the treatment of $H_2N-R_1$.

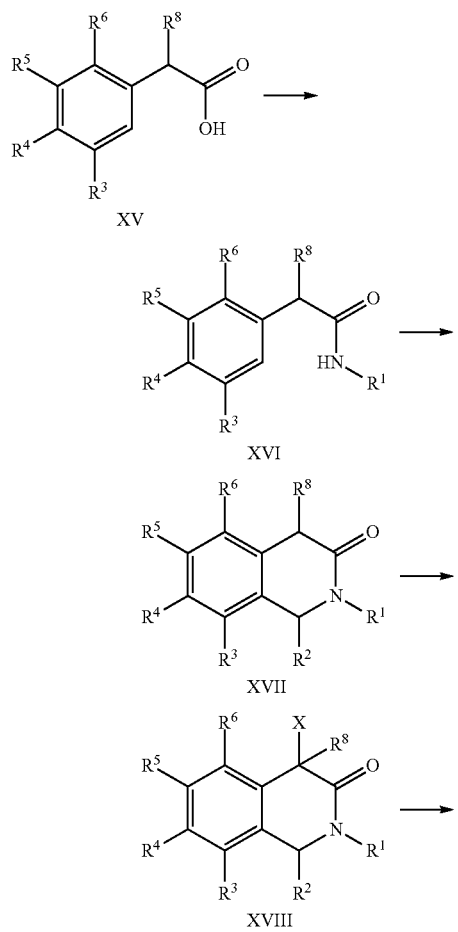

Scheme 4

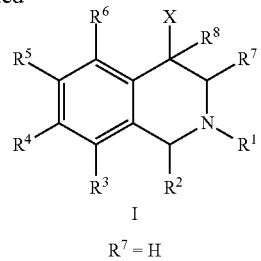

Conversion of the amides of Formula (XVI) to the dihydroisoquinolinones of Formula (XVII) proceeds with aldehydes $R_2CHO$ in the presence of acidic medium such as, but not limited to polyphosphoric acid, pyrophosphoric acid or Eaton's reagent (phosphorus pentoxide, 7.7 wt % solution in methanesulfonic acid).

Treatment of the dihydroisoquinolinones of Formula (XVII) with a compound of Formula X-halide (preferably bromide), or a compound of Formula X—$OSO_2CF_3$ in the presence of a metal catalyst with a base in an inert solvent gives dihydroisoquinolinones of Formula (XVIII). Metal catalysts may include, but are not limited to, salts or phosphine complexes of Cu, Pd, or Ni [eg. $Pd(OAc)_2$, CuI, $PdCl_2(PPh_3)_2$, $PdCl_2dppf$, $NiCl_2(PPh_3)_2$]. The preferred metal catalysts may be generated in situ by mixing metal salts (preferably $Pd(OAc)_2$) with phosphine ligands (preferably 2,8,9-tri-i-butyl-2,5,8,9-tetraaza-1-phosphabicyclo [3.3.3]undecane, 2-dicyclohexylphosphino-2',4',6'-triisopropylbiphenyl or 2,2'-bis(diphenylphosphino)-1,1'-binaphthyl). Bases may include, but are not limited to, alkaline earth metal carbonates, alkaline earth metal bicarbonates, alkaline earth metal hydroxides, alkali metal carbonates, alkali metal bicarbonates, alkali metal phosphate, alkali metal hydroxides, alkali metal hydrides, alkali metal alkoxides (preferably sodium t-butoxide), alkaline earth metal hydrides, alkali metal dialkylamides, alkali metal bis(trialkylsilyl)amides (preferably sodium bis(trimethylsilyl)amide), alkyl amines (preferably diisopropylethylamine or triethylamine) or aromatic bases (preferably pyridine). Inert solvents may include, but are not limited to acetonitrile, cyclic ethers (preferably tetrahydrofuran or 1,4-dioxane), N,N-dialkylacetamides (preferably dimethylacetamide), N,N-dialkylformamides (preferably dimethylformamide), dialkylsulfoxides (preferably dimethylsulfoxide), aromatic hydrocarbons (preferably toluene). Preferred reaction temperatures range from room temperature up to the boiling point of the solvent employed. The reactions may be run in conventional glassware or in one of many commercially available parallel synthesizer units.

Reduction of dihydroisoquinolinones of Formula (XVIII) to the compounds of Formula (I) proceeds with reducing agents including for example, but not limited to, sodium borohydride, lithium borohydride, borane, diisobutylaluminum hydride, and lithium aluminum hydride. The reductions are carried out from 0° C. to elevated temperature up to the reflux point of the solvent employed. If borane is used, it may be employed as a complex for example, but not limited to, borane-methyl sulfide complex, borane-piperidine complex, or borane-tetrahydrofuran complex. One skilled in the art will understand the optimal combination of reducing agents and reaction conditions needed or may seek guidance from the text of Larock, R. C., *Comprehensive Organic Transformations*, VCH Publishers, New York, p. 604 (1989), which is hereby incorporated by reference in its entirety.

Compounds of Formula (I) wherein $R^4$ is aryl, heteroaryl, or $NR^9R^{10}$ and $R^7$=H, may be obtained using the similar methodology described for Scheme 4 or as outlined in Scheme 5.

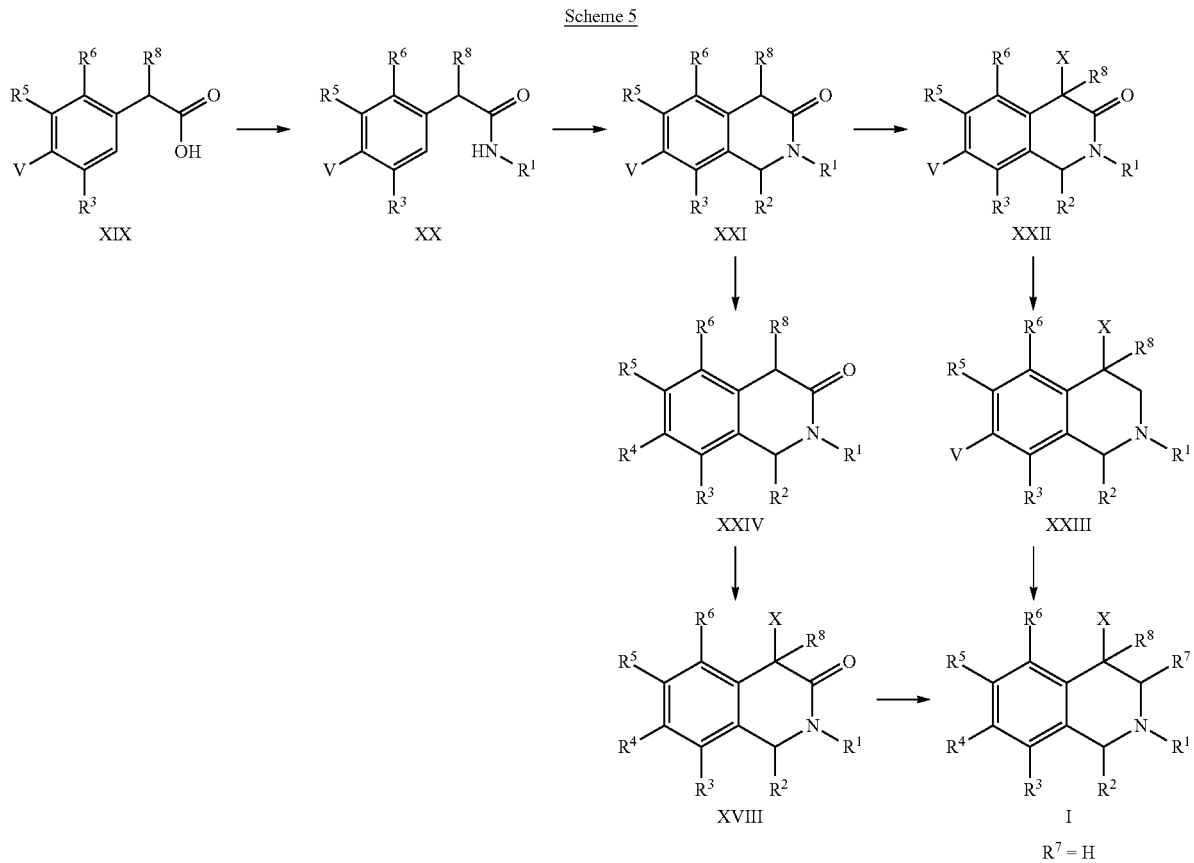

Scheme 5

Compounds of Formula (XIX; V=Br, Cl or $OSO_2CF_3$) may be obtained from commercial sources and are conveniently converted to compounds of Formula (XXIII) via the chemical steps as described for the conversion of compounds of Formula (XV) to compounds of Formula (I) in Scheme 4. The target compounds of Formula (I) of this invention may be prepared by treatment of compounds of Formula (XXIII) with an aryl or heteroaryl boronic acids or aryl, heteroaryl boronic acid esters or $HNR^9R^{10}$, in the presence of a metal catalyst with or without a base in an inert solvent. Metal catalysts may include, but are not limited to, salts or phosphine complexes of Cu, Pd, or Ni [e.g., $Pd(OAc)_2$, CuI, $PdCl_2(PPh_3)_2$, $PdCl_2dppf$, and $NiCl_2(PPh_3)_2$]. The preferred metal catalysts may be generated in situ by mixing metal salts (preferably $Pd(OAc)_2$) with phosphine ligands. Bases may include, but are not limited to, alkaline earth metal carbonates, alkaline earth metal bicarbonates, alkaline earth metal hydroxides, alkali metal carbonates, alkali metal bicarbonates, alkali metal phosphate, alkali metal hydroxides, alkali metal hydrides, alkali metal alkoxides, alkaline earth metal hydrides, alkali metal dialkylamides, alkali metal bis(trialkylsilyl)amides (preferably sodium bis(trimethylsilyl)amide), trialkyl amines (preferably diisopropylethylamine or triethylamine) or aromatic amines (preferably pyridine). Inert solvents may include, but are not limited to acetonitrile, cyclic ethers (preferably tetrahydrofuran or 1,4-dioxane), N,N-dialkylacetamides (preferably dimethylacetamide), N,N-dialkylformamides (preferably dimethylformamide), dialkylsulfoxides (preferably dimethylsulfoxide), aromatic hydrocarbons (preferably toluene). Preferred reaction temperatures range from room temperature up to the boiling point of the solvent employed. The reactions may be run in conventional glassware or in one of many commercially available parallel synthesizer units.

Alternatively, compounds of Formula (XXIII) may be converted to the correspondent boronic acids or boronic acid esters, wherein V=$B(OH)_2$ or $B(OR^a)(OR^b)$ (where $R^a$ and $R^b$ are lower alkyl, ie. $C_1$-$C_6$, or taken together, $R^a$ and $R^b$ are lower alkylene, ie. $C_2$-$C_{12}$) using well known methods. Treatment of these so formed boronic acids or boronic acid esters with an aryl or heteroaryl halide or aryl or heteroaryl triflate, in the presence of a metal catalyst with or without a base in an inert solvent may afford the compounds of Formula (I). Metal catalysts may include, but are not limited to, salts or phosphine complexes of Cu, Pd, or Ni [e.g., $Pd(OAc)_2$, CuI, $PdCl_2$ $(PPh_3)_2$, $PdCl_2dppf$, and $NiCl_2(PPh_3)_2$]. Bases may include, but are not limited to, alkaline earth metal carbonates, alkaline earth metal bicarbonates, alkaline earth metal hydroxides, alkali metal carbonates, alkali metal bicarbonates, alkali metal phosphate, alkali metal hydroxides, alkali metal hydrides, alkali metal alkoxides (preferably sodium t-butoxide), alkaline earth metal hydrides, alkali metal dialkylamides, alkali metal bis(trialkylsilyl)amides (preferably sodium bis(trimethylsilyl)amide), trialkyl amines (preferably diisopropylethylamine or triethylamine) or aromatic amines (preferably pyridine).

Inert solvents may include, but are not limited to acetonitrile, cyclic ethers (preferably tetrahydrofuran or 1,4-dioxane), N,N-dialkylacetamides (preferably dimethylacetamide), N,N-dialkylformamides (preferably dimethylformamide), dialkylsulfoxides (preferably dimethylsulfoxide), aromatic hydrocarbons (preferably toluene). Preferred reaction temperatures range from room temperature up to the boiling point of the solvent employed. The reactions may be run in conventional glassware or in one of many commercially available parallel synthesizer units.

Treatment of dihydroisoquinolinones of Formula (XXI) with an aryl or heteroaryl boronic acid, or aryl or heteroaryl boronate ester, or $HNR^9R^{10}$ in the presence of a metal catalyst with or without a base in an inert solvent generates compounds of Formula (XXIV). Metal catalysts may include, but are not limited to, salts or phosphine complexes of Cu, Pd, or Ni [e.g., $Pd(OAc)_2$, CuI, $PdCl_2(PPh_3)_2$, $PdCl_2dppf$, and $NiCl_2(PPh_3)_2$]. The preferred metal catalysts may be generated in situ by mixing metal salts (preferably $Pd(OAc)_2$) with phosphine ligands (preferably 2,8,9-tri-i-butyl-2,5,8,9-tetraaza-1-phosphabicyclo[3.3.3]undecane, 2-dicyclohexylphosphino-2',4',6'-triisopropylbiphenyl or 2,2'-bis(diphenylphosphino)-1,1'-binaphthyl) or CuI with L-proline. Bases may include, but are not limited to, alkaline earth metal carbonates, alkaline earth metal bicarbonates, alkaline earth metal hydroxides, alkali metal carbonates, alkali metal bicarbonates, alkali metal phosphate (preferably $K_3PO_4$), alkali metal hydroxides, alkali metal hydrides, alkali metal alkoxides (preferably sodium t-butoxide), alkaline earth metal hydrides, alkali metal dialkylamides, alkali metal bis(trialkylsilyl)amides (preferably sodium bis(trimethylsilyl)amide), trialkyl amines (preferably diisopropylethylamine or triethylamine) or aromatic amines (preferably pyridine). Inert solvents may include, but are not limited to acetonitrile, cyclic ethers (preferably tetrahydrofuran or 1,4-dioxane), N,N-dialkylacetamides (preferably dimethylacetamide), N,N-dialkylformamides (preferably dimethylformamide), dialkylsulfoxides (preferably dimethylsulfoxide), aromatic hydrocarbons (preferably toluene). Preferred reaction temperatures range from room temperature up to the boiling point of the solvent employed. The reactions may be run in conventional glassware or in one of many commercially available parallel synthesizer units.

Finally, conversion compounds of Formula (XXIV) to compounds of Formula (XVIII), then to the compounds of Formula (I) may be achieved similarly by the methods described for the conversion of compounds of Formula (XVII) to compounds of Formula (I) (Scheme 4).

Enantiomerically enriched compounds of Formula (XVIII) and compounds of Formula (XXII) may be obtained by using chiral ligands such as for example, but not limited to, (+) or (−)-2,2'-bis(diphenylphosphino)-1,1'-binaphthyl.

The methods that are described for the synthetic routes used in Scheme 4 and Scheme 5 are also applicable to the preparation of compounds of Formula (I) wherein X is monocyclic aryl or monocyclic heteroaryl.

Compounds of Formula (I) may be obtained in enantiomerically pure (R) and (S) form by crystallization with chiral salts such as, but not limited to, (+)-di-p-toluoyl-D-tartaric acid salt, (−)-di-p-toluoyl-L-tartaric acid salt, (1S)-(+)-10 camphor sulfonic acid salt, (+)-dibenzoyl-D-tartaric acid salt, (−)-dibenzoyl-L-tartaric acid salt, L-(+)-tartric acid salt, D-(−)-tartric acid salt, D-(+)-malic acid salt, L-(−)-malic acid salt, S-(+)-mandelic acid salt, R-(−)-mandelic acid, S-(−)-Mosher's acid [α-methoxy-α-(trifluoromethyl)phenylacetic acid] salt, R-(+)-Mosher's acid [α-methoxy-α-(trifluoromethyl)phenylacetic acid] salt. Additional chiral salts may be described in the book of Eliel et al., *Stereochemistry of Organic Compounds*, Wiley-Interscience Publication:New York, p. 334 (1994), which is hereby incorporated by reference in its entirety.

The resolution procedure may be performed under a wide variety of conditions familiar to one skilled in the art of organic synthesis. Typical solvents include acetonitrile, tetrahydrofuran, methyl ethyl ketone, acetone, methanol, ethanol, isopropyl alcohol and a mixture of two or more of these solvents. The resolution procedure may at stages have temperatures ranging from −50° C. up to the boiling point of the solvent employed.

Alternatively, compounds of Formula (I) may be obtained in enantiomerically pure (R) and (S) form from the corresponding racemic mixture through chiral HPLC employing commercially available chiral columns.

Compounds of Formula (I) in enantiomerically pure (R) or (S) form may be converted to the corresponding racemic mixture of compounds by the treatment with a base in the presence or absence of a crown ether catalyst in an inert solvent. Bases may include, but are not limited to, alkali metal hydroxide, alkali metal hydrides, alkali metal alkoxides (preferably sodium t-butoxide), alkali metal alkanes, alkali metal dialkylamides, alkali metal bis(trialkylsilyl) amides (preferably potassium bis(trimethylsilyl)amide). Inert solvents may include, but are not limited to, acetonitrile, ethers (preferably tetrahydrofuran or 1,4-dioxane), N,N-dialkylformamides (preferably dimethylformamide), dialkylsulfoxides (preferably dimethylsulfoxide), aromatic hydrocarbons (preferably toluene). When alkali metal alkoxide is the base, an alcohol such as, but not limited to, ethanol, isopropanol, n-butanol, t-butanol, isobutanol or ethylene glycol is preferred as a co-solvent or to be the solely solvent. Typical crown ether is 18-Crown-6. Preferred reaction temperatures range from 0° C. up to the boiling point of the solvent employed. This reaction may also be carried out in a pressurized vessel or microwave reactor.

The synthetic methodologies described for Scheme 4 and Scheme 5 are amenable to large scale (multi-kilogram scale) synthetic process.

It will be appreciated that compounds useful according to the present invention may contain asymmetric centers. These asymmetric centers may independently be in either the R or S configuration and such compounds are able to rotate a plane of polarized light in a polarimeter. If said plane of polarized light is caused by the compound to rotate in a counterclockwise direction, the compound is said to be the (−) stereoisomer of the compound. If said plane of polarized light is caused by the compound to rotate in a clockwise direction, the compound is said to be the (+) stereoisomer of the compound. It will be apparent to those skilled in the art that certain compounds useful according to the invention may also exhibit geometrical isomerism. It is to be understood that the present invention includes individual geometrical isomers and stereoisomers and mixtures thereof, including racemic mixtures, of compounds of Formula (I) hereinabove. Such isomers can be separated from their mixtures, by the application or adaptation of known methods, for example chromatographic techniques and recrystallization techniques, or they are separately prepared from the appropriate isomers of their intermediates.

Radiolabelled compounds of the invention are synthesized by a number of means well known to those of ordinary skill in the art, e.g., by using starting materials incorporating therein one or more radioisotopes. Compounds of the present invention where a stable radioisotope, such as carbon-14, tritium, iodine-121, or another radioisotope, has been introduced synthetically are useful diagnostic agents for identifying areas of the brain or central nervous system that may be affected by disorders where norepinephrine, dopamine or serotonin transporters and their uptake mechanism are implicated.

The present invention provides compositions containing the compounds described herein, including, in particular, pharmaceutical compositions comprising therapeutically effective amounts of the compounds and pharmaceutically acceptable carriers.

It is a further object of the present invention to provide kits having a plurality of active ingredients (with or without carrier) which, together, may be effectively utilized for carrying out the novel combination therapies of the invention.

It is another object of the invention to provide a novel pharmaceutical composition which is effective, in and of itself, for utilization in a beneficial combination therapy because it includes a plurality of active ingredients which may be utilized in accordance with the invention.

The present invention also provides kits or single packages combining two or more active ingredients useful in treating the disease. A kit may provide (alone or in combination with a pharmaceutically acceptable diluent or carrier), the compound of formula (I) and the additional active ingredient (alone or in combination with diluent or carrier) selected from a serotonin 1A receptor antagonist, a selective neurokinin-1 receptor antagonist, and a norepinephrine precursor.

In practice, compounds of the present invention may generally be administered parenterally, intravenously, subcutaneously intramuscularly, colonically, nasally, intraperitoneally, rectally or orally.

The products according to the invention may be presented in forms permitting administration by the most suitable route and the invention also relates to pharmaceutical compositions containing at least one product according to the invention which are suitable for use in human or veterinary medicine. These compositions may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations.

The choice of vehicle and the content of active substance in the vehicle are generally determined in accordance with the solubility and chemical properties of the product, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation or microfiltration.

Suitable compositions containing the compounds of the invention may be prepared by conventional means. For example, compounds of the invention may be dissolved or suspended in a suitable carrier for use in a nebulizer or a suspension or solution aerosol, or may be absorbed or adsorbed onto a suitable solid carrier for use in a dry powder inhaler.

Solid compositions for rectal administration include suppositories formulated in accordance with known methods and containing at least one compound of Formula (I).

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.01 to about 100, preferably about 0.01 to about 10 mg/kg body weight per day by inhalation, from about 0.01 to about 100, preferably 0.1 to 70, more especially 0.5 to 10 mg/kg body weight per day by oral administration, and from about 0.01 to about 50, preferably 0.01 to 10 mg/kg body weight per day by intravenous administration. In each particular case, the doses will be determined in accordance with the factors distinctive to the subject to be treated, such as age, weight, general state of health and other characteristics which can influence the efficacy of the medicinal product.

The products according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

The present invention provides compounds which inhibit synaptic norepinephrine, dopamine and serotonin uptake and are therefore believed to be useful in treating a disorder which is created by or is dependent upon decreased availability of serotonin, norepinephrine or dopamine. Although the compounds of the Formula (I) inhibit synaptic norepinephrine, dopamine and serotonin uptake, in any individual compound these inhibitory effects may be manifested at the same or vastly different concentrations or doses. As a result, some compounds of the Formula (I) are useful in treating such a disorder at doses at which synaptic norepinephrine uptake may be substantially inhibited but at which synaptic serotonin uptake or dopamine uptake is not substantially inhibited, or vice versa. Also, some compounds of the Formula (I) are useful in treating such a disorder at doses at which synaptic dopamine uptake may be substantially inhibited but at which synaptic norepinephrine or serotonin uptake is not substantially inhibited, or vice versa. And, conversely, some compounds of the Formula (I) are useful in treating such a disorder at doses at which synaptic serotonin uptake may be substantially inhibited but at which synaptic norepinephrine or dopamine uptake is not substantially inhibited, or vice versa. Other compounds of Formula (I) are useful in treating such a disorder at doses at which synaptic norepinephrine, dopamine and serotonin uptake are substantially inhibited.

The present invention provides compounds where the inhibitory effects on serotonin and norepinephrine uptake occurs at similar or even the same concentrations of these compounds while the effects on inhibition of dopamine uptake occurs at vastly different concentrations or doses. As a result, some compounds of the Formula (I) are useful in treating such a disorder at doses at which synaptic serotonin and norepinephrine uptake may be substantially inhibited but at which synaptic dopamine uptake is not substantially inhibited, or vice versa.

The present invention provides compounds where the inhibitory effects on serotonin and dopamine uptake occurs at similar or even the same concentrations of these compounds while the effects on inhibition of norepinephrine uptake occurs at vastly different concentrations or doses. As a result, some compounds of the Formula (I) are useful in treating such a disorder at doses at which synaptic serotonin and dopamine uptake may be substantially inhibited but at which synaptic norepinephrine uptake is not substantially inhibited, or vice versa.

The present invention provides compounds where the inhibitory effects on norepinephrine and dopamine uptake occurs at similar or even the same concentrations of these compounds while the effects on inhibition of dopamine uptake occurs at vastly different concentrations or doses. As a result, some compounds of the Formula (I) are useful in treating such a disorder at doses at which synaptic norepinephrine and dopamine uptake may be substantially inhibited but at which synaptic serotonin uptake is not substantially inhibited, or vice versa.

The present invention provides compounds where the inhibitory effects on norepinephrine, dopamine and serotonin uptake occur at similar or even the same concentration. As a result, some compounds of the Formula (I) are useful in treating such a disorder at doses at which synaptic norepinephrine, dopamine and serotonin uptake may all be substantially inhibited.

The concentrations or doses at which a test compound inhibits synaptic norepinephrine, dopamine and serotonin uptake is readily determined by the use of standard assay and techniques well known and appreciated by one of ordinary skill in the art. For example, the degree of inhibition at a particular dose in rats can be determined by the method of Dudley, *J Pharmacol Exp Ther* 217:834-840 (1981), which is hereby incorporated by reference in its entirety.

The therapeutically effective inhibitory dose is one that is effective in substantially inhibiting synaptic norepinephrine uptake, synaptic dopamine uptake, or synaptic serotonin uptake or inhibiting the synaptic uptake of two or more of norepinephrine, dopamine and serotonin uptake. The therapeutically effective inhibitory dose can be readily determined by those skilled in the art by using conventional range finding techniques and analogous results obtained in the test systems described above.

Compounds of this invention provide a particularly beneficial therapeutic index relative to other compounds available for the treatment of similar disorders. Without intending to be limited by theory, it is believed that this is due, at least in part, to some of the compounds having higher binding affinities for one or two of the neurotransmitter transporters, e.g. selectivity towards the norepinephrine transporter protein ("NET") over the transporters for other neurochemicals, e.g., the dopamine transporter protein ("DAT") and the serotonin transporter protein ("SERT").

Other compounds of this invention may demonstrate selectivity towards the SERT over the transporters for other neurochemicals, e.g., the DAT and the NET.

Still other compounds of this invention may demonstrate selectivity towards the DAT over the transporters for other neurochemicals, e.g., the SERT and the NET.

Other compounds of this invention may demonstrate selectivity towards the SERT and the NET over the transporter for other neurochemical, e.g., the DAT.

Still other compounds of this invention may demonstrate selectivity towards the SERT and the DAT over the transporter for other neurochemical, e.g., the NET.

Still other compounds of this invention may demonstrate selectivity towards the NET and the DAT over the transporter for other neurochemical, e.g., the SERT.

Finally other compounds possess nearly identical affinity towards the NET, the DAT and the SERT.

Binding affinities are demonstrated by a number of means well known to ordinarily skilled artisans, including, without limitation, those described in the Examples section hereinbelow. Briefly, for example, protein-containing extracts from cells, e.g., HEK293E cells, expressing the transporter proteins are incubated with radiolabelled ligands for the proteins. The binding of the radioligands to the proteins is reversible in the presence of other protein ligands, e.g., the compounds of this invention; said reversibility, as described below, provides a means of measuring the compounds' binding affinities for the proteins (Ki). A higher Ki value for a compound is indicative that the compound has less binding affinity for a protein than is so for a compound with a lower Ki; conversely, lower Ki values are indicative of greater binding affinities.

Accordingly, the difference in compound selectivity for proteins is indicated by a lower Ki for the protein for which the compound is more selective, and a higher Ki for the protein for which the compound is less selective. Thus, the higher the ratio in Ki values of a compound for protein A over protein B, the greater is the compounds' selectivity for the latter over the former (the former having a higher Ki and the latter a lower Ki for that compound). Compounds provided herein possess a wide range of selectivity profiles for the norepinephrine, dopamine and serotonin transporters as reflected by the ratios of the experimentally determined Ki values.

Selected compounds ("mono action transporter reuptake inhibitors") of the present invention have potent binding affinity for each of the biogenic amine transporters NET, DAT or SERT. For example, selected compounds of this invention possess potent (NET Ki<100 nM) and selective binding affinity for NET, where the Ki ratio of DAT/NET and SERT/NET is greater than 10:1. Other selected compounds of the present invention possess potent (SERT Ki<100 nM) and selective binding affinity for SERT, where the Ki ratio of NET/SERT and DAT/SERT is greater than 10:1. Other selected compounds of the present invention possess potent (DAT Ki<100 nM) and selective binding affinity for DAT, where the Ki ratio of NET/DAT and SERT/DAT is greater than 10:1.

Selected compounds ("dual action transporter reuptake inhibitors") of the present invention have potent binding affinity for two of the biogenic amine transporters NET, DAT or SERT. For example, selected compounds of this invention possess potent (NET & SERT Ki values <100 nM) and selective binding affinity for NET and SERT, where the Ki ratio of DAT/NET and DAT/SERT is greater than 10:1 while the Ki ratio of SERT/NET or NET/SERT is less than 10:1. Other selected compounds of this invention possess potent (NET & DAT Ki values <100 nM) and selective binding affinity for NET and DAT, where the Ki ratio of SERT/NET and SERT/DAT is greater than 10:1 while the Ki ratio of DAT/NET or NET/DAT is less than 10:1. Other selected compounds of this invention possess potent (DAT & SERT Ki values <100 nM) and selective binding affinity for DAT and SERT, where the Ki ratio of NET/DAT and SERT/DAT is greater than 10:1 while the Ki ratio of SERT/NET or NET/SERT is less than 10:1.

Selected compounds ("triple action transporter reuptake inhibitors") of the present invention have potent binding affinity simultaneously for all three of the biogenic amine transporters, NET, DAT or SERT. For example, selected compounds of this invention possess potent (NET, DAT & SERT Ki values <100 nM) where the Ki ratios of NET/DAT, NET/SERT, DAT/NET, DAT/SERT, SERT/NET and SERT/DAT are all less than 10:1.

Selected compounds of the present invention have potent binding affinity (Ki values <100 nM) for one, two or three of the biogenic amine transporters, NET, DAT and SERT where the Ki ratios for any of NET/SERT, NET/DAT, DAT/NET, DAT/SERT, SERT/NET and SERT/DAT fall outside of the bounds defined for the "mono-, dual or triple action transporter reuptake inhibitors" defined above.

Selected compounds of the present invention have less potent binding affinity (Ki values between 100 nM and 1000 nM) for one, two or three of the biogenic amine transporters, NET, DAT and SERT where the Ki ratios for any of NET/SERT, NET/DAT, DAT/NET, DAT/SERT, SERT/NET and SERT/DAT fall within the bounds defined for the "mono-, dual or triple action transporter reuptake inhibitors" defined above.

Finally, selected compounds of the present invention have less potent binding affinity (Ki values between 100 nM and 1000 nM) for one, two or three of the biogenic amine transporters, NET, DAT and SERT where the Ki ratios for any of NET/SERT, NET/DAT, DAT/NET, DAT/SERT, SERT/NET and SERT/DAT fall outside of the bounds defined for the "mono-, dual or triple action transporter reuptake inhibitors" defined above.

The present invention provides methods of treating subjects afflicted with various neurological and psychiatric disorders by administering to said subjects a dose of a pharmaceutical composition provided herein. Said disorders include, without limitation, attention deficit disorder hyperactivity disorder (ADHD), cognition impairment, anxiety disorders, especially generalized anxiety disorder (GAD), panic disorder, bipolar disorder, also known as manic depression or manic-depressive disorder, obsessive compulsive disorder (OCD), posttraumatic stress disorder (PTSD), acute stress disorder, social phobia, simple phobia, premenstrual dysphoric disorder (PMDD), social anxiety disorder (SAD), major depressive disorder (MDD), supranuclear palsy, eating disorders, especially obesity, anorexia nervosa, bulimia nervosa, and binge eating disorder, analgesia (including neuropathic pain, especially diabetic neuropathy), substance abuse disorders (including chemical dependencies) like nicotine addiction, cocaine addiction, alcohol and amphetamine addiction, Lesch-Nyhan syndrome, neurodegenerative diseases like Parkinson's disease, late luteal phase syndrome or narcolepsy, psychiatric symptoms anger such as, rejection sensitivity, movement disorders, like extrapyramidal syndrome, Tic disorders and restless leg syndrome (RLS), tardive dyskinesia, supranuclear palsy, sleep related eating disorder (SRED), night eating syndrome (NES), urinary incontinence (including stress urinary incontinence (SUI) and mixed incontinence), migraine, fibromyalgia syndrome (FS), chronic fatigue syndrome (CFS), sexual dysfunction especially premature ejaculation and male impotence, thermoregulatory disorders (e.g., hot flashes that may be associated with menopause), and lower back pain.

The compounds provided herein are particularly useful in the treatment of these and other disorders due, at least in part, to their ability to selectively bind to the transporter proteins for certain neurochemicals with a greater affinity than to the transporter proteins for other neurochemicals.

The compounds of the invention, their methods or preparation and their biological activity will appear more clearly from the examination of the following examples which are presented as an illustration only and are not to be considered as limiting the invention in its scope.

EXAMPLES

The following examples are provided to illustrate embodiments of the present invention but are by no means intended to limit its scope.

Unless otherwise noted, reagents and solvents were used as received from commercial suppliers. All reactions were done under nitrogen atmosphere unless stated otherwise. Progress of the reactions was monitored by TLC, GC or HPLC. Thin-layer chromatography (TLC) was performed using Analtech or EMD silica gel plates and visualized by ultraviolet (UV) light (254 nm). GC was performed under the following conditions: Hewlett Packard 5-MS column, 30 m×0.25 mm×0.25 µm, injection temperature 150° C., initial temperature 100° C., initial time 2.0 minutes, final temperature 320° C., rate 20° C./minute. HPLC was performed under the following conditions: Phenomenex Synergi polar-RP, 4µ, 150×4.6 mm; or Phenomenex Luna C18(2), 4µ, 150×4.6 mm; acetonitrile:water (containing TFA or acetic acid), eluant at 1 ml/minute, detection at 220 nm, 230 nm or 254 nm. Proton nuclear magnetic resonance spectra were obtained on a Bruker AV 500 or a Bruker AV-300 spectrometer. Spectra are given in ppm (δ) and coupling constants, J, are reported in Hertz. Tetramethylsilane was used as an internal standard for proton spectra and the solvent peak was used as the reference peak for carbon spectra. Mass spectra were obtained on a Perkin Elmer Sciex 100 atmospheric pressure ionization (APCI) mass spectrometer, a Finnigan LCQ Duo LCMS ion trap electrospray ionization (ESI) mass spectrometer or a Thermofinnigan AQA. Purification using preparative HPLC was performed using a Phenomenex Luna 10µ C18(2) column (250×21.20 mm) on a Varian Prostar with UV detection at 220, 230, or 254 nm. Chiral resolution was performed on a CHIRALCEL OD, CHIRALPAK AD, CHIRACEL OJ or CHIRALPAK ADH column. Chromatography refers to flash chromatography, which was carried out on silica gel (EMD silica gel 60 Å) or medium pressure liquid chromatography, carried out on a CombiFlash Companion or a Biotage Horizon system. Optical rotations were measured on a Perkin Elmer polarimeter (model 341 or model 343) on free bases. Elemental analyses were carried out by Robertson Microlit Laboratories, Inc or Quantitative Technologies Inc. Reported yields are not optimized.

Example 1

Preparation of 4-(Benzo[b]thiophen-2-yl)-1,2,3,4-tetrahydroisoquinoline

Step A: The product from Step A of Example 3 (0.34 g, 1.3 mmol) in $CH_3OH$ (10 ml) was stirred for 10 minutes at room temperature under a $N_2$ atmosphere. Sodium cyanoborohydride (0.49 g, 7.8 mmol) was added and stirred for 2 hours. The addition of 3M HCl (4 ml dropwise) turned the reaction from a milky white solution to yellow/green and back to a milky white solution. The mixture was basified with 2N $Na_2CO_3$ solution and then concentrated in vacuo to a white solid. The residue was partitioned in $H_2O$ (30 ml) and EtOAc (30 ml). The mixture was extracted with EtOAc (3×30 ml). The combined organic layer was washed with brine (50 ml), dried over $Na_2SO_4$, filtered and concentrated in vacuo. Chromatography ($SiO_2$, 250 g, 1:49 methanol:EtOAc) afforded the pure product as an oil (0.29 g); HPLC 94.2% purity; $^1$H NMR (500 MHz, $CDCl_3$) δ 7.70 (d, J=7.84 Hz, 1H), 7.61 (d, J=7.76 Hz, 1H), 7.20 (m, 3H), 7.11 (d, J=3.85 Hz, 2H), 7.05 (d, J=7.47 Hz, 1H), 6.89 (s, 1H), 4.32 (t, J=5.16 Hz, 1H), 4.06 (dd, J=24.6, 16.6 Hz, 2H), 3.39 (dd, J=13.0, 4.64 Hz, 1H), 3.30 (dd, J=13.0, 4.64, 1H) 1.88-2.10 (b s, 1H); ESI MS m/z 266 [M+1].

Step B: The product from Step A (0.18 g, 6.8 mmol) was stirred in EtOH (3.0 ml) and fumaric acid (0.08 g, 6.8 mmol) dissolved in $CH_3OH$ (0.5 ml) was added. Part of the reaction mixture precipitated but stirring was continued for 1 hour then diethyl ether (2 ml) was added and the reaction mixture was filtered to give a white solid (0.16 g); HPLC 98.6% purity; $^1$H NMR (500 MHz, DMSO-$d_6$) δ, 7.83 (d, J=7.90 Hz, 1H), 7.74 (d, J=7.76 Hz, 1H), 7.32 (m, 1H), 7.26 (m, 2H), 7.16 (t, J=4.92 Hz, 1H), 7.10 (m, 3H), 6.55 (s, 1H), 4.50 (t, J=7.20 Hz, 1H), 4.06 (d, J=16.1 Hz, 1H), 3.99 (d, J=16.1 Hz, 1H), 3.36 (dd, J=12.4, 4.9 Hz, 1H), 3.16 (dd, J=12.4, 6.15 Hz, 1H); ESI MS m/z 266 [M+1].

Example 2

Preparation of (+)-4-(Benzo[b]furan-2-yl)-2-methyl-1,2,3,4-tetrahydroisoquinoline, hydrochloride salt and (−)-4-(benzo[b]furan-2-yl)-2-methyl-1,2,3,4-tetrahydroisoquinoline, hydrochloride salt Racemic 4-(benzo[b]furan-2-yl)-2-methyl-1,2,3,4-tetrahydroisoquinoline was prepared from 2-benzo[b]furanboronic acid and 4-bromoisoquinoline as described in Example 36 (Steps D to F). This racemic compound (120 mg) was separated on semi-prep chiral HPLC (chiralcel OD-H, 1×25 cm, eluent: 3% isopropanol in heptane, flow: 3.1 ml/minute, 500 μl injections, 20 mg/injections). The resulting free bases were dissolved in ethyl acetate and treated with a 2 M solution of HCl in diethyl ether (2 equiv) to give (+)-4-(benzo[b]furan-2-yl)-2-methyl-1,2,3,4-tetrahydroisoquinoline, hydrochloride salt (13 mg, 99.6% AUC HPLC, 100% AUC chiral HPLC): $^1$H NMR (300 MHz, Acetone-$d_6$) δ 7.71-7.80 (m, 1H), 7.50-7.58 (m, 1H), 7.31-7.45 (m, 2H), 7.01-7.23 (m, 5H); 5.35-5.50 (m, 1H), 4.47-4.70 (m, 2H), 3.70-4.00 (m, 2H), 3.11 (s, 3H), 2.43 (s, 3H); EI MS m/z=263 $[C_{18}H_{17}NO]^+$; $[α]^{25}_D$ +37° (c 0.5, MeOH, free base) and (−)-4-(benzo[b]furan-2-yl)-2-methyl-1,2,3,4-tetrahydroisoquinoline, hydrochloride salt (49 mg, 99.7% AUC HPLC, 100% chiral HPLC): $^1$H NMR (300 MHz, Acetone-$d_6$) δ 7.64-7.71 (m, 1H), 7.42-7.49 (m, 1H), 7.25-7.36 (m, 2H), 6.93-7.15 (m, 4H), 5.22-4.40 (m, 1H), 3.40-4.60 (m, 2H), 3.60-3.90 (m, 2H), 3.02 (s, 3H), 2.35 (s, 3H); EI MS m/z=263 $[C_{18}H_{17}NO]^+$; $[α]^{25}_D$ −40° (c 0.5, MeOH, free base).

Example 3

Preparation of 4-(Benzo[b]thiophen-2-yl)-2-ethyl-1,2,3,4-tetrahydroisoquinoline, fumarate salt Step A: A mixture of 4-bromoisoquinoline (0.64 g, 3.0 mmol) in ethylene glycol dimethyl ether (4 ml), benzothiophene-2-boronic acid (0.69 g, 4.0 mmol), and 2 N $Na_2CO_3$ (3 ml) were degassed for 5 minutes then purged under $N_2$ atmosphere for 5 minutes twice. A catalytic amount of $Pd(PPh_3)_4$ (0.36 g, 0.3 mmol) was added and the reaction was degassed and purged with $N_2$. The reaction heated to 80° C. with stirring for 12 hours during which the solution turned a dark brown color. The reaction was cooled to room temperature, diluted with $H_2O$ (20 ml) and extracted with EtOAc (3×50 ml). The combined organic layer was washed with brine (30 ml), dried with $Na_2SO_4$, filtered and concentrated in vacuo. Chromatography ($SiO_2$, 200 g, 1:3 ethyl acetate/hexanes) afforded the pure product as an oil (0.65 g); HPLC 99.5% purity; $^1$HNMR (500 MHz, $CDCl_3$) δ 9.27 (s, 1H), 8.70 (s, 1H), 8.29 (d, J=8.48 Hz, 1H), 8.05 (d, J=8.1 Hz, 1H), 7.86-7.91 (m, 2H), 7.72-7.75 (m, 1H), 7.64-7.67 (m, 1H), 7.5 (s, 1H), 7.37-7.44 (m, 2H); ESI MS m/z 262 [M+1].

Step B: The product from Step A (0.35 g, 1.3 mmol) was stirred in methylene chloride (10 ml) and cooled in an ice bath under $N_2$. Ethyl triflate (0.2 ml, 1.6 mmol) was added and stirred at room temperature for 2 hours (ESI MS showed M+1=290), thin-layer chromatography indicated no starting material. The reaction mixture was concentrated in vacuo and $CH_3OH$ (30 ml) was added with stirring under $N_2$ atmosphere. Sodium cyanoborohydride (0.2 g, 3.2 mmol) was added and the reaction mixture stirred overnight. The reaction mixture was concentrated in vacuo and partitioned in $H_2O$ (30 ml) and EtOAc (30 ml). The mixture was extracted with EtOAc (3×30 ml). The combined organic layer was washed with brine (50 ml), dried over $Na_2SO4$, filtered and concentrated in vacuo. Chromatography ($SiO2$, 150 g, 1:5 ethyl acetate/hexanes) afforded the pure product as an oil (0.26 g); HPLC 97.3% purity; $^1$HNMR (500 MHz, $CDCl_3$) δ 7.7 (d, J=7.92 Hz, 1H), 7.66 (d, J=7.81 Hz, 1H) 7.25-7.28 (m, 1H), 7.18-7.22 (m, 1H), 7.13 (t, J=10.7 Hz, 3H), 7.07 (t, J=9.04 Hz, 2H), 4.53 (t, J=7.33 Hz, 1H), 3.77 (d, J=14.9 Hz, 1H), 3.68 (d, J=14.9 Hz, 1H), 3.02 (dd, J=11.4, 4.86 Hz, 1H), 2.91 (dd, J=11.4, 6.27 Hz, 1H), 2.56-2.67 (m, 2H), 1.17 (t, J=9.57 Hz, 3H); ESI MS m/z 294 [M+1].

Step C: The product from Step B (0.25 g, 0.85 mmol) was stirred in EtOH (2.5 ml) and added fumaric acid (0.09 g, 0.85 mmol). The reaction mixture was gently heated until a precipitate formed. The mixture was left in freezer for 1 hour then triturated with diethyl ether and filtered to give a white solid (0.16 g), HPLC 98.5% purity; $^1$HNMR (500 MHz, $CD_3OD$) δ 7.78 (d, J=7.95 Hz, 1H), 7.75 (d, J=8.07 Hz, 1H), 7.28-7.35 (m, 4H), 7.24 (t, J=10.6 Hz, 2H), 7.17 (d, J=7.78 Hz, 1H), 6.67 (s, 2H), 4.94 (dd, J=9.79, 5.79 Hz, 1H), 4.39 (d, J=15.2 Hz, 1H), 4.28 (d, J=15.2 Hz, 1H), 3.73-3.77 (m, 1H), 3.42 (dd, J=12.1, 10.0 Hz, 1H), 3.15-3.20 (m, 2H), 1.37 (t, J=9.70 Hz, 3H); ESI MS m/z 294 [M+1].

Example 4

Preparation of (+)-4-(benzofuran-2-yl)-2,7-dimethyl-1,2,3,4-tetrahydroisoquinoline, hydrochloride salt and (−)-4-(benzofuran-2-yl)-2,7-dimethyl-1,2,3,4-tetrahydroisoquinoline, hydrochloride salt Racemic 4-benzofuran-2-yl-2,7-dimethyl-1,2,3,4-tetrahydroisoquinoline was prepared from 2-acetylbenzofuran and 3-tolylmethylamine as described in Example 26. This racemic compound (105 mg) was separated on semi-prep chiral HPLC (chiralcel OD-H, 1×25 cm, eluent: 3% ethanol in heptane, flow: 4 ml/minute, 500 µl injections, 5 mg/injections). The resulting free bases were dissolved in ethyl acetate and treated with a 2 M solution of HCl in diethyl ether (2 equiv) to give (+)-4-benzofuran-2-yl-2,7-dimethyl-1,2,3,4-tetrahydroisoquinoline, hydrochloride salt (39 mg, 100% AUC HPLC, 99.4% AUC chiral HPLC): $^1$H NMR (300 MHz, Acetone-$d_6$) δ 7.63-7.70 (m, 1H), 7.20-7.47 (m, 6H), 7.00-7.08 (m, 2H), 5.31-5.43 (m, 1H), 4.43-4.62 (m, 2H), 3.70-3.88 (m, 2H), 3.01 (s, 3H); EI MS m/z=277 [$C_{19}H_{19}NO$]$^+$, $[\alpha]^{25}_D$ +20° (c 1.0, MeOH, free base) and (−)-4-benzofuran-2-yl-2,7-dimethyl-1,2,3,4-tetrahydroisoquinoline, hydrochloride salt (40 mg, 100% AUC HPLC, 100% chiral HPLC): $^1$H NMR (300 MHz, Acetone-$d_6$) δ 7.63-7.69 (m, 1H), 7.21-7.47 (m, 6H), 7.00-7.10 (m, 2H), 5.32-5.45 (m, 1H), 4.43-4.66 (m, 2H), 3.67-3.90 (m, 2H), 3.02 (s, 3H); EI MS m/z=277 [$C_{19}H_{19}NO$]$^+$; $[\alpha]^{25}_D$ −17° (c 1.0, MeOH, free base).

Example 5

Preparation of 4-(benzofuran-2-yl)-2,5-dimethyl-1,2,3,4-tetrahydroisoquinoline, maleate salt 4-benzofuran-2-yl-2,5-dimethyl-1,2,3,4-tetrahydroisoquinoline, maleate salt (99.3% AUC HPLC) was prepared as described in Example 26 from 2-acetylbenzofuran and 3-tolylmethylamine: $^1$H NMR (300 MHz, MeOD) δ 7.17-7.49 (m, 7H), 6.20 (s, 1H), 6.14 (s, 2H), 4.87 (s, 1H), 4.62 (d, J=15.3 Hz, 1H), 4.41 (d, J=15.6 Hz, 1H), 4.11 (d, J=12.6 Hz, 2H), 3.81 (dd, J=12.6, 5.1 Hz, 1H), 3.05 (s, 3H), 2.22 (s, 3H), EI MS m/z=278 [$C_{19}H_{19}NO+H$]$^+$. Anal. Calcd. for $C_{23}H_{23}NO_5$: C, 70.07; H, 5.85; N, 3.55 with 0.11% $H_2O$. Found: C, 66.80; H, 5.65; N, 3.29.

Example 6

Preparation of 4-(benzofuran-2-yl)-2,8-dimethyl-1,2,3,4-tetrahydroisoquinoline, maleate salt 4-benzofuran-2-yl-2,8-dimethyl-1,2,3,4-tetrahydroisoquinoline, maleate salt (99.0% AUC HPLC) was prepared as described in Example 26 from 2-acetylbenzofuran and 2-tolylmethylamine: $^1$H NMR (300 MHz, MeOD) δ 7.57 (d, J=6.9 Hz, 1H), 7.43 (d, J=8.1 Hz, 1H), 7.10-7.31 (m, 5H), 6.67 (s, 1H), 6.21 (s, 2H), 4.87-4.89 (m, 1H), 4.51 (s, 2H), 3.89-3.93 (m, 2H), 3.15 (s, 3H), 2.35 (s, 3H), EI MS m/z=278 [$C_{19}H_{19}NO+H$]$^+$. Anal. Calcd. for $C_{23}H_{23}NO_5$: C, 69.39; H, 6.00; N, 3.45 with 0.46% $H_2O$ and 2.5% EtOH. Found: C, 68.38; H, 6.30; N, 3.30.

Example 7

Preparation of 4-(5-chloro-1-benzofuran-2-yl)-2-methyl-1,2,3,4-tetrahydroisoquinoline, hydrochloride salt 4-(5-Chloro-1-benzofuran-2-yl)-2-methyl-1,2,3,4-tetrahydroisoquinoline, hydrochloride salt (16 mg, 95.8% AUC HPLC) was prepared from 5-chlorosalicylaldehyde as described in Example 8: $^1$H NMR (400 MHz, DMSO-$d_6$) δ 7.50-7.63 (m, 1H), 7.34-7.49 (m, 2H), 7.06-7.25 (m, 4H), 6.80-6.93 (m, 1H), 4.74-4.96 (m, 1H), 4.26-4.53 (m, 2H), 3.47-3.83 (m, 2H), 2.81 (br s, 3H); DI MS m/z 299 [$C_{18}H_{16}ClNO+H$]$^+$.

Example 8

Preparation of 4-(5-fluoro-benzofuran-2-yl)-2-methyl-1,2,3,4-tetrahydroisoquinoline, hydrochloride salt Step A: Chloromethyl trimethylsilane (5.0 g, 41 mmol) and sodium iodide (6.1 g, 41 mmol) were added to a mixture of 5-fluorosalicylaldehyde (5.2 g, 37 mmol) and potassium carbonate (15.2 g, 110 mmol) in DMF (100 ml). The resulting mixture was heated at 65° C. for 15 hours then cooled to room temperature, quenched with water and extracted with diethyl ether twice. The combined organic extracts were washed with water and dried over anhydrous magnesium sulfate to give the desired intermediate as an off-white solid (7.7 g, 93%, 97.2% AUC HPLC): $^1$H NMR (500 MHz, DMSO-$d_6$) δ 10.30-10.10 (m, 1H), 7.50-7.30 (m, 1H), 7.30-7.10 (m, 2H), 3.65 (br s, 2H), 0.20 (br s, 9H).

Step B: A mixture of the product from Step A (7.7 g, 34 mmol) and cesium fluoride (15.6 g, 103 mmol) in DMF (100 ml) was heated at 95° C. for 3 days. The resulting mixture was diluted with saturated aqueous sodium bicarbonate and extracted with diethyl ether and dichloromethane. The combined organic extracts were washed with water and brine, and dried over anhydrous magnesium sulfate to give a crude residue. This residue was diluted with MTBE, washed with water and brine, and dried to afford the desired hydroxydihydrobenzofuran intermediate as a brown liquid (3.9 g, 76.2% AUC GC): $^1$H NMR (500 MHz, CDCl$_3$) δ 6.91 (dd, J=7.6, 2.9 Hz, 1H), 6.78 (td, J=8.9, 2.9 Hz, 1H), 6.60 (dd, J=8.9, 4.1 Hz, 1H), 5.12 (dd, J=6.6, 2.5 Hz, 1H), 4.36 (dd, J=10.7, 6.7 Hz, 1H), 4.23 (dd, J=10.7, 2.6 Hz, 1H), 2.57 (br s, 1H).

Step C: The product from Step B (3.7 g, 24.0 mmol) was dehydrated with thionyl chloride (10 equiv) in pyridine (75 ml) to afford the benzofuran intermediate (1.97 g, 60%, 89.1% AUC HPLC) as described in Example 9 (Step B).

Step D: 4-(5-Fluoro-1-benzofuran-2-yl)-2-methyl-1,2,3,4-tetrahydroisoquinoline, hydrochloride salt (99.1% AUC HPLC) was prepared from the product from Step C and 4-bromoisoquinoline as described in Example 10 using an alternative procedure to generate the hydrochloride salt. The free base (53 mg, 188 mmol) was dissolved in ethyl acetate (2 ml) and treated with HCl in diethyl ether (92 µl, 2M) at room temperature. Solids started to precipitate. MTBE was added and the resulting mixture was filtered to give the desired hydrochloride salt as a yellow solid (36 mg, 77%, 95.2% AUC HPLC): $^1$H NMR (400 MHz, D$_2$O) δ 7.05-7.49 (m, 7H), 6.95-7.00 (td, J=9.6, 2.3 Hz, 1H), 4.59-4.81 (m, 3H), 3.65-4.03 (m, 2H), 3.00 (br s, 3H); DI MS m/z 282 [$C_{18}H_{16}FNO+H$]$^+$.

Example 9

Preparation of 4-(7-fluoro-benzofuran-2-yl)-2-methyl-1,2,3,4-tetrahydroisoquinoline, hydrochloride salt Step A: Iodomethyl trimethylsilane (6.0 ml, 40 mmol) was added to a mixture of 3-fluorosalicylaldehyde (5.0 g, 36 mmol) and potassium carbonate (15.2 g, 110 mmol) in dimethylformamide (100 ml). The resulting mixture was heated at 60° C. for 6 hours after which additional iodomethyl trimethylsilane was added. After stirring at 60° C. for 15 hours, the mixture was cooled to room temperature and the solids were removed by filtration. Cesium fluoride (16.4 g, 108 mmol) was added to the filtrate and the resulting mixture was heated at 105° C. for 36 hours. The mixture was extracted with methylene chloride, washed with water and dried over anhydrous magnesium sulfate to give a red/brown oil (3.6 g) which solidified on standing. These crude solids were triturated with hexanes to give light brown needles (2.3 g, 42%): $^1$H NMR (500 MHz, DMSO-$d_6$) δ 7.06 (d, J=7.6 Hz, 1H), 7.00 (dd, J=11.4, 8.5 Hz, 1H), 6.75 (ddd, J=12.0, 7.9, 4.4 Hz, 1H), 5.61 (d, J=5.7 Hz, 1H), 5.18 (br s, 1H), 4.46 (dd, J=10.1, 6.9 Hz, 1H), 4.19 (dd, J=10.1, 2.8 Hz, 1H).

Step B: Thionyl chloride (11.0 ml, 150 mmol) was added over a period of 5 minutes to a solution of the product from Step A (2.3 g, 15 mmol) in pyridine (12 ml) at 0° C. and the resulting mixture was stirred at 0° C. for 90 minutes. Dichloromethane (100 ml) was added and the reaction was quenched carefully with 10% aqueous sodium bicarbonate (200 ml) to reach pH 5. Solid sodium bicarbonate (30 g) was then added followed by water (100 ml). The two layers were separated and the aqueous phase was extracted with dichloromethane (100 ml). The combined organic layers were washed with a 5% aqueous sodium bicarbonate (100 ml) and water (100 ml), and were dried over anhydrous magnesium sulfate. The crude was dissolved in dichloromethane and washed with 1N HCl twice and water to remove any residual pyridine. The organic layer was dried over anhydrous magnesium sulfate to give the desired benzofuran (1.5 g, 73%, 98.3% AUC HPLC): $^1$H NMR (500 MHz, DMSO-$d_6$) δ 7.95 (d, J=1.9 Hz, 1H), 7.36 (d, J=7.6 Hz, 1H), 7.17-7.05 (m, 2H), 6.94 (t, J=2.5 Hz, 1H).

Step C: 4-(7-Fluoro-1-benzofuran-2-yl)-2-methyl-1,2,3,4-tetrahydroisoquinoline, hydrochloride salt (99.1% AUC HPLC) was prepared from the product from Step B and 4-bromoisoquinoline as described in Example 10: 1H NMR (500 MHz, CDCl$_3$) δ 7.07-7.38 (m, 5H), 6.92-7.04 (m, 2H), 6.81-6.87 (m, 1H), 4.57 (d, J=16.1 Hz, 1H), 4.29-4.50 (m, 1H), 4.11-4.28 (m, 1H), 3.73-3.83 (m, 1H), 3.51-3.66 (m, 1H), 3.00 (br s, 3H); DI MS m/z 282 [$C_{18}H_{16}FNO+H$]$^+$.

Example 10

Preparation of 4-(5-methoxy-benzofuran-2-yl)-2-methyl-1,2,3,4-tetrahydroisoquinoline, hydrochloride salt Step A: 5-Methoxybenzofuran (1 g, 6.8 mmol) was dissolved in tetrahydrofuran (10 ml) and cooled to −30° C. The solution was treated with n-BuLi (3.5 ml, 8.9 mmol, 2.5 M in hexanes) over 30 minutes, maintaining the internal temperature at −30° C. during the addition to give a red solution. After 1 hour at −30° C., trimethyl borate (1 ml, 8.8 mmol) was added over 10 minutes and the solution became pale brown. The resulting solution was allowed to warm slowly to 10° C. over 2 hours after which it was quenched with 6 M HCl (10 ml) and extracted with ethyl acetate (30 ml). The organics were washed with water (30 ml) and brine (30 ml) and were dried over anhydrous magnesium sulfate. After filtration, the organic solution was concentrated and the boronic acid precipitated by adding hexanes. The crystals were filtered and washed with hexanes to give an off-white solid (983 mg, 76%): $^1$H NMR (500 MHz, DMSO-$d_6$) δ 8.53 (br s, 2H), 4.47 (br d, J=8.8 Hz, 1H), 7.20 (br s, 1H), 6.94 (br dd, J=8.8, 2.5 Hz, 1H), 3.79 (br s, 3H).

Step B: A solution of the product from Step A (1.0 g, 5.1 mmol) in 1,2-dimethoxyethane (10 ml) was treated with aqueous sodium carbonate (6.0 ml, 2 M solution), 4-bromoisoquinoline (1.0 g, 4.8 mmol) and catalytic palladium acetate and triphenylphosphine. The mixture was heated at reflux for 2 hours. Additional palladium acetate and triphenylphosphine were added and the reaction was refluxed overnight. The reaction was cooled to room temperature and diluted with water. The product was extracted with methylene chloride twice, washed with water and dried over anhydrous magnesium sulfate to give a brown oil (1.5 g, 83.1% AUC HPLC).

Step C: A solution of the product from Step B (1.5 g, 5.5 mmol) in chloroform (20 ml) was treated with iodomethane (1.0 ml, 16.4 mmol) and heated at 60° C. for 3.5 hours. Additional iodomethane was added and the mixture was heated at 60° C. overnight. The resulting slurry was cooled to ambient temperature. The solids were filtered off and washed with chloroform to give the desired methylated isoquinoline as a yellow solid (1.7 g, 84% from 4-bromoisoquinoline, 90.8% AUC HPLC): $^1$H NMR (500 MHz, DMSO-$d_6$) δ 10.03 (s, 1H), 9.22 (s, 1H), 8.85 (d, J=8.5 Hz, 1H), 8.62-8.54 (m, 1H), 8.45-8.36 (m, 1H), 8.22-8.14 (m, 1H), 7.81 (s, 1H), 7.72 (d, J=9.2 Hz, 1H), 7.36 (br d, J=1.9 Hz, 1H), 7.11 (br dd, J=8.8, 2.2 Hz, 1H), 4.55 (s, 3H), 3.87 (s, 3H).

Step D: The product from Step C (0.50 g, 1.2 mmol) was slurried in methanol (25 ml) and treated with sodium cyanoborohydride (0.17 mg, 1.7 mmol) and a few drops of a solution of bromocresol green in methanol. The resulting green mixture was treated with a 2.0 M solution of hydrogen chloride in diethyl ether until the color of the solution turned yellow. The mixture was stirred for 2 hours at room temperature maintaining the yellow color by adding more hydrogen chloride in ether. An aqueous solution of sodium hydroxide (10 ml, 3.0 M) was added to quench the reaction and the mixture was extracted with ethyl acetate. The organic extracts were washed with water and brine, and were dried over anhydrous magnesium sulfate to give a crude yellow oil (0.28 g). The corresponding hydrochloride salt was prepared by passing a stream of hydrogen chloride gas through a solution of the crude in ethyl acetate. The organics were reduced in volume and treated with hexanes to precipitate the desired salt. The slurry was filtered and washed with hexanes to give a pale yellow solid (0.24 g, 60%, 100% AUC HPLC): $^1$H NMR (400 MHz, DMSO-$d_6$) δ 7.60-6.80 (m, 8H), 5.15-4.82 (m, 1H), 4.70-4.30 (m, 2H), 4.20-3.55 (m, 5H), 3.00 (s, 3H); DI MS m/z=294 [$C_{19}H_{19}NO_2+H$]$^+$.

Example 11

Preparation of (+)-4-(7-methoxybenzo[b]furan-2-yl)-2-methyl-1,2,3,4-tetrahydroisoquinoline, hydrochloride salt and (−)-4-(7-methoxybenzo[b]furan-2-yl)-2-methyl-1,2,3,4-tetrahydroisoquinoline, hydrochloride salt Racemic 4-(7-methoxybenzo[b]furan-2-yl)-2-methyl-1,2,3,4-tetrahydroisoquinoline was prepared from 2-(7- methoxybenzo[b]furan) boronic acid and 4-bromoisoquinoline as described in Example 36 (Steps D to F). This racemic compound (260 mg) was separated on semi-prep chiral HPLC (chiralcel OD-H, 1×25 cm, eluent: 2% ethanol in heptane, flow: 3.7 ml/min, 500 μl injections, 20 mg/injections). The resulting free bases were dissolved in ethyl acetate and treated with a 2 M solution of HCl in diethyl ether (2 equiv) to give (+)-4-(7-methoxybenzo[b]furan-2-yl)-2-methyl-1,2,3,4-tetrahydroisoquinoline, hydrochloride salt (48 mg, 95.0% AUC HPLC, 100% AUC chiral HPLC): $^1$H NMR (300 MHz, MeOD) δ 7.25-7.40 (m, 4H), 7.13-7.19 (m, 2H), 6.90 (dd, J=6.0, 3.0 Hz, 1H), 6.70 (br s, 1H), 4.75-4.92 (m, 1H), 4.59 (d, J=5.1 Hz, 2H), 3.95 (s, 3H), 3.90-3.98 (m, 1H), 3.22-3.33 (m, 1H), 3.10 (s, 3H); EI MS m/z=294 $[C_{19}H_{19}NO_2+H]^+$, $[\alpha]^{25}_D$ +5.3° (c 1.0, MeOH, free base) and (−)-4-(7-methoxybenzo[b]furan-2-yl)-2-methyl-1,2,3,4-tetrahydroisoquinoline, hydrochloride salt (48 mg, 97.3% AUC HPLC, 100% chiral HPLC): $^1$H NMR (300 MHz, MeOD) δ 7.25-7.40 (m, 4H), 7.13-7.19 (m, 2H), 6.85-6.92 (m, 1H), 6.70 (br s, 1H), 4.78-4.92 (m, 1H), 4.50-4.56 (m, 2H), 3.95 (s, 3H), 3.85-3.95 (m, 2H), 3.09 (s, 3H); EI MS m/z=294 $[C_{19}H_{19}NO_2+H]^+$; $[\alpha]^{25}_D$ −10.4° (c 1.0, MeOH, free base).

Example 12

Preparation of 4-(benzo[b]furan-3-yl)-2-methyl-1,2,3,4-tetrahydroisoquinoline, hydrochloride salt Step A: A solution of 2-methoxyphenylacetone (5 g, 30.5 mmol) in N,N-dimethylformamide dimethyl acetal (8.7 ml, 73.1 mmol) was stirred at 80° C. for 4 hours. The mixture was concentrated under vacuum. The resulting residue was dissolved in dichloromethane (40 ml), cooled to 0° C. and treated with a solution of boron tribromide (5 ml, 52.9 mmol) in dichloromethane (10 ml). After stirring at 0° C. for 1 hour, additional boron tribromide (5 ml, 52.9 mmol) was added. The mixture was stirred at 0° C. for 10 more minutes and was poured into a mixture of ice and saturated aqueous sodium bicarbonate. The resulting mixture was extracted with dichloromethane three times. The combined organic extracts were washed with water once and dried over anhydrous sodium sulfate to give 3-acetylbenzofuran (4.7 g, 96%, 94.5% AUC HPLC): $^1$H NMR (300 MHz, CDCl$_3$) δ 8.16-8.19 (m, 2H), 7.44-7.48 (m, 1H), 7.29-7.32 (m, 2H), 2.50 (s, 3H).

Step B: A solution of tetrabutylammonium tribromide (12.3 g, 25.4 mmol) in dichloromethane (60 ml) was added dropwise to a solution of the product from Step A (3.7 g, 23.1 mmol) in dichloromethane (15 ml) and methanol (15 ml) at room temperature. At completion of the addition, the resulting red-orange solution was stirred at room temperature for 15 hours. The mixture was concentrated under vacuum and the residue was taken into ethyl acetate and water. The layers were separated and the aqueous phase was extracted with ethyl acetate. The combined organic extracts were washed with saturated aqueous sodium bicarbonate and brine and dried over anhydrous sodium sulfate to give the desired bromo compound (5.5 g, 99%): $^1$H NMR (300 MHz, CDCl$_3$) δ 8.41 (s, 1H), 8.22-8.26 (m, 1H), 7.56-7.60 (m, 1H), 7.41-7.44 (m, 2 H), 4.36 (s, 2H).

Step C: Benzylmethylamine (2.8 g, 23.0 mmol) was added dropwise to a solution of the product from Step B (5.5 g, 23.0 mmol) in dichloromethane (45 ml) at 0° C. At completion of the addition, the resulting mixture was stirred at this temperature for 15 minutes and diisopropylethylamine (4.4 ml, 25.3 mmol) was added dropwise. The mixture was stirred at room temperature for 15 hours after which it was quenched with saturated aqueous sodium bicarbonate and extracted with dichloromethane twice. The combined organic extracts were washed with saturated aqueous sodium bicarbonate and dried over anhydrous sodium sulfate. Concentration of the filtrate and purification by chromatography (9:1 heptane/ethyl acetate) gave the desired intermediate (3.2 g, 50%): $^1$H NMR (300 MHz, CDCl$_3$) δ 8.69 (s, 1H); 8.26-8.29 (m, 1H), 7.53-7.56 (m, 1H), 7.28-7.41 (m, 7H), 3.68 (s, 2H), 3.61 (s, 2H), 2.39 (s, 3H).

Step D: Sodium borohydride (0.43 g, 11.3 mmol) was added to a solution of the product from Step C (3.2 g, 11.4 mmol) in methanol (35 ml) at 0° C. The resulting mixture was stirred at room temperature for 15 hours. Methanol was removed in vacuo. The residue was taken into water and was extracted with dichloromethane twice. The combined organic extracts were washed with water and brine and dried over anhydrous sodium sulfate to give the desired alcohol intermediate (2.4 g, 75%) after chromatography: $^1$H NMR (300 MHz, CDCl$_3$) δ 7.60 (s, 1H), 7.46-7.49 (m, 2H), 7.17-7.39 (m, 7H), 5.03 (dd, J=11.1, 0.6 Hz, 1H), 3.82 (d, J=12.9 Hz, 1H), 3.58 (d, J=13.2 Hz, 1H), 2.94 (dd, J=12.3, 10.8 Hz, 1H), 2.68 (dd, J=12.3, 3.3 Hz, 1H), 2.41 (s, 3H).

Step E: Aluminum chloride (2.0 g, 15.3 mmol) was added portionwise to a solution of the product from Step D (2.4 g, 8.5 mmol) in dichloromethane (90 ml) at 0° C. At the end of the addition, the mixture was stirred for 1.5 hours at 0° C., poured onto ice and dichloromethane and stirred for an additional 15 minutes. The mixture was washed with water and saturated aqueous sodium bicarbonate, extracted with dichloromethane and dried over sodium sulfate. The resulting crude was purified by chromatography (4:1 heptane/ethyl acetate) and preparative TLC (1:1 heptane/ethyl acetate) to give 4-benzofuran-3-yl-2-methyl-1,2,3,4-tetrahydroisoquinoline (0.13 g, 6%, 99.6% AUC HPLC): $^1$H NMR (300 MHz, CDCl$_3$) δ 7.46-7.51 (m, 2H), 7.26-7.32 (m, 2H), 7.08-7.18 (m, 5H), 4.53 (t, J=3.6 Hz, 1H), 4.14 (dd, J=14.4, 7.2 Hz, 1H), 3.81 (d, J=15.0 Hz, 1H), 3.69 (d, J=14.7 Hz, 1H), 3.05 (ddd, J=11.4, 5.7, 1.2 Hz, 1H), 2.82 (dd, J=11.1, 8.1 Hz, 1H), 2.48 (s, 3H).

Step F: The product from Step E (0.12 g, 0.48 mmol) was dissolved in ethyl acetate (2 ml) and treated with 2 M HCl in diethyl ether (0.48 ml, 0.95 mmol) to give 4-Benzofuran-3-yl-2-methyl-1,2,3,4-tetrahydroisoquinoline, hydrochloride salt (0.12 g, 88%, 99.3% AUC HPLC) after filtration: $^1$H NMR (300 MHz, DMSO-d$_6$) δ 8.18 (br s, 1H), 7.62 (d, J=8.4 Hz, 1H), 6.88-7.36 (m, 7H), 4.90-5.02 (m, 1H), 4.52-4.70 (m, 2H), 3.61-3.82 (m, 2H), 2.95 (s, 3H); EI MS m/z=264 $[C_{18}H_{17}NO+H]^+$. Anal. Calcd. for $C_{18}H_{18}ClNO$: C, 72.11; H, 6.05; N, 4.67. Found: C, 71.97; H, 6.31; N, 4.52.

Example 13

Preparation of 4-(benzo[b]furan-4-yl)-2-methyl-1,2,3,4-tetrahydroisoquinoline, maleate salt 4-Benzo[b]furan-4-yl-2-methyl-1,2,3,4-tetrahydroisoquinoline was prepared from 3-bromophenol as described in Example 14 (Steps A and B) and converted to its maleate salt (0.39 g, 100% AUC HPLC) as described in Example 69: $^1$H NMR (300 MHz, MeOD) δ 7.74 (d, J=2.4 Hz, 1H), 7.52-7.55 (m, 1H), 7.15-7.38 (m, 5H), 6.90 (d, J=7.8 Hz, 1H), 6.50-6.51 (m, 1H), 6.26 (s, 2H), 4.92-4.99 (m, 1H), 4.62-4.68 (m, 2H), 3.86-3.94 (m, 1H), 3.58-3.68 (m, 1H), 3.11 (s, 3H); EI MS m/z=264 [C$_{18}$H$_{17}$NO+H]$^+$. Anal. Calcd. for C$_{22}$H$_{21}$NO$_5$: C, 69.64; H, 5.58; N, 3.69. Found: C, 69.36; H, 5.80; N, 3.34.

Example 14

Preparation of (+)-4-(benzo[b]furan-5-yl)-2-methyl-1,2,3,4-tetrahydroisoquinoline, hydrochloride salt and (−)-4-(benzo[b]furan-5-yl)-2-methyl-1,2,3,4-tetrahydroisoquinoline, hydrochloride salt Step A: A mixture of 4-bromophenol (5.0 g, 29 mmol), bromoacetaldehyde diethyl acetal (4.5 ml, 30 mmol), potassium carbonate (4.1 g, 30 mmol) and potassium iodide (0.2 g, 1 mmol) in butanone (30 ml) was stirred at 80° C. for 8 days. The mixture was cooled to room temperature, diluted with water and extracted with ethyl acetate three times. The combined organic extracts were washed with aqueous sodium hydroxide (1 M), water and brine, dried over anhydrous sodium sulfate and concentrated under vacuum to give the desired product (3.8 g, 46%, 100% AUC GC) after chromatography (9:1 heptane/ethyl acetate): $^1$H NMR (300 MHz, CDCl$_3$) δ 7.38 (dt, J=9.0, 3.3 Hz, 2H), 6.83 (dt, J=9.0, 3.3 Hz, 2H), 4.83 (t, J=5.1 Hz, 1H), 3.99 (d, J=5.1 Hz, 2H), 3.78 (qd, J=9.3, 7.2 Hz, 2H), 3.65 (qd, J=9.3, 7.2 Hz, 2H), 1.26 (t, J=7.2 Hz, 6H).

Step B: 4-Benzo[b]furan-5-yl-2-methyl-1,2,3,4-tetrahydroisoquinoline (0.5 g, 98.1%) was prepared from the product from Step A as described in Example 40 (Steps B to E): H NMR (300 MHz, CDCl$_3$) δ 7.62 (d, J=2.1 Hz, 1H), 7.42-7.45 (m, 2H), 7.05-7.19 (m, 4H), 7.00 (d, J=7.5 Hz, 1H), 6.72 (dd, J=2.4, 0.9 Hz, 1H), 4.40 (t, J=7.2 Hz, 1H), 3.80 (d, J=15.0 Hz, 1H), 3.67 (d, J=14.7 Hz, 1H), 3.09 (ddd, J=11.4, 5.7, 1.2 Hz, 1H), 2.64 (dd, J=11.4, 8.7 Hz, 1H), 2.46 (s, 3H).

Step C: The product from Step B was separated on semi-prep chiral HPLC (chiralcel OD-H, 1×25 cm, eluent: 2% ethanol in heptane (0.1% Et$_3$N), flow: 4 ml/minute, 500 µl injections, 5 mg/injection). The resulting free bases were dissolved in ethyl acetate and treated with a 2 M solution of HCl in diethyl ether (2 equiv) to give (+)-4-benzo[b]furan-5-yl-2-methyl-1,2,3,4-tetrahydroisoquinoline, hydrochloride salt (33 mg, 99% AUC HPLC, 100% AUC chiral HPLC): $^1$H NMR (300 MHz, MeOD, free base) δ 7.81 (d, J=2.1 Hz, 1H), 7.57 (br s, 1H), 7.53 (d, J=8.7 Hz, 1H), 7.16-7.40 (m, 4H), 6.92 (d, J=7.8 Hz, 1H), 6.84 (br s, 1H), 4.60-4.85 (m, 3H), 3.82-3.94 (m, 1H), 3.59 (t, J=12.3 Hz, 1H), 3.11 (s, 3H); EI MS m/z=264 [C$_{18}$H$_{17}$NO+H]$^+$; [α]$^{25}_D$ +37° (c 1.0, MeOH, free base), and (−)-4-benzo[b]furan-5-yl-2-methyl-1,2,3,4-tetrahydroisoquinoline, hydrochloride salt (28 mg, 99.5% AUC HPLC, 100% chiral HPLC): $^1$H NMR (300 MHz, MeOD) δ 7.81 (d, J=2.1 Hz, 1H), 7.57 (br s, 1H), 7.54 (d, J=8.7 Hz, 1H), 7.25-7.38 (m, 3H), 7.18 (dd, J=8.7, 1.8 Hz, 1H), 6.92 (d, J=7.8 Hz, 1H), 6.84 (br s, 1H), 4.55-4.88 (m, 3H), 3.80-3.96 (m, 1H), 3.59 (t, J=11.7 Hz, 1H), 3.11 (s, 3H); EI MS m/z=264 [C$_{18}$H$_{17}$NO+H]$^+$, [α]$^{25}_D$ −37° (c 1.0, MeOH, free base).

Example 15

Preparation of 4-(benzo[b]furan-5-yl)-2,7-dimethyl-1,2,3,4-tetrahydroisoquinoline, maleate salt 4-Benzo[b]furan-5-yl-2,7-dimethyl-1,2,3,4-tetrahydroisoquinoline was prepared from 7-methylcinnamic acid and 5-bromofuran as described in Example 41 (Steps A to H) and was converted to the corresponding maleate salt (0.29 g, 98.3% AUC HPLC) as in Example 69: 1H NMR (300 MHz, MeOD) δ 7.79 (d, J=1.8 Hz, 1H), 7.50-7.53 (m, 2H), 7.07-7.18 (m, 3H), 6.80-6.83 (m, 2H), 6.24 (s, 2H), 4.67 (dd, J=10.8, 6.0 Hz, 1H), 4.51-4.58 (m, 2H), 3.87 (dd, J=12.0, 5.7 Hz, 1H), 3.54-3.63 (m, 1H), 3.09 (s, 3H), 2.34 (s, 3H); EI MS m/z=278 [C$_{19}$H$_{19}$NO+H]$^+$. Anal. Calcd. for C$_{23}$H$_{23}$NO$_5$: C, 69.97; H, 5.91; N, 3.52 with 0.08 equiv EtOH. Found: C, 69.31; H, 5.88; N, 3.39.

Example 16

Preparation of 4-(benzo[b]furan-5-yl)-7-fluoro-2-methyl-1,2,3,4-tetrahydroisoquinoline, hydrochloride salt 4-Benzo[b]furan-5-yl-7-fluoro-2,methyl-1,2,3,4-tetrahydroisoquinoline, hydrochloride salt (0.26 g, 96.5% AUC HPLC) was prepared from 7-fluorocinnamic acid and 5-bromofuran as described in Example 41: $^1$H NMR (300 MHz, DMSO-d$_6$) δ 11.65 (br s, 1H) 8.03 (d, J=2.1 Hz, 1H), 7.62 (d, J=8.4 Hz, 1H), 7.55 (s, 1H), 6.96-7.50 (m, 4H), 6.78 (br s, 1H), 4.66-4.74 (m, 1H), 4.53 (br s, 1H), 3.45-3.80 (m, 2H), 2.94 (s, 3H), 2.51 (s, 3H); EI MS m/z=282 [C$_{18}$H$_{16}$FNO+H]$^+$. Anal. Calcd. for C$_{18}$H$_{17}$ClFNO: C, 67.21; H, 5.51; N, 4.36 with 1.1 equiv HCl. Found: C, 67.32; H, 5.41; N, 4.19.

Example 17

Preparation of 4-(benzo[b]furan-6-yl)-2-methyl-1,2,3,4-tetrahydroisoquinoline, maleate salt 4-Benzo[b]furan-6-yl-2-methyl-1,2,3,4-tetrahydroisoquinoline was prepared from 3-bromophenol as described in Example 14 (Steps A and B) and converted to its maleate salt (0.28 g, 98.2% AUC HPLC) as described in Example 69: $^1$H NMR (300 MHz, MeOD) δ 7.79 (d, J=2.1 Hz, 1H), 7.65 (d, J=8.1 Hz, 1H), 7.25-7.42 (m, 4H), 7.14 (dd, J=8.1, 1.5 Hz, 1H), 6.96 (d, J=7.8 Hz, 1H), 6.86-6.87 (m, 1H), 6.26 (s, 2H), 4.60-4.76 (m, 3H), 3.86-3.92 (m, 1H), 3.62 (t, J=12.0 Hz, 1H), 3.09 (s, 3H); EI MS m/z=264 [C$_{18}$H$_{17}$NO+H]$^+$. Anal. Calcd. for C$_{22}$H$_{21}$NO$_5$: C, 69.64; H, 5.58; N, 3.69. Found: C, 69.67; H, 5.65; N, 3.39.

Example 18

Preparation of 4-(benzo[b]furan-6-yl)-7-fluoro-2-methyl-1,2,3,4-tetrahydroisoquinoline, hydrochloride salt 4-Benzo[b]furan-6-yl-7-fluoro-2,methyl-1,2,3,4-tetrahydroisoquinoline, hydrochloride salt (0.21 g, 97.3% AUC HPLC) was prepared from 7-fluorocinnamic acid and 6-bromofuran as described in Example 41: $^1$H NMR (300 MHz, DMSO-d$_6$) δ 11.53 (br s, 1H) 8.02 (d, J=2.4 Hz, 1H), 7.68 (d, J=8.1 Hz, 1H), 7.53 (be s, 1H), 6.97-7.20 (m, 4H), 6.79 (br s, 1H), 4.68-4.74 (m, 1H), 4.53 (br s, 21H), 3.39-3.82 (m, 2H), 2.92 (s, 3H), 2.50 (s, 3H); EI MS m/z=282 [C$_{18}$H$_{16}$FNO+H]$^+$. Anal. Calcd. for C$_{18}$H$_{17}$ClFNO: C, 67.20; H, 5.51; N, 4.36 with 1.1 equiv HCl. Found: C, 67.30; H, 5.66; N, 4.30.

Example 19

Preparation of 4-(benzo[b]furan-7-yl)-2-methyl-1,2,3,4-tetrahydroisoquinoline, maleate salt 4-Benzo[b]furan-7-yl-2-methyl-1,2,3,4-tetrahydroisoquinoline was prepared from 2-bromophenol as described in Example 14 (Steps A and B) and converted to its maleate salt (0.64 g, 100% AUC HPLC) as described in Example 69: $^1$H NMR (300 MHz, MeOD) δ 7.74 (d, J=2.1 Hz, 1H), 7.64 (dd, J=7.8, 1.2 Hz, 1H), 7.15-7.33 (m, 5H), 6.90 (d, J=2.1 Hz, 2H), 6.26 (s, 2H), 5.06-5.12 (m, 1H), 4.64 (s, 2H), 3.79-3.96 (m, 2H), 3.11 (s, 3H); EI MS m/z=264 $[C_{18}H_{17}NO+H]^+$. Anal. Calcd. for $C_{22}H_{21}NO_5$: C, 69.64; H, 5.58; N, 3.69. Found: C, 69.67; H, 5.82; N, 3.49.

Example 20

Preparation of (+) and (−)-4-(benzo[b]thiophen-5-yl)-1,2,3,4-tetrahydroisoquinoline, fumarate salt Step A: To a solution of isoquinoline-4-boronic acid (378 mg, 2.013 mmol) and 5-bromobenzothiophene (286 mg, 1.342 mmol) in dichloroethane (8 mL), sodium carbonate (2 M aqueous, 2 mL, 4 mmol) was added and the solution degassed by alternately evacuating and releasing to argon three times. To this heterogenic mixture was added palladium tetrakistriphenylphosphine (76 mg, 0.6711 mmol), the reaction mixture was degassed 3 times and heated to 90° C. with agitation for 12 hours. To this mixture was added EtOAc (100 mL), the mixture washed with water (3×100 mL), and dried over anhydrous sodium sulfate. Purification by column chromatography (SiO$_2$, 30 g, 50% ethyl acetate/hexane) provided the product as a white solid (316 mg): 1H NMR (CDCl$_3$, 300 MHz) δ 9.29 (s, 1H), 8.55 (s, 1H), 8.06-7.97 (m, 4H), 7.68-7.65 (m, 2H), 7.56-7.42 (m, 3H). ESI-MS calc. for $C_{17}H_{11}NS$ $[M+H]^+$ 262. Found 262.

Step B: To a solution of product from Step A (400 mg, 1.530 mmol) in anhydrous THF (15 mL) at 0° C. was added lithium borohydride (1 M soln in THF, 18 mL, 18 mmol) and the reaction mixture stirred at room temperature for 24 hours. Methanol (50 mL) was added, the mixture stirred at room temperature for 15 minutes, and concentrated to dryness. The residue was dissolved in EtOAc (250 mL), the organic layer was washed with water (50 mL) and brine (50 mL), and dried over anhydrous sodium sulfate. Purification by column chromatography (SiO$_2$, 30 g, 33% to 100% ethyl acetate/hexane then 10% MeOH/chloroform) provided the product as a colorless oil (228 mg): $^1$H NMR (CDCl$_3$, 300 MHz) δ 7.80 (d, J=8.3, 1H), 7.49 (s, 1H), 7.41 (d, J=5.4, 1H), 7.25-7.07 (m, 4H), 6.92 (d, J=7.5, 1H), 4.25-4.07 (m, 5H), 3.43 (dd, J=5.2, 10.0, 1H), 3.15 (dd, J=6.5, 13.0, 1H). ESI MS calc. for $C_{17}H_{15}NS$ $[M+H]^+$ 266. Found 266.

Step C: The free base was converted to its acetate by concentrating a solution of product from Step B (65 mg, 0.245 mmol) in acetic acid (5 mL) to dryness. Lyophilization from acetonitrile (2 mL) and water (2 mL) provided the racemic product as a white solid (45 mg): mp 118-120° C. $^1$H NMR (CD$_3$OD, 300 MHz) δ 7.85 (d, J=9.0, 1H), 7.72 (d, J=7.4, 1H), 7.8 (d, J=5.5, 1H), 7.33 (d, J=5.1, 1H), 7.23-7.11 (m, 4 H), 6.86 (d, J=7.6, 1H), 4.47-4.22 (m, 3H), 3.62-3.57 (m, 1H), 3.32-3.30 (m, 1H), (1.92 (s, 3H). ESI MS calcd. for $C_{17}H_{15}NS$ $[M+H]^+$ 266. Found 266.

Step D: Single enantiomers were obtained through chiral chromatography (Chiralpak AD, 10% isopropanol/heptane with 0.1% diethylamine) of product from Step B. (+)-enantiomer (80 mg): $[α]_D$ +6.0 (0.15, Methanol). (−)-enantiomer (80 mg): $[α]_D$ −30.7 (0.15, Methanol).

Step E: To a solution of the (−)-enantiomer obtained from Step D (73 mg) in ethanol (5 mL) was added a solution of fumaric acid (32 mg) in methanol (1 mL) at 0° C. The solution was stirred at 0° C. for 2 hours, then concentrated, and the residue was washed with ethanol. The fumarate salt was isolated as a white powder (73 mg): mp 192-197° C.; HPLC>99% ee (Chiralpak AD column); $^1$H NMR (CD$_3$OD, 300 MHz) δ 7.89 (d, J=8.3, 1H), 7.69 (s, 1H), 7.59 (d, J=5.5, 1H), 7.34-7.16 (m, 5H), 6.90 (d, J=6.7, 1H), 6.67 (s, 2H), 4.58-4.32 (m, 3H), 3.73-3.67 (m, 1H), 3.44-3.40 (m, 1H). ESI MS calcd. for $C_{17}H_{15}NS$ $[M+H]^+$ 266. Found 266.

The fumarate of the (+)-enantiomer was obtained similarly. (+)-enantiomer; mp 165-172° C. HPLC 95.7% ee (Chiralpak AD column).

Example 21

Preparation of 4-(benzothiophen-2-yl)-2-methyl-1,2,3,4-tetrahydroisoquinoline 4-(benzothiophen-2-yl)-2-methyl-1,2,3,4-tetrahydroisoquinoline was prepared from 2-benzothiophenboronic acid and 4-bromoisoquinoline as described in Example 36 (Steps D to F): mp 89-91° C.; $^1$H NMR (500 MHz, CDCl$_3$) δ 7.72 (d, J=7.9 Hz, 1H), 7.67 (d, J=7.5 Hz, 1H), 7.32-7.23 (m, 3H), 7.07-7.17 (m, 4H), 4.55 (t, J=5.0 Hz, 1H), 3.77 (d, J=15.0 Hz, 1H), 3.62 (d, J=15.0 Hz, 1H), 3.00 (dd, J=12.0, 5.0 Hz, 1H), 2.89 (dd, J=12.0, 6.0 Hz, 1H), 2.48 (s, 3H); IR (KBr) 2945, 2783, 1493, 1458 cm$^{-1}$; CI MS m/z=280 $[C_{18}H_{17}NS+H]^+$; HPLC 99.1%, $t_r$=16.07 min. Anal. Calcd. For $C_{18}H_{17}NS$: C, 77.38; H, 6.13; N, 5.01. Found; C, 77.23; H, 6.16; N, 4.97.

Example 22

Preparation of 4-(benzothiophen-2-yl)-2,8-dimethyl-1,2,3,4-tetrahydroisoquinoline, maleate salt 4-Benzothiophen-2-yl-2,8-dimethyl-1,2,3,4-tetrahydroisoquinoline, maleate salt (98.7% AUC HPLC) was prepared as described in Example 26 from 2-acetylbenzothiophene and 2-tolylmethylamine: $^1$H NMR (300 MHz, MeOD) δ 7.75-7.83 (m, 2H), 7.19-7.39 (m, 5H), 7.08 (t, J=4.5 Hz, 1H), 6.21 (s, 2H), 5.03 (dd, J=9.6, 5.7 Hz, 1H), 4.57 (d, J=15.6 Hz, 1H), 4.45 (d, J=15.6 Hz, 1H), 3.93 (dd, J=12.0, 5.4 Hz, 1H), 3.72 (dd, J=12.0, 9.9 Hz, 1H), 3.14 (s, 3H), 2.35 (s, 3H), EI MS m/z=294 $[C_{19}H_{19}NS+H]^+$. Anal. Calcd. for $C_{23}H_{23}NO_4S$: C, 66.83; H, 5.74; N, 3.33; S, 7.61 with 0.36% H$_2$O and 2.00% EtOH. Found: C, 65.68; H, 5.60; N, 3.20; S, 7.70.

Example 23

Preparation of 4-(4-fluorobenzo[b]thiophen-2-yl)-2-methyl-1,2,3,4-tetrahydroisoquinoline, maleate salt 4-(4-Fluorobenzo[b]thiophen-2-yl)-2-methyl-1,2,3,4-tetrahydroisoquinoline, maleate salt (45 mg, 95.6% AUC HPLC) was prepared from 3-fluorobenzenethiol and bromoacetaldehyde diethyl acetal as described in Example 36: $^1$H NMR (300 MHz, DMSO-d$_6$) δ 7.56 (d, J=7.8 Hz, 1H), 7.31 (s, 1H), 6.95-7.19 (m, 6H), 5.89 (s, 2H), 4.74 (t, J=6.3 Hz, 1H), 3.98-4.21 (m, 2H), 3.32-3.59 (m, 2H), 2.64 (s, 3H); EI MS m/z=298 $[C_{18}H_{16}FNS+H]^+$.

Example 24

Preparation of 4-(benzo[b]thiophen-5-yl)-2-ethyl-1,2,3,4-tetrahydroisoquinoline

To a solution of product from Step A in Example 20 (100 mg, 0.383 mmol) in anhydrous dichloromethane (2.5 mL) at 0° C. was added ethyl triflate (60 µL, 0.459 mmol). The mixture was stirred at room temperature for 2 hours, concentrated to dryness and redissolved in methanol (5 mL)/dichloromethane (5 mL). To this solution was added sodium cyanoborohydride (240 mg, 2.00 mmol), the mixture stirred at room temperature for 12 hours and concentrated to dryness. The residue was dissolved in ethyl acetate (25 mL) and the organic layer was washed with saturated sodium bicarbonate solution (25 mL), brine (25 mL) and dried over anhydrous sodium sulfate. Purification by semi preparative HPLC provided the product as colorless oil (81 mg): ESI MS calcd. for $C_{19}H_{19}NS$ [M+H]$^+$ 394. Found 394.

Example 25

Preparation of 4-(benzothiophen-2-yl)-2,5-dimethyl-1,2,3,4-tetrahydroisoquinoline, maleate salt 4-Benzothiophen-2-yl-2,5-dimethyl-1,2,3,4-tetrahydroisoquinoline, maleate salt (97.3% AUC HPLC) was prepared as described in Example 26 from 2-acetylbenzothiophene and 3-tolylmethylamine: $^1$H NMR (300 MHz, MeOD) δ 7.82 (t, J=5.1 Hz, 1H), 7.67 (t, J=4.2 Hz, 1H), 7.28-7.41 (m, 4H), 7.20 (d, J=7.5 Hz, 3H), 6.23 (s, 3H), 5.00 (t, J=4.2 Hz, 1H), 4.64 (d, J=15.6 Hz, 1H), 4.45 (d, J=15.6 Hz, 1H), 3.94 (d, J=3.6 Hz, 2H), 3.05 (s, 3H), 2.18 (s, 3H), EI MS m/z=294 [$C_{19}H_{19}NS+H$]$^+$. Anal. Calcd. for $C_{25}H_{25}NO_6S$: C, 63.34; H, 5.28; N, 2.96; S, 6.76 with 1.28% $H_2O$. Found: C, 63.76; H, 5.45; N, 2.76; S, 6.53.

Example 26

Preparation of 4-(benzothiophen-2-yl)-2,7-dimethyl-1,2,3,4-tetrahydroisoquinoline, maleate salt Step A: A solution of tetrabutylammonium tribromide (15.0 g, 312 mmol) in dichloromethane (80 ml) was added dropwise to a solution of 2-acetylbenzothiophene (5.0 g, 28 mmol) in dichloromethane (20 ml) and methanol (20 ml) at room temperature. At completion of the addition, the resulting red-orange solution was stirred at room temperature for 15 hours. The mixture was concentrated under vacuum and the residue was taken into ethyl acetate and water. The layers were separated and the aqueous phase was extracted with ethyl acetate. The combined organic extracts were washed with saturated aqueous sodium bicarbonate and brine and dried over anhydrous sodium sulfate to give the desired bromo compound (7.3 g, 100%): $^1$HNMR (300 MHz, CDCl$_3$) δ 8.07 (s, 1H), 7.91 (dd, J=12.0, 8.1 Hz, 2 H), 7.42-7.53 (m, 2H), 4.47 (s, 2H).

Step B: 3-Tolylmethylamine (1.6 g, 11.7 mmol) was added dropwise to a solution of the product from Step A (3.0 g, 11.7 mmol) in dichloromethane (25 mL) at 0° C. At completion of the addition, the resulting mixture was stirred at 0° C. for 15 minutes and diisopropylethyl amine (2.3 ml, 12.9 mmol) was added dropwise. The mixture was stirred at room temperature for 15 hours after which it was quenched with saturated aqueous sodium bicarbonate and extracted with dichloromethane twice. The combined organic extracts were washed with saturated aqueous sodium bicarbonate and dried over sodium sulfate to give the desired intermediate (1.8 g, 49%) after chromatography (9:1 heptane/ethyl acetate): $^1$H NMR (300 MHz, CDCl$_3$) δ 7.99 (s, 1H), 7.78 (d, J=7.8 Hz, 2H), 7.29-7.41 (m, 2H), 6.98-7.18 (m, 4H), 3.67 (s, 2H), 3.60 (s, 2H), 2.34 (s, 3H), 2.27 (s, 3H).

Step C: Sodium borohydride (0.2 g, 5.8 mmol) was added to a solution of the product from Step B (1.8 g, 5.8 mmol) in methanol (20 ml) at 0° C. The resulting mixture was stirred at room temperature for 15 hours. Methanol was removed in vacuo. The residue was taken into water and extracted with dichloromethane three times. The combined organic extracts were washed with water and brine and dried over sodium sulfate to give the desired alcohol (1.6 g, 86%) after chromatography (9:1 to 2:1 heptane/ethyl acetate): $^1$H NMR (300 MHz, CDCl$_3$) δ 7.73 (dd,☐7.81-7.85 (m, 1H), J=6.6, 1.5 Hz, 1H), 7.23-7.38 (m, 4H), 7.12-7.15 (m, 3H), 5.10 (dd, J=10.8, 3.9 Hz, 1H), 3.73 (d, J=12.9 Hz, 1H), 3.57 (d, J=13.2 Hz, 1H), 2.85 (dd, J=12.6, 10.2 Hz, 1H), 2.74 (dd, J=12.6, 3.9 Hz, 1H), 2.38 (s, 3H), 2.35 (s, 3H).

Step D: Aluminum chloride (1.20 g, 8.7 mmol) was added portionwise to a solution of the product from Step C (1.50 g, 4.8 mmol) in dichloromethane (60 ml) at 0° C. At the end of the addition, the mixture was stirred at 0° C. for 1.5 hours, poured onto ice and dichloromethane and stirred for an additional 15 minutes. The mixture was washed with water and saturated aqueous sodium bicarbonate, extracted with dichloromethane and dried over sodium sulfate to give a crude mixture containing a 2 to 1 ratio of regioisomers. Purification by chromatography (4:1 to 2:1 heptane/ethyl acetate) afforded 4-benzothiophen-2-yl-2,7-dimethyl-1,2,3,4-tetrahydroisoquinoline (0.57 g, 40%, 99.1% AUC HPLC): $^1$H NMR (300 MHz, CDCl$_3$) δ 7.58-7.66 (m, 7.13-7.24 (m, 2H), 7.07 (s, 1H), 6.96 (s,☐2H), J=7.5 Hz, 1H), 6.84 (d, J=11.4 Hz, 1H), 4.44 (t, J=5.4 Hz, 1H), 3.65 (d, J=15.0 Hz, 1H), 3.51 (d, J=15.0 Hz, 1H), 2.91 (dd, J=11.7, 5.1 Hz, 1H), 2.80 (dd, J=11.4, 6.3 Hz, 1H), 2.40 (s, 3H), 2.22 (s, 3H) and 4-benzothiophen-2-yl-2,5-dimethyl-1,2,3,4-tetrahydroisoquinoline (0.21 g, 15%, 96.0% AUC HPLC): $^1$H NMR (300 MHz, CDCl$_3$) δ 7.74 (d, J 7.63 (dd,☐=7.8 Hz, 1H), J=6.9, 1.2 Hz, 1H), 7.16-7.32 (m, 3H), 7.03 (t, J=14.7 Hz, 1H), 6.89 (s, 1H), 4.45 (br s, 1H), 4.02 (d, J=15.0 Hz, 1H), 3.40 (d, J=15.0 Hz, 1H), 3.13 (dt, J=11.4, 1.8 Hz, 1H), 2.79 (dd, J=11.4, 4.2 Hz, 1H), 2.42 (s, 3H), 2.19 (s, 3H).

Step E: 4-Benzothiophen-2-yl-2,7-dimethyl-1,2,3,4-tetrahydroisoquinoline (0.57 g) was crystallized with maleic acid (1 equiv) in ethanol to give 4-benzothiophen-2-yl-2,7-dimethyl-1,2,3,4-tetrahydroisoquinoline, maleate salt (0.20 g, 26%, 99.5% AUC HPLC): $^1$H NMR (300 MHz, MeOD) δ 7.76-7.84 (m, 2H), 7.31-7.40 (m, 3H), 7.12-7.18 (m, 3H), 6.25 (s, 2.7H, maleic acid), 5.00 (dd, J=9.6, 6.0 Hz, 1H), 4.58 (d, J=15.3 Hz, 1H), 4.52 (d, J=15.9 Hz, 1H), 3.98 (dd, J=12.3, 5.7 Hz, 1H), 3.74 (dd, J=12.0, 10.2 Hz, 1H), 3.13 (s, 3H), 2.37 (s, 3H), EI MS m/z=294 [$C_{19}H_{19}NS+H$]$^+$. Anal. Calcd. for $C_{23}H_{23}NO_4S$: C, 64.70; H, 5.43; N, 3.08; S, 7.05 with 0.39% $H_2O$ and 1.35 equiv of maleic acid. Found: C, 62.86; H, 5.25; N, 2.90; S, 7.20.

Example 27

Preparation of 4-(benzo[b]thiophen-5-yl)-4-hydroxy-2-methyl-1,2,3,4-tetrahdro-isoquinoline, fumarate salt Step A: To a solution of 5-bromo-1-benzothiophene (511 mg, 2.4 mmol) at −75° C., was added t-butyllithium (1.7 M in pentane, 1.6 mL, 2.6 mmol) dropwise. The reaction mixture was stirred at −75° C. for 1 hour. To the resulting dark brown mixture was added 2-methyl-2,3-dihydro-1H-isoquinolin-4-one (323 mg, 2.0 mmol), which was prepared using the method described by Hanna et al., *J. Med. Chem.* 17(9):1020-1023 (1974), which is hereby incorporated by reference in its entirety. The reaction mixture was stirred for 15 hours with gradually warming up. The mixture was quenched with saturated ammonium chloride and extracted with ethyl acetate (3×50 ml). The combined organic extracts were washed with saturated sodium chloride, dried over anhydrous sodium sulfate, filtered, and concentrated in vacuo. Purification by medium pressure silica gel chromatography (10-40% ethyl acetate/hexanes) followed by preparative HPLC afforded the product (65 mg, 11%): $^1$H NMR (CDCl$_3$, 500 MHz) δ 7.81 (d, 1H, J=8.5 Hz), 7.69 (d, 1H, J=8.5 Hz), 7.34-7.23 (m, 4H), 7.20 (s, 1H), 7.18 (d, 1H, J=7.3 Hz), 7.10 (d, 1H, J=7.6 Hz), 3.91 (s, 1H), 3.84 (d, 1H, J=15.0 Hz), 3.53 (d, 1H, J=15.0 Hz), 3.11 (dd, 1H, J=1.4, 11.6 Hz), 2.87 (d, 1H, J=11.6 Hz), 2.50 (s, 3H), ESI MS m/z=296 [M+H]$^+$.

Step B: The product from Step A (59.1 mg, 0.2 mmol) was dissolved in ethanol (1 mL) and added a solution of fumaric acid (24 mg, 0.2 mmol) in methanol (0.5 mL). The solvent was removed under reduced pressure. The residue was triturated with ethyl acetate. The resulting precipitate was collected by filtration, washed with ethyl acetate, and dried at 50° C. under vacuum to provide the product as a white solid (60 mg, 73%): $^1$H NMR (CD$_3$OD, 500 MHz) δ 7.81 (d, 1H, J=7.2 Hz), 7.71 (d, 1H, J=7.2 Hz), 7.40 (d, 1H, J=7.8 Hz), 7.36-7.23 (m, 4H), 7.25 (d, 1H, J=7.6 Hz), 7.20 (s, 1H), 6.70 (s, 2H), 4.25 (d, 1H, J=15.4 Hz), 4.20 (d, 1H, J=15.4 Hz), 3.54 (d, 1H, J=12.1 Hz), 3.48 (d, 1H, J=12.1 Hz), 2.83 (s, 3H), ESI MS m/z=296 [M+H]$^+$.

Example 28

Preparation of 4-(5-fluorobenzo[b]thiophen-2-yl)-2-methyl-1,2,3,4-tetrahydroisoquinoline, maleate salt 4-(5-Fluorobenzo[b]thiophen-2-yl)-2-methyl-1,2,3,4-tetrahydroisoquinoline, maleate salt (638 mg, 97.6% AUC HPLC) was prepared from 4-fluorobenzenethiol and bromoacetaldehyde diethyl acetal as described in Example 36: $^1$H NMR (300 MHz, DMSO-d$_6$) δ 7.98 (dd, J=5.1, 3.6 Hz, 1H), 7.69 (dd, J=2.4, 9.9 Hz, 1H), 7.44 (s, 1H), 7.18-7.38 (m, 5H), 6.13 (s, 2H), 4.86-4.99 (m, 1H), 4.40 (d, J=11.4 Hz, 1H), 4.27 (d, J=15.3 Hz, 1H), 3.41-3.79 (m, 2H), 2.87 (s, 3H); EI MS m/z=298 [C$_{18}$H$_{16}$FNS+H]$^+$. Anal. Calcd. for C$_{22}$H$_{20}$FNO$_4$S: C, 63.32; H, 4.89; N, 3.36 with 0.83% H$_2$O. Found: C, 63.07; H, 4.60; N, 3.46.

Example 29

Preparation of 4-(6-fluorobenzo[b]thiophen-2-yl)-2-methyl-1,2,3,4-tetrahydroisoquinoline, maleate salt 4-(6-Fluorobenzo[b]thiophen-2-yl)-2-methyl-1,2,3,4-tetrahydroisoquinoline, maleate salt (252 mg 96.5% AUC HPLC) was prepared from 3-fluorobenzenethiol and bromoacetaldehyde diethyl acetal as described in Example 36: $^1$H NMR (300 MHz, DMSO-d$_6$) δ 7.82-7.86 (m, 2H), 7.41 (s, 1H), 7.21-7.34 (m, 4H), 7.15 (d, J=7.2 Hz, 1H), 6.09 (s, 2H), 4.89 (t, J=7.8 Hz, 1H), 4.40 (d, J=15.3 Hz, 1H), 4.26 (d, J=15.3 Hz, 1H), 3.42-3.73 (m, 2H), 2.86 (s, 3H); EI MS m/z=298 [C$_{18}$H$_{16}$FNS+H]$^+$. Anal. Calcd. for C$_{22}$H$_{20}$FNO$_4$S: C, 63.40; H, 4.90; N, 3.36; S, 7.68 with 0.70% H$_2$O. Found: C, 62.97; H, 4.70; N, 3.01; S, 7.60.

Example 30

Preparation of 4-(7-fluorobenzo[b]thiophen-2-yl)-2-methyl-1,2,3,4-tetrahydroisoquinoline, maleate salt 4-(7-Fluorobenzo[b]thiophen-2-yl)-2-methyl-1,2,3,4-tetrahydroisoquinoline, maleate salt (617 mg, 99.7% AUC HPLC) was prepared from 2-fluorobenzenethiol and bromoacetaldehyde diethyl acetal as described in Example 36: 1H NMR (300 MHz, DMSO-d$_6$) δ 7.68 (d, J=7.8 Hz, 1H), 7.53 (s, 1H), 7.41 (dt, J=7.8, 5.4 Hz, 1H), 7.16-7.34 (m, 5H), 6.10 (s, 2H), 4.86-4.98 (m, 1H), 4.37 (d, J=15.6 Hz, 1H), 4.20 (d, J=13.8 Hz, 1H), 3.39-3.71 (m, 2H), 2.83 (s, 3H); EI MS m/z=298 [C$_{18}$H$_{16}$FNS+H]$^+$. Anal. Calcd. for C$_{22}$H$_{20}$FNO$_4$S: C, 63.51; H, 4.86; N, 3.37; S, 7.70 with 0.54% H$_2$O. Found: C, 63.22; H, 4.49; N, 3.29; S, 7.94.

Example 31

Preparation of 4-(4-chlorobenzo[b]thiophen-2-yl)-2-methyl-1,2,3,4-tetrahydroisoquinoline, maleate salt 4-(4-Chlorobenzo[b]thiophen-2-yl)-2-methyl-1,2,3,4-tetrahydroisoquinoline, maleate salt (290 mg, 96.1% AUC HPLC) was prepared from 3-chlorobenzenethiol and bromoacetaldehyde diethyl acetal as described in Example 36: $^1$H NMR (300 MHz, DMSO-d$_6$) δ 7.97 (d, J=7.9 Hz, 1H), 7.23-7.57 (m, 7H), 6.15 (s, 2H), 4.96-5.13 (m, 1H), 4.47 (d, J=15.5 Hz, 1H), 4.32 (d, J=15.4 Hz, 1H), 3.52-3.85 (m, 2H), 2.91 (s, 3H); EI MS m/z=314 [C$_{18}$H$_{16}$ClNS+H]$^+$. Anal. Calcd. for C$_{22}$H$_{20}$ClNO$_4$S: C, 60.65; H, 4.73; N, 3.22; S, 7.35 with 1.24% H$_2$O. Found: C, 60.31; H, 4.49; N, 3.14; S, 7.64.

Example 32

Preparation of 4-(5-chlorobenzo[b]thiophen-2-yl)-2-methyl-1,2,3,4-tetrahydroisoquinoline 4-(5-Chlorobenzo[b]thiophen-2-yl)-2-methyl-1,2,3,4-tetrahydroisoquinoline was prepared from 4-chlorobenzenethiol and bromoacetaldehyde diethyl acetal as described in Example 36 (Steps A to F): 1H NMR (300 MHz, CDCl$_3$) δ 7.57 (d, J=1.8 Hz, 1H), 7.54 (d, J=8.4 Hz, 1H), 7.01-7.14 (m, 6H), 4.45 (t, J=5.1 Hz, 1H), 3.73 (d, J=15.0 Hz, 1H), 3.52 (d, J=15.0 Hz, 1H), 2.87 (ddd, J=18.3, 11.4, 4.8 Hz, 2H), 2.41 (s, 3H); EI MS m/z=314 [C$_{18}$H$_{16}$ClNS+H]$^+$.

Example 33

Preparation of 4-(6-chlorobenzo[b]thiophen-2-yl)-2-methyl-1,2,3,4-tetrahydroisoquinoline, maleate salt 4-(6-Chlorobenzo[b]thiophen-2-yl)-2-methyl-1,2,3,4-tetrahydroisoquinoline, maleate salt (364 mg, 100% AUC HPLC) was prepared from 3-chlorobenzenethiol and bromoacetaldehyde diethyl acetal as described in Example 36: 1H NMR (300 MHz, DMSO-d$_6$) δ 8.08 (s, 1H), 7.83 (d, J=8.4 Hz, 1H), 7.24-7.43 (m, 5H), 7.15 (d, J=7.5 Hz, 1H), 6.09 (s, 2H), 4.89 (t, J=6.6 Hz, 1H), 4.37 (d, J=14.7 Hz, 1H), 4.23 (d, J=14.4 Hz, 1H), 3.45-3.75 (m, 2H), 2.84 (s, 3H); EI MS m/z=314 [C$_{18}$H$_{16}$ClNS+H]$^+$. Anal. Calcd. for C$_{22}$H$_{20}$ClNO$_4$S: C, 61.46; H, 4.69; N, 3.26; S, 7.46. Found: C, 61.24; H, 4.51; N, 3.36; S, 7.53.

Example 34

Preparation of 4-(7-chlorobenzo[b]thiophen-2-yl)-2-methyl-1,2,3,4-tetrahydroisoquinoline, maleate salt 4-(7-Chlorobenzo[b]thiophen-2-yl)-2-methyl-1,2,3,4-tetrahydroisoquinoline, maleate salt (373 mg, 98.4% AUC HPLC) was prepared from 2-chlorobenzenethiol and bromoacetaldehyde diethyl acetal as described in Example 36: $^1$H NMR (300 MHz, DMSO-d$_6$) δ 7.82 (d, J=6.6 Hz, 1H), 7.54 (s, 1H), 7.21-7.49 (m, 5H), 7.17 (d, J=7.2 Hz, 1H), 6.10 (s, 2H), 4.85-5.03 (m, 1H), 4.39 (d, J=14.4 Hz, 1H), 4.23 (d, J 13.5 Hz, 1H), 3.38-3.75 (m, 2H), 2.84 (s, 3H); EI MS m/z=314 [$C_{18}H_{16}ClNS+H$]$^+$. Anal. Calcd. for $C_{22}H_{20}NO_4S$: C, 60.14; H, 4.78; N, 3.19; with 2.06% $H_2O$. Found: C, 58.57; H, 4.84; N, 2.92.

Example 35

Preparation of 4-(4-methoxybenzo[b]thiophen-2-yl)-2-methyl-1,2,3,4-tetrahydroisoquinoline, maleate salt 4-(4-Methoxybenzo[b]thiophen-2-yl)-2-methyl-1,2,3,4-tetrahydroisoquinoline, maleate salt (73 mg, 99.1% AUC HPLC) was prepared from 3-methoxybenzenethiol and bromoacetaldehyde diethyl acetal as described in Example 36: $^1$H NMR (300 MHz, MeOD) δ 7.25-7.41 (m, 7H), 6.87 (d, J=7.8 Hz, 1H), 6.25 (s, 2H), 4.99-5.04 (m, 1H), 4.50-4.61 (m, 2H), 3.93-3.98 (m, 4H), 3.69-3.76 (m, 1H), 3.09 (s, 3H); EI MS m/z=310 [$C_{19}H_{19}NOS+H$]$^+$.

Example 36

Preparation of 4-(5-methoxybenzothiophen-2-yl)-2-methyl-1,2,3,4-tetrahydroisoquinoline, maleate salt Step A: Bromoacetaldehyde diethyl acetal (10.2 ml, 68 mmol) was added dropwise to a suspension of 4-methoxybenzenethiol (10.0 g, 71 mmol) and potassium carbonate (9.8 g, 71 mmol) in acetone (120 ml) at room temperature. After stirring under these conditions for 15 hours, the reaction mixture was filtered through diatomaceous earth, rinsed with acetone and the filtrate was concentrated under vacuum. The resulting residue was taken into water and ethyl acetate. The two layers were separated and the aqueous phase was extracted with ethyl acetate twice. The combined organic extracts were washed with aqueous sodium hydroxide (1 M) and brine, dried over sodium sulfate and concentrated under vacuum. The crude material was purified by chromatography (19:1 heptane/ethyl acetate) to give the desired product (16.2 g, 89%, 94.1% AUC GC): $^1$H NMR (300 MHz, CDCl$_3$) δ 7.38-7.43 (m, 2H), 6.83-6.87 (m, 2H), 4.61 (t, J=5.7 Hz, 1H), 3.80 (s, 3H), 3.49-3.71 (m, 4H), 3.02 (d, J=6.0 Hz, 2H), 1.19 (t, J=7.5 Hz, 6H).

Step B: A solution of the product from Step A (15.0 g, 58.5 mmol) in chlorobenzene (65 ml) was added dropwise to a solution of polyphosphoric acid (125 g) in chlorobenzene (375 ml) heated to 135° C. After stirring at 135° C. for 1.5 hours, the mixture was cooled below 50° C. The chlorobenzene layer was poured out of the reaction flask and was concentrated under vacuum. Meanwhile, water was added to the reaction vessel to decompose polyphosphoric acid. The resulting aqueous phase was added to the residue from the chlorobenzene layer. Additional water and dichloromethane were added and the two phases were separated. The aqueous layer was extracted with dichloromethane twice. The combined organic extracts were dried with sodium sulfate and concentrated under vacuum. The crude material was purified by chromatography (15:1 heptane/ethyl acetate) to give the cyclized product (4.5 g, 47%, 100% AUC GC): $^1$H NMR (300 MHz, CDCl$_3$) δ 7.87 (d, J=9.0 Hz, 1H), 7.58 (d, J=5.4 Hz, 1H), 7.39-7.42 (m, 2H), 7.14 (dd, J=9.0, 2.4 Hz, 1H), 4.01 (s, 3H).

Step C: N,N,N',N'-Tetramethylethylenediamine (2.0 ml, 13.4 mmol) was added dropwise to a solution of the product from Step B (2.0 g, 12.2 mmol) in tetrahydrofuran (50 ml) at −40° C. At completion of the addition, the mixture was stirred for 15 minutes under these conditions. n-Butyllithium (9.0 mL, 1.6 M) was added dropwise and the resulting mixture was stirred for 1 hour allowing the temperature to reach −30° C. Trimethyl borate (1.5 ml, 13.4 mmol) was added dropwise and the mixture was allowed to warm to 20° C. overnight. The reaction was quenched with 1 M hydrochloric acid, extracted with ethyl acetate three times and dried over anhydrous sodium sulfate to give the desired crude boronic acid (2.6 g, quantitative). This material was used in the next step without purification.

Step D: The crude from Step C (2.5 g, 12.0 mmol) was added to a solution of 4-bromoisoquinoline (1.7 g, 8.0 mmol) and triphenylphosphine (0.4 g, 1.6 mmol) in 1,2-dimethoxyethane (40 ml). The mixture was degassed three times with argon. Palladium acetate (0.2 g, 0.8 mmol) was added and the suspension was stirred at room temperature for 20 minutes. Aqueous sodium carbonate (9.6 ml, 2 M solution) was added and the suspension was degassed three times with argon. After stirring at 85° C. for 15 hours, the cooled mixture was diluted with water and extracted with dichloromethane twice. The combined extracts were dried with sodium sulfate, concentrated under vacuum and purified by chromatography (5:1 heptane/ethyl acetate) to give the desired isoquinoline (1.8 g, 76%, 97.9% AUC HPLC) after purification by chromatography: $^1$H NMR (300 MHz, CDCl$_3$) δ 9.21 (s, 1H), 8.62 (s, 1H), 8.24 (d, J=8.1 Hz, 1H), 7.99 (d, J=7.8 Hz, 1H), 7.58-7.71 (m, 3H), 7.38 (s, 1H), 7.26 (d, J=2.1 Hz, 1H), 7.19 (s, 1H), 6.99 (dd, J=9.0, 2.4 Hz, 1H), 3.84 (s, 3H).

Step E: A solution of the product from Step D (1.8 g, 6.2 mmol) and iodomethane (1.2 ml, 18.5 mmol) in chloroform (40 ml) was stirred at 60° C. for 15 hours. The cooled mixture was concentrated under vacuum to afford the methylated crude material (2.6 g, 97%, 79% AUC HPLC): $^1$H NMR (300 MHz, CDCl$_3$) δ 10.83 (s, 1H), 8.71 (d, J=8.1 Hz, 1H), 8.46 (d, J=8.4 Hz, 1H), 8.34 (s, 1H), 8.10 (dt, J=7.2, 1.2 Hz, 1H), 7.96 (t, J=7.2 Hz, 1H), 7.68-7.74 (m, 2H), 7.32 (d, J=2.4 Hz), 7.07 (dd, J=9.0, 2.7 Hz, 1H), 4.75 (s, 3H), 3.85 (s, 3H).

Step F: Sodium cyanoborohydride (0.85 g, 13.5 mmol) followed by two drops of a methanolic solution of bromocresol green was added to a solution of the crude from Step E (2.6 g, 6.0 mmol) in methanol (10 ml). A blue color was observed. Methanolic HCl was added until the reaction mixture turned yellow. The resulting mixture was stirred at room temperature for 1 hour with periodic addition of methanolic HCl to maintain the yellow color. The mixture was quenched by adding aqueous sodium hydroxide (10 ml, 3 M) and extracted with ethyl acetate twice. The organic extracts were washed with brine, dried over magnesium sulfate and concentrated to give the desired tetrahydroisoquinoline (1.6 g, 86%, 99.3% AUC HPLC) after purification by chromatography (5:1 heptane/ethyl acetate): $^1$H NMR (300 MHz, CDCl$_3$) δ 7.60 (d, J=8.7 Hz, 1H), 7.09-7.21 (m, 6H), 6.92 (dd, J=8.7, 2.4 Hz, 1H), 4.55 (t, J=10.8 Hz, 1H), 3.86 (s, 3H), 3.79 (d, J=15.0 Hz, 1H), 3.64 (d, J=15.0 Hz, 1H), 3.02 (dd, J=11.4, 4.5 Hz, 1H), 2.91 (dd, J=11.4, 6.0 Hz, 1H), 2.50 (s, 3H).

Step G: The product from Step F (1.6 g) was crystallized with maleic acid in dichloromethane. The resulting solids were triturated with MTBE and dried under high vacuum to give 4-(5-methoxybenzothiophen-2-yl)-2-methyl-1,2,3,4-tetrahydroisoquinoline, maleate salt (2.1 g, 95%, 99.3% AUC HPLC): $^1$H NMR (300 MHz, MeOD) δ 7.68 (d, J=9.0 Hz, 1H), 7.25-7.37 (m, 6H), 6.99 (dd, J=9.0, 2.7 Hz, 1H), 6.24 (s, 2H), 5.04 (dd, J=9.9, 6.0 Hz, 1H), 4.59 (s, 2H), 3.99 (dd, J=12.6, 6.0 Hz, 1H), 3.85 (s, 3H), 3.75 (dd, J=12.3, 10.2 Hz, 1H), 3.11 (s, 3H), EI MS m/z=310 [C$_{19}$H$_{19}$NOS+H]$^+$. Anal. Calcd. for C$_{23}$H$_{23}$NO$_5$S: C, 63.17; H, 5.44; N, 3.15; S, 7.20 with 1.7% H$_2$O. Found: C, 62.94; H, 5.42; N, 2.75; S, 6.80.

Example 37

Preparation of 4-(6-methoxybenzo[b]thiophen-2-yl)-2-methyl-1,2,3,4-tetrahydroisoquinoline 4-(6-Methoxybenzo[b]thiophen-2-yl)-2-methyl-1,2,3,4-tetrahydroisoquinoline (29 mg, 96.9% AUC HPLC) was prepared from 3-methoxybenzenethiol and bromoacetaldehyde diethyl acetal as described in Example 36 (Steps A to F): $^1$H NMR (300 MHz, CDCl$_3$) δ 7.57 (d, J=8.7 Hz, 1H), 7.24 (d, J=2.4 Hz, 1H), 7.09-7.22 (m, 4H), 7.07 (s, 1H), 6.95 (dd, J=2.4, 8.7 Hz, 1H), 4.54 (t, J=5.4 Hz, 1H), 3.85 (s, 3H), 3.78 (d, J=15.0 Hz, 1H), 3.65 (d, J=15.0 Hz, 1H), 3.02 (dd, J=4.8, 11.4 Hz, 1H), 2.90 (dd, J=6.3, 11.4 Hz, 1H), 2.51 (s, 3H); EI MS m/z=310 [C$_{19}$H$_{19}$NOS+H]$^+$.

Example 38

Preparation of 4-(benzo[b]thiophen-3-yl)-2-methyl-1,2,3,4-tetrahydroisoquinoline 4-(Benzo[b]thiophen-3-yl)-2-methyl-1,2,3,4-tetrahydroisoquinoline was prepared from 3-benzo[b]thiophene boronic acid and 4-bromoisoquinoline as described in Example 36 (Steps D to F): $^1$H NMR (300 MHz, CDCl$_3$) δ 7.55-7.58 (m,□7.88-7.82 (m, 1H), 1H), 7.22-7.27 (m, 2H), 6.90-7.10 (m, 5H), 4.69 (dd, J=6.9, 6.6 Hz, 1H), 3.72 (d, J=15.0 Hz, 1H), 3.63 (d, J=15.0 Hz, 1H), 3.00 (dd, J=11.4, 5.4 Hz, 1 H), 2.73 (dd, J=11.4, 8.1 Hz, 1H), 2.38 (s, 3H); EI MS m/z=280 [C$_{18}$H$_{17}$NS+H]$^+$.

Example 39

Preparation of 4-(benzo[b]thiophen-4-yl)-2-methyl-1,2,3,4,tetrahydroisoquinoline, maleate salt 4-(Benzo[b]thiophen-4-yl)-2-methyl-1,2,3,4-tetrahydroisoquinoline, maleate salt (0.13 g, 99.6% AUC HPLC) was prepared from 3-bromobenzenethiol as described in Example 69: $^1$H NMR (300 MHz, DMSO-d$_6$) δ 7.87 (d, J=7.9 Hz, 1H), 7.68 (d, J=5.5 Hz, 1H), 7.01-7.34 (m, 6H), 6.62 (d, J=7.7 Hz, 1H), 4.87-4.92 (m, 1H), 4.39 (q, J=15.5 Hz, 2H), 3.60-3.64 (m, 1H), 3.4 (t, J=11.4 Hz, 1H), 2.78 (s, 3H); EI MS m/z=280 [C$_{18}$H$_{17}$NS+H]$^+$. Anal. Calcd. for C$_{22}$H$_{21}$NO$_4$S: C, 64.60; H, 5.48; N, 3.42; S, 7.83. Found: C, 66.55; H, 5.52; N, 3.46; S, 7.87.

Example 40

Preparation of (+)-4-(benzo[b]thiophen-5-yl)-2-methyl-1,2,3,4-tetrahydroisoquinoline, hydrochloride salt and (−)-4-(benzo[b]thiophen-5-yl)-2-methyl-1,2,3,4-tetrahydroisoquinoline, hydrochloride salt Step A: Bromoacetaldehyde diethyl acetal (19 ml, 132 mmol) was added dropwise to a suspension of 4-bromobenzenethiol (25 g, 126 mmol) and potassium carbonate (18 g, 132 mmol) in acetone (200 ml) at room temperature. After stirring for 15 hours under these conditions, the reaction mixture was filtered through diatomaceous earth, rinsed with acetone and the filtrate was concentrated under vacuum. The resulting residue was taken into water and ethyl acetate. The two layers were separated and the aqueous phase was extracted with ethyl acetate twice. The combined organic extracts were washed with aqueous sodium hydroxide (1 M) and brine, dried over anhydrous sodium sulfate and concentrated under vacuum to give the desired product (35 g, 91%, 100% AUC GC) after chromatography (9:1 heptane/ethyl acetate): $^1$H NMR (300 MHz, CDCl$_3$) □δ 7.24-7.45□□m, 4H), 4.64 (t, J=5.5 Hz, 1H), 3.49-3.74 (m, 4H), 1.71 (d, J=5.5 Hz, 2H), 1.18-1.27 (m, 6H).

Step B: A solution of the product from Step A (35 g, 92 mmol) in chlorobenzene (50 ml) was added dropwise to a solution of polyphosphoric acid (100 g) in chlorobenzene (250 ml) at 135° C. After stirring at 135° C. for 1 hour, the mixture was cooled below 50° C. The chlorobenzene layer was poured out of the reaction flask and was concentrated under vacuum. Meanwhile, water was added to the reaction vessel at 0° C. to decompose polyphosphoric acid. The resulting aqueous phase was added to the residue from the chlorobenzene layer. Additional water and dichloromethane were added and the two phases were separated. The aqueous layer was extracted with dichloromethane twice. The combined organic extracts were dried with anhydrous sodium sulfate and concentrated under vacuum to give the cyclized product (18 g, 72%) after chromatography (100% heptane): $^1$H NMR (300 MHz, CDCl$_3$) δ 7.98□□d□□J=1.8 Hz, 1H), 7.76 (d, J=8.6 Hz, 1H), 7.44-7.50 (m, 2H), 7.29 (d, J=5.8 Hz, 1H).

Step C: Isoquinolin-4-ylboronic acid (2.4 g, 14.0 mmol) was added to a solution of the product from Step B (2.0 g, 9.4 mmol) and triphenylphosphine (0.5 g, 1.9 mmol) in 1,2-dimethoxyethane (50 ml). The suspension was degassed with nitrogen. Palladium acetate (0.2 g, 0.9 mmol) was added and the batch was stirred at room temperature for 20 minutes. Aqueous sodium carbonate (11.3 ml, 2 M solution) was added and the suspension was degassed again with nitrogen. The mixture was stirred at 85° C. for 3.5 hours, cooled, diluted with water and extracted with ethyl acetate twice. The combined organic extracts were dried over anhydrous sodium sulfate, concentrated under vacuum and purified by chromatography (5:1 heptane/ethyl acetate) to give the desired isoquinoline (1.8 g, 74%, 98% AUC HPLC): $^1$H NMR (300 MHz, CDCl$_3$) δ 9.30□□s, 1H), 8.59□□s, 1H), 7.95-8.07□□m, 4H), 7.43-7.72 (μ, 5H).

Step D: A solution of the product from Step C (1.8 g, 7.0 mmol) and iodomethane (1.3 ml, 21.0 mmol) in chloroform (30 ml) was stirred at 60° C. for 15 hours. The cooled mixture was concentrated under vacuum to afford the methylated crude material (3.1 g, 81.9% AUC HPLC): $^1$H NMR (300 MHz, DMSO-d$_6$) δ 10.99 (s, 1H), 8.81 (d, J=8.1 Hz, 1H), 8.27 (s, 1H), 8.02-8.17 (m, 4H), 7.49-7.55 (m, 4H), 4.86 (s, 3H).

Step E: Sodium cyanoborohydride (1.1 g, 17.3 mmol) followed by two drops of a methanolic solution of bromocresol green was added to a solution of the crude from Step D (3.1 g, 7.7 mmol) in methanol (50 ml). A blue color was observed. Methanolic HCl was added until the reaction mixture turned yellow. The resulting mixture was stirred at room temperature for 5 hour with periodic addition of methanolic HCl to maintain the yellow color. The mixture was quenched by adding aqueous sodium hydroxide (3 M) and extracted with ethyl acetate twice. The combined organic extracts were washed with brine, dried over anhydrous magnesium sulfate and concentrated to give the desired tetrahydroisoquinoline (1.5 g, 78% for 2 steps, 97.4% AUC HPLC) after purification by chromatography (3:1 heptane/ethyl acetate): $^1$H NMR (300 MHz, CDCl$_3$) δ 7.81 (d, J=8.3 Hz, 1H), 7.68 (s, 1H), 7.44 (d, J=5.5 Hz, 1H), 7.3 (s, 1H), 7.10-7.22 (m, 4H), 6.91 (d, J=7.6 Hz, 1H), 4.42 (t, J=7.5 Hz, 1H), 3.81 (d, J=15.0 Hz, 1H), 3.68 (d, J=14.7 Hz, 1H), 3.10 (ddd, J=11.4, 5.7, 1.2 Hz, 1H), 2.63-2.69 (m, 1H), 2.46 (s, 3H).

Step F: The racemic compound from Step E (105 mg) was separated on semi-prep chiral HPLC (chiralcel OD-H, 1×25 cm, eluent: 3% isopropanol in heptane, flow: 4 ml/minute, 500 μl injections, 5 mg/injection). The resulting free bases were dissolved in ethyl acetate and treated with a 2 M solution of HCl in diethyl ether (2 equiv) to give (+)-4-benzo[b]thiophen-5-yl-2-methyl-1,2,3,4-tetrahydroisoquinoline, hydrochloride salt (47 mg, 100% AUC HPLC, 100% AUC chiral HPLC): $^1$H NMR (300 MHz, MeOD) δ 7.94 (d, J=8.4 Hz, 1H), 7.82 (s, 1H), 7.65 (d, J □=5.4 Hz, 1H), 7.19-7.37 (m, 5H), 6.93 (d, J=7.5 Hz, 1H), 4.64-4.81 (m, 3H), 3.90-3.96 (m, 1H), 3.62 (t, J=12.3 Hz, 1H), 3.12 (s, 3H); EI MS m/z=280 [C$_{18}$H$_{17}$NS+H]$^+$; [α]$^{25}$$_D$ +60° (c 1.0, MeOH, free base), and (−)-4-benzo[b]thiophen-5-yl-2-methyl-1,2,3,4-tetrahydroisoquinoline, hydrochloride salt (46 mg, 99.7% AUC HPLC, 100% chiral HPLC): $^1$H NMR (300 MHz, MeOD) δ 7.94 (dd, J=8.4, 2.4 Hz, 1H), 7.82 (s, 1H), 7.65 (dd, J□=5.4, 2.4 Hz, 1H), 7.19-7.39 (m, 5H), 6.93 (d, J=7.8 Hz, 1H), 4.64-4.82 (m, 3H), 3.86-3.96 (m, 1H), 3.61 (t, J=12.6 Hz, 1H), 3.12 (s, 3H); EI MS m/z=280 [C$_{18}$H$_{17}$NS+H]$^+$, [α]$^{25}$$_D$ −60° (c 1.0, MeOH, free base).

Example 41

Preparation of 4-(benzo[b]thiophen-5-yl)-2,7-dimethyl-1,2,3,4-tetrahydroisoquinoline, hydrochloride salt Step A: Ethyl chloroformate (28 ml, 293 mmol) was added dropwise to a solution of 4-methylcinnamic acid (40 g, 247 mmol) and triethylamine (69 ml, 492 mmol) in acetone (300 ml) at 0° C. and the resulting mixture was stirred at 0° C. for 1 hour. A solution of sodium azide (26 g, 400 mmol) in water (100 ml) was added dropwise keeping the temperature of the mixture below 5° C. At completion of the addition, the mixture was stirred at room temperature for 2 hours. Water (400 ml) was added and acetone was removed under vacuum (note: the bath temperature of the rotary evaporator was kept at 40° C. and a blastshield was placed in front of the rotary evaporator). The resulting slurry was extracted with toluene (3×100 ml). The combined organic extracts were dried over anhydrous magnesium sulfate and filtered. The filtrate was added dropwise to a solution of tributylamine (120 ml, 503 mmol) in diphenyl ether (200 ml) at 190° C. Toluene was distilled off the reaction mixture as the addition progressed. At the end of the addition, the mixture was stirred at 210° C. for 2 hours and was cooled to room temperature. The resulting slurry was filtered and rinsed with heptane to give the desired isoquinolone (24 g, 62%) as a yellow solid: $^1$H NMR (300 MHz, CDCl$_3$) δ 8.25 (s, 1H), 7.47-7.51 (m, 2H), 7.18 (d, J=6.9 Hz, 1H), 6.57 (d, J=6.9 Hz, 1H), 2.52 (s, 3H).

Step B: A solution of bromine (4.8 ml, 94 mmol) in acetic acid (50 ml) was added dropwise to a solution of the product from Step A (15.0 g, 94 mmol) in acetic acid (300 ml) at room temperature. The mixture was stirred at room temperature for 4 hours, poured into iced water, extracted with dichloromethane three times and dried over magnesium sulfate to give the desired product (24.2 g): $^1$H NMR (300 MHz, CDCl$_3$) δ 8.24 (s, 1H), 7.80 (d, J=8.4 Hz, 1H), 7.63 (dd, J=8.4, 1.8 Hz, 1H), 7.39 (s, 1H), 2.55 (s, 3H).

Step C: A solution of the product from Step B (24.2 g, 102 mmol) in phosphorus oxychloride (250 ml) was stirred at 110° C. for 4 hours. The mixture was cooled to room temperature and phosphorus oxychloride was evaporated under vacuum. The residue was quenched with saturated sodium bicarbonate at 0° C. and extracted with dichloromethane three times. The combined organic extracts were washed with saturated sodium bicarbonate and dried over magnesium sulfate to give the desired material (22.0 g, 91% for 2 steps): $^1$H NMR (300 MHz, CDCl$_3$) δ 8.41 (s, 1H), 8.10 (d, J=0.6 Hz, 1H), 8.06 (d, J=8.7 Hz, 1H), 7.69 (dd, J=8.7, 1.5 Hz, 1H), 2.63 (s, 3H).

Step D: Red phosphorus (3.9 g, 125 mmol) was added to a solution of the product from Step C (9.5 g, 27 mmol) in hydriodic acid (22.7 ml, 57 wt. % in water) and the mixture was stirred at 140° C. for 5 hours. After cooling to room temperature, the mixture was poured into saturated sodium bicarbonate (500 ml, containing 10 g of sodium sulfite). Dichloromethane (250 ml) was added and the mixture was filtered through diatomaceous earth to remove phosphorus. The filtrate was extracted with dichloromethane three times and dried over magnesium sulfate to give 4-bromo-7-methylisoquinoline (4.6 g, 76%, 98.3% AUC GC) after purification by chromatography (5:1 heptane/ethyl acetate): $^1$H NMR (300 MHz, CDCl$_3$) δ 9.01 (s, 1H), 8.61 (s, 1H), 7.96 (d, J=8.7 Hz, 1H), 7.64 (s, 1H), 7.56 (d, J=8.7 Hz, 1H), 2.53 (s, 3H).

Step E: Bis(pinacolato)diboron (1.3 g, 5.12 mmol), dichloro[1,1'-bis(diphenylphosphino)ferrocene]palladium (II) dichloromethane (0.1 g, 0.14 mmol) and potassium acetate (1.4 g, 14.26 mmol) were charged in a 100 ml 3 neck round-bottomed flask which had been dried with a heat gun under vacuum and cooled under nitrogen prior to use. The mixture was degassed with nitrogen three times. A solution of 5-bromothiophene (1.0 g, 4.69 mmol) in dimethyl sulfoxide (20 ml) was added, the mixture was degassed again three times and was stirred at 85° C. for 1.5 hours. After cooling to room temperature, the mixture was filtered through diatomaceous earth and rinsed with water and ethyl acetate. Additional water was added to the filtrate which was extracted with ethyl acetate three times. The combined organic extracts were washed with brine once and dried over sodium sulfate to give the desired material (0.8 g, 64%, 100% AUC GC) after chromatography (9:1 to 5:1 heptane/ethyl acetate): $^1$H NMR (300 MHz, CDCl$_3$) δ 8.24 (s, 1H), 7.81 (d, J=8.1 Hz, 1H), 7.68 (dd, J=8.1, 0.6 Hz, 1H), 7.34 (d, J=5.4 Hz, 1H), 7.28 (dd, J=5.4, 0.6 Hz, 1H), 1.30 (s, 12H).

Step F: An aqueous solution of sodium bicarbonate (4.30 ml, 2 M) was added to a solution of the bromoisoquinoline from Step D (0.64 g, 2.9 mmol), the product from Step E (0.75 g, 2.9 mmol) and triphenylphosphine (0.30 g, 1.2 mmol) in DMF (20 ml) at room temperature. The resulting mixture was degassed with nitrogen three times. Palladium (II) acetate (0.07 g, 0.3 mmol) was added, the mixture was degassed with nitrogen three times and stirred at 80° C. for 15 hours. After cooling to room temperature, the mixture was filtered through diatomaceous earth and rinsed with water and ethyl acetate. The filtrate was washed with water twice and brine, and dried over magnesium sulfate to give the desired coupled isoquinoline (0.70 g, 88%) after chromatography (5:1 to 3:1 heptane/ethyl acetate): $^1$H NMR (300 MHz, CDCl$_3$) δ 7.94 (d, J=8.4 Hz, 1H), 7.88 (d, J=1.2 Hz, 1H), 7.75-7.78 (m, 2H), 7.47 (d, J=5.4 Hz, 1H), 7.40-7.44 (m, 2H), 7.34 (d, J=5.4 Hz, 1H), 2.50 (s, 3H).

Step G: The product from Step F (0.7 g, 2.5 mmol) was methylated according to the procedure described in Example 40 (Step D) to give the desired methylated isoquinoline (1.0 g, 95%): ¹H NMR (300 MHz, DMSO-d₆) δ 9.93 (s, 1H), 8.79 (d, J=0.9 Hz, 1H), 8.30-8.33 (m, 2H), 8.07-8.16 (m, 3H), 7.96 (d, J=5.7 Hz, 1H), 7.58-7.63 (m, 2H), 4.53 (s, 3H), 2.65 (s, 3H).

Step H: The product from Step G (1.01 g, 2.4 mmol) was reduced following the procedure described in Example 40 (Step E) to give the desired tetrahydroisoquinoline (0.38 g, 53%, 97.3% AUC HPLC): ¹H NMR (300 MHz, CDCl₃) δ 7.80 (d, J=8.4 Hz, 1H), 7.68 (d, J=1.5 Hz, 1H), 7.43 (d, J=5.4 Hz, 1H), 7.28-7.29 (m, 1H), 7.20 (dd, J=8.4, 1.8 Hz, 1H), 6.89-6.94 (m, 2H), 6.79 (d, J=7.8 Hz, 1H), 4.38 (t, J=7.8 Hz, 1H), 3.76 (d, J=14.7 Hz, 1H), 3.63 (d, J=15.0 Hz, 1H), 3.08 (ddd, J=11.4, 5.7, 1.2 Hz, 1H), 2.63 (dd, J=11.4, 8.4 Hz, 1H), 2.45 (s, 3H), 2.32 (s, 3H).

Step I: 4-Benzo[b]thiophen-5-yl-2,7-dimethyl-1,2,3,4-tetrahydroisoquinoline, hydrochloride salt (0.24 g, 64%) was prepared by dissolving the product from Step H (0.33 g, 1.1 mmol) in ethyl acetate and treating the resulting solution with 2 M hydrochloride in diethyl ether (2 equiv) at room temperature: 1H NMR (300 MHz, DMSO-d₆) δ 11.52 (br s, 1H)☐☐8.01 (d, J=8.1 Hz, 1H), 7.79-7.82 (m, 2H), 7.45 (d, J=4.2 Hz, 1H), 7.18 (d, J=8.4 Hz, 1H), 7.07 (s, 1H), 7.05 (d, J=6.3 Hz, 1H), 6.64 (d, J=7.8 Hz, 1H), 4.64-4.75 (m, 1H), 4.49 (s, 2H), 3.45-3.82 (m, 2H), 2.92 (s, 3H), 2.28 (s, 3H); EI MS m/z=294 [C₁₉H₁₉NS+H]⁺. Anal. Calcd. for C₁₉H₂₀ClNS: C, 68.44; H, 6.03; N, 4.20 with 1.1 equiv HCl. Found: C, 68.49; H, 5.76; N, 4.05.

Example 42

Preparation of 4-(2-methylbenzo[b]thiophen-5-yl)-2-methyl-1,2,3,4-tetrahydroisoquinoline, hydrochloride salt Step A: A mixture of 4-bromothiophenol (5.0 g, 26.4 mmol), 2,3-dichloro-1-propene (2.6 g, 23.8 mmol) and potassium carbonate (4.4 g, 31.7 mmol) in acetone (20 ml) was stirred at 55° C. for 6 hours. After cooling to room temperature, acetone was removed under vacuum and the residue was taken into water and extracted with ethyl acetate twice. The combined organic layers were washed with 1 M sodium hydroxide, water and brine, dried over anhydrous sodium sulfate, filtered and concentrated under vacuum. Diethylaniline (30 ml) was added to the residue and the resulting mixture was stirred at 185° C. for 15 hours. Ethyl acetate was added to the cooled mixture and diethylaniline was removed by washing with 1 M HCl four times. The organic layer was dried over sodium carbonate to give 5-bromo-2-methylbenzothiophene (5.3 g, 88%, 95.1% AUC GC): ¹H NMR (300 MHz, CDCl₃) δ 7.70 (s, 1H), 7.52 (d, J=8.7 Hz, 1H), 7.26 (dd, J=8.7, 1.8 Hz, 1H), 6.83 (s, 1H), 2.51 (s, 3H).

Step B: 4-(2-methylbenzo[b]thiophen-5-yl)-2-methyl-1,2,3,4-tetrahydroisoquinoline was prepared from 5-bromo-2-methylbenzothiophene and isoquinolin-4-ylboronic acid as described in Example 40 (Steps C to E). The free base was dissolved in ethyl acetate and treated with 2 M hydrogen chloride in diethyl ether (2 equiv) to give the corresponding hydrochloride salt (0.41 g, 98.8% AUC HPLC): ¹H NMR (300 MHz, DMSO-d₆) δ 11.09 (br s, 1H), 7.88 (d, J=8.4 Hz, 1H), 7.63 (s, 1H), 7.09-7.27 (m, 5H), 6.76 (d, J=7.5 Hz, 1H), 4.69 (dd, J=10.8, 6.3 Hz, 1H), 4.55 (br s, 2H), 3.54-3.83 (m, 2H), 2.94 (s, 1H), 2.57 (s, 3H); EI MS m/z=293 [C₁₉H₁₉NS]⁺. Anal. Calcd. for C₁₉H₂₀ClNS: C, 68.61; H, 6.10; N, 4.21 with 0.73% H₂O. Found: C, 68.35; H, 6.55; N, 4.00.

Example 43

Preparation of 4-(benzo[b]thiophen-5-yl)-7-fluoro-2-methyl-1,2,3,4-tetrahydroisoquinoline, hydrochloride salt 4-(Benzo[b]thiophen-5-yl)-7-fluoro-2,methyl-1,2,3,4-tetrahydroisoquinoline, hydrochloride salt (0.31 g, 99.5% AUC HPLC) was prepared from 7-fluorocinnamic acid and 5-bromothiophene as described in Example 41: 1H NMR (300 MHz, DMSO-d₆) δ 11.48 (br s, 1H)☐☐8.03 (d, J=8.1 Hz, 1H), 7.81-7.82 (m, 2H), 7.46 (d, J=5.1 Hz, 1H), 7.20 (d, J=8.7 Hz, 1H), 7.00-7.08 (m, 1H), 6.79 (br s, 1H), 4.68-4.76 (m, 1H), 4.54 (s, 2H), 3.54-3.82 (m, 3H), 2.93 (s, 3H), 2.51 (s, 3H); EI MS m/z=298 [C₁₈H₁₆FNS+H]⁺. Anal. Calcd. for C₁₈H₁₇ClFNS: C, 64.01; H, 5.07; N, 4.15 with 1.1 equiv HCl. Found: C, 63.91; H, 5.50; N, 3.86.

Example 44

Preparation of 4-(benzo[b]thiophen-6-yl)-2-methyl-1,2,3,4-tetrahydroisoquinoline, maleate salt 4-(Benzo[b]thiophen-6-yl)-2-methyl-1,2,3,4-tetrahydroisoquinoline, maleate salt (0.09 g, 99.7% AUC HPLC) was prepared from 3-bromobenzenethiol as described in Example 69: ¹H NMR (300 MHz, DMSO-d₆) δ 7.80-7.86 (m, 2H), 7.71 (d, J=5.4 Hz, 1H), 7.39 (d, J=5.4 Hz, 1H), 7.11-7.22 (m, 4H), 6.76 (d, J=7.6 Hz, 1H), 6.00 (s, 2H), 4.53-4.59 (m, 1H), 4.34-4.46 (m, 2H), 3.65-3.81 (m, 1H), 3.46 (t, J=11.3 Hz, 1H), 3.26 (s, 3H); EI MS m/z=280 [C₁₈H₁₇NS+H]⁺. Anal. Calcd. for C₂₂H₂₁NO₄S: C, 66.82; H, 5.35; N, 3.54; S, 8.11. Found: C, 66.76; H, 5.26; N, 3.42; S, 7.97.

Example 45

Preparation of 4-indol-1-yl-2-methyl-1,2,3,4-tetrahydroisoquinoline, hydrochloride salt Step A: 4-Indol-1-ylisoquinoline (0.88 g, 3.6 mmol) and iodomethane (0.67 ml, 10.8 mmol) in chloroform (18 ml) were stirred at 60° C. for 15 hours. The cooled mixture was concentrated under vacuum to afford the methylated crude material (1.5 g, 76.4% AUC HPLC): ¹H NMR (300 MHz, CDCl₃) δ 11.05 (s, 1H), 8.86-8.89 (m, 1H), 8.39-8.42 (m, 1H), 8.08-8.13 (m, 2H), 7.89-7.92 (m, 1H), 7.77-7.80 (m, 1H), 7.58 (d, J=3.3 Hz, 1H), 7.24-7.30 (m, 2H), 7.09-7.12 (m, 1H), 6.93 (d, J=3.3 Hz, 1H), 4.86 (s, 3H).

Step B: Sodium cyanoborohydride (0.55 g, 8.7 mmol) followed by two drops of a methanolic solution of bromocresol green was added to a solution of the crude from Step A (1.5 g, 3.9 mmol) in methanol (20 ml). A blue color was observed. Methanolic HCl was added until the reaction mixture turned yellow. The resulting mixture was stirred at room temperature for 5 hours with periodic addition of methanolic HCl to maintain the yellow color. The mixture was quenched by adding aqueous sodium hydroxide (3 M) and extracted with ethyl acetate twice. The combined organic extracts were washed with brine, dried over anhydrous magnesium sulfate and concentrated to give the desired tetrahydroisoquinoline (0.65 g, 64% for 2 steps, 94.9% AUC HPLC) after purification twice by chromatography (5:1 heptane/ethyl acetate): ¹H NMR (300 MHz, CDCl₃) δ 7.57 (d, J=7.8 Hz, 1H), 7.29 (d, J=8.1 Hz, 1H), 7.01-7.19 (m, 3H), 6.94 (d, J=3.0 Hz, 1H), 6.87 (d, J=7.8 Hz, 1H), 6.39-6.40 (m, 1H), 5.70-5.74 (m, 1H), 3.66 (s, 2H), 3.00 (dd, J=11.4, 5.1 Hz, 1H), 2.82 (dd, J=11.4, 6.9 Hz, 1H), 2.37 (s, 3H).

Step C: The product from Step B (37 mg, 0.14 mmol) was dissolved in ethyl acetate (1 mL) and treated with a 2 M solution of HCl in diethyl ether (0.14 mL) to give 4-indol-1-yl-2-methyl-1,2,3,4-tetrahydroisoquinoline, hydrochloride salt (28 mg, 64%, 98% AUC HPLC): $^1$H NMR (300 MHz, MeOD) δ 7.62 (d, J=7.5 Hz, 1H), 7.09-7.40 (m, 8H), 6.59 (s, 1H), 6.29 (m, 1H), 4.59-4.78 (m, 2H), 3.81-4.08 (m, 2H), 3.15 (s, 3H); EI MS m/z=263 $[C_{18}H_{18}N_2+H]^+$; Anal. Calcd. for $C_{18}H_{18}N_2$ with 1.2 HCl: C, 70.59; H, 6.27; N, 9.15. Found: C, 70.74; H, 6.41; N, 8.96.

Example 46

Preparation of 4-(1H-Indazol-5-yl)-2-methyl-1,2,3,4-tetrahydroisoquinoline

Step A: Indole (3.00 g, 25.6 mmol) and di-tert-butyl-dicarbonate (6.15 g, 28.2 mmol) were combined as described for the synthesis of Example 48, Step A. The crude product was carried onto Step B upon concentration in vacuo.

Step B: The crude product obtained from Step A and triisopropyl borate (7.22 g, 38.4 mmol) were combined as described for the synthesis of Example 48, Step B to afford, upon recrystalization, the product as a white solid (3.41 g, 51% over Steps A and B): $^1$H NMR (300 MHz, CD$_3$OD) δ 8.10 (d, J=7.7 Hz, 1H), 7.54 (d, J=6.3 Hz, 1H), 7.28-7.17 (m, 2H), 6.63 (s, 1H), 1.68 (s, 9H).

Step C: The boronic acid obtained in Step B (1.50 g, 5.74 mmol) and 4-bromoisoquinoline (956 mg, 4.60 mmol) were combined as described for the synthesis of Example 48, Step C to afford, after chromatography, the product as a white solid (1.05 g, 66%). $^1$H NMR (300 MHz, CDCl$_3$) δ 9.29 (s, 1H), 8.57 (s, 1H), 8.37 (d, J=8.3 Hz, 1H), 8.07-8.01 (m, 1H), 7.68-7.62 (m, 4H), 7.42-7.32 (m, 2H), 6.72 (s, 1H), 0.87 (s, 9H).

Step D: The product obtained in Step C (1.05 g, 3.05 mmol) and methyl triflate (551 mg, 3.36 mmol) were combined as described for the synthesis of Example 48, Step D to afford a yellow salt that was carried onto Step E.

Step E: The crude product obtained in Step D and sodium cyanoborohydride (767 mg, 12.2 mmol) were combined as described for the synthesis of Example 48, Step E to afford the product (698 mg, 87% over Steps D and E) as a light brown solid.

Step F: The product obtained in Step E and maleic acid (340 mg, 2.93 mmol) were combined as described for the synthesis of Example 48, Step F to afford, after recrystallization, the product (530 mg, 48%) as a white solid. mp 167-169 C; $^1$H NMR (300 MHz, CD$_3$OD) δ 7.48 (d, J=7.8 Hz, 1H), 7.35-7.27 (m, 4H), 7.15-6.97 (m, 3H), 6.34 (s, 1H), 6.24 (s, 2H), 4.84-4.80 (m, 1H), 4.53 (d, J=4.6 Hz, 2H), 3.91-3.87 (m, 1H), 3.73-3.69 (m, 1H), 3.07 (s, 3H); ESI-MS m/z 263 $[C_{18}H_{18}N_2+H]^+$; Anal. Calcd for $C_{18}H_{18}N_2$—$C_4H_4O_4$: C, 69.83; H, 5.86; N, 7.40. Found: C, 69.52; H, 5.86; N, 7.18.

Example 47

Preparation of 4-(1H-Indazol-5-yl)-2,7-dimethyl-1,2,3,4-tetrahydroisoquinoline

Step A: To a mixture of 1H-Indole-2-carboxylic acid (2.50 g, 15.5 mmol) and acetyl chloride (31 mL, 0.43 mol) in Et$_2$O (31.5 mL) was added phosphorus pentachloride (3.55 g, 17.1 mmol) in portions, and the mixture was then heated under reflux for 1.5 hours. The cooled reaction mixture was concentrated under reduced pressure, and the crude product obtained thus was recrystallized from heptanes to give 1H-indole-2-carbonyl chloride (2.04 g, 73%) as yellow needles.

Step B: To an ice-cold biphasic mixture of 40% aqueous KOH (7.88 g of KOH in 19.7 g of solution) and Et$_2$O (67 mL) was added 1-methyl-3-nitro-1-nitrosoguanidine (4.35 g, 29.5 mmol) over 15 minutes. After 30 minutes, the bright yellow Et$_2$O solution of diazomethane was decanted into an ice-cooled Erlenmeyer flask containing KOH pellets. After 2 hours, the ice-cold diazomethane solution was decanted into a second, ice-cooled Erlenmeyer flask. The acid chloride (2.04 g, 11.4 mmol) was added to the above solution over 15 minutes. The resultant mixture was stirred at 0° C. for 1 hour, and then stored at −30° C. overnight. Nitrogen was bubbled through the cold reaction mixture for 30 minutes, which was then diluted with EtOAc (60 mL). The reaction mixture was washed with water and brine, dried (MgSO$_4$), filtered and concentrated to give the crude product, which was used as such in Step C.

Step C: To an ice-cold suspension of the crude product from Step B in Et$_2$O (50 mL) was added 48% HBr (3 mL) dropwise. After 30 minutes, the reaction mixture was diluted with Et$_2$O (25 mL) and washed with water. The aqueous layer was re-extracted with Et$_2$O (25 mL). The organic extracts were combined, washed with brine, dried (MgSO$_4$), filtered and concentrated under reduced pressure to give the crude product (1.88 g, crude), which was used in Step D without further purification.

Synthesis of m-tolylamine: To a solution of m-tolualdehyde (6.4 mL, 54.0 mmol) in MeOH (50 mL) was added 40% aqueous methylamine (4.3 mL, 55.1 mmol). After 20 minutes, the mixture was cooled in an ice-bath, and sodium borohydride (3.07 g, 81.1 mmol) was added in small portions over 20 minutes. The mixture was then warmed to room temperature and stirred overnight. The reaction mixture was then concentrated under reduced pressure, and partitioned between water and CH$_2$Cl$_2$ (100 mL each). The aqueous layer was re-extracted with CH$_2$Cl$_2$ (2×50 mL), and the organic extracts were combined and washed with 2 N HCl (3×30 mL). The aqueous layer was washed with CH$_2$Cl$_2$ (50 mL), treated with concentrated NH$_4$OH (until pH 12), and extracted with CH$_2$Cl$_2$ (3×100 mL). The organic extracts were combined, washed with brine, dried (MgSO$_4$), filtered and concentrated under reduced pressure to give m-tolylamine (5.46 g, 75%), which was used in Step D without further purification. $^1$H NMR (300 MHz, CDCl$_3$) δ 7.26-7.05 (m, 4H), 3.72 (s, 2H), 2.46 (s, 3H), 2.35 (s, 3H).

Step D: To an ice-cold solution of the product from Step C (1.88 g, crude) in CH$_2$Cl$_2$ (15.8 mL) was added methyl m-tolylamine (1.1 g, 7.9 mmol), followed by diisopropylethylamine (1.8 mL, 10.6 mmol). The reaction mixture kept cold for 30 minutes, and then stirred at room temperature overnight. The reaction mixture was diluted with water, and the product was extracted in CH$_2$Cl$_2$ (3×40 mL). The organic extracts were combined, washed with brine, and concentrated under reduced pressure. Purification by flash column chromatography (90:10 CH$_2$Cl$_2$/hexanes, then CH$_2$Cl$_2$, 99:1 CH$_2$Cl$_2$/MeOH and 98:2 CH$_2$Cl$_2$/MeOH) gave partially purified product (1.86 g), which was used in Step E as such. $^1$H NMR (300 MHz, CDCl$_3$) δ 9.84 (br s, 1H), 7.69 (d, J=8.0 Hz, 1H), 7.41-7.09 (m, 8H), 3.75 (s, 2H), 3.67 (s, 2H), 2.42 (s, 3H), 2.35 (s, 3H).

Step E: To a mixture of the product from Step D (1.86 g) and DMAP (40 mg, 0.31 mmol) in $CH_3CN$ (25 mL) was added $Boc_2O$ (1.46 g, 6.68 mmol), and the mixture was stirred at room temperature for 45 minutes. The mixture was then diluted with water and $CH_2Cl_2$ (50 mL each). The organic layer was separated out, washed with brine, and concentrated under reduced pressure. Purification by flash column chromatography (gradient, 95:5 hexanes/EtOAc to 75:25 hexanes/EtOAc) gave the product (1.02 g, 17% over 5 steps) as a pale yellow oil: $^1H$ NMR (300 MHz, $CDCl_3$) δ 8.04 (d, J=8.4 Hz, 1H), 7.59 (d, J=7.8 Hz, 1H), 7.42-7.39 (m, 1H), 7.27-7.25 (m, 2H), 7.16 (d, J=7.3 Hz, 1H), 7.08-7.03 (m, 4H), 3.64 (s, 2H), 3.60 (s, 2H), 2.37 (s, 3H), 2.28 (s, 3H), 1.59 (s, 9H).

Step F: To an ice-cold solution of the product from Step E (1.02 g, 2.60 mmol) in MeOH (6.7 mL) was added $NaBH_4$ (0.11 g, 2.86 mmol) in small portions. The reaction mixture was stirred at room temperature overnight, at which point additional $NaBH_4$ (30 mg, 0.79 mmol) was added to the mixture and the stirring was continued for 2 hours more. The reaction mixture was then concentrated to dryness. Purification by flash chromatography (gradient, 95:5 hexanes/EtOAc to 60:40 EtOAc/hexanes) gave the desired product (0.29 g, 28%) as a yellow oil: 7.99 (d, J=8.3 Hz, 1H), 7.49 (d, J=7.2 Hz, 1H), 7.26-7.06 (m, 6H), 6.70 (s, 1H), 5.35-5.25 (m, 1H), 3.67 (d, J=13.0 Hz, 1H), 3.51 (d, J=13.0 Hz, 1H), 3.00-2.90 (m, 1H), 2.70-2.60 (m, 1H), 2.32 (s, 3H), 2.31 (s, 3H), 1.67 (s, 9H).

Step G: A solution of the product from Step F above (0.29 g, 0.74 mmol) in 1,2-dichloroethane (2.4 mL) was added dropwise via addition funnel to methanesulfonic acid (2.7 mL) at 40° C. After 30 minutes, the reaction mixture was cooled to room temperature, and poured over ice. The pH of the resultant mixture was adjusted to pH 9 with concentrated $NH_4OH$, and the product was extracted into $CH_2Cl_2$ (4×15 mL). The organic extracts were combined, washed with brine, dried ($Na_2SO_4$), filtered and concentrated under reduced pressure. Purification by flash column chromatography (gradient, 90:10 hexanes/EtOAc containing 0.05% TEA to 55:45 hexanes/EtOAc) containing 0.05% TEA) gave the desired product (59 mg, 29%) as a brown oil.

Step H: To a solution of the product from Step G above (59 mg, 0.21 mmol) in EtOH (0.5 mL) at −30° C. was added maleic acid (24 mg, 0.21 mmol). The above solution was diluted with EtOH (1 mL) and added dropwise to $Et_2O$ (50 ml) at −30° C. The precipitate formed was filtered, washed with $Et_2O$ and dried. The off-white solid obtained was then triturated with EtOAc/hexanes, filtered and dried under reduced pressure to the product (47 mg, 51%) as an off-white solid: $^1H$ NMR (300 MHz, $CD_3OD$) δ 7.47 (d, J=8.1 Hz, 1H), 7.28 (d, J=8.0 Hz, 1H), 7.11-6.96 (m, 5H), 6.31 (br s, 1H), 6.25 (s, 2H), 4.76-4.72 (m, 1H), 4.42 (br s, 2H), 3.83-3.79 (m, 1H), 3.60-3.50 (m, 1H), 3.01 (s, 3H), 2.00 (s, 3H); ESI MS m/z 277 $[C_{19}H_{20}N_2+H]^+$; Anal. Calcd for $C_{19}H_{20}N_2 \cdot 1.25C_4H_4O_4 \cdot 0.5H_2O$: C, 66.82; H, 6.10; N, 6.49. Found: C, 67.16; H, 6.25; N, 6.29.

Example 48

Preparation of 4-(5-methoxy-1H-Indazol-5-yl)-2-methyl-1,2,3,4-tetrahydroisoquinoline, maleate salt Step A: To a solution of 5-methoxyindole (3.00 g, 20.4 mmol) in $CH_3CN$ (15 mL) was added di-tert-butyl-dicarbonate (4.90 g, 22.4 mmol) and a catalytic amount of DMAP. The solution was stirred at room temperature overnight. The reaction mixture was diluted with cold 1 N HCl (30 mL) and extracted with EtOAc (3×30 mL). The organic phase was dried ($Na_2CO_3$) and concentrated under reduced pressure. Purification by flash column chromatography ($CH_2Cl_2$) gave N-tert-butyl-carboxylate-5-methoxyindole (4.89 g, 97%) as a white solid. $^1H$ NMR (300 MHz, $CDCl_3$) δ 8.01 (d, J=8.3 Hz, 1H), 7.56 (d, J=3.3 Hz, 1H), 7.02 (s, 1H), 6.922 (dd, J=9.0 Hz, 2.5 Hz, 1H), 6.49 (d, J=3.6 Hz, 1H), 3.85 (s, 3H), 1.66 (s, 9H).

Step B: To an ice-cold solution of N-tert-butyl-carboxylate-5-methoxyindole (2.45 g, 9.90 mmol) and triisopropyl borate (2.83 g, 15.1 mmol) in THF (12.5 mL) was added 2.0 M LDA (6.3 mL in THF, 12.5 mL). The reaction mixture was stirred at 0° C. for 1 h, after which it was quenched with 2 N HCl (aq, 30 mL), and then extracted with $CH_2Cl_2$ (40 mL). The organic phase was dried ($Na_2SO_4$) and concentrated under reduced pressure. Recrystalization of the concentrate in 1:1 $CH_3CN/H_2O$ (40 mL) yielded N-tert-butyl-carboxylate-5-methoxy-2-indoleboronic acid (2.70 g, 94%) as a white solid. $^1H$ NMR (300 MHz, DMSO-$d_6$) δ 8.18 (s, 2H), 7.95 (d, J=8.9 Hz, 1H), 7.07 (d, J=2.5 Hz, 1H), 6.87 (dd, J=9.0 Hz, 2.6 Hz, 1H), 6.55 (s, 1H), 3.77 (s, 3H), 1.59 (s, 9H).

Step C: A mixture of 4-bromoisoquinoline (1.05 g, 5.04 mmol), the product obtained in Step B (2.20 g, 7.56 mmol), DME (13 mL) and 2 M $Na_2CO_3$ (6.3 mL, 12.6 mmol) was degassed (five times, vacuum/argon). To this mixture was added $Pd(PPh_3)_4$ (291 mg, 0.252 mmol). The resulting mixture was degassed (five times, vacuum/argon) and then heated to reflux overnight. The cooled reaction mixture was filtered, and the filter cake was washed with $CH_2Cl_2$. The filtrate was treated with 1 N NaOH (aq, 20 mL) and extracted with $CH_2Cl_2$ (2×20 mL). The combined organic phase was dried ($Na_2SO_4$) and concentrated under reduced pressure. Purification by flash column chromatography (1:1 EtOAc/hexanes, the mixture was loaded on to the column as a solution in $CH_2Cl_2$) gave the product (1.12 g, 59%) as a clear oil. $^1H$ NMR (300 MHz, $CDCl_3$) δ 9.29 (s, 1H), 8.55 (s, 1H), 8.26 (d, J=9.0 Hz, 1H), 8.05-8.02 (m, 1H), 7.68-7.63 (m, 3H), 7.09 (d, J=2.5 Hz, 1H), 7.03 (dd, J=9.0 Hz, 2.6 Hz, 1H), 6.64 (s, 1H), 3.90 (s, 3H), 0.87 (s, 9H).

Step D: Methyl triflate (120 mg, 0.732 mmol) was added dropwise to an ice-cold solution of the product from Step C (250 mg, 0.668 mmol) in $CH_2Cl_2$ (2.3 mL). The resulting slurry was stirred for 30 minutes at room temperature. Excess methyl triflate was quenched with MeOH and the resulting solution was concentrated in vacuo to afford the pyridinium salt as a yellow solid, which was carried onto Step E without further purification.

Step E: Sodium cyanoborohydride (105 mg, 1.67 mmol) was added to a solution of the product from Step C in MeOH (5 mL). The reaction was stirred overnight at room temperature. MeOH was removed in vacuo and the residue was diluted with $CH_2Cl_2$. The solution was washed with 1 N NaOH (aq), dried ($Na_2SO_4$) and concentrated in vacuo. The crude oil was carried onto Step F.

Step F: A solution of the product from Step E and maleic acid (83 mg, 0.711 mmol) in EtOH (5 mL) was stirred at −30° C. for 1 h. The slurry formed was filtered under reduced pressure and washed with EtOAc to give the product (120 mg, 36% over Steps E and F) as a white solid: mp 117-120° C.; $^1H$ NMR (300 MHz, $CD_3OD$) δ 7.35-7.26 (m, 3H), 7.19-7.13 (m, 2H), 7.00 (s, 1H), 6.75 (dd, J=8.8 Hz, 2.4 Hz, 1H), 6.27-6.24 (m, 3H), 4.82-4.77 (m, 1H), 4.54 (d, J=3.7 Hz, 2H), 3.92-3.87 (m, 1H), 3.79 (s, 3H), 3.74-3.69 (m, 1H), 3.08 (s, 3H); ESI-MS m/z 293 $[C_{19}H_{20}N_2O+H]^+$; Anal. Calcd for $C_{19}H_{20}N_2O \cdot 1.5C_4H_4O_4$: C, 64.37; H, 5.62; N, 6.01. Found: C, 64.00; H, 5.87; N, 6.17.

Example 49

Preparation of 4-(1H-Indol-5-yl)-2-methyl-1,2,3,4-tetrahydroisoquinoline

Step A: 5-Bromo-N-tert-butyl-indolecarboxylate (1.28 mg, 4.34 mmol) and 4-isoquinolineboronic acid (900 mg, 5.20 mmol) were combined as described for the synthesis of Example 48, Step C to afford, after chromatography, the product (314 mg, 21%) as a brown oil. $^1$H NMR (300 MHz, CDCl$_3$) δ 9.26 (s, 1H), 8.54 (s, 1H), 8.28 (d, J=8.4 Hz, 1H), 8.07-8.04 (m, 1H), 7.97-7.94 (m, 1H), 7.70-7.60 (m, 4H), 7.46 (dd, J=8.5 Hz, 1.7 Hz), 6.66 (d, J=3.6 Hz, 1H), 1.72 (s, 9H).

Step B: The product obtained in Step A (314 mg, 0.918 mmol) and methyl triflate (164 mg, 1.00 mmol) were reacted as described for the synthesis of Example 48, Step D to afford a yellow salt that was carried onto Step C.

Step C: The crude product obtained in Step B and sodium cyanoborohydride (231 mg, 3.67 mmol) were combined as described for the synthesis of Example 48, Step E. The reaction mixture was then concentrated in vacuo, diluted with CH$_2$Cl$_2$ and washed with 1 N NaOH (aq). The organic phase was dried (Na$_2$SO$_4$) and concentrated under reduced pressure. Purification by flash column chromatography (2:5 EtOAc/hexanes, the mixture was loaded on to the column as a solution in CH$_2$Cl$_2$) gave the product (217 mg, 65% over Steps B and C) as a clear oil. $^1$H NMR (300 MHz, CDCl$_3$) δ 8.04 (d, J=8.7 Hz, 1H), 7.58 (d, J=3.6 Hz, 1H), 7.39 (d, J=1.5 Hz, 1H), 7.16-7.02 (m, 4H), 6.87 (d, J=7.7 Hz, 1H), 6.50 (d, J=3.7 Hz, 1H), 4.38 (t, J=7.0 Hz, 1H), 3.82-3.61 (m, 2H), 3.11-3.05 (m, 1H), 2.65-2.58 (m, 1H), 2.44 (s, 3H), 1.66 (s, 9H).

Step D: To a solution of the product obtained in Step C (217 mg, 0.599 mmol) in CH$_2$Cl$_2$ (10 mL) was added TFA (5 mL). The solution was stirred at room temperature for 3 h, after which the solution was concentrated in vacuo. The concentrate was then dissolved in EtOH (10 mL), to which was added concentrated NH$_4$OH (6 mL). The solution was stirred at room temperature for 30 minutes and concentrated in vacuo, after which the concentrate was dissolved in CH$_2$Cl$_2$ (30 mL) and washed with 2 N NaOH (aq). The organic phase was dried (Na$_2$SO$_4$) and concentrated under reduced pressure. Purification by flash column chromatography (98/1.5/0.5 CH$_2$Cl$_2$/MeOH/NH$_4$OH, the mixture was loaded on to the column as a solution in CH$_2$Cl$_2$) gave the product (40 mg, 25%) as a light brown solid. $^1$H NMR (500 MHz, CDCl$_3$) δ 8.24 (s, 1H), 7.48 (s, 1H), 7.29 (d, J=8.4 Hz, 1H), 7.16-7.08 (m, 3H), 7.03 (t, J=7.4 Hz, 1H), 6.99 (d, J=7.4 Hz, 1H), 6.91 (d, J=7.7 Hz, 1H), 6.48 (s, 1H), 4.39 (t, J=7.5 Hz, 1H), 3.82 (d, J=14.8 Hz, 1H), 3.62 (d, J=14.8 Hz, 1H), 3.13-3.01 (m, 1H), 2.62 (t, J=10.4 Hz, 1H), 2.45 (3H).

Step E: The product obtained in Step D and maleic acid (19 mg, 0.167 mmol) were combined as described for the synthesis of Example 48, Step F to afford, after recrystalization, the product (38 mg, 55%) as an off-white solid: mp 185-189° C.; $^1$H NMR (500 MHz, CD$_3$OD) δ 7.44 (m, 1H), 7.38 (d, J=8.4 Hz, 1H), 7.31-7.21 (m, 4H), 6.97 (d, J=7.7 Hz, 1H), 6.92 (dd, J=8.4 Hz, 1.6 Hz, 1H), 6.41 (d, J=2.5 Hz, 1H), 6.24 (s, 2H), 4.64-4.55 (m, 3H), 3.87-3.83 (m, 3H), 3.65-3.58 (m, 1H), 3.07 (s, 3H); ESI-MS m/z 263 [C18H$_{18}$N$_2$+H]$^+$; Anal. Calcd for C$_{18}$H$_{18}$N$_2$·1.3C$_4$H$_4$O$_4$: C, 67.50; H, 5.66; N, 6.80. Found: C, 67.43; H, 5.66; N, 6.78.

Example 50

Preparation of 2-methyl-4-(2-methylbenzo[b]thiazol-5-yl)-1,2,3,4-tetrahydroisoquinoline, hydrochloride salt Step A: Sodium nitrite (0.9 g, 13 mmol) was added portionwise to a suspension of 2-methyl-5-aminobenzothiazole dihydrochloride (2.0 g, 8 mmol) in hydrobromic acid (24 ml) at 0° C. The resulting mixture was added dropwise to a solution of copper(I) bromide (4.0 g, 14 mmol) in hydrobromic acid (50 ml) at 0° C. After stirring at 0° C. for 2 hours, water was added. The reaction mixture was basified to pH 9 using aqueous ammonium hydroxide and was extracted with ethyl acetate. The combined organic layers were dried over magnesium sulfate to give 2-methyl-5-bromobenzothiazole (1.0 g, 52%, 82% AUC GC) after chromatography (9:1 heptane/ethyl acetate): $^1$H NMR (300 MHz, DMSO-d$_6$) δ 8.12 (d, J=1.8 Hz, 8.02 (dd,☐1H) J=8.4, 1.5 Hz, 1H), 7.56 (dd, J=8.7, 2.1 Hz, 1H), 2.81 (s, 3H).

Step B: 2-methyl-4-(2-methylbenzo[b]thiazol-5-yl)-1,2,3,4-tetrahydroisoquinoline, hydrochloride salt (0.06 g, 97.4% AUC HPLC) was prepared from the product from Step A and 4-bromoisoquinoline as described in Example 41 (Steps E to I): $^1$H NMR (300 MHz, MeOD) δ 7.98 (d, J=8.4 Hz, 1H), 7.85 (s, 1H), 7.24-7.36 (m, 4H), 6.92 (d, J=7.8 Hz, 1H), 4.75-4.85 (m, 1H), 4.65 (br s, 2H), 3.85-4.00 (m, 1H), 3.55-3.68 (m, 1H), 3.07 (s, 3H), 2.87 (s, 3H); EI MS m/z=295 [C$_{18}$H$_{18}$N$_2$S+H]$^+$. Anal. Calcd. for C$_{18}$H$_{19}$ClN$_2$S: C, 61.91; H, 5.45; N, 8.02 with 1.5 equiv HCl. Found: C, 61.61; H, 5.79; N, 7.90.

Example 51

Preparation of 4-(1H-Inden-2-yl)-2-methyl-1,2,3,4-tetrahydroisoquinoline, maleate salt Step A: Trifluoro-methanesulfonic acid 1H-inden-2-yl ester was synthesized in 87% yield following a procedure published in Huffman et al., *J. Med. Chem.* 39:3875-3877 (1996), which is hereby incorporated by reference in its entirety, using 2-indanone: $^1$H NMR (300 MHz, CDCl$_3$) δ 8.05 (s, 1H), 7.43-7.20 (m, 4H), 6.68 (s, 1H), 3.66 (s, 2H).

Step B: A solution of trifluoromethanesulfonic acid 1H-inden-2-yl ester (2.58 g, 10.39 mmol), bis(pinacolato)diboron (5.28 g, 20.79 mmol) and KOAc (3.06 g, 31.18 mmol) in DMSO (54 mL) was purged with argon. To this mixture was added PdCl$_2$dppf-CH$_2$Cl$_2$ (0.679 g, 0.83 mmol). The resulting mixture was purged with argon and heated to 80° C. for 5 h. The cooled reaction mixture was diluted with water (50 mL) and extracted with CH$_2$Cl$_2$ (1×200 mL, 2×100 mL). The combined organic layers was concentrated to a smaller volume under reduced pressure. The residue was diluted with EtOAc (200 mL), washed with water (1×50 mL, 2×25 mL), brine (2×25 mL), dried (Na$_2$SO$_4$), and concentrated under reduced pressure to afford 2-(1H-inden-2-yl)-4,4,5,5-tetramethyl-[1,3,2]dioxaborolane as a black oil, which carried onto Step C without further purification.

Step C: A solution of the product obtained in Step B (~10 mmol), 4-bromoisoquinoline (1.39 g, 6.66 mmol) and Pd(PPh$_3$)$_4$ (0.46 g, 0.40 mmol) in DMF (33 mL) was purged with argon. To this mixture was added a solution of Cs$_2$CO$_3$ (8.68 g, 26.64 mmol) in water (13 mL). The resulting mixture was purged with argon and heated to 88° C. overnight. The cooled reaction mixture was diluted with water (25 mL) and extracted with EtOAc (3×150 mL). The combined organic layer was concentrated under reduced pressure. Purification by flash chromatography (1:1:1: $CH_2Cl_2$/hexanes/EtOAc) gave the product (0.649 g, 40%) as a brown solid: $^1H$ NMR (300 MHz, $CDCl_3$) δ 9.18 (s, 1H), 8.57 (s, 1H), 8.28 (d, 1H, J=8.5 Hz), 8.02 (d, 1H, J=8.2 Hz), 7.77-7.45 (m, 4H), 7.40-7.18 (m, 2H), 3.94 (s, 2H).

Step D: Methyl triflate (0.153 mL, 1.35 mmol) was added dropwise to an ice-cold solution of the product from Step C (0.30 g, 1.23 mmol) in $CH_2Cl_2$ (5 mL). The resulting solution was stirred at 0° C. for 1.5 hours and then at room temperature for 0.5 h. The mixture was concentrated to dryness under reduced pressure to afford the pyridinium salt as a yellow solid, which was carried onto Step E without further purification.

Step E: Sodium cyanoborohydride (0.144 g, 2.26 mmol) was added to a solution of the product from Step C in MeOH (6 mL). The reaction was stirred at room temperature overnight. The mixture was diluted with water (10 mL) and 2 N NaOH (10 mL), and was extracted with $CH_2Cl_2$ (3×100 mL). The combined organic solution was dried ($Na_2SO_4$) and concentrated under reduced pressure. Purification by flash chromatography (eluent: 98: to 96:4 to 92:8 $CH_2Cl_2$/MeOH) gave the product (0.24 g, 75% over two step) as an oil.

Step F: A solution of the product from Step E (0.236 g, 0.90 mmol) and maleic acid (0.107 g, 0.92 mmol) in EtOH (2 mL) was cooled to −20° C. The slurry formed was filtered under reduced pressure and washed with EtOH to give the product as an off-white solid (0.135 g, 39%): mp 184-187° C.; $^1H$ NMR (300 MHz, $CD_3OD$) δ 7.43-7.19 (m, 7H), 7.14 (td, 1H, J=7.3, 1.2 Hz), 6.75 (s, 1H), 6.22 (s, 2H), 4.66-4.55 (m, 1H), 4.50 (s, 2H), 3.83-3.69 (m, 1H), 3.68-3.57 (m, 1H), 3.46-3.32 (m, 2H), 3.13 (s, 3H); ESI m/z 261 $[C_{19}H_{19}N+H]^+$. Anal. Calcd for $C_{19}H_{19}N·1.05C_4H_4O_4$: C, 72.71; H, 6.10; N, 3.65. Found: C, 72.78; H, 6.17; N, 3.65.

Example 52

Preparation of 4-(indan-5-yl)-2-methyl-1,2,3,4-tetrahydroisoquinoline, hydrochloride salt 4-Indan-5-yl-2-methyl-1,2,3,4-tetrahydroisoquinoline was prepared from 5-acetylindane and benzylamine as described in Example 58 (Steps A to D). It was dissolved in ethyl acetate and treated with 2 M hydrogen chloride in diethyl ether (2 equiv) to give the corresponding hydrochloride salt (2.15 g, 99.4% AUC HPLC): $^1H$ NMR (300 MHz, $CDCl_3$) δ $^1H$ NMR (300 MHz, MeOD) δ 7.22-7.34 (m, 4H), 7.11 (s, 1H), 7.02 (d, J=6.9 Hz, 1H), 6.91 (d, J=6.9 Hz, 3H), 4.54-4.66 (m, 3H), 3.81-3.87 (m, 1H), 3.51 (t, J=12.3 Hz, 1H), 3.10 (s, 3 H), 2.87-2.94 (m, 4H), 2.03-2.14 (m, 2H), EI MS m/z=264 $[C_{19}H_{21}N+H]^+$. Anal. Calcd. for $C_{19}H_{22}ClN$: C, 76.11; H, 7.40; N, 4.67. Found: C, 75.87; H, 7.57; N, 4.52.

Example 53

Preparation of 2-methyl-4-(naphthalen-1-yl)-1,2,3,4-tetrahydroisoquinoline

2-Methyl-4-naphthalen-1-yl-1,2,3,4-tetrahydroisoquinoline (0.16 g, 99.5% AUC HPLC) was prepared from 1-naphthaleneboronic acid and 4-bromoisoquinoline as described in Example 56: $^1H$ NMR (300 MHz, $CDCl_3$) δ 7.92 (dd, J=4.5, 4.8 Hz, 1H),□ 7.77 (d, J=8.4 Hz, 1H), 7.47-7.57 (m, 2H), 7.40 (t, J=7.7 Hz, 1H), 7.15-7.22 (m, 3H), 7.05-7.10 (m, 1H), 6.89 (d, J=7.8 Hz, 1H), 5.17 (br s, 1H), 3.72-3.88 (m, 2H), 3.16 (dd, J=11.4, 5.7 Hz, 1 H), 2.72-2.88 (m, 1H), 2.45 (s, 3H); EI MS m/z=274 $[C_{20}H_{19}N+H]^+$.

Example 54

Preparation of 2-methyl-4-(4-methylnaphthalen-1-yl)-1,2,3,4-tetrahydroisoquinoline 2-Methyl-4-(4-methylnaphthalen-1-yl)-1,2,3,4-tetrahydroisoquinoline (0.17 g, 98.9% AUC HPLC) was prepared from 4-methyl-1-naphthaleneboronic acid and 4-bromoisoquinoline as described in Example 56: $^1H$ NMR (300 MHz, $CDCl_3$) δ 8.07-8.10 (m, 1H),□ 7.50-7.60 (m, 2H), 7.30-7.26 (m, 6H), 6.90 (d, J=7.5 Hz, 1H), 5.14 (br s, 1H), 3.70-3.82 (m, 2H), 3.16 (dd, J=11.4, 5.7 Hz, 1 H), 2.70-2.88 (m, 1H), 2.70 (s, 3H), 2.44 (s, 3H); EI MS m/z=288 $[C_{21}H_{21}N+H]^+$.

Example 55

Preparation of 2-methyl-4-(naphthalen-2-yl)-1,2,3,4-tetrahydroisoquinoline

Step A: 2-Naphthaleneboronic acid (1.2 g, 7.2 mmol) was added to a solution of 4-bromoisoquinoline (1.0 g, 4.8 mmol) and triphenylphosphine (0.3 g, 0.9 mmol) in 1,2-dimethoxyethane (10 ml). The mixture was degassed with argon. Palladium(II) acetate (0.1 g, 0.5 mmol) was added and the suspension was stirred at room temperature for 20 minutes. Aqueous sodium carbonate (5.8 ml, 2 M) was added and the suspension was degassed with argon. After stirring at 85° C. for 3 hours, the cooled mixture was diluted with water and extracted with dichloromethane once. The combined extracts were dried with sodium sulfate, concentrated under vacuum and purified by chromatography (5:1 heptane/ethyl acetate) to give the desired product (1.1 g, 90%, 95% AUC GC): $^1H$ NMR (300 MHz, $CDCl_3$) δ 9.32 (s, 1H), 8.62 (s, 1H), 7.92-8.12 (m, 6H), 7.56-7.72 (m, 5 H).

Step B: A solution of the product from Step A (1.0 g, 4 mmol) and iodomethane (0.8 ml, 12 mmol) in chloroform (15 ml) was stirred at 60° C. for 2 hours. The mixture was concentrated under vacuum to afford the desired intermediate (1.0 g, 61%, 86% AUC HPLC): $^1H$ NMR (300 MHz, $CDCl_3$) δ 10.79 (s, 1H), 8.58 (d, J=8.1 Hz, 1H), 8.09 (d, J=1.2 Hz, 1H), 7.74-7.93 (m, 7H), 7.37-7.43 (m, 3H), 4.63 (s, 3H).

Step C: Sodium cyanoborohydride (0.34 g, 5.4 mmol) followed by two drops of a methanolic bromocresol green solution were added to a solution of the product from Step C (0.97 g, 2.4 mmol) in methanol (40 ml). A blue color was observed. Methanolic HCl (3 M) was added until a yellow color was obtained. The resulting mixture was stirred at room temperature for 1 hour with periodic addition of methanolic HCl to maintain the yellow color. The mixture was quenched by adding aqueous sodium hydroxide (20 ml, 3 M) and extracted with ethyl acetate twice. The organic extracts were washed with brine, dried over magnesium sulfate and concentrated to give 2-methyl-4-naphthalen-2-yl-1,2,3,4-tetrahydroisoquinoline (0.61 g, 93%, 96% AUC HPLC) as a white solid: $^1H$ NMR (300 MHz, $CDCl_3$) δ 7.62-7.69 (m, 3H),□ 7.57 (s, 1H), 7.28-7.36 (m, 2H), 7.14 (dd, J=8.4, 1.5 Hz, 1H), 6.90-7.06 (m, 3H), 6.76 (d, J=7.8 Hz, 1H), 4.36 (dd, J=8.4, 6.3 Hz, 1H), 3.72 (d, J=15.0 Hz, 1H), 3.58 (d, J=14.7 Hz, 1H), 3.02 (ddd, J=11.7, 6.0, 1.5 Hz, 1 H), 2.59 (dd, J=11.4, 9.0 Hz, 1H), 2.35 (s, 3H); EI MS m/z=274 $[C_{20}H_{19}N+H]^+$.

Example 56

Preparation of 2,5-dimethyl-4-(naphthalen-2-yl)-1,2,3,4-tetrahydroisoquinoline, maleate salt 2,5-Dimethyl-4-naphthalen-2-yl-1,2,3,4-tetrahydroisoquinoline, maleate salt (0.16 g, 98.5% AUC HPLC) was prepared as described in Example 58: $^1$H NMR (300 MHz, MeOD) δ 7.84-7.92 (m, 2H), 7.69-7.73 (m, 1H), 7.44-7.51 (m, 2H), 7.34-7.39 (m, 3H), 7.22-7.24 (m, 2H),☐ 6.17 (s, 2H), 4.86 (t, J=5.7 Hz, 1H), 4.66 (d, J=15.3 Hz, 1H), 4.47 (d, J=15.3 Hz, 1H), 3.97 (dd, J=12.6, 6.0 Hz, 1H), 3.72-3.85 (m, 1H), 3.01 (s, 3H), 1.94 (s, 3H), EI MS m/z=288 $[C_{21}H_{21}N+H]^+$. Anal. Calcd. for $C_{25}H_{25}NO_4$: C, 72.59; H, 6.38; N, 3.35 with 2.00% $H_2O$ and 1.37% EtOH. Found: C, 72.24; H, 6.38; N, 3.05.

Example 57

Preparation of 2,7-dimethyl-4-(naphthalen-2-yl)-1,2,3,4-tetrahydroisoquinoline, maleate salt Step A: A solution of tetrabutylammonium tribromide (15.6 g, 32 mmol) in dichloromethane (80 ml) was added dropwise to a solution of 2-acetylnaphthalene (5.0 g, 29 mmol) in dichloromethane (20 ml) and methanol (20 ml) at room temperature. At completion of the addition, the resulting red-orange solution was stirred at room temperature for 15 hours. The mixture was concentrated under vacuum and the residue was taken into ethyl acetate and water. The layers were separated and the aqueous phase was extracted with ethyl acetate. The combined organic extracts were washed with saturated aqueous sodium bicarbonate and brine and dried over anhydrous sodium sulfate to give the desired bromo compound (7.6 g, 100%): $^1$HNMR (300 MHz, CDCl$_3$) δ 8.05 (s, 1H), 7.04 (dd, J=4.2, 1.8 Hz, 1 H), 8.02 (d, J=1.8 Hz, 1H), 7.56-7.67 (m, 2H), 4.59 (s, 2H).

Step B: 3-Tolylmethylamine (2.7 g, 20 mmol) was added dropwise to a solution of the product from Step A (5.0 g, 20 mmol) in dichloromethane (25 ml) at 0° C. At completion of the addition, the resulting mixture was stirred at 0° C. for 15 minutes and diisopropylethylamine (3.8 ml, 22 mmol) was added dropwise. The mixture was stirred at room temperature for 15 hours after which it was quenched with saturated aqueous sodium bicarbonate and extracted with dichloromethane twice.

The combined organic extracts were washed with saturated aqueous sodium bicarbonate and dried over sodium sulfate to give the desired intermediate (2.7 g, 45%) after chromatography (19:1 to 9:1 heptane/ethyl acetate): $^1$H NMR (300 MHz, CDCl$_3$) δ 8.50 (s, 1H), 8.03 (dd, J=8.7, 1.8 Hz, 1H), 7.87-7.95 (m, 3H), 7.56-7.64 (m, 2H), 7.11-7.28 (m, 4H), 3.92 (s, 2H), 3.71 (s, 2H), 2.44 (s, 3H), 2.36 (s, 3H).

Step C: Sodium borohydride (0.34 g, 8.9 mmol) was added to a solution of the product from Step B (2.70 g, 8.9 mmol) in methanol (40 ml) at 0° C. The resulting mixture was stirred at room temperature for 15 hours. Methanol was removed in vacuo. The residue was taken into water and extracted with dichloromethane three times. The combined organic extracts were washed with water and brine and dried over sodium sulfate to give the desired alcohol (1.5 g, 55%) after chromatography (19:1 to 3:1 heptane/ethyl acetate): $^1$H NMR (300 MHz, CDCl$_3$) δ 7.84-7.88 (m, 4H),☐ 7.47-7.52 (m, 3H), 7.27 (t, J=7.5 Hz, 1H), 7.12-7.17 (m, 3H), 6.46 (dd, J=9.6, 3.9 Hz, 1H), 3.77 (d, J=12.9 Hz, 1H), 3.55 (d, J=12.9 Hz, 1H), 2.62-2.75 (m, 2H), 2.39 (s, 3H), 2.38 (s, 3H).

Step D: Aluminum chloride (1.20 g, 8.8 mmol) was added portionwise to a solution of the product from Step C (1.50 g, 4.9 mmol) in dichloromethane (40 ml) at 0° C. At the end of the addition, the mixture was stirred at 0° C. for 1.5 hours, poured onto ice and dichloromethane and stirred for an additional 15 minutes. The mixture was washed with water and saturated aqueous sodium bicarbonate, extracted with dichloromethane and dried over sodium sulfate to give a crude mixture containing a 1.4 to 1 ratio of regioisomers. Purification by chromatography (5:1 to 1:1 heptane/ethyl acetate) afforded 4-naphthalen-2-yl-2,7-dimethyl-1,2,3,4-tetrahydroisoquinoline (0.23 g, 16%, 98.7% AUC HPLC): $^1$H NMR (300 MHz, CDCl$_3$) δ 7.59-7.73 (m, 4H),☐ 7.31-7.39 (m, 2H), 7.19 (dd, J=8.4, 1.5 Hz, 1H), 6.84 (s, 1H), 6.78 (d, J=7.8 Hz, 1H), 6.67 (d, J=7.8 Hz, 1H), 4.32 (t, J=7.8 Hz, 1H), 3.67 (d, J=15.0 Hz, 1H), 3.53 (d, J=15.0 Hz, 1H), 2.99 (ddd, J=11.4, 5.4, 1.2 Hz, 1H), 2.56 (dd, J=11.4, 9.0 Hz, 1H), 2.35 (s, 3H), 2.21 (s, 3H) and 4-naphthalen-2-yl-2,5-dimethyl-1,2,3,4-tetrahydroisoquinoline (0.44 g, 31%, 99.1% AUC HPLC): $^1$H NMR (300 MHz, CDCl$_3$) δ 7.63-7.72 (m, 3H),☐ 7.41 (s, 1H), 7.29-7.34 (m, 2H), 7.18-7.21 (m, 1H), 7.08 (t, J=7.5 Hz, 1H), 6.95 (d, J=7.5 Hz, 1H), 6.92 (d, J=7.2 Hz, 1H), 4.22 (t, J=3.9 Hz, 1H), 3.87 (d, J=15.0 Hz, 1H), 3.35 (d, J=14.7 Hz, 1H), 2.75-2.83 (m, 2H), 2.79 (dd, J=11.4, 4.2 Hz, 1H), 2.23 (s, 3H), 1.83 (s, 3H).

Step E: 4-Naphthalen-2-yl-2,7-dimethyl-1,2,3,4-tetrahydroisoquinoline (0.18 g) was crystallized with maleic acid (1 equiv) in reagent alcohol to give 4-naphthalen-2-yl-2,7-dimethyl-1,2,3,4-tetrahydroisoquinoline, maleate salt (0.07 g, 27%, 99.4% AUC HPLC): $^1$H NMR (300 MHz, MeOD) δ 7.80-7.91 (m, 4H), 7.51-7.54 (m, 2H), 7.29 (d, J=8.4, 1.5 Hz, 1H), 7.08-7.149 (m, 2H), 6.84 (d, J=7.8 Hz, 1H),☐ 6.26 (s, 2H), 6.74 (dd, J=10.5, 6.6 Hz, 1H), 4.62 (d, J=15.3 Hz, 1H), 4.56 (d, J=15.6 Hz, 1H), 3.91 (dd, J=12.0, 6.0 Hz, 1H), 3.66 (t, J=11.7 Hz, 1H), 3.10 (s, 3H), 2.36 (s, 3H), EI MS m/z=288 $[C_{21}H_{21}N+H]^+$.

Example 58

Preparation of 2,8-dimethyl-4-naphthalen-2-yl-1,2,3,4-tetrahydroisoquinoline, hydrochloride salt Step A: o-Tolualdehyde was converted to methyl-(2-methyl-benzyl)-amine via reductive amination using aqueous methyl amine and NaBH$_4$. Methyl-(2-methyl-benzyl)-amine was then alkylated with 2-bromo-2'-acetonaphthone followed by reduction by NaBH$_4$ to give 2-[methyl-(2-methyl-benzyl)-amino]-1-naphthalen-2-yl-ethanol as a clear, light yellow oil: $^1$H NMR (300 MHz, CDCl$_3$) δ 7.78-7.87 (m, 4 H), 7.40-7.51 (m, 3 H), 7.14-7.30 (m, 4 H), 4.89 (dd, J=10.1, 3.9 Hz, 1 H), 3.71 (d, J=12.9 Hz, 1 H), 3.54 (d, J=12.9 Hz, 1 H), 2.70 (dd, J=12.3, 10.3 Hz, 1 H), 2.62 (dd, J=12.4, 3.9 Hz, 1 H), 2.41 (s, 3 H), 2.35 (s, 3 H); Cl MS m/z 306 $[C_{21}H_{23}NO+H]^+$.

Step B: The product from Step A (1.25 g, 4.1 mmol) was dissolved in trifluoroacetic acid (TFA, 7.5 mL), then trifluoroacetic anhydride (TFAA, 7.5 mL) was added. After stirring for 24 h, the solvents were removed in vacuo, the residue was dissolved in MeOH, and the solvent was removed in vacuo. The residue was dissolved in aqueous NH$_4$OH, then extracted twice with CH$_2$Cl$_2$. The extract was dried over Na$_2$SO$_4$, filtered, the solvent was removed in vacuo, and the residue was purified by column chromatography on silica gel (40 g) eluting with 5% to 30% EtOAc/hexanes with 1% Et$_3$N to give 2,8-dimethyl-4-naphthalen-2-yl-1,2,3,4-tetrahydroisoquinoline (0.73 g, 61%) as a clear, dark yellow oil: $^1$H NMR (300 MHz, CDCl$_3$) δ 7.66-7.88

(m, 4 H), 7.38-7.48 (m, 2 H), 7.26 (dd, J=8.3, 1.6 Hz, 1 H), 6.93-7.04 (m, 2 H), 6.74 (d, J=7.2 Hz, 1 H), 4.45 (t, J=6.9 Hz, 1 H), 3.75 (d, J=15.4 Hz, 1 H), 3.51 (d, J=15.4 Hz, 1 H), 3.06 (ddd, J=11.2, 5.6, 0.9 Hz, 1 H), 2.67 (ddd, J=11.4, 8.5 Hz, 1 H), 2.48 (s, 3 H), 2.27 (s, 3H).

Step C: Using ethereal HCl and methanol, the product from Step B (0.73 g, 2.5 mmol) was converted to its hydrochloride salt (136 mg, 17%, 98.4% AUC HPLC) as a white amorphous solid: mp 210-214° C.; $^1$H NMR (300 MHz, CD$_3$OD) δ 7.76-7.90 (m, 4 H), 7.47-7.55 (m, 2 H), 7.26 (dd, J=8.6, 1.6 Hz, 1 H), 7.10-7.21 (m, 2 H), 6.77 (d, J=7.3 Hz, 1 H), 4.78 (dd, J=11.2, 6.0 Hz, 1H), 4.65 (d, J=15.7 Hz, 1 H), 4.48 (d, J=15.6 Hz, 1 H), 3.87 (dd, J=12.1, 6.0 Hz, 1 H), 3.66 (t, J=11.8 Hz, 1 H), 3.13 (s, 3 H), 2.36 (s, 3 H), IR (KBr) 3434, 2926, 2546, 1459, 754, 479 cm$^{-1}$; Cl MS m/z 288 [C$_{21}$H$_{21}$N+H]$^+$; Anal. Calcd. for C$_{21}$H$_{21}$N.HCl.0.5 H$_2$O: C, 75.77; H, 6.96; N, 4.21. Found: C, 76.04; H, 6.85; N, 4.14.

Example 59

Preparation of 4-(8-chloronaphthalen-2-yl)-2-methyl-1,2,3,4-tetrahydroisoquinoline, maleate salt Step A: 7-Bromo-3,4-dihydronaphthalen-1-one was prepared from bromobenzene and succinic anhydride as described in Example 64 (Steps A to C).

Step B: Sodium acetate (12.4 g, 150 mmol) was added to a solution of hydroxylamine hydrochloride (10.6 g, 150 mmol) in methanol (230 ml) at room temperature and the resulting mixture was stirred at room temperature for 30 minutes. The product from Step A (30.9 g, 140 mmol) was added portionwise over 1 hour and the mixture was stirred at room temperature for 2.5 hours. Water (300 ml) was added, the mixture became clear at first and then solids started to precipitate. The suspension was stirred at room temperature for 1 hour and then was filtered. The resulting solids were azeotroped with ethyl acetate three times to give the desired oxime (28.3 g, 86%): $^1$H NMR (300 MHz, DMSO-d$_6$) δ 7.94 (d, J=0.9 Hz, 1H), 7.40 (dd, J=8.4, 1.2 Hz, 1H), 7.15 (d, J=8.1 Hz, 1H), 2.61-2.68 (m, 4H), 1.68-1.78 (m, 2H).

Step C: Concentrated sulfuric acid (33.9 ml, 636 mmol) was added to a mixture of the product from Step B (28.3 g, 118 mmol), and acetic anhydride (33.9 ml, 359 mmol) in acetic acid (170 ml) at room temperature and the resulting mixture was stirred at 95° C. for 1 hour. After cooling to room temperature, water (170 ml) was added. The mixture was basified to pH 13 with 6 M sodium hydroxide and was extracted with methyl tert-butyl ether. The combined organic extracts were dried over magnesium sulfate to give 2-amino-7-bromonaphthalene (14 g, 53%) after purification by chromatography (19:1 hexanes/ethyl acetate).

Step D: A mixture of the product from Step C (6.0 g, 30 mmol) and 6 M HCl (13.4 ml) was stirred at room temperature until a solid formed. The mixture was cooled to 0° C. and a solution of sodium nitrite (1.9 g, 30 mmol) in water (5.6 ml) was slowly added keeping the temperature below 5° C. The resulting brown slurry was stirred at 0° C. for 15 minutes and then a solution of copper(I) chloride (3.3 g, 30 mmol) in 6 M HCl (15.4 ml) was added. The mixture was stirred at 0° C. for 10 minutes, then warmed to room temperature and stirred at 60° C. for 30 minutes. After cooling to room temperature, dichloromethane was added. The mixture was filtered through diatomaceous earth and the filtrate was extracted with dichloromethane three times. The combined organic layers were washed with water and dried over magnesium sulfate to give 7-bromo-1-chloronaphthalene (2.8 g, 43%) after chromatography (100% hexanes): $^1$H NMR (300 MHz, DMSO-d$_6$) δ 8.30 (d, J=1.8 Hz, 1H), 7.96-8.02 (m, 2H), 7.74-7.78 (m, 2H), 7.55 (t, J=7.8 Hz, 1H).

Step E: 4-(8-Chloronaphthalen-2-yl)-2-methyl-1,2,3,4-tetrahydroisoquinoline, maleate salt (0.29 g, 99.5% AUC HPLC) was prepared from the product from Step D as described in Example 63 (Steps C and D): $^1$H NMR (300 MHz, DMSO-d$_6$) δ 8.12 (s, 1H), 8.04 (d, J=8.4 Hz, 1H), 7.96 (d, J=8.4 Hz, 1H), 7.74 (dd, J=7.2, 0.9 Hz, 1H), 7.53 (d, J=8.4 Hz, 1H), 7.42 (dd, J=8.4, 1.5 Hz, 1H), 7.29-7.32 (m, 2H), 7.18-7.25 (m, 1H), 6.83 (d, J=7.5 Hz, 1H), 6.05 (s, 2H), 4.79 (dd, J=10.5, 6.3 Hz, 1H), 4.54 (d, J=15.3 Hz, 1H), 4.44 (d, J=15.3 Hz, 1H), 3.80 (dd, J=12.0, 6.3 Hz, 1H), 3.56 (t, J=11.4 Hz, 1H), 2.90 (s, 3H); EI MS m/z=308 [C$_{20}$H$_{18}$ClN+H]$^+$. Anal. Calcd. for C$_{24}$H$_{22}$ClNO$_4$: C, 67.35; H, 5.23; Cl, 8.28; N, 3.27 with 0.95% H$_2$O. Found: C, 67.55; H, 5.53; Cl, 8.45; N, 3.15.

Example 60

Preparation of 4-(8-fluoronaphthalen-2-yl)-2-methyl-1,2,3,4-tetrahydroisoquinoline, maleate salt Step A: 2-Amino-7-bromonaphthalene (14 g) was prepared as described in Example 60 (Step A to C).

Step B: A solution of the product from Step A (5 g, 21 mmol) in methyl tert-butyl ether (20 ml) was treated with a solution of hydrogen chloride in diethyl ether (16.9 ml, 2 M) and the resulting mixture was stirred at room temperature. After 30 minutes, solids had precipitated and were filtered and washed with methyl tert-butyl ether. These solids were added to 6 M HCl (57.7 ml) and the resulting suspension was cooled to 0° C. Sodium nitrite (4.7 g, 70 mmol) followed by sodium tetrafluoroborate (7.4 g, 70 mmol) were added portionwise keeping the temperature at 0° C. The mixture was stirred at 0° C. for 30 minutes, then filtered. The filtrate was washed with ice cold water and extracted with ice cold methyl tert-butyl ether to give 7-bromo-1-fluoronaphthalene (4 g, 85%): H NMR (300 MHz, DMSO-d$_6$) δ 8.18 (d, J=1.8 Hz, 1H), 7.97 (dd, J=9.0, 1.8 Hz, 1H), 7.80 (d, J=8.1 Hz, 1H), 7.72 (dd, J=8.7, 2.1 Hz, 1H), 7.55 (td, J=7.8, 5.4 Hz, 1H), 7.39 (ddd, J=10.8, 7.8, 0.9 Hz, 1H).

Step C: 4-(8-Fluoronaphthalen-2-yl)-2-methyl-1,2,3,4-tetrahydroisoquinoline, maleate salt (0.23 g, 96.5% AUC HPLC) was prepared from the product from Step B as described in Example 63 (Steps C and D): $^1$H NMR (300 MHz, DMSO-d$_6$) δ 7.99-8.04 (m, 2H), 7.79 (d, J=8.1 Hz, 1H), 7.19-7.56 (m, 6H), 6.84 (d, J=7.5 Hz, 1H), 6.05 (s, 2H), 4.77 (dd, J=10.5, 6.6 Hz, 1H), 4.54 (d, J=15.3 Hz, 1H), 4.44 (d, J=15.6 Hz, 1H), 3.78 (dd, J=12.0, 6.3 Hz, 1H), 3.57 (t, J=11.1 Hz, 1H), 2.91 (s, 3H); EI MS m/z=292 [C$_{20}$H$_{18}$FN+H]$^+$. Anal. Calcd. for C$_{24}$H$_{22}$FNO$_4$: C, 70.47; H, 5.47; F, 4.64; N, 3.43 with 0.38% H$_2$O. Found: C, 70.33; H, 5.78; F, 4.38; N, 3.30.

Example 61

Preparation of 4-(6-methoxynaphthalen-2-yl)-2-methyl-1,2,3,4-tetrahydroisoquinoline 4-(6-Methoxynaphthalene-2-yl)-2-methyl-1,2,3,4-tetrahydroisoquinoline was prepared from 6-methoxy-2-naphthaleneboronic acid and 4-bromoisoquinoline as described in Example 56: $^1$H NMR (300 MHz, CDCl$_3$) δ 7.55-7.63 (m, 3H), 6.96-7.16 (m, 6H), 6.82 (d, J=7.8 Hz, 1H), 4.35 (dd, J=8.4, 6.0 Hz, 1H), 3.84 (s, 3H), 3.74 (d, J=14.7 Hz, 1H), 3.59 (d, J=15.0 Hz, 1H), 3.03 (ddd, J=11.4, 5.7, 1.2 Hz, 1H), 2.59 (dd, J=11.4, 9.0 Hz, 1H), 2.39 (s, 3H); EI MS m/z=304 $[C_{21}H_{21}NO+H]^+$.

Example 62

Preparation of 4-(7-methoxynaphthalen-2-yl)-2-methyl-1,2,3,4-tetrahydroisoquinoline, maleate salt Step A: Sodium hydroxide (20 ml, 1M) and dimethyl sulfate (15.0 ml, 158 mmol) were added dropwise to a solution of 2,7-dihydroxynaphthalene (6.6 g, 40 mmol) in dichloromethane (100 ml) and water (60 ml). Additional sodium hydroxide (20 ml, 1M) and dimethyl sulfate (15.0 ml, 158 mmol) were added and the resulting mixture was stirred at room temperature for 2 hours. The two phases were separated and the aqueous layer was extracted with dichloromethane twice. The combined organic extracts were washed with 1 M HCl, dried over magnesium sulfate and concentrated under vacuum. The crude material was purified by column chromatography (5:1 heptane/ethyl acetate) to give 2-hydroxy-7-methoxynaphthalene (2.1 g, 30%, 100% AUC HPLC): $^1$H NMR (300 MHz, CDCl$_3$) δ 7.66-7.70 (m, 2H), 6.94-7.08 (m, 4H), 4.90 (s, 1H), 3.92 (s, 3H).

Step B: Triflic anhydride (6.7 ml, 6.6 mmol) was added to a solution of the product from Step A (1.0 g, 5.7 mmol) and triethylamine (1.9 ml, 13.3 mmol) in dichloromethane at −23° C. After completion of the addition, the mixture was allowed to warm to room temperature and stirred for 3 hours. The reaction mixture was diluted with water and extracted with ethyl acetate twice. The combined organic extracts were washed with brine and dried over sodium sulfate to give the product (1.9 g, 100% AUC GC): $^1$H NMR (300 MHz, CDCl$_3$) δ 7.66-7.86 (m, 3H), 7.15-7.25 (m, 3H), 3.95 (s, 3H).

Step C: Isoquinolin-4-ylboronic acid (0.76 g, 4.4 mmol) was added to a solution of the product from Step B (0.9 g, 2.9 mmol) and triphenylphosphine (0.15 g, 0.6 mmol) in 1,2-dimethoxyethane (15 ml). The suspension was degassed with nitrogen. Palladium acetate (0.06 g, 0.3 mmol) was added and the batch was stirred at room temperature for 20 minutes. Aqueous sodium carbonate (3.5 ml, 2 M solution) was added and the suspension was degassed again with nitrogen. The mixture was stirred at 85° C. for 3.5 hours, cooled, diluted with water and extracted with ethyl acetate twice. The combined organic extracts were dried over anhydrous sodium sulfate, concentrated under vacuum and purified by chromatography (5:1 heptane/ethyl acetate) to give the desired isoquinoline (0.46 g, 55%, 98.7% AUC HPLC): H NMR (300 MHz, CDCl$_3$) δ 9.30 (s, 1H), 8.59 (s, 1H), 8.06-8.10 (m, 1H), 7.83-8.00 (m, 4H), 7.64-7.69 (m, 2H), 7.50 (dd, J=8.1, 1.5 Hz, 1H), 7.24-7.27 (m, 2H), 3.96 (s, 3H).

Step D: 4-(7-Methoxynaphthalen-2-yl)-2-methyl-1,2,3,4-tetrahydroisoquinoline was prepared from the product from Step C as described in Example 56 (Steps B and C) and converted to the corresponding maleate salt (0.15 g, 99.0% AUC HPLC) by crystallization with maleic acid (1 equiv) in ethanol: $^1$H NMR (300 MHz, DMSO-d$_6$) δ 7.83 (dd, J=8.4, 4.3 Hz, 2H), 7.73 (s, 1H), 7.16-7.30 (m, 6H), 6.84 (d, J=7.6 Hz, 1H), 6.05 (s, 2H), 4.61-4.67 (m, 1H), 4.43-4.55 (m, 2H), 3.87 (s, 3H), 3.78 (dd, J=6.0, 11.4 Hz, 1H), 3.55 (t, J=11.2 Hz, 1H), 2.93 (s, 3H); EI MS m/z=304 $[C_{21}H_{21}NO+H]^+$. Anal. Calcd. for $C_{25}H_{25}NO_5$: C, 71.58; H, 6.01; N, 3.34. Found: C, 71.55; H, 6.22; N, 3.28.

Example 63

Preparation of 4-(8-methoxynaphthalen-2-yl)-2-methyl-1,2,3,4-tetrahydroisoquinoline, maleate salt Step A: Bromobenzene (150 ml, 1.42 mol) was added in one portion to a mixture of aluminum chloride (109 g, 0.82 mmol) and succinic anhydride (41 g, 0.41 mol) in cyclohexane (200 ml) at 80° C. and the resulting mixture was stirred at 80° C. for 2 hours. After cooling below 40° C., the mixture was slowly poured into 6 M HCl (200 ml) and ice, and yellow solids precipitated. Methyl tert-butyl ether was added to dissolve the solids and the phases were separated. The organic layer was washed with water three times and was extracted into 2 M NaOH. The aqueous extracts were acidified to pH 1 with 6 M HCl, extracted with methyl tert-butyl ether, dried with magnesium sulfate and concentrated to a residue. This material was recrystallized by dissolving the residue in 50:35:15 cyclohexane/toluene/isopropanol at 70° C. followed by cooling to room temperature, filtering and azeotroping the resulting solids with hexanes to give the desired compound (57 g, 55%) as a white solid: $^1$H NMR (300 MHz, DMSO-d$_6$) δ 7.89-7.93 (m, 2H), 7.72-7.77 (m, 2H), 3.23 (t, J=6.0 Hz, 2H), 2.58 (t, J=6.6 Hz, 2H).

Step B: A mixture of the product from Step A (57 g, 223 mmol), potassium hydroxide (43 g, 760 mmol) and hydrazine hydrate (26 ml, 830 mmol) in diethylene glycol (2865 ml) was stirred at 195° C. for 3 hours. After cooling below 40° C., the mixture was diluted with water (300 ml), poured into 3 M NaOH and washed with dichloromethane three times. Brine was added to break up the emulsion. The aqueous layer was acidified to pH 1 with 6 M HCl and extracted with methyl tert-butyl ether three times. The combined organic extracts were dried over magnesium sulfate to give 4-(4-bromophenyl)butyric acid (41 g, 75%): $^1$H NMR (300 MHz, DMSO-d$_6$) δ 7.44-7.48 (m, 2H), 7.14-7.20 (m, 2H), 2.56 (t, J=7.2 Hz, 2H), 2.20 (t, J=7.5 Hz, 2H), 1.72-1.82 (m, 2H).

Step C: The product from Step B (97 g, 397 mmol) was added to polyphosphoric acid (580 g) and the resulting mixture was stirred at 90° C. for 10 minutes. After cooling to 0° C., 6 M NaOH (2 l) was added and the mixture was extracted with methyl tert-butyl ether. The organic extracts were dried over magnesium sulfate to give 7-bromo-3,4-dihydronaphthalen-1-one (49 g, 55%) after chromatography (6:1 to 4:1 heptane/ethyl acetate) and recrystallization from cyclohexane: $^1$H NMR (300 MHz, DMSO-d$_6$) δ 7.91 (d, J=2.1 Hz, 1H), 7.71 (dd, J=8.1, 2.1 Hz, 1H), 7.34 (d, J=8.1 Hz, 1H), 2.90 (t, J=6.0 Hz, 2H), 2.61 (t, J=6.3 Hz, 2H), 1.99-2.07 (m, 2H).

Step D: A solution of tetrabutylammonium tribromide (11.8 g, 24.4 mmol) in dichloromethane (80 ml) was added dropwise to a solution of the product from Step C (5.0 g, 22.2 mmol) in dichloromethane (20 ml) and methanol (20 ml) at room temperature over 1 hour. At completion of the addition, the mixture was stirred at room temperature for 15 hours and was then concentrated. The residue was taken into dichloromethane and was washed with saturated sodium bicarbonate three times. The organic layer was concentrated and the residue was dissolved in dimethylformamide (100 ml). Lithium carbonate (5.3 g, 71.1 mmol) and lithium bromide (4.1 g, 46.6 mmol) were added and the resulting mixture was stirred at 140° C. for 1.5 hours. After cooling to room temperature, the solids were filtered and rinsed with ethyl acetate. The filtrate was washed with water four times and dried over sodium sulfate to give 7-bromonaphthalen- 1-ol (2.7 g, 56%): $^1$H NMR (300 MHz, CDCl$_3$) δ 8.41 (d, J=1.8 Hz, 1H), 7.68 (d, J=8.7 Hz, 1H), 7.57 (dd, J=8.7, 1.8 Hz, 1H), 7.41 (d, J=8.4 Hz, 1H), 7.28-7.35 (m, 1H), 6.62 (d, J=7.2 Hz, 1H), 5.80 (br s, 1H).

Step E: Potassium carbonate (3.3 g, 23.9 mmol) and methyl iodide (1.5 ml, 23.9 mmol) were added to a solution of the product from Step D (2.7 g, 11.9 mmol) in acetone (40 ml) at room temperature and the mixture was stirred at 65° C. for 2 hours. The solids were filtered, rinsed with ethyl acetate and the filtrate was evaporated. The residue was dissolved in ethyl acetate and washed with water twice. The aqueous layers were extracted with ethyl acetate. The combined organic extracts were washed with brine and dried over sodium sulfate to give 7-bromo-1-methoxynaphthalene (2.5 g, 88%) after chromatography (19:1 heptane/ethyl acetate): $^1$H NMR (300 MHz, CDCl$_3$) δ 8.49 (d, J=2.1 Hz, 1H), 7.68 (d, J=8.7 Hz, 1H), 7.59 (dd, J=8.7, 2.1 Hz, 1H), 7.39-7.43 (m, 2H), 6.85 (dd, J=5.4, 3.0 Hz, 1H), 3.15 (s, 3H).

Step F: 4-(8-Methoxynaphthalen-2-yl)-2-methyl-1,2,3,4-tetrahydroisoquinoline, maleate salt (0.29 g, 96.2% AUC HPLC) was prepared from the product from Step E as described in Example 63 (Steps C and D): $^1$H NMR (300 MHz, MeOD) δ 8.18 (s, 1H), 7.84 (d, J=8.4 Hz, 1H), 7.23-7.47 (m, 6H), 6.93-7.00 (m, 2H), 6.23 (s, 2H), 4.76-4.82 (m, 1H), 4.62 (br s, 2H), 3.88-3.96 (m, 1H), 3.59-3.70 (m, 1H), 3.10 (s, 3H); EI MS m/z=304 [C$_{21}$H$_{21}$NO+H]$^+$. Anal. Calcd. for C$_{25}$H$_{25}$NO$_5$: C, 71.05; H, 6.10; N, 3.27 with 0.2% H$_2$O and 0.17 EtOH. Found: C, 70.53; H, 6.04; N, 3.13.

Example 64

Preparation of 2-methyl-4-(5,6,7,8-tetrahydronaphthalen-2-yl)-1,2,3,4-tetrahydroisoquinoline, hydrochloride salt 2-Methyl-4-(5,6,7,8-tetrahydronaphthalen-2-yl)-1,2,3,4-tetrahydroisoquinoline was prepared from 6-acetyltetralin and benzylamine as described in Example 58 (Steps A to D). It was dissolved in ethyl acetate and treated with 2 M hydrogen chloride in diethyl ether (2 equiv) to give the corresponding hydrochloride salt (0.43 g, 98.6% AUC HPLC): $^1$H NMR (300 MHz, MeOD) δ 7.22-7.34 (m, 3H), 7.08 (d, J=7.8 Hz, 1H), 6.94 (br s, 3H), 4.49-4.62 (m, 3H), 3.81 (dd, J=12.0, 6.0 Hz, 1H), 3.53 (t, J=11.7 Hz, 1H), 3.08 (s, 3 H), 2.76 (br s, 4H), 1.82 (br s, 4H); EI MS m/z=278 [C$_{20}$H$_{23}$N+H]$^+$. Anal. Calcd. for C$_{20}$H$_{24}$ClN: C, 75.60; H, 7.59; N, 4.41 with 1.1 equiv HCl. Found: C, 75.44; H, 8.11; N, 4.26.

Example 65

Preparation of 4-(2H-chromen-3-yl)-2-methyl-1,2,3,4-tetrahydroisoquinoline, maleate salt Step A: To an ice-cold suspension of NaH (0.49 g, 12.4 mmol, 60% dispersion in oil) in THF (34.3 mL) was added salicylaldehyde (1.1 mL, 10.3 mmol) over 25 minutes. After 2.5 hours at 0° C., trimethyl-2-phosphonoacrylate (1.6 mL, 10.3 mmol) was added to the reaction mixture over 10 minutes. The icebath was removed, and the reaction mixture was stirred at room temperature for 2 hours, and then at 70° C. for 2 hours. The cooled reaction mixture was quenched with water, and the product was extracted into Et$_2$O (3×75 mL). The Et$_2$O extract was washed with brine, dried (Na$_2$SO$_4$), filtered and concentrated under reduced pressure. The residue obtained was re-dissolved in Et$_2$O (100 mL), washed with 10% NaHSO$_3$ and brine, dried (MgSO$_4$), filtered and concentrated to give the product (1.96 g, quantitative, crude) as a white solid: $^1$H NMR (300 MHz, CDCl$_3$) δ 7.44 (s, 1H), 7.23-7.20 (m, 1H), 7.13 (dd, J=7.2, 1.6 Hz, 1H), 6.92 (td, J=7.4, 0.9 Hz, 1H), 6.84 (d, J=8.1 Hz, 1H), 5.00 (d, J=1.3 Hz, 2H), 3.82 (s, 3H).

Step B: To an ice-cold solution of the ester (1.96 g, 10.3 mmol) from Step A in 2:1:1 THF/H$_2$O/MeOH (120 mL) was added LiOH.H$_2$O (0.87 g, 20.6 mmol). The icebath was removed, and the reaction mixture was heated under reflux for 30 minutes. The cooled reaction mixture was concentrated under reduced pressure, and acidified to pH 3-4 with concentrated HCl. The white precipitate formed was filtered, re-dissolved in CH$_2$Cl$_2$/MeOH, dried (MgSO$_4$), filtered and concentrated to give 2H-chromene-3-carboxylic acid (1.43 g, 79% over 2 steps): $^1$H NMR (300 MHz, DMSO-d$_6$) δ 7.45 (s, 1H), 7.34-7.31 (m, 1H), 7.25 (dd, J=7.9, 1.5 Hz, 1H), 6.95 (td, J=7.4, 0.9 Hz, 1H), 6.85 (d, J=8.1 Hz, 1H), 4.91 (d, J=1.3 Hz, 2H).

Step C: To a solution of LiOAc.2H$_2$O (0.16 g, 1.62 mmol) in 97:3 CH$_3$CN/H$_2$O (30 mL) was added 6-chloro-2H-1-benzopyran-3-carboxylic acid (1.43 g, 8.12 mmol), followed by NBS (1.52 g, 8.53 mmol) and the mixture was stirred at room temperature for 5 hours. The reaction mixture was then concentrated to dryness under reduced pressure. Purification by flash column chromatography (gradient, hexanes, then 98:2 to 90:10 hexanes/Et$_2$O) gave 3-bromo-6-chloro-2H-chromene (0.47 g, 27%) as a pale yellow oil: $^1$H NMR (300 MHz, CDCl$_3$) δ 7.14-7.10 (m, 1H), 6.94-6.88 (m, 2H), 6.79 (d, J=8.1 Hz, 1H), 6.75 (s, 1H), 4.88 (d, J=1.5 Hz, 2H).

Step D: To a mixture of the pinacol diborane (0.62 g, 2.45 mmol), KOAc (0.65 g, 6.68 mmol) and the bromide (0.47 g, 2.23 mmol) from Step C above was added DMSO (21.8 mL). The solution was degassed (three times, vacuum/argon), and PdCl$_2$dppfCH$_2$Cl$_2$ (110 mg, 0.13 mmol) was added to it. The reaction mixture was degassed again (three times, vacuum/argon), and heated at 80° C. for 3.5 hours. The cooled reaction mixture was diluted with water, extracted with CH$_2$Cl$_2$ (3×50 mL), washed with brine (50 mL), dried (Na$_2$SO$_4$), filtered and concentrated to give the crude boronate ester, which was used in the next step without further purification.

Step E: To a mixture of the crude boronate ester from Step D above and 4-bromoquinoline (0.42 g, 2.03 mmol) in DMF (8.4 mL) was added a solution of Cs2CO3 (2.64 g, 8.11 mmol) in water (3.8 mL). The mixture was degassed (three times, vacuum/argon), and Pd(PPh$_3$)$_4$ (0.16 g, 0.14 mmol) was added to it. The reaction mixture was degassed again (three times, vacuum/argon), and heated at 80° C. overnight. The cooled reaction mixture was diluted with water, extracted with CH$_2$Cl$_2$ (3×50 mL), washed with brine (50 mL), dried (Na$_2$SO$_4$), filtered and concentrated under reduced pressure. Purification by flash column chromatography (gradient, 95:5 to 70:30 hexanes/EtOAc) yielded partially purified product (0.36 g), which was used in Step F without further purification.

Step F: To an ice-cold solution of the product from Step E above (0.36 g) in CH$_2$Cl$_2$ (4.68 mL) was added methyl triflate (0.17 mL, 1.53 mmol) dropwise. The icebath was removed, and the mixture was stirred at room temperature for 40 minutes. The reaction was quenched with MeOH (1 mL), and the reaction mixture was concentrated under reduced pressure and used as such in Step G.

Step G: To a solution of the crude product from Step F above in MeOH (48 mL) was added sodium cyanoborohydride (0.19 g, 3.06 mmol), and the reaction mixture was stirred at room temperature overnight. The reaction mixture was concentrated, diluted with water, and extracted with $CH_2Cl_2$ (5×25 mL). The organic extracts were combined, washed with brine, dried ($Na_2SO_4$) and concentrated under reduced pressure. Purification by flash column chromatography (gradient, 90:10 to 70:30 hexanes/EtOAc) gave partially purified product (0.20 g), which was subjected to flash chromatography (eluent: 90:10 EtOAc/hexanes and 80:20 EtOAc/hexanes), followed by reverse phase HPLC (TFA salt obtained was converted to the corresponding free base with concentrated $NH_4OH$) to obtain the desired product (54 mg, 8% over 4 steps) as a pale yellow oil: $^1$H NMR (300 MHz, $CDCl_3$) δ 7.26-6.86 (m, 7H), 6.76 (d, J=7.6 Hz, 1H), 6.33 (s, 1H), 4.74 (dd, J=14.5, 1.3 Hz, 1H), 4.50 (dd, J=14.5, 1.3 Hz, 1H), 3.90-3.80 (m, 1H), 3.58 (d, J=3.0 Hz, 1H), 2.85-2.75 (m, 1H), 2.61 (dd, J=11.5, 6.8 Hz, 1H), 2.42 (s, 3H).

Step H: To a solution of the product from Step G (54 mg, 0.18 mmol) in EtOH (0.5 mL) was added maleic acid (21 mg, 0.18 mmol), and the solution was cooled to −30° C. The thick slurry formed was diluted with EtOH (0.5 mL), and warmed to room temperature. The clear yellow solution obtained was concentrated under reduced pressure to obtain a foam, which was triturated with EtOAc, followed by EtOAc/hexanes to give the desired product (26 mg, 36%) as an off-white solid: $^1$H NMR (500 MHz, $CD_3OD$) δ 7.37-7.35 (m, 3H), 7.27 (br s, 1H), 7.14-7.11 (m, 1H), 7.03 (br s, 1H), 6.89 (br s, 1H), 6.77-6.76 (m, 1H), 6.50-6.40 (br s, 1H), 6.25 (s, 2H), 4.65-4.62 (m, 1H), 4.52-4.50 (m, 1H), 4.45 (s, 2H), 4.23 (br s, 1H), 3.70 (br s, 1H), 3.50-3.40 (m, 1H), 3.04 (s, 3H); ESI MS m/z 278 $[C_{19}H_{19}$ NO+H]$^+$; Anal. Calcd for $C_{19}H_{19}NO—C_4H_4O_4$-0.25$H_2O$: C, 69.42; H, 5.95; N, 3.52. Found: C, 69.28; H, 5.58; N, 3.47.

Example 66

4-(8,9-Dihydro-7H-benzocyclohepten-6-yl)-2-methyl-1,2,3,4-tetrahydroisoquinoline, maleate salt Step A: 8-Bromo-6,7-dihydro-5H-benzocycloheptene was synthesized following a procedure published in Paquette et al., J. Org. Chem. 56:6199-6205 (1991), which is hereby incorporated by reference in its entirety. $^1$H NMR (300 MHz, $CDCl_3$) δ 7.17-7.03 (m, 4H), 6.94 (s, 1H), 2.95-2.79 (m, 4H), 2.00-2.89 (m, 2H).

Step B: 8-Bromo-6,7-dihydro-5H-benzocycloheptene (1.0 g, 4.48 mmol), and bis(pinacolato)diboron (2.28 g, 8.98 mmol) were reacted as described for the synthesis of Example 67, Step D. The crude product was used without further purification in Step C.

Step C: The product from Step B (~0.48 mmol), and 4-bromoisoquinoline (0.865 g, 4.07 mmol) were reacted as described for the synthesis of Example 67, Step E to afford, after chromatography, the product as an off-white solid (1.08 g, 82% over 2 steps): $^1$H NMR (300 MHz, $CDCl_3$) δ 9.19 (s, 1H), 8.47 (s, 1H), 8.06-7.97 (m, 2H), 7.74-7.50 (m, 2H), 7.24-7.14 (m, 4H), 6.62 (s, 1H), 3.05-3.00 (m, 2H), 2.74-2.67 (m, 2H), 2.28-2.17 (m, 2H).

Step D: The product from Step C (1.0 g, 3.68 mmol), and methyl triflate (0.46 mL, 4.06 mmol) were reacted as described for the synthesis of Example 67, Step F to afford a yellow solid, which was carried onto Step E without further purification.

Step E: The product from Step D (~3.68 mmol), and sodium cyanoborohydride (0.578 g, 9.20 mmol) were combined as described for the synthesis of Example 67, Step G to afford, after chromatography, the product as an off-white solid (1.08 g, quantitative over 2 steps). $^1$H NMR (300 MHz, DMSO-$d_6$) δ 7.25-7.05 (m, 8H), 6.50 (s, 1H), 3.85 (t, 1H, J=6.7 Hz), 3.57 (d, ½ AB, 1H, J=15.0 Hz), 3.43 (d, ½ AB, 1H, J=15.0 Hz), 2.91-2.79 (m, 1H), 2.69-2.60 (m, 2H), 2.56-2.46 (m, 2H), 2.33 (s, 3H), 2.12-1.81 (m, 3H).

Step F: The product from Step E (1.0 g, 3.45 mmol) and maleic acid (0.43 g, 0.74 mmol) in EtOH (3 mL) at room temperature was stirred using an ultrasound generator. The slurry was filtered under reduced pressure to give the desired product (0.926 g, 93%) as a white solid: mp 178-180° C.; $^1$H NMR (300 MHz, $CD_3OD$) δ 7.43-7.30 (m, 3H), 7.28-7.22 (m, 1H), 7.20-7.12 (m, 4H), 6.68 (s, 1H), 4.48 (s, 2H), 4.26 (dd, 1H, J=11.4, 6.5 Hz), 3.79 (dd, 1H, J=12.2, 6.4 Hz), 3.49 (t, 1H, J=11.6 Hz), 3.07 (s, 3H), 2.89-2.71 (m, 2H), 2.11-1.89 (m, 4H) ESI m/z 289 $[C_{21}H_{23}N+H]^+$. Anal. Calcd for $C_{21}H_{23}N—C_4H_4O_4$: C, 74.05; H, 6.71; N, 3.45. Found: C, 73.91; H, 6.73; N, 3.43.

Example 67

Preparation of 4-(benzo[b]thiophen-7-yl)-2-methyl-1,2,3,4,tetrahydroisoquinoline, maleate salt 4-Benzo[b]thiophen-7-yl-2-methyl-1,2,3,4-tetrahydroisoquinoline was prepared from 2-bromobenzenethiol as described in Example 40 (Steps A to E) and was converted to the corresponding maleate salt (0.14 g, 99.2% AUC HPLC) by crystallization with maleic acid (1 equiv) in ethanol (2 ml): $^1$H NMR (300 MHz, DMSO-$d_6$) δ 7.91 (d, J=7.9 Hz, 1H), 7.79 (d, J=5.4 Hz, 1H), 7.56 (d, J=5.4 Hz, 1H), 7.47 (t, J=7.5 Hz, 1H), 7.35 (d, J=3.8 Hz, 2H), 7.20-7.28 (m, 2H), 6.82 (d, J=6.2 Hz, 1H), 6.09 (s, 2H), 4.89-4.95 (m, 1H), 4.54 (s, 2H), 3.76-3.87 (m, 1H), 3.57-3.65 (m, 1H), 2.96 (s, 3H); EI MS m/z=280 $[C_{18}H_{17}NS+H]^+$. Anal. Calcd. for $C_{22}H_{21}NO_4S$: C, 64.60; H, 5.48; N, 3.42; S, 7.83 with 3.2% $H_2O$. Found: C, 64.11; H, 5.56; N, 2.98; S, 7.87.

Example 68

Preparation of 4-hydroxy-7-Methoxy-2-methyl-4-(quinolin-6-yl)-1,2,3,4-tetrahdro-isoquinoline, fumarate Step A: To solution of 6-bromoquinoline (624 mg, 3.0 mmol) at −75° C., was added t-butyllithium (1.7 M in pentane, 1.95 mL, 3.3 mmol) dropwise. The reaction mixture was stirred at −75° C. for 1 hour. To the resulting dark brown mixture was added 7-methoxy-2-methyl-2,3-dihydro-1H-isoquinolin-4-one (383 mg, 2.0 mmol), which was prepared using the method described by Hanna et al., J. Med. Chem., 17(9):1020-1023 (1974), which is hereby incorporated by reference in its entirety. The reaction mixture was stirred for 15 hours with gradually warming up. The mixture was quenched with saturated ammonium chloride and extracted with ethyl acetate (3×50 ml). The combined organic extracts were washed with saturated sodium chloride, dried over anhydrous sodium sulfate, filtered, and concentrated in vacuo. Purification by medium pressure silica gel chromatography (0-5% methanol/dichloromethane) afforded the product (225 mg, 35%): $^1$H NMR ($CDCl_3$, 300 MHz) δ 8.90 (dd, 1H, J=1.7, 4.3 Hz), 8.22-8.18 (m, 2H), 8.00 (d, 1H, J=8.9 Hz), 7.50 (dd, 1H, J=2.0, 8.9 Hz), 7.41 (dd, 1H, J=4.3, 8.3 Hz), 6.85 (d, 1H, J=8.6 Hz), 6.68 (dd, 1H, J=2.6, 8.6 Hz), 6.60 (d, 1H, J=2.5 Hz), 4.50 (br s, 1H), 3.80 (s, 3H), 3.69 (d, 1H, J=15.0 Hz), 3.43 (d, 1H, J=15.0 Hz), 2.98 (d, 1H, J=11.7 Hz), 2.75 (d, 1H, J=11.7 Hz), 2.44 (s, 3H), ESI MS m/z=321 [M+H]+.

Step B: The product from Step A (45 mg, 0.14 mmol) was dissolved in ethanol (1 mL) and added a solution of fumaric acid (17 mg, 0.14 mmol) in methanol (0.5 mL). The solvent was removed under reduced pressure. The residue was triturated with ethyl acetate. The resulting precipitate was collected by filtration, washed with ethyl acetate, and dried at 50° C. under vacuum to provide the product as an off-white solid (35 mg, 57%): $^1$H NMR (CD$_3$OD, 500 MHz) δ 8.87 (dd, 1H, J=1.6, 4.3 Hz), 8.39 (d, 1H, J=7.7 Hz), 8.20 (d, 1H, J=1.8 Hz), 7.98 (d, 1H, J=8.9 Hz), 7.64 (dd, 1H, J=2.0, 8.9 Hz), 7.58 (dd, 1H, J=4.3, 8.3 Hz), 6.89-6.81 (m, 3H), 6.70 (s, 2H), 4.38 (d, 1H, J=15.5 Hz), 4.27 (d, 1H, J=15.5 Hz), 3.81 (s, 3H), 3.53 (d, 1H, J=12.3 Hz), 3.43 (d, 1H, J=12.3 Hz), 2.88 (s, 3H). ESI MS m/z=321 [M+H]+.

Example 69

Preparation of 7-methoxy-2-methyl-4-(quinolin-6-yl)-1,2,3,4-tetrahdroisoquinoline, fumarate salt Step A: The product from Step A of Example 70 (250 mg, 0.78 mmol) was heated at reflux in HCl/Ethanol (prepared by mixing 1.5 mL of acetyl chloride with 25 mL of ethanol) for 2 hours. The solvent was removed under reduced pressure. The residue was redissolved in methanol (25 mL) and sodium borohydride (300 mg, 7.8 mmol) was added to the solution. The reaction mixture was stirred at room temperature for 4 hours. ESI MS analysis indicated that the reaction was not complete. Additional sodium cyanoborohydride (250 mg, 4 mmol) was added to this mixture. The resulting reaction mixture was stirred at room temperature for 16 hours. The mixture was then quenched with water and extracted with ethyl acetate (3×50 ml). The combined organic extracts were washed with saturated sodium chloride, dried over anhydrous sodium sulfate, filtered, and concentrated in vacuo. Purification by medium pressure silica gel chromatography (0-5% methanol/dichloromethane) afforded the product (105 mg, 44%): $^1$H NMR (CD$_3$OD, 500 MHz) δ 8.80 (dd, 1H, J=1.6, 4.3 Hz), 8.30 (d, 1H, J=8.4 Hz), 7.95 (d, 1H, J=8.7 Hz), 7.77 (d, 1H, J=1.8 Hz), 7.56 (dd, 1H, J=1.9, 8.7 Hz), 7.51 (dd, 1H, J=4.3, 8.3 Hz), 6.74-6.66 (m, 3H), 4.48 (dd, 1H, J=6.2, 8.9 Hz), 3.81 (d, 1H, J=15.0 Hz), 3.76 (s, 3H), 3.66 (d, 1H, J=15.0 Hz), 3.17-3.13 (m, 1H), 2.67 (dd, 1H, J=9.4, 11.6 Hz), 2.75 (d, 1H, J=11.7 Hz), 2.44 (s, 3H), ESI MS m/z=305 [M+H]+.

Step B: The product from Step A (51 mg, 0.16 mmol) was dissolved in ethanol (1 mL) and added a solution of fumaric acid (19 mg, 0.16 mmol) in methanol (0.5 mL). The solvent was removed under reduced pressure. The residue was triturated with ethyl acetate. The resulting precipitate was collected by filtration, washed with ethyl acetate, and dried at 50° C. under vacuum to provide the product as an off-white solid (55 mg, 82%): $^1$H NMR (CD$_3$OD, 500 MHz) δ 8.85 (dd, 1H, J=1.6, 4.3 Hz), 8.34 (d, 1H, J=8.2 Hz), 8.01 (d, 1H, J=8.8 Hz), 7.87 (d, 1H, J=1.6 Hz), 7.60-7.54 (m, 2H), 6.83 (s, 1H), 6.79 (d, 2H, J=1.4 Hz), 4.72 (dd, 1H, J=6.1, 10.6 Hz), 4.37 (s, 2H), 3.79 (s, 3H), 3.71 (dd, 1H, J=6.1, 12.1 Hz), 3.39 (d, 1H, J=11.1 Hz), 2.91 (s, 3H), ESI MS m/z=305 [M+H]+.

Example 70

Preparation of (+)-4-(benzo[b]thiophen-2-yl)-2-methyl-7-(pyridazin-3-yl)-1,2,3,4-tetrahydroisoquinoline, maleate salt and (−)-4-(benzo[b]thiophen-2-yl)-2-methyl-7-(pyridazin-3-yl)-1,2,3,4-tetrahydroisoquinoline, maleate salt Step A: To a solution of 2-acetylbenzo[b]thiophene (5.0 g, 28 mmol) in chloroform (120 mL) was added pyridinium bromide perbromide (9.6 g, 28 mmol) in two batches. The reaction solution was stirred at room temperature for 2 hours, and then was washed with water, aqueous HCl (2 M), water and brine. The resultant solution was dried over sodium sulfate and concentrated under reduced pressure to give the desired bromoketone (7.4 g, crude) as a brown solid, which was used in the next step without further purification: $^1$H NMR (CDCl$_3$, 500 MHz) δ 8.07 (s, 1H), 7.94-7.87 (m, 2H), 7.52-7.25 (m, 2H), 4.46 (s, 2H).

Step B: To a solution of 3-methoxybenzyl methylamine (4.3 g, 29 mmol) in dichloromethane (150 mL) were added triethylamine (10 mL) and the bromoketone (7.3 g, 29 mmol) from Step A above. The reaction solution was stirred at room temperature for 2 hours, and then was quenched with aqueous saturated sodium bicarbonate. The organic extract was separated, washed with water and brine, dried over sodium sulfate and concentrated under reduced pressure. The crude product was purified by flash column chromatography (90:10 to 85:15 hexanes/ethyl acetate) to give the desired product (7.1 g, 76% over 2 steps) as a reddish oil: 1H NMR (CDCl$_3$, 500 MHz) δ 8.09 (s, 1H), 7.86 (d, J=8.0 Hz, 2H), 7.45 (dd, J=8.0, 1.1 Hz, 1H), 7.40 (dd, J=8.0, 1.0 Hz, 1H), 7.24 (d, J=8.1 Hz, 1H), 6.97-6.95 (m, 2H), 6.83 (d, J=8.5 Hz, 1H), 3.78 (s, 3H), 3.76 (s, 2H), 3.70 (s, 2H), 2.43 (s, 3H); ESI-MS m/z 326 [M+H]+.

Step C: To a solution of the ketone (7.1 g, 22 mmol) from Step B above in methanol (100 mL) at 0° C. was added sodium borohydride (0.89 g, 24 mmol) in small portions. The reaction solution was stirred at 0° C. for 1 hour. The solvent was then removed under reduced pressure and the residue obtained was dissolved in dichloromethane. The resultant solution was washed with aqueous saturated sodium bicarbonate and brine, dried over sodium sulfate and concentrated under reduced pressure to give the desired alcohol (6.9 g, 96% crude) as a yellow oil. The crude product was used in the next step without further purification: $^1$H NMR (CDCl$_3$, 500 MHz) δ 7.81 (d, J=7.9 Hz, 1H), 7.70 (d, J=8.1 Hz, 1H), 7.33-7.23 (m, 3H), 7.21 (s, 1H), 6.91-6.87 (m, 3H), 5.07 (dd, J=10.1, 3.5 Hz, 1H), 4.40-4.03 (m, 1H), 3.81 (s, 3H), 3.72 (d, J=13.0 Hz, 1H), 3.56 (d, J=13.0 Hz, 1H), 2.83 (dd, J=12.4, 10.2 Hz, 1H), 2.72 (dd, J=12.4, 3.7 Hz, 1H), 2.34 (s, 3H); ESI-MS m/z 328 [M+H]+.

Step D: To a solution of the alcohol (6.9 g, 21 mmol) from Step C above in dichloromethane (150 mL) was added methanesulfonic acid (14 mL, 210 mmol) dropwise. After the addition, the reaction solution was stirred at room temperature for 20 minutes, and then was added slowly to ice-cold aqueous sodium hydroxide (120 mL, 2 M) and stirred for 20 minutes. The organic extract was separated and the aqueous extract was washed with dichloromethane twice. The combined organic extract was washed with water and brine, dried over sodium sulfate and concentrated under reduced pressure. The crude product was purified by flash column chromatography (95:5 to 50:50 hexanes/ethyl acetate) to give the desired cyclized product (3.4 g, 52%) as a reddish oil: $^1$H NMR (CDCl$_3$, 500 MHz) δ 7.72 (d, J=8.0 Hz, 1H), 7.67 (d, J=8.0 Hz, 1H), 7.29-7.23 (m, 2H), 7.13 (s, 1H), 7.06 (d, J=8.5 Hz, 1H), 6.69 (d, J=2.7 Hz, 1H), 6.61 (d, J=2.6 Hz, 1H), 4.50 (t, J=5.3 Hz, 1H), 3.77 (s, 3H), 3.73 (d, J=14.5 Hz, 1H), 3.59 (d, J=14.5 Hz, 1H), 2.99 (dd, J=11.5, 4.9 Hz, 1H), 2.87 (dd, J=11.4, 6.2 Hz, 1H), 2.47 (s, 3H); ESI-MS m/z 310 [M+H]$^+$.

Step E: To a solution of the 7-methoxy tetrahydroisoquinoline (1.6 g, 5.1 mmol) from Step D above in acetic acid (25 mL) was added aqueous hydrogen bromide (25 mL, 48%). The reaction solution was heated at 100° C. for 20 hours, and then cooled to room temperature and concentrated under reduced pressure. The residue obtained was taken up in a mixture of dichloromethane, water and a small amount of methanol. The resultant solution was quenched carefully with aqueous saturated sodium bicarbonate until pH>8. The organic extract was separated, washed with water and brine, dried over sodium sulfate and concentrated under reduced pressure to give the desired phenol (1.6 g, crude) as a brown solid, which was used in the next step without further purification: $^1$H NMR (CDCl$_3$, 500 MHz) δ 7.72 (d, J=7.7 Hz, 1H), 7.67 (d, J=7.7 Hz, 1H), 7.29 (td, J=7.3, 1.2 Hz, 1H), 7.23 (td, J=7.3, 1.3 Hz, 1H), 7.13 (s, 1H), 7.01 (d, J=8.4 Hz, 1H), 6.59 (dd, J=8.4, 2.5 Hz, 1H), 6.53 (d, J=2.3 Hz, 1H), 4.49 (t, J=5.7 Hz, 1H), 3.68 (d, J=15.1 Hz, 1H), 3.57 (d, J=15.0 Hz, 1H), 3.00 (dd, J=11.6, 5.4 Hz, 1H), 2.85 (dd, J=11.5, 6.4 Hz, 1H), 2.47 (s, 3H), 1.90-1.45 (m, 1H); ESI-MS m/z 296 [M+H]$^+$.

Step F: To a solution of this phenol (1.6 g, 5.1 mmol) from Step E above in dichloromethane (50 mL) at 0° C. were successively added pyridine (0.80 mL, 10 mmol) and triflic anhydride (1.1 mL, 6.6 mmol) dropwise. The resultant reaction solution was stirred at 0° C. for 1 hour, and then was quenched with aqueous saturated sodium bicarbonate. The organic extract was separated and the aqueous layer was extracted with dichloromethane twice. The combined organic extract was washed with 1:1 water/brine, dried over sodium sulfate and concentrated under reduced pressure to give the crude product. Purification by flash column chromatography (dichloromethane to 98:2 dichloromethane/methanol) gave the desired triflate (1.6 g, 73% over two steps) as a yellow oil: $^1$H NMR (CDCl$_3$, 500 MHz) δ 7.74 (d, J=8.0 Hz, 1H), 7.70 (d, J=7.8 Hz, 1H), 7.32-7.24 (m, 3H), 7.16 (s, 1H), 7.02-7.00 (m, 2H), 4.54 (t, J=5.4 Hz, 1H), 3.78 (d, J=15.4 Hz, 1H), 3.65 (d, J=15.4 Hz, 1H), 3.01 (dd, J=11.6, 5.0 Hz, 1H), 2.91 (dd, J=11.6, 6.0 Hz, 1H), 2.50 (s, 3H); ESI-MS m/z 428 [M+H]$^+$.

Step G: To a mixture of the triflate (1.0 g, 2.3 mmol) from Step F above, bis(pinacolato)diboron (0.65 g, 2.6 mmol) and potassium acetate (0.69 g, 7.0 mmol) was added dimethyl sulfoxide (15 mL). The resultant solution was purged with argon for 10 minutes, and then 1,1'-bis(diphenylphosphino)ferrocenedichloropalladium (57 mg, 0.07 mmol) was added to it. The reaction solution was degassed again with argon for 5 minutes and heated at 80° C. for 1 hour. The reaction solution was then cooled to room temperature, diluted with ethyl acetate, washed with water and brine, dried over sodium sulfate and concentrated under reduced pressure. The crude product was purified by flash column chromatography (dichloromethane to 95:5 dichloromethane/methanol) to give the desired product (1.3 g, crude) as a reddish oil, which was used in the next step without further purification: $^1$H NMR (CDCl$_3$, 500 MHz) δ 7.72 (d, J=7.9 Hz, 1H), 7.67 (d, J=7.9 Hz, 1H), 7.56-7.54 (m, 2H), 7.29 (td, J=7.3, 1.1 Hz, 1H), 7.23 (td, J=8.2, 2.6 Hz, 1H), 7.16 (d, J=7.5 Hz, 1H), 7.13 (s, 1H), 4.57 (t, J=5.3 Hz, 1H), 3.77 (d, J=14.9 Hz, 1H), 3.63 (d, J=14.9 Hz, 1H), 3.00 (dd, J=11.3, 4.8 Hz, 1H), 2.89 (dd, J=11.4, 6.1 Hz, 1H), 2.48 (s, 3H), 1.33 (s, 12H); ESI-MS m/z 406 [M+H]$^+$.

Step H: To a mixture of the boronate ester (1.3 g, crude) from Step G above, 3,6-dichloropyridazine (0.69 g, 4.6 mmol) and sodium carbonate (0.75 g, 7.1 mmol) were added N,N-dimethylformamide (20 mL) and water (5.1 mL). The reaction solution was purged with argon for 10 minutes, and then 1,1'-bis(diphenylphosphino)ferrocenedichloropalladium (94 mg, 0.12 mmol) was added to it. The reaction solution was degassed again with argon for 5 minutes and heated at 80° C. for 2 hours. The reaction solution was then cooled to room temperature, diluted with ethyl acetate, washed with water and brine, dried over sodium sulfate and concentrated under reduced pressure. The crude product was purified using the Biotage MPLC system (dichloromethane to 95:5 dichloromethane/methanol) to give the partially purified product (0.83 g, 91%) as a light brown solid, which was used in the next step without further purification: $^1$H NMR (CDCl$_3$, 500 MHz) δ 7.87 (s, 1H), 7.80-7.69 (m, 4H), 7.54 (d, J=9.0 Hz, 1H), 7.53-7.24 (m, 3H), 7.20 (s, 1H), 4.62 (br s, 1H), 3.86 (d, J=15.3 Hz, 1H), 3.74 (d, J=15.0 Hz, 1H), 3.07-3.04 (m, 1H), 2.96-2.92 (m, 1H), 2.53 (s, 3H); ESI-MS m/z 392 [M+H]$^+$.

Step I: To a partially dissolved solution of the chloropyridazine (0.40 g, 1.0 mmol) from Step H above in a mixture of ethanol (55 mL) and methanol (20 mL) were added hydrazine monohydrate (2.0 mL, 42 mmol) and palladium on carbon (150 mg). The reaction solution was heated under reflux for 16 hours, and then was cooled to room temperature, filtered through a plug of celite and concentrated under reduced pressure. The crude product was purified by flash column chromatography (dichloromethane to 97:3 dichloromethane/methanol) to give the desired product (0.21 g, 59%) as a light yellow foam: $^1$H NMR (CDCl$_3$, 500 MHz) δ 9.14 (dd, J=4.9, 1.5 Hz, 1H), 7.93 (d, J=1.5 Hz, 1H), 7.82 (dd, J=8.6, 1.6 Hz, 1H), 7.77-7.73 (m, 2H), 7.70 (d, J=7.8 Hz, 1H), 7.51 (dd, J=9.2, 5.4 Hz, 1H), 7.33-7.23 (m, 3H), 7.20 (s, 1H), 4.63 (t, J=5.4 Hz, 1H), 3.87 (d, J=15.1 Hz, 1H), 3.75 (d, J=15.0 Hz, 1H), 3.06 (dd, J=11.6, 4.9 Hz, 1H), 2.94 (dd, J=11.6, 6.1 Hz, 1H), 2.53 (s, 3H).

Step J: To a solution of the 7-pyridazinyl tetrahydroisoquinoline (0.21 g, 0.60 mmol) from Step I above in a mixture of methanol (10 mL) and dichloromethane (3 mL) was added maleic acid (69 mg, 0.60 mmol). The reaction solution was concentrated under reduced pressure to ~3 mL and diluted with water (10 mL). The resultant solution was lyophilized overnight to give 4-(benzo[b]thiophen-2-yl)-2-methyl-7-(pyridazin-3-yl)-1,2,3,4-tetrahydroisoquinoline, maleate salt (280 mg, 99%) as a light yellow solid: mp 113-115° C.; $^1$H NMR (CD$_3$OD, 500 MHz) δ 9.18 (dd, J=4.9, 1.5 Hz, 1H), 8.20 (dd, J=8.7, 1.5 Hz, 1H), 8.09 (s, 1H), 8.02 (dd, J=7.7, 1.2 Hz, 1H), 7.84-7.79 (m, 3H), 7.44 (d, J=8.3 Hz, 1H), 7.40-7.32 (m, 3H), 6.24 (s, 2H), 5.09 (dd, J=9.8, 6.0 Hz, 1H), 4.65 (br s, 2H), 3.98 (dd, J=12.4, 6.0 Hz, 1H), 3.75 (t, J=11.6 Hz, 1H), 3.08 (s, 3H); ESI-MS m/z 358 [M+H]$^+$.

Step K: The free base of 4-(benzo[b]thiophen-2-yl)-2-methyl-7-(pyridazin-3-yl)-1,2,3,4-tetrahydroisoquinoline, maleate salt (0.28 g) was resolved by preparative chiral HPLC (CHIRALPAK OD column, using 80:20:0.1 heptane/2-propanol/diethylamine as the eluent) to give the (+)-enantiomer [[α]$^{25}_D$ +122.7° (c 0.11, chloroform)] and the (−)-enantiomer [[α]$^{25}_D$ −39.1° (c 0.11, chloroform)]. The (+)-enantiomer (0.11 g, 0.31 mmol) was dissolved in a mixture of methanol (3 mL) and dichloromethane (3 mL) and one equivalent of maleic acid (35 mg, 0.31 mmol) was added to the solution. The resultant solution was concentrated under reduced pressure and the residue obtained was dissolved in a mixture of methanol (5 mL) and water (25 mL) and lyophilized overnight to provide (+)-4-(benzo[b]thiophen-2-yl)-2-methyl-7-(pyridazin-3-yl)-1,2,3,4-tetrahydroisoquinoline, maleate salt (0.14 g, 98%, >99% AUC HPLC) as a white solid: mp 99-102° C.; $^1$H NMR (CD$_3$OD, 500 MHz) δ 9.18 (dd, J=4.9, 1.5 Hz, 1H), 8.20 (dd, J=8.7, 1.5 Hz, 1H), 8.08 (s, 1H), 8.02 (dd, J=7.7, 1.2 Hz, 1H), 7.84-7.77 (m, 3H), 7.44 (d, J=8.3 Hz, 1H), 7.40-7.32 (m, 3H), 6.25 (s, 2H), 5.09 (dd, J=9.8, 6.0 Hz, 1H), 4.63 (br s, 2H), 3.97 (dd, J=12.4, 6.0 Hz, 1H), 3.73 (t, J=11.6 Hz, 1H), 3.09 (s, 3H); ESI-MS m/z 358 [M+H]$^+$; Anal. Calcd. For C$_{22}$H$_{19}$N$_3$S—C$_4$H$_4$O$_4$—H$_2$O: C, 63.53; H, 5.13; N, 8.55. Found: C, 63.66; H, 4.90; N, 8.43. The (−)-enantiomer (0.11 g, 0.31 mmol) was dissolved in a mixture of methanol (3 mL) and dichloromethane (3 mL) and one equivalent of maleic acid (35 mg, 0.31 mmol) was added to the solution. The resultant solution was concentrated under reduced pressure and the residue obtained was dissolved in a mixture of methanol (5 mL) and water (25 mL) and lyophilized overnight to provide (−)-4-(benzo[b]thiophen-2-yl)-2-methyl-7-(pyridazin-3-yl)-1,2,3,4-tetrahydroisoquinoline, maleate salt (0.14 g, 98%, >99% AUC HPLC) as a white solid: mp 100-104° C.; $^1$H NMR (CD$_3$OD, 500 MHz) δ 9.18 (dd, J=4.9, 1.5 Hz, 1H), 8.20 (dd, J=8.7, 1.5 Hz, 1H), 8.08 (s, 1H), 8.02 (dd, J=7.7, 1.2 Hz, 1H), 7.84-7.77 (m, 3H), 7.44 (d, J=8.3 Hz, 1H), 7.40-7.32 (m, 3H), 6.25 (s, 2H), 5.09 (dd, J=9.8, 6.0 Hz, 1H), 4.63 (br s, 2H), 3.97 (dd, J=12.4, 6.0 Hz, 1H), 3.73 (t, J=11.6 Hz, 1H), 3.09 (s, 3H); ESI-MS m/z 358 [M+H]$^+$; Anal. Calcd. For C$_{22}$H$_{19}$N$_3$S—C$_4$H$_4$O$_4$—H$_2$O: C, 63.53; H, 5.13; N, 8.55. Found: C, 63.46; H, 5.07; N, 8.43.

Example 71

Preparation of (+/−)-4-(benzo[b]thiophen-2-yl)-2-methyl-7-(pyrazin-2-yl)-1,2,3,4-tetrahydroisoquinoline, maleate salt Step A: To a solution of 2-acetylbenzo[b]thiophene (5.0 g, 28 mmol) in chloroform (120 mL) was added pyridinium bromide perbromide (9.6 g, 28 mmol) in two batches. The reaction solution was stirred at room temperature for 2 hours, and then was washed with water, aqueous HCl (2 M), water and brine. The resultant solution was dried over sodium sulfate and concentrated under reduced pressure to give the desired bromoketone (7.4 g, crude) as a brown solid, which was used in the next step without further purification: $^1$H NMR (CDCl$_3$, 500 MHz) δ 8.07 (s, 1H), 7.94-7.87 (m, 2H), 7.52-7.25 (m, 2H), 4.46 (s, 2H).

Step B: To a solution of 3-methoxybenzyl methylamine (4.3 g, 29 mmol) in dichloromethane (150 mL) were added triethylamine (10 mL) and the bromoketone (7.3 g, 29 mmol) from Step A above. The reaction solution was stirred at room temperature for 2 hours, and then was quenched with aqueous saturated sodium bicarbonate. The organic extract was separated, washed with water and brine, dried over sodium sulfate and concentrated under reduced pressure. The crude product was purified by flash column chromatography (90:10 to 85:15 hexanes/ethyl acetate) to give the desired product (7.1 g, 76% over 2 steps) as a reddish oil: $^1$H NMR (CDCl$_3$, 500 MHz) δ 8.09 (s, 1H), 7.86 (d, J=8.0 Hz, 2H), 7.45 (dd, J=8.0, 1.1 Hz, 1H), 7.40 (dd, J=8.0, 1.0 Hz, 1H), 7.24 (d, J=8.1 Hz, 1H), 6.97-6.95 (m, 2H), 6.83 (d, J=8.5 Hz, 1H), 3.78 (s, 3H), 3.76 (s, 2H), 3.70 (s, 2H), 2.43 (s, 3H); ESI-MS m/z 326 [M+H]$^+$.

Step C: To a solution of the ketone (7.1 g, 22 mmol) from Step B above in methanol (100 mL) at 0° C. was added sodium borohydride (0.89 g, 24 mmol) in small portions. The reaction solution was stirred at 0° C. for 1 hour. The solvent was then removed under reduced pressure and the residue obtained was dissolved in dichloromethane. The resultant solution was washed with aqueous saturated sodium bicarbonate and brine, dried over sodium sulfate and concentrated under reduced pressure to give the desired alcohol (6.9 g, 96% crude) as a yellow oil. The crude product was used in the next step without further purification: $^1$H NMR (CDCl$_3$, 500 MHz) δ 7.81 (d, J=7.9 Hz, 1H), 7.70 (d, J=8.1 Hz, 1H), 7.33-7.23 (m, 3H), 7.21 (s, 1H), 6.91-6.87 (m, 3H), 5.07 (dd, J=10.1, 3.5 Hz, 1H), 4.40-4.03 (m, 1H), 3.81 (s, 3H), 3.72 (d, J=13.0 Hz, 1H), 3.56 (d, J=13.0 Hz, 1H), 2.83 (dd, J=12.4, 10.2 Hz, 1H), 2.72 (dd, J=12.4, 3.7 Hz, 1H), 2.34 (s, 3H); ESI-MS m/z 328 [M+H]$^+$.

Step D: To a solution of the alcohol (6.9 g, 21 mmol) from Step C above in dichloromethane (150 mL) was added methanesulfonic acid (14 mL, 210 mmol) dropwise. After the addition, the reaction solution was stirred at room temperature for 20 minutes, and then was added slowly to ice-cold aqueous sodium hydroxide (120 mL, 2 M) and stirred for 20 minutes. The organic layer was separated and the aqueous layer was extracted with dichloromethane twice. The combined organic extract was washed with water and brine, dried over sodium sulfate and concentrated under reduced pressure. The crude product was purified by flash column chromatography (95:5 to 50:50 hexanes/ethyl acetate) to give the desired product (3.4 g, 52%) as a reddish oil: $^1$H NMR (CDCl$_3$, 500 MHz) δ 7.72 (d, J=8.0 Hz, 1H), 7.67 (d, J=8.0 Hz, 1H), 7.29-7.23 (m, 2H), 7.13 (s, 1H), 7.06 (d, J=8.5 Hz, 1H), 6.69 (d, J=2.7 Hz, 1H), 6.61 (d, J=2.6 Hz, 1H), 4.50 (t, J=5.3 Hz, 1H), 3.77 (s, 3H), 3.73 (d, J=14.5 Hz, 1H), 3.59 (d, J=14.5 Hz, 1H), 2.99 (dd, J=11.5, 4.9 Hz, 1H), 2.87 (dd, J=11.4, 6.2 Hz, 1H), 2.47 (s, 3H); ESI-MS m/z 310 [M+H]$^+$.

Step E: To a solution of the 7-methoxy tetrahydroisoquinoline (1.6 g, 5.1 mmol) from Step D above in acetic acid (25 mL) was added aqueous hydrogen bromide (25 mL, 48%). The reaction solution was heated at 100° C. for 20 hours, and then cooled to room temperature and concentrated under reduced pressure. The residue obtained was taken up in a mixture of dichloromethane, water and small amount of methanol. The resultant solution was quenched carefully with aqueous saturated sodium bicarbonate until pH>8. The organic extract was separated, washed with water and brine, dried over sodium sulfate and concentrated under reduced pressure to give the desired phenol (1.6 g, crude) as a brown solid, which was used in the next step without further purification: $^1$H NMR (CDCl$_3$, 500 MHz) δ 7.72 (d, J=7.7 Hz, 1H), 7.67 (d, J=7.7 Hz, 1H), 7.29 (td, J=7.3, 1.2 Hz, 1H), 7.23 (td, J=7.3, 1.3 Hz, 1H), 7.13 (s, 1H), 7.01 (d, J=8.4 Hz, 1H), 6.59 (dd, J=8.4, 2.5 Hz, 1H), 6.53 (d, J=2.3 Hz, 1H), 4.49 (t, J=5.7 Hz, 1H), 3.68 (d, J=15.1 Hz, 1H), 3.57 (d, J=15.0 Hz, 1H), 3.00 (dd, J=11.6, 5.4 Hz, 1H), 2.85 (dd, J=11.5, 6.4 Hz, 1H), 2.47 (s, 3H), 1.90-1.45 (m, 1H); ESI-MS m/z 296 [M+H]$^+$.

Step F: To a solution of this phenol (1.6 g, 5.1 mmol) from Step E above in dichloromethane (50 mL) at 0° C. were successively added pyridine (0.80 mL, 10 mmol) and triflic anhydride (1.1 mL, 6.6 mmol) dropwise. The resultant reaction solution was stirred at 0° C. for 1 hour, and then was quenched with aqueous saturated sodium bicarbonate. The organic extract was separated and the aqueous layer was extracted with dichloromethane twice. The combined organic extract was washed with 1:1 water/brine, dried over sodium sulfate and concentrated under reduced pressure to give the crude product. Purification by flash column chromatography (dichloromethane to 98:2 dichloromethane/ methanol) gave the desired triflate (1.6 g, 73% over two steps) as a yellow oil: $^1$H NMR (CDCl$_3$, 500 MHz) δ 7.74 (d, J=8.0 Hz, 1H), 7.70 (d, J=7.8 Hz, 1H), 7.32-7.24 (m, 3H), 7.16 (s, 1H), 7.02-7.00 (m, 2H), 4.54 (t, J=5.4 Hz, 1H), 3.78 (d, J=15.4 Hz, 1H), 3.65 (d, J=15.4 Hz, 1H), 3.01 (dd, J=11.6, 5.0 Hz, 1H), 2.91 (dd, J=11.6, 6.0 Hz, 1H), 2.50 (s, 3H); ESI-MS m/z 428 [M+H]$^+$.

Step G: To a mixture of the triflate (1.0 g, 2.3 mmol) from Step F above, bis(pinacolato)diboron (0.65 g, 2.6 mmol) and potassium acetate (0.69 g, 7.0 mmol) was added dimethyl sulfoxide (15 mL). The resultant solution was purged with argon for 10 minutes, and then 1,1'-bis(diphenylphosphino)ferrocenedichloropalladium (57 mg, 0.07 mmol) was added to it. The reaction solution was degassed again with argon for 5 minutes and heated at 80° C. for 1 hour. The reaction solution was then cooled to room temperature, diluted with ethyl acetate, washed with water and brine, dried over sodium sulfate and concentrated under reduced pressure. The crude product was purified by flash column chromatography (dichloromethane to 95:5 dichloromethane/methanol) to give the desired product (1.3 g, crude) as a reddish oil, which was used in the next step without further purification: $^1$H NMR (CDCl$_3$, 500 MHz) δ 7.72 (d, J=7.9 Hz, 1H), 7.67 (d, J=7.9 Hz, 1H), 7.56-7.54 (m, 2H), 7.29 (td, J=7.3, 1.1 Hz, 1H), 7.23 (td, J=8.2, 2.6 Hz, 1H), 7.16 (d, J=7.5 Hz, 1H), 7.13 (s, 1H), 4.57 (t, J=5.3 Hz, 1H), 3.77 (d, J=14.9 Hz, 1H), 3.63 (d, J=14.9 Hz, 1H), 3.00 (dd, J=11.3, 4.8 Hz, 1H), 2.89 (dd, J=11.4, 6.1 Hz, 1H), 2.48 (s, 3H), 1.33 (s, 12H); ESI-MS m/z 406 [M+H]$^+$.

Step H: To a mixture of the boronate ester (0.12 g, 0.3 mmol) from Step G above, 2-chloropyrazine (0.053 mL, 0.59 mmol) and sodium carbonate (95 mg, 0.90 mmol) were added dimethylformamide (3 mL) and water (0.75 mL). The reaction solution was purged with argon for 10 minutes, and then 1,1'-bis(diphenylphosphino)ferrocenedichloropalladium (12 mg, 0.015 mmol) was added to it. The reaction solution was degassed again with argon for 5 minutes and heated at 80° C. for 3 hours. The reaction solution was then cooled to room temperature, diluted with ethyl acetate, washed with water and brine, dried over sodium sulfate and concentrated under reduced pressure. The crude product was purified by preparative thin layer chromatography (95:5 dichloromethane/methanol) to give the desired product (67 mg, 62%) as a light yellow solid: $^1$H NMR (CDCl$_3$, 500 MHz) δ 8.99 (d, J=1.5 Hz, 1H), 8.61 (dd, J=2.5, 1.6 Hz, 1H), 8.49 (d, J=2.5 Hz, 1H), 7.79 (s, 1H), 7.75-7.68 (m, 3H), 7.32-7.25 (m, 3H), 7.19 (s, 1H), 4.63 (t, J=5.6 Hz, 1H), 3.87 (d, J=15.0 Hz, 1H), 3.74 (d, J=15.0 Hz, 1H), 3.07-3.04 (m, 1H), 2.96-2.92 (m, 1H), 2.53 (s, 3H). To a solution of the newly obtained 7-pyrazinyl tetrahydroisoquinoline (67 mg, 0.19 mmol) in methanol (2 mL) was added maleic acid (22 mg, 0.19 mmol), followed by slow addition of water (10 mL). The resultant reaction solution was lyophilized overnight to give (+/−)-4-(benzo[b]thiophen-2-yl)-2-methyl-7-(pyrazin-2-yl)-1,2,3,4-tetrahydroisoquinoline, maleate salt (87 mg) as an off-white solid: mp 102-105° C.; $^1$H NMR (CD$_3$OD, 500 MHz) δ 9.14 (d, J=1.5 Hz, 1H), 8.69 (dd, J=2.5, 1.6 Hz, 1H), 8.56 (d, J=2.5 Hz, 1H), 8.06-8.03 (m, 2H), 7.83 (d, J=7.3 Hz, 1H), 7.78 (d, J=7.5 Hz, 1H), 7.42-7.32 (m, 4H), 6.25 (s, 2H), 5.08-5.05 (m, 1H), 4.60 (app s, 2H), 3.94 (dd, J=11.6, 5.3 Hz, 1H), 3.74-3.68 (m, 1H), 3.08 (s, 3H); ESI-MS m/z 358 [M+H]$^+$.

Example 72

Preparation of (+/−)-4-(benzo[b]thiophen-2-yl)-2-methyl-7-(pyrimidin-2-yl)-1,2,3,4-tetrahydroisoquinoline, maleate salt Step A: To a solution of 2-acetylbenzo[b]thiophene (5.0 g, 28 mmol) in chloroform (120 mL) was added pyridinium bromide perbromide (9.6 g, 28 mmol) in two batches. The reaction solution was stirred at room temperature for 2 hours, and then was washed with water, aqueous HCl (2 M), water and brine. The resultant solution was dried over sodium sulfate and concentrated under reduced pressure to give the desired bromoketone (7.4 g, crude) as a brown solid, which was used in the next step without further purification: $^1$H NMR (CDCl$_3$, 500 MHz) δ 8.07 (s, 1H), 7.94-7.87 (m, 2H), 7.52-7.25 (m, 2H), 4.46 (s, 2H).

Step B: To a solution of 3-methoxybenzyl methylamine (4.3 g, 29 mmol) in dichloromethane (150 mL) were added triethylamine (10 mL) and the bromoketone (7.3 g, 29 mmol) from Step A above. The reaction solution was stirred at room temperature for 2 hours, and then was quenched with aqueous saturated sodium bicarbonate. The organic extract was separated, washed with water and brine, dried over sodium sulfate and concentrated under reduced pressure. The crude product was purified by flash column chromatography (90:10 to 85:15 hexanes/ethyl acetate) to give the desired product (7.1 g, 76% over 2 steps) as a reddish oil: 1H NMR (CDCl$_3$, 500 MHz) δ 8.09 (s, 1H), 7.86 (d, J=8.0 Hz, 2H), 7.45 (dd, J=8.0, 1.1 Hz, 1H), 7.40 (dd, J=8.0, 1.0 Hz, 1H), 7.24 (d, J=8.1 Hz, 1H), 6.97-6.95 (m, 2H), 6.83 (d, J=8.5 Hz, 1H), 3.78 (s, 3H), 3.76 (s, 2H), 3.70 (s, 2H), 2.43 (s, 3H); ESI-MS m/z 326 [M+H]$^+$.

Step C: To a solution of the ketone (7.1 g, 22 mmol) from Step B above in methanol (100 mL) at 0° C. was added sodium borohydride (0.89 g, 24 mmol) in small portions. The reaction solution was stirred at 0° C. for 1 hour. The solvent was then removed under reduced pressure and the residue obtained was dissolved in dichloromethane. The resultant solution was washed with aqueous saturated sodium bicarbonate and brine, dried over sodium sulfate and concentrated under reduced pressure to give the desired alcohol (6.9 g, 96% crude) as a yellow oil. The crude product was used in the next step without further purification: $^1$H NMR (CDCl$_3$, 500 MHz) δ 7.81 (d, J=7.9 Hz, 1H), 7.70 (d, J=8.1 Hz, 1H), 7.33-7.23 (m, 3H), 7.21 (s, 1H), 6.91-6.87 (m, 3H), 5.07 (dd, J=10.1, 3.5 Hz, 1H), 4.40-4.03 (m, 1H), 3.81 (s, 3H), 3.72 (d, J=13.0 Hz, 1H), 3.56 (d, J=13.0 Hz, 1H), 2.83 (dd, J=12.4, 10.2 Hz, 1H), 2.72 (dd, J=12.4, 3.7 Hz, 1H), 2.34 (s, 3H); ESI-MS m/z 328 [M+H]$^+$.

Step D: To a solution of the alcohol (6.9 g, 21 mmol) from Step C above in dichloromethane (150 mL) was added methanesulfonic acid (14 mL, 210 mmol) dropwise. After the addition, the reaction solution was stirred at room temperature for 20 minutes, and then was added slowly to ice-cold aqueous sodium hydroxide (120 mL, 2 M) and stirred for 20 minutes. The organic layer was separated and the aqueous layer was extracted with dichloromethane twice. The combined organic extract was washed with water and brine, dried over sodium sulfate and concentrated under reduced pressure. The crude product was purified by flash column chromatography (95:5 to 50:50 hexanes/ethyl acetate) to give the desired product (3.4 g, 52%) as a reddish oil: $^1$H NMR (CDCl$_3$, 500 MHz) δ 7.72 (d, J=8.0 Hz, 1H), 7.67 (d, J=8.0 Hz, 1H), 7.29-7.23 (m, 2H), 7.13 (s, 1H), 7.06 (d, J=8.5 Hz, 1H), 6.69 (d, J=2.7 Hz, 1H), 6.61 (d, J=2.6 Hz, 1H), 4.50 (t, J=5.3 Hz, 1H), 3.77 (s, 3H), 3.73 (d, J=14.5 Hz, 1H), 3.59 (d, J=14.5 Hz, 1H), 2.99 (dd, J=11.5, 4.9 Hz, 1H), 2.87 (dd, J=11.4, 6.2 Hz, 1H), 2.47 (s, 3H); ESI-MS m/z 310 [M+H]$^+$.

Step E: To a solution of the 7-methoxy tetrahydroisoquinoline (1.6 g, 5.1 mmol) from Step D above in acetic acid (25 mL) was added aqueous hydrogen bromide (25 mL, 48%). The reaction solution was heated at 100° C. for 20 hours, and then cooled to room temperature and concentrated under reduced pressure. The residue obtained was taken up in a mixture of dichloromethane, water and small amount of methanol. The resultant solution was quenched carefully with aqueous saturated sodium bicarbonate until pH>8. The organic extract was separated, washed with water and brine, dried over sodium sulfate and concentrated under reduced pressure to give the desired phenol (1.6 g, crude) as a brown solid, which was used in the next step without further purification: $^1$H NMR (CDCl$_3$, 500 MHz) δ 7.72 (d, J=7.7 Hz, 1H), 7.67 (d, J=7.7 Hz, 1H), 7.29 (td, J=7.3, 1.2 Hz, 1H), 7.23 (td, J=7.3, 1.3 Hz, 1H), 7.13 (s, 1H), 7.01 (d, J=8.4 Hz, 1H), 6.59 (dd, J=8.4, 2.5 Hz, 1H), 6.53 (d, J=2.3 Hz, 1H), 4.49 (t, J=5.7 Hz, 1H), 3.68 (d, J=15.1 Hz, 1H), 3.57 (d, J=15.0 Hz, 1H), 3.00 (dd, J=11.6, 5.4 Hz, 1H), 2.85 (dd, J=11.5, 6.4 Hz, 1H), 2.47 (s, 3H), 1.90-1.45 (m, 1H); ESI-MS m/z 296 [M+H]$^+$.

Step F: To a solution of this phenol (1.6 g, 5.1 mmol) from Step E above in dichloromethane (50 mL) at 0° C. were successively added pyridine (0.80 mL, 10 mmol) and triflic anhydride (1.1 mL, 6.6 mmol) dropwise. The resultant reaction solution was stirred at 0° C. for 1 hour, and then was quenched with aqueous saturated sodium bicarbonate. The organic extract was separated and the aqueous layer was extracted with dichloromethane twice. The combined organic extract was washed with 1:1 water/brine, dried over sodium sulfate and concentrated under reduced pressure to give the crude product. Purification by flash column chromatography (dichloromethane to 98:2 dichloromethane/methanol) gave the desired triflate (1.6 g, 73% over two steps) as a yellow oil: $^1$H NMR (CDCl$_3$, 500 MHz) δ 7.74 (d, J=8.0 Hz, 1H), 7.70 (d, J=7.8 Hz, 1H), 7.32-7.24 (m, 3H), 7.16 (s, 1H), 7.02-7.00 (m, 2H), 4.54 (t, J=5.4 Hz, 1H), 3.78 (d, J=15.4 Hz, 1H), 3.65 (d, J=15.4 Hz, 1H), 3.01 (dd, J=11.6, 5.0 Hz, 1H), 2.91 (dd, J=11.6, 6.0 Hz, 1H), 2.50 (s, 3H); ESI-MS m/z 428 [M+H]$^+$.

Step G: To a mixture of the triflate (1.0 g, 2.3 mmol) from Step F above, bis(pinacolato)diboron (0.65 g, 2.6 mmol) and potassium acetate (0.69 g, 7.0 mmol) was added dimethyl sulfoxide (15 mL). The resultant solution was purged with argon for 10 minutes, and then 1,1'-bis(diphenylphosphino)ferrocenedichloropalladium (57 mg, 0.07 mmol) was added to it. The reaction solution was degassed again with argon for 5 minutes and heated at 80° C. for 1 hour. The reaction solution was then cooled to room temperature, diluted with ethyl acetate, washed with water and brine, dried over sodium sulfate and concentrated under reduced pressure. The crude product was purified by flash column chromatography (dichloromethane to 95:5 dichloromethane/methanol) to give the desired product (1.3 g, crude) as a reddish oil, which was used in the next step without further purification: $^1$H NMR (CDCl$_3$, 500 MHz) δ 7.72 (d, J=7.9 Hz, 1H), 7.67 (d, J=7.9 Hz, 1H), 7.56-7.54 (m, 2H), 7.29 (td, J=7.3, 1.1 Hz, 1H), 7.23 (td, J=8.2, 2.6 Hz, 1H), 7.16 (d, J=7.5 Hz, 1H), 7.13 (s, 1H), 4.57 (t, J=5.3 Hz, 1H), 3.77 (d, J=14.9 Hz, 1H), 3.63 (d, J=14.9 Hz, 1H), 3.00 (dd, J=11.3, 4.8 Hz, 1H), 2.89 (dd, J=11.4, 6.1 Hz, 1H), 2.48 (s, 3H), 1.33 (s, 12H); ESI-MS m/z 406 [M+H]$^+$.

Step H: To a mixture of the boronate ester (0.12 g, 0.3 mmol) from Step G above, 2-chloropyrimidine (68 mg, 0.59 mmol) and sodium carbonate (95 mg, 0.90 mmol) were added N,N-dimethylformamide (3 mL) and water (0.75 mL). The reaction solution was purged with argon for 10 minutes, and then 1,1'-bis(diphenylphosphino)ferrocenedichloropalladium (12 mg, 0.015 mmol) was added to the solution. The reaction solution was degassed again with argon for 5 minutes and heated at 80° C. for 3 hours. The reaction solution was then cooled to room temperature, diluted with ethyl acetate, washed with water and brine, dried over sodium sulfate and concentrated under reduced pressure. The crude product was purified by preparative thin layer chromatography (95:5 dichloromethane/methanol) to give the desired product (34 mg, 31%) as a light yellow oil: $^1$H NMR (CDCl$_3$, 500 MHz) δ 8.79 (d, J=4.8 Hz, 2H), 8.20-8.18 (m, 2H), 7.74 (d, J=8.0 Hz, 1H), 7.68 (d, J=7.8 Hz, 1H), 7.31-7.25 (m, 3H), 7.18 (s, 1H), 7.17 (t, J=4.7 Hz, 1H), 4.64-4.62 (m, 1H), 3.87 (d, J=15.0 Hz, 1H), 3.73 (d, J=15.0 Hz, 1H), 3.10-2.93 (m, 2H), 2.52 (s, 3H). To a solution of the 7-pyrimidinyl tetrahydroisoquinoline (34 mg, 0.095 mmol) in methanol (2 mL) was added maleic acid (11 mg, 0.095 mmol), followed by slow addition of water (10 mL). The resultant reaction solution was lyophilized overnight to give (+/−)-4-(benzo[b]thiophen-2-yl)-2-methyl-7-(pyrimidin-2-yl)-1,2,3,4-tetrahydroisoquinoline, maleate salt (42 mg) as a light yellow solid: mp 103-106° C.; $^1$H NMR (CD$_3$OD, 500 MHz) δ 8.86 (d, J=4.9 Hz, 2H), 8.36-8.34 (m, 2H), 7.83 (d, J=7.8 Hz, 1H), 7.78 (d, J=7.4 Hz, 1H), 7.40-7.32 (m, 5H), 6.25 (s, 2H), 5.07 (dd, J=9.1, 5.8 Hz, 1H), 4.62 (br s, 2H), 3.96 (dd, J=12.3, 5.6 Hz, 1H), 3.77-3.62 (m, 1H), 3.09 (s, 3H); ESI-MS m/z 358 [M+H]$^+$.

Example 73

Preparation of (+/−)-4-(benzo[b]thiophen-2-yl)-2-methyl-7-(pyrimidin-5-yl)-1,2,3,4-tetrahydroisoquinoline, maleate salt Step A: To a solution of 2-acetylbenzo[b]thiophene (5.0 g, 28 mmol) in chloroform (120 mL) was added pyridinium bromide perbromide (9.6 g, 28 mmol) in two batches. The reaction solution was stirred at room temperature for 2 hours, and then was washed with water, aqueous HCl (2 M), water and brine. The resultant solution was dried over sodium sulfate and concentrated under reduced pressure to give the desired bromoketone (7.4 g, crude) as a brown solid, which was used in the next step without further purification: $^1$H NMR (CDCl$_3$, 500 MHz) δ 8.07 (s, 1H), 7.94-7.87 (m, 2H), 7.52-7.25 (m, 2H), 4.46 (s, 2H).

Step B: To a solution of 3-methoxybenzyl methylamine (4.3 g, 29 mmol) in dichloromethane (150 mL) were added triethylamine (10 mL) and the bromoketone (7.3 g, 29 mmol) from Step A above. The reaction solution was stirred at room temperature for 2 hours, and then was quenched with aqueous saturated sodium bicarbonate. The organic extract was separated, washed with water and brine, dried over sodium sulfate and concentrated under reduced pressure. The crude product was purified by flash column chromatography (90:10 to 85:15 hexanes/ethyl acetate) to give the desired product (7.1 g, 76% over 2 steps) as a reddish oil: 1H NMR (CDCl$_3$, 500 MHz) δ 8.09 (s, 1H), 7.86 (d, J=8.0 Hz, 2H), 7.45 (dd, J=8.0, 1.1 Hz, 1H), 7.40 (dd, J=8.0, 1.0 Hz, 1H), 7.24 (d, J=8.1 Hz, 1H), 6.97-6.95 (m, 2H), 6.83 (d, J=8.5 Hz, 1H), 3.78 (s, 3H), 3.76 (s, 2H), 3.70 (s, 2H), 2.43 (s, 3H); ESI-MS m/z 326 [M+H]$^+$.

Step C: To a solution of the ketone (7.1 g, 22 mmol) from Step B above in methanol (100 mL) at 0° C. was added sodium borohydride (0.89 g, 24 mmol) in small portions. The reaction solution was stirred at 0° C. for 1 hour. The solvent was then removed under reduced pressure and the residue obtained was dissolved in dichloromethane. The resultant solution was washed with aqueous saturated sodium bicarbonate and brine, dried over sodium sulfate and concentrated under reduced pressure to give the desired alcohol (6.9 g, 96% crude) as a yellow oil. The crude product was used in the next step without further purification: $^1$H NMR (CDCl$_3$, 500 MHz) δ 7.81 (d, J=7.9 Hz, 1H), 7.70 (d, J=8.1 Hz, 1H), 7.33-7.23 (m, 3H), 7.21 (s, 1H), 6.91-6.87 (m, 3H), 5.07 (dd, J=10.1, 3.5 Hz, 1H), 4.40-4.03 (m, 1H), 3.81 (s, 3H), 3.72 (d, J=13.0 Hz, 1H), 3.56 (d, J=13.0 Hz, 1H), 2.83 (dd, J=12.4, 10.2 Hz, 1H), 2.72 (dd, J=12.4, 3.7 Hz, 1H), 2.34 (s, 3H); ESI-MS m/z 328 [M+H]$^+$.

Step D: To a solution of the alcohol (6.9 g, 21 mmol) from Step C above in dichloromethane (150 mL) was added methanesulfonic acid (14 mL, 210 mmol) dropwise. After the addition, the reaction solution was stirred at room temperature for 20 minutes, and then was added slowly to ice-cold aqueous sodium hydroxide (120 mL, 2 M) and stirred for 20 minutes. The organic layer was separated and the aqueous layer was extracted with dichloromethane twice. The combined organic extract was washed with water and brine, dried over sodium sulfate and concentrated under reduced pressure. The crude product was purified by flash column chromatography (95:5 to 50:50 hexanes/ethyl acetate) to give the desired product (3.4 g, 52%) as a reddish oil: $^1$H NMR (CDCl$_3$, 500 MHz) δ 7.72 (d, J=8.0 Hz, 1H), 7.67 (d, J=8.0 Hz, 1H), 7.29-7.23 (m, 2H), 7.13 (s, 1H), 7.06 (d, J=8.5 Hz, 1H), 6.69 (d, J=2.7 Hz, 1H), 6.61 (d, J=2.6 Hz, 1H), 4.50 (t, J=5.3 Hz, 1H), 3.77 (s, 3H), 3.73 (d, J=14.5 Hz, 1H), 3.59 (d, J=14.5 Hz, 1H), 2.99 (dd, J=11.5, 4.9 Hz, 1H), 2.87 (dd, J=11.4, 6.2 Hz, 1H), 2.47 (s, 3H); ESI-MS m/z 310 [M+H]$^+$.

Step E: To a solution of the 7-methoxy tetrahydroisoquinoline (1.6 g, 5.1 mmol) from Step D above in acetic acid (25 mL) was added aqueous hydrogen bromide (25 mL, 48%). The reaction solution was heated at 100° C. for 20 hours, and then cooled to room temperature and concentrated under reduced pressure. The residue obtained was taken up in a mixture of dichloromethane, water and small amount of methanol. The resultant solution was quenched carefully with aqueous saturated sodium bicarbonate until pH>8. The organic extract was separated, washed with water and brine, dried over sodium sulfate and concentrated under reduced pressure to give the desired phenol (1.6 g, crude) as a brown solid, which was used in the next step without further purification: $^1$H NMR (CDCl$_3$, 500 MHz) δ 7.72 (d, J=7.7 Hz, 1H), 7.67 (d, J=7.7 Hz, 1H), 7.29 (td, J=7.3, 1.2 Hz, 1H), 7.23 (td, J=7.3, 1.3 Hz, 1H), 7.13 (s, 1H), 7.01 (d, J=8.4 Hz, 1H), 6.59 (dd, J=8.4, 2.5 Hz, 1H), 6.53 (d, J=2.3 Hz, 1H), 4.49 (t, J=5.7 Hz, 1H), 3.68 (d, J=15.1 Hz, 1H), 3.57 (d, J=15.0 Hz, 1H), 3.00 (dd, J=11.6, 5.4 Hz, 1H), 2.85 (dd, J=11.5, 6.4 Hz, 1H), 2.47 (s, 3H), 1.90-1.45 (m, 1H); ESI-MS m/z 296 [M+H]$^+$.

Step F: To a solution of this phenol (1.6 g, 5.1 mmol) from Step E above in dichloromethane (50 mL) at 0° C. were successively added pyridine (0.80 mL, 10 mmol) and triflic anhydride (1.1 mL, 6.6 mmol) dropwise. The resultant reaction solution was stirred at 0° C. for 1 hour, and then was quenched with aqueous saturated sodium bicarbonate. The organic extract was separated and the aqueous layer was extracted with dichloromethane twice. The combined organic extract was washed with 1:1 water/brine, dried over sodium sulfate and concentrated under reduced pressure to give the crude product. Purification by flash column chromatography (dichloromethane to 98:2 dichloromethane/methanol) gave the desired triflate (1.6 g, 73% over two steps) as a yellow oil: $^1$H NMR (CDCl$_3$, 500 MHz) δ 7.74 (d, J=8.0 Hz, 1H), 7.70 (d, J=7.8 Hz, 1H), 7.32-7.24 (m, 3H), 7.16 (s, 1H), 7.02-7.00 (m, 2H), 4.54 (t, J=5.4 Hz, 1H), 3.78 (d, J=15.4 Hz, 1H), 3.65 (d, J=15.4 Hz, 1H), 3.01 (dd, J=11.6, 5.0 Hz, 1H), 2.91 (dd, J=11.6, 6.0 Hz, 1H), 2.50 (s, 3H); ESI-MS m/z 428 [M+H]$^+$.

Step G: To a mixture of the triflate (1.0 g, 2.3 mmol) from Step F above, bis(pinacolato)diboron (0.65 g, 2.6 mmol) and potassium acetate (0.69 g, 7.0 mmol) was added dimethyl sulfoxide (15 mL). The resultant solution was purged with argon for 10 minutes, and then 1,1'-bis(diphenylphosphino)ferrocenedichloropalladium (57 mg, 0.07 mmol) was added to it. The reaction solution was degassed again with argon for 5 minutes and heated at 80° C. for 1 hour. The reaction solution was then cooled to room temperature, diluted with ethyl acetate, washed with water and brine, dried over sodium sulfate and concentrated under reduced pressure. The crude product was purified by flash column chromatography (dichloromethane to 95:5 dichloromethane/methanol) to give the desired product (1.3 g, crude) as a reddish oil, which was used in the next step without further purification: $^1$H NMR (CDCl$_3$, 500 MHz) δ 7.72 (d, J=7.9 Hz, 1H), 7.67 (d, J=7.9 Hz, 1H), 7.56-7.54 (m, 2H), 7.29 (td, J=7.3, 1.1 Hz, 1H), 7.23 (td, J=8.2, 2.6 Hz, 1H), 7.16 (d, J=7.5 Hz, 1H), 7.13 (s, 1H), 4.57 (t, J=5.3 Hz, 1H), 3.77 (d, J=14.9 Hz, 1H), 3.63 (d, J=14.9 Hz, 1H), 3.00 (dd, J=11.3, 4.8 Hz, 1H), 2.89 (dd, J=11.4, 6.1 Hz, 1H), 2.48 (s, 3H), 1.33 (s, 12H); ESI-MS m/z 406 [M+H]$^+$.

Step H: To a mixture of the boronate ester (0.12 g, 0.3 mmol) from Step G above, 5-bromopyrimidine (94 mg, 0.59 mmol) and sodium carbonate (95 mg, 0.90 mmol) were added N,N-dimethylformamide (3 mL) and water (0.75 mL). The reaction solution was purged with argon for 10 minutes, and then 1,1'-bis(diphenylphosphino)ferrocenedichloropalladium (12 mg, 0.015 mmol) was added to the solution. The reaction solution was degassed again with argon for 5 minutes and heated at 80° C. for 3 hours. The reaction solution was then cooled to room temperature, diluted with ethyl acetate, washed with water and brine, dried over sodium sulfate and concentrated under reduced pressure. The crude product was purified by preparative thin layer chromatography (95:5 dichloromethane/methanol) to give the desired product (49 mg, 45%) as a light yellow solid: $^1$H NMR (CDCl$_3$, 500 MHz) δ 9.19 (s, 1H), 8.92 (s, 2H), 7.74 (d, J=8.0 Hz, 1H), 7.70 (d, J=7.8 Hz, 1H), 7.32-7.25 (m, 5H), 7.21 (s, 1H), 4.63-4.61 (m, 1H), 3.85 (d, J=15.1 Hz, 1H), 3.72 (d, J=15.1 Hz, 1H), 3.08-3.04 (m, 1H), 2.97-2.93 (m, 1H), 2.53 (s, 3H). To a solution of the 7-pyrimidinyl tetrahydroisoquinoline (49 mg, 0.14 mmol) in methanol (2 mL) was added maleic acid (16 mg, 0.14 mmol), followed by slow addition of water (10 mL). The resultant reaction solution was lyophilized overnight to give (+/−)-4-(benzo[b]thiophen-2-yl)-2-methyl-7-(pyrimidin-5-yl)-1,2,3,4-tetrahydroisoquinoline, maleate salt (64 mg) as an off-white solid: mp 103-107° C.; $^1$H NMR (CD$_3$OD, 500 MHz) δ 9.16 (s, 1H), 9.09 (s, 2H), 7.82 (dd, J=7.9, 5.7 Hz, 1H), 7.78 (d, J=7.5 Hz, 1H), 7.70-7.68 (m, 2H), 7.42-7.32 (m, 4H), 6.25 (s, 2H), 5.06 (dd, J=9.9, 5.9 Hz, 1H), 4.58 (app s, 2H), 3.93 (dd, J=12.2, 5.9 Hz, 1H), 3.70 (dd, J=9.8, 6.5 Hz, 1H), 3.07 (s, 3H); ESI-MS m/z 358 [M+H]$^+$.

Example 74

Preparation of (+/−)-4-(benzo[b]thiophen-2-yl)-2-methyl-7-(3,5-dimethylisoxazol-4-yl)-1,2,3,4-tetrahydroisoquinoline, maleate salt Step A: To a solution of 2-acetylbenzo[b]thiophene (5.0 g, 28 mmol) in chloroform (120 mL) was added pyridinium bromide perbromide (9.6 g, 28 mmol) in two batches. The reaction solution was stirred at room temperature for 2 hours, and then was washed with water, aqueous HCl (2 M), water and brine. The resultant solution was dried over sodium sulfate and concentrated under reduced pressure to give the desired bromoketone (7.4 g, crude) as a brown solid, which was used in the next step without further purification: ¹H NMR (CDCl₃, 500 MHz) δ 8.07 (s, 1H), 7.94-7.87 (m, 2H), 7.52-7.25 (m, 2H), 4.46 (s, 2H).

Step B: To a solution of 3-methoxybenzyl methylamine (4.3 g, 29 mmol) in dichloromethane (150 mL) were added triethylamine (10 mL) and the bromoketone (7.3 g, 29 mmol) from Step A above. The reaction solution was stirred at room temperature for 2 hours, and then was quenched with aqueous saturated sodium bicarbonate. The organic extract was separated, washed with water and brine, dried over sodium sulfate and concentrated under reduced pressure. The crude product was purified by flash column chromatography (90:10 to 85:15 hexanes/ethyl acetate) to give the desired product (7.1 g, 76% over 2 steps) as a reddish oil: 1H NMR (CDCl₃, 500 MHz) δ 8.09 (s, 1H), 7.86 (d, J=8.0 Hz, 2H), 7.45 (dd, J=8.0, 1.1 Hz, 1H), 7.40 (dd, J=8.0, 1.0 Hz, 1H), 7.24 (d, J=8.1 Hz, 1H), 6.97-6.95 (m, 2H), 6.83 (d, J=8.5 Hz, 1H), 3.78 (s, 3H), 3.76 (s, 2H), 3.70 (s, 2H), 2.43 (s, 3H); ESI-MS m/z 326 [M+H]⁺.

Step C: To a solution of the ketone (7.1 g, 22 mmol) from Step B above in methanol (100 mL) at 0° C. was added sodium borohydride (0.89 g, 24 mmol) in small portions. The reaction solution was stirred at 0° C. for 1 hour. The solvent was then removed under reduced pressure and the residue obtained was dissolved in dichloromethane. The resultant solution was washed with aqueous saturated sodium bicarbonate and brine, dried over sodium sulfate and concentrated under reduced pressure to give the desired alcohol (6.9 g, 96% crude) as a yellow oil. The crude product was used in the next step without further purification: ¹H NMR (CDCl₃, 500 MHz) δ 7.81 (d, J=7.9 Hz, 1H), 7.70 (d, J=8.1 Hz, 1H), 7.33-7.23 (m, 3H), 7.21 (s, 1H), 6.91-6.87 (m, 3H), 5.07 (dd, J=10.1, 3.5 Hz, 1H), 4.40-4.03 (m, 1H), 3.81 (s, 3H), 3.72 (d, J=13.0 Hz, 1H), 3.56 (d, J=13.0 Hz, 1H), 2.83 (dd, J=12.4, 10.2 Hz, 1H), 2.72 (d, J=12.4, 3.7 Hz, 1H), 2.34 (s, 3H); ESI-MS m/z 328 [M+H]⁺.

Step D: To a solution of the alcohol (6.9 g, 21 mmol) from Step C above in dichloromethane (150 mL) was added methanesulfonic acid (14 mL, 210 mmol) dropwise. After the addition, the reaction solution was stirred at room temperature for 20 minutes, and then was added slowly to ice-cold aqueous sodium hydroxide (120 mL, 2 M) and stirred for 20 minutes. The organic layer was separated and the aqueous layer was extracted with dichloromethane twice. The combined organic extract was washed with water and brine, dried over sodium sulfate and concentrated under reduced pressure. The crude product was purified by flash column chromatography (95:5 to 50:50 hexanes/ethyl acetate) to give the desired product (3.4 g, 52%) as a reddish oil: ¹H NMR (CDCl₃, 500 MHz) δ 7.72 (d, J=8.0 Hz, 1H), 7.67 (d, J=8.0 Hz, 1H), 7.29-7.23 (m, 2H), 7.13 (s, 1H), 7.06 (d, J=8.5 Hz, 1H), 6.69 (d, J=2.7 Hz, 1H), 6.61 (d, J=2.6 Hz, 1H), 4.50 (t, J=5.3 Hz, 1H), 3.77 (s, 3H), 3.73 (d, J=14.5 Hz, 1H), 3.59 (d, J=14.5 Hz, 1H), 2.99 (dd, J=11.5, 4.9 Hz, 1H), 2.87 (dd, J=11.4, 6.2 Hz, 1H), 2.47 (s, 3H); ESI-MS m/z 310 [M+H]⁺.

Step E: To a solution of the 7-methoxy tetrahydroisoquinoline (1.6 g, 5.1 mmol) from Step D above in acetic acid (25 mL) was added aqueous hydrogen bromide (25 mL, 48%). The reaction solution was heated at 100° C. for 20 hours, and then cooled to room temperature and concentrated under reduced pressure. The residue obtained was taken up in a mixture of dichloromethane, water and small amount of methanol. The resultant solution was quenched carefully with aqueous saturated sodium bicarbonate until pH>8. The organic extract was separated, washed with water and brine, dried over sodium sulfate and concentrated under reduced pressure to give the desired phenol (1.6 g, crude) as a brown solid, which was used in the next step without further purification: ¹H NMR (CDCl₃, 500 MHz) δ 7.72 (d, J=7.7 Hz, 1H), 7.67 (d, J=7.7 Hz, 1H), 7.29 (td, J=7.3, 1.2 Hz, 1H), 7.23 (td, J=7.3, 1.3 Hz, 1H), 7.13 (s, 1H), 7.01 (d, J=8.4 Hz, 1H), 6.59 (dd, J=8.4, 2.5 Hz, 1H), 6.53 (d, J=2.3 Hz, 1H), 4.49 (t, J=5.7 Hz, 1H), 3.68 (d, J=15.1 Hz, 1H), 3.57 (d, J=15.0 Hz, 1H), 3.00 (dd, J=11.6, 5.4 Hz, 1H), 2.85 (dd, J=11.5, 6.4 Hz, 1H), 2.47 (s, 3H), 1.90-1.45 (m, 1H); ESI-MS m/z 296 [M+H]⁺.

Step F: To a solution of this phenol (1.6 g, 5.1 mmol) from Step E above in dichloromethane (50 mL) at 0° C. were successively added pyridine (0.80 mL, 10 mmol) and triflic anhydride (1.1 mL, 6.6 mmol) dropwise. The resultant reaction solution was stirred at 0° C. for 1 hour, and then was quenched with aqueous saturated sodium bicarbonate. The organic extract was separated and the aqueous layer was extracted with dichloromethane twice. The combined organic extract was washed with 1:1 water/brine, dried over sodium sulfate and concentrated under reduced pressure to give the crude product. Purification by flash column chromatography (dichloromethane to 98:2 dichloromethane/methanol) gave the desired triflate (1.6 g, 73% over two steps) as a yellow oil: ¹H NMR (CDCl₃, 500 MHz) δ 7.74 (d, J=8.0 Hz, 1H), 7.70 (d, J=7.8 Hz, 1H), 7.32-7.24 (m, 3H), 7.16 (s, 1H), 7.02-7.00 (m, 2H), 4.54 (t, J=5.4 Hz, 1H), 3.78 (d, J=15.4 Hz, 1H), 3.65 (d, J=15.4 Hz, 1H), 3.01 (dd, J=11.6, 5.0 Hz, 1H), 2.91 (dd, J=11.6, 6.0 Hz, 1H), 2.50 (s, 3H); ESI-MS m/z 428 [M+H]⁺.

Step G: To a mixture of the triflate (1.0 g, 2.3 mmol) from Step F above, bis(pinacolato)diboron (0.65 g, 2.6 mmol) and potassium acetate (0.69 g, 7.0 mmol) was added dimethyl sulfoxide (15 mL). The resultant solution was purged with argon for 10 minutes, and then 1,1'-bis(diphenylphosphino)ferrocenedichloropalladium (57 mg, 0.07 mmol) was added to it. The reaction solution was degassed again with argon for 5 minutes and heated at 80° C. for 1 hour. The reaction solution was then cooled to room temperature, diluted with ethyl acetate, washed with water and brine, dried over sodium sulfate and concentrated under reduced pressure. The crude product was purified by flash column chromatography (dichloromethane to 95:5 dichloromethane/methanol) to give the desired product (1.3 g, crude) as a reddish oil, which was used in the next step without further purification: ¹H NMR (CDCl₃, 500 MHz) δ 7.72 (d, J=7.9 Hz, 1H), 7.67 (d, J=7.9 Hz, 1H), 7.56-7.54 (m, 2H), 7.29 (td, J=7.3, 1.1 Hz, 1H), 7.23 (td, J=8.2, 2.6 Hz, 1H), 7.16 (d, J=7.5 Hz, 1H), 7.13 (s, 1H), 4.57 (t, J=5.3 Hz, 1H), 3.77 (d, J=14.9 Hz, 1H), 3.63 (d, J=14.9 Hz, 1H), 3.00 (dd, J=11.3, 4.8 Hz, 1H), 2.89 (dd, J=11.4, 6.1 Hz, 1H), 2.48 (s, 3H), 1.33 (s, 12H); ESI-MS m/z 406 [M+H]⁺.

Step H: To a mixture of the boronate ester (0.12 g, 0.3 mmol) from Step G above, 4-iodo-3,5-dimethylisoxazole (0.13 g, 0.59 mmol) and sodium carbonate (95 mg, 0.90 mmol) were added N,N-dimethylformamide (3 mL) and water (0.75 mL). The reaction solution was purged with argon for 10 minutes, and then 1,1'-bis(diphenylphosphino)ferrocenedichloropalladium (12 mg, 0.015 mmol) was added to the solution. The reaction solution was degassed again with argon for 5 minutes and heated at 80° C. for 3 hours. The reaction solution was then cooled to room temperature, diluted with ethyl acetate, washed with water and brine, dried over sodium sulfate and concentrated under reduced pressure. The crude product was purified by preparative thin layer chromatography (95:5 dichloromethane/ methanol) to give the desired product (28 mg, 25%): $^1$H NMR (CDCl$_3$, 500 MHz) δ 7.74 (d, J=8.0 Hz, 1H), 7.70 (d, J=7.9 Hz, 1H), 7.32 (td, J=7.3, 1.1 Hz, 1H), 7.28-7.21 (m, 3H), 7.00 (dd, J=7.9, 1.6 Hz, 1H), 6.97 (s, 1H), 4.59 (app s, 1H), 3.80 (d, J=15.0 Hz, 1H), 3.67 (d, J=15.2 Hz, 1H), 3.06-3.04 (m, 1H), 2.94 (dd, J=11.3, 5.9 Hz, 1H), 2.52 (s, 3H), 2.38 (s, 3H), 2.25 (s, 3H); ESI-MS m/z 375 [M+H]$^+$. To a solution of the 7-isoxazole tetrahydroisoquinoline (28 mg, 0.075 mmol) in methanol (2 mL) was added maleic acid (8.7 mg, 0.075 mmol), followed by slow addition of water (10 mL). The resultant reaction solution was lyophilized overnight to give (+/−)-4-(benzo[b]thiophen-2-yl)-2-methyl-7-(3,5-dimethylisoxazol-4-yl)-1,2,3,4-tetrahydroisoquinoline, maleate salt (35 mg) as a light yellow solid: mp 92-95° C.; $^1$H NMR (CD$_3$OD, 500 MHz) δ 7.83 (d, J=7.8 Hz, 1H), 7.78 (d, J=7.3 Hz, 1H), 7.39-7.29 (m, 6H), 6.25 (s, 2H), 5.05 (dd, J=9.9, 5.6 Hz, 1H), 4.59 (app s, 2H), 3.97 (dd, J=12.2, 5.6 Hz, 1H), 3.77-3.72 (m, 1H), 3.09 (s, 3H), 2.42 (s, 3H), 2.26 (s, 3H); ESI-MS m/z 375 [M+H]$^+$.

Example 75

Preparation of (+)-4-(benzo[b]thiophen-2-yl)-2-methyl-7-(morpholin-4-yl)-1,2,3,4-tetrahydroisoquinoline, maleate salt and (−)-4-(benzo[b]thiophen-2-yl)-2-methyl-7-(morpholin-4-yl)-1,2,3,4-tetrahydroisoquinoline, maleate salt Step A: To a solution of 2-acetylbenzo[b]thiophene (5.0 g, 28 mmol) in chloroform (120 mL) was added pyridinium bromide perbromide (9.6 g, 28 mmol) in two batches. The reaction solution was stirred at room temperature for 2 hours, and then was washed with water, aqueous HCl (2 M), water and brine. The resultant solution was dried over sodium sulfate and concentrated under reduced pressure to give the desired bromoketone (7.4 g, crude) as a brown solid, which was used in the next step without further purification: $^1$H NMR (CDCl$_3$, 500 MHz) δ 8.07 (s, 1H), 7.94-7.87 (m, 2H), 7.52-7.25 (m, 2H), 4.46 (s, 2H).

Step B: To a solution of 3-methoxybenzyl methylamine (4.3 g, 29 mmol) in dichloromethane (150 mL) were added triethylamine (10 mL) and the bromoketone (7.3 g, 29 mmol) from Step A above. The reaction solution was stirred at room temperature for 2 hours, and then was quenched with aqueous saturated sodium bicarbonate. The organic extract was separated, washed with water and brine, dried over sodium sulfate and concentrated under reduced pressure. The crude product was purified by flash column chromatography (90:10 to 85:15 hexanes/ethyl acetate) to give the desired product (7.1 g, 76% over 2 steps) as a reddish oil: 1H NMR (CDCl$_3$, 500 MHz) δ 8.09 (s, 1H), 7.86 (d, J=8.0 Hz, 2H), 7.45 (dd, J=8.0, 1.1 Hz, 1H), 7.40 (dd, J=8.0, 1.0 Hz, 1H), 7.24 (d, J=8.1 Hz, 1H), 6.97-6.95 (m, 2H), 6.83 (d, J=8.5 Hz, 1H), 3.78 (s, 3H), 3.76 (s, 2H), 3.70 (s, 2H), 2.43 (s, 3H); ESI-MS m/z 326 [M+H]$^+$.

Step C: To a solution of the ketone (7.1 g, 22 mmol) from Step B above in methanol (100 mL) at 0° C. was added sodium borohydride (0.89 g, 24 mmol) in small portions. The reaction solution was stirred at 0° C. for 1 hour. The solvent was then removed under reduced pressure and the residue obtained was dissolved in dichloromethane. The resultant solution was washed with aqueous saturated sodium bicarbonate and brine, dried over sodium sulfate and concentrated under reduced pressure to give the desired alcohol (6.9 g, 96% crude) as a yellow oil. The crude product was used in the next step without further purification: $^1$H NMR (CDCl$_3$, 500 MHz) δ 7.81 (d, J=7.9 Hz, 1H), 7.70 (d, J=8.1 Hz, 1H), 7.33-7.23 (m, 3H), 7.21 (s, 1H), 6.91-6.87 (m, 3H), 5.07 (dd, J=10.1, 3.5 Hz, 1H), 4.40-4.03 (m, 1H), 3.81 (s, 3H), 3.72 (d, J=13.0 Hz, 1H), 3.56 (d, J=13.0 Hz, 1H), 2.83 (dd, J=12.4, 10.2 Hz, 1H), 2.72 (dd, J=12.4, 3.7 Hz, 1H), 2.34 (s, 3H); ESI-MS m/z 328 [M+H]$^+$.

Step D: To a solution of the alcohol (6.9 g, 21 mmol) from Step C above in dichloromethane (150 mL) was added methanesulfonic acid (14 mL, 210 mmol) dropwise. After the addition, the reaction solution was stirred at room temperature for 20 minutes, and then was added slowly to ice-cold aqueous sodium hydroxide (120 mL, 2 M) and stirred for 20 minutes. The organic layer was separated and the aqueous layer was washed with dichloromethane twice. The combined organic extract was washed with water and brine, dried over sodium sulfate and concentrated under reduced pressure. The crude product was purified by flash column chromatography (95:5 to 50:50 hexanes/ethyl acetate) to give the desired cyclized product (3.4 g, 52%) as a reddish oil: $^1$H NMR (CDCl$_3$, 500 MHz) δ 7.72 (d, J=8.0 Hz, 1H), 7.67 (d, J=8.0 Hz, 1H), 7.29-7.23 (m, 2H), 7.13 (s, 1H), 7.06 (d, J=8.5 Hz, 1H), 6.69 (d, J=2.7 Hz, 1H), 6.61 (d, J=2.6 Hz, 1H), 4.50 (t, J=5.3 Hz, 1H), 3.77 (s, 3H), 3.73 (d, J=14.5 Hz, 1H), 3.59 (d, J=14.5 Hz, 1H), 2.99 (dd, J=11.5, 4.9 Hz, 1H), 2.87 (dd, J=11.4, 6.2 Hz, 1H), 2.47 (s, 3H); ESI-MS m/z 310 [M+H]$^+$.

Step E: To a solution of the 7-methoxy tetrahydroisoquinoline (1.6 g, 5.1 mmol) from Step D above in acetic acid (25 mL) was added aqueous hydrogen bromide (25 mL, 48%). The reaction solution was heated at 100° C. for 20 hours, and then cooled to room temperature and concentrated under reduced pressure. The residue obtained was taken up in a mixture of dichloromethane, water and small amount of methanol. The resultant solution was quenched carefully with aqueous saturated sodium bicarbonate until pH>8. The organic extract was separated, washed with water and brine, dried over sodium sulfate and concentrated under reduced pressure to give the desired phenol (1.6 g, crude) as a brown solid, which was used in the next step without further purification: $^1$H NMR (CDCl$_3$, 500 MHz) δ 7.72 (d, J=7.7 Hz, 1H), 7.67 (d, J=7.7 Hz, 1H), 7.29 (td, J=7.3, 1.2 Hz, 1H), 7.23 (td, J=7.3, 1.3 Hz, 1H), 7.13 (s, 1H), 7.01 (d, J=8.4 Hz, 1H), 6.59 (dd, J=8.4, 2.5 Hz, 1H), 6.53 (d, J=2.3 Hz, 1H), 4.49 (t, J=5.7 Hz, 1H), 3.68 (d, J=15.1 Hz, 1H), 3.57 (d, J=15.0 Hz, 1H), 3.00 (dd, J=11.6, 5.4 Hz, 1H), 2.85 (dd, J=11.5, 6.4 Hz, 1H), 2.47 (s, 3H), 1.90-1.45 (m, 1H); ESI-MS m/z 296 [M+H]$^+$.

Step F: To a solution of this phenol (1.6 g, 5.1 mmol) from Step E above in dichloromethane (50 mL) at 0° C. were successively added pyridine (0.80 mL, 10 mmol) and triflic anhydride (1.1 mL, 6.6 mmol) dropwise. The resultant reaction solution was stirred at 0° C. for 1 hour, and then was quenched with aqueous saturated sodium bicarbonate. The organic extract was separated and the aqueous layer was extracted with dichloromethane twice. The combined organic extract was washed with 1:1 water/brine, dried over sodium sulfate and concentrated under reduced pressure to give the crude product. Purification by flash column chromatography (dichloromethane to 98:2 dichloromethane/methanol) gave the desired triflate (1.6 g, 73% over two steps) as a yellow oil: $^1$H NMR (CDCl$_3$, 500 MHz) δ 7.74 (d, J=8.0 Hz, 1H), 7.70 (d, J=7.8 Hz, 1H), 7.32-7.24 (m, 3H), 7.16 (s, 1H), 7.02-7.00 (m, 2H), 4.54 (t, J=5.4 Hz, 1H), 3.78 (d, J=15.4 Hz, 1H), 3.65 (d, J=15.4 Hz, 1H), 3.01 (dd, J=11.6, 5.0 Hz, 1H), 2.91 (dd, J=11.6, 6.0 Hz, 1H), 2.50 (s, 3H); ESI-MS m/z 428 [M+H]$^+$.

Step G: To a solution of the triflate (0.10 g, 0.23 mmol) from Step F above in toluene (2.5 mL) were added cesium carbonate (67 mg, 0.14 mmol), 2-(dicyclohexylphosphino)-2',4',6'-tri-i-propyl-1,1'-biphenyl (0.19 g, 0.58 mmol) and morpholine (41 µL, 0.47 mmol). The reaction mixture was purged with argon for 5 minutes, and then palladium acetate (8 mg, 0.04 mmol) was added. The reaction flask was capped and heated in a microwave oven (160° C.) for 2 hours. The reaction solution was then cooled to room temperature, filtered through a plug of celite and concentrated under reduced pressure. The crude product obtained was purified using flash column chromatography (dichloromethane to 95:5 dichloromethane/MeOH) to give the desired product (57 mg, 68%) as a yellow foam: $^1$H NMR (CDCl$_3$, 500 MHz) δ 7.72 (d, J=7.9 Hz, 1H), 7.67 (d, J=7.9 Hz, 1H), 7.31-7.22 (m, 2H), 7.13 (s, 1H), 7.05 (d, J=8.6 Hz, 1H), 6.71 (dd, J=8.6, 2.7 Hz, 1H), 6.60 (d, J=2.5 Hz, 1H), 4.49 (t, J=5.4 Hz, 1H), 3.85-3.83 (m, 4H), 3.72 (d, J=14.9 Hz, 1H), 3.58 (d, J=15.0 Hz, 1H), 3.13-3.11 (m, 4H), 2.99 (dd, J=11.3, 5.0 Hz, 1H), 2.86 (dd, J=11.4, 6.2 Hz, 1H), 2.47 (s, 3H).

Step H: To a solution of the 7-morpholinyl tetrahydroisoquinoline (56 mg, 0.15 mmol) from Step G above in methanol (5 mL) was added maleic acid (18 mg, 0.15 mmol). The resultant solution was concentrated under reduced pressure to ~2 mL and diluted with water (5 mL). The resultant solution was lyophilized overnight to give the corresponding maleate salt (73 mg, 99%) as a light yellow solid: mp 110-113° C.; $^1$H NMR (CD$_3$OD, 500 MHz) δ 7.80 (dd, J=7.8, 0.6 Hz, 1H), 7.75 (d, J=7.4 Hz, 1H), 7.38-7.30 (m, 3H), 7.10 (d, J=8.7 Hz, 1H), 6.95 (dd, J=8.7, 2.4 Hz, 1H), 6.80 (d, J=2.5 Hz, 1H), 6.25 (s, 2H), 4.91 (dd, J=9.7, 6.1 Hz, 1H), 4.50 (d, J=15.2 Hz, 1H), 4.45 (d, J=15.4 Hz, 1H), 3.91 (dd, J=12.2, 5.6 Hz, 1H), 3.83-3.81 (m, 4H), 3.71-3.60 (m, 1H), 3.17-3.15 (m, 4H), 3.06 (s, 3H); ESI-MS m/z 365 [M+H]$^+$.

Step I: The free base of product from Step H (0.27 g) was resolved by preparative chiral HPLC (CHIRALPAK AD column, using 80:20:0.1 heptane/isopropanol/diethylamine as the eluent) to give the (+)-enantiomer [[α]$^{25}_D$ +44.8° (c 0.11, methanol)] and the (−)-enantiomer [[α]$^{25}_D$ −45.5° (c 0.13, methanol)]. To a solution of the (+)-enantiomer (0.13 g, 0.36 mmol) in methanol (5 mL) was added maleic acid (41 mg, 0.35 mmol), followed by slow addition of water (25 mL). The resultant solution was lyophilized overnight to give (+)-4-(benzo[b]thiophen-2-yl)-2-methyl-7-(morpholine-4-yl)-1,2,3,4-tetrahydroisoquinoline, maleate salt (0.17 g, 97%, AUC HPLC>99%) as an off-white solid: mp 142-146° C.; $^1$H NMR (CD$_3$OD, 500 MHz) δ 7.80 (dd, J=7.8, 0.6 Hz, 1H), 7.75 (d, J=7.5 Hz, 1H), 7.74-7.29 (m, 3H), 7.10 (d, J=8.7 Hz, 1H), 6.95 (dd, J=8.7, 2.2 Hz, 1H), 6.80 (d, J=2.3 Hz, 1H), 6.25 (s, 2H), 4.92 (dd, J=9.6, 5.9 Hz, 1H), 4.50 (d, J=15.2 Hz, 1H), 4.45 (d, J=15.3 Hz, 1H), 3.91 (dd, J=12.4, 5.9 Hz, 1H), 3.83-3.80 (m, 4H), 3.70-3.59 (m, 1H), 3.18-3.15 (m, 4H), 3.06 (s, 3H); ESI-MS m/z 365 [M+H]$^+$; Anal. Calcd. For C$_{22}$H$_{24}$N$_2$OS-1.125C$_4$H$_4$O$_4$-0.75H$_2$O: C, 62.56; H, 5.95; N, 5.51. Found: C, 62.45; H, 5.95; N, 5.14. To a solution of the (−)-enantiomer (0.13 g, 0.36 mmol) in methanol (5 mL) was added maleic acid (40 mg, 0.35 mmol), followed by slow addition of water (25 mL). The resultant solution was lyophilized overnight to give (−)-4-(benzo[b]thiophen-2-yl)-2-methyl-7-(morpholine-4-yl)-1,2,3,4-tetrahydroisoquinoline, maleate salt (0.16 g, 98%, AUC HPLC>99%) as an off-white solid: mp 142-145° C.; $^1$H NMR (CD$_3$OD, 500 MHz) δ 7.80 (dd, J=7.8, 0.6 Hz, 1H), 7.75 (d, J=7.5 Hz, 1H), 7.74-7.29 (m, 3H), 7.10 (d, J=8.7 Hz, 1H), 6.95 (dd, J=8.7, 2.2 Hz, 1H), 6.80 (d, J=2.3 Hz, 1H), 6.25 (s, 2H), 4.92 (dd, J=9.6, 5.9 Hz, 1H), 4.50 (d, J=15.2 Hz, 1H), 4.45 (d, J=15.3 Hz, 1H), 3.91 (dd, J=12.4, 5.9 Hz, 1H), 3.83-3.80 (m, 4H), 3.70-3.59 (m, 1H), 3.18-3.15 (m, 4H), 3.06 (s, 3H); ESI-MS m/z 365 [M+H]$^+$; Anal. Calcd. For C$_{22}$H$_{24}$N$_2$OS—C$_4$H$_4$O$_4$—H$_2$O: C, 62.63; H, 6.06; N, 5.62. Found: C, 62.45; H, 5.89; N, 5.32.

Example 76

Preparation of (+)-4-(benzo[b]thiophen-2-yl)-2-methyl-7-(piperidin-1-yl)-1,2,3,4-tetrahydroisoquinoline, maleate salt and (−)-4-(benzo[b]thiophen-2-yl)-2-methyl-7-(piperidin-1-yl)-1,2,3,4-tetrahydroisoquinoline, maleate salt Step A: To a solution of 2-acetylbenzo[b]thiophene (5.0 g, 28 mmol) in chloroform (120 mL) was added pyridinium bromide perbromide (9.6 g, 28 mmol) in two batches. The reaction solution was stirred at room temperature for 2 hours, and then was washed with water, aqueous HCl (2 M), water and brine. The resultant solution was dried over sodium sulfate and concentrated under reduced pressure to give the desired bromoketone (7.4 g, crude) as a brown solid, which was used in the next step without further purification: $^1$H NMR (CDCl$_3$, 500 MHz) δ 8.07 (s, 1H), 7.94-7.87 (m, 2H), 7.52-7.25 (m, 2H), 4.46 (s, 2H).

Step B: To a solution of 3-methoxybenzyl methylamine (4.3 g, 29 mmol) in dichloromethane (150 mL) were added triethylamine (10 mL) and the bromoketone (7.3 g, 29 mmol) from Step A above. The reaction solution was stirred at room temperature for 2 hours, and then was quenched with aqueous saturated sodium bicarbonate. The organic extract was separated, washed with water and brine, dried over sodium sulfate and concentrated under reduced pressure. The crude product was purified by flash column chromatography (90:10 to 85:15 hexanes/ethyl acetate) to give the desired product (7.1 g, 76% over 2 steps) as a reddish oil: 1H NMR (CDCl$_3$, 500 MHz) δ 8.09 (s, 1H), 7.86 (d, J=8.0 Hz, 2H), 7.45 (dd, J=8.0, 1.1 Hz, 1H), 7.40 (dd, J=8.0, 1.0 Hz, 1H), 7.24 (d, J=8.1 Hz, 1H), 6.97-6.95 (m, 2H), 6.83 (d, J=8.5 Hz, 1H), 3.78 (s, 3H), 3.76 (s, 2H), 3.70 (s, 2H), 2.43 (s, 3H); ESI-MS m/z 326 [M+H]$^+$.

Step C: To a solution of the ketone (7.1 g, 22 mmol) from Step B above in methanol (100 mL) at 0° C. was added sodium borohydride (0.89 g, 24 mmol) in small portions. The reaction solution was stirred at 0° C. for 1 hour. The solvent was then removed under reduced pressure and the residue obtained was dissolved in dichloromethane. The resultant solution was washed with aqueous saturated sodium bicarbonate and brine, dried over sodium sulfate and concentrated under reduced pressure to give the desired alcohol (6.9 g, 96% crude) as a yellow oil. The crude product was used in the next step without further purification: $^1$H NMR (CDCl$_3$, 500 MHz) δ 7.81 (d, J=7.9 Hz, 1H), 7.70 (d, J=8.1 Hz, 1H), 7.33-7.23 (m, 3H), 7.21 (s, 1H), 6.91-6.87 (m, 3H), 5.07 (dd, J=10.1, 3.5 Hz, 1H), 4.40-4.03 (m, 1H), 3.81 (s, 3H), 3.72 (d, J=13.0 Hz, 1H), 3.56 (d, J=13.0 Hz, 1H), 2.83 (dd, J=12.4, 10.2 Hz, 1H), 2.72 (dd, J=12.4, 3.7 Hz, 1H), 2.34 (s, 3H); ESI-MS m/z 328 [M+H]$^+$.

Step D: To a solution of the alcohol (6.9 g, 21 mmol) from Step C above in dichloromethane (150 mL) was added methanesulfonic acid (14 mL, 210 mmol) dropwise. After the addition, the reaction solution was stirred at room temperature for 20 minutes, and then was added slowly to ice-cold aqueous sodium hydroxide (2 M) and stirred for 20 minutes. The organic layer was separated and the aqueous layer was washed with dichloromethane twice. The combined organic extract was washed with water and brine, dried over sodium sulfate and concentrated under reduced pressure. The crude product was purified by flash column chromatography (95:5 to 50:50 hexanes/ethyl acetate) to give the desired cyclized product (3.4 g, 52%) as a reddish oil: $^1$H NMR (CDCl$_3$, 500 MHz) δ 7.72 (d, J=8.0 Hz, 1H), 7.67 (d, J=8.0 Hz, 1H), 7.29-7.23 (m, 2H), 7.13 (s, 1H), 7.06 (d, J=8.5 Hz, 1H), 6.69 (d, J=2.7 Hz, 1H), 6.61 (d, J=2.6 Hz, 1H), 4.50 (t, J=5.3 Hz, 1H), 3.77 (s, 3H), 3.73 (d, J=14.5 Hz, 1H), 3.59 (d, J=14.5 Hz, 1H), 2.99 (dd, J=11.5, 4.9 Hz, 1H), 2.87 (dd, J=11.4, 6.2 Hz, 1H), 2.47 (s, 3H); ESI-MS m/z 310 [M+H]$^+$.

Step E: To a solution of the 7-methoxy tetrahydroisoquinoline (1.6 g, 5.1 mmol) from Step D above in acetic acid (25 mL) was added aqueous hydrogen bromide (25 mL, 48%). The reaction solution was heated at 100° C. for 20 hours, and then cooled to room temperature and concentrated under reduced pressure. The residue obtained was taken up in a mixture of dichloromethane, water and small amount of methanol. The resultant solution was quenched carefully with aqueous saturated sodium bicarbonate until pH>8. The organic extract was separated, washed with water and brine, dried over sodium sulfate and concentrated under reduced pressure to give the desired phenol (1.6 g, crude) as a brown solid, which was used in the next step without further purification: $^1$H NMR (CDCl$_3$, 500 MHz) δ 7.72 (d, J=7.7 Hz, 1H), 7.67 (d, J=7.7 Hz, 1H), 7.29 (td, J=7.3, 1.2 Hz, 1H), 7.23 (td, J=7.3, 1.3 Hz, 1H), 7.13 (s, 1H), 7.01 (d, J=8.4 Hz, 1H), 6.59 (dd, J=8.4, 2.5 Hz, 1H), 6.53 (d, J=2.3 Hz, 1H), 4.49 (t, J=5.7 Hz, 1H), 3.68 (d, J=15.1 Hz, 1H), 3.57 (d, J=15.0 Hz, 1H), 3.00 (dd, J=11.6, 5.4 Hz, 1H), 2.85 (dd, J=11.5, 6.4 Hz, 1H), 2.47 (s, 3H), 1.90-1.45 (m, 1H); ESI-MS m/z 296 [M+H]$^+$.

Step F: To a solution of this phenol (1.6 g, 5.1 mmol) from Step E above in dichloromethane (50 mL) at 0° C. were successively added pyridine (0.80 mL, 10 mmol) and triflic anhydride (1.1 mL, 6.6 mmol) dropwise. The resultant reaction solution was stirred at 0° C. for 1 hour, and then was quenched with aqueous saturated sodium bicarbonate. The organic extract was separated and the aqueous layer was extracted with dichloromethane twice. The combined organic extract was washed with 1:1 water/brine, dried over sodium sulfate and concentrated under reduced pressure to give the crude product. Purification by flash column chromatography (dichloromethane to 98:2 dichloromethane/methanol) gave the desired triflate (1.6 g, 73% over two steps) as a yellow oil: $^1$H NMR (CDCl$_3$, 500 MHz) δ 7.74 (d, J=8.0 Hz, 1H), 7.70 (d, J=7.8 Hz, 1H), 7.32-7.24 (m, 3H), 7.16 (s, 1H), 7.02-7.00 (m, 2H), 4.54 (t, J=5.4 Hz, 1H), 3.78 (d, J=15.4 Hz, 1H), 3.65 (d, J=15.4 Hz, 1H), 3.01 (dd, J=11.6, 5.0 Hz, 1H), 2.91 (dd, J=11.6, 6.0 Hz, 1H), 2.50 (s, 3H); ESI-MS m/z 428 [M+H]$^+$.

Step G: To a solution of the triflate (0.60 g, 1.4 mmol) from Step F above in toluene (18 mL) were added cesium carbonate (1.15 g, 3.5 mmol) and 2-(dicyclohexylphosphino)-2',4',6'-tri-i-propyl-1,1'-biphenyl (0.40 g, 0.85 mmol). The reaction mixture was purged with argon for 10 minutes and then palladium(II) acetate (47 mg, 0.21 mmol) was added to it. The resultant solution was purged with argon for 5 minutes, and then piperidine (0.29 mL, 2.8 mmol) was added via syringe. The reaction flask was capped and heated at 100° C. for 20 hours, and then was cooled to room temperature, filtered through a plug of celite and concentrated under reduced pressure. The crude product obtained was purified by flash column chromatography (dichloromethane to 96:4 dichloromethane/methanol) to give the desired product (0.38 g, 74%) as a yellow foam: $^1$H NMR (CD$_3$OD, 500 MHz) δ 7.73 (d, J=7.8 Hz, 1H), 7.69 (d, J=7.5 Hz, 1H), 7.31-7.23 (m, 2H), 7.19 (s, 1H), 6.97 (d, J=8.5 Hz, 1H), 6.79 (t, J=6.5 Hz, 1H), 6.72 (d, J=1.5 Hz, 1H), 4.59 (br s, 1H), 3.72 (d, J=15.0 Hz, 1H), 3.60 (d, J=15.1 Hz, 1H), 3.15-3.10 (m, 5H), 2.76 (dd, J=11.2, 8.7 Hz, 1H), 2.45 (s, 3H), 1.72-1.57 (m, 6H); ESI-MS m/z 363 [M+H]$^+$.

Step H: The 7-piperidinyl tetrahydroisoquinoline (0.42 g, 1.2 mmol) from Step G above was resolved by preparative chiral HPLC (CHIRALCEL OJ column, using 80:20:0.1 heptane/ethanol/diethylamine as the eluent) to give the (+)-enantiomer [[α]$^{25}_D$ +52.7° (c 0.15, methanol)] and the (−)-enantiomer [[α]$^{25}_D$ −55.6° (c 0.14, methanol)]. The (+)-enantiomer (0.20 g, 0.55 mmol) was dissolved in methanol (5 mL) and maleic acid (64 mg, 0.55 mmol) was added to it. To this solution was added water (25 mL). The resultant solution was lyophilized overnight to provide (+)-4-(benzo[b]thiophen-2-yl)-2-methyl-7-(piperidin-1-yl)-1,2,3,4-tetrahydroisoquinoline, maleate salt (0.26 g, 98%, >99% AUC HPLC) as an off-white solid: mp 114-116° C.; $^1$H NMR (CD$_3$OD, 500 MHz) δ 7.80 (dd, J=8.3, 1.0 Hz, 1H), 7.75 (d, J=7.3 Hz, 1H), 7.37-7.28 (m, 3H), 7.07 (d, J=8.7 Hz, 1H), 6.94 (dd, J=8.7, 2.5 Hz, 1H), 6.79 (d, J=2.5 Hz, 1H), 6.24 (s, 2H), 4.90 (dd, J=9.6, 6.0 Hz, 1H), 4.48 (d, J=15.3 Hz, 1H), 4.43 (d, J=15.3 Hz, 1H), 3.89 (dd, J=12.4, 6.0 Hz, 1H), 3.63 (t, J=10.4 Hz, 1H), 3.20-3.18 (m, 4H), 3.05 (s, 3H), 1.72-1.58 (m, 6H); ESI-MS m/z 363 [M+H]$^+$; Anal. Calcd. For C$_{23}$H$_{25}$N$_2$S—C$_4$H$_4$O$_4$-1.5H$_2$O: C, 64.14; H, 6.58; N, 5.54. Found: C, 63.94; H, 6.20; N, 5.40.

The (−)-enantiomer (0.20 g, 0.55 mmol) was dissolved in methanol (5 mL) and maleic acid (63 mg, 0.55 mmol) was added. To this solution was added water (25 mL) and the resultant solution was lyophilized overnight to provide (−)-4-(benzo[b]thiophen-2-yl)-2-methyl-7-(piperidin-1-yl)-1,2,3,4-tetrahydroisoquinoline, maleate salt (0.25 g, 98%, >99% AUC HPLC) as an off-white solid: mp 113-115° C.; $^1$H NMR (CD$_3$OD, 500 MHz) δ 7.80 (dd, J=8.3, 1.0 Hz, 1H), 7.75 (d, J=7.3 Hz, 1H), 7.37-7.28 (m, 3H), 7.07 (d, J=8.7 Hz, 1H), 6.94 (dd, J=8.7, 2.5 Hz, 1H), 6.79 (d, J=2.5 Hz, 1H), 6.24 (s, 2H), 4.90 (dd, J=9.6, 6.0 Hz, 1H), 4.48 (d, J=15.3 Hz, 1H), 4.43 (d, J=15.3 Hz, 1H), 3.89 (dd, J=12.4, 6.0 Hz, 1H), 3.63 (t, J=10.4 Hz, 1H), 3.20-3.18 (m, 4H), 3.05 (s, 3H), 1.72-1.58 (m, 6H); ESI-MS m/z 363 [M+H]$^+$; Anal. Calcd. For C$_{23}$H$_{25}$N$_2$S—C$_4$H$_4$O$_4$-0.75H$_2$O: C, 65.90; H, 6.45; N, 5.69. Found: C, 65.74; H, 6.27; N, 5.51.

Example 77

Preparation of (+/−)-4-(benzo[b]thiophen-2-yl)-2-methyl-7-(pyrrolidin-1-yl)-1,2,3,4-tetrahydroisoquinoline, maleate salt Step A: To a solution of 2-acetylbenzo[b]thiophene (5.0 g, 28 mmol) in chloroform (120 mL) was added pyridinium bromide perbromide (9.6 g, 28 mmol) in two batches. The reaction solution was stirred at room temperature for 2 hours, and then was washed with water, aqueous HCl (2 M), water and brine. The resultant solution was dried over sodium sulfate and concentrated under reduced pressure to give the desired bromoketone (7.4 g, crude) as a brown solid, which was used in the next step without further purification: $^1$H NMR (CDCl$_3$, 500 MHz) δ 8.07 (s, 1H), 7.94-7.87 (m, 2H), 7.52-7.25 (m, 2H), 4.46 (s, 2H).

Step B: To a solution of 3-methoxybenzyl methylamine (4.3 g, 29 mmol) in dichloromethane (150 mL) were added triethylamine (10 mL) and the bromoketone (7.3 g, 29 mmol) from Step A above. The reaction solution was stirred at room temperature for 2 hours, and then was quenched with aqueous saturated sodium bicarbonate. The organic extract was separated, washed with water and brine, dried over sodium sulfate and concentrated under reduced pressure. The crude product was purified by flash column chromatography (90:10 to 85:15 hexanes/ethyl acetate) to give the desired product (7.1 g, 76% over 2 steps) as a reddish oil: 1H NMR (CDCl$_3$, 500 MHz) δ 8.09 (s, 1H), 7.86 (d, J=8.0 Hz, 2H), 7.45 (dd, J=8.0, 1.1 Hz, 1H), 7.40 (dd, J=8.0, 1.0 Hz, 1H), 7.24 (d, J=8.1 Hz, 1H), 6.97-6.95 (m, 2H), 6.83 (d, J=8.5 Hz, 1H), 3.78 (s, 3H), 3.76 (s, 2H), 3.70 (s, 2H), 2.43 (s, 3H); ESI-MS m/z 326 [M+H]$^+$.

Step C: To a solution of the ketone (7.1 g, 22 mmol) from Step B above in methanol (100 mL) at 0° C. was added sodium borohydride (0.89 g, 24 mmol) in small portions. The reaction solution was stirred at 0° C. for 1 hour. The solvent was then removed under reduced pressure and the residue obtained was dissolved in dichloromethane. The resultant solution was washed with aqueous saturated sodium bicarbonate and brine, dried over sodium sulfate and concentrated under reduced pressure to give the desired alcohol (6.9 g, 96% crude) as a yellow oil. The crude product was used in the next step without further purification: $^1$H NMR (CDCl$_3$, 500 MHz) δ 7.81 (d, J=7.9 Hz, 1H), 7.70 (d, J=8.1 Hz, 1H), 7.33-7.23 (m, 3H), 7.21 (s, 1H), 6.91-6.87 (m, 3H), 5.07 (dd, J=10.1, 3.5 Hz, 1H), 4.40-4.03 (m, 1H), 3.81 (s, 3H), 3.72 (d, J=13.0 Hz, 1H), 3.56 (d, J=13.0 Hz, 1H), 2.83 (dd, J=12.4, 10.2 Hz, 1H), 2.72 (dd, J=12.4, 3.7 Hz, 1H), 2.34 (s, 3H); ESI-MS m/z 328 [M+H]$^+$.

Step D: To a solution of the alcohol (6.9 g, 21 mmol) from Step C above in dichloromethane (150 mL) was added methanesulfonic acid (14 mL, 210 mmol) dropwise. After the addition, the reaction solution was stirred at room temperature for 20 minutes, and then was added slowly to ice-cold aqueous sodium hydroxide (120 mL, 2 M) and stirred for 20 minutes. The organic layer was separated and the aqueous layer was extracted with dichloromethane twice. The combined organic extract was washed with water and brine, dried over sodium sulfate and concentrated under reduced pressure. The crude product was purified by flash column chromatography (95:5 to 50:50 hexanes/ethyl acetate) to give the desired product (3.4 g, 52%) as a reddish oil: $^1$H NMR (CDCl$_3$, 500 MHz) δ 7.72 (d, J=8.0 Hz, 1H), 7.67 (d, J=8.0 Hz, 1H), 7.29-7.23 (m, 2H), 7.13 (s, 1H), 7.06 (d, J=8.5 Hz, 1H), 6.69 (d, J=2.7 Hz, 1H), 6.61 (d, J=2.6 Hz, 1H), 4.50 (t, J=5.3 Hz, 1H), 3.77 (s, 3H), 3.73 (d, J=14.5 Hz, 1H), 3.59 (d, J=14.5 Hz, 1H), 2.99 (dd, J=11.5, 4.9 Hz, 1H), 2.87 (dd, J=11.4, 6.2 Hz, 1H), 2.47 (s, 3H); ESI-MS m/z 310 [M+H]$^+$.

Step E: To a solution of the 7-methoxy tetrahydroisoquinoline (1.6 g, 5.1 mmol) from Step D above in acetic acid (25 mL) was added aqueous hydrogen bromide (25 mL, 48%). The reaction solution was heated at 100° C. for 20 hours, and then cooled to room temperature and concentrated under reduced pressure. The residue obtained was taken up in a mixture of dichloromethane, water and small amount of methanol. The resultant solution was quenched carefully with aqueous saturated sodium bicarbonate until pH>8. The organic extract was separated, washed with water and brine, dried over sodium sulfate and concentrated under reduced pressure to give the desired phenol (1.6 g, crude) as a brown solid, which was used in the next step without further purification: $^1$H NMR (CDCl$_3$, 500 MHz) δ 7.72 (d, J=7.7 Hz, 1H), 7.67 (d, J=7.7 Hz, 1H), 7.29 (td, J=7.3, 1.2 Hz, 1H), 7.23 (td, J=7.3, 1.3 Hz, 1H), 7.13 (s, 1H), 7.01 (d, J=8.4 Hz, 1H), 6.59 (dd, J=8.4, 2.5 Hz, 1H), 6.53 (d, J=2.3 Hz, 1H), 4.49 (t, J=5.7 Hz, 1H), 3.68 (d, J=15.1 Hz, 1H), 3.57 (d, J=15.0 Hz, 1H), 3.00 (dd, J=11.6, 5.4 Hz, 1H), 2.85 (dd, J=11.5, 6.4 Hz, 1H), 2.47 (s, 3H), 1.90-1.45 (m, 1H); ESI-MS m/z 296 [M+H]$^+$.

Step F: To a solution of this phenol (1.6 g, 5.1 mmol) from Step E above in dichloromethane (50 mL) at 0° C. were successively added pyridine (0.80 mL, 10 mmol) and triflic anhydride (1.1 mL, 6.6 mmol) dropwise. The resultant reaction solution was stirred at 0° C. for 1 hour, and then was quenched with aqueous saturated sodium bicarbonate. The organic extract was separated and the aqueous layer was extracted with dichloromethane twice. The combined organic extract was washed with 1:1 water/brine, dried over sodium sulfate and concentrated under reduced pressure to give the crude product. Purification by flash column chromatography (dichloromethane to 98:2 dichloromethane/methanol) gave the desired triflate (1.6 g, 73% over two steps) as a yellow oil: $^1$H NMR (CDCl$_3$, 500 MHz) δ 7.74 (d, J=8.0 Hz, 1H), 7.70 (d, J=7.8 Hz, 1H), 7.32-7.24 (m, 3H), 7.16 (s, 1H), 7.02-7.00 (m, 2H), 4.54 (t, J=5.4 Hz, 1H), 3.78 (d, J=15.4 Hz, 1H), 3.65 (d, J=15.4 Hz, 1H), 3.01 (dd, J=11.6, 5.0 Hz, 1H), 2.91 (dd, J=11.6, 6.0 Hz, 1H), 2.50 (s, 3H); ESI-MS m/z 428 [M+H]$^+$.

Step G: To a solution of the triflate (0.11 g, 0.26 mmol) from Step F above in toluene (3 mL) were added cesium carbonate (0.21 g, 0.66 mmol) and 2-(dicyclohexylphosphino)-2',4',6'-tri-i-propyl-1,1'-biphenyl (37 mg, 0.08 mmol) and the reaction mixture was purged with argon for 10 minutes. To this solution was added palladium(II) acetate (4.7 mg, 0.02 mmol). The reaction solution was purged with argon again for 5 minutes, and then pyrrolidine (44 µL, 0.52 mmol) was added via syringe. The reaction flask was capped and heated at 100° C. for 20 hours. The reaction solution was then cooled to room temperature, filtered through a plug of celite and concentrated under reduced pressure. The crude product obtained was purified by flash column chromatography (99:1 dichloromethane/methanol), followed by preparative thin layer chromatography (66:34 hexanes/ethyl acetate) to give the desired product (60 mg, 66%) as a white foam: $^1$H NMR (CD$_3$OD, 500 MHz) δ 7.71 (d, J=8.1 Hz, 1H), 7.65 (d, J=7.8 Hz, 1H), 7.28-7.25 (m, 1H), 7.22 (dd, J=8.1, 1.2 Hz, 1H), 7.13 (s, 1H), 6.98 (d, J=8.5 Hz, 1H), 6.38 (dd, J=8.0, 2.6 Hz, 1H), 6.25 (d, J=2.5 Hz, 1H), 4.48 (t, J=5.6 Hz, 1H), 3.72 (d, J=14.7 Hz, 1H), 3.58 (d, J=14.7 Hz, 1H), 3.26-3.23 (m, 4H), 2.99-2.96 (m, 1H), 2.85 (dd, J=14.4, 6.3 Hz, 1H), 2.46 (s, 3H), 1.99-1.95 (m, 4H); ESI-MS m/z 349 [M+H]$^+$.

Step H: To a solution of the 7-pyrrolidine tetrahydroisoquinoline (60 mg, 0.17 mmol) from Step G above in methanol (2 mL) was added maleic acid (20 mg, 0.17 mmol), followed by slow addition of water (10 mL). The resultant solution was lyophilized overnight to give (+/−)-4-(benzo[b]thiophen-2-yl)-2-methyl-7-(pyrrolidin-1-yl)-1,2,3,4-tetrahydroisoquinoline, maleate salt (79 g, 98%) as a white solid: mp 105-108° C.; $^1$H NMR (CD$_3$OD, 500 MHz) δ 7.80 (d, J=7.9 Hz, 1H), 7.74 (d, J=7.6 Hz, 1H), 7.37-7.27 (m, 3H), 7.02 (d, J=8.5 Hz, 1H), 6.57 (dd, J=8.4, 2.1, Hz, 1H), 6.38 (d, J=2.2 Hz, 1H), 6.24 (s, 2H), 4.90-4.84 (m, 1H), 4.50 (d, J=15.0 Hz, 1H), 4.44 (d, J=15.0 Hz, 1H), 3.90 (dd, J=12.5, 6.1 Hz, 1H), 3.69-3.56 (m, 1H), 3.31-3.26 (m, 4H), 3.06 (s, 3H), 2.05-2.01 (m, 4H); ESI-MS m/z 349 [M+H]$^+$.

Example 78

Preparation of (+)-4-(benzo[b]thiophen-2-yl)-2-methyl-7-(morpholine-4-ylmethyl)-1,2,3,4-tetrahydroisoquinoline, maleate salt Step A: To a solution of the (+)-enantiomer, free base from Step H in Example 79 (0.25 g, 0.82 mmol) in toluene (10 mL) at −78° C. was added diisobutylaluminum hydride (0.90 mL, 0.90 mmol, 1 M in toluene). After the addition, the reaction solution was slowly warmed to room temperature and stirred overnight. To the resultant reaction mixture was then slowly added a saturated solution of Rochelle's salt and the slurry obtained was stirred vigorously for 2 hours. The organic phase was separated and the aqueous solution was extracted with ethyl acetate twice. The combined organic extract was washed with brine, dried over sodium sulfate and concentrated under reduced pressure. The crude product obtained was purified by preparative thin layer chromatography (95:5 dichloromethane/methanol) to give the desired product (78 mg, 30%) as a colorless oil: $^1$H NMR (CDCl$_3$, 500 MHz) δ 9.95 (s, 1H), 7.73 (d, J=8.1 Hz, 1H), 7.70 (d, J=7.9 Hz, 1H), 7.63-7.61 (m, 2H), 7.33-7.25 (m, 3H), 7.18 (s, 1H), 4.61 (t, J=5.4 Hz, 1H), 3.84 (d, J=15.2 Hz, 1H), 3.70 (d, J=15.2 Hz, 1H), 3.04 (dd, J=11.6, 5.0 Hz, 1H), 2.93 (dd, J=11.6, 5.9 Hz, 1H), 2.52 (s, 3H).

Step B: To a solution of the aldehyde (78 mg, 0.25 mmol) from Step A above in dichloromethane (8 mL) at room temperature were added morpholine (28 µL, 0.32 mmol), sodium triacetoxyborohydride (80 mg, 0.38 mmol), acetic acid (5 µL) and 4Å molecular sieves (0.5 g). The reaction solution was stirred at room temperature overnight, and then was diluted with dichloromethane, washed with aqueous sodium carbonate (2 M), dried over sodium sulfate and concentrated under reduced pressure. The crude product obtained was purified by preparative thin layer chromatography (94:6 dichloromethane/methanol) to give the desired product (68 mg, 72%) as a white foam: $[\alpha]^{24}_D$ +37.2° (c 0.11, methanol); $^1$H NMR (CDCl$_3$, 500 MHz) δ 7.72 (d, J=8.0 Hz, 1H), 7.68 (d, J=7.9 Hz, 1H), 7.30-7.23 (m, 2H), 7.16 (s, 1H), 7.11-7.05 (m, 3H), 4.54 (t, J=5.0 Hz, 1H), 3.75 (d, J=15.0 Hz, 1H), 3.73-3.69 (m, 4H), 3.62 (d, J=14.9 Hz, 1H), 3.44 (s, 2H), 3.00 (dd, J=11.5, 4.9 Hz, 1H), 2.89 (dd, J=11.4, 6.1 Hz, 1H), 2.49 (s, 3H), 2.45-2.41 (m, 4H); ESI-MS m/z 379 [M+H]$^+$.

To a solution of the tetrahydroisoquinoline (62 mg, 0.16 mmol) in methanol (3 mL) was added maleic acid (38 mg, 0.33 mmol), followed by water (15 mL). The resultant solution was lyophilized overnight to give (+/−)-4-(benzo[b]thiophen-2-yl)-2-methyl-7-(morpholine-4-ylmethyl)-1,2,3,4-tetrahydroisoquinoline, maleate salt (94 mg, 91%, AUC HPLC>99%): mp 80-82° C.; $^1$H NMR (CD$_3$OD, 500 MHz) δ 7.80 (d, J=7.9 Hz, 1H), 7.76 (d, J=7.5 Hz, 1H), 7.40-7.31 (m, 6H), 6.26 (s, 4H), 5.01 (dd, J=9.6, 5.8 Hz, 1H), 4.50-4.47 (m, 2H), 4.19 (s, 2H), 3.90-3.85 (m, 5H), 3.64 (dd, J=12.3, 10.2 Hz, 1H), 3.13-3.09 (m, 4H), 3.03 (s, 3H); ESI-MS m/z 379 [M+H]$^+$; Anal. Calcd. For C$_{22}$H$_{24}$N$_2$OS·2C$_4$H$_4$O$_4$·1.875H$_2$O: C, 57.77; H, 5.90; N, 4.35. Found: C, 58.09; H, 5.58; N, 3.95.

Example 79

Preparation of (+)-4-(benzo[b]thiophen-2-yl)-2-methyl-1,2,3,4-tetrahydroisoquinoline-7-carbonitrile, maleate salt and (−)-4-(benzo[b]thiophen-2-yl)-2-methyl-1,2,3,4-tetrahydroisoquinoline-7-carbonitrile, maleate salt Step A: To a solution of 2-acetylbenzo[b]thiophene (5.0 g, 28 mmol) in chloroform (120 mL) was added pyridinium bromide perbromide (9.6 g, 28 mmol) in two batches. The reaction solution was stirred at room temperature for 2 hours, and then was washed with water, aqueous HCl (2 M), water and brine. The resultant solution was dried over sodium sulfate and concentrated under reduced pressure to give the desired bromoketone (7.4 g, crude) as a brown solid, which was used in the next step without further purification: $^1$H NMR (CDCl$_3$, 500 MHz) δ 8.07 (s, 1H), 7.94-7.87 (m, 2H), 7.52-7.25 (m, 2H), 4.46 (s, 2H).

Step B: To a solution of 3-methoxybenzyl methylamine (4.3 g, 29 mmol) in dichloromethane (150 mL) were added triethylamine (10 mL) and the bromoketone (7.3 g, 29 mmol) from Step A above. The reaction solution was stirred at room temperature for 2 hours, and then was quenched with aqueous saturated sodium bicarbonate. The organic extract was separated, washed with water and brine, dried over sodium sulfate and concentrated under reduced pressure. The crude product was purified by flash column chromatography (90:10 to 85:15 hexanes/ethyl acetate) to give the desired product (7.1 g, 76% over 2 steps) as a reddish oil: $^1$H NMR (CDCl$_3$, 500 MHz) δ 8.09 (s, 1H), 7.86 (d, J=8.0 Hz, 2H), 7.45 (dd, J=8.0, 1.1 Hz, 1H), 7.40 (dd, J=8.0, 1.0 Hz, 1H), 7.24 (d, J=8.1 Hz, 1H), 6.97-6.95 (m, 2H), 6.83 (d, J=8.5 Hz, 1H), 3.78 (s, 3H), 3.76 (s, 2H), 3.70 (s, 2H), 2.43 (s, 3H); ESI-MS m/z 326 [M+H]$^+$.

Step C: To a solution of the ketone (7.1 g, 22 mmol) from Step B above in methanol (100 mL) at 0° C. was added sodium borohydride (0.89 g, 24 mmol) in small portions. The reaction solution was stirred at 0° C. for 1 hour. The solvent was then removed under reduced pressure and the residue obtained was dissolved in dichloromethane. The resultant solution was washed with aqueous saturated sodium bicarbonate and brine, dried over sodium sulfate and concentrated under reduced pressure to give the desired alcohol (6.9 g, 96% crude) as a yellow oil. The crude product was used in the next step without further purification: $^1$H NMR (CDCl$_3$, 500 MHz) δ 7.81 (d, J=7.9 Hz, 1H), 7.70 (d, J=8.1 Hz, 1H), 7.33-7.23 (m, 3H), 7.21 (s, 1H), 6.91-6.87 (m, 3H), 5.07 (dd, J=10.1, 3.5 Hz, 1H), 4.40-4.03 (m, 1H), 3.81 (s, 3H), 3.72 (d, J=13.0 Hz, 1H), 3.56 (d, J=13.0 Hz, 1H), 2.83 (dd, J=12.4, 10.2 Hz, 1H), 2.72 (dd, J=12.4, 3.7 Hz, 1H), 2.34 (s, 3H); ESI-MS m/z 328 [M+H]$^+$.

Step D: To a solution of the alcohol (6.9 g, 21 mmol) from Step C above in dichloromethane (150 mL) was added methanesulfonic acid (14 mL, 210 mmol) dropwise. After the addition, the reaction solution was stirred at room temperature for 20 minutes, and then was added slowly to ice-cold aqueous sodium hydroxide (120 mL, 2 M) and stirred for 20 minutes. The organic layer was separated and the aqueous layer was extracted with dichloromethane twice. The combined organic extract was washed with water and brine, dried over sodium sulfate and concentrated under reduced pressure. The crude product was purified by flash column chromatography (95:5 to 50:50 hexanes/ethyl acetate) to give the desired product (3.4 g, 52%) as a reddish oil: $^1$H NMR (CDCl$_3$, 500 MHz) δ 7.72 (d, J=8.0 Hz, 1H), 7.67 (d, J=8.0 Hz, 1H), 7.29-7.23 (m, 2H), 7.13 (s, 1H), 7.06 (d, J=8.5 Hz, 1H), 6.69 (d, J=2.7 Hz, 1H), 6.61 (d, J=2.6 Hz, 1H), 4.50 (t, J=5.3 Hz, 1H), 3.77 (s, 3H), 3.73 (d, J=14.5 Hz, 1H), 3.59 (d, J=14.5 Hz, 1H), 2.99 (dd, J=11.5, 4.9 Hz, 1H), 2.87 (dd, J=11.4, 6.2 Hz, 1H), 2.47 (s, 3H); ESI-MS m/z 310 [M+H]$^+$.

Step E: To a solution of the 7-methoxy tetrahydroisoquinoline (1.6 g, 5.1 mmol) from Step D above in acetic acid (25 mL) was added aqueous hydrogen bromide (25 mL, 48%). The reaction solution was heated at 100° C. for 20 hours, and then cooled to room temperature and concentrated under reduced pressure. The residue obtained was taken up in a mixture of dichloromethane, water and small amount of methanol. The resultant solution was quenched carefully with aqueous saturated sodium bicarbonate until pH>8. The organic extract was separated, washed with water and brine, dried over sodium sulfate and concentrated under reduced pressure to give the desired phenol (1.6 g, crude) as a brown solid, which was used in the next step without further purification: $^1$H NMR (CDCl$_3$, 500 MHz) δ 7.72 (d, J=7.7 Hz, 1H), 7.67 (d, J=7.7 Hz, 1H), 7.29 (td, J=7.3, 1.2 Hz, 1H), 7.23 (td, J=7.3, 1.3 Hz, 1H), 7.13 (s, 1H), 7.01 (d, J=8.4 Hz, 1H), 6.59 (dd, J=8.4, 2.5 Hz, 1H), 6.53 (d, J=2.3 Hz, 1H), 4.49 (t, J=5.7 Hz, 1H), 3.68 (d, J=15.1 Hz, 1H), 3.57 (d, J=15.0 Hz, 1H), 3.00 (dd, J=11.6, 5.4 Hz, 1H), 2.85 (dd, J=11.5, 6.4 Hz, 1H), 2.47 (s, 3H), 1.90-1.45 (m, 1H); ESI-MS m/z 296 [M+H]$^+$.

Step F: To a solution of this phenol (1.6 g, 5.1 mmol) from Step E above in dichloromethane (50 mL) at 0° C. were successively added pyridine (0.80 mL, 10 mmol) and triflic anhydride (1.1 mL, 6.6 mmol) dropwise. The resultant reaction solution was stirred at 0° C. for 1 hour, and then was quenched with aqueous saturated sodium bicarbonate. The organic extract was separated and the aqueous layer was extracted with dichloromethane twice. The combined organic extract was washed with 1:1 water/brine, dried over sodium sulfate and concentrated under reduced pressure to give the crude product. Purification by flash column chromatography (dichloromethane to 98:2 dichloromethane/methanol) gave the desired triflate (1.6 g, 73% over two steps) as a yellow oil: $^1$H NMR (CDCl$_3$, 500 MHz) δ 7.74 (d, J=8.0 Hz, 1H), 7.70 (d, J=7.8 Hz, 1H), 7.32-7.24 (m, 3H), 7.16 (s, 1H), 7.02-7.00 (m, 2H), 4.54 (t, J=5.4 Hz, 1H), 3.78 (d, J=15.4 Hz, 1H), 3.65 (d, J=15.4 Hz, 1H), 3.01 (dd, J=11.6, 5.0 Hz, 1H), 2.91 (dd, J=11.6, 6.0 Hz, 1H), 2.50 (s, 3H); ESI-MS m/z 428 [M+H]$^+$.

Step G: To a solution of the triflate (1.8 g, 4.3 mmol) from Step F above in N,N-dimethylformamide (15 mL) was added zinc cyanide (1.0 g, 8.6 mmol). The reaction solution was purged with argon for 10 minutes, and then tetrakis(triphenylphosphine) palladium(0) (0.50 g, 0.43 mmol) was added to it. The resultant solution was degassed with argon for 5 minutes and heated at 120° C. for 4 hours. The reaction mixture was then cooled to room temperature, diluted with water, extracted with ethyl acetate. The organic extract was washed with brine, dried over sodium sulfate and concentrated under reduced pressure. The crude product was purified by flash column chromatography (83:17 to 66:34 eluent hexanes/ethyl acetate) to give the desired product (0.50 g, 38%) as a yellow foam: $^1$H NMR (CDCl$_3$, 500 MHz) δ 7.74 (d, J=8.0 Hz, 1H), 7.69 (d, J=7.8 Hz, 1H), 7.40-7.26 (m, 5H), 7.17 (s, 1H), 4.57 (t, J=5.3 Hz, 1H), 3.77 (d, J=15.3 Hz, 1H), 3.64 (d, J=15.4 Hz, 1H), 3.02 (dd, J=11.6, 5.0 Hz, 1H), 2.91 (dd, J=11.6, 5.2 Hz, 1H), 2.51 (s, 3H).

Step H: The 7-carbonitrile-tetrahydroisoquinoline (0.67 g) from Step G above was resolved by preparative chiral HPLC (CHIRALPAK AD column, using 85:15:0.1 heptane/ethanol/diethylamine as the eluent) to give the (+)-enantiomer [[α]$^{25}_D$ +129.3° (c 0.16, methanol)] and the (−)-enantiomer [[α]$^{25}_D$ −133.6° (c 0.11, methanol)]. The (+)-enantiomer (83 mg, 0.27 mmol) was dissolved in methanol (3 mL) and treated with maleic acid (32 mg, 0.27 mmol), followed by slow addition of water (10 mL). The resultant solution was lyophilized overnight to give (+)-4-(benzo[b]thiophen-2-yl)-2-methyl-1,2,3,4-tetrahydroisoquinoline-7-carbonitrile, maleate salt (105 mg, 91%, AUC HPLC>99%) as a yellow solid: mp 91-94° C.; 1H NMR (CD$_3$OD, 500 MHz) δ 7.82 (d, J=7.8 Hz, 1H), 7.78 (d, J=7.5 Hz, 1H), 7.71 (s, 1H), 7.64 (d, J=8.0 Hz, 1H), 7.41-7.32 (m, 4H), 6.26 (s, 3H), 5.05 (dd, J=9.6, 6.0 Hz, 1H), 4.51 (app s, 2H), 3.89 (dd, J=12.4, 5.9 Hz, 1H), 3.66 (dd, J=12.0, 10.3 Hz, 1H), 3.03 (s, 3H); ESI-MS m/z 305 [M+H]$^+$; Anal. Calcd. For C$_{19}$H$_{16}$N$_2$S·1.5C$_4$H$_4$O$_4$·1.5H$_2$O: C, 59.40; H, 4.98; N, 5.54. Found: C, 59.36; H, 4.60; N, 5.64.

Step I: To a solution of the (−)-enantiomer (0.18 g, 0.59 mmol) as prepared from Step H methanol (3 mL) was added maleic acid (68 mg, 0.59 mmol), followed by slow addition of water (15 mL). The resultant solution was lyophilized overnight to provide (−)-4-(benzo[b]thiophen-2-yl)-2-methyl-1,2,3,4-tetrahydroisoquinoline-7-carbonitrile, maleate salt (0.24 g, 96%, 97.1% AUC HPLC) as a light yellow solid: mp 80-84° C.; $^1$H NMR (CD$_3$OD, 500 MHz) δ 7.82 (d, J=7.8 Hz, 1H), 7.78 (d, J=7.5 Hz, 1H), 7.71 (s, 1H), 7.64 (d, J=8.0 Hz, 1H), 7.41-7.32 (m, 4H), 6.26 (s, 3H), 5.01 (dd, J=9.6, 6.0 Hz, 1H), 4.46 (app s, 2H), 3.84 (dd, J=12.4, 5.6 Hz, 1H), 3.62 (dd, J=12.0, 10.3 Hz, 1H), 3.00 (s, 3H); ESI-MS m/z 305 [M+H]$^+$.

Example 80

Preparation of (+/−)-4-(benzo[b]thiophen-4-yl)-2-methyl-7-(morpholin-4-yl)-1,2,3,4-tetrahydroisoquinoline, maleate salt Step A: To a solution of the 3-bromothiophenol (14.8 g, 78 mmol) in N,N-dimethylformamide (270 mL) at 0° C. was added sodium hydride (3.6 g, 90 mmol) in batches. After the addition, the reaction solution was stirred at room temperature for 30 minutes, and bromoacetaldehyde dimethyl acetal (9.7 mL, 82 mmol) was added to it. The reaction mixture was stirred at room temperature for 2 hours. The resultant solution was diluted with ethyl acetate, washed with water and brine, dried over sodium sulfate and concentrated under reduced pressure. The crude product was purified by flash column chromatography (hexanes to 95:5 hexanes/ethyl acetate) to give the desired product (20.6 g, 95%) as a light yellow oil: $^1$H NMR (CDCl$_3$, 500 MHz) δ 7.51 (t, J=1.8 Hz, 1H), 7.32-7.28 (m, 2H), 7.14 (t, J=7.9 Hz, 1H), 4.53 (t, J=5.5 Hz, 1H), 3.38 (s, 6H), 3.11 (d, J=5.5 Hz, 2H).

Step B: To a solution of polyphosphoric acid (90 g) in chlorobenzene (250 mL) under reflux was added a solution of the thiophenol acetal (27.6 g, 99.6 mmol) from Step A above in chlorobenzene (120 mL) dropwise. After the addition, the reaction solution was heated under reflux for 2 hours and then cooled to room temperature. The top layer was separated; the bottom layer was diluted with water and then extracted with dichloromethane twice. The combined organic extract was washed with water and aqueous saturated sodium bicarbonate and dried concentrated under reduced pressure. The crude product was purified by flash column chromatography (hexanes) to give a 1:1 mixture of 4-bromobenzo[b]thiophene and 6-bromobenzo[b]thiophene (15.5 g, 73%), which was used in the next step without further purification or characterization.

Step C: To a solution of the isomeric bromobenzo[b]thiophene (14.2 g, 66.5 mmol) from Step B above in N,N-dimethylformamide (130 mL) were added pyridine (7.5 mL) and copper(I) cyanide (7.75 g). The reaction mixture was heated under reflux for 20 hours. The reaction solution was then cooled to 60° C. and poured into a solution of ethylene diamine in water. The resultant mixture was stirred for 30 minutes and extracted with diethyl ether and ethyl acetate. The combined organic extract was washed with 1:1 brine/water, dried over sodium sulfate and concentrated under reduced pressure. The crude product obtained was purified by flash column chromatography (95:5 to 91:9 hexanes/ethyl acetate) to give 4-cyanobenzo[b]thiophene (4.15 g, 39%) as a light yellow solid, and 6-cyanobenzo[b]thiophene (4.34 g, 41%) as a reddish oil: $^1$H NMR for 4-cyanobenzo[b]thiophene (CDCl$_3$, 500 MHz) δ 8.10 (d, J=8.2 Hz, 1H), 7.74-7.70 (m, 2H), 7.62 (dd, J=5.5, 0.6 Hz, 1H), 7.43 (d, J=7.8 Hz, 1H); ¹H NMR for 6-cyanobenzo[b]thiophene (CDCl₃, 500 MHz) δ 8.22 (app s, 1H), 7.90 (d, J=8.3 Hz, 1H), 7.72 (d, J=5.4 Hz, 1H), 7.59 (d, J=8.3 Hz, 1H), 7.42 (dd, J=5.4, 0.5 Hz, 1H).

Step D: To a reaction flask equipped with mechanical stirrer under argon were added copper(I) bromide (0.19 g, 1.3 mmol) and methylmagnesium bromide (26 mL, 78 mmol, 3 M in diethyl ether) at −78° C. To the resultant slurry was then added a solution of the 4-cyanobenzo[b]thiophene (4.15 g, 26.1 mmol) from Step C above in tetrahydrofuran (50 mL) dropwise and the reaction mixture was stirred at room temperature for 16 hours. The reaction solution was then added slowly to aqueous saturated ammonium chloride while stirring. The resultant mixture was then extracted with ethyl acetate twice. The combined organic extract was washed with water and brine, dried over sodium sulfate and concentrated under reduced pressure. The crude product obtained was purified by flash column chromatography (94:6 hexanes/ethyl acetate) to give the partially purified product (5.9 g, crude), which was used in the next step without further purification: ¹H NMR (CDCl₃, 500 MHz) δ 8.37 (d, J=5.5 Hz, 1H), 8.08 (d, J=8.1 Hz, 1H), 7.96 (d, J=7.5 Hz, 1H), 7.65 (d, J=5.6 Hz, 1H), 7.43 (t, J=7.7 Hz, 1H), 2.73 (s, 3H).

Step E: To a solution of the methylketone (5.9 g, 24 mmol) from Step D above in chloroform (100 mL) was added pyridinium bromide perbromide (8.0 g, 24 mmol) in two batches. The reaction solution was stirred at room temperature for 2 hours, and then was washed with water, aqueous HCl (2 M), water and brine. The resultant solution was dried over sodium sulfate and concentrated under reduced pressure to give the desired bromoketone (6.4 g, crude), which was used in the next step without purification: ¹H NMR (CDCl₃, 500 MHz) δ 8.34 (dd, J=5.5, 0.6 Hz, 1H), 8.13 (d, J=8.0 Hz, 1H), 7.97 (dd, J=7.6, 0.8 Hz, 1H), 7.70 (d, J=5.6 Hz, 1H), 7.45 (t, J=7.8 Hz, 1H), 4.59 (s, 2H).

Step F: To a solution of 3-methoxybenzyl methylamine (4.4 g, 29 mmol) in dichloromethane (150 mL) were added triethylamine (10 mL) and the bromoketone (6.4 g, 24 mmol) from Step E above. The reaction solution was stirred at room temperature for 18 hours, and then was quenched with aqueous saturated sodium bicarbonate (100 mL). The organic extract was separated, washed with water and brine, dried over sodium sulfate and concentrated under reduced pressure. The crude product obtained was purified by flash column chromatography (86:14 hexanes/ethyl acetate) to give the desired product (3.9 g, 46% over 3 steps) as a light yellow oil: ¹H NMR (CDCl₃, 500 MHz) δ 8.29 (d, J=5.6 Hz, 1H), 8.06 (d, J=8.1 Hz, 1H), 7.95 (d, J=7.5 Hz, 1H), 7.63 (d, J=5.6 Hz, 1H), 7.37 (t, J=7.8 Hz, 1H), 7.22 (t, J=7.7 Hz, 1H), 6.93-6.90 (m, 2H), 6.80 (dd, J=7.7, 2.5 Hz, 1H), 3.88 (s, 2H), 3.77 (s, 3H), 3.69 (s, 2H), 2.42 (s, 3H).

Step G: To a solution of the ketone (3.9 g, 12 mmol) from Step F above in methanol (80 mL) at 0° C. was added sodium borohydride (0.5 g, 13 mmol) in small portions. The reaction solution was stirred at 0° C. for 2 hours, and then the solvent was removed under reduced pressure. The residue obtained was dissolved in dichloromethane, washed with aqueous saturated sodium bicarbonate and brine. The organic extract was dried over sodium sulfate and concentrated under reduced pressure to give the desired alcohol (6.9 g, 96% crude) as a yellow oil, which was used in the next step without further purification: ¹H NMR (CDCl₃, 500 MHz) δ 7.80 (d, J=8.1 Hz, 1H), 7.46 (d, J=7.2 Hz, 1H), 7.41 (d, J=5.6 Hz, 1H), 7.37 (d, J=5.6 Hz, 1H), 7.33 (t, J=7.7 Hz, 1H), 7.27 (t, J=7.8 Hz, 1H), 6.93 (d, J=7.6 Hz, 1H), 6.90 (br s, 1H), 6.84 (dd, J=8.2, 2.5 Hz, 1H), 5.20 (dd, J=10.6, 3.3 Hz, 1H), 4.44-4.03 (m, 1H), 3.82 (s, 3H), 3.76 (d, J=13.0 Hz, 1H), 3.52 (d, J=13.0 Hz, 1H), 2.77 (dd, J=12.6, 11.2 Hz, 1H), 2.64 (dd, J=12.6, 3.4 Hz, 1H), 2.42 (s, 3H); ESI-MS m/z 328 [M+H]⁺.

Step H: To a solution of the alcohol (3.9 g, 12 mmol) from Step G above in dichloromethane (150 mL) were added phosphorus pentoxide (2 g) and methanesulfonic acid (1.6 mL, 24 mmol) dropwise at room temperature. After stirring for 2 hours, a solution of additional methanesulfonic acid (1.6 mL, 24 mmol) in dichloromethane (3 mL) was added to it. After the addition, the reaction solution was stirred at room temperature for 1 hour, and then the organic layer was separated and washed with aqueous saturated sodium bicarbonate, water and brine. The resultant organic extract was dried over sodium sulfate and concentrated under reduced pressure. The crude product obtained was purified by flash column chromatography (95:5 to 50:50 hexanes/ethyl acetate) to give the desired product (1.4 g, 38%) as a yellow oil: ¹H NMR (CDCl₃, 500 MHz) δ 7.77 (d, J=8.1 Hz, 1H), 7.39 (d, J=5.5 Hz, 1H), 7.28-7.25 (m, 2H), 7.10 (d, J=7.2 Hz, 1H), 6.76 (d, J=8.5 Hz, 1H), 6.66 (d, J=2.5 Hz, 1H), 6.62 (dd, J=8.5, 2.6 Hz, 1H), 4.79-4.76 (m, 1H), 3.81 (d, J=15.3 Hz, 1H), 3.78 (s, 3H), 3.64 (d, J=15.0 Hz, 1H), 3.13-3.08 (m, 1H), 2.68 (dd, J=11.5, 8.2 Hz, 1H), 2.43 (s, 3H); ESI-MS m/z 310 [M+H]⁺.

Step I: To a solution of the 7-methoxy tetrahydroisoquinoline (1.4 g, 4.5 mmol) from Step H above in acetic acid (25 mL) was added 48% aqueous hydrogen bromide (25 mL). The resultant mixture was heated at 100° C. for 20 hours, and then cooled to room temperature and concentrated under reduced pressure. The residue obtained was dissolved in dichloromethane and quenched carefully with aqueous saturated sodium bicarbonate until pH>8. The organic extract was separated, washed with water and brine, dried over sodium sulfate and concentrated under reduced pressure to give the desired phenol (1.4 g, crude) as a gray foam, which was used in the next step without further purification: ¹H NMR (CDCl₃, 500 MHz) δ 7.77 (d, J=8.1 Hz, 1H), 7.38 (d, J=5.5 Hz, 1H), 7.28-7.24 (m, 2H), 7.10 (d, J=7.3 Hz, 1H), 6.70 (d, J=8.3 Hz, 1H), 6.56-6.50 (m, 2H), 4.78-4.75 (m, 1H), 3.77 (d, J=15.0 Hz, 1H), 3.60 (d, J=15.0 Hz, 1H), 3.15-3.11 (m, 1H), 2.68 (dd, J=11.5, 9.5 Hz, 1H), 2.44 (s, 3H), 1.95-1.56 (m, 1H).

Step J: To a solution of the phenol (1.4 g, 4.5 mmol) from Step I above in dichloromethane (50 mL) at 0° C. was added pyridine (0.73 mL, 9.0 mmol), followed by triflic anhydride (1.0 mL, 5.9 mmol) dropwise. The reaction solution was stirred at 0° C. for 1 hour, and then quenched with aqueous saturated sodium bicarbonate. The organic extract was separated, washed with water and brine, dried over sodium sulfate and concentrated under reduced pressure. The crude product was purified by flash column chromatography (dichloromethane to 98:2 dichloromethane/methanol) to give the desired triflate (1.6 g, 85% over two steps) as a reddish oil: ¹H NMR (CDCl₃, 500 MHz) δ 7.81 (d, J=8.1 Hz, 1H), 7.44 (d, J=5.5 Hz, 1H), 7.28-7.22 (m, 2H), 7.07-7.04 (m, 2H), 6.94 (app s, 2H), 4.83-4.80 (m, 1H), 3.86 (d, J=15.3 Hz, 1H), 3.68 (d, J=15.3 Hz, 1H), 3.16-3.11 (m, 1H), 2.72 (dd, J=11.6, 9.1 Hz, 1H), 2.46 (s, 3H); ESI-MS m/z 428 [M+H]⁺.

Step K: To a solution of the triflate (0.10 g, 0.23 mmol) from Step J above in toluene (2.5 mL) were added cesium carbonate (67 mg, 0.14 mmol), 2-(dicyclohexylphosphino)-2',4',6'-tri-i-propyl-1,1'-biphenyl (0.19 g, 0.58 mmol) and morpholine (41 μL, 0.47 mmol). The reaction mixture was purged with argon for 5 minutes, and then palladium(II) acetate (8 mg, 0.04 mmol) was added. The reaction flask was capped, heated in a microwave oven (160° C.) for 45 minutes, and then cooled to room temperature. The reaction solution was filtered through a plug of celite and concentrated. The crude product obtained was purified by flash column chromatography (dichloromethane to 97:3 dichloromethane/methanol) to give the desired product (11 mg, 13%) as a yellow oil: $^1$H NMR (CDCl$_3$, 500 MHz) δ 7.77 (d, J=8.0 Hz, 1H), 7.39 (d, J=5.4 Hz, 1H), 7.28-7.24 (m, 2H), 7.10 (d, J=7.4 Hz, 1H), 6.75 (d, J=8.1 Hz, 1H), 6.65-6.63 (m, 2H), 4.77 (br s, 1H), 3.86-3.84 (m, 4H), 3.79 (d, J=14.5 Hz, 1H), 3.64 (d, J=14.5 Hz, 1H), 3.14-3.11 (m, 5H), 2.71-2.68 (m, 1H), 2.44 (s, 3H); ESI-MS m/z 365 [M+H]$^+$.

Step L: To a solution of the 7-morpholinyl tetrahydroisoquinoline (11 mg, 0.03 mmol) from Step K above in methanol (1 mL) was added maleic acid (3.5 mg, 0.03 mmol), followed by water (5 mL). The resultant solution was lyophilized overnight to give (+/−)-4-(benzo[b]thiophen-4-yl)-2-methyl-7-(morpholin-4-yl)-1,2,3,4-tetrahydroisoquinoline, maleate salt (15 mg, 99%) as a light yellow solid: mp 103-107° C.; $^1$H NMR (CD$_3$OD, 500 MHz) δ 7.92 (d, J=8.1 Hz, 1H), 7.61 (d, J=4.8 Hz, 1H), 7.36 (t, J=7.6 Hz, 1H), 7.34-7.10 (m, 2H), 6.87-6.84 (m, 2H), 6.75 (br s, 1H), 6.25 (s, 2H), 5.02-4.98 (m, 1H), 4.67-4.50 (m, 2H), 3.87 (dd, J=12.1, 6.1 Hz, 1H), 3.86-3.82 (m, 4H), 3.72-3.54 (m, 1H), 3.16-3.13 (m, 4H), 3.08 (s, 3H); ESI-MS m/z 365 [M+H]$^+$.

Example 81

Preparation of (+/−)-4-(benzo[b]thiophen-4-yl)-2-methyl-7-(pyridazin-3-yl)-1,2,3,4-tetrahydroisoquinoline, maleate salt Step A: To a solution of the 3-bromothiophenol (14.8 g, 78 mmol) in N,N-dimethylformamide (270 mL) at 0° C. was added sodium hydride (3.6 g, 90 mmol) in batches. After the addition, the reaction solution was stirred at room temperature for 30 minutes, and bromoacetaldehyde dimethyl acetal (9.7 mL, 82 mmol) was added to it. The reaction mixture was stirred at room temperature for 2 hours. The resultant solution was diluted with ethyl acetate, washed with water and brine, dried over sodium sulfate and concentrated under reduced pressure. The crude product was purified by flash column chromatography (hexanes to 95:5 hexanes/ethyl acetate) to give the desired product (20.6 g, 95%) as a light yellow oil: $^1$H NMR (CDCl$_3$, 500 MHz) δ 7.51 (t, J=1.8 Hz, 1H), 7.32-7.28 (m, 2H), 7.14 (t, J=7.9 Hz, 1H), 4.53 (t, J=5.5 Hz, 1H), 3.38 (s, 6H), 3.11 (d, J=5.5 Hz, 2H).

Step B: To a solution of polyphosphoric acid (90 g) in chlorobenzene (250 mL) under reflux was added a solution of the thiophenol acetal (27.6 g, 99.6 mmol) from Step A above in chlorobenzene (120 mL) dropwise. After the addition, the reaction solution was heated under reflux for 2 hours and then cooled to room temperature. The top layer was separated; the bottom layer was diluted with water and then extracted with dichloromethane twice. The combined organic extract was washed with water and aqueous saturated sodium bicarbonate and dried concentrated under reduced pressure. The crude product was purified by flash column chromatography (hexanes) to give a 1:1 mixture of 4-bromobenzo[b]thiophene and 6-bromobenzo[b]thiophene (15.5 g, 73%), which was used in the next step without further purification or characterization.

Step C: To a solution of the isomeric bromobenzo[b]thiophene (14.2 g, 66.5 mmol) from Step B above in N,N-dimethylformamide (130 mL) were added pyridine (7.5 mL) and copper(I) cyanide (7.75 g). The reaction mixture was heated under reflux for 20 hours. The reaction solution was then cooled to 60° C. and poured into a solution of ethylene diamine in water. The resultant mixture was stirred for 30 minutes and extracted with diethyl ether and ethyl acetate. The combined organic extract was washed with 1:1 brine/water, dried over sodium sulfate and concentrated under reduced pressure. The crude product obtained was purified by flash column chromatography (95:5 to 91:9 hexanes/ethyl acetate) to give 4-cyanobenzo[b]thiophene (4.15 g, 39%) as a light yellow solid, and 6-cyanobenzo[b]thiophene (4.34 g, 41%) as a reddish oil: $^1$H NMR for 4-cyanobenzo[b]thiophene (CDCl$_3$, 500 MHz) δ 8.10 (d, J=8.2 Hz, 1H), 7.74-7.70 (m, 2H), 7.62 (dd, J=5.5, 0.6 Hz, 1H), 7.43 (d, J=7.8 Hz, 1H); $^1$H NMR for 6-cyanobenzo[b]thiophene (CDCl$_3$, 500 MHz) δ 8.22 (app s, 1H), 7.90 (d, J=8.3 Hz, 1H), 7.72 (d, J=5.4 Hz, 1H), 7.59 (d, J=8.3 Hz, 1H), 7.42 (dd, J=5.4, 0.5 Hz, 1H).

Step D: To a reaction flask equipped with mechanical stirrer under argon were added copper(I) bromide (0.19 g, 1.3 mmol) and methylmagnesium bromide (26 mL, 78 mmol, 3 M in diethyl ether) at −78° C. To the resultant slurry was then added a solution of the 4-cyanobenzo[b]thiophene (4.15 g, 26.1 mmol) from Step C above in tetrahydrofuran (50 mL) dropwise and the reaction mixture was stirred at room temperature for 16 hours. The reaction solution was then added slowly to aqueous saturated ammonium chloride while stirring. The resultant mixture was then extracted with ethyl acetate twice. The combined organic extract was washed with water and brine, dried over sodium sulfate and concentrated under reduced pressure. The crude product obtained was purified by flash column chromatography (94:6 hexanes/ethyl acetate) to give the partially purified product (5.9 g, crude), which was used in the next step without further purification: $^1$H NMR (CDCl$_3$, 500 MHz) δ 8.37 (d, J=5.5 Hz, 1H), 8.08 (d, J=8.1 Hz, 1H), 7.96 (d, J=7.5 Hz, 1H), 7.65 (d, J=5.6 Hz, 1H), 7.43 (t, J=7.7 Hz, 1H), 2.73 (s, 3H).

Step E: To a solution of the methylketone (5.9 g, 24 mmol) from Step D above in chloroform (100 mL) was added pyridinium bromide perbromide (8.0 g, 24 mmol) in two batches. The reaction solution was stirred at room temperature for 2 hours, and then was washed with water, aqueous HCl (2 M), water and brine. The resultant solution was dried over sodium sulfate and concentrated under reduced pressure to give the desired bromoketone (6.4 g, crude), which was used in the next step without purification: $^1$H NMR (CDCl$_3$, 500 MHz) δ 8.34 (dd, J=5.5, 0.6 Hz, 1H), 8.13 (d, J=8.0 Hz, 1H), 7.97 (dd, J=7.6, 0.8 Hz, 1H), 7.70 (d, J=5.6 Hz, 1H), 7.45 (t, J=7.8 Hz, 1H), 4.59 (s, 2H).

Step F: To a solution of 3-methoxybenzyl methylamine (4.4 g, 29 mmol) in dichloromethane (150 mL) were added triethylamine (10 mL) and the bromoketone (6.4 g, 24 mmol) from Step E above. The reaction solution was stirred at room temperature for 18 hours, and then was quenched with aqueous saturated sodium bicarbonate (100 mL). The organic extract was separated, washed with water and brine, dried over sodium sulfate and concentrated under reduced pressure. The crude product obtained was purified by flash column chromatography (86:14 hexanes/ethyl acetate) to give the desired product (3.9 g, 46% over 3 steps) as a light yellow oil: $^1$H NMR (CDCl$_3$, 500 MHz) δ 8.29 (d, J=5.6 Hz, 1H), 8.06 (d, J=8.1 Hz, 1H), 7.95 (d, J=7.5 Hz, 1H), 7.63 (d, J=5.6 Hz, 1H), 7.37 (t, J=7.8 Hz, 1H), 7.22 (t, J=7.7 Hz, 1H), 6.93-6.90 (m, 2H), 6.80 (dd, J=7.7, 2.5 Hz, 1H), 3.88 (s, 2H), 3.77 (s, 3H), 3.69 (s, 2H), 2.42 (s, 3H).

Step G: To a solution of the ketone (3.9 g, 12 mmol) from Step F above in methanol (80 mL) at 0° C. was added sodium borohydride (0.5 g, 13 mmol) in small portions. The reaction solution was stirred at 0° C. for 2 hours, and then the solvent was removed under reduced pressure. The residue obtained was dissolved in dichloromethan, washed with aqueous saturated sodium bicarbonate and brine. The organic extract was dried over sodium sulfate and concentrated under reduced pressure to give the desired alcohol (6.9 g, 96% crude) as a yellow oil, which was used in the next step without further purification: $^1$H NMR (CDCl$_3$, 500 MHz) δ 7.80 (d, J=8.1 Hz, 1H), 7.46 (d, J=7.2 Hz, 1H), 7.41 (d, J=5.6 Hz, 1H), 7.37 (d, J=5.6 Hz, 1H), 7.33 (t, J=7.7 Hz, 1H), 7.27 (t, J=7.8 Hz, 1H), 6.93 (d, J=7.6 Hz, 1H), 6.90 (br s, 1H), 6.84 (dd, J=8.2, 2.5 Hz, 1H), 5.20 (dd, J=10.6, 3.3 Hz, 1H), 4.44-4.03 (m, 1H), 3.82 (s, 3H), 3.76 (d, J=13.0 Hz, 1H), 3.52 (d, J=13.0 Hz, 1H), 2.77 (dd, J=12.6, 11.2 Hz, 1H), 2.64 (dd, J=12.6, 3.4 Hz, 1H), 2.42 (s, 3H); ESI-MS m/z 328 [M+H]$^+$.

Step H: To a solution of the alcohol (3.9 g, 12 mmol) from Step G above in dichloromethane (150 mL) were added phosphorus pentoxide (2 g) and methanesulfonic acid (1.6 mL, 24 mmol) dropwise at room temperature. After stirring for 2 hours, a solution of additional methanesulfonic acid (1.6 mL, 24 mmol) in dichloromethane (3 mL) was added. After the addition, the reaction solution was stirred at room temperature for 1 hour, and then the organic layer was separated and washed with aqueous saturated sodium bicarbonate, water and brine. The resultant organic extract was dried over sodium sulfate and concentrated under reduced pressure. The crude product obtained was purified by flash column chromatography (95:5 to 50:50 hexanes/ethyl acetate) to give the desired product (1.4 g, 38%) as a yellow oil: $^1$H NMR (CDCl$_3$, 500 MHz) δ 7.77 (d, J=8.1 Hz, 1H), 7.39 (d, J=5.5 Hz, 1H), 7.28-7.25 (m, 2H), 7.10 (d, J=7.2 Hz, 1H), 6.76 (d, J=8.5 Hz, 1H), 6.66 (d, J=2.5 Hz, 1H), 6.62 (dd, J=8.5, 2.6 Hz, 1H), 4.79-4.76 (m, 1H), 3.81 (d, J=15.3 Hz, 1H), 3.78 (s, 3H), 3.64 (d, J=15.0 Hz, 1H), 3.13-3.08 (m, 1H), 2.68 (dd, J=11.5, 8.2 Hz, 1H), 2.43 (s, 3H); ESI-MS m/z 310 [M+H]$^+$.

Step I: To a solution of the 7-methoxy tetrahydroisoquinoline (1.4 g, 4.5 mmol) from Step H above in acetic acid (25 mL) was added 48% aqueous hydrogen bromide (25 mL). The resultant mixture was heated at 100° C. for 20 hours, and then cooled to room temperature and concentrated under reduced pressure. The residue obtained was dissolved in dichloromethane and quenched carefully with aqueous saturated sodium bicarbonate until pH>8. The organic extract was separated, washed with water and brine, dried over sodium sulfate and concentrated under reduced pressure to give the desired phenol (1.4 g, crude) as a gray foam, which was used in the next step without further purification: $^1$H NMR (CDCl$_3$, 500 MHz) δ 7.77 (d, J=8.1 Hz, 1H), 7.38 (d, J=5.5 Hz, 1H), 7.28-7.24 (m, 2H), 7.10 (d, J=7.3 Hz, 1H), 6.70 (d, J=8.3 Hz, 1H), 6.56-6.50 (m, 2H), 4.78-4.75 (m, 1H), 3.77 (d, J=15.0 Hz, 1H), 3.60 (d, J=15.0 Hz, 1H), 3.15-3.11 (m, 1H), 2.68 (dd, J=11.5, 9.5 Hz, 1H), 2.44 (s, 3H), 1.95-1.56 (m, 1H).

Step J: To a solution of the phenol (1.4 g, 4.5 mmol) from Step I above in dichloromethane (50 mL) at 0° C. was added pyridine (0.73 mL, 9.0 mmol), followed by triflic anhydride (1.0 mL, 5.9 mmol) dropwise. The reaction solution was stirred at 0° C. for 1 hour, and then quenched with aqueous saturated sodium bicarbonate. The organic extract was separated, washed with water and brine, dried over sodium sulfate and concentrated under reduced pressure. The crude product was purified by flash column chromatography (dichloromethane to 98:2 dichloromethane/methanol) to give the desired triflate (1.6 g, 85% over two steps) as a reddish oil: $^1$H NMR (CDCl$_3$, 500 MHz) δ 7.81 (d, J=8.1 Hz, 1H), 7.44 (d, J=5.5 Hz, 1H), 7.28-7.22 (m, 2H), 7.07-7.04 (m, 2 H), 6.94 (app s, 2H), 4.83-4.80 (m, 1H), 3.86 (d, J=15.3 Hz, 1H), 3.68 (d, J=15.3 Hz, 1H), 3.16-3.11 (m, 1H), 2.72 (dd, J=11.6, 9.1 Hz, 1H), 2.46 (s, 3H); ESI-MS m/z 428 [M+H]$^+$.

Step K: To a solution of the triflate (1.4 g, 3.3 mmol) from Step J above in dimethyl sulfoxide (22 mL) were added bis(pinacolato)diboron (0.91 g, 3.6 mmol) and potassium acetate (0.98 g, 10 mmol). The reaction solution was purged with argon for 10 minutes, and then 1,1'-bis(diphenylphosphino)ferrocenedichloropalladium (81 mg, 0.10 mmol) was added to it. The reaction solution was degassed with argon for 5 minutes, heated at 80° C. for 1 hour, and then cooled to room temperature. The resultant reaction solution was diluted with ethyl acetate, washed with water and brine, dried over sodium sulfate and concentrated under reduced pressure. The crude product obtained was purified by flash column chromatography (dichloromethane to 95:5 dichloromethane/methanol) to give the desired product (1.4 g, crude), which was used in the next step without further purification: $^1$H NMR (CDCl$_3$, 500 MHz) δ 7.78 (d, J=8.1 Hz, 1H), 7.59 (s, 1H), 7.47 (d, J=7.7 Hz, 1H), 7.38 (d, J=5.4 Hz, 1H), 7.27-7.24 (m, 2H), 7.08 (d, J=7.2 Hz, 1H), 6.87 (d, J=7.7 Hz, 1H), 4.85 (t, J=7.1 Hz, 1H), 3.88 (d, J=14.7 Hz, 1H), 3.67 (d, J=14.9 Hz, 1H), 3.14 (dd, J=11.7, 6.1 Hz, 1H), 2.70 (dd, J=11.4, 9.4 Hz, 1H), 2.44 (s, 3H), 1.34 (s, 12H).

Step L: To a reaction flask with the boronate ester (1.4 g, crude) from Step K above, 3,6-dichloropyridazine (0.98 g, 6.6 mmol) and sodium carbonate (1.08 g, 10 mmol) were added N,N-dimethylformamide (30 mL) and water (7.6 mL). The resultant solution was purged with argon for 10 minutes, and then 1,1'-bis(diphenylphosphino)ferrocenedichloropalladium (0.14 g, 0.17 mmol) was added. The reaction solution was degassed again with argon for 5 minutes, heated at 80° C. for 2 hours, and then cooled to room temperature. The resultant solution was diluted with ethyl acetate, washed with water and brine, dried over sodium sulfate and concentrated under reduced pressure. The crude product was purified using the Biotage MPLC system (99:1 to 95:5 dichloromethane/methanol) to give the partially purified product (0.97 g, 75%) as a pink foam, which was used in the next step without further purification: $^1$H NMR (CDCl$_3$, 500 MHz) δ 7.94 (d, J=1.4 Hz, 1H), 7.80 (t, J=8.2 Hz, 2H), 7.64 (dd, J=8.1, 1.7 Hz, 1H), 7.54 (d, J=9.0 Hz, 1H), 7.41 (d, J=5.3 Hz, 1H), 7.31-7.26 (m, 2H), 7.14 (d, J=7.1 Hz, 1H), 7.01 (d, J=8.1 Hz, 1H), 4.89 (t, J=7.8 Hz, 1H), 3.97 (d, J=15.0 Hz, 1H), 3.75 (d, J=15.0 Hz, 1H), 3.20-3.16 (m, 1H), 2.76 (dd, J=11.6, 8.2 Hz, 1H), 2.49 (s, 3H); ESI-MS m/z 392 [M+H]$^+$.

Step M: To a solution of chloropyridazine (0.55 g, 1.4 mmol) from Step L above in a mixture of ethanol (30 mL) and methanol (30 mL) was added hydrozine (1.4 mL, 28 mmol) and palladium on carbon (0.11 g). The reaction solution was heated under reflux for 16 hours, then cooled to room temperature, filtered through a plug of celite and concentrated under reduced pressure. The crude product was purified by flash column chromatography (dichloromethane to 97:3 dichloromethane/methanol) to give the desired product (0.28 g, 54%) as a light yellow foam: $^1$H NMR (CDCl$_3$, 500 MHz) δ 9.14 (dd, J=4.9, 1.6 Hz, 1H), 7.99 (d, J=1.4 Hz, 1H), 7.82 (td, J=8.6, 1.6 Hz, 2H), 7.67 (dd, J=8.1, 1.7 Hz, 1H), 7.51 (dd, J=8.1, 4.8 Hz, 1H), 7.41 (d, J=5.4 Hz, 1H), 7.29 (t, J=7.8 Hz, 2H), 7.15 (d, J=7.0 Hz, 1H), 7.02 (d, J=8.1 Hz, 1H), 4.90 (t, J=6.9 Hz, 1H), 3.98 (d, J=15.0 Hz, 1H), 3.76 (d, J=14.9 Hz, 1H), 3.18 (dd, J=11.6, 6.0 Hz, 1H), 2.76 (dd, J=11.5, 9.2 Hz, 1H), 2.49 (s, 3H); ESI-MS m/z 358 [M+H]$^+$.

Step N: To a solution of the 7-pyridazinyl tetrahydroisoquinoline (0.28 g, 0.71 mmol) from Step M above in methanol (3 mL) was added maleic acid (84 mg, 0.71 mmol), followed by slow addition of water (15 mL). The resultant solution was lyophilized overnight to give (+/−)-4-(benzo[b]thiophen-4-yl)-2-methyl-7-(pyridazin-3-yl)-1,2,3,4-tetrahydroisoquinoline, maleate salt (0.32 g, 95%) as a light yellow solid: mp 94-97° C.; $^1$H NMR (CD$_3$OD, 500 MHz) δ 9.17 (dd, J=4.9, 1.5 Hz, 1H), 8.18 (dd, J=8.7, 1.5 Hz, 1H), 8.14 (d, J=1.2 Hz, 1H), 7.97 (d, J=8.1 Hz, 1H), 7.91 (dd, J=8.2, 1.4 Hz, 1H), 7.81 (dd, J=8.7, 5.0 Hz, 1H), 7.65 (d, J=5.6 Hz, 1H), 7.40 (t, J=7.7 Hz, 1H), 7.31-7.23 (m, 2H), 7.08 (d, J=8.3 Hz, 1H), 6.25 (s, 2H), 5.19 (dd, J=11.3, 6.6 Hz, 1H), 4.79 (app s, 2H), 3.97 (dd, J=12.4, 6.3 Hz, 1H), 3.76 (t, J=12.0 Hz, 1H), 3.14 (s, 3H); ESI-MS m/z 358 [M+H]$^+$.

Example 82

Preparation of (+)-4-(4-methoxy-benzo[b]thiophen-5-yl)-2-methyl-1,2,3,4-tetrahydroisoquinoline, fumarate salt and (−)-4-(4-methoxy-benzo[b]thiophen-5-yl)-2-methyl-1,2,3,4-tetrahydroisoquinoline, fumarate salt Step A: 5-Bromo-4-methoxy-benzothiophene was prepared by following the procedures described in literature (Chenard et al., *J. Org. Chem.*, 48:4312-4317 (1983), which is hereby incorporated by reference in its entirety). A mixture of 5-bromo-4-methoxy-benzothiophene (2.43 g, 10 mmol), isoquinolin-4-boronic acid (2.08 g, 12 mmol) and cesium carbonate (9.77 g, 30 mmol) in 1,2-dimethoxyethane (50 mL) and water (10 mL) was degassed with argon. Pd(PPh$_3$)$_4$ (693 mg, 0.6 mmol) was added and the reaction mixture was heated at reflux for 15 hours. The cooled reaction mixture was diluted with water and extracted with ethyl acetate twice. The combined organic extracts were washed with brine, dried over anhydrous sodium sulfate and concentrated. Purification by column chromatography (silica gel, 10% to 50% ethyl acetate/hexanes) gave the desired product (2.02 g, 69%): $^1$H NMR (CDCl$_3$, 500 MHz) δ 9.31 (s, 1H), 9.27 (s, 1H), 8.07-8.05 (m, 1H), 7.75 (d, J=8.2 Hz, 1H), 7.70-7.62 (m, 3H), 7.56 (d, J=5.4 Hz, 1H), 7.50 (d, J=5.5 Hz, 1H), 7.31 (d, J=8.2 Hz, 1H), 3.52 (s, 3H); ESI-MS m/z=292 [M+H]$^+$.

Step B: To an ice-cooled solution of the product from Step A (1.0 g, 3.43 mmol) in dichloromethane (15 mL) was added methyl triflate (676 mg, 4.12 mmol). The reaction mixture was stirred at 0° C. for 0.5 hour. The solvent was then removed under the reduced pressure to provide the desired product (1.6 g, >99% crude yield): ESI MS m/z=306 [M]$^+$. This crude product was used in the next step without further purification.

Step C: To a solution of the crude product from Step B (1.6 g, 3.43 mmol) in methanol (50 mL) was added sodium cyanoborohydride (260 mg, 4.12 mmol). The reaction mixture was stirred at room temperature for 0.5 hour. The solvent was removed under reduced pressure. The residue was diluted with water and extracted with ethyl acetate twice. The combined extracts were washed with brine, dried over sodium sulfate and concentrated. Purification by column chromatography (silica gel, 10% to 50% ethyl acetate/hexanes) provided the desired product (700 mg, 66% for 2 steps): $^1$H NMR (CDCl$_3$, 500 MHz) δ 7.51 (d, J=8.6 Hz, 1H), 7.47 (dd, J=5.6, 0.6 Hz, 1H), 7.42 (d, J=5.6 Hz, 1H), 7.13-7.09 (m, 2H), 7.06-7.04 (m, 1H), 6.99 (d, J=8.4 Hz, 1H), 6.84 (d, J=7.7 Hz, 1H), 4.90-4.89 (m, 1H), 3.95 (s, 3H), 3.81 (d, J=14.8 Hz, 1H), 3.64 (d, J=14.8 Hz, 1H), 3.09-3.06 (m, 1H), 2.60 (dd, J=11.4, 9.0 Hz, 1H), 2.45 (s, 3H); ESI MS m/z=310 [M+H]$^+$. This material was resolved by preparative chiral HPLC (CHIRALPAK AD column, using 99:1:0.1 heptane/IPA/diethyl amine as the eluent) to give the (+)-enantiomer [[α]$^{25}_D$ +66.4° (c 0.1, methanol)](323 mg, 98.6% AUC HPLC) and the (−)-enantiomer [[α]$^{25}_D$ −36.0° (c 0.1, methanol)](346 mg, >99% AUC HPLC).

Step D: To a solution of the (+)-enantiomer from Step C (103 mg, 0.333 mmol) in methanol (2 mL) was added fumaric acid (39 mg, 0.333 mmol). The solvent was removed under reduced pressure. The residue was triturated with ethyl acetate and diethyl ether. The resulting precipitate was collected by filtration, washed with diethyl ether, and dried at 50° C. under vacuum to provide (+)-4-(4-methoxy-benzo[b]thiophen-5-yl)-2-methyl-1,2,3,4-tetrahydroisoquinoline, fumarate salt as a white solid (85 mg, 60%, >99% AUC HPLC): mp 97-99° C.; $^1$H NMR (CD$_3$OD, 500 MHz) δ 7.70-7.57 (m, 2H), 7.50 (d, J=5.5 Hz, 1H), 7.29-7.26 (m, 2H), 7.22-7.15 (m, 1H), 7.08 (d, J=8.3 Hz, 1H), 6.89 (d, J=7.7 Hz, 1H), 6.69 (s, 2H), 5.02-4.99 (m, 1H), 4.48 (d, J=15.0 Hz, 1H), 4.42 (d, J=15.0 Hz, 1H), 3.77 (s, 3H), 3.72-3.65 (m, 1H), 3.52-3.46 (m, 1H), 2.98 (s, 3H); ESI MS m/z=310 [M+H]$^+$.

Step E: To a solution of the (−)-enantiomer from Step C (106 mg, 0.342 mmol) in methanol (2 mL) was added fumaric acid (40 mg, 0.342 mmol). The solvent was removed under reduced pressure. The residue was triturated with ethyl acetate and diethyl ether. The resulting precipitate was collected by filtration, washed with diethyl ether, and dried at 50° C. under vacuum to provide (−)-4-(4-methoxy-benzo[b]thiophen-5-yl)-2-methyl-1,2,3,4-tetrahydroisoquinoline, fumarate salt as a white solid (70 mg, 48%, >99% AUC HPLC): mp 94-96° C.; $^1$H NMR (CD$_3$OD, 500 MHz) δ 7.66-7.61 (m, 2H), 7.50 (d, J=5.5 Hz, 1H), 7.26 (d, J=4.0 Hz, 2H), 7.22-7.18 (m, 1H), 7.08 (d, J=8.3 Hz, 1H), 6.89 (d, J=7.6 Hz, 1H), 6.68 (s, 2H), 4.67 (dd, J=9.9, 6.1 Hz, 1H), 4.49 (d, J=15.1 Hz, 1H), 4.43 (d, J=15.1 Hz, 1H), 3.76 (s, 3H), 3.72-3.68 (m, 1H), 3.53-3.46 (m, 1H), 2.98 (s, 3H); ESI MS m/z=310 [M+H]$^+$.

Example 83

Preparation of (+)-4-(4-methoxy-benzo[b]thiophen-5-yl)-2-methyl-7-(pyridazin-3-yl)-1,2,3,4-tetrahydroisoquinoline, maleate salt Step A: Bis(pinacolato)diboron (217 mg, 0.854 mmol) was added to a mixture of the crude product from Step A of the Example 85 (390 mg, 0.776 mmol) and potassium acetate (229 mg, 2.33 mmol) in dimethyl sulfoxide (5 mL). The reaction mixture was degassed with argon. PdCl$_2$(dppf) (34 mg, 0.047 mmol) was added and the reaction mixture was stirred at 80° C. for 2 hours, cooled, diluted with water and extracted with ethyl acetate twice. The combined organic extracts were washed with brine, dried over anhydrous sodium sulfate and concentrated to give the desired boronate (546 mg, >99% crude yield). ESI MS m/z=436 [M+H]$^+$. This crude product was used in the next step without further purification.

Step B: 3,6-Dichloropyridazine (180 mg, 1.17 mmol) was added to a mixture of the crude product from Step A (546 mg, 0.776 mmol) and sodium carbonate (2M, 1.2 mL, 2.4 mmol) in dimethyl formamide (6 mL). The reaction mixture was degassed with argon. PdCl$_2$(dppf) (34 mg, 0.047 mmol) was added and the reaction mixture was stirred at 100° C. for 1.5 hours, cooled, diluted with water and extracted with ethyl acetate twice. The combined organic extracts were washed with brine, dried over anhydrous sodium sulfate and concentrated. Purification by column chromatography (silica gel, 2% to 8% MeOH/CH$_2$Cl$_2$ gave the desired product (177 mg, 54% for 3 steps): $^1$H NMR (CDCl$_3$, 500 MHz) δ 7.88 (d, J=1.2 Hz, 1H), 7.78 (d, J=9.0 Hz, 1H), 7.66 (dd, J=8.1, 1.7 Hz, 1H), 7.55-7.52 (m, 2H), 7.49 (d, J=5.5 Hz, 1H), 7.44 (d, J=5.5 Hz, 1H), 7.01 (d, J=8.3 Hz, 2H), 4.96-4.92 (m, 1H), 3.97 (s, 3H), 3.92 (d, J=15.0 Hz, 1H), 3.73 (d, J=15.0 Hz, 1H), 3.14-3.10 (m, 1H), 2.65 (dd, J=11.4, 9.0 Hz, 1H), 2.49 (s, 3H); ESI MS m/z=422 [M+H]$^+$.

Step C: To a solution of the product from Step B (177 mg, 0.419 mmol) in ethanol (10 mL) was added hydrazine (210 mg, 4.19 mmol) and 10% Pd/C (80 mg). The reaction mixture was heated at reflux for 4 h. The mixture was then filtered through celite and the celite pad was washed with methanol. The filtrate was concentrated and purified by column chromatography (silica gel, 3% to 5% MeOH/CH$_2$Cl$_2$ to provide the desired product (100 mg, 62%): $^1$H NMR (CDCl$_3$, 300 MHz) δ 9.13 (dd, J=4.9, 1.5 Hz, 1H), 7.94 (d, J=1.5 Hz, 1H), 7.82 (dd, J=8.6, 1.6 Hz, 1H), 7.70 (dd, J=8.1, 1.8 Hz, 1H), 7.55-7.48 (m, 3H), 7.44 (d, J=5.5 Hz, 1H), 7.03-7.00 (m, 2H), 4.95 (dd, J=8.1, 6.5 Hz, 1H), 3.97 (s, 3H), 3.94 (d, J=15.1 Hz, 1H), 3.73 (d, J=15.1 Hz, 1H), 3.16-3.09 (m, 1H), 2.65 (dd, J=11.4, 9.0 Hz, 1H), 2.49 (s, 3H); ESI-MS m/z=388 [M+H]$^+$.

Step D: To a solution of the product from Step C (92 mg, 0.237 mmol) in methanol (3 mL) was added maleic acid (27 mg, 0.237 mmol). The solvent was removed under reduced pressure to provide (+)-4-(4-methoxy-benzo[b]thiophen-5-yl)-2-methyl-7-(pyridazin-3-yl)-1,2,3,4-tetrahydroisoquinoline, maleate salt as an off-white solid (119 mg, 96%, >99% AUC HPLC): $^1$HNMR (CD$_3$OD, 500 MHz) δ 9.19 (dd, J=4.8, 1.3 Hz, 1H), 8.17 (dd, J=8.7, 1.4 Hz, 1H), 8.09 (s, 1H), 7.94 (dd, J=8.2, 1.4 Hz, 1H), 7.80 (dd, J=8.7, 4.9 Hz, 1H), 7.70 (d, J=8.4 Hz, 1H), 7.65 (d, J=5.6 Hz, 1H), 7.53 (d, J=5.6 Hz, 1H), 7.16-7.11 (m, 2H), 6.23 (s, 2H), 5.11-5.07 (m, 1H), 4.72 (d, J=15.2 Hz, 1H), 4.67 (d, J=15.2 Hz, 1H), 3.87-3.82 (m, 1H), 3.81 (s, 3H), 3.73-3.68 (m, 1H), 3.12 (s, 3H); ESI MS m/z=388 [M+H]$^+$; Anal. Calcd. For C$_{23}$H$_{21}$N$_3$OS.C$_4$H$_4$O$_4$.H$_2$O: C, 62.17; H, 5.22; N, 8.06. Found: C, 62.43; H, 5.09; N, 7.71.

Example 84

Preparation of (+)-4-(4-Methoxy-benzothiophen-5-yl)-2-methyl-7-(6-methyl-pyridazin-3-yl)-1,2,3,4-tetrahydroisoquinoline, maleate salt Step A: 3-Chloro-6-methyl-pyridazine (230 mg, 1.78 mmol) was added to a mixture of the crude product from Step A of Example 83 (545 g, 1.19 mmol) and sodium carbonate (2M, 1.8 mL, 3.6 mmol) in dimethyl formamide (10 mL). The reaction mixture was degassed with argon. PdCl$_2$(dppf) (52 mg, 0.071 mmol) was added and the reaction mixture was stirred at 100° C. for 3 hours, cooled, diluted with water and extracted with ethyl acetate twice. The combined organic extracts were washed with brine, dried over anhydrous sodium sulfate and concentrated. Purification by column chromatography (silica gel, 3% to 6% MeOH/CH$_2$Cl$_2$ gave the desired product (300 mg, 63% for 3 steps): $^1$H NMR (CDCl$_3$, 500 MHz) δ 7.90 (d, J=1.3 Hz, 1H), 7.72-7.67 (m, 2H), 7.53 (d, J=8.4 Hz, 1H), 7.48 (d, J=5.5 Hz, 1H), 7.44 (d, J=5.5 Hz, 1H), 7.35 (d, J=8.7 Hz, 1H), 7.03-6.98 (m, 2H), 4.96-4.93 (m, 1H), 3.97 (s, 3H), 3.92 (d, J=14.9 Hz, 1H), 3.73 (d, J=14.9 Hz, 1H), 3.14-3.10 (m, 1H), 2.74 (s, 3H), 2.65 (dd, J=11.4, 9.0 Hz, 1H), 2.49 (s, 3H); ESI MS m/z=402 [M+H]$^+$.

Step B: To a solution of the product from Step A (102 mg, 0.254 mmol) in methanol (3 mL) was added maleic acid (29.5 mg, 0.254 mmol). The solvent was removed under reduced pressure to provide (+)-4-(4-methoxy-benzothiophen-5-yl)-2-methyl-7-(6-methyl-pyridazin-3-yl)-1,2,3,4-tetrahydroisoquinoline, maleate salt as a light brown solid (122 mg, 93%, 95.3% AUC HPLC): $^1$H NMR (CD$_3$OD, 500 MHz) δ 8.07 (s, 1H), 8.06 (d, J=8.8 Hz, 1H), 7.91 (dd, J=8.2, 1.6 Hz, 1H), 7.71-7.64 (m, 3H), 7.53 (d, J=5.5 Hz, 1H), 7.16 (d, J=8.3 Hz, 1H), 7.11 (d, J=8.2 Hz, 1H), 6.24 (s, 2H), 5.09-5.08 (m, 1H), 4.75-4.72 (m, 2H), 3.91-3.87 (m, 1H), 3.80 (s, 3H), 3.79-3.75 (m, 1H), 3.15 (s, 3H), 2.72 (s, 3H); ESI MS m/z=402 [M+H]$^+$.

Example 85

Preparation of (+)-4-(4-methoxy-benzo[b]thiophen-5-yl)-2-methyl-7-(morpholin-4-yl)-1,2,3,4-tetrahydroisoquinoline, maleate salt Step A: Triflic anhydride (416 mg, 1.74 mmol) was added to a solution of the (+)-enantiomer from Step F of the Example 87 (434 mg, 1.33 mmol) and triethylamine (202 mg, 2.0 mmol) in dichloromethane (15 mL) at 0° C. The reaction mixture was stirred at 0° C. for 0.5 hour and then diluted with water and extracted with dichloromethane twice. The combined organic extracts were washed with brine, dried over sodium sulfate and concentrated to give the desired triflate (670 mg, >99% crude yield): ESI-MS m/z=458 [M+H]$^+$. This crude product was used in the next step without further purification.

Step B: To a solution of the crude product from Step A (280 mg, 0.557 mmol) in toluene (20 mL) was added morpholine (97 mg, 1.11 mmol), cesium carbonate (544 mg, 1.67 mmol), X-Phos (159 mg, 0.334 mmol), and Pd(OAc)$_2$ (19 mg, 0.084 mmol). The reaction mixture was degassed with argon, heated at reflux for 15 hours and then allowed to cool to room temperature. The mixture was diluted with ethyl acetate and filtered through celite. The filtrate was washed with brine, dried over anhydrous sodium sulfate and concentrated. Purification by column chromatography (silica gel, 2% to 4% MeOH/CH$_2$Cl$_2$ gave the desired product (96 mg, 44% for 2 steps): [α]$^{25}_D$ +55.0° (c 0.1, methanol); $^1$H NMR (CDCl$_3$, 500 MHz) δ 7.51 (d, J=8.4 Hz, 1H), 7.47 (d, J=5.5 Hz, 1H), 7.42 (d, J=5.5 Hz, 1H), 7.00 (d, J=8.4 Hz, 1H), 6.74 (d, J=8.4 Hz, 1H), 6.66-6.63 (m, 2H), 4.83-4.80 (m, 1H), 3.96 (s, 3H), 3.84 (t, J=4.8 Hz, 4H), 3.76 (d, J=14.8 Hz, 1H), 3.61 (d, J=14.8 Hz, 1H), 3.11 (t, J=4.8 Hz, 4H), 3.06 (dd, J=11.2, 5.6 Hz, 1H), 2.57 (dd, J=11.2, 9.0 Hz, 1H), 2.44 (s, 3H); ESI-MS m/z=395 [M+H]$^+$.

Step C: To a solution of the product from Step B (86 mg, 0.218 mmol) in methanol (2 mL) was added maleic acid (25 mg, 0.218 mmol). The solvent was removed under reduced pressure to provide (+)-4-(4-methoxy-benzothiophen-5-yl)-2-methyl-7-(morpholin-4-yl)-1,2,3,4-tetrahydroisoquinoline, maleate salt as an off-white solid (111 mg, 97%, 98.7% AUC HPLC): $^1$HNMR (CD$_3$OD, 500 MHz) δ 7.67-7.62 (m, 2H), 7.51-7.50 (m, 1H), 7.08 (d, J=8.2 Hz, 1H), 6.89-6.87 (m, 1H), 6.83-6.78 (m, 2H), 6.25 (s, 2H), 4.91-4.89 (m, 1H), 4.56-4.53 (m, 2H), 3.82-3.79 (m, 8H), 3.58-3.56 (m, 1H), 3.14-3.12 (m, 4H), 3.09 (s, 3H); ESI MS m/z=395 [M+H]$^+$; Anal. Calcd. For C$_{23}$H$_{26}$N$_2$O$_2$S.C$_4$H$_4$O$_4$.0.75H$_2$O: C, 61.87; H, 6.06; N, 5.34. Found: C, 62.01; H, 5.83; N, 4.94.

Example 86

Preparation of (+/−)-4-(4-methoxy-benzo[b]thiophen-5-yl)-2-methyl-1,2,3,4-tetrahydroisoquinoline-5-ol, maleate salt Step A: To a solution of the 5-hydroxy regioisomer from Step E of the Example 87 (96 mg, 0.295 mmol) in methanol (3 mL) was added maleic acid (34.6 mg, 0.295 mmol). The solvent was removed under reduced pressure to provide (+/−)-4-(4-methoxy-benzothiophen-5-yl)-2-methyl-1,2,3,4-tetrahydroisoquinoline-5-ol, maleate salt as an off-white solid (130 mg, 99%, >99% AUC HPLC): $^1$H NMR (CD$_3$OD, 500 MHz) δ 7.57-7.47 (m, 3H), 7.22-7.19 (m, 1H), 6.85-6.74 (m, 3H), 6.21 (s, 2H), 5.01 (t, J=6.8 Hz, 1H), 4.57 (d, J=14.8 Hz, 1H), 4.43 (d, J=14.8 Hz, 1H), 3.87 (s, 3H), 3.86 (bs, 1H), 3.53 (bs, 1H), 3.01 (s, 3H); ESI MS m/z=326 [M+H]$^+$.

Example 87

Preparation of (−)-4-(4-methoxy-benzo[b]thiophen-5-yl)-2-methyl-1,2,3,4-tetrahydroisoquinoline-7-ol, maleate salt and (+)-4-(4-methoxy-benzothiophen-5-yl)-2-methyl-1,2,3,4-tetrahydroisoquinoline-7-[b]l, maleate salt Step A: 5-Bromo-4-methoxy-benzothiophene was prepared by following the procedures described in literature (Chenard et al., *J. Org. Chem.*, 48:4312-4317 (1983) which is hereby incorporated by reference in its entirety). A mixture of 5-bromo-4-methoxy-benzothiophene (9.39 g, 38.6 mmol), n-butyl vinyl ether (19.3 g, 193 mmol), potassium carbonate (6.4 g, 46.3 mmol), dppp (1.05 g, 2.55 mmol) and Pd(OAc)$_2$ (260 mg, 1.16 mmol) in DMF (100 mL) and water (10 mL) was heated at reflux for 6 h. The mixture was allowed to cool to room temperature and then 2 N HCl (150 mL) was added. The resulting mixture was stirred at room temperature for 0.5 hour and extracted with ethyl acetate three times. The combined organic extracts were washed with saturated sodium bicarbonate and brine, dried over anhydrous sodium sulfate and concentrated. Purification by column chromatography (silica gel, 5% to 15% ethyl acetate/hexanes) gave the desired product (7.06 g, 88%): $^1$H NMR (CDCl$_3$, 500 MHz) δ 7.71 (d, J=8.5 Hz, 1H), 7.64 (dd, J=8.5, 0.5 Hz, 1H), 7.54 (dd, J=5.5, 0.5 Hz, 1H), 7.47 (d, J=5.5 Hz, 1H), 4.04 (s, 3H), 2.73 (s, 3H).

Step B: To a mixture of the product from Step A (7.06 g, 34.2 mmol) in ethyl acetate (75 mL) and chloroform (60 mL) was added copper(II) bromide (15.45 g, 68.4 mmol). The reaction mixture was heated at reflux for 4 hours. The mixture was allowed to cool to room temperature and then filtered through celite. The filtrate was concentrated and purified by column chromatography (silica gel, 5% to 20% ethyl acetate/hexanes) to provide the desired product (6.37 g, 65%): $^1$H NMR (CDCl$_3$, 500 MHz) δ 7.74 (d, J=8.5 Hz, 1H), 7.67 (dd, J=8.5, 0.5 Hz, 1H), 7.56 (dd, J=5.5, 0.5 Hz, 1H), 7.51 (d, J=5.5 Hz, 1H), 4.68 (s, 2H), 4.11 (s, 3H).

Step C: To a solution of the product from Step B (4.37 g, 15.3 mmol) in dichloromethane (60 mL) was added diisopropylethylamine (2.97 g, 23.0 mmol) and N-(3-hydroxybenzyl)methylamine (2.52 g, 18.4 mmol). The reaction mixture was stirred at room temperature for 4 hours and then diluted with dichloromethane (100 mL). The mixture was washed with water and brine, dried over sodium sulfate and concentrated. Purification by column chromatography (silica gel, 1% to 4% methanol/dichloromethane) provided the desired product (3.96 g, 81%): $^1$H NMR (CDCl$_3$, 300 MHz) δ 7.62 (s, 2H), 7.48 (dd, J=10.0, 5.6 Hz, 2H), 7.15 (t, J=7.7 Hz, 1H), 6.89-6.84 (m, 2H), 6.75-6.72 (m, 1H), 3.93 (s, 2H), 3.92 (s, 3H), 3.68 (s, 2H), 2.43 (s, 3H). ESI-MS m/z=342 [M+H]$^+$.

Step D: To an ice-cooled solution of the product from Step C (3.96 g, 11.6 mmol) in methanol (60 mL) was added sodium borohydride (910 mg, 24 mmol). The reaction mixture was stirred at 0° C. for 1 hour. The solvent was removed under reduced pressure. The residue was partitioned between dichloromethane and water. The organic extracts were washed with brine, dried over sodium sulfate and concentrated to provide the desired product (3.90 g, 98% crude yield): ESI-MS m/z=344 [M+H]$^+$. This crude product was used in the next step without further purification.

Step E: To a solution of the product from Step D (3.60 g, 10.5 mmol) in dichloromethane (300 mL) was added methanesulfonic acid (7.41 g, 77.1 mmol) dropwise. The reaction mixture was stirred at room temperature for 20 minutes. The mixture was then cooled in an icebath and saturated sodium bicarbonate (250 mL) was added. The organic layer was separated and the aqueous was extracted with dichloromethane. The combined extracts were washed with brine, dried over sodium sulfate and concentrated. Purification by column chromatography (silica gel, 1% to 6% methanol/dichloromethane) provided the 5-hydroxy regioisomer (1.56 g, 46%) and the 7-hydroxy regioisomer (1.09 g, 32%). The 5-hydroxy regioisomer: $^1$H NMR (CDCl$_3$, 500 MHz) δ 7.50 (d, J=8.4 Hz, 1H), 7.46 (d, J=5.5 Hz, 1H), 7.42-7.40 (m, 2H), 7.05 (t, J=7.8 Hz, 1H), 6.70 (d, J=7.6 Hz, 1H), 6.58 (d, J=8.0 Hz, 1H), (5.60 (br s, 1H), 4.63 (t, J=4.8 Hz, 1H), 4.05 (s, 3H), 3.84 (d, J=14.9 Hz, 1H), 3.46 (d, J=14.9 Hz, 1H), 2.91 (dd, J=11.5, 5.5 Hz, 1H), 2.78 (dd, J=11.5, 4.3 Hz, 1H), 2.38 (s, 3H); ESI MS m/z=326 [M+H]$^+$. The 7-hydroxy regioisomer: $^1$H NMR (CDCl$_3$, 500 MHz) δ 7.52 (d, J=8.4 Hz, 1H), 7.45 (d, J=5.5 Hz, 1H), 7.41 (d, J=5.5 Hz, 1H), 6.99 (d, J=8.4 Hz, 1H), 6.66 (d, J=8.4 Hz, 1H), 6.52 (dd, J=8.4, 2.5 Hz, 1H), 6.43 (br s, 1H), 4.81 (dd, J=9.1, 8.1 Hz, 1H), 3.89 (s, 3H), 3.68 (d, J=14.9 Hz, 1H), 3.53 (d, J=14.9 Hz, 1H), 3.09 (dd, J=11.4, 5.9 Hz, 1H), 2.59 (dd, J=11.3, 9.7 Hz, 1H), 2.44 (s, 3H); ESI-MS m/z=326 [M+H]$^+$.

Step F: The 7-hydroxy regioisomer from Step E (1.03 g) was resolved by preparative chiral HPLC (CHIRALCEL OD column, using 80:20:0.1 heptane/IPA/diethylamine as the eluent) to give the (−)-enantiomer [[α]$^{25}_D$ −48.1° (c 0.104, methanol)](493 mg, >99% AUC HPLC) and the (+)-enantiomer [[α]$^{25}_D$ +58.3° (c 0.108, methanol)](485 mg, >99% AUC HPLC).

Step G: To a solution of the (−)-enantiomer from Step F (50 mg, 0.154 mmol) in methanol (2 mL) was added maleic acid (18 mg, 0.154 mmol). The solvent was removed under reduced pressure to provide (−)-4-(4-methoxy-benzo[b]thiophen-5-yl)-2-methyl-1,2,3,4-tetrahydroisoquinoline-7-ol, maleate salt as a white solid (65 mg, 95%, 97.5% AUC HPLC): $^1$H NMR (CD$_3$OD, 500 MHz) δ 7.67-7.61 (m, 2H), 7.50 (d, J=5.5 Hz, 1H), 7.08 (d, J=8.1 Hz, 1H), 6.73-6.68 (m, 3H), 6.25 (s, 2H), 4.92-4.90 (m, 1H), 4.53-4.51 (m, 2H), 3.80-3.78 (m, 1H), 3.79 (s, 3H), 3.63-3.61 (m, 1H), 3.08 (s, 3H); ESI-MS m/z=326 [M+H]$^+$.

Step H: To a solution of the (+)-enantiomer from Step F (50 mg, 0.154 mmol) in methanol (2 mL) was added maleic acid (18 mg, 0.154 mmol). The solvent was removed under reduced pressure to provide (+)-4-(4-methoxy-benzothiophen-5-yl)-2-methyl-1,2,3,4-tetrahydroisoquinoline-7-ol, maleate salt as a white solid (65 mg, 95%, >99% AUC HPLC): $^1$H NMR (CD$_3$OD, 500 MHz) δ 7.67-7.61 (m, 2H), 7.50 (d, J=5.5 Hz, 1H), 7.08 (d, J=8.2 Hz, 1H), 6.74-6.68 (m, 3H), 6.24 (s, 2H), 4.90-4.86 (m, 1H), 4.53-4.51 (m, 2H), 3.79 (s, 3H), 3.79-3.76 (m, 1H), 3.65-3.62 (m, 1H), 3.08 (s, 3H); ESI MS m/z=326 [M+H]$^+$.

Example 88

Preparation of (+)-5-(2-methyl-1,2,3,4-tetrahydroisoquinolin-4-yl)-benzo[b]thiophen-4-ol, fumarate salt and (−)-5-(2-methyl-1,2,3,4-tetrahydroisoquinolin-4-yl)-benzo[b]thiophen-4-ol, fumarate salt Step A: A mixture of the (+)-enantiomer from Step C of Example 82 (220 mg, 0.711 mmol) in 48% HBr (5 mL) and acetic acid (1 mL) was heated at reflux for 2 hours. The solvent and excess HBr was removed under reduced pressure. The residue was partitioned with ethyl acetate and saturated sodium bicarbonate. The aqueous layer was extracted with ethyl acetate. The combined extracts were washed with brine, dried over sodium sulfate and concentrated. Purification by column chromatography (silica gel, 20% to 50% ethyl acetate/hexanes) provided the desired phenol (100 mg, 48%, >99% AUC HPLC): $[\alpha]^{25}_D$ +220.0° (c 0.12, methanol)]; $^1$H NMR (CDCl$_3$, 500 MHz) δ 13.84 (s, 1H), 7.40 (d, J=5.5 Hz, 1H), 7.29 (d, J=8.1 Hz, 1H), 7.23 (d, J=8.1 Hz, 1H), 7.19 (d, J=5.5 Hz, 1H), 7.13-7.04 (m, 4H), 4.16 (d, J=5.1 Hz, 1H), 4.11 (dd, J=14.7, 1.2 Hz, 1H), 3.59 (d, J=14.7 Hz, 1H), 3.31 (d, J=11.9 Hz, 1H), 2.97 (dd, J=11.9, 5.3 Hz, 1H), 2.61 (s, 3H); ESI-MS m/z=296 [M+H]$^+$.

Step B: To a solution of the product from Step A (98 mg, 0.33 mmol) in methanol (3 mL) was added fumaric acid (39 mg, 0.33 mmol). The solvent was removed under reduced pressure. The residue was triturated with ethyl acetate and diethyl ether. The resulting precipitate was collected by filtration, washed with diethyl ether, and dried at 50° C. under vacuum to provide (+)-5-(2-methyl-1,2,3,4-tetrahydroisoquinolin-4-yl)-benzo[b]thiophen-4-ol, fumarate salt as a white solid (80 mg, 71%, >99% AUC HPLC): mp 213-215° C.; $^1$H NMR (CD$_3$OD, 500 MHz) δ 7.39 (d, J=5.3 Hz, 1H), 7.34-7.30 (m, 2H), 7.17-7.08 (m, 4H), 7.03 (d, J=7.7 Hz, 1H), 6.70 (s, 0.8H), 4.52-4.50 (m, 1H), 4.23 (d, J=15.0 Hz, 1H), 3.90 (d, J=11.3 Hz, 1H), 3.38-3.26 (m, 2H), 2.73 (s, 3H). ESI-MS m/z=296 [M+H]$^+$.

Step C: A mixture of the (−)-enantiomer from Step D of Example 82 (240 mg, 0.775 mmol) in 48% HBr (5 mL) and acetic acid (1 mL) was heated at reflux for 2 hours. The solvent and excess HBr was removed under reduced pressure. The residue was partitioned between ethyl acetate and saturated sodium bicarbonate. The aqueous layer was extracted with ethyl acetate. The combined extracts were washed with brine, dried over sodium sulfate and concentrated. Purification by column chromatography (silica gel, 10% to 50% ethyl acetate/hexanes) provided the desired phenol product (110 mg, 48%, >99% AUC HPLC): $[\alpha]^{25}_D$ −211.3° (c 0.12, methanol)]; $^1$H NMR (CDCl$_3$, 500 MHz) δ 13.84 (s, 1H), 7.40 (d, J=5.4 Hz, 1H), 7.30 (d, J=8.1 Hz, 1H), 7.23 (d, J=8.1 Hz, 1H), 7.19 (d, J=5.4 Hz, 1H), 7.13-7.04 (m, 4H), 4.16 (d, J=4.8 Hz, 1H), 4.11 (d, J=14.7 Hz, 1H), 3.59 (d, J=14.7 Hz, 1H), 3.31 (d, J=11.9 Hz, 1H), 2.97 (dd, J=11.9, 5.3 Hz, 1H), 2.61 (s, 3H). ESI MS m/z=296 [M+H]$^+$.

Step D: To a solution of the product from Step C (106 mg, 0.359 mmol) in methanol (3 mL) was added fumaric acid (42 mg, 0.359 mmol). The solvent was removed under reduced pressure. The residue was triturated with ethyl acetate and diethyl ether. The resulting precipitate was collected by filtration, washed with diethyl ether, and dried at 50° C. under vacuum to provide (−)-5-(2-methyl-1,2,3,4-tetrahydroisoquinolin-4-yl)-benzo[b]thiophen-4-ol, fumarate salt as a white solid (95 mg, 75%, >99% AUC HPLC): mp 214-216° C.; $^1$H NMR (CD$_3$OD, 500 MHz) δ 7.40 (d, J=5.4 Hz, 1H), 7.35-7.31 (m, 2H), 7.16-7.09 (m, 4H), 7.03 (d, J=7.7 Hz, 1H), 6.70 (s, 1H), 4.55-4.54 (m, 1H), 4.25 (d, J=14.9 Hz, 1H), 3.95-3.94 (m, 1H), 3.41-3.26 (m, 2H), 2.76 (s, 3H). ESI-MS m/z=296 [M+H]$^+$.

Example 89

Preparation of (+)-5-(2-ethyl-1,2,3,4-tetrahydroisoquinolin-4-yl)-benzo[b]thiophen-4-ol, fumarate salt and (−)-5-(2-ethyl-1,2,3,4-tetrahydroisoquinolin-4-yl)-benzo[b]thiophen-4-ol, fumarate salt Step A: A mixture of the (+)-enantiomer from Step B of Example 90 (225 mg, 0.695 mmol) in 48% HBr (5 mL) and acetic acid (1 mL) was heated at reflux for 2 hours. The solvent and excess HBr was removed under reduced pressure. The residue was partitioned between ethyl acetate and saturated sodium bicarbonate. The aqueous layer was extracted with ethyl acetate. The combined extracts were washed with brine, dried over sodium sulfate and concentrated. Purification by column chromatography (silica gel, 0% to 2% methanol/dichloromethane) provided the desired phenol (130 mg, 60%, >99% AUC HPLC): $[\alpha]^{25}_D$ +250.8° (c 0.13, methanol)]; $^1$H NMR (CDCl$_3$, 300 MHz) δ 13.84 (s, 1H), 7.41 (d, J=5.5 Hz, 1H), 7.29 (d, J=8.1 Hz, 1H), 7.25-7.17 (m, 2H), 7.11-7.06 (m, 4H), 4.22-4.16 (m, 2H), 3.57 (d, J=14.6 Hz, 1H), 3.40 (d, J=11.7 Hz, 1H), 2.93 (dd, J=11.9, 5.2 Hz, 1H), 2.79 (q, J=7.3 Hz, 2H), 1.29 (t, J=7.3 Hz, 3H); ESI-MS m/z=310 [M+H]$^+$.

Step B: To a solution of the product from Step A (124 mg, 0.40 mmol) in methanol (3 mL) was added fumaric acid (47 mg, 0.40 mmol). The solvent was removed under reduced pressure. The residue was triturated with ethyl acetate and diethyl ether. The resulting precipitate was collected by filtration, washed with diethyl ether, and dried at 50° C. under vacuum to provide (+)-5-(2-ethyl-1,2,3,4-tetrahydroisoquinolin-4-yl)-benzo[b]thiophen-4-ol, fumarate salt as a white solid (120 mg, 70%, >99% AUC HPLC): mp 158-159° C.; $^1$H NMR (CD$_3$OD, 500 MHz) δ 7.45 (d, J=5.4 Hz, 1H), 7.39-7.34 (m, 2H), 7.21-7.09 (m, 4H), 7.00-6.97 (m, 1H), 6.70 (s, 2H), 4.74-4.73 (m, 1H), 4.39 (d, J=15.0 Hz, 1H), 4.19-4.17 (m, 1H), 3.53-3.46 (m, 2H), 3.14-3.12 (m, 2H), 1.37 (t, J=7.2, 3H); ESI-MS m/z=310 [M+H]$^+$.

Step C: A mixture of the (−)-enantiomer from Step B of Example 90 (230 mg, 0.711 mmol) in 48% HBr (5 mL) and acetic acid (1 mL) was heated at reflux for 2 hours. The solvent and excess HBr was removed under reduced pressure. The residue was partitioned between ethyl acetate and saturated sodium bicarbonate. The aqueous layer was extracted with ethyl acetate. The combined extracts were washed with brine, dried over sodium sulfate and concentrated. Purification by column chromatography (silica gel, 0% to 4% methanol/dichloromethane) provided the desired phenol (115 mg, 52%, >99% AUC HPLC): $[\alpha]^{25}_D$ −266.4° (c 0.13, methanol)], $^1$H NMR (CDCl$_3$, 300 MHz) δ 13.84 (s, 1H), 7.41 (d, J=5.5 Hz, 1H), 7.29 (d, J=8.1 Hz, 1H), 7.25-7.17 (m, 2H), 7.11-7.06 (m, 4H), 4.22-4.16 (m, 2H), 3.57 (d, J=14.6 Hz, 1H), 3.40 (d, J=11.7 Hz, 1H), 2.93 (dd, J=11.9, 5.2 Hz, 1H), 2.79 (q, J=7.3 Hz, 2H), 1.29 (t, J=7.3 Hz, 3H); ESI-MS m/z=310 [M+H]$^+$.

Step D: To a solution of the product from Step C (109 mg, 0.352 mmol) in methanol (3 mL) was added fumaric acid (41 mg, 0.352 mmol). The solvent was removed under reduced pressure. The residue was triturated with ethyl acetate and diethyl ether. The resulting precipitate was collected by filtration, washed with diethyl ether, and dried at 50° C. under vacuum to provide (−)-5-(2-ethyl-1,2,3,4-tetrahydroisoquinolin-4-yl)-benzo[b]thiophen-4-ol, fumarate salt as a white solid (60 mg, 41%, >99% AUC HPLC): mp 155-157° C.; $^1$H NMR (CD$_3$OD, 500 MHz) δ 7.46 (d, J=5.5 Hz, 1H), 7.40-7.35 (m, 2H), 7.21-7.10 (m, 4H), 6.99-6.98 (m, 1H), 6.70 (s, 1.8H), 4.76-4.75 (m, 1H), 4.39 (d, J=14.9 Hz, 1H), 4.21-4.20 (m, 1H), 3.53-3.44 (m, 2H), 3.15-3.13 (m, 2H), 1.37 (t, J=7.1, 3H); ESI MS m/z=310 [M+H]$^+$.

Example 90

Preparation of (+)-4-(4-methoxy-benzo[b]thiophen-5-yl)-2-ethyl-1,2,3,4-tetrahydroisoquinoline, fumarate salt and (−)-4-(4-methoxy-benzo[b]thiophen-5-yl)-2-methyl-1,2,3,4-tetrahydroisoquinoline, fumarate salt Step A: To an ice-cooled solution of the product from Step A of Example 82, (1.0 g, 3.43 mmol) in dichloromethane (15 mL) was added ethyl triflate (672 mg, 3.77 mmol). The reaction mixture was stirred at 0° C. for 0.5 hour. The solvent was then removed under the reduced pressure to provide the desired product (1.7 g, >99% crude yield): ESI-MS m/z=320 [M]$^+$. This crude product was used in the next step without further purification.

Step B: To a solution of the crude product from Step A (1.7 g, 3.43 mmol) in methanol (50 mL) was added sodium cyanoborohydride (260 mg, 4.12 mmol). The reaction mixture was stirred at room temperature for 1 hour. The solvent was removed under reduced pressure. The residue was diluted with water and extracted with ethyl acetate twice. The combined extracts were washed with brine, dried over sodium sulfate and concentrated. Purification by column chromatography (silica gel, 30% ethyl acetate/hexanes) provided the desired product (710 mg, 64% for 2 steps): $^1$H NMR (CDCl$_3$, 500 MHz) δ 7.52 (d, J=8.4 Hz, 1H), 7.47 (d, J=5.5 Hz, 1H), 7.42 (d, J=5.5 Hz, 1H), 7.13-7.10 (m, 2H), 7.05-7.01 (m, 2H), 6.83 (d, J=7.7 Hz, 1H), 4.91-4.88 (m, 1H), 3.94 (s, 3H), 3.93 (d, J=14.7 Hz, 1H), 3.64 (d, J=14.7 Hz, 1H), 3.20-3.16 (m, 1H), 2.64-2.56 (m, 3H), 1.17 (t, J=7.2 Hz, 3H). ESI MS m/z=324 [M+H]$^+$. This material was resolved by preparative chiral HPLC (CHIRALPAK AD column, using 98:2:0.1 heptane/IPA/diethylamine as the eluent) to give the (+)-enantiomer [[α]$^{25}_D$ +51.2° (c 0.1, methanol)](331 mg, >99% AUC HPLC) and the (−)-enantiomer [[α]$^{25}_D$ −88.5° (c 0.1, methanol)](342 mg, >99% AUC HPLC).

Step C: To a solution of the (+)-enantiomer from Step B (106 mg, 0.328 mmol) in methanol (2 mL) was added fumaric acid (38 mg, 0.328 mmol). The solvent was removed under reduced pressure. The residue was triturated with ethyl acetate and diethyl ether. The resulting precipitate was collected by filtration, washed with diethyl ether, and dried at 50° C. under vacuum to provide (+)-4-(4-methoxy-benzo[b]thiophen-5-yl)-2-ethyl-1,2,3,4-tetrahydroisoquinoline, fumarate salt as an off-white solid (94 mg, 65%, 98.6% AUC HPLC): mp 91-92° C.; $^1$H NMR (CD$_3$OD, 500 MHz) δ 7.66 (dd, J=8.2, 0.5 Hz, 1H), 7.62 (d, J=5.6 Hz, 1H), 7.51 (dd, J=5.6, 0.5 Hz, 1H), 7.31-7.26 (m, 2H), 7.23-7.19 (m, 1H), 7.10 (d, J=8.3 Hz, 1H), 6.90 (d, J=7.7 Hz, 1H), 6.68 (s, 2H), 5.00 (dd, J=11.2, 6.3 Hz, 1H), 4.57 (d, J=15.1 Hz, 1H), 4.43 (d, J=15.1 Hz, 1H), 3.77 (s, 3H), 3.77-3.74 (m, 1H), 3.51-3.46 (m, 1H), 3.32-3.28 (m, 2H), 1.42 (t, J=7.3 Hz, 3H); ESI MS m/z=324 [M+H]$^+$.

Step D: To a solution of the (−)-enantiomer from Step B (112 mg, 0.346 mmol) in methanol (2 mL) was added fumaric acid (40 mg, 0.346 mmol). The solvent was removed under reduced pressure. The residue was triturated with ethyl acetate and diethyl ether. The resulting precipitate was collected by filtration, washed with diethyl ether, and dried at 50° C. under vacuum to provide (−)-4-4-(methoxybenzo[b]thiophen-5-yl)-2-ethyl-1,2,3,4-tetrahydroisoquinoline, fumarate salt as an off-white solid (70 mg, 46%, 98.8% AUC HPLC): mp 88-90° C.; $^1$H NMR (CD$_3$OD, 500 MHz) δ 7.66 (d, J=8.4 Hz, 1H), 7.62 (d, J=5.5 Hz, 1H), 7.51 (d, J=5.5 Hz, 1H), 7.31-7.26 (m, 2H), 7.23-7.19 (m, 1H), 7.10 (d, J=8.3 Hz, 1H), 6.90 (d, J=7.7 Hz, 1H), 6.68 (s, 2H), 5.01 (dd, J=11.2, 6.3 Hz, 1H), 4.59 (d, J=15.2 Hz, 1H), 4.45 (d, J=15.5 Hz, 1H), 3.79-3.76 (m, 1H), 3.76 (s, 3H), 3.53-3.48 (m, 1H), 3.34-3.30 (m, 2H), 1.43 (t, J=7.3 Hz, 3H); ESI-MS m/z=324 [M+H]$^+$.

Example 91

Preparation of (+)-5-(2-methyl-1,2,3,4-tetrahydroisoquinolin-4-yl)-benzo[b]thiophene-4-carbonitrile, fumarate salt and (−)-5-(2-Methyl-1,2,3,4-tetrahydroisoquinolin-4-yl)-benzo[b]thiophene-4-carbonitrile, fumarate salt Step A: The racemic product from Step C in Example 82 (0.063 g, 2.0 mmol) was dissolved in hydrobromic acid (25 mL) and refluxed for 3.5 hours.

The solution was concentrated in vacuo and redissolved in methanol and concentrated. The solid was treated with saturated sodium bicarbonate solution and extracted with methylene chloride. The extract was washed with brine solution, then dried over sodium sulfate, filtered and evaporated to an off-white solid (0.58 g, 96%). ESI-MS m/z 296 [M+H]$^+$.

Step B: The product from Step A (0.57 g, 0.002 mmol) was dissolved in methylene chloride. The mixture was cooled in an ice bath and added triethylamine (0.41 mL) and trifluoromethanesulfonic anhydride (0.40 mL) and stirred for 3 hours. Saturated sodium chloride solution was added to the mixture and extracted with methylene chloride twice. The combined organic extract was dried over sodium sulfate, filtered and concentrated to a yellow solid (0.84 g, 99%); ESI-MS m/z 428 [M+H]$^+$.

Step C: The product from Step B (0.84 g, 2.0 mmol) and zinc cyanide (0.46 g, 4.0 mmol) in N,N-dimethylformamide was degassed with argon. Tetrakis-(triphenylphosphine)palladium(0) (0.23 g, 0.2 mmol), tris(dibenzylideneacetone)-dipalladium(0) (0.72 g, 0.79 mmol), and 1,1'-bis(diphenylphosphino)ferrocene (0.17 g, 0.31 mmol) were added and the reaction mixture was then heated to 100° C. for 4 hours. The reaction was cooled to room temperature and diluted with ethyl acetate.

The mixture was first washed with saturated sodium bicarbonate solution, then with brine and extracted with ethyl acetate. The organic extract was dried over sodium sulfate, filtered and concentrated in vacuo. The oil was purified by column chromatography (silca gel, 20% ethyl acetate/hexanes) to give the desired product as a yellow oil (0.09 g, 15%): $^1$H NMR (500 MHz, CDCl$_3$) δ 7.90 (d, J=8.5 Hz, 1H), 7.68 (d, J=5.5 Hz, 1H), 7.63-7.62 (m, 1H), 7.20-7.17 (m, 2H), 7.14 (d, J=7.0 Hz, 1H), 7.11-7.08 (m, 1H), 6.87 (d, J=7.7 Hz, 1H), 4.86 (t, J=5.7 Hz, 1H), 3.80 (d, J=14.9 Hz, 1H), 3.64 (d, J=15.0 Hz, 1H), 3.06 (dd, J=11.6, 5.4 Hz, 1H), 2.78 (dd, J=11.6, 6.2 Hz, 1H), 2.42 (s, 3H).

This compound was resolved by preparative chiral HPLC (CHIRALPAK AD column, using 90% heptane/10% isopropyl alcohol/0.1% diethylamine) to give the (+)-enantiomer $[\alpha]^{25}_D$ +68.6° (c=0.08, methanol) and the (−)-enantiomer $[\alpha]^{25}_D$ −75.0° (c=0.05, methanol). The (+)-enantiomer (30 mg, 99 mmol) was converted to the fumaric acid salt by dissolving the free base in a minimal amount of ethanol, adding one equivalent of fumaric acid in enough methanol to completely dissolve the acid, then combining the two solutions and stirring for 2 hours. The solution was concentrated to a minimal volume, then refrigerated at −30° C. until crystal formation occurred. Filtration yielded the 5-(2-methyl-1,2,3,4-tetrahydroisoquinolin-4-yl)-benzo[b]thiophene-4-carbonitrile, fumarate salt (14.8 mg, >99%, 93.8% AUC HPLC) as an off-white solid: $^1$H NMR (500 MHz, CD$_3$OD) δ 8.17 (d, J=8.5 Hz, 1H), 7.98 (d, J=5.5 Hz, 1H), 7.60 (d, J=5.5 Hz, 1H), 7.30-7.17 (m, 4H), 6.80 (d, J=5.5 Hz, 1H), 6.71 (d, J=2.0 Hz, 2H), 5.05 (d, J=6.2 Hz, 1H), 4.26-4.19 (m, 2H), 3.61 (d, J=5.1 Hz, 1H), 3.27-3.23 (m, 1H), 2.82 (s, 3H).

The same procedure was used to transform the (−)-enantiomer (37.0 mg, 115.0 mmol) to give 5-(2-methyl-1,2,3,4-tetrahydroisoquinolin-4-yl)-benzo[b]thiophene-4-carbonitrile, fumarate salt (10.7 mg, >99%) as an off-white solid: $^1$H NMR (500 MHz, CD$_3$OD) δ 8.17 (d, J=8.5 Hz, 1H), 7.98 (d, J=5.5 Hz, 1H), 7.60 (d, J=5.5 Hz, 1H), 7.30-7.18 (m, 4H), 6.81 (d, J=7.8 Hz, 1H), 6.7 (s, 2H), 5.08-5.05 (m, 1H), 4.30-4.21 (m, 2H), 3.63 (t, J=5.9 Hz, 1H), 3.26 (d, J=10.6 Hz, 1H), 2.82 (d, J=5.4 Hz, 3H).

Example 92

Preparation of (+)-4-(benzo[b]thiophen-5-yl)-2-methyl-1,2,3,4-tetrahdro-isoquinoline-4-ol, fumarate salt and (−)-4-(benzothiophen-5-yl)-2-methyl-1,2,3,4-tetrahdro-isoquinoline-4-ol Step A: To a solution of 5-bromobenzothiophene (511 mg, 2.4 mmol) at −75° C., was added t-butyllithium (1.7 M in pentane, 1.6 mL, 2.6 mmol) dropwise. The reaction mixture was stirred at −75° C. for 1 hour. To the resulting dark brown mixture was added 2-methyl-2,3-dihydro-1H-isoquinolin-4-one (323 mg, 2.0 mmol), which was prepared using the method described by Hanna et al., *J. Med. Chem.*, 17(9): 1020-1023 (1974), which is hereby incorporated by reference in its entirety. The reaction mixture was stirred for 15 hours with gradual warming up. The mixture was quenched with saturated ammonium chloride and extracted with ethyl acetate (3×50 ml). The combined organic extracts were washed with saturated sodium chloride, dried over anhydrous sodium sulfate, filtered, and concentrated in vacuo. Purification by medium pressure silica gel chromatography (10-40% ethyl acetate/hexanes) followed by preparative HPLC afforded 4-(benzo[b]thiophen-5-yl)-2-methyl-1,2,3,4-tetrahdro-isoquinoline-4-ol (65 mg, 11%) and 4-(5-bromobenzo[b]thiophen-2-yl)-2-methyl-1,2,3,4-tetrahydroisoquinoline-4-ol (58 mg, 8%). 4-(Benzothiophen-5-yl)-2-methyl-1,2,3,4-tetrahydroisoquinoline-4-ol: $^1$H NMR (CDCl$_3$, 500 MHz) δ 7.81 (d, J=8.5 Hz, 1H), 7.69 (d, J=8.5 Hz, 1H), 7.34-7.23 (m, 4H), 7.20 (s, 1H), 7.18 (d, J=7.3 Hz, 1H), 7.10 (d, J=7.6 Hz, 1H), 3.91 (s, 1H), 3.84 (d, J=15.0 Hz, 1H), 3.53 (d, J=15.0 Hz, 1H), 3.11 (dd, J=11.6, 1.4 Hz, 1H), 2.87 (d, J=11.6 Hz, 1H), 2.50 (s, 3H); ESI MS m/z=296 [M+H]$^+$. 4-(5-Bromobenzothiophen-2-yl)-2-methyl-1,2,3,4-tetrahydroisoquinoline-4-ol: $^1$H NMR (CDCl$_3$, 300 MHz) δ 7.81 (d, J=1.8 Hz, 1H), 7.66 (d, J=8.5 Hz, 1H), 7.38 (dd, J=8.5, 1.9 Hz, 1H), 7.30-7.23 (m, 2H), 7.18 (d, J=7.3 Hz, 1H), 7.11 (s, 1H), 7.07 (d, J=7.6 Hz, 1H), 3.69 (d, J=15.0 Hz, 1H), 3.48 (d, J=15.0 Hz, 1H), 3.10 (dd, J=11.6, 1.3 Hz, 1H), 2.83 (d, J=11.6 Hz, 1H), 2.47 (s, 3H); ESI MS m/z=374 [M+H]$^+$.

Step B: The 4-(benzothiophen-5-yl)-2-methyl-1,2,3,4-tetrahydroisoquinoline-4-ol from Step A (59.1 mg, 0.2 mmol) was dissolved in ethanol (1 mL) and added a solution of fumaric acid (24 mg, 0.2 mmol) in methanol (0.5 mL). The solvent was removed under reduced pressure. The residue was triturated with ethyl acetate. The resulting precipitate was collected by filtration, washed with ethyl acetate, and dried at 50° C. under vacuum to provide 4-(benzothiophen-5-yl)-2-methyl-1,2,3,4-tetrahydroisoquinoline-4-ol, fumarate salt as a white solid (60 mg, 73%, >99% AUC HPLC): mp 172-174° C.; $^1$H NMR (CD$_3$OD, 500 MHz) δ 7.81 (d, J=7.2 Hz, 1H), 7.71 (d, J=7.2 Hz, 1H), 7.40 (d, J=7.8 Hz, 1H), 7.36-7.23 (m, 4H), 7.25 (d, J=7.6 Hz, 1H), 7.20 (s, 1H), 6.70 (s, 2H), 4.25 (d, J=15.4 Hz, 1H), 4.20 (d, J=15.4 Hz, 1H), 3.54 (d, J=12.1 Hz, 1H), 3.48 (d, J=12.1 Hz, 1H), 2.83 (s, 3H); ESI MS m/z=296 [M+H]$^+$.

Step C: This compound from Step B was resolved by preparative chiral HPLC (CHIRALPAK AD column) to give the (+)-enantiomer $[\alpha]^{25}_D$ +69.1° (c=0.06, methanol) and the (−)-enantiomer $[\alpha]^{25}_D$ −72.7° (c=0.06, methanol).

Step D: The (+)-enantiomer (0.14 g, 0.47 mmol) was converted to the fumaric acid salt by dissolving the free base in a minimal amount of ethanol, adding one equivalent of fumaric acid in enough methanol to completely dissolve the acid, then combining the two solutions and stirring over 2 hours. The solution was concentrated to a minimal volume, then refrigerated at −30° C. until crystal formation occurred. Filtration yielded 4-benzo[b]thiophen-5-yl-2-methyl-1,2,3,4-tetrahydroisoquinoline-4-ol, maleate salt (124 mg, 64%, >99% AUC HPLC) as an off-white solid: mp 95-97° C.; $^1$H NMR (500 MHz, CD$_3$OD) δ 8.03 (d, J=1.2 Hz, 1H), ☐ 7.88 (d, J=8.5 Hz, 1H), 7.61 (d, J=5.4 Hz, 1H), 7.38-7.34 (m, 2H), 7.30-7.23 (m, 3H), 7.00 (d, J=7.5 Hz, 1H), 6.69 (s, 2H), 4.46 (d, J=15.4 Hz, 1H), 4.34 (d, J=15.3 Hz, 1H), 3.58 (d, J=12.3 Hz, 1H), 3.48 (d, J=12.4 Hz, 1H) 2.92 (s, 3H).

Example 93

Preparation of (+)-4-benzo[b]thiophen-5-yl-2,4-dimethyl-1,2,3,4-tetrahydroisoquinoline fumaric acid salt and (−)-4-benzo[b]thiophen-5-yl-2,4-dimethyl-1,2,3,4-tetrahydroisoquinoline fumaric acid salt Step A: N-Methylbenzylamine (0.26 mL, 2.0 mmol) was added to a stirred solution of 1-benzothiophen-5-yl-2-bromo-ethanone (0.5 g, 1.99 mmol), from Step C of Example 96, in tetrahydrofuran (10 mL) and N,N-diisopropylethylamine (0.45 mL, 2.6 mmol) under N$_2$ over 3.0 hours. The solvent was removed and water was added to the residue and extracted with ethyl acetate three times. The organic extract was dried over sodium sulfate, filtered and concentrated to a yellow oil. The oil was purified by column chromatography (silica gel, 25% ethyl acetate/hexanes) to provide the desired product (0.36 g, 62%) as a yellow oil: $^1$HNMR (500 MHz, CDCl$_3$) δ 8.43 (d, J=0.9 Hz, 1H), 7.95-7.89 (m, 2H), 7.51 (d, J=5.4 Hz, 1H), 7.41-7.27 (m, 6H), 3.85 (s, 2H), 3.71 (s, 2H), 2.40 (s, 3H).

Step B: The product from Step A (0.35 g, 1.2 mmol) was dissolved in anhydrous diethyl ether (2.0 mL) and the solution was added dropwise to a solution of methyl magnesium iodide (0.8 mL, 2.4 mmol) in diethyl ether (8 mL) cooled at −65° C. The reaction mixture was allowed to warm to room temperature over 3 hours then concentrated (0.29 g, 80% crude yield) as a yellow oil: This crude product was used in the next step without further purification. ESI-MS m/z 312 [M+H]$^+$.

Step C: Methanesulfonic acid (10 mL) was heated to 40° C. under nitrogen. The crude product from Step B (0.29 g, 0.9 mmol) was dissolved in dichloroethane (6 mL) and added to the warm acid, then the mixture was heated to 80° C. After stirring for 30 minutes at 80° C., the mixture was poured over ice and adjusted to pH 9-10 by the addition of concentrated ammonium hydroxide. The solution was extracted twice with methylene chloride. The organic layers were combined and dried over sodium sulfate, filtered and concentrated to a brown oil. The oil was purified by column chromatography (silica gel, 25%-100% ethyl acetate/hexanes) to give the desired product (99 mg, 37%) as a colorless oil: $^1$HNMR (500 MHz, CDCl$_3$) δ 7.73-7.69 (m, 2H), 7.38-7.35 (m, 1H), 7.27-7.24 (m, 1H), 7.21-7.06 (m, 4H), 6.91 (d, J=7.9 Hz, 1H), 3.73 (d, J=14.7 Hz, 1H), 3.60 (d, J=14.7 Hz, 1H), 2.73 (d, J=11.5 Hz, 1H), 2.66 (d, J=11.5 Hz, 1H), 2.35 (s, 3H), 1.82 (s, 3H).

Step D: The product from Step C (0.10 g, 0.34 mmol) was converted to the fumaric acid salt by dissolving the freebase in a minimal amount of ethanol, adding one equivalent of fumaric acid in enough methanol to completely dissolve the acid, then combining the two solutions and stirring for 2 hours. The solution was concentrated to a minimal volume, then refrigerated at −30° C. until crystal formation occurred. Filtration yielded (+/−)-4-benzo[b]thiopen-5-yl-2,4-dimethyl-1,2,3,4-tetrahydroisoquinoline, fumarate salt (98.5 mg, 86%) as an off-white solid: $^1$HNMR (500 MHz, CDCl$_3$) δ 7.84 (d, J=8.5 Hz, 1H), 7.72 (s, 1H), 7.57 (d, J=5.4 Hz, 1H), 7.32-7.20 (m, 5H), 7.08 (d, J=7.7 Hz, 1H), 6.69 (s, 2H), 4.29 (m, 2H), 3.56 (d, J=12.4 Hz, 1H), 3.40 (d, J=12.4 Hz, 1H), 2.83 (s, 3H), 1.92 (s, 3H).

Step E: The free-base from Step D (58.8 mg, 212 mmol) was resolved by preparative chiral HPLC (CHIRALPAK AD column, using 90% heptane/10% isopropyl alcohol/0.1% diethylamine) to give the (+)-enantiomer $[\alpha]^{25}_D$ +39.6° (c 0.06, methanol) and the (−)-enantiomer $[\alpha]^{25}_D$ −31.6° (c 0.06, methanol). The (+)-enantiomer (8.5 mg, 0.03 mmol) was converted to the fumaric acid salt by dissolving the free-base in a minimal amount of ethanol, adding one equivalent of fumaric acid in enough methanol to completely dissolve the acid, then combining the two solutions and stirring for 2 hours. The solution was concentrated to a minimal volume, then refrigerated at −30° C. until crystal formation occurred. Filtration yielded 4-benzo[b]thiopen-5-yl-2,4-dimethyl-1,2,3,4-tetrahydroisoquinoline, fumarate salt, (12.0 mg, >99%, 97.3% AUC HPLC) as an off-white solid: mp 95-97° C.; $^1$H NMR (500 MHz, CD$_3$OD) δ 7.81 (d, J=8.6 Hz, 1H), □ 7.71 (d, J=1.4 Hz, 1H), 7.55 (d, J=5.4 Hz, 1H), 7.30 (d, J=5.4 Hz, 1H), 7.26-7.18 (m, 4H), 7.03 (d, J=6.9 Hz, 1H), 6.69 (s, 2H), 4.12-4.07 (m, 2H), 3.35-3.34 (m, 1H), 3.19-3.20 (m, 1H), 2.67 (s, 3H), 1.89 (s, 3H).

The same procedure was used to transform the (−)-enantiomer (12 mg, 0.04 mmol) to its fumaric salt to give 4-benzo[b]thiopen-5-yl-2,4-dimethyl-1,2,3,4-tetrahydroisoquinoline, fumerate salt (16.5 mg, >99%, 98.5% AUC HPLC) as an off-white solid: mp 95-97° C.; $^1$H NMR (500 MHz, CD$_3$OD) δ 7.81 (d, J=8.6 Hz, 1H), □ 7.71 (s, 1H), 7.54 (d, J=5.4 Hz, 1H), 7.30-7.29 (m, 1H), 7.24-7.18 (m, 4H), 7.02 (d, J=7.5 Hz, 1H), 6.69 (s, 2H), 4.07-4.02 (m, 2H), 3.27-3.26 (m, 1H), 3.16-3.17 (m, 1H), 2.65 (s, 3H), 1.88 (s, 3H).

Example 94

Preparation of (+/−)4-Benzo[b]thiophen-5-yl-2-methyl-1,2,3,4-tetrahydroisoquinoline-4-carbonitrile, fumarate salt Step A: Tin(IV) chloride in dichloromethane (0.51 mL, 1.0 M) was added dropwise to a suspension of 4-benzo[b]thiophen-5-yl-2-methyl-1,2,3,4-tetrahydroisoquinolin-4-ol (300 mg, 1.02 mmol) from Example 92, and trimethylsilylcyanide (0.68 mL, 5.1 mmol) in dichloromethane (4.5 mL) at 0° C. The resulting solution was allowed to stir at room temperature overnight, then additional tin(IV) chloride in dichloromethane (1.02 mL, 1.0 M) was added and the solution stirred at room temperature for an additional 24 hours. Potassium carbonate (636 mg, 4.60 mmol), potassium fluoride hydrate (435 mg, 7.49 mmol) and then water (0.135 mL, 7.50 mmol) were added and the mixture stirred overnight. Silica gel (2.5 g) and enough water to make the mixture stirrable were added and the mixture filtered. The filter pad was washed with ethyl acetate. The organic layer was washed with saturated sodium bicarbonate, dried over sodium sulfate and concentrated under vacuum. The crude material was filtered through a plug of silica (1:1 hexane/ethyl acetate). The filtrate was concentrated under vacuum. The residue was purified by column chromatography (95:5, then 90:10 hexane/ethyl acetate) to give 4-benzo[b]thiophen-5-yl-2-methyl-1,2,3,4-tetrahydroisoquinoline-4-carbonitrile (17 mg, 6%). Recrystallization from ethanol gave 10 mg white solid. The carbonitrile (10 mg, 0.033 mmol) was converted to the fumarate salt by dissolving in a minimum amount of methanol and treated with a solution of fumaric acid (3.0 mg, 0.026 mmol) in methanol. The solution was concentrated to dryness and the residue dissolved in 1:1 acetonitrile/water and lyophilized to give 4-benzo[b]thiophen-5-yl-2-methyl-1,2,3,4-tetrahydroisoquinoline-4-carbonitrile, fumarate salt (13 mg, 94%, >99.0% AUC HPLC): mp 170-172° C.; $^1$H NMR (500 MHz, CDCl$_3$) δ 7.92 (d, J=1.8 Hz, 1H), 7.89 (d, J=11.5 Hz, 1H), 7.63 (d, J=5.5 Hz, 1H), 7.38 (d, J=5.5 Hz, 1H), 7.35-7.32 (m, 1H), 7.28-7.20 (m, 3H), 7.04 (d, J=8.00 Hz, 1H), 6.75 (s, 1.4H), 3.90 (d, J=15.2 Hz, 1H), 3.70 (d, J=15.2 Hz, 1H), 3.34 (d, J=12.0 Hz, 1H), 2.95 (d, J=12.0 Hz, 1H), 2.48 (s, 3H).

Example 95

Preparation of (+)-4-benzo[b]thiophen-5-yl-2-methyl-1,2,3,4-tetrahydroisoquinoline-7-ol, fumarate salt To a solution of the (+)-enantiomer obtained from Step F of Example 96 (free base, 0.5 g, 1.6 mmol) in AcOH (20 mL) was added HBr (20 mL, 48%). The reaction was refluxed for 3.5 h. After cooled to room temperature, the solvent was removed under vacuum. The residue was neutralized with saturated aqueous NaHCO$_3$ solution. The product was extracted with EtOAc (2×100 mL). The organic layers were combined, washed with brine (100 mL), dried (Na$_2$SO$_4$) and concentrated to give an off-white solid, which was purified using medium pressure chromatography (eluent: MeOH/dichloromethane 1:99 to 5:95) to give (+)-4-benzo[b]thiophen-5-yl-2-methyl-1,2,3,4-tetrahydroisoquinoline-7-ol as a white solid (460 mg, 1.5 mmol, 96%): $[\alpha]^{25}_D$ +85° (c 0.02, methanol). The solid (28 mg, 0.09 mmol) was dissolved in MeOH (5 mL) and to this solution was added fumaric acid (11 mg, 0.10 mmol). The solution was concentrated to less than 1 mL. To this solution was added water (5 mL). The resulting suspension was then lyophilized on a freeze dryer to give (+)-4-benzo[b]thiophen-5-yl-7-hydroxy-2-methyl-1,2,3,4-tetrahydroisoquinoline, fumarate salt (33 mg, 85%, >99% AUC HPLC) as a white solid: mp 155-157° C.; H NMR (500 MHz, CD$_3$OD) δ 7.88 (d, J=8.3 Hz, 1H), 7.71 (s, 1H), 7.59 (d, J=5.5 Hz, 1H), 7.34 (d, J=5.5 Hz, 1H), 7.17 (dd, J=8.3, 1.6 Hz, 1H), 6.73-6.71 (m, 1H), 6.69 (s, 2H), 6.66-6.64 (m, 2H), 4.54 (dd, J=11.2, 6.2 Hz, 1H), 4.32 (s, 2H), 3.68 (dd, J=12.2, 6.0 Hz, 1H), 3.32-3.31 (m, 1H), 2.91 (s, 3H); ESI-MS m/z 296 [M+H]$^+$.

Example 96

Preparation of (+)-4-benzo[b]thiophen-5-yl-7-methoxy-2-methyl-1,2,3,4-tetrahydroisoquinoline, fumarate salt Step A: A mixture of CuCN (86 g, 960 mmol), 5-bromobenzo[b]thiophene (157 g, 723 mmol), pyridine (80 mL) and DMF (1400 mL) was heated at reflux for 14 h. After cooled to 80° C., the reaction mixture was poured into a cold aqueous solution of ethylenediamine (400 mL in 2 L water) cooled by an icebath. The product was extracted with ether (2×1.5 L). The ether layer was washed with brine (1 L), dried (Na$_2$SO$_4$), and concentrated. The residue was recrystallized from CHCl$_3$/Hexanes (50 mL/2000 mL) to give benzo[b]thiophene-5-carbonitrile (106 g, 90%) as a white solid: $^1$H NMR (300 MHz, CDCl$_3$) δ 8.15 (s, 1H), 7.97 (d, J=8.3 Hz, 1H), 7.61 (d, J=5.4 Hz, 1H), 7.56 (d, J=8.3 Hz, 1H), 7.41 (d, J=5.4 Hz, 1H).

Step B: To a cold (-78° C.) mixture of methylmagnesium bromide in THF (3 M, 693 mL, 2.08 mol) and CuBr (5.5 g, 38 mmol) was added a solution of benzo[b]thiophene-5-carbonitrile (106 g, 667 mmol) and TBSCl (199 g, 1.32 mol) in THF (500 mL). The cooling bath was removed, and the reaction mixture was allowed to warm up to room temperature. The mixture was stirred at room temperature for 40 minutes. The reaction mixture was poured into ice water (100 mL) slowly. The product was extracted with dichloromethane (2×100 mL). The organic layer was washed with saturated aqueous NH$_4$Cl solution (100 mL), brine (100 mL), dried (Na$_2$SO$_4$) and concentrated to give the desired product (860 mg, 78%) as an off-white solid: $^1$H NMR (300 MHz, CDCl$_3$) δ 8.43 (s, 1H), 7.95-7.94 (m, 2H), 7.53 (d, J=5.4 Hz, 1H), 7.44 (d, J=5.4 Hz, 1H), 2.69 (s, 3H).

Step C: To a solution of the product obtained in Step B (1-benzo[b]thiophen-5-yl-ethanone) (60 g, 340 mmol) in CHCl$_3$ (1 L) was added pyridinium tribromide (110 g, 343 mmol) at room temperature. The mixture was stirred with a mechanic stirrer at room temperature for 6 hours. It was washed with 1 N HCl (2×1 L) to remove pyridine. The organic layer was then washed with brine, dried (Na$_2$SO$_4$) and concentrated. The residue was purified by medium pressure chromatograph (eluent: CH$_2$Cl$_2$/hex 30:70) to the desired product (50 g, 57%) as a white solid: $^1$H NMR (300 MHz, CDCl$_3$) δ 8.48 (s, 1H), 7.97-7.96 (m, 2H), 7.56 (d, J=5.4 Hz, 1H), 7.47 (d, J=5.4 Hz, 1H), 4.54 (s, 2H).

Step D: To a cold (0° C.) and stirred solution of 3-methoxy-N-benzylamine (46 g, 305 mmol) and diisopropylethylamine (40 mL, 276 mmol) in CH$_2$Cl$_2$ (500 mL) was added the product obtained from Step C (71 g, 276 mmol) in CH$_2$Cl$_2$ (500 mL) solution. The reaction was then stirred at 0° C. for 2 hours. It was washed with water (500 mL), saturated aqueous NaHCO$_3$ (500 mL), brine, dried and concentrated to give the desired product as a light yellow liquid (107 g, crude, quant.): $^1$H NMR (300 Hz, CDCl$_3$) δ 8.43 (s, 1H), 7.94-7.92 (m, 2H), 7.51 (d, J=5.4 Hz, 1H), 7.40 (d, J=5.4 Hz, 1H), 7.25-7.21 (m, 1H), 6.93-6.80 (m, 3H), 3.83 (s, 2H), 3.76 (s, 3H), 3.67 (s, 2H), 2.40 (s, 3H); ESI-MS m/z 326 [M+H]$^+$.

Step E: To a cold (0° C.) and stirred solution of the product obtained from Step D (107 g, crude mmol) in methanol (1000 mL) was slowly added NaBH$_4$ (11 g, 290 mmol). The resulting solution was stirred at 0° C. for 3 hours. The solvent was removed, and the residue was taken up with water (500 mL). The product was extracted with dichloromethane (2×1000 mL). The organic layers were combined, washed with brine, dried and concentrated to give the desired product (107 g, crude, quant.) as a thick liquid: $^1$H NMR (300 MHz, CDCl$_3$) δ 7.85-7.82 (m, 2H), 7.43 (d, J=5.4 Hz, 1H), 7.32-7.30 (m, 2H), 6.95-6.80 (m, 4H), 4.88 (dd, J=6.9, 3.6 Hz, 1H), 3.81-3.81 (m, 4H), 3.74 (d, J=12.9 Hz, 1H), 3.52 (d, J=12.9 Hz, 1H), 2.65-2.58 (m, 2H), 2.35 (s, 3H); ESI-MS m/z 328 [M+H]$^+$.

Step F: To a solution of the product obtained from Step E (25.0 g, 76.5 mmol) in CH$_2$Cl$_2$ (500 mL) was added MsOH (74 g, 770 mmol) slowly at room temperature. The solution was stirred at room temperature for 15 minutes. The mixture was slowly added to an ice-cooled NaOH solution (2 N, 500 mL). The organic layer was separated, and the aqueous layer was extracted with dichloromethane (200 mL) one more time. The organic layers were combined, washed with water (500 mL) and brine 300 mL), dried (Na$_2$SO$_4$) and concentrated. The residue was purified by flash column chromatography (eluent: MeOH/EtOAc/Hex 1:9:15) to give 4-benzo[b]thiophen-5-yl-7-methoxy-2-methyl-1,2,3,4-tetrahydroisoquinoline (12.5 g, 53%) as a foam solid. It was then resolved by a CHRIALPAK AD column (eluent: 10 IPA/90Heptane/0.1 DEA). A small amount of (+)-enantiomer [[α]$^{25}_D$ +74.3° (c 0.07, methanol)](65 mg, 0.21 mmol) was dissolved in methanol (5 mL), and to this solution was added fumaric acid (24 mg, 0.21 mmol). The solution was concentrated to less than 1 mL. To this solution was added water (5 mL). The resulting suspension was then lyophilized on a freeze dryer to give (+)-4-benzo[b]thiophen-5-yl-7-methoxy-2-methyl-1,2,3,4-tetrahydroisoquinoline, fumarate (55 mg, 62%, >99% AUC HPLC) as a white solid: mp 103-105° C.; $^1$H NMR (500 MHz, CD$_3$OD) δ 7.89 (d, J=8.3 Hz, 1H), 7.72 (s, 1H), 7.60 (d, J=5.4 Hz, 1H), 7.34 (d, J=5.5 Hz, 1H), 7.17 (dd, J=8.3, 1.6 Hz, 1 H), 6.84-6.80 (m, 3H), 6.72 (s, 4H), 4.60 (dd, J=10.5, 6.0 Hz, 1H), 4.48-4.42 (m, 2H), 3.37-3.74 (m, 4H), 3.44 (t, J=10.5 Hz, 1H), 2.98 (s, 3H); ESI-MS m/z 310 [M+H]$^+$.

Example 97

Preparation of (+)-4-benzo[b]thiophen-5-yl-2-methyl-7-pyridazin-3-yl-1,2,3,4-tetrahydroisoquinoline, fumarate salt Step A: To a solution of the product obtained according to Example 95 (free base, 6.0 g, 20.3 mmol) in dichloromethane (200 ml) cooled to 0° C. was added triflic anhydride (11.2 g, 40.7 mmol). After stirred at room temperature for 1 h, the reaction material was poured into a saturated aqueous NaHCO$_3$ solution (200 mL). The organic layer separated was washed with brine (300 mL), dried (Na$_2$SO$_4$) and concentrated to give the desired triflate (9.0 g, quant., crude) as a light yellow oil: $^1$H NMR (300 MHz, CDCl$_3$) δ 7.80 (d, J=8.3 Hz, 1H), 7.61 (s, 1H), 7.44 (d, J=5.5 Hz, 1H), 7.28-7.26 (m, 1H), 7.15 (d, J=8.3 Hz, 1H), 7.05-7.03 (m, 1H), 6.97-6.94 (m, 2H), 4.39 (t, J=12.0 Hz, 1H), 3.81 (d, J=15.0 Hz, 1H), 3.67 (d, J=15.0 Hz, 1H), 3.09 (dd, J=10.5, 6.0 Hz, 1H), 2.64 (dd, J=11.6, 8.7 Hz, 1H), 2.45 (s, 3H); ESI-MS 428 [M+H]+.

Step B: A mixture of the triflate (2.5 g, crude, 5.9 mmol) obtained from Step A, bis(pincolato)diboron (1.49 g, 5.9 mmol), KOAc (1.74 g, 17.7 mmol), and DMSO (20 mL) was purged with argon. PdCl$_2$dppf (722 mg, 0.77 mmol) was added to the mixture, and the system was purged again with argon. The mixture was heated at 100° C. for 3 hours. After cooled to room temperature, the reaction was diluted with dichloromethane (100 mL), and filtered through celite. The filtrate was washed with H$_2$O (100 mL) and brine (100 mL), dried (Na$_2$SO$_4$) and concentrated to give the desired borane ester (5.2 g, crude) as a dark oil: $^1$H NMR (300 MHz, CDCl$_3$) δ 7.78 (d, J=8.3 Hz, 1H), 7.64 (s, 1H), 7.57 (s, 1H), 7.49 (d, J=7.8 Hz, 1H), 7.41 (d, J=5.4 Hz, 1H), 7.26 (s, 1H), 7.15 (d, J=8.2 Hz, 1H), 6.90 (d, J=7.9 Hz, 1H), 4.42-4.40 (m, 1H), 3.80 (d, J=15.9 Hz, 1H), 3.66 (d, J=15.9 Hz, 1H), 3.10-3.08 (m, 1H), 2.62 (t, J=11.4 Hz, 1H), 2.43 (s, 3H), 1.33 (s, 12H); ESI-MS 406 [M+H]+.

Step C: A mixture of the ester (5.2 g, crude, 5.9 mmol) obtained from Step B, 3-pyridazinylchloride (1.0 g, 8.8 mmol), Na$_2$CO$_3$ (1.93 g, 17.9 mmol), H$_2$O (5 mL), and DMF (25 mL) was purged with argon. PdCl$_2$dppf (722 mg, 0.88 mmol) was added. The mixture was heated at 100° C. for 5 hours. After cooled to room temperature, the reaction was diluted with dichloromethane (100 mL), and filtered through celite. The filtrate was washed with water (200 mL) and brine (200 mL), dried (Na$_2$SO$_4$) and concentrated. The residue was purified by a medium pressure chromatography (eluent: MeOH/EtOAc 1:9) to give (+)-4-benzo[b]thiophen-5-yl-2-methyl-7-pyridazin-3-yl-1,2,3,4-tetrahydroisoquinoline (390 mg, 19% for three steps) as a light-brown oil. It was dissolved in MeOH (5 mL) at room temperature, and to this solution was added fumaric acid (125 mg, 1.07 mmol). The solution was concentrated to about 2 mL. Water (20 mL) was added to the solution. The resulting suspension was lyophilized on a freeze dryer overnight to give (+)-4-benzo[b]thiophen-5-yl-2-methyl-7-pyridazin-3-yl-1,2,3,4-tetrahydroisoquinoline, fumarate salt (355 mg, 59%, >99% AUC HPLC) as a light-brown solid: $[\alpha]^{25}_D$ +7.3° (c 0.07, methanol); mp 122-124° C.; $^1$H NMR (500 MHz, CD$_3$OD) δ 9.15 (d, J=4.9 Hz, 1H), 8.17 (d, J=8.7 Hz, 1H), 8.04 (s, 1H), 7.93-7.88 (m, 2H), 7.80-7.77 (m, 2H), 7.61 (d, J=5.5 Hz, 1H), 7.35 (d, J=5.5 Hz, 1H), 7.22 (d, J=8.3 Hz, 1H), 7.11 (d, J=8.2 Hz, 1H), 6.71 (s, 4H), 4.71 (dd, J=10.5, 6.5 Hz, 1H), 4.52 (d, J=15.1 Hz, 1H), 4.44 (d, J=15.1 Hz, 1H), 3.73 (dd, J=12, 0, 6.0 Hz, 1H), 3.42-3.38 (m, 1H), 2.91 (s, 3H); ESI-MS 358 [M+H]+; Anal Calcd. For C$_{22}$H$_{19}$N$_3$S.1.75C$_4$H$_4$O$_4$: C, 62.13; H, 4.67; N, 7.50. Found: C, 61.80; H, 4.81; N, 7.17.

Example 98

Preparation of (+)-[6-(4-benzo[b]thiophen-5-yl-2-methyl-1,2,3,4-tetrahydroisoquinolin-7-yl)-pyridazin-3-yl]-dimethyl-amine, fumarate salt Step A: A mixture of the product obtained from Step B of Example 97 (2.0 g, crude), 3,6-dichloropyridazine (1.0 g), Na$_2$CO$_3$ (1.56 g, 14.7 mmol), H$_2$O (4 mL), and DMF (20 mL) was purged with argon. PdCl$_2$dppf (600 mg, 0.74 mmol) was added. The mixture was heated at 80° C. for 4 hours, and at 85° C. for 1 hour. After cooled to room temperature, the reaction was diluted with dichloromethane (200 mL), and filtered through celite. The filtrate was washed with water (200 mL) and brine (200 mL), dried (Na$_2$SO$_4$) and concentrated. The residue was purified by medium pressure chromatography (eluent: MeOH/EtOAc/hexanes 1:9:10) to give the desired product (410 mg, 87%) as an off-white solid. $^1$H NMR (300 MHz, CDCl$_3$) δ 7.89 (b, 1H), 7.82 (d, J=8.3 Hz, 1H), 7.81 (d, J=8.9 Hz, 1H), 7.68-7.65 (m, 2H), 7.54 (d J=8.9 Hz, 1H), 7.44 (d, J=5.4 Hz, 1H), 7.29-7.27 (m, 1H), 7.19 (d, J=5.4 Hz, 1H), 7.06 (d, J=8.1 Hz, 1H), 4.48-4.43 (m, 1H), 3.90 (d, J=15.1 Hz, 1H), 3.75 (d, J=15.1 Hz, 1H), 3.13 (dd, J=11.8, 5.6 Hz, 1H), 2.71-2.64 (m, 1H), 2.48 (s, 3H); ESI-MS 392 [M+H]+.

Step B: A mixture of the product obtained from Step A (200 mg, 0.51 mmol), Me$_2$NH (40% aq solution, 4 mL, 35 mmol) and DMF (10 mL) was placed in a sealed tube. The tube was then heated at 110° C. for 14 h. After cooled to room temperature, the reaction was diluted with dichloromethane (50 mL) and washed with water, brine, dried and concentrated. The residue was purified by a medium pressure chromatography (eluent: MeOH/EtOAc 1:9) to give [6-(4-benzo[b]thiophen-5-yl-2-methyl-1,2,3,4-tetrahydroisoquinolin-7-yl)-pyridazin-3-yl]-dimethylamine (200 mg, 98%) as a yellow semi-solid. The compound was dissolved in methanol (2 mL), and to this solution was added fumaric acid (60 mg, 0.52 mmol). To this solution was added water (15 mL). The resulting suspension was lyophilized on a freeze dryer overnight to give (+)-[6-(4-benzo[b]thiophen-5-yl-2-methyl-1,2,3,4-tetrahydroisoquinolin-7-yl)-pyridazin-3-yl]-dimethylamine, fumarate salt (230 mg, 88%, 98.0% AUC HPLC) as an off-white solid: $[\alpha]^{25}_D$ +32.5° (c 0.08, methanol); mp 116-119° C.; $^1$H NMR (500 MHz, CD$_3$OD) δ 7.92 (d, J=8.3 Hz, 1H), 7.87 (bs, 1H), 7.81 (d, J=10.0 Hz, 1H), 7.77 (bs, 1H), 7.75 (d, J=8.3 Hz, 1H), 7.61 (d, J=5.4, 1H), 7.35 (d, J=5.4 Hz, 1H), 7.22 (d, J=8.3 Hz, 1H), 7.19 (d, J=9.6 Hz, 1H), 7.04 (d, J=8.3 Hz, 1H), 6.71 (s, 4H), 4.73-4.67 (m, 1H), 4.60-4.49 (m, 2H), 3.81-3.77 (m, 1H), 3.50-3.43 (m, 1H), 3.21 (s, 6H), 2.99 (s, 3H); ESI-MS m/z 401 [M+H]+; Anal Calcd. For C$_{22}$H$_{24}$N$_4$S.2.0C$_4$H$_4$O$_4$.0.25H$_2$O: C, 60.32; H, 5.14; N, 8.79. Found: C, 60.03; H, 4.94; N, 8.87.

Example 99

Preparation of (+)-4-benzo[b]thiophen-5-yl-2-methyl-7-pyridazin-4-yl-1,2,3,4-tetrahydroisoquinoline and (−)-4-benzo[b]thiophen-5-yl-2-methyl-7-pyridazin-4-yl-1,2,3,4-tetrahydroisoquinoline Step A: A mixture of (−)-4-benzo[b]thiophen-5-yl-7-methoxy-2-methyl-1,2,3,4-tetrahydroisoquinoline (10.00 g, 32.3 mmol) which was obtained according to Step F in the preparation of Example 98 and sodium ethanethiolate (11.3 g, 134.3 mmol) in DMF (250 mL) was heated at 140° C. under an N$_2$ atmosphere for 14 hours. The reaction mixture was cooled in an ice bath before addition of saturated NH$_4$Cl (250 mL). The aqueous phase was extracted with DCM (3×750 mL) and the combined organic extracts washed with water (3×500 mL), brine, dried over Na$_2$SO$_4$ and concentrated in vacuo. The crude material was purified by silica gel column chromatography (eluent: 5% MeOH/CH$_2$Cl$_2$) to afford (−)-4-benzo[b]thiophen-5-yl-2-methyl-1,2,3,4-tetrahydroisoquinoline-7-ol (6.64 g, 70%) as an orange-brown solid: $^1$H NMR (300 MHz, CDCl$_3$) δ 7.76 (d, J=8.3 Hz, 1H), 7.62 (s, 1H), 7.40 (d, J=5.4 Hz, 1H), 7.26-7.20 (m, 2H), 7.13 (d, J=8.4 Hz, 1H), 6.66 (d, J=8.3 Hz, 1H), 6.50-6.40 (m, 2H), 4.34 (dd, J=9.0, 6.0 Hz, 1H), 3.68 (d, J=15.0 Hz, 1H), 3.54 (d, J=15.0 Hz, 1H), 3.11 (dd, J=11.5, 5.7 Hz, 1H), 2.58 (dd, J=11.3, 9.7 Hz, 1H), 2.43 (s, 3H); ESI-MS m/z=296 [M+H]+.

Step B: To a solution of (−)-4-benzo[b]thiophen-5-yl-2-methyl-1,2,3,4-tetrahydroisoquinoline-7-ol (6.64 g, 22.5 mmol) in dichloromethane (210 ml) cooled to 0° C. was added triflic anhydride (4.92 mL, 29.2 mmol). After stirring for 2 hours the reaction was allowed to warm to room temperature for 30 minutes, then poured into a saturated aqueous NaHCO$_3$ solution (200 ml). The organic layer separated was washed with water (200 mL) and brine, dried (Na$_2$SO$_4$) and the volitiles removed in vacuo. The crude material was purified by silica gel column chromatography (eluent: Et$_2$O) to afford (−)-trifluoro-methanesulfonic acid-4-benzo[b]thiophen-yl-2-methyl-1,2,3,4-tetrahydroisoquino-7-yl ester (7.88 g, 82%) as a yellow oil: $^1$H NMR (300 MHz, CDCl$_3$) δ 7.80 (d, J=8.3 Hz, 1H), 7.61 (s, 1H), 7.44 (d, J=5.5 Hz, 1H), 7.28-7.26 (m, 1H), 7.15 (d, J=8.3 Hz, 1H), 7.05-7.03 (m, 1H), 6.97-6.94 (m, 2H), 4.39 (t, J=12.0 Hz, 1H), 3.81 (d, J=15.0 Hz, 1H), 3.67 (d, J=15.0 Hz, 1H), 3.09 (dd, J=10.5, 6.0 Hz, 1H), 2.64 (dd, J=11.6, 8.7 Hz, 1H), 2.45 (s, 3H); ESI-MS m/z=428 [M+H]$^+$.

Step C: To a solution of 2,2,6,6-tetramethylpiperidine (4.75 mL, 28.1 mmol) in THF (120 mL) at −30° C. under N$_2$ was added n-BuLi (11.28 mL of 2.5 M solution in hexanes, 28.1 mmol). The solution was allowed to warm to 0° C. for 30 minutes then cooled to −78° C. A solution of pyridazine (2.04 ml, 28.1 mmol) in THF (9 mL) was added dropwise. The deep red solution was stirred at −78° C. for 30 minutes before addition of ZnCl$_2$ (112.30 mL of a 0.5 M solution in THF, 56.3 mmol). The resulting brown suspension was allowed to warm to room temperature and a solution of (−)-trifluoro-methanesulfonic acid-4-benzo[b]thiophen-yl-2-methyl-1,2,3,4-tetrahydroisoquino-7-yl ester (6.00 g, 14.1 mmol) in THF (36 mL) was added followed by tetrakis(triphenylphosphine)palladium(0) (1.62 g, 1.41 mmol). The system was flushed with argon and the mixture heated at 70° C. for 14 hours. After cooling to room temperature saturated NH$_4$Cl (200 mL) was added and the mixture partitioned with EtOAc (500 mL) and water (300 mL). The layers were filtered in order to allow separation of the organic phase. The organic phase was washed with brine, dried over Na$_2$SO$_4$ and concentrated in vacuo. The resulting residue was partially purified by column chromatography (eluent: 5% MeOH/CH$_2$Cl$_2$) to obtain a mixture of the 3- and 4-pyridazyl regioisomers. This material was dissolved in EtOAc (15 mL) and the solution left to stand overnight. The precipitated solid was filtered to afford (−)-4-benzo[b]thiophen-5-yl-2-methyl-7-pyridazin-3-yl-1,2,3,4-tetrahydroisoquinoline (0.92 g, 18%) as a light brown solid.

The remaining mother-liquor was concentrated in vacuo and the residue eluted through a 120 g ISCO combi-flash column (eluent: 5% MeOH/EtOAc) to afford a further amount of Example 99 [(−)-enantiomer](1.01 g, 20%) plus additional mixed fractions containing mostly the regioisomeric product. The mixed fractions were concentrated in vacuo and purified using a 40 g ISCO combi-flash column (eluent: 5 to 10% MeOH/EtOAc) to afford (−)-4-benzo[b]thiophen-5-yl-2-methyl-7-pyridazin-4-yl-1,2,3,4-tetrahydroisoquinoline (210 mg, 4%) as an off-white solid: $^1$H NMR (500 MHz, CDCl$_3$) δ 9.45 (m, 1H), 9.20 (dd, J=5.4, 1.0 Hz, 1H), 7.82 (d, J=8.3 Hz, 1H), 7.69 (s, 1H), 7.62 (dd, J=5.4, 2.5 Hz, 1H), 7.46 (d, J=9.7 Hz, 1H), 7.42 (s, 1H), 7.37 (dd, J=8.1, 1.8 Hz, 1H), 7.29 (d, J=5.4 Hz, 1H), 7.18 (dd, J=8.3, 1.5 Hz, 1H), 7.08 (d, J=8.1 Hz, 1H), 4.45 (t, J=6.5 Hz, 1H), 3.88 (d, J=15.0 Hz, 1H), 3.74 (d, J=15.0 Hz, 1H), 3.18 (dd, J=11.5, 5.6 Hz, 1H), 2.69 (dd, J=11.5, 8.7 Hz, 1H), 2.48 (s, 3H); ESI-MS m/z=358 [M+H]$^+$.

Step D: To a solution of (−)-4-benzo[b]thiophen-5-yl-2-methyl-7-pyridazin-4-yl-1,2,3,4-tetrahydroisoquinoline (210 mg, 0.59 mmol) in tert-butanol (6 mL) was added potassium tert-butoxide (396 mg, 3.53 mmol). The mixture was heated under an N$_2$ atmosphere at 95° C. for 20 hours. After cooling to room temperature, saturated NH$_4$Cl (3 mL) was added and the mixture extracted with EtOAc (30 ml). The organic extract was washed with brine, dried over Na$_2$SO$_4$ and concentrated in vacuo. The residue was purified by chromatography using a 12 g ISCO combi-flash column (eluent: 10% MeOH/EtOAc) to afford (+/−)-4-benzo[b]thiophen-5-yl-2-methyl-7-pyridazin-4-yl-1,2,3,4-tetrahydroisoquinoline as an off-white solid (200 mg, 95%). The racemate was resolved using a Chiralpak AD column (eluent: 20 IPA/80Hep/0.1 DEA) to afford (+)-4-benzo[b]thiophen-5-yl-2-methyl-7-pyridazin-4-yl-1,2,3,4-tetrahydroisoquinoline (77 mg, 77%) as an off-white solid: [[α]$^{25}_D$ +77.4° (c 0.10, methanol)] and (−)-4-benzo[b]thiophen-5-yl-2-methyl-7-pyridazin-4-yl-1,2,3,4-tetrahydroisoquinoline (75 mg, 75%) as an off-white solid: [[α]$^{25}_D$ −77.7° (c 0.08, methanol)].

Example 100

Preparation of (+)-4-benzo[b]thiophen-5-yl-2-methyl-7-morpholin-4-yl-1,2,3,4-tetrahydroisoquinoline, fumarate salt A mixture of the product obtained from Step A of Example 97 (2.5 g, crude), morpholine (1.03 g, 11.8 mmol), Pd(OAc)$_2$ (198 mg, 0.88 mmol), X-phos (1.67 g, 3.51 mmol), Cs$_2$CO$_3$ (5.58 g, 17.6 mmol) and toluene (20 mL) was placed in a microwave reaction vessel. The vessel was heated in a microwave reactor (program: 10 min ramp, 160° C., 30 minutes). After cooled to room temperature, the reaction was diluted with dichloromethane (100 mL), and filtered through celite. The filtrate was washed with saturated aqueous ammonium chloride solution (100 mL) and brine (100 mL), dried (Na$_2$SO$_4$) and concentrated. The residue was purified by medium pressure chromatography (eluent: MeOH/EtOAc/hexanes 1:19:20) followed by another medium pressure chromatography (eluent: MeOH/CH$_2$Cl$_2$ 1:39 to 1:19) to give 4-benzo[b]thiophen-5-yl-2-methyl-7-morpholin-4-yl-1,2,3,4-tetrahydroisoquinoline (320 mg, 14% for three steps) as a colorless oil. It was then dissolved in MeOH (5 mL), and to this solution was added fumaric acid (100 mg, 0.86 mmol). The solution was concentrated to about 2 mL. Water (20 mL) was added to the resulting solution, which was then lyophilized on a freeze dryer for 48 hours to give (+)-4-benzo[b]thiophen-5-yl-2-methyl-7-morpholin-4-yl-1,2,3,4-tetrahydroisoquinoline, fumarate salt (284 mg, 56%, 98.6% AUC HPLC) as an off-white solid: [α]$^{25}_D$ +12.7° (c 0.06, methanol); mp 118-120° C.; $^1$H NMR (500 MHz, CD$_3$OD) δ 7.89 (d, J=8.5 Hz, 1H), 7.72 (s, 1H), 7.60 (d, J=5.4 Hz, 1H), 7.33 (d, J=5.4 Hz, 1H), 7.17 (d, J=8.3 Hz, 1H), 6.88-6.85 (m, 1H), 6.80-6.78 (m, 2H), 6.71 (s, 4H), 4.58 (dd, J=10.9, 6.0 Hz, 1H), 4.44-4.37 (m, 2H), 3.82-3.80 (m, 4H), 3.74 (dd, J=12.0, 6.1 Hz, 1H), 3.43-3.38 (m, 1H), 3.14-3.12 (m, 4H), 2.96 (s, 3H); ESI-MS m/z 365 [M+H]$^+$; Anal Calcd. For C$_{22}$H$_{24}$N$_2$OS.1.75C$_4$H$_4$O$_4$.0.5H$_2$O: C, 60.3; H, 5.60; N, 4.85. Found: C, 60.61; H, 5.57; N, 4.62.

Example 101

Preparation of (+/−)-(4-benzo[b]thiophen-5-yl-2-methyl-7-morpholin-4-ylmethyl-1,2,3,4-tetrahydroisoquinoline, fumarate salt A mixture of the product obtained in Example 103 (free base, 69 mg, 0.22 mmol), di(ethylene glycol) di-p-tosylate (92.5 mg, 0.22 mmol), Na$_2$CO$_3$ (71 mg, 0.67 mmol) and acetonitrile was refluxed overnight. After cooled to room temperature, the solid was filtered. The filtrate was diluted with dichloromethane (50 mL), washed with brine (100 mL), dried (Na$_2$SO$_4$) and concentrated. The residue was purified by a medium pressure chromatography (eluent: NH$_4$OH/MeOH/CH$_2$Cl$_2$ 3:27:970), followed by preparative HPLC to give (+/−)-(4-benzo[b]thiophen-5-yl-2-methyl-7-morpholin-4-ylmethyl-1,2,3,4-tetrahydroisoquinoline (26 mg, 31%) as a semi-solid. The solid was dissolved in methanol (2 mL), and to this solution was added fumaric acid (8.0 mg, 0.069 mmol). The solution was concentrated to about 1 mL, and to this solution was added water (5 mL). The resulting suspension was lyophilized on a freeze dryer overnight to give (+/−)-(4-benzo[b]thiophen-5-yl-2-methyl-7-morpholin-4-ylmethyl-1,2,3,4-tetrahydroisoquinoline, fumarate salt (30 mg, 87%) as a white solid: mp 115-118° C.; $^1$H NMR (500 MHz, CD$_3$OD) δ 7.89 (d, J=8.4 Hz, 1H), 7.73 (s, 1H), 7.60 (d, J=5.4 Hz, 1H), 7.34 (d, J=5.4 Hz, 1H), 7.26 (s, 1H), 7.21 (d, J=8.0 Hz, 1H), 7.16 (d, J=8.4 Hz, 1H), 6.90 (d, J=8.0 Hz, 1H), 6.70 (s, 3H), 4.62-4.61 (m, 1H), 4.40-4.30 (m, 2H), 3.71-3.63 (m, 7H), 3.34-3.32 (m, 1H), 2.89 (s, 3H), 2.59 (m, 4H); ESI-MS m/z 379 [M+H]$^+$.

Example 102

Preparation of (+/−)-(4-benzo[b]thiophen-5-yl-2-methyl-1,2,3,4-tetrahydroisoquinolin-7-ylmethyl)-dimethyl-amine, fumarate salt Step A: To a cold (0° C.) solution of (+/−)-4-benzo[b]thiophen-5-yl-2-methyl-1,2,3,4-tetrahydroisoquinoline-7-carbonitrile (180 mg, 0.59 mmol), which was obtained in the same manner as that of the product of Example 104, in THF (5 mL) was added LAH in THF (1.8 mL, 1.0 M, 1.8 mmol). The reaction was allowed to warm up to room temperature and stirred at room temperature for 5 hours. The reaction was quenched by ice water. The product was extracted with dichloromethane (2×100 mL). The organic layers were combined, washed with brine (100 mL), dried (Na$_2$SO$_4$) and concentrated. The residue was purified by medium pressure chromatography (eluent: NH$_4$OH/MeOH/DCM 1:9:190) to give 4-benzo[b]thiophen-yl-2-methyl-1,2,3,4-tetrahydroisoquinoline-7-carbaldehyde (35 mg, 19%) as a colorless oil: ESI-MS m/z 308 [M+H]$^+$.

Step B: To a solution of the product obtained from Step A (35 mg, 0.11 mmol) in THF (2 mL) was added dimethylamine in THF (0.12 mL, 2.0M) at room temperature. After stirred at room temperature for 2 h, NaBH$_4$ (13 mg, 0.34 mmol) was added to the reaction at room temperature. The reaction was further stirred at room temperature for 3 hours. The reaction was poured into saturated aqueous ammonium chloride solution (50 mL), and the product was extracted with dichloromethane (2×50 mL). The organic layers were combined, washed with brine (50 mL), dried (Na$_2$SO$_4$) and concentrated. The residue was purified by biotage column (eluent: NH$_4$OH/MeOH/DCM 3:27:970), followed by HPLC to give (+/−)-(4-benzo[b]thiophen-5-yl-2-methyl-1,2,3,4-tetrahydroisoquinolin-7-ylmethyl)-dimethyl-amine (10 mg, 26%) as a colorless thick oil. The compound was dissolved in methanol (2 mL), and to this solution was added fumaric acid (5.0 mg, 0.043 mmol). The solution was concentrated to about 1 mL, and to this solution was added water (5 mL). The resulting suspension was lyophilized on a freeze dryer overnight to give (+/−)-(4-benzo[b]thiophen-5-yl-2-methyl-1,2,3,4-tetrahydroisoquinolin-7-ylmethyl)-dimethyl-amine, fumarate salt (14 mg, 85%) as a white solid: mp 123-125° C.; NMR (500 MHz, CD$_3$OD) δ 7.85 (d, J=8.3 Hz, 1H), 7.70 (s, 1H), 7.58 (d, J=5.4 Hz, 1H), 7.32-7.31 (m, 2H), 7.22 (d, J=8.3 Hz, 1H), 7.15 (d, J=8.3 Hz, 1H), 6.99 (d, J=8.0 Hz, 1H), 6.70 (s, 5H), 4.58-4.52 (m, 1H), 4.19 (s, 2H), 4.02-3.94 (m, 2H), 3.43-3.38 (m, 1H), 2.95-2.94 (m, 1H), 2.80 (s, 6H), 2.65 (s, 3H); ESI-MS m/z 337 [M+H]$^+$.

Example 103

Preparation of (+)-C-(4-benzo[b]thiophen-5-yl-2-methyl-1,2,3,4-tetrahydroisoquinoline-7-yl)-methyl-amine, fumarate salt To a cold (0° C.) and stirred solution of the product obtained according to Example 104 (freebase, 120 mg, 0.40 mmol) in THF (5 mL) was added LAH in THF (1.2 mL, 1.2 mmol). The reaction was allowed to warm up to room temperature, and stirred for 24 h at room temperature. The reaction mixture was slowly added to ice water, and the product was extracted with dichloromethane (2×100 mL). The organic layers were combined, washed with brine (100 mL), dried (Na$_2$SO$_4$) and concentrated. The residue was purified by medium pressure chromatography (eluent: NH$_4$OH/MeOH/CH$_2$Cl$_2$ 1:9:190) to give C-(4-benzo[b]thiophen-5-yl-2-methyl-1,2,3,4-tetrahydroisoquinoline-7-yl)-methylamine (86 mg, 70%) [[α]$^{25}_D$ +71.1° (c 0.045, methanol)]. This compound (16 mg, 0.052 mmol) was dissolved in methanol (2 mL), and to the solution was added fumaric acid (6.0 mg, 0.052 mmol). The solution was concentrated to about 1 mL, and to this solution was added water (5 mL). The resulting suspension was lyophilized on a freeze dryer overnight to give C-(4-benzo[b]thiophen-5-yl-2-methyl-1,2,3,4-tetrahydroisoquinoline-7-yl)-methylamine, fumarate salt (18 mg, 56%, 95.3% AUC HPLC): mp 143-145° C.; $^1$H NMR (500 MHz, CD$_3$OD) δ 7.86 (d, J=8.4 Hz, 1H), 7.71 (s, 1H), 7.59 (d, J=5.4 Hz, 1H), 7.31 (d, J=5.4 Hz, 1H), 7.29 (s, 1H), 7.22 (d, J=8.1 Hz, 1H), 7.14 (d, J=8.4 Hz, 1H), 6.95 (d, J=8.1 Hz, 1H), 6.67 (s, 5H), 4.62-4.60 (m, 1H), 4.29-4.15 (m, 2H), 4.08 (s, 2H), 3.59-3.55 (m, 1H), 3.20-3.15 (m, 1H), 2.79 (s, 3H); ESI-MS m/z 309 [M+H]$^+$; Anal Calcd. For C$_{19}$H$_{20}$N$_2$S.2.5C$_4$H$_4$O$_4$.2.25H$_2$O: C, 54.50; C, 5.44; N, 4.38. Found: C, 54.72; H, 5.37; N, 4.04.

Example 104

Preparation of (+)-4-benzo[b]thiophen-5-yl-2-methyl-1,2,3,4-tetrahydroisoquinoline-7-carbonitrile, fumarate salt A mixture of the product obtained from Step A of Example 97 (300 mg, 0.702 mmol), zinc cynide (165 mg, 1.40 mmol) and DMF (6 mL) was purged with argon. To the mixture was added Pd(PPh$_3$)$_4$ (123 mg, 0.105 mmol) and the mixture was further purged with argon. It was heated at 120° C. for 4 h. After cooled to room temperature, the reaction was diluted with dichloromethane (100 mL), and filtered through celite. The filtrate was washed with brine (100 mL), dried (Na$_2$SO$_4$) and concentrated. The residue was purified by medium pressure chromatography (eluent: MeOH/EtOAc/hexanes 3:57:140) to a give (+)-4-benzo[b]thiophen-5-yl-2-methyl-1,2,3,4-tetrahydroisoquinoline-7-carbonitrile (68 mg, 32%) [[α]$^{25}_D$ +97.8° (c 0.05, methanol)] as a colorless semi-solid. The compound (68 mg, 0.22 mmol) was dissolved in methanol (2 mL), and to this solution was added fumaric acid (26 mg, 0.07 mmol). The solution was concentrated to about 1 mL, and to this solution was added water (5 mL). The resulting suspension was lyophilized on a freeze dryer overnight to give (+)-4-benzo[b]thiophen-5-yl-2-methyl-1,2,3,4-tetrahydroisoquinoline-7-carbonitrile, fumarate salt (50 mg, 53%, 96% AUC HPLC) as a white solid: mp 112-114° C.; $^1$H NMR (500 MHz, CD$_3$OD) δ 7.88 (d, J=8.3 Hz, 1H), 7.71 (s, 1H), 7.63 (s, 1H), 7.60 (d, J=5.4 Hz, 1H), 7.46 (d, J=7.8 Hz, 1H), 7.33 (d, J=5.4 Hz, 1H), 7.16 (d, J=8.4 Hz, 1H), 7.06 (d, J=8.1 Hz, 1H), 6.72 (s, 3H), 4.59 (dd, J=10.0, 6.3 Hz, 1H), 4.22 (d, J=15.5 Hz, 1H), 4.09 (d, J=15.5 Hz, 1H), 3.49 (dd, J=11.9, 6.0 Hz, 1H), 3.10-3.08 (m, 1H), 2.73 (s, 3H); ESI-MS m/z 305 [M+H]$^+$; Anal Calcd. For C$_{19}$H$_{16}$N$_2$S.1.75C$_4$H$_4$O$_4$.H$_2$O: C, 59.42; H, 4.79; N, 5.33. Found: C, 59.27; H, 4.43; N, 5.33.

Example 105

Preparation of (+/−)-4-(benzo[b]thiophen-5-yl)-1,2-dimethyl-1,2,3,4-tetrahydroisoquinoline, fumarate salt Step A: A mixture of 5-bromo-benzo[b]thiophene (1.28 g, 6.0 mmol), isoquinolin-4-boronic acid (1.04 g, 6 mmol) and cesium carbonate (1.95 g, 6.0 mmol) in 1,2-dimethoxyethane (50 mL) and 2 M sodium carbonate (6 mL) was degassed with argon. Pd(PPh$_3$)$_4$ (416 mg, 0.36 mmol) was added and the reaction mixture was heated at reflux for 15 hours. The cooled reaction mixture was diluted with water and extracted with ethyl acetate twice. The combined organic extracts were washed with brine, dried over anhydrous sodium sulfate and concentrated. Purification by column chromatography (silica gel, 10% to 30% ethyl acetate/hexanes) gave the desired product (510 mg, 32%): $^1$H NMR (CDCl$_3$, 500 MHz) δ 9.28 (s, 1H), 8.55 (s, 1H), 8.07-8.02 (m, 2H), 7.96-7.93 (m, 2H), 7.69-7.62 (m, 2H), 7.55 (d, J=5.4 Hz, 1H), 7.49 (dd, J=8.2, 1.6 Hz, 1H), 7.42 (dd, J=5.4, 0.4 Hz, 1H); ESI-MS m/z=262 [M+H]$^+$.

Step B: To an ice-cooled solution of the product from Step A (240 mg, 0.918 mmol) in dichloromethane (4 mL) was added methyl triflate (181 mg, 1.102 mmol). The reaction mixture was stirred at room temperature for 1 hour. The solvent was removed under the reduced pressure and the residue was dissolved in THF, cooled in an ice-bath and treated with methyl magnesium iodide (3M in ether, 0.62 mL, 1.86 mmol). The reaction mixture was stirred at 0° C. for 2 hours, quenched with saturated ammonium chloride and extracted with ethyl acetate three times. The combined extracts were washed with brine, dried over anhydrous sodium sulfate and concentrated to provide the desired product (300 mg, >99% crude yield): ESI MS m/z=292 [M+H]$^+$. This crude product was used in the next step without further purification.

Step C: To a solution of the crude product from Step B (300 mg, 0.918 mmol) in methanol (25 mL) was added sodium cyanoborohydride (300 mg, 4.77 mmol). The reaction mixture was stirred at room temperature overnight. Another two portions of cyanoborohydride (300 mg, 4.77 mmol) were added and the reaction mixture was stirred at room temperature overnight to complete the reaction. The reaction mixture was then quenched with water and extracted with ethyl acetate three times. The combined extracts were washed with brine, dried over sodium sulfate and concentrated. Purification by column chromatography (silica gel, 15% to 40% ethyl acetate/hexanes) provided the desired product (70 mg, 26% for 3 steps): $^1$H NMR (CDCl$_3$, 300 MHz) δ 7.79 (d, J=8.3 Hz, 1H), 7.65 (d, J=1.4 Hz, 1H), 7.42 (d, J=5.5 Hz, 1H), 7.28-7.12 (m, 4H), 7.03 (t, J=8.0 Hz, 1H), 6.81 (d, J=7.7 Hz, 1H), 4.41 (dd, J=9.4, 5.1 Hz, 1H), 3.71 (q, J=6.4 Hz, 1H), 3.18 (dd, J=11.6, 5.1 Hz, 1H), 2.74 (dd, J=11.6, 9.6 Hz, 1H), 2.48 (s, 3H), 1.50 (d, J=6.4 Hz, 3H); ESI MS m/z=294 [M+H]$^+$.

Step D: To a solution of the product from Step C (67 mg, 0.228 mmol) in methanol (2 mL) was added fumaric acid (27 mg, 0.228 mmol). The solvent was removed under reduced pressure. The residue was triturated with ethyl acetate and diethyl ether. The resulting precipitate was collected by filtration, washed with diethyl ether, and dried at 50° C. under vacuum to provide (+/−)-4-(benzothiophen-5-yl)-1,2-dimethyl-1,2,3,4-tetrahydroisoquinoline, fumarate salt as a white solid (70 mg, 75%, 98.0% AUC HPLC): mp 179-181° C.; $^1$H NMR (CD$_3$OD, 500 MHz) δ 7.89 (d, J=8.3 Hz, 1H), 7.73 (d, J=1.4 Hz, 1H), 7.60 (d, J=5.5 Hz, 1H), 7.40 (d, J=8.0 Hz, 1H), 7.35-7.31 (m, 2H), 7.21-7.14 (m, 2H), 6.87 (d, J=7.8 Hz, 1H), 6.69 (s, 2H), 4.70-4.63 (m, 2H), 3.74 (dd, J=12.4, 5.8 Hz, 1H), 3.56-3.51 (m, 1H), 2.96 (s, 3H), 1.78 (d, J=6.7 Hz, 3H); ESI MS m/z=294 [M+H]$^+$.

Example 106

Preparation of (+/−)-4-(benzo[b]thiophen-5-yl)-8-methoxy-2-methyl-1,2,3,4-tetrahydroisoquinoline, fumarate salt Step A: To a solution of 2-anisaldehyde (5.56 g, 40 mmol) in methanol (40 mL) was added methylamine (40 wt % solution in water, 6.9 mL, 80 mol) and acetic acid (240 mg, 4 mmol). The reaction mixture was stirred at room temperature for 16 hours and then cooled in an ice bath. To this ice-cooled mixture was added sodium borohydride (1.51 g, 40 mmol) in portions. The reaction mixture was stirred at room temperature for 3 hours. Most of the solvent was removed under the reduced pressure. The residue was diluted with water (100 mL) and ethyl acetate (100 mL). The organic layer was separated and the aqueous layer was extracted with ethyl acetate twice. The combined extracts were washed with brine, dried over sodium sulfate and concentrated to provide the desired 2-methoxybenzyl methylamine (4.7 g, 79%): $^1$H NMR (CDCl$_3$, 500 MHz) δ 7.23 (d, J=7.4 Hz, 2H), 6.91 (t, J=7.4 Hz, 1H), 6.86 (d, J=7.9 Hz, 1H), 3.83 (s, 3H), 3.75 (s, 2H), 2.42 (s, 3H); ESI MS m/z=152 [M+H]$^+$. This crude product was used in the next step without further purification.

Step B: To an ice-cooled mixture of the product from Step A (348 mg, 2.3 mmol) and diisopropylethylamine (394 mg, 3.0 mmol) in dichloromethane (10 mL) was added 1-(benzothiophen-5-yl)-2-bromo-ethanone (see Example 96 for preparation) (600 mg, 2.03 mmol). The reaction mixture was stirred at room temperature for 4 hours and then diluted with dichloromethane (100 mL). The mixture was washed with water and brine, dried over sodium sulfate and concentrated to provide the desired product (800 mg, >99% crude yield): ESI-MS m/z=326 [M+H]$^+$. This crude product was used in the next step without further purification.

Step C: To an ice-cooled solution of the product from Step B (800 mg, 2.0 mmol) in methanol (10 mL) was added sodium borohydride (80 mg, 2.1 mmol). The reaction mixture was stirred at 0° C. for 1 hour. The solvent was removed under reduced pressure. The residue was partitioned between dichloromethane and water. The aqueous was extracted with dichloromethane twice. The combined extracts were washed with brine, dried over sodium sulfate and concentrated to provide the desired product (700 mg, 99% crude yield): ESI-MS m/z=328 [M+H]$^+$. This crude product was used in the next step without further purification.

Step D: To an ice-cooled solution of the crude product from Step C (500 mg, 1.43 mmol) in dichloromethane (300 mL) was added methanesulfonic acid (1 mL, 15.4 mmol) dropwise. The reaction mixture was stirred at room temperature overnight. Another 1 mL of methanesulfonic acid was added and the reaction mixture was stirred at room temperature overnight. The mixture was adjusted to pH>8 by adding saturated sodium bicarbonate. The organic layer was separated and the aqueous was extracted with dichloromethane twice. The combined extracts were washed with brine, dried over sodium sulfate and concentrated. Purification by column chromatography (silica gel, 10 to 30% ethyl acetate/hexanes) provided the desired product (37 mg, 8% for 4 steps): $^1$H NMR (CDCl$_3$, 500 MHz) δ 7.78 (d, J=8.3 Hz, 1H), 7.65 (d, J=1.4 Hz, 1H), 7.41 (d, J=5.4 Hz, 1H), 7.26 (d, J=6.0 Hz, 1H), 7.17 (dd, J=8.3, 1.6 Hz, 1H), 7.03 (t, J=7.9 Hz, 1H), 6.69 (d, J=8.1 Hz, 1H), 6.50 (d, J=7.8 Hz, 1H), 4.39-4.37 (m, 1H), 3.86 (s, 3H), 3.84 (d, J=15.8 Hz, 1H), 3.49 (d, J=15.8 Hz, 1H), 3.05-3.01 (m, 1H), 2.61 (dd, J=11.4, 8.5 Hz, 1H), 2.46 (s, 3H); ESI-MS m/z=310 [M+H]$^+$.

Step E: To a solution of the product from Step D (37 mg, 0.119 mmol) in methanol (1 mL) was added fumaric acid (14 mg, 0.119 mmol). The solvent was removed under reduced pressure. The residue was triturated with ethyl acetate and diethyl ether. The resulting precipitate was collected by filtration, washed with diethyl ether, and dried at 50° C. under vacuum to provide (+/−)-4-(benzo[b]thiophen-5-yl)-8-methoxy-2-methyl-1,2,3,4-tetrahydroisoquinoline, fumarate salt as a white solid (40 mg, 91%, >99% AUC HPLC): mp 197-199° C.; $^1$HNMR (CD$_3$OD, 500 MHz) δ 7.85 (d, J=8.4 Hz, 1H), 7.69 (d, J=1.3 Hz, 1H), 7.58 (d, J=5.4 Hz, 1H), 7.32 (d, J=5.6 Hz, 1H), 7.15-7.12 (m, 2H), 6.86 (d, J=8.2 Hz, 1H), 6.66 (s, 1H), 6.46 (d, J=7.6 Hz, 1H), 4.60-4.56 (m, 1H), 4.35 (d, J=15.8 Hz, 1H), 3.90 (d, J=15.8 Hz, 1H), 3.89 (s, 3H), 3.52-3.48 (m, 1H), 3.15-3.11 (m, 1H), 2.80 (s, 3H); ESI-MS m/z=310 [M+H]$^+$.

Example 107

Preparation of (+/−)-4-benzo[b]thiophen-5-yl-8-methoxy-2-methy-1,2,3,4-tetrahydroisoquinolin-4-ol Step A: To a mixture of (2-iodo-6-methoxy-phenyl)-methanol (2.00 g, 7.65 mmol) in chloroform (35 mL) was added manganese (IV) oxide (17.96 g, 206.5 mmol). The reaction mixture was heated at reflux for 24 hours. The cooled reaction mixture was filtered through a small pad of diatomaceous earth. The filtrate was concentrated. Purification by flash column chromatography (silica gel; 10:90 ethyl acetate/hexanes) provided the desired product (0.43 g, 22%) as a yellow oil: $^1$H NMR (CDCl$_3$, 300 MHz) δ 10.25 (s, 1H), 7.59 (d, J=7.7 Hz, 1H), 7.13 (t, J=8.0 Hz, 1H), 6.99 (d, J=8.4 Hz, 1H), 3.91 (s, 3H).

Step B: The product from Step A (0.43 g, 1.64 mmol), and methylamine (40% aqueous solution in water, 0.14 mL, 1.67 mmol) was stirred in methanol (2.5 mL) at room temperature for 30 minutes. The reaction mixture was then cooled to 0° C. and treated with sodium borohydride (90 mg, 2.46 mmol). The reaction mixture was stirred at 0° C. for 1 hour, warmed to room temperature and stirred for an additional 3.5 hours. The reaction mixture was diluted with water, extracted with methylene chloride three times, dried over sodium sulfate, filtered, and the solvent was evaporated to afford the desired product (0.42 g, 93%) as a yellow oil: $^1$H NMR (CDCl$_3$, 500 MHz) δ 7.42 (d, J=7.9 Hz, 1H), 6.92 (t, J=8.1 Hz, 1H), 6.84 (d, J=7.8 Hz, 1H), 3.85 (s, 2H), 3.80 (s, 3H), 2.43 (s, 3H).

Step C: Product from Step B (0.43 g, 1.55 mmol) and N,N-diisopropylethylamine (0.26 g, 2.02 mmol) in methylene chloride (4 mL) was cooled to 0° C. and treated with 1-benzo[b]thiophen-5-yl-2-bromo-ethanone, which was prepared according to Step C in Example 98, (0.475 g, 1.86 mmol), portionwise over a period of 10 minutes. The reaction mixture was warmed to room temperature and stirred overnight. The reaction mixture was washed with water three times, dried over sodium sulfate, filtered, and the solvent was evaporated. Purification by column chromatography (40 g silica gel; 70:30 hexanes/ethyl acetate) afforded the product (0.39 g, 56%) as a light, yellow solid: $^1$H NMR (CDCl$_3$, 500 MHz) δ 8.49 (s, 1H), 7.94 (d, J=8.5 Hz, 1H), 7.86 (d, J=8.5 Hz, 1H), 7.54 (d, J=8.0 Hz, 1H), 7.48 (d, J=5.5 Hz, 1H), 7.40 (d, J=5.4 Hz, 1H), 6.97 (t, J=8.1 Hz, 1H), 6.86 (d, J=8.2 Hz, 1H), 3.86 (s, 2H), 3.79 (s, 2H), 3.73 (s, 3H), 2.45 (s, 3H).

Step D: To the product from Step C (0.39 g, 0.864 mmol) in THF (4 mL) was added n-butyllithium (1.6 M in hexane, 0.7 mL, 1.12 mmol) dropwise at −70° C. The reaction mixture was stirred for an additional 10 minutes. The reaction mixture was quenched with water and an aqueous solution of ammonium chloride (5 mL). The solution was extracted with ethyl acetate four times, washed with brine three times, dried over sodium sulfate, filtered, and concentrate in vacuo. Purification by column chromatography (40 g silica gel; 60:40 ethyl acetate/hexane) afforded 4-benzo[b]thiophen-5-yl-8-methoxy-2-methyl-1,2,3,4-tetrahydroisoquinolin-4-ol (0.15 g, 53%, 99% AUC HPLC) as an off-white solid: $^1$H NMR (CDCl$_3$, 500 MHz) δ 8.06 (s, 1H), 7.79 (d, J=8.5 Hz, 1H), 7.43 (d, J=5.4 Hz, 1H), 7.32 (d, J=5.4 Hz, 1H), 7.29-7.26 (m, 1H), 7.08 (t, J=8.0 Hz, 1H), 6.75 (d, J=7.5 Hz, 1H), 6.56 (d, J=7.8 Hz, 1H), 4.10 (d, J=8.7 Hz, 1H), 3.86 (s, 3H), 3.26 (d, J=15.9 Hz, 1H), 2.90 (d, J=11.5 Hz, 1H), 2.75 (d, J=11.5 Hz, 1H), 2.52 (s, 3H); ESI MS m/z 326 [M+H]$^+$.

Example 108

Preparation of (+)-4-benzo[b]-thiophen-5-yl-7-fluoro-2-methyl-1,2,3,4-tetrahydroisoquinolin-4-ol, fumaric acid salt and (−)-4-Benzo[b]-thiophen-5-yl-7-fluoro-2-methyl-1,2,3,4-tetrahydroisoquinolin-4-ol, fumaric acid salt Step A: A solution of sodium nitrite (4.5 g, 65 mmol) in water (75 mL) was cooled, and added to 2-amino-5-fluorobenzoic acid (10.0 g, 65 mmol) in 2 N hydrochloric acid (150 mL) at −5° C. and the mixture was stirred for 30 minutes.

In a separate vessel potassium iodide (21.5 g, 130 mmol) and copper (I) iodide (6.2 g, 32.5 mmol) was dissolved in water (75 mL) and cooled to −5° C. To this solution was added the above diazonium solution dropwise. The resulting red-brown precipitate which formed was allowed to warm to room temperature over a period of 4 hours. The precipitate was isolated by filtration and the solid was rinsed with water and dried under vacuum for over 24 hours. The brown solid was suspended in tert-butyl methyl ether and heated to 56° C.; the inorganic salt was filtered off. The filtrate was concentrated to a slurry and hexanes was added, causing more precipitate to form. The mixture was allowed to stir for over 1 hour, then filtered and rinsed with hexanes and dried further in a vacuum oven to provide 5-fluoro-2-iodo-benzoic acid (9.0 g, 52%): $^1$H NMR (500 MHz, CD$_3$OD) δ 8.01 (dd, J=8.7, 5.4 Hz, 1H), □ 7.55 (dd, J=9.2, 3.0 Hz, 1H), 7.05-7.01 (m, 1H).

Step B: The product of Step A (9.0 g, 34 mmol) was dissolved in tetrahydrofuran (50 mL) and cooled in an ice bath under nitrogen. A 2.0 M solution of borane-methylsulfide complex (42 mL, 8.5 mmol) in tetrahydrofuran was added dropwise and the mixture was stirred for 30 minutes. The ice bath was removed and the reaction mixture was refluxed for 2 hours at 70° C. The solvent was concentrated in vacuo and the residue was dissolved in saturated ammonium chloride and extracted twice with methylene chloride. The organic extract was washed with brine, dried over sodium sulfate, filtered, and concentrated in vacuo to afford the desired product (6.2 g, 73%) as an off-white solid: $^1$H NMR (500 MHz, CDCl$_3$) δ 7.78-7.69 (m, 1H), 7.31-7.22 (m, 1H), 6.83-6.75 (m, 1H), 4.64 (s, 2H), 2.04 (s, 1H).

Step C: The product from Step B (6.2 g, 25.0 mmol) was dissolved in chloroform (170 mL) and the solution was added to a suspension of manganese (IV) oxide (43.0 g, 675 mmol) in chloroform (150 mL) and the mixture was stirred overnight at 75° C. The reaction mixture was filtered through a pad of diatomaceous earth and concentrated in vacuo to afford the desired product (3.7 g, 60% crude yield) as a yellow solid: $^1$H NMR (500 MHz, CDCl$_3$) δ 10.01 (d, J=3.0 Hz, 1H), 7.92 (dd, J=8.7, 5.0 Hz, 1H), □ 7.60 (dd, J=8.6, 3.1 Hz, 1H), 7.10-7.06 (m, 1H).

Step D: The crude product from Step C (3.7 g, 14.8 mmol) was dissolved in methanol (20 mL) and 40% aqueous solution of N-methylamine (1.3 mL, 15.0 mmol) and the mixture stirred for 1.5 hours. The reaction mixture was then cooled in an ice bath and sodium borohydride (0.8 g, 22.0 mmol) was added portionwise and the mixture stirred at room temperature for over 2 hours. The mixture was concentrated under vacuum and the residue was dissolved in water (20 mL) and extracted with ethyl acetate (3×30 mL). The combined organic extracts were washed with brine (20 mL), dried over sodium sulfate and concentrated in vacuo to a yellow oil (3.3 g, 83% crude yield): $^1$H NMR (500 MHz, CDCl$_3$) δ 7.74-7.67 (m 1H), □ 7.12-7.02 (m, 1H), 6.68-6.64 (m, 1H), 3.66 (s, 2H), 2.39 (s, 3H), 1.58 (brs, 1H).

Step E: To a solution of 1-benzo[b]thiophen-5-yl-2-bromo-ethanone (see Example 98, Step C, was added N,N-diisopropylethylamine (0.51 mL, 2.9 mmol) and the mixture was stirred at room temperature for over 4 hours. The reaction mixture was quenched with water (5 mL) and the organic layer was dried over sodium sulfate, filtered and concentrated in vacuo then purified by column chromatography (5-40% ethyl acetate/hexanes) to give the desired product (0.97 g, 92%) as a yellow oil: $^1$H NMR (500 MHz, CDCl$_3$) δ 8.47 (d, J=1.0 Hz, 1H), □ 7.96-7.91 (m, 2H), 7.77 (dd, J=8.6, 5.6 Hz, 1H), 7.52 (d, J=5.4 Hz, 1H), 7.42 (d, J=5.4 Hz, 1H), 7.30 (dd, J=9.7, 3.1 Hz, 1H), 6.76-6.72 (m, 1H), 3.98 (s, 2H), 3.74 (s, 2H), 2.45 (s, 3H).

Step F: A 1.6 M solution of n-butyllithium in hexanes (3.3 mL, 5.3 mmol) was added to a cooled (−60° C.) solution of the product obtained in Step E (1.7 g, 4.1 mmol) in anhydrous tetrahydrofuran over 10 minutes. The reaction mixture was quenched with water (10 mL) and saturated ammonium chloride (5 mL). The organic layer was dried over sodium sulfate, concentrated in vacuo and purified by column chromatography (5-50% ethyl acetate/hexanes) to give the desired product (0.72 g, 60%): $^1$H NMR (500 MHz, CDCl$_3$) δ 8.08 (s, 1H), 7.89 (d, J=1.5 Hz, 1H), 7.79 (d, J=8.5 Hz, 1H), 7.54 (d, J=5.4 Hz, 1H), □ 7.32 (d, J=5.4 Hz, 1H), 7.26 (dd, J=8.5, 1.7 Hz, 1H), 7.05 (dd, J=8.6, 5.7 Hz, 1H), 6.94-6.86 (m, 2H), 3.84 (d, J=15.2 Hz, 1H), 3.58 (d, J=15.2 Hz, 1H), 2.96 (dd, J=11.9, 1.1 Hz, 1H), 2.81 (d, J=11.9 Hz, 1H), 2.42 (s, 3H).

Step G: This compound from Step F was resolved by preparative chiral HPLC (CHIRALCEL OJ column, using 90% heptane/10% isopropyl alcohol/0.1% diethylamine) to give the (+)-enantiomer [α]$^{25}_D$ +73.8° (0.07, methanol) and the (−)-enantiomer [α]$^{25}_D$ −60.0° (0.06, methanol). The (+)-enantiomer (14 mg, 0.05 mmol) was converted to the fumaric acid salt by dissolving the freebase in a minimal amount of ethanol, adding one equivalent of fumaric acid in enough methanol to completely dissolve the acid, then combining the two solutions and stirring for 2 hours. The solution was concentrated to a minimal volume, then refrigerated at −30° C. until crystal formation occurred. Filtration yielded 4-benzo[b]thiophen-5-yl-7-fluoro-2-methyl-1,2,3,4-tetrahydroisoquinolin-4-ol, fumerate salt (12.0 mg, >99%, 97.3% AUC HPLC) as an off-white solid: mp 95-97.0° C.; $^1$H NMR (500 MHz, CD$_3$OD) δ 8.00 (d, J=1.3 Hz, 1H), □ 7.87 (d, J=8.5 Hz, 1H), 7.60 (d, J=5.4 Hz, 1H), 7.37 (d, J=5.4 Hz, 1H), 7.28 (dd, J=1.5, 8.5 Hz, 1H), 7.06-6.97 (m, 3H), 6.71 (s, 2H), 4.32 (d, J=15.5 Hz, 1H), 4.18 (d, J=15.6 Hz, 1H), 3.43-3.35 (m, 2H), 2.81 (s, 3H).

The same procedure was used to transform the (−)-enantiomer (15 mg, 0.05 mmol) to the 4-benzo[b]thiophen-5-yl-7-fluoro-2-methyl-1,2,3,4-tetrahydroisoquinolin-4-ol, fumarate salt (16.5 mg, >99%, 98.5% AUC HPLC) as an off-white solid: mp 95-97° C.; $^1$H NMR (500 MHz, CD$_3$OD) δ 8.00 (d, J=1.2 Hz, 1H), 7.87 (d, J=8.5 Hz, 1H), 7.60 (d, J=5.4 Hz, 1H), 7.37 (d, J=5.5 Hz, 1H), 7.28 (dd, J=1.4 Hz, 8.5 Hz, 1H), 7.06-6.97 (m, 3H), 6.71 (s, 2H), 4.32 (d, J=15.5 Hz, 1H), 4.18 (d, J=15.4 Hz, 1H), 3.42-3.34 (m, 2H), 2.81 (s, 3H).

Example 109

Preparation of (+/−)-4-benzo[b]thiophen-5-yl-2-cyclopropyl-1,2,3,4-tetrahydroisoquinoline, fumarate salt A mixture of 4-benzo[b]thiophen-5-yl-1,2,3,4-tetrahydroisoquinoline (250 mg, 0.94 mmol, the preparation of which was described in Example 20), (1-ethoxycyclopropoxy)trimethylsilane (987 mg, 5.66 mmol), acetic acid (600 mg, 9.42 mmol), sodium cyanoborohydride (296 mg, 4.72 mmol), and molecular sieves (4 Å) was heated at reflux temperature for 16 hours, then cooled to room temperature. The mixture was treated with water, concentrated in vacuo, the residue dissolved in ethyl acetate and washed with 1N NaOH solution, then brine. The organic layer was dried over magnesium sulfate, concentrated and the residue purified by column chromatography (SiO$_2$, 12 g, 85% to 0% hexanes/ethyl acetate) to provide the desired tetrahydroisoquinoline (87 mg, 30%). This material was dissolved in methanol and treated with a solution of fumaric acid in methanol (5 mL) at 0° C. The solution was stirred at room temperature for 12 hours, then concentrated, and the solid was washed with diethyl ether providing 4-benzo[b]thiophen-5-yl-2-cyclopropyl-1,2,3,4-tetrahydroisoquinoline, fumarate salt (100 mg, 95.5% AUC HPLC): $^1$H NMR (CD$_3$OD, 300 MHz) δ 7.84 (d, J=8.3 Hz, 1H), 7.70 (d, J=1.4 Hz, 1H), 7.56 (d, J=5.5 Hz, 1H), 7.32 (d, J=5.1 Hz, 1H), 7.20-7.07 (m, 4H), 6.84 (d, J=7.5 Hz, 1H), 6.73 (s, 2H), 4.48-4.43 (m, 1H), 4.23-4.10 (m, 2H), 3.57-3.47 (m, 2H), 3.13-3.06 (m, 1H), 2.21-2.18 (m, 1H), 0.71-0.64 (m, 4H); ESI-MS m/z=306 [+H]$^+$.

Example 110

Preparation of (+/−)-(4-benzo[b]thiophen-5-yl-3,4-dihydro-1H-isoquinolin-2-yl)acetonitrile, fumarate salt A mixture of 4-benzo[b]thiophen-5-yl-1,2,3,4-tetrahydroisoquinoline (250 mg, 0.94 mmol, the preparation of which was described in Example 20), chloroacetonitrile (285 mg, 3.77 mmol), and cesium carbonate (614 mg, 1.88 mmol) in DMF (2 mL) was stirred at room temperature for 3 hours. The mixture was diluted with ethyl acetate, washed with 5% LiOH solution, then brine, and the organic layer dried over magnesium sulfate, and concentrated. The residue was purified by column chromatography ($SiO_2$, 12 g, 85% to 0% hexane/ethyl acetate) to provide the desired tetrahydroisoquinoline (90 mg, 31%). This material was dissolved in methanol and treated with a solution of fumaric acid in methanol (5 mL) at 0° C. The solution was stirred at room temperature for 12 hours, then concentrated, and the solid was washed with diethyl ether providing (4-benzo[b]thiophen-5-yl-3,4-dihydro-1H-isoquinolin-2-yl)-acetonitrile, fumarate salt (91 mg, 73%, 97.6% AUC HPLC): $^1$H NMR (DMSO-$d_6$, 300 MHz) δ 7.91 (d, J=8.3 Hz, 1H), 7.74-7.68 (m, 2H), 7.39 (d, J=5.4 Hz, 1H), 7.24-7.06 (m, 4H), 6.83 (d, J=7.6 Hz, 1H), 6.63 (s, 2H), 4.43-4.39 (m, 1H), 3.99-3.76 (m, 4H), 3.12-3.07 (m, 1H), 2.83-2.77 (m, 1H); ESI-MS m/z=306 $[M+H]^+$.

Example 111

Preparation of (+/−)-[2-(4-Benzo[b]thiophen-5-yl-3,4-dihydro-1H-isoquinolin-2-yl)-ethyl]dimethylamine, fumarate salt Step A: A mixture of 4-benzo[b]thiophen-5-yl-1,2,3,4-tetrahydroisoquinoline (250 mg, 0.94 mmol, the preparation of which was described in Example 20), 2-dimethylaminoethylchloride, hydrochloride salt (271 mg, 1.89 mmol), and cesium carbonate (1.23 g, 3.77 mmol) in DMF (4 mL) was stirred at room temperature for 3 days. The mixture was diluted with ethyl acetate, washed with 5% LiOH solution, then brine, and the organic layer dried over magnesium sulfate, and concentrated. The residue was purified by column chromatography ($SiO_2$, 12 g, 85% to 0% hexane/ethyl acetate) to provide the desired tetrahydroisoquinoline (7.0 mg, 2%). This material was dissolved in methanol and treated with a solution of fumaric acid in methanol (5 mL) at 0° C. The solution was stirred at room temperature for 12 hours, then concentrated, and the solid was washed with diethyl ether providing [2-(4-benzo[b]thiophen-5-yl-3,4-dihydro-1H-isoquinolin-2-yl)-ethyl]dimethylamine, fumarate salt (9.2 mg, 98%, 97.2% AUC HPLC): $^1$H NMR (CD$_3$OD, 500 MHz) δ 7.82 (d, J=8.3 Hz, 1H), 7.63 (d, J=1.4 Hz, 1H), 7.54 (d, J=5.5 Hz, 1H), 7.29-7.28 (m, 1H), 7.20-7.10 (m, 4H), 6.90-6.88 (m, 1H), 6.75 (s, 2H), 4.46-4.44 (m, 1H), 4.04-3.94 (m, 2H), 3.16-2.98 (m, 6H), 2.64 (s, 3H), 2.60 (s, 3H); ESI-MS m/z=337 $[M+H]^+$.

Example 112

Preparation of (+/−)-2-(4-Benzo[b]thiophen-5-yl-3,4-dihydro-1H-isoquinolin-2-yl)-ethanol, fumarate salt Step A: A mixture of 4-benzo[b]thiophen-5-yl-1,2,3,4-tetrahydroisoquinoline (40 mg, 0.15 mmol, the preparation of which was described in Example 20), 2-bromoethanol (23 mg, 0.18 mmol), and cesium carbonate (98 mg, 0.30 mmol) in DMF (4 mL) was stirred at room temperature for 12 hours. The mixture was diluted with ethyl acetate, washed with 5% LiOH solution, then brine, and the organic layer dried over magnesium sulfate, and concentrated. The residue was purified by column chromatography ($SiO_2$, 12 g, 85% to 0% hexane/ethyl acetate) to provide the desired tetrahydroisoquinoline (13 mg, 28%). This material was dissolved in methanol and treated with a solution of fumaric acid in methanol (5 mL) at 0° C. The solution was stirred at room temperature for 12 hours, then concentrated, and the solid was washed with diethyl ether providing 2-(4-benzo[b]thiophen-5-yl-3,4-dihydro-1H-isoquinolin-2-yl)ethanol, fumarate salt (18 mg, 99%, 96.0% AUC HPLC): $^1$H NMR (CD$_3$OD, 500 MHz) δ 7.92 (d, J=8.4 Hz, 1H), 7.79 (d, J=0.9 Hz, 1H), 7.62 (d, J=5.4 Hz, 1H), 7.36-7.30 (m, 3H), 7.25-7.20 (m, 2H), 6.92 (d, J=7.8 Hz, 1H), 6.74 (s, 2H), 4.77-4.74 (m, 1H), 4.69 (s, 2H), 4.01-3.97 (m, 3H), 3.65-3.58 (m, 1H), 3.48-3.46 (m, 2H), ESI-MS m/z=310 $[M+H]^+$.

Example 113

Preparation of (+)-4-(7-Methoxy-benzothiophen-6-yl)-2-methyl-1,2,3,4-tetrahydroisoquinoline, fumarate salt and (−)-4-(7-Methoxy-benzothiophen-6-yl)-2-methyl-1,2,3,4-tetrahydroisoquinoline, fumarate salt Step A: 2-(3-Thienyl)ethanol (4.26 g, 33.0 mmol) was dissolved in acetonitrile (10 mL) and was added to a cooled solution of dibromo-triphenylphosphorane (14.01 g, 33.0 mmol) in acetonitrile (20 mL) and pyridine (2.68 mL, 33.0 mmol) and was stirred for 2 hours. The solvents were concentrated and the residue was dissolved in ether (50 mL) and washed with saturated sodium bicarbonate solution, water, and brine. The organic layer was dried over sodium sulfate, filtered and concentrated to a semi-solid. The crude product was purified by column chromatography (silica gel, 10% ethyl acetate/hexanes) to give 3-(2-bromoethyl)thiophene (3.96 g, 62%) as a pale yellow oil: $^1$H NMR (500 MHz, CDCl$_3$) δ 7.28 (dd, J=4.9, 2.9 Hz, 1H), 7.06 (t, J=1.0 Hz, 1H), 6.97 (dd, J=4.9, 1.1 Hz, 1H), 3.56 (t, J=7.5 Hz, 2H), 3.20 (t, J=7.5 Hz, 2H).

Step B: The product from Step A (3.96 g, 21.0 mmol) was dissolved in tetrahydrofuran and was slowly added dropwise to a cooled mixture of sodium hydride (0.83 g, 40.0 mmol) in tetrahydrofuran (60 mL) and diethylmalonate (3.32 g, 21.0 mmol). The mixture stirred for an additional 10 minutes before the ice bath was removed, then stirred for an hour at room temperature. A catalytic amount of sodium iodide was added to the reaction mixture and stirred for 48 hours. The mixture was concentrated to a solid and redissolved in ethyl acetate, then washed with water and extracted with ethyl acetate twice. The organic extracts were dried over sodium sulfate, filtered and concentrated to a yellow oil. The oil was purified by column chromatography (silca gel, 10% ethyl acetate/hexanes) to give the desired malonate (3.0 g, 54%) as a colorless oil: $^1$H NMR (500 MHz, CDCl$_3$) δ 7.26-7.25 (m, 1H), 6.98-6.94 (m, 2H), 4.22-4.17 (m, 4H), 3.34 (t, J=7.5 Hz, 1H), 2.71-2.68 (m, 2H), 2.25-2.20 (m, 2H), 1.28-1.26 (m, 6H).

Step C: The product from Step B (3.0 g, 11.0 mmol) was dissolved in a 20% solution of potassium hydroxide (20 mL) and heated to 60° C. for 2.5 hours. The reaction mixture was returned to room temperature then cooled in an ice bath and added cold 6 N hydrogen chloride solution (25 mL) and diethyl ether (25 mL). The ice bath was removed and the reaction was heated to 40° C. overnight. The reaction was returned to room temperature and the aqueous layer was saturated with sodium chloride. The organic layer was extracted with diethyl ether twice, dried over sodium sulfate, filtered and concentrated to give 2-(2-thiophen-3-yl-ethyl)-malonic acid (2.4 g, 99%) as an oil: $^1$H NMR (500 MHz, CDCl$_3$) δ 7.24 (dd, J=4.6, 2.9 Hz, 1H), 6.99-6.95 (m, 2H), 3.34 (t, J=7.3 Hz, 1H), 2.76-2.73 (m, 2H), 2.26-2.12 (m, 2H).

Step D: The product from Step C (2.4 g, 11.0 mmol) was dissolved in 2-methoxyethyl ether (20 mL) and refluxed for 24 hours. The reaction was cooled to room temperature and basified to pH 9 with concentrated ammonium hydroxide. The mixture was extracted once with diethyl ether and set aside. The aqueous layer was acidified with concentrated hydrochloride acid and extracted four times with diethyl ether. The extract were combined and dried over sodium sulfate, filtered and concentrated to give 4-thiophen-3-yl-butyric acid (1.8 g, 95%) as an oil.

Step E: The product from Step D (1.8 g, 11.0 mmol) was dissolved in 2-methoxyethyl ether (2 mL) and added thionyl chloride (0.89 mL, 12.2 mmol) and pyridine (1 drop) and heated to 70° C. for 24 hours. The mixture was purified by column chromatography (silica gel, 0-15% ethyl acetate/hexanes as an eluent) to provide 5,6-dihydro-4H-benzothiophen-7-one (1.16 g, 72%): $^1$H NMR (500 MHz, CDCl$_3$) δ 7.61 (d, J=4.9 Hz, 1H), 6.97 (d, J=4.9 Hz, 1H), 2.89-2.87 (m, 2H), 2.63-2.60 (m, 2H), 2.21-2.16 (m, 2H).

Step F: The product from Step E (1.16 g, 7.6 mmol) was dissolved in chloroform (20 mL) and added to a hot suspension (70° C.) of cupric bromide (6.9 g, 30.0 mmol), ethyl acetate (15 mL) and stirred for 48 hours. The reaction mixture was returned to room temperature and filtered over a pad of diatomaceous earth. The filtrate was concentrated and re-dissolved in diethyl ether. Activated aluminum oxide, neutral for chromatography 50-200 micron was used to get rid of most of dark color. The suspension was filtered over a pad of diatomaceous earth and sodium sulfate. The mixture was concentrated to give 6,6-dibromo-5,6-dihydro-4H-benzothiophen-7-one (1.95 g, 87% crude) as a brown solid: $^1$H NMR (500 MHz, CDCl$_3$) δ 7.75 (d, J=4.9 Hz, 1H), 6.99 (d, J=4.9 Hz, 1H), 3.13-3.11 (m, 2H), 3.01-2.99 (m, 2H).

Step G: The product from Step F (1.90 g, 6.0 mmol) was dissolved in N,N-dimethylformamide (15 mL) and added sodium carbonate (3.25 g, 30.0 mmol) and heated to 100° C. for over 1.5 hours. The suspension was then stirred for 24 hours at room temperature. The reaction was filtered over sodium sulfate and rinsed with diethyl ether (50 mL). The filtrate was acidified to pH 1 with concentrated hydrochloride acid. The organic layer was washed (2×50 mL) with water, then extracted with 5% aqueous solution of potassium hydroxide (3×50 mL). The basic aqueous solution was acidified with concentrated hydrochloric acid and extracted (3×50 mL) with diethyl ether. The combined ether extracts were dried over sodium sulfate, filtered and concentrated to give 6-bromo-benzothiophen-7-ol (1.09 g, 77% crude) as a red-brown solid: $^1$H NMR (500 MHz, CDCl$_3$) δ 7.45-7.42 (m, 2H), 7.31-7.29 (m, 2H), 5.93 (s, 1H).

Step H: The product from Step G (1.08 g, 4.7 mmol) was dissolved in acetone (10 mL) and potassium carbonate (1.30 g, 9.4 mmol) and dimethyl sulfate (0.9 mL, 9.4 mmol) were added and the mixture was stirred at 50° C. for 24 hours. The mixture was cooled to room temperature and filtered over sodium sulfate. The reaction mixture was then concentrated to an oil and redissolved in methanol (10 mL), and sodium hydroxide (1.5 g) was added to decompose excess dimethyl sulfate. The mixture was stirred for 1 hour. Methanol was removed and the residue was dissolved in water (5 mL) and extracted (2×30 mL) with diethyl ether. The combined organic extract was dried over sodium sulfate, filtered and concentrated to an oil. The oil was purified on column chromatography (silica gel, 0-100% ethyl acetate/hexanes as an eluent) to give 6-bromo-7-methoxy-benzothiophene (0.96 g, 84%): $^1$H NMR (500 MHz, CDCl$_3$) δ 7.50 (d, J=8.4 Hz, 1H), 7.44-7.41 (m, 2H), 7.32 (d, J=5.4 Hz, 1H), 4.05 (s, 3H).

Step I: The product from Step H (0.59 g, 2.4 mmol), 4-isoquinoline boronic acid (0.63 g, 3.6 mmol), triphenyl phosphine (0.13 g, 0.5 mmol), 2 N sodium carbonate (1.5 mL) and ethylene glycol dimethyl ether (10 mL) were all added in a reaction vessel and evacuated, then purged under argon atmosphere for 15 minutes. Palladium acetate was then added to the reaction and the mixture was heated to 80° C. for 6 hours. The reaction was diluted with water (5 mL) and extracted with ethyl acetate three times. The extracts were combined and washed with brine, was dried over sodium sulfate, filtered and concentrated to a brown oil. The oil was purified on column chromatography (silica gel, 5-90% ethyl acetate/hexanes as an eluent) to give 4-(7-methoxy-benzothen-6-yl)-isoquinoline (0.50 g, 70%) as a yellow oil: $^1$H NMR (300 MHz, CDCl$_3$) δ 9.33 (s, 1H), 8.60 (s, 1H), 8.10-8.07 (m, 1H), 7.73-7.65 (m, 4H), 7.56 (d, J=5.4 Hz, 1H), 7.47 (d, J=5.4 Hz, 1H), 7.36 (d, J=8.1 Hz, 1H), 3.57 (s, 3H).

Step J: The product from Step I (0.99 g, 3.4 mmol) was dissolved in methylene chloride (10 mL) and methyl triflate (0.46 mL, 0.41 mmol) was added and stirred for 30 minutes. The solvent was concentrated to a yellow solid. The solid was re-dissolved in methanol (10 mL) and cooled in an ice bath. Sodium cyanoborohydride (1.29 g, 21 mmol) was added to the reaction mixture and stirred for 15 minutes then the reaction was allowed to warm up to room temperature over 2 hours. The reaction mixture was concentrated and partitioned between water (20 ml) and ethyl acetate (40 ml). The mixture was extracted with ethyl acetate (2×30 ml). The combined extract was washed with brine (50 ml), and the organic layer was dried over sodium sulfate, filtered and concentrated in vacuo. The oil was purified by column chromatography (silica gel, 10-70% ethyl acetate hexanes as an eluent) to give 4-(7-methoxy-benzothiophen-6-yl)-2-methyl-1,2,3,4-tetrahydroisoquinoline (0.61 g, 58%) as a yellow oil: $^1$H NMR (300 MHz, CDCl$_3$) δ 7.47 (d, J=8.2 Hz, 1H), 7.41 (d, J=5.4 Hz, 1H), 7.30 (d, J=5.4 Hz, 1H), 7.13-7.00 (m, 4H), 6.84 (d, J=7.6 Hz, 1H), 4.91-4.86 (m, 1H) 3.98 (s, 3H), 3.82 (d, J=14.8 Hz, 1H), 3.64 (d, J=14.8 Hz, 1H), 3.11-3.05 (m, 1H), 2.62 (dd, J=11.3, 9.0 Hz, 1H), 2.45 (s, 3H); ESI-MS mz 310 [M+H]$^+$.

This compound was resolved by preparative chiral HPLC (CHIRALPAK AD column, using 95% heptane/5% isopropyl alcohol/0.1% diethylamine) to give the (+)-enantiomer [[α]$^{25}_D$ +74.7° (c=0.19, methanol)] and the (−)-enantiomer [[α]$^{25}_D$ −84.0° (c=0.1, methanol)]. The (+)-enantiomer (58 mg, 0.2 mmol) was converted to the fumaric acid salt by dissolving the oil in a minimal amount of ethanol, adding one equivalent of fumaric acid in enough methanol to completely dissolve the acid, then combining the two solutions and stirring for 2 hours. The solution was concentrated to a minimal volume, then refrigerated at −30° C. until crystal formation occurred. Filtration yielded (+)-4-(7-methoxy-benzo[b]thiophen-6-yl)-2-methyl-1,2,3,4-tetrahydroisoquinoline, fumarate salt (14.8 mg, >99%, 96.2% AUC HPLC) as an off-white solid: mp 98-99° C.; $^1$H NMR (500 MHz, CD$_3$OD) δ 7.61-7.58 (m, 2H), 7.39 (d, J=5.3 Hz, 1H), ☐ 7.26 (d, J=3.2 Hz, 2H), 7.21-7.18 (m, 1H), 7.10 (d, J=8.2 Hz, 1H), 6.89 (d, J=7.7 Hz, 1H), 6.70 (s, 2H), 4.98 (dd, J=10.8, 6.3 Hz, 1H), 4.45-4.34 (m, 2H), 3.80 (s, 3H), 3.67-3.64 (m, 1H), 3.45-3.41 (m, 1H), 2.94 (s, 3H).

The same procedure was used to transform the (−)-enantiomer (63.6 mg, 0.21 mmol) to its salt to give (−)-4-(7-methoxy-benzothiophen-6-yl)-2-methyl-1,2,3,4-tetrahydroisoquinoline, fumarate salt (10.7 mg, >99%, 97.4% AUC HPLC) as an off-white solid: mp 98-99° C.; $^1$H NMR (500 MHz, CD$_3$OD) δ 7.61-7.58 (m, 2H), 7.39 (d, J=5.3 Hz, 1H), ☐ 7.26 (d, J=3.2 Hz, 2H), 7.21-7.18 (m, 1H), 7.10 (d, J=8.2 Hz, 1H), 6.89 (d, J=7.7 Hz, 1H), 6.70 (s, 2H), 4.98 (dd, J=10.8, 6.3 Hz, 1H), 4.45-4.34 (m, 2H), 3.80 (s, 3H), 3.67-3.64 (m, 1H), 3.45-3.41 (m, 1H), 2.94 (s, 3H).

Example 114

Preparation of (+/−)-4-benzo[b]thiophen-6-yl-2-methyl-1,2,3,4-tetrahydroisoquinolin-7-ol, maleate salt Step A: A mixture of 3-methoxy-thiophenol (25.0 g, 175.0 mmol), potassium carbonate (26.6 g, 192.0 mmol), and bromoacetaldehyde-dimethyl-acetal (32.3 mL, 175.0 mmol) was added in acetone (250.0 mL). The reaction mixture was stirred for over 24 hours. Water was added to the reaction and the mixture was extracted with ethyl acetate three times. The combined organic layer was washed with saturated sodium bicarbonate, saturated sodium chloride, dried over sodium sulfate, filtered and concentrated to give the desired product (48.0 g, 99% crude) as an oil: $^1$H NMR (500 MHz, CDCl$_3$) δ 7.20-7.17 (m, 1H), 6.96-6.92 (m, 2H), 6.73-6.71 (m, 1H), 4.65 (t, J=5.5 Hz, 1H), 3.79 (s, 3H), 3.68 (dd, J=9.3, 7.0 Hz, 2H), 3.55 (dd, J=9.3, 7.0 Hz, 2H), 3.14 (d, J=5.6 Hz, 2H), 1.21 (t, J=7.1 Hz, 6H).

Step B: The product from Step A (15.0 g, 58.5 mmol) was dissolved in methylene chloride (125 mL) and the solution was added to a solution of boron trifluoride diethyl etherate (7.86 mL, 62 mmol) in methylene chloride (900 mL) at room temperature under nitrogen. The reaction mixture was stirred for 30 minutes. Saturated sodium bicarbonate solution was added to the mixture until both phases were clear. The organic layer was extracted with methylene chloride twice. The combined organic extracts were dried over sodium sulfate and concentrated to an oil. The oil was purified by column chromatography (100% hexanes) to give the desired 6-methoxy benzothiophene (5.0 g, 52%) as a colorless oil: $^1$H NMR (500 MHz, CDCl$_3$) δ 7.50 (d, J=5.6 Hz, 1H), 7.46 (d, J=8.1 Hz, 1H), 7.3 (d, J=5.6 Hz, 1H), 7.29-7.25 (m, 1H), 6.75 (d, J=7.8 Hz, 1H), 3.96 (s, 3H).

Step C: The product from Step B (9.1 g, 55.0 mmol) was added neat to pyridine hydrochloride (25.6 g, 22 mmol) at 200° C. for over 2.5 hours. The mixture was allowed to cool then ice water was added and extracted with methylene chloride twice. The combined extract was dried over sodium sulfate, filtered and concentrated to an oil. The oil solidified on standing, which was then triturated with hexanes to give the desired product (4.42 g, 53.4%): $^1$H NMR (500 MHz, CDCl$_3$) δ 7.67 (d, J=8.6 Hz, 1H), 7.31 (d, J=2.2 Hz, 1H), 7.26-7.22 (m, 2H), 6.91 (dd, J=8.6, 2.3 Hz, 1H), 4.81 (s, 1H).

Step D: The product from Step C (2.9 g, 19.0 mmol) was dissolved in methylene chloride (40 mL) and triethylamine (4.0 mL, 29.0 mmol). The reaction mixture was cooled in an ice bath and trifluoromethanesulfonic anhydride (3.75 mL, 21.0 mmol) was added and was stirred for 30 minutes. Saturated sodium chloride solution was added to the mixture and extracted with methylene chloride twice. The organic extracts were dried over sodium sulfate, filtered and concentrated to a yellow solid (5.4 g, 99%): $^1$H NMR (500 MHz, CDCl$_3$) δ 7.86 (d, J=8.8 Hz, 1H), 7.81 (d, J=2.2 Hz, 1H), 7.56 (d, J=5.4 Hz, 1H), 7.37 (d, J=5.5 Hz, 1H), 7.28 (dd, J=8.7, 2.3 Hz, 1H).

Step E: A mixture of the product from Step D (5.4 g, 19 mmol), n-butyl vinyl ether (9.84 mL), triethylamine (5.33 mL, 38 mmol) and 1,3-bis(diphenylphosphino)propane (4.73 g, 11 mmol) in N,N-dimethylformamide was degassed with argon and stirred. Palladium(II) acetate was then added to the reaction mixture, which was then heated to 100° C. over 4 hours. The cooled reaction mixture was filtered over a pad of diatomaceous earth and concentrated to a yellow solid. The solid was dissolved in 1 N hydrochloric acid (50.0 mL) and stirred for 1 hour. The mixture was then concentrated and purified by column chromatography (5-25% ethyl acetate/hexanes as the eluent) to give the desired ketone (2.95 g, 87.5%) as a yellow solid: $^1$H NMR (500 MHz, CDCl$_3$) δ 8.52-8.51 (m, 1H), 7.97 (dd, J=8.4, 1.6 Hz, 1H), 7.88 (d, J=8.4 Hz, 1H), 7.67 (d, J=5.5 Hz, 1H), 7.41-7.39 (m, 1H), 2.68 (s, 3H).

Step F: The product from Step E (2.9 g, 16 mmol) was dissolved in ethyl acetate (20 mL) and added to a suspension of copper(II) bromide (7.35 g, 33.0 mmol) in chloroform (40 mL). The reaction mixture was refluxed for 3 hours then allowed to cool to room temperature. The mixture was filtered over a pad of diatomaceous earth and concentrated to a brown solid, which was purified by column chromatography (5-10% ethyl acetate/hexanes) to give the desired product (3.71 g, 88.5%): $^1$H NMR (500 MHz, CDCl$_3$) δ 8.56-8.55 (m, 1H), 7.98 (dd, J=8.4, 1.6 Hz, 1H), 7.90 (d, J=8.4 Hz, 1H), 7.72 (d, J=5.5 Hz, 1H), 7.41 (dd, J=5.4, 0.5 Hz, 1H), 4.53 (s, 2H).

Step G: The product from Step F (3.70 g, 14.5 mmol), 4-hydroxy-N-methyl benzylamine (2.37 g, 17.5 mmol) and N,N-diisopropylethylamine (2.8 mL, 16.0 mmol) were suspended in methylene chloride and stirred for over 24 hours. Water was added to the reaction mixture and was extracted with methylene chloride. The organic layer was then washed with 1N HCl, then with saturated sodium chloride solution. The solution was dried over sodium sulfate, filtered, concentrated in vacuo and purified by column chromatography (2-10% methanol/methylene chloride as the eluent) to give the desired product (2.94 g, 65%): $^1$H NMR (500 MHz, CDCl$_3$) δ 8.52 (d, J=0.5 Hz, 1H), 7.95 (dd, J=8.4, 1.5 Hz, 1H), 7.84 (d, J=8.4 Hz, 1H), 7.66 (d, J=5.4 Hz, 1H), 7.38 (d, J=5.4 Hz, 1H), 7.20 (d, J=7.8 Hz, 1H), 6.92-6.90 (m, 2H), 6.77-6.75 (m, 1H), 3.86 (s, 2H), 3.65 (s, 2H), 2.40 (s, 3H).

Step H: The product from Step G (2.94 g, 9.0 mmol) was dissolved in methanol and cooled in an ice bath. Sodium borohydride (0.43 g, 11.0 mmol) was added to the reaction mixture and stirred at room temperature for 1 hour. The methanol was concentrated in vacuo and the solid was re-dissolved in methylene chloride, washed with water twice and extracted with methylene chloride twice. The combined organic extract was washed with brine, dried over sodium sulfate, filtered and concentrated to a yellow solid (2.75 g, 93%): $^1$H NMR (500 MHz, CDCl$_3$) δ 7.91 (s, 1H), 7.77 (d, J=8.2 Hz, 1H), 7.41 (d, J=5.4 Hz, 1H), 7.32-7.30 (m, 2H), 7.20 (t, J=7.7 Hz, 1H), 6.87 (d, J=7.6 Hz, 1H), 6.81 (s, 1H), 6.75 (d, J=8.1 Hz, 1H), 4.88 (dd, J=3.6, 10.3 Hz, 1H), 3.71 (d, J=13.1 Hz, 1H), 3.49 (d, J=12.1 Hz, 1H), 2.67-2.56 (m, 2H), 2.34 (s, 3H); ESI-MS m/z 314 [M+H]$^+$.

Step I: The product from Step H (2.75 g, 8.8 mmol) was dissolved in methylene chloride (80 mL) and added to a solution of methanesulfonic acid (7.0 mL, 105 mmol) in methylene chloride (400 mL) and stirred for 10 minutes. The reaction mixture was cooled in an ice bath, then quenched with saturated sodium bicarbonate solution and stirred for 1 hour. The organic layer was washed with saturated sodium chloride solution, dried over sodium sulfate. The mixture was filtered, concentrated and purified by column chromatography (10% methanol/methylene chloride) to give the desired 4-benzo[b]thiophen-6-yl-2-methyl-1,2,3,4-tetrahydroisoquinolin-7-ol (0.98 g, 38%): $^1$H NMR (500 MHz, CDCl$_3$) δ 7.72 (t, J=8.2 Hz, 2H), 7.38 (d, J=5.4 Hz, 1H), 7.29 (d, J=5.3 Hz, 1H), 7.18 (d, J=8.1 Hz, 1H), 6.73 (d, J=8.3 Hz, 1H), 6.54 (dd, J=2.6 Hz, 8.3 Hz, 1H), 6.49 (s, 1H), 4.33 (t, J=5.9 Hz, 1H), 3.67 (d, J=14.9 Hz, 1H), 3.56 (d, J=7.4 Hz, 1H), 3.09-3.05 (m, 1H), 2.59 (t, J=8.9 Hz, 1H), 2.42 (s, 3H).

Step J: The product from Step I (0.10 g, 0.35 mmol) was converted to the maleic acid salt by dissolving the free base in a minimal amount of ethanol, adding one equivalent of maleic acid in enough methanol to completely dissolve the acid, then combining the two solutions and stirring over 1 hour. The solution was concentrated to a minimal volume, then refrigerated at −30° C. until crystal formation occurred to give 4-benzo[b]thiophen-6-yl-2-methyl-1,2,3,4-tetrahydroisoquinolin-7-ol, maleate salt (0.13 g, 90%, 98.7% AUC HPLC): $^1$H NMR (500 MHz, CD$_3$OD) δ 7.84 (d, J=8.2 Hz, 1H), 7.79 (s, 1H), 7.59 (d, J=5.4 Hz, 1H), 7.37 (d, J=5.4 Hz, 1H), 7.20 (d, J=8.2 Hz, 1H) 6.74-6.6.8 (m, 3H), 6.23 (s, 2H), 4.61-4.59 (m, 1H), 4.52-4.48 (m, 2H), 3.84-3.82 (m, 1H), 3.49-3.47 (m, 1H), 3.05 (s, 3H).

Example 115

Preparation of (+)-4-benzo[b]thiophen-6-yl-2-methyl-7-pyridazin-3-yl-1,2,3,4-tetrahydroisoquinoline, maleate salt and (−)-4-Benzo[b]thiophen-6-yl-2-methyl-7-pyridazin-3-yl-1,2,3,4-tetrahydroisoquinoline, maleate salt Step A: The product from Step J (1.54 g, 3.6 mmol) in Step K of the preparation of Example 148, bis(pinacolato)diborane (1.4 g, 5.4 mmol), potassium acetate (1.06 g, 10.8 mmol) in dimethlysulfoxide (50.0 mL) and degassed with argon. [1,1'-bis(diphenylphosphino)ferrocene]dichloropalladium(II), complex with dichloromethane (0.24 g, 0.3 mmol) was added and the mixture was heated to 100° C. for 4 hours. The reaction mixture was filtered over a pad of diatomaceous earth and rinsed with ethyl acetate. The mixture was washed with water twice and once with brine, then extracted with ethyl acetate three times. The combined organic extract was dried over sodium sulfate and concentrated to a dark brown oil (1.4 g, 99%): $^1$H NMR (500 MHz, CDCl$_3$) δ 7.65 (d, J=8.1 Hz, 1H), 7.62 (s, 1H), 7.50 (s, 1H), 7.43 (d, J=7.4 Hz, 1H), 7.33-7.31 (m, 2H), 7.22 (d, J=5.4 Hz, 1H), 7.09 (d, J=6.7 Hz, 1H), 4.39-4.36 (m, 1H), 3.76 (d, J=14.9 Hz, 1H), 3.62 (d, J=14.7 Hz, 1H), 3.06-3.03 (m, 1H), 2.61-2.56 (m, 1H), 2.39 (s, 3H); ESI-MS m/z 406 [M+H]$^+$.

Step B: The product from Step A (1.0 g, 2.6 mmol), 3,6-dichloropyridazine (0.59 g, 3.9 mmol), 2 M sodium carbonate (4.0 mL), and [1,1'-bis(diphenylphosphino)-ferrocene]dichloropalladium(II), complex with dichloromethane (0.15 g, 0.18 mmol) in N,N-dimethylformamide was heated to 100° C. for 4 hours. Water was added to the reaction mixture and extracted with ethyl acetate. The organic layer was washed with saturated sodium chloride solution and extracted with ethyl acetate twice. The combined organic layer was dried over sodium sulfate, concentrated in vacuo and purified by column chromatography (2-10% methanol/methylene chloride) to give the desired product (0.39 g, 45%): $^1$H NMR (500 MHz, CDCl$_3$) δ 7.88 (s, 1H), 7.80-7.78 (m, 1H), 7.74 (s, 1H), 7.67 (d, J=8.1 Hz, 1H), 7.53 (d, J=8.9 Hz, 1H), 7.40 (d, J=5.4 Hz, 1H), 7.31 (d, J=5.8 Hz, 1H), 7.21 (dd, J=1.5 Hz, 8.1 Hz, 1H), 7.06 (d, J=8.1 Hz, 1H), 4.45 (t, J=6.5 Hz, 1H), 3.88 (d, J=15.0 Hz, 1H), 3.74 (d, J=15.0 Hz, 1H), 3.14-3.10 (m, 1H), 2.71-2.67 (m, 1H), 2.47 (s, 3H).

Step C: The product from Step B (0.38 g, 0.98 mmol) was dissolved in ethanol (50 mL) and hydrazine monohydrate (0.47 mL, 9.8 mmol). Palladium on carbon (10 wt. %, 0.20 g) was added to the reaction mixture and heated to 100° C. for 4 hours. The mixture was cooled to room temperature and was filtered over a pad of diatomaceous earth, then rinsed with methylene chloride. The mixture was concentrated in vacuo and purified by column chromatography (2-10% methanol/methylene chloride) to give the desired product (0.21 g, 60%): $^1$H NMR (500 MHz, CDCl$_3$) δ 9.14 (d, J=4.8 Hz, 1H), 7.94 (s, 1H), 7.82 (d, J=8.6 Hz, 1H), 7.76 (s, 1H), 7.74 (s, 1H), 7.71 (d, J=8.1 Hz, 1H), 7.52-7.50 (m, 1H), 7.40 (d, J=5.4, 1H), 7.31 (d, J=5.4 Hz, 1H), 7.22 (d, J=8.2 Hz, 1H), 7.06 (d, J=8.1 Hz, 1H), 4.46 (t, J=6.4 Hz, 1H), 3.88 (d, J=14.9 Hz, 1H), 3.75 (d, J=14.9 Hz, 1H), 3.14-3.11 (m, 1H), 2.71-2.67 (m, 1H), 2.48 (s, 3H).

This compound was resolved by preparative chiral HPLC (CHIRALPAK AD column, using 80% heptane/20% ethanol/0.1% diethylamine) to give the (+)-enantiomer $[α]^{25}_D$ +53.3° (c=0.105, methanol) and the (−)-enantiomer $[α]^{25}_D$ −67.9° (c=0.109, methanol).

Step D: The (+)-enantiomer (0.09 g, 0.25 mmol) from Step C was converted to the maleic acid salt by dissolving the free base in a minimal amount of methanol, adding one equivalent of maleic acid in enough methanol to completely dissolve the acid, then combining the two solutions and stirring over 1 hour. The solution was concentrated to a minimal volume, then refrigerated at −30° C. until crystal formation occurred. Filtration yielded (+)-4-benzo[b]thiophen-6-yl-2-methyl-7-pyridazin-3-yl-1,2,3,4-tetrahyrdo-isoquinoline, maleate salt (86.0 mg, 99%, >99% AUC HPLC) as a brown solid: $^1$H NMR (500 MHz, CD$_3$OD) δ 9.17 (d, J=4.8 Hz, 1H), 8.18 (d, J=8.7 Hz, 1H), 8.09 (s, 1H), 7.94 (dd, J=1.6 Hz, 8.1 Hz, 1H), 7.89 (s, 1H), 7.87 (s, 1H), 7.81-7.79 (m, 1H), 7.62 (d, J=5.4 Hz, 1H), 7.39 (d, J=5.4 Hz, 1H), 7.27 (d, J=8.2 Hz, 1H), 7.14 (d, J=8.2 Hz, 1H), 6.24 (s, 2H), 4.81-4.77 (m, 2H), 4.70 (s, 2H), 3.94-3.90 (m, 1H), 3.69-3.66 (m, 1H), 3.10 (s, 3H).

The same procedure was used to transform the (−)-enantiomer, (0.09 mg, 0.25 mmol) to its maleic salt to give 4-benzo[b]thiophen-6-yl-2-methyl-7-pyridazin-3-yl-1,2,3,4-tetrahyrdo-isoquinoline, maleate salt (16.5 mg, 98.9%, >99% AUC HPLC) as an off-white solid: $^1$H NMR (500 MHz, CD$_3$OD) δ 9.17 (d, J=4.9 Hz, 1H), 8.17 (d, J=8.6 Hz, 1H), 8.08 (s, 1H), 7.94 (d, J=6.6 Hz, 1H), 7.89 (s, 1H), 7.87 (s, 1H), 7.81-7.79 (m, 1H), 7.62 (d, J=5.4 Hz, 1H), 7.39 (d, J=5.4 Hz, 1H), 7.26 (d, J=8.2 Hz, 1H), 7.14 (d, J=8.2 Hz, 1H), 6.24 (s, 2H), 4.79-4.77 (m, 1H), 4.68 (s, 2H), 3.93-3.89 (m, 1H), 3.67-3.65 (m, 1H), 3.09 (s, 3H).

Example 116

Preparation of (+/−)-4-benzo[b]thiophen-7-yl-2-methyl-1,2,3,4-tetrahydroisoquinoline, hydrochloric salt and (−)-4-benzo[b]thiophen-7-yl-2-methyl-1,2,3,4-tetrahydroisoquinoline, hydrochloric salt Step A: In a sealed tube, a solution of 7-bromobenzothiophene (330 mg, 1.55 mmol), 4-tributylstannanyl-isoquinoline (648 mg, 1.55 mmol) and triphenyl phosphine (41 mg, 0.155 mmol) in DMF (3 mL) was degassed by freeze/thaw. Triethylamine (108 μL, 0.775 mmol), palladium (II) acetate (17 mg, 0.078 mmol), and cuprous iodide (59 mg, 0.31 mmol) were added and the reaction mixture was heated to 100° C. for 3 days. The crude product was obtained via aqueous work up using CH$_2$Cl$_2$ as extracting solvent.

Step B: Methyl trifluoromethanesulfonate (179 μL, 1.58 mmol) was added to a solution of the crude product from Step A (375 mg, 1.44 mmol) and methylenechloride (3 mL) and stirred at room temperature for 3 hours. The solvent was evaporated. The residue was diluted with methanol (3 mL) and treated with sodium cyanoborohydride (226 mg, 3.6 mmol) and stirred at room temperature overnight. The solvent was evaporated and the residue was diluted with methylene chloride, washed with an aqueous solution of sodium hydroxide, dried over sodium sulfate and concentrated down to dryness.

This product was resolved by chiral HPLC (Chiralpak AD, 97:3 heptane/IPA with 0.1% diethylamine). The (+)enantiomer (127 mg, 35%) was obtained $[\alpha]^{24}_D$ +42.6° (c 0.6, methanol).

Step C: A solution of the product from Step B (127 mg, 0.455 mmol) and a 2N solution of HCl (455 μL, 0.909 mmol) in methylene chloride (1 mL) was stirred at room temperature. The solvent was evaporated. The residue was diluted with diethyl ether and filtered to afford (+/−)4-benzo[b]thiophen-7-yl-2-methyl-1,2,3,4-tetrahydroisoquinoline (97 mg, 68%) as a pale green solid: m.p. 228-230° C.; $^1$H NMR (CDCl$_3$, 500 MHz) δ 13.63 (br, 1H), 7.82 (d, J=7.7 Hz, 1H), 7.46-7.14 (m, 7H), 6.93-6.92 (m, 1H), 5.47-5.43 (m, 1H), 4.91 (d, J=14.9 Hz, 1H), 4.26 (d, J=13.6 Hz, 1H), 3.80-3.76 (m, 1H), 3.48-3.46 (m, 1H), 2.98 (s, 3H); ESI-MS m/z 280 [M+H]$^+$. Anal. Calcd. For C18H$_{17}$NS—HCl-0.25H$_2$O: C, 67.48; H, 5.82; N, 4.37; Cl, 11.07. Found: C, 67.78; H, 5.45; N, 4.24; Cl, 11.00.

Example 117

Preparation of (+/−)-4-benzofuran-2-yl-2-methyl-7-pyridazin-3-yl-1,2,3,4-tetrahydroisoquinoline, maleate salt Step A: To a solution of benzofuran-2-yl methyl ketone (10 g, 62.4 mmol) in carbon disulfide (80 mL) was added a solution of bromine (3.2 mL, 62.4 mmol) in carbon disulfide (80 mL) dropwise over 3 hours. The reaction mixture was filtered and the filtrate was concentrated under reduced pressure. The crude product obtained was purified by recrystallization from hot ethanol to give the desired α-bromoketone (10.14 g, 68%, two crops) as greenish-yellow crystals: $^1$H NMR (500 MHz, CDCl$_3$) δ 7.74 (d, J=7.9 Hz, 1H), 7.66 (d, J=0.8 Hz, 1H), 7.60 (dd, J=8.5, 0.6 Hz, 1H), 7.52 (td, J=7.2, 1.2 Hz, 1H), 7.35 (td, J=7.5, 0.8 Hz, 1H), 4.45 (s, 2H).

Step B: To a mixture of (3-methoxybenzyl)methylamine (4.7 g, 40 mmol) and triethylamine (8.6 mL, 62 mmol) in dichloromethane (62 mL) was added the α-bromoketone from Step A (7.4 g, 31 mmol) in small portions. The reaction mixture was stirred at room temperature for 2 hours, and then poured into water. The organic layer was separated, washed with water twice and brine, dried over sodium sulfate, filtered and concentrated under reduced pressure. The crude material was purified by column chromatography (85:15 hexanes/ethyl acetate, then 80:20 and 75:25 hexanes/ethyl acetate) to give the desired tertiary amine (6.78 g, 70%) as a brownish orange oil: $^1$H NMR (500 MHz, CDCl$_3$) δ 7.69 (d, J=7.8 Hz, 1H), 7.60 (d, J=0.9 Hz, 1H), 7.56 (dd, J=8.7, 0.8 Hz, 1H), 7.49-7.45 (m, 1H), 7.32-7.29 (m, 1H), 7.23 (d, J=8.0 Hz, 1H), 6.98-6.93 (m, 2H), 6.83-6.81 (m, 1H), 3.79 (s, 5H), 3.71 (s, 2H), 2.45 (s, 3H).

Step C: To an ice-cold solution of the product from Step B (6.78 g, 21.9 mmol) in methanol (56.5 mL) was added sodium borohydride (0.91 g, 24.1 mmol) in small portions. The reaction mixture was stirred at room temperature for 2 hours, and then concentrated under reduced pressure. The residue obtained was partitioned between dichloromethane and water. The organic layer was separated out, and the aqueous layer was re-extracted with dichloromethane twice.

The combined organic extract was washed with brine, dried over sodium sulfate, filtered and concentrated to give the desired alcohol (6.1 g, 89%) as a brownish orange oil: $^1$H NMR (300 MHz, CDCl$_3$) δ 7.60-7.50 (m, 1H), 7.45 (d, J=8.2 Hz, 1H), 7.40-7.10 (m, 3H), 6.95-6.68 (m, 4H), 4.91 (dd, J=9.8 Hz, 3.7 Hz, 1H), 3.78 (s, 3H), 3.70 (d, J=14.9 Hz, 1H), 3.59-3.51 (m, 1H), 3.00 (dd, J=12.4, 9.9 Hz, 1H), 2.77 (dd, J=12.4, 3.7 Hz, 1H), 2.32 (s, 3H).

Step D: To a solution of the crude product from Step C (6.1 g, 19.6 mmol) in dichloromethane (128 mL) was added methanesulfonic acid (12.7 mL, 196 mmol) dropwise via addition funnel. The dark brown mixture was stirred at room temperature for 40 minutes, and then added dropwise to an ice-cold solution of sodium hydroxide (128 mL, 2 M). The mixture obtained was diluted with water, and the organic layer was separated out. The aqueous layer was re-extracted with dichloromethane twice, and the combined organic extract was washed with brine, dried over sodium sulfate, filtered and concentrated under reduced pressure. The crude product was purified by column chromatography (95:5 to 70:30 hexanes/ethyl acetate, gradient), and the partially purified product obtained was dissolved in dichloromethane and washed with 2 M HCl (Note: The hydrochloride salt of the desired product could not be extracted into the aqueous layer). The organic layer was concentrated, and re-purified by column chromatography (90:10 dichloromethane/methanol) to give the hydrochloride salt of the desired product. A solution of the hydrochloride salt in dichloromethane was washed with a saturated solution of sodium bicarbonate, dried over sodium sulfate, filtered and concentrated to give the desired product (1.3 g, 23%) as a pale yellow oil: $^1$H NMR (500 MHz, CDCl$_3$) δ 7.44-7.00 (m, 2H), 7.21 (td, J=8.0, 1.5 Hz, 1H), 7.16 (td, J=7.4, 1.1 Hz, 1H), 7.10 (d, J=8.5 Hz, 1H), 6.73 (dd, J=8.5, 2.7 Hz, 1H), 6.63 (d, J=2.6 Hz, 1H), 6.34 (d, J=0.7 Hz, 1H), 4.38 (t, J=5.8 Hz, 1H), 3.79 (s, 3H), 3.71 (d, J=15.0 Hz, 1H), 3.58 (d, J=15.0 Hz, 1H), 3.06 (dd, J=11.4, 6.5 Hz, 1H), 2.95 (dd, J=11.4, 5.2 Hz, 1H), 2.45 (s, 3H). The undesired 5-methoxy regioisomer was also isolated (0.99 g, 17%) as a yellow solid.

Step E: To a solution of the product from Step D (1.3 g, 4.4 mmol) in acetic acid (20 mL) was added a solution of hydrogen bromide in acetic acid (20 mL, 33% solution). The mixture was heated at 100° C. overnight, and the cooled reaction mixture was concentrated under reduced pressure. The residue obtained was diluted with water and dichloromethane, and basified with a saturated solution of sodium bicarbonate. The organic layer was separated, and the aqueous layer was re-extracted with dichloromethane twice. The combined organic extract was dried over sodium sulfate, filtered and concentrated under reduced pressure to give the desired phenol (1.18 g, 96%) as a brown foam: H NMR (300 MHz, CDCl$_3$) δ 7.44-7.39 (m, 2H), 7.26-7.15 (m, 2H), 7.03 (d, J=8.3 Hz, 1H), 6.62 (dd, J=8.3, 2.6 Hz, 1H), 6.51 (d, J=2.1 Hz, 1H), 6.36 (s, 1H), 4.39 (t, J=5.9 Hz, 1H), 3.64 (d, J=15.1 Hz, 1H), 3.54 (d, J=15.1 Hz, 1H), 3.11-2.95 (m, 2H), 2.46 (s, 3H).

To an ice-cold solution of the phenol (1.18 g, 4.23 mmol) in dichloromethane (42 mL) were added pyridine (0.7 mL, 8.5 mmol) and triflic anhydride (0.9 mL, 5.5 mmol). The reaction mixture was stirred at 0° C. for 45 minutes, and then quenched with a saturated solution of sodium bicarbonate.

The organic layer was separated, and the aqueous layer was re-extracted with dichloromethane twice. The combined organic layer was dried over sodium sulfate, filtered and concentrated under reduced pressure. The crude product was purified by column chromatography (90:10 dichloromethane/hexanes, then dichloromethane) to give the desired triflate (1.34 g, 74%) as a yellow oil: $^1$H NMR (300 MHz, CDCl$_3$) δ 7.49-7.47 (m, 1H), 7.42 (d, J=8.1 Hz, 1H), 7.29-7.19 (m, 3H), 7.08-7.00 (m, 2H), 6.39 (s, 1H), 4.44 (t, J=5.8 Hz, 1H), 3.74 (d, J=15.5 Hz, 1H), 3.65 (d, J=15.3 Hz, 1H), 3.08 (dd, J=11.6, 6.7 Hz, 1H), 2.99 (dd, J=11.6, 5.2 Hz, 1H), 2.47 (s, 3H).

Step F: To a degassed mixture (Ar, 10 minutes) of the triflate from Step E (1.02 g, 2.48 mmol), potassium acetate (0.73 g, 7.44 mmol) and bis(pinacolato)diboron (0.69 g, 2.72 mmol) in dimethyl sulfoxide (16 mL) was added dichlorobis (phosphinoferrocene)palladium(II) (0.06 g, 0.07 mmol), and the mixture was heated at 80° C. for 3 hours. The cooled reaction mixture was partitioned between ethyl acetate and water, and the aqueous layer was re-extracted with dichloromethane. The combined organic extract was dried over sodium sulfate, filtered and concentrated under reduced pressure. The crude product was purified by column chromatography (dichloromethane, then 99:1 and 98:2 dichloromethane/methanol) to give the partially purified boronate ester (0.99 g) as a pale yellow oil: $^1$H NMR (300 MHz, CDCl$_3$) δ 7.65-7.55 (m, 2H), 7.45-7.30 (m, 2H), 7.26-7.10 (m, 3H), 6.34 (s, 1H), 4.45 (t, J=5.6 Hz, 1H), 3.74 (d, J=15.2 Hz, 1H), 3.62 (d, J=14.9 Hz, 1H), 3.07 (dd, J=11.5, 6.5 Hz, 1H), 3.04-2.90 (m, 1H), 2.45 (s, 3H), 1.34 (s, 12H).

To a mixture of the boronate ester (0.99 g, 2.56 mmol) and 3,6-dichloropyridazine (0.76 g, 5.11 mmol) in dimethylformamide (22 mL) was added a solution of sodium carbonate (0.83 g, 7.87 mmol) in water (5.7 mL). The solution was degassed (Ar, 10 minutes), and dichlorobis(phosphinoferrocene)palladium(II) (0.17 g, 0.20 mmol) was added to it. The reaction mixture was heated at 80° C. for 4 hours, cooled and partitioned between dichloromethane and water. The aqueous layer was then re-extracted with dichloromethane twice, and the combined organic extract was dried over sodium sulfate, filtered and concentrated under reduced pressure. The crude product was purified by column chromatography (dichloromethane, then 99:1, 98:2, 97:3 and 96:4 dichloromethane/methanol) to give the desired product (0.41 g, 43%) as a brown solid: $^1$H NMR (300 MHz, CDCl$_3$) δ 7.88 (d, J=1.3 Hz, 1H), 7.82-7.70 (m, 2H), 7.55 (d, J=9.0 Hz, 1H), 7.50-7.40 (m, 2H), 7.35 (d, J=8.2 Hz, 1H), 7.26-7.15 (m, 2H), 6.43 (s, 1H), 4.52 (t, J=5.9 Hz, 1H), 3.83 (d, J=15.2 Hz, 1H), 3.74 (d, J=15.2 Hz, 1H), 3.11 (dd, J=11.5, 6.8 Hz, 1H), 3.03 (dd, J=11.4, 5.4 Hz, 1H), 2.48 (s, 3H).

Step G: To a solution of the product from Step F (0.2 g, 0.5 mmol) in ethanol (10 mL) and methanol (7 mL) was added hydrazine monohydrate (0.5 g, 10 mmol), followed by 10% palladium on carbon (50 mg). The mixture was heated at 70° C. overnight, and cooled to room temperature. Additional hydrazine monohydrate (0.25 g, 5.0 mmol) and 10% palladium on carbon (50 mg) were added to the reaction mixture, which was then heated under reflux for 90 minutes. The cooled reaction mixture was filtered through celite, and the filtrate was concentrated under reduce pressure. The crude product was purified by flash column chromatography (90:10 dichloromethane/hexanes, then dichloromethane, and finally 99:1, 98:2, 97:3, 96:4 and 95:5 dichloromethane/methanol) to give the desired pyridazine derivative (0.11 g, 61%) as an off-white foam: $^1$H NMR (500 MHz, CDCl$_3$) δ 9.16 (dd, J=4.9, 1.6 Hz, 1H), 7.94 (d, J=1.4 Hz, 1H), 7.84 (dd, J=8.6, 1.6 Hz, 1H), 7.81 (dd, J=8.1, 1.9 Hz, 1H), 7.52 (dd, J=8.6, 4.9 Hz, 1H), 7.48 (dd, J=7.8, 1.1 Hz, 1H), 7.43 (dd, J=8.3, 0.6 Hz, 1H), 7.35 (d, J=8.1 Hz, 1H), 7.26-7.17 (m, 2H), 6.43 (s, 1H), 4.52 (t, J=5.9 Hz, 1H), 3.83 (d, J=15.1 Hz, 1H), 3.75 (d, J=15.1 Hz, 1H), 3.11 (dd, J=11.4, 6.7 Hz, 1H), 3.04 (dd, J=11.5, 5.2 Hz, 1H), 2.51 (s, 3H).

Step H: To a solution of the product from Step G (0.11 g, 0.31 mmol) in methanol (2 mL) was added maleic acid (36 mg, 0.31 mmol). The solution was diluted with water (12 mL) after 1 hour, and then lyophilized to give (+/−)-4-benzofuran-2-yl-2-methyl-7-pyridazin-3-yl-1,2,3,4-tetrahydroisoquinoline, maleate salt (142 mg, theoretical yield, 98.6% AUC HPLC) as a pale yellow solid: mp 96-98° C.; $^1$H NMR (500 MHz, CD$_3$OD) δ 9.18 (dd, J=4.9, 1.5 Hz, 1H), 8.20 (dd, J=8.7, 1.5 Hz, 1H), 8.10 (s, 1H), 8.03 (d, J=8.2 Hz, 1H), 7.81 (dd, J=8.7, 4.9 Hz, 1H), 7.59 (d, J=7.9 Hz, 1H), 7.47-7.37 (m, 2H), 7.32-7.21 (m, 2H), 6.78 (br s, 1H), 6.24 (s, 2H), 4.97 (t, J=7.1 Hz, 1H), 4.63 (app s, 2H), 3.94 (app d, J=6.6 Hz, 2H), 3.11 (s, 3H); ESI-MS m/z 342 [M+H]$^+$.

Example 118

Preparation of (+/−)-4-benzofuran-2-yl-2-methyl-7-morpholin-4-yl-1,2,3,4-tetrahydroisoquinoline, maleate salt Step A: To a solution of benzofuran-2-yl methyl ketone (10 g, 62.4 mmol) in carbon disulfide (80 mL) was added a solution of bromine (3.2 mL, 62.4 mmol) in carbon disulfide (80 mL) dropwise over 3 hours. The reaction mixture was filtered and the filtrate was concentrated under reduced pressure. The crude product obtained was purified by recrystallization from hot ethanol to give the desired α-bromoketone (10.14 g, 68%, two crops) as greenish-yellow crystals: $^1$H NMR (500 MHz, CDCl$_3$) δ 7.74 (d, J=7.9 Hz, 1H), 7.66 (d, J=0.8 Hz, 1H), 7.60 (dd, J=8.5, 0.6 Hz, 1H), 7.52 (td, J=7.2, 1.2 Hz, 1H), 7.35 (td, J=7.5, 0.8 Hz, 1H), 4.45 (s, 2H).

Step B: To a mixture of (3-methoxybenzyl)methylamine (4.7 g, 40 mmol) and triethylamine (8.6 mL, 62 mmol) in dichloromethane (62 mL) was added the α-bromoketone from Step A (7.4 g, 31 mmol) in small portions. The reaction mixture was stirred at room temperature for 2 hours, and then poured into water. The organic layer was separated, washed with water twice and brine, dried over sodium sulfate, filtered and concentrated under reduced pressure. The crude material was purified by column chromatography (85:15 hexanes/ethyl acetate, then 80:20 and 75:25 hexanes/ethyl acetate) to give the desired tertiary amine (6.78 g, 70%) as a brownish orange oil: $^1$H NMR (500 MHz, CDCl$_3$) δ 7.69 (d, J=7.8 Hz, 1H), 7.60 (d, J=0.9 Hz, 1H), 7.56 (dd, J=8.7, 0.8 Hz, 1H), 7.49-7.45 (m, 1H), 7.32-7.29 (m, 1H), 7.23 (d, J=8.0 Hz, 1H), 6.98-6.93 (m, 2H), 6.83-6.81 (m, 1H), 3.79 (s, 5H), 3.71 (s, 2H), 2.45 (s, 3H).

Step C: To an ice-cold solution of the product from Step B (6.78 g, 21.9 mmol) in methanol (56.5 mL) was added sodium borohydride (0.91 g, 24.1 mmol) in small portions. The reaction mixture was stirred at room temperature for 2 hours, and then concentrated under reduced pressure. The residue obtained was partitioned between dichloromethane and water. The organic layer was separated out, and the aqueous layer was re-extracted with dichloromethane twice.

The combined organic extract was washed with brine, dried over sodium sulfate, filtered and concentrated to give the desired alcohol (6.1 g, 89%) as a brownish orange oil: $^1$H NMR (300 MHz, CDCl$_3$) δ 7.60-7.50 (m, 1H), 7.45 (d, J=8.2 Hz, 1H), 7.40-7.10 (m, 3H), 6.95-6.68 (m, 4H), 4.91 (dd, J=9.8 Hz, 3.7 Hz, 1H), 3.78 (s, 3H), 3.70 (d, J=14.9 Hz, 1H), 3.59-3.51 (m, 1H), 3.00 (dd, J=12.4, 9.9 Hz, 1H), 2.77 (dd, J=12.4, 3.7 Hz, 1H), 2.32 (s, 3H).

Step D: To a solution of the crude product from Step C (6.1 g, 19.6 mmol) in dichloromethane (128 mL) was added methanesulfonic acid (12.7 mL, 196 mmol) dropwise via addition funnel. The dark brown mixture was stirred at room temperature for 40 minutes, and then added dropwise to an ice-cold solution of sodium hydroxide (128 mL, 2 M). The mixture obtained was diluted with water, and the organic layer was separated out. The aqueous layer was re-extracted with dichloromethane twice, and the combined organic extract was washed with brine, dried over sodium sulfate, filtered and concentrated under reduced pressure. The crude product was purified by column chromatography (95:5 to 70:30 hexane/ethyl acetate, gradient), and the partially purified product obtained was dissolved in dichloromethane and washed with 2 M HCl (Note: The hydrochloride salt of the desired product could not be extracted into the aqueous layer). The organic layer was concentrated, and re-purified by column chromatography (90:10 dichloromethane/methanol) to give the hydrochloride salt of the desired product. A solution of the hydrochloride salt in dichloromethane was washed with a saturated solution of sodium bicarbonate, dried over sodium sulfate, filtered and concentrated to give the desired product (1.3 g, 23%) as a pale yellow oil: $^1$H NMR (500 MHz, CDCl$_3$) δ 7.44-7.00 (m, 2H), 7.21 (td, J=8.0, 1.5 Hz, 1H), 7.16 (td, J=7.4, 1.1 Hz, 1H), 7.10 (d, J=8.5 Hz, 1H), 6.73 (dd, J=8.5, 2.7 Hz, 1H), 6.63 (d, J=2.6 Hz, 1H), 6.34 (d, J=0.7 Hz, 1H), 4.38 (t, J=5.8 Hz, 1H), 3.79 (s, 3H), 3.71 (d, J=15.0 Hz, 1H), 3.58 (d, J=15.0 Hz, 1H), 3.06 (dd, J=11.4, 6.5 Hz, 1H), 2.95 (dd, J=11.4, 5.2 Hz, 1H), 2.45 (s, 3H). The undesired 5-methoxy regioisomer was also isolated (0.99 g, 17%) as a yellow solid.

Step E: To a solution of the product from Step D (1.3 g, 4.4 mmol) in acetic acid (20 mL) was added a solution of hydrogen bromide in acetic acid (20 mL, 33% solution). The mixture was heated at 100° C. overnight, and the cooled reaction mixture was concentrated under reduced pressure. The residue obtained was diluted with water and dichloromethane, and basified with a saturated solution of sodium bicarbonate. The organic layer was separated, and the aqueous layer was re-extracted with dichloromethane twice. The combined organic extract was dried over sodium sulfate, filtered and concentrated under reduced pressure to give the desired phenol (1.18 g, 96%) as a brown foam: H NMR (300 MHz, CDCl$_3$) δ 7.44-7.39 (m, 2H), 7.26-7.15 (m, 2H), 7.03 (d, J=8.3 Hz, 1H), 6.62 (dd, J=8.3, 2.6 Hz, 1H), 6.51 (d, J=2.1 Hz, 1H), 6.36 (s, 1H), 4.39 (t, J=5.9 Hz, 1H), 3.64 (d, J=15.1 Hz, 1H), 3.54 (d, J=15.1 Hz, 1H), 3.11-2.95 (m, 2H), 2.46 (s, 3H).

To an ice-cold solution of the phenol (1.18 g, 4.23 mmol) in dichloromethane (42 mL) were added pyridine (0.7 mL, 8.5 mmol) and triflic anhydride (0.9 mL, 5.5 mmol). The reaction mixture was stirred at 0° C. for 45 minutes, and then quenched with a saturated solution of sodium bicarbonate. The organic layer was separated out, and the aqueous layer was re-extracted with dichloromethane twice. The combined organic layer was dried over sodium sulfate, filtered and concentrated under reduced pressure. The crude product was purified by column chromatography (90:10 dichloromethane/hexanes, then dichloromethane) to give the desired triflate (1.34 g, 74%) as a yellow oil: $^1$H NMR (300 MHz, CDCl$_3$) δ 7.49-7.47 (m, 1H), 7.42 (d, J=8.1 Hz, 1H), 7.29-7.19 (m, 3H), 7.08-7.00 (m, 2H), 6.39 (s, 1H), 4.44 (t, J=5.8 Hz, 1H), 3.74 (d, J=15.5 Hz, 1H), 3.65 (d, J=15.3 Hz, 1H), 3.08 (dd, J=11.6, 6.7 Hz, 1H), 2.99 (dd, J=11.6, 5.2 Hz, 1H), 2.47 (s, 3H).

Step F: To a mixture of the triflate from Step E (0.1 g, 0.24 mmol), 2-(dicyclohexylphosphino)-2',4',6'-triisopropylbiphenyl (69 mg, 0.14 mmol) and cesium carbonate (0.20 g, 0.61 mmol) in toluene (2.6 mL) was added morpholine (42 µL, 0.49 mmol), and the mixture was degassed (Ar, 10 minutes). Palladium (II) acetate (8 mg, 0.04 mmol) was added to the mixture, which was then heated under reflux overnight. The cooled reaction mixture was diluted with methanol, filtered through celite, and the filtrate was concentrated under reduced pressure.

This reaction was repeated twice more (0.24 mmol of triflate per run), and the combined crude product was partially purified by column chromatography (dichloromethane, then 98:2, 97:3 and 96:4 dichloromethane/methanol) to give the desired product (103 mg) as a brown oil. This material was purified further by preparative thin layer chromatography (Analtech 1 mm plates; eluent 95:5 dichloromethane/methanol) to give the desired product (23 mg, 9%) as a pale yellow oil: $^1$H NMR (500 MHz, CDCl$_3$) δ 7.45-7.43 (m, 1H), 7.41 (d, J=8.0 Hz, 1H), 7.22-7.18 (m, 1H), 7.16 (td, J=7.5, 1.1 Hz, 1H), 7.09 (d, J=8.5 Hz, 1H), 6.75 (dd, J=8.5, 2.6 Hz, 1H), 6.62 (d, J=2.5 Hz, 1H), 6.35 (s, 1H), 4.37 (t, J=5.7 Hz, 1H), 3.85 (t, J=4.8 Hz, 4H), 3.69 (d, J=15.2 Hz, 1H), 3.57 (d, J=14.9 Hz, 1H), 3.13 (t, J=4.8 Hz, 4H), 3.05 (dd, J=11.4, 6.5 Hz, 1H), 2.94 (dd, J=11.4, 5.2 Hz, 1H), 2.45 (s, 3H).

To a solution of the morpholine derivative (23 mg, 0.06 mmol) in methanol (2 mL) was added maleic acid (7.5 mg, 0.06 mmol), and the mixture was stirred at room temperature for 1 hour. The solution was concentrated to dryness, and the residue was triturated with diethyl ether (2 mL) and methanol (2-3 drops) twice. The supernatant was removed via pipette, and the residue was dissolved in methanol (2 mL) and water (10 mL), and the solution was lyophilized to give (+/−)-4-benzofuran-2-yl-2-methyl-7-morpholin-4-yl-1,2,3,4-tetrahydroisoquinoline, maleate salt (26 mg, 86%, 98.4% AUC HPLC) as a tan solid: mp 95-97° C.; $^1$H NMR (500 MHz, CD$_3$OD) δ 7.55 (d, J=7.6 Hz, 1H), 7.42 (d, J=8.0 Hz, 1H), 7.29-7.25 (m, 1H), 7.22 (td, J=7.4, 0.9 Hz, 1H), 7.15 (br s, 1H), 7.00-6.95 (m, 1H), 6.82 (d, J=2.4 Hz, 1H), 6.75-6.50 (br s, 1H), 6.25 (s, 2H), 4.80-4.75 (m, 2H), 4.60-4.40 (m, 2H), 3.88 (br s, 1H), 3.82 (app t, J=4.8 Hz, 4H), 3.16 (app t, J=4.8 Hz, 4H), 3.08 (s, 3H); ESI-MS m/z 349 [M+H]$^+$.

Example 119

Preparation of (+)-4-(1H-Indol-6-yl)-2-methyl-1,2,3,4-tetrahydroisoquinoline, fumarate salt Step A: Racemic 4-(1H-indol-6-yl)-2-methyl-1,2,3,4-tetrahydroisoquinoline was prepared from 6-bromo-1H-indole by a method similar to the one described in Example 122 (Steps A to D). This racemic compound (450 mg) was separated on semi-prep chiral HPLC (Chiralcel OD, 90% heptane/isopropanol with 0.1% diethylamine). Each of the resulting enantiomers was dissolved in methanol and treated with a solution of maleic acid in methanol (5 mL) at 0° C. The solution was stirred at room temperature overnight, then concentrated, and the solid was slurried with diethyl ether, filtration provided (+)-4-(1H-indol-6-yl)-2-methyl-1,2,3,4-tetrahydroisoquinoline, fumarate salt [160 mg, 42%, >99% AUC HPLC, 100% AUC chiral HPLC (free base)]: $^1$H NMR (CD$_3$OD, 300 MHz) δ 7.55 (d, J=8.2 Hz, 1H), 7.31-7.21 (m, 5H), 6.99 (d, J=7.7 Hz, 1H), 6.85 (dd, J=8.2, 1.5 Hz, 1H), 6.74 (s, 4H), 6.46-6.44 (m, 1H), 4.67-4.58 (m, 3H), 3.89-3.83 (m, 1H), 3.64-3.60 (m, 1H), 3.07 (s, 3H); ESI-MS m/z=263 [M+H]$^+$, $[\alpha]_D^{25}$ +108.0° (c 0.08, MeOH, free base), Anal. Calcd. for $C_{18}H_{18}N_2 \cdot 2C_4H_4O_4 \cdot 0.375\ H_2O$: C, 62.29; H, 5.38; N, 5.59. Found: C, 61.94; H, 5.19; N, 6.18.

Example 120

Preparation of (+/−)-4-(3-chloro-1H-indol-6-yl)-2-methyl-1,2,3,4-tetrahydroisoquinoline, maleate salt Step A: To a solution of 4-bromo-2-nitrotoluene (7.9 g, 36.6 mmol) in dimethylformamide (73 mL) were added N,N-dimethylformamide dimethylacetal (14.5 mL, 110 mmol) and pyrrolidine (4.7 mL), and the mixture was heated at 110° C. for 90 minutes. The cooled reaction mixture was diluted with diethyl ether, and washed with water. The aqueous layer was re-extracted with diethyl ether twice, and the combined organic extract was dried over sodium sulfate, filtered and concentrated under reduced pressure. The residue obtained was dissolved in aqueous acetic acid (245 mL, 80%), and heated to 75° C. Zinc powder (20.8 g, 318 mmol) was added to the hot solution in small portions over 2 hours. The reaction mixture was then heated at 85° C. for 3 hours and 30 minutes, cooled to room temperature and then to 0° C. The precipitate formed was removed by filtration, and the filtrate was diluted with ethyl acetate and washed with water twice. The organic extract was dried over sodium sulfate, filtered and concentrated under reduced pressure to give a brown oil. The crude product was purified by flash column chromatography (95:5 hexanes/ethyl acetate, then 90:10 hexanes/ethyl acetate) to give 6-bromoindole as a grey solid (2.61 g, 36%): H NMR (500 MHz, CDCl$_3$) δ 8.14 (br s, 1H), 7.53 (s, 1H), 7.49 (d, J=8.4 Hz, 1H), 7.21 (dd, J=8.4, 1.7 Hz, 1H), 7.17-7.15 (m, 1H), 6.53-6.51 (m, 1H).

Step B: To an ice-cold solution of 6-bromoindole (0.5 g, 2.55 mmol) in methanol (10 mL) was added N-chlorosuccinimide (0.34 g, 2.55 mmol) in small portions. The reaction mixture was stirred at 0° C. for 15 minutes, and at room temperature for 1 hour, and then poured into ice-cold water. The aqueous mixture was extracted with diethyl ether four times, and the combined organic extract was washed with brine, dried over sodium sulfate, filtered and concentrated under reduced pressure. The residue obtained was dissolved in dichloromethane, dried over sodium sulfate, filtered and concentrated under reduced pressure. To this residue was added di-t-butyldicarbonate (0.56 g, 2.55 mmol), followed by N,N-dimethylaminopyridine (25 mg) and acetonitrile (7 mL), and the mixture was stirred for 30 minutes. The reaction mixture was poured into water, and the product was extracted into ethyl acetate twice. The combined organic extract was washed with brine, dried over sodium sulfate, filtered and concentrated under reduced pressure. The crude product was purified by column chromatography (95:5 hexanes/ethyl acetate) to give the desired compound (0.61 g, 72%) as a brown solid: $^1$H NMR (500 MHz, CDCl$_3$) δ 8.38 (br s, 1H), 7.53 (s, 1H), 7.46-7.41 (m, 2H), 1.66 (s, 9H).

Step C: To a mixture of the product from Step B (0.15 g, 0.45 mmol) and isoquinoline-4-boronic acid (0.10 g, 0.54 mmol) in ethylene glycol dimethyl ether (2.1 mL) was added a solution of cesium carbonate (0.45 mL, 2 M), and the mixture was degassed (Ar, 10 minutes). Tetrakis(triphenylphosphine)palladium (0) (26 mg, 0.02 mmol) was added to the mixture, which was then heated under reflux for 5 hours. The cooled reaction mixture was partitioned between ethyl acetate and water, and the aqueous layer was re-extracted with ethyl acetate twice. The combined organic layer was dried over sodium sulfate, filtered and concentrated under reduced pressure. The crude product was purified by flash column chromatography (98:2 dichloromethane/methanol) to give the desired product (82 mg, 48%) as a pink foam: $^1$H NMR (500 MHz, CDCl$_3$) δ 9.28 (s, 1H), 8.55 (s, 1H), 8.32 (br s, 1H), 8.06 (d, J=7.6 Hz, 1H), 7.95 (d, J=8.2 Hz, 1H), 7.74 (d, J=8.0 Hz, 1H), 7.68-7.64 (m, 3H), 7.47 (dd, J=8.0, 1.4 Hz, 1H), 1.60 (s, 9H).

Step D: To an ice-cold solution of the product from Step C (80 mg, 0.21 mmol) in dichloromethane was added methyl triflate (26 μL, 0.23 mmol) dropwise. The reaction mixture was stirred at 0° C. for 15 minutes, and then concentrated to dryness. The residue was taken up in methanol (2.5 mL), and cooled to 0° C. Sodium cyanoborohydride (0.13 g, 2.11 mmol) was added in small portions, and the reaction mixture was stirred at 0° C. for 1 hour and 15 minutes. The reaction mixture was concentrated and partitioned between water and dichloromethane. The aqueous layer was re-extracted with dichloromethane, and the combined organic extract was dried over sodium sulfate, filtered and concentrated under reduced pressure. The crude product was purified by preparative thin layer chromatography (Analtech 1 mm plates; eluent: 95:5 dichloromethane/methanol) to give the desired product (55 mg, 65%) as a white solid: $^1$H NMR (500 MHz, CDCl$_3$) δ 8.00 (br s, 1H), 7.54 (s, 1H), 7.48 (d, J=8.1 Hz, 1H), 7.15-7.04 (m, 4H), 6.87 (d, J=7.7 Hz, 1H), 4.42 (t, J=6.7 Hz, 1H), 3.76 (d, J=15.1 Hz, 1H), 3.65 (d, J=14.8 Hz, 1H), 3.07 (dd, J=11.5, 5.4 Hz, 1H), 2.64 (dd, J=11.3, 8.5 Hz, 1H), 2.44 (s, 3H), 1.59 (s, 9H).

To a solution of the above-obtained chloroindole derivative (55 mg, 0.14 mmol) in dioxanes (3 mL) was added 2 M HCl (5 mL, solution in ether), and the mixture was stirred at room temperature for 5 days. The reaction mixture was concentrated, dissolved in 4 M HCl (5 mL, solution in dioxanes), and stirred overnight. The reaction mixture was concentrated, and the crude product was purified by preparative thin layer chromatography (Analtech 1 mm plates; eluent: 95:4.5:0.5 dichloromethane/methanol/concentrated ammonium hydroxide) to give the desired product (25 mg, 60%) as a buff-colored solid: $^1$H NMR (500 MHz, CDCl$_3$) δ 8.00 (br s, 1H), 7.54 (s, 1H), 7.48 (d, J=8.1 Hz, 1H), 7.15-7.04 (m, 5H), 6.87 (d, J=7.7 Hz, 1H), 4.42 (t, J=6.7 Hz, 1H), 3.76 (d, J=15.1 Hz, 1H), 3.65 (d, J=14.8 Hz, 1H), 3.07 (dd, J=11.5, 5.4 Hz, 1H), 2.64 (dd, J=11.3, 8.5 Hz, 1H), 2.44 (s, 3H).

To a mixture of the freebase of the desired product (25 mg, 0.08 mmol) and maleic acid (9.6 mg, 0.08 mmol) were added methanol (2 mL) and dichloromethane (2 mL) and the mixture was stirred for 1 hour. The solution was concentrated, and the residue was dissolved in methanol and water and lyophilized to give (+/−)-4-(3-chloro-1H-indol-6-yl)-2-methyl-1,2,3,4-tetrahydroisoquinoline, maleate salt (34 mg, quantitative, 93.9% AUC HPLC at 254 nm, 98.2% AUC HPLC at 220 nm) as an off-white solid: mp 94-98° C.; $^1$H NMR (500 MHz, CD$_3$OD) δ 7.53 (d, J=8.2 Hz, 1H), 7.40-7.20 (m, 5H), 6.96 (d, J=7.7 Hz, 2H), 6.25 (s, 2H), 4.71-4.40 (m, 3H), 3.90-3.85 (m, 1H), 3.79 (br s, 1H), 3.07 (s, 3H); ESI MS m/z 297 [M+H]$^+$.

Example 121

Preparation of (+/−)-4-(1-benzyl-1H-indol-5-yl)-2-methyl-1,2,3,4-tetrahydroisoquinoline, maleate salt Step A: To an ice-cold solution of 5-bromoindole (2 g, 10.2 mmol) in DMF (17.6 mL) was added potassium tert-butoxide (2.40 g, 21.4 mmol). The mixture was stirred at room temperature for 30 minutes, and cooled to 0° C. again. Benzyl bromide (2.4 mL, 1.96 mmol) was added dropwise to the reaction mixture, which was then stirred at room temperature for 1 hour and 45 minutes. The reaction mixture was poured into ice-cold water (400 mL), and stirred for 15 minutes. The off-white precipitate formed was filtered, washed with water, and dried under reduced pressure at 45° C. overnight to give the desired benzylated compound (2.70 g, 92%) as an off-white solid: $^1$H NMR (500 MHz, DMSO-$d_6$) δ 7.74 (d, J=1.8 Hz, 1H), 7.56 (d, J=3.0 Hz, 1H), 7.42 (d, J=8.8 Hz, 1H), 7.34-7.15 (m, 6H), 6.48 (d, J=2.8 Hz, 1H), 5.42 (s, 2H).

Step B: To a mixture of the product from Step A (0.50 g, 1.77 mmol) and isoquinoline-4-boronic acid (0.4 g, 2.13 mmol) in ethylene glycol dimethyl ether (8.1 mL) was added a solution of cesium carbonate (1.77 mL, 2 M), and the mixture was degassed (Ar, 10 minutes). Tetrakis(triphenylphosphine)palladium (0) (0.10 g, 0.89 mmol) was added to the mixture, which was then heated under reflux for 5 hours. The cooled reaction mixture was partitioned between ethyl acetate and water, and the aqueous layer was re-extracted with ethyl acetate twice. The combined organic layer was dried over sodium sulfate, filtered and concentrated under reduced pressure. The crude product was purified by flash column chromatography (80:20 hexanes/ethyl acetate, then 70:30 to 60:40 hexanes/ethyl acetate) to give the desired product (0.33 g, 56%) as a pink solid: $^1$H NMR (500 MHz, $CDCl_3$) δ 9.24 (s, 1H), 8.54 (s, 1H), 8.06-7.95 (m, 2H), 7.78 (d, J=1.3 Hz, 1H), 7.67-7.57 (m, 2H), 7.42 (d, J=8.4 Hz, 1H), 7.36-7.29 (m, 4H), 7.24 (d, J=3.1 Hz, 1H), 7.21-7.18 (m, 2H), 6.64 (d, J=3.1 Hz, 1H), 5.40 (s, 2H).

Step C: To an ice-cold solution of the product from Step B (0.06 g, 0.17 mmol) in dichloromethane was added methyl triflate (21 μL, 0.19 mmol) dropwise. The reaction mixture was stirred at 0° C. for 10 minutes, and concentrated to dryness. The residue was taken up in methanol (1.9 mL), and cooled to 0° C. Sodium cyanoborohydride (53 mg, 0.85 mmol) was added in small portions, and the reaction mixture was stirred at 0° C. for 20 minutes. Methanol (12 mL) and dichloromethane (6 mL) were added to the reaction mixture, followed by sodium cyanoborohydride (53 mg, 0.85 mmol). The mixture was warmed to room temperature and stirred overnight. The mixture was poured into water, and extracted with ethyl acetate. The organic extract was dried over sodium sulfate, filtered and concentrated under reduced pressure. The crude product was partially purified by preparative thin layer chromatography (Analtech 1 mm plates; eluent: 93:7 dichloromethane/methanol) to give the desired product (40 mg).

This reaction was repeated once more with the product from Step B (0.25 g, 0.75 mmol). The crude product of the reaction was partially purified by column chromatography (dichloromethane, then 98:2 and 97:3 dichloromethane/methanol) to give the desired product (225 mg, partially pure).

The two batches were combined and purified by preparative reverse phase HPLC (Phenomenex Luna C18 (2) column). The solution of the trifluoroacetate salt of the desired product obtained was concentrated (to remove the acetonitrile) and then basified with saturated sodium bicarbonate solution. The basic solution was extracted with dichloromethane four times, and the combined organic extract was dried over sodium sulfate, filtered and concentrated to give the desired product (58 mg, 18%): $^1$H NMR (500 MHz, $CDCl_3$) δ 7.48 (s, 1H), 7.30-7.26 (m, 3H), 7.20 (d, J=8.4 Hz, 1H), 7.15-6.97 (m, 8H), 6.48 (d, J=3.1 Hz, 1H), 5.29 (s, 2H), 4.38 (t, J=7.3 Hz, 1H), 3.80 (d, J=14.8 Hz, 1H), 3.61 (d, J=14.7 Hz, 1H), 3.09 (dd, J=11.4, 5.7 Hz, 1H), 2.61 (dd, J=11.4, 9.3 Hz, 1H), 2.43 (s, 3H).

To a solution of the above-obtained product (57 mg, 0.16 mmol) in methanol (2 mL) was added maleic acid (19 mg, 0.16 mmol), and the mixture was stirred for 40 minutes. To this solution were added methanol (6 mL) and water (18 mL), and the mixture was lyophilized to give (+/−)-4-(1-benzyl-1H-indol-5-yl)-2-methyl-1,2,3,4-tetrahydroisoquinoline, maleate salt, (75 mg, 99%, 97.6% AUC HPLC) as an off-white solid: mp 81-85° C.; $^1$H NMR (500 MHz, $CD_3OD$) δ 7.45 (br s, 1H), 7.35-7.20 (m, 8H), 7.13 (d, J=7.1 Hz, 2H), 7.05-6.84 (m, 2H), 6.48 (d, J=3.1 Hz, 1H), 5.38 (s, 2H), 6.24 (s, 2H), 4.68-4.42 (m, 3H), 3.85-3.78 (m, 1H), 3.68-3.56 (br m, 1H), 3.05 (s, 3H); ESI MS m/z 353 [M+H]$^+$.

Example 122

Preparation of (+)-4-(1H-Indazol-5-yl)-2-methyl-1, 2,3,4-tetrahydroisoquinoline, fumarate salt and (−)-4-(1H-Indazol-5-yl)-2-methyl-1,2,3,4-tetrahydroisoquinoline, fumarate salt Step A: To a solution of isoquinoline-4-boronic acid (1.90 g, 10.1 mmol) and 5-bromoindazole-1-carboxylic acid tert-butyl ester (2.00 g, 6.74 mmol) in dimethoxyethane (40 mL) was added a solution of aqueous cesium carbonate (2 M, 6.7 mL, 13.47 mmol) and the solution degassed by alternately evacuating and releasing to argon three times. To this heterogeneous mixture was added tetrakis(triphenylphosphine)palladium (389 mg, 0.337 mmol), the reaction mixture was degassed three times and heated to 85° C. with agitation for 2 hours. The mixture was cooled, EtOAc (150 mL) was added, the organic layer washed with water (3×50 mL), and dried over anhydrous sodium sulfate then concentrated. The residue was purified by column chromatography ($SiO_2$, 40 g, 100% to 50% hexane/ethyl acetate) to provide the product as a yellow solid (910 mg, 45%): $^1$H NMR ($CDCl_3$, 300 MHz) δ 9.29 (s, 1H), 8.53 (s, 1H), 8.34 (d, J=8.5 Hz, 1H), 8.27 (d, J=0.7 Hz, 1H), 8.09-8.07 (m, 1H), 7.88-7.85 (m, 2H), 7.71-7.65 (m, 3H), 1.77 (s, 9H); ESI MS m/z=346 [M+H]$^+$.

Step B: To a solution of product from Step A (910 mg, 2.64 mmol) in anhydrous dichloromethane (40 mL) at 0° C. was added methyl trifluoromethanesulfonate (328 μL, 0.289 mmol). The mixture was stirred at 0° C. for 1 hour, concentrated to dryness and redissolved in methanol (100 mL). To this solution was added sodium cyanoborohydride (1.66 g, 26.3 mmol), the mixture stirred at room temperature for 12 hours and concentrated to dryness. The residue was dissolved in ethyl acetate (250 mL) and the organic layer was washed with sodium hydroxide solution (0.05 M, 50 mL), brine (2×100 mL), dried over anhydrous sodium sulfate and concentrated. The residue was purified by column chromatography ($SiO_2$, 40 g, 100% to 50% hexane/ethyl acetate) to provide the desired tetrahydroisoquinoline as colorless oil (540 mg, 74%): ESI MS m/z=364 [M+H]$^+$.

Step C: To a solution of the product in Step B (540 mg) in dichloromethane (20 mL) at 0° C. was added TFA (10 mL). The mixture was stirred at room temperature for 2 hours and concentrated. The residue was purified by column chromatography ($SiO_2$, 40 g, 100% to 50% hexane/ethyl acetate then 90% ethyl acetate/methanol+1% ammonium hydroxide) to provide the product as white solid (530 mg, 95%). $^1$H NMR ($CD_3OD$, 300 MHz) δ 7.97 (s, 1H), 7.60 (s, 1H), 7.46 (d, J=8.7 Hz, 1H), 7.16-7.02 (m, 4H), 6.80 (d, J=7.6 Hz, 1H), 4.46-4.41 (m, 1 H), 3.87 (d, J=4.9 Hz, 1H), 3.62 (d, J=4.7 Hz, 1H), 3.18-3.06 (m, 1H), 2.65-2.61 (m, 1H), 2.24 (s, 3H). ESI-MS m/z=264 [M+H]$^+$.

Step D: Single enantiomers were obtained through chiral HPLC (Chiralcel OD, 99% heptane/1% isopropanol with 0.1% diethylamine) of product from Step C. (+)-enantiomer: HPLC>99% ee (Chiralpak AD column. $[\alpha]_D^{25}$ +102.9° (c 0.07, methanol). (−)-enantiomer: HPLC>99% ee (Chiralpak AD column. $[\alpha]_D^{25}$ −54.0° (c 0.1, methanol).

Step E: To a solution of each of the single enantiomers obtained from Step D (320 mg, 1.22 mmol) in methanol (25 mL) was added a solution of fumaric acid (141 mg, 1.22 mmol) in methanol (15 mL) at 0° C. The solution was stirred at room temperature for 5 h, concentrated, and the residue was slurried with diethyl ether. (+)-4-(1H-Indazol-5-yl)-2-methyl-1,2,3,4-tetrahydroisoquinoline, fumarate salt and (−)-4-(1H-Indazol-5-yl)-2-methyl-1,2,3,4-tetrahydroisoquinoline, fumarate salt were obtained by filtration as a white powder (399 mg, 87%): $^1$H NMR (CD$_3$OD, 300 MHz) δ 8.03 (d, J=0.9 Hz, 1H), 7.71 (s, 1H), 7.55 (d, J=8.7 Hz, 1H), 7.33-7.19 (m, 4H), 6.91 (d, J=8.7 Hz, 1H), 6.71 (s, 2H), 4.76-4.70 (m, 1H), 4.57 (s, 3H), 3.84 (dd, J=12.2, 6.1 Hz, 1H), 3.05 (m, 3H). ESI MS m/z=264 [M+H]$^+$. (+)-enantiomer; mp 105-114° C. HPLC>99% AUC. Anal. Calcd. For C$_{17}$H$_{17}$N$_3$.2.25C$_4$H$_4$O$_4$.H$_2$O: C, 57.56; H, 5.20; N, 7.75. Found: C, 57.57; H, 4.99; N, 7.57. (−)-enantiomer: mp>200° C. HPLC 96.9% AUC.

Step F: To an ice-cold solution of the (+)-enantiomer obtained from Step D (38 mg, 0.125 mmol) in DMF (2 mL) was added NaH (60% in mineral oil, 9 mg, 0.190 mmol) and the suspension stirred at 0° C. for 1 hour. To this mixture was added a solution of α-bromo-m-tolunitrile (24.4 mg, 0.124 mmol) in DMF (2 mL) 0° C., and the solution was warmed to room temperature and stirred for 3 hours. The mixture was quenched with water (2 mL), extracted with EtOAc (2×50 mL), and concentrated. The residue was purified by column chromatography (SiO$_2$, 12 g, 50% to 100% ethyl acetate/hexane) to provide the target compound as a colorless oil (15.4 mg, 33%): $^1$H NMR (CD$_3$OD, 300 MHz) δ 8.06 (s, 1H), 7.64-7.48 (m, 6H), 7.23-7.16 (m, 3H), 7.09-7.05 (m, 1H), 6.84-6.81 (m, 1H), 5.69 (s, 2H), 4.49-4.44 (m, 1H), 3.90-3.85 (d, J=4.9 Hz, 1H), 3.67-3.63 (d, J=4.9 Hz, 1H), 3.18-3.13 (m, 1H), 2.66-2.59 (m, 1H), 2.47 (s, 3H). ESI MS m/z=379 [M+H]$^+$. $[\alpha]_D^{25}$ +26.2° (c 0.07, methanol). HPLC>99% ee (Chiralpak AD column).

Step G: To a solution of the product obtained from Step D (14 mg, 0.037 mmol) in methanol (3 mL) was added a solution of maleic acid (4 mg, 0.037 mmol) in methanol (1 mL) at 0° C. The solution was stirred at room temperature overnight, then concentrated, and the solid was washed with ethanol and diethyl ether providing the target compound as a white powder (13.4 mg, 73%): mp 83-88° C. HPLC>99% AUC. $^1$H NMR (CD$_3$OD, 500 MHz) δ 8.08 (s, 1H), 7.70-7.46 (m, 6H), 7.31-7.19 (m, 4H), 6.92-6.90 (m, 1H), 6.24 (s, 2H), 5.70 (s, 2H), 4.68-4.65 (m, 1H), 4.42 (s, 2H), 3.74-3.70 (m, 1H), 3.42-3.38 (m, 1H), 2.94 (s, 3H); ESI-MS m/z=379 [M+H]$^+$.

Example 123

Preparation of (+) 4-(6-methoxy-1H-indazol-5-yl)-2-methyl-1,2,3,4-tetrahydroisoquinoline, maleate salt Step A: Racemic 4-(6-methoxy-1H-indazol-5-yl)-2-methyl-1,2,3,4-tetrahydroisoquinoline was prepared from 5-bromo-6-methoxy-1H-indazole as described in Example 1 (Steps A to D). This racemic compound (500 mg) was separated on semi-prep chiral HPLC (Chiralcel OJ, 80% heptane/20% ethanol with 0.1% diethylamine). Each resulting enantiomer was dissolved in methanol and treated with a solution of maleic acid in methanol (5 mL) at 0° C. The solution was stirred at room temperature overnight, then concentrated, and the solid was washed with diethyl ether providing 4-(6-methoxy-1H-indazol-5-yl)-2-methyl-1,2,3,4-tetrahydroisoquinoline, maleate salt (single enantiomer), maleate salt [130 mg, 54%, >99% AUC HPLC, 100% AUC chiral HPLC (free base)]: $^1$H NMR (CD$_3$OD, 500 MHz) δ 7.88 (s, 1H), 7.30-7.25 (m, 4H), 7.07 (s, 1H), 7.00-6.94 (m, 1H), 6.25 (s, 2H), 4.94-4.93 (m, 1H), 4.60-4.50 (m, 2H), 3.90-3.70 (m, 5H), 3.07 (m, 3H); ESI-MS m/z=294 [M+H], $[\alpha]_D^{25}$ +28.0° (c 0.05, MeOH, free base); Anal. Calcd. for C$_{18}$H$_{19}$N$_3$.1.25C$_4$H$_4$O$_4$. 0.75H$_2$O: C, 61.12; H, 5.69; N, 9.30. Found: C, 61.11; H, 5.33; N, 9.19, and (+)-4-(6-methoxy-1H-indazol-5-yl)-2-methyl-1,2,3,4-tetrahydroisoquinoline, maleate salt [48 mg, 54%, 98.0% AUC HPLC, 100% AUC chiral HPLC (free base)]: $^1$H NMR (CD$_3$OD, 500 MHz) δ 7.88 (s, 1H), 7.30-7.25 (m, 4H), 7.07 (s, 1H), 7.00-6.94 (m, 1H), 6.25 (s, 6H), 4.94-4.93 (m, 1H), 4.60-450 (m, 2H), 3.90-3.70 (m, 5H), 3.07 (m, 3H), ESI MS m/z=294 [M+H], $[\alpha]_D^{25}$ +4.0° (c 0.08, MeOH, free base).

Example 124

Preparation of (+)-4-(7-chloro-1H-indazol-5-yl)-2-methyl-1,2,3,4-tetrahydoisoquinoline, maleate salt Step A: A mixture of isoquinolin-4-ylboronic acid (1.00 g, 5.78 mmol), 5-bromo-7-chloro-1H-indazole (892 mg, 3.85 mmol), 2.0 M sodium carbonate (3.85 mL, 7.71 mmol) and dimethoxyethane was degassed with argon. Tetrakis(triphenylphosphine)palladium(0) (233 mg, 0.193 mmol) was added, the mixture degassed again with argon, then heated to 85° C. for 24 hours. The reaction was cooled and partitioned between ethyl acetate and water, the organic layer washed with and dried with sodium sulfate. The solvent was removed under vacuum and the residue purified by column chromatography (9/1 to 6/4 hexanes/ethyl acetate gradient) to give 4-(7-chloro-1H-indazol-5-yl)-isoquinoline (777 mg, 72%): $^1$H NMR (300 MHz, CDCl$_3$) δ 10.52 (s, 1H) 9.31 (s, 1H), 8.53 (s, 1H), 8.22 (s, 1H), 8.09 (dd, J=7.4, 1.62 Hz, 1H), 7.28 (dd, J=7.4, 1.2 Hz, 1H), 7.87 (d, J=9.0 Hz, 1H), 7.81 (d, J=1.2 Hz, 1H), 7.72-7.64 (m, 2H), 7.57 (d, J=1.3 Hz, 1H).

Step B: To a suspension of the product derived from Step A (776 mg, 2.77 mmol) and di-t-butyl dicarbonate (909 mg, 4.16 mmol) in acetonitrile (18 mL) was added 4-dimethylaminopyridine. The resulting solution was stirred overnight, the solvent removed under vacuum, and the residue purified by column chromatography (3:1 hexanes/ethyl acetate) to give the desired BOC-protected product (778 mg, 74%): $^1$H NMR (500 MHz, CDCl$_3$) δ 9.26 (s, 1H), 8.76 (s, 1H), 8.53 (s, 1H), 8.07 (d, J=7.9 Hz, 1H), 7.88 (d, J=8.3, Hz, 1H), 7.73-7.67 (m, 3H), 7.54 (d, J=1.3 Hz, 1H), 1.75 (s, 9H).

Step C: To a 0° C. solution of the product obtained from Step B (758 mg, 2.00 mmol) in dichloromethane was added anisole (1 mL) and methyl trifluoromethanesulfonate (344 mg, 2.09 mmol). The solution was allowed to warm to 10° C. over 1.5 hours and concentrated to dryness under vacuum. Anisole (1 mL) was charged to the flask and the mixture dissolved in methanol. Sodium cyanoborohydride (503 mg, 8.00 mmol) was then added and the reaction stirred for 2.5 hours. The reaction was poured into a mixture of brine (196 mL) and water (30 mL) and extracted with ethyl acetate three times and the combined organic layers washed with brine, dried with sodium sulfate, concentrated under vacuum, and the residue purified by column chromatography (75:25 to 60:40 hexanes/ethyl acetate gradient) to give the desired tetrahydoisoquinoline (655 mg, 82%): $^1$H NMR (500 MHz, CDCl$_3$) δ 8.56 (s, 1H), 7.34 (s, 1H), 7.26 (s, 1H), 7.21 (d, J=1.2 Hz, 1H), 7.18-6.89 (m, 3H), 4.27 (t, J=6.50 Hz, 1H), 3.71 (d, J=15.0 Hz, 1H), 3.67 (d, J=15.0 Hz, 1H), 2.99 (dd, J=11.4, 5.4 Hz, 1H), 2.66 (dd, J=11.6, 7.70 Hz, 1H), 2.44 (s, 3H), 1.71 (s, 9H).

Step D: To a solution of the product derived from Step C (655 mg, 1.65 mmol) in methanol (18.3 mL) was added 1N HCl in ether (17.9 mL, 17.9 mmol). The solution stirred overnight, concentrated under vacuum and the residue purified by column chromatography (95:5:0.2 to 90:10:0.2 dichloromethane/methanol/concentrated ammonium hydroxide gradient) to give the desired deprotected indazole (427 mg, 84%): $^1$H NMR (500 MHz, CDCl$_3$) δ 10.18 (s, 1H), 8.04 (s, 1H), 7.49 (d, J=1.0 Hz, 1H), 7.26-7.06 (m, 3H), 6.87 (d, J=7.8 Hz, 1H), 4.36 (t, J=6.50 Hz, 1H), 3.72 (d, J=14.9 Hz, 1H), 3.69 (d, J=15.0 Hz, 1H), 3.03 (dd, J=11.5, 5.5 Hz, 1H), 2.65 (dd, J=11.5, 7.80 Hz, 1H), 2.44 (s, 3H).

This compound was resolved by preparative chiral HPLC (CHIRALPAK AD column, using 8:2:0.01 heptane/IPA/triethylamine as the eluent) to give the (+)-enantiomer [[α]$^{25}_D$ +45.1° (c 0.04, methanol)] and the (−)-enantiomer [[α]$^{25}_D$ −81.3° (c 0.03, methanol)]. The (+)-enantiomer (105 mg, 0.353 mmol) was converted to its maleate salt by dissolving in absolute ethanol (1 mL), adding one equivalent of maleic acid in ethanol and concentrating to dryness under vacuum. The residue was dissolved in 1:1 acetonitrile/water and lyophilized to give (+)-4-(7-chloro-1H-indazol-5-yl)-2-methyl-1,2,3,4-tetrahydoisoquinoline, maleate salt as an off-white solid (143 mg, 98%, >99% AUC HPLC): mp 107.4-110.9° C.; $^1$H NMR (500 MHz, CD$_3$OD) δ 8.12 (s, 1H), 7.66 (s, 1H), 7.35-7.25 (m, 4H), 6.94 (d, J=7.7 Hz, 1H), 6.24 (s, 2H) 4.71 (dd, J=10.4, 6.2 Hz, 1H), 4.58 (d, J=15.3 Hz, 1H), 4.54 (d, J=15.3 Hz, 1H), 3.85 (dd, J=12.4, 6.4 Hz, 1H), 3.58 (t, J=11.8 Hz, 1H), 3.05 (s, 3H); ESI-MS m/z 298 [M+H]$^+$.

Example 125

Preparation of (−)-4-(7-chloro-1H-indazol-5-yl)-2-methyl-1,2,3,4-tetrahydoisoquinoline, maleate salt The free base of the (−)-enantiomer (112 mg, 0.376 mmol) from Step D in example 126 was converted to its maleate salt by dissolving in absolute ethanol (1 mL), adding one equivalent of maleic acid in ethanol and concentrating to dryness under vacuum. The residue was dissolved in 1:1 acetonitrile/water and lyophilized to give (−)-4-(7-chloro-1H-indazol-5-yl)-2-methyl-1,2,3,4-tetrahydoisoquinoline, maleate salt as a white solid (143 mg, 92%, >99% AUC HPLC): mp 104-110° C.; $^1$H NMR (500 MHz, CD$_3$OD) δ 8.12 (s, 1H), 7.67 (s, 1H), 7.35-7.25 (m, 4H), 6.95 (d, J=7.8 Hz, 1H), 6.24 (s, 2H), 4.73 (dd, J=11.0, 6.3 Hz, 1H), 4.63 (d, J=15.3 Hz, 1H), 4.57 (d, J=15.3 Hz, 1H), 3.85 (dd, J=12.3, 6.2 Hz, 1H), 3.63 (t, J=11.8 Hz, 1H), 3.08 (s, 3H); ESI-MS m/z 298 [M+H]$^+$.

Example 126

Preparation of (+)-4-(1H-Indazol-6-yl)-2-methyl-1,2,3,4-tetrahydroisoquinoline, fumarate salt and (−)-4-(1H-Indazol-6-yl)-2-methyl-1,2,3,4-tetrahydroisoquinoline, fumarate salt Racemic 4-(7-methyl-1H-indazol-5-yl)-2-methyl-1,2,3,4-tetrahydroisoquinoline was prepared from 5-bromo-7-methyl-1H-indazole by a method similar to the one described in Example 131 (Steps A to D). This racemic compound (180 mg) was separated on semi-prep chiral HPLC (Chiralpak AD, 80% heptane/20% isopropanol with 0.1% diethylamine). The resulting free bases were dissolved in methanol and treated with a solution of maleic acid in methanol (5 mL) at 0° C. The solution was stirred at room temperature overnight, then concentrated, and the solid was washed with diethyl ether providing (+)-4-(7-methyl-1H-indazol-5-yl)-2-methyl-1,2,3,4-tetrahydroisoquinoline, maleate salt [23 mg, 9%, >99% AUC HPLC, 96.6% AUC chiral HPLC (free base)]: $^1$H NMR (CD$_3$OD, 500 MHz) δ 8.01 (s, 1H), 7.52 (s, 1H), 7.31-7.23 (m, 3H), 6.98-6.93 (m, 2H), 6.23 (s, 2H), 4.70-4.56 (m, 3H), 3.88-3.84 (m, 1H), 3.64-3.60 (m, 1H), 3.08 (s, 3H), 2.52 (s, 3H), ESI MS m/z=278 [C$_{18}$H$_{19}$N$_3$+H], [α]$_D^{25}$ +51.7° (c 0.07, MeOH, free base), and (−)-4-(7-methyl-1H-indazol-5-yl)-2-methyl-1,2,3,4-tetrahydroisoquinoline, maleate salt [71 mg, 71%, 92.7% AUC HPLC, 91.3% AUC chiral HPLC, (free base)]: 1H NMR (CD$_3$OD, 500 MHz) δ 8.01 (s, 1H), 7.52 (s, 1H), 7.31-7.23 (m, 3H), 6.98-6.93 (m, 2H), 6.23 (s, 2H), 4.70-4.56 (m, 3H), 3.88-3.84 (m, 1H), 3.64-3.60 (m, 1H), 3.08 (s, 3H), 2.52 (s, 3H), ESI-MS m/z=278 [M+H], [α]$_D^{25}$ −43.5° (c 0.06, MeOH, free base).

Example 127

Preparation of (+/−)-4-(1H-indazol-5-yl-2-methyl-7-(morpholine-4-yl)-1,2,3,4-tetrahydroisoquinoline, maleate salt Step A: To a solution of Boc-protected 5-bromo-indazole (2.0 g, 6.7 mmol) and n-butyl vinylether (4.4 mL, 33.6 mmol) in dioxane (20 mL) were added tri-t-butyl phosphine (0.41 g, 2.0 mmol) and N-methyldicyclohexylamine (1.6 mL, 7.4 mmol). The reaction solution was purged with argon for 5 minutes and then tris(dibenzylideneacetone)dipalladium (0.37 g, 0.4 mmol) was added to it. The reaction flask was purged with argon for 5 minutes and then was capped and heated at 40° C. for 16 hours. The reaction mixture was then cooled to room temperature and diluted with ethyl acetate. The organic solution was washed with water, aqueous saturated ammonium chloride and brine, dried over sodium sulfate and concentrated under reduced pressure. The residue obtained was dissolved in a mixture of tetrahydrofuran (60 mL) and water (30 mL) and treated with acetic acid (5 mL). The resultant solution was stirred at room temperature for 2 hours and then the solvent was removed under reduced pressure. The residue obtained was diluted with ethyl acetate, washed with water twice, aqueous saturated sodium bicarbonate twice and brine, dried over sodium sulfate and concentrated under reduced pressure. The crude product obtained was purified using the Biotage MPLC system (95:5 to 65:35 hexanes/ethyl acetate) to give the desired product (0.91 g, 52%) as a reddish oil: $^1$H NMR (CDCl$_3$, 500 MHz) δ 8.38 (t, J=0.7 Hz, 1H), 8.28 (s, 1H), 8.25 (d, J=8.9 Hz, 1H), 8.16 (dd, J=8.9, 1.5 Hz, 1H), 2.69 (s, 3H), 1.74 (s, 9H).

Step B: To a solution of the methyl ketone (0.85 g, 3.2 mmol) from Step A above in tetrahydrofuran (12 mL) were added 2-pyrrolidinone hydrotribromide (1.75 g, 3.4 mmol) and 2-pyrrolidinone (0.26 mL). The reaction solution was heated under reflux for 1 hour and then was cooled to room temperature and filtered to remove the precipitate formed. The filtrate obtained was concentrated under reduced pressure to give the crude product, which was purified using the Biotage MPLC system (95:5 to 63:37 hexanes/ethyl acetate) to provide the desired product (0.91 g, 70%) as a yellow solid: $^1$H NMR (CDCl$_3$, 500 MHz) δ 8.44 (d, J=1.2 Hz, 1H), 8.30 (s, 1H), 8.29 (d, J=9.0 Hz, 1H), 8.18 (dd, J=8.8 Hz, 1H), 4.51 (s, 2H), 1.74 (s, 9H).

Step C: To a solution of methyl-(3-morpholin-4-yl-benzyl)-amine (0.11 g, 0.51 mmol) in dichloromethane (5 mL) were added the α-bromomethyl ketone (0.16 g, 0.47 mmol) from Step B above and N,N-diisopropylethylamine (0.13 mL, 0.77 mmol). The reaction solution was stirred at room temperature for 3 hours and then was diluted with dichloromethane. The solution obtained was washed with water, dried over sodium sulfate and concentrated under reduced pressure. The crude product obtained was partially purified by flash column chromatography (98:2 dichloromethane/methanol) to give the desired product (0.22 g), which was used in the next step without further purifications: $^1$H NMR (CDCl$_3$, 500 MHz) δ 8.38 (s, 1H), 8.23 (d, J=0.5 Hz, 1H), 8.21 (d, J=8.8 Hz, 1H), 8.16 (dd, J=8.8, 1.5 Hz, 1H), 7.23 (t, J=7.8 Hz, 1H), 6.91 (s, 1H), 6.85-6.81 (m, 2H), 3.87-3.82 (m, 4H), 3.79 (s, 2H), 3.62 (s, 2H), 3.17-3.12 (m, 4H), 2.39 (s, 3H), 1.74 (s, 9H); ESI-MS m/z 465 [M+H]$^+$.

Step D: To a solution of the ketone (0.22 g, 0.47 mmol) from Step C above in methanol (15 mL) at 0° C. was added sodium borohydride (19 mg, 0.52 mmol). The reaction mixture was stirred for 45 minutes and the solvent was then removed under reduced pressure. The residue obtained was dissolved in dichloromethane, washed with water and aqueous saturated sodium bicarbonate, dried over sodium sulfate and concentrated under reduced pressure. The crude product was purified by flash column chromatography (98:2 to 95:5 dichloromethane/methanol) to give the desired product (0.13 g, 58% over 2 steps) as a light yellow oil: $^1$H NMR (CDCl$_3$, 500 MHz) δ 8.15-8.13 (m, 2H), 7.75 (d, J=0.6 Hz, 1H), 7.49 (dd, J=8.8, 1.5 Hz, 1H), 7.27-7.23 (m, 1H), 6.89 (s, 1H), 6.86-6.83 (m, 2H), 4.87 (dd, J=10.0, 4.0 Hz, 1H), 4.26-4.06 (m, 1H), 3.88-3.86 (m, 4H), 3.73 (d, J=13.0 Hz, 1H), 3.50 (d, J=13.0 Hz, 1H), 3.18-3.16 (m, 4H), 2.61-2.57 (m, 2H), 2.36 (s, 3H), 1.72 (s, 9H).

Step E: To a solution of the alcohol (0.12 g, 0.25 mmol) from Step D above in dichloromethane (6 mL) was added N,N-diisopropylethylamine (70 µL, 0.50 mmol), followed by methanesulfonyl chloride (23 µL, 0.30 mmol). The reaction solution was stirred at room temperature for 90 minutes, and then methanesulfonic acid (0.16 mL, 2.5 mmol) was added to it in two batches. The reaction mixture was stirred at room temperature for 2 hours, and then was quenched with aqueous saturated sodium bicarbonate and extracted with dichloromethane twice. The combined organic extract was dried over sodium sulfate and concentrated under reduced pressure. The crude product obtained was purified by preparative thin layer chromatography (95:4.5:0.5 ethyl acetate/methanol/concentrated ammonium hydroxide) to give the desired product (10 mg, 11%) as a white foam: $^1$H NMR (CDCl$_3$, 500 MHz) δ 10.15-9.73 (br s, 1H), 8.00 (d, J=0.5 Hz, 1H), 7.59 (s, 1H), 7.39 (d, J=8.9 Hz, 1H), 7.23 (dd, J=8.7, 1.5 Hz, 1H), 6.78 (d, J=8.5 Hz, 1H), 6.68-6.62 (m, 2H), 4.34-4.31 (m, 1H), 3.86-3.83 (m, 4H), 3.72 (d, J=14.9 Hz, 1H), 3.63 (d, J=14.9 Hz, 1H), 3.14-3.11 (m, 4H), 3.06-3.00 (m, 1H), 2.61 (dd, J=11.2, 8.5 Hz, 1H), 2.43 (s, 3H); ESI-MS m/z 349 [M+H]$^+$.

Step F: To a solution of the 7-morpholinyl tetrahydroisoquinoline (10 mg, 0.028 mmol) from Step E above in methanol (2 mL) was added maleic acid (6.6 mg, 0.057 mmol), followed by water (10 mL) The resultant solution was lyophilized overnight to give (+/−)-4-(1H-indazol-5-yl)-2-methyl-7-(morpholine-4-yl)-1,2,3,4-tetrahydroisoquinoline, maleate salt (16 mg, 96%) as a light yellow solid: mp 71-75° C.; $^1$H NMR (CD$_3$OD, 500 MHz) δ 8.02 (s, 1H), 7.78-7.57 (m, 1H), 7.55 (d, J=8.6 Hz, 1H), 7.21 (d, J=8.5 Hz, 1H), 6.89 (d, J=7.9 Hz, 1H), 6.82-6.81 (m, 2H), 6.28 (s, 5H), 4.65-4.43 (m, 3H), 3.86-3.80 (m, 5H), 3.63-3.44 (m, 1H), 3.15-3.13 (m, 4H), 3.07 (s, 3H); ESI-MS m/z 349 [M+H]$^+$.

Example 128

Preparation of (+)-3-[5-(2-methyl-1,2,3,4-tetrahydroisoquinolin-4-yl)indazol-1-ylmethyl]-benzonitrile, maleate salt Step A: To a solution of isoquinoline-4-boronic acid (1.90 g, 10.1 mmol) and 5-bromoindazole-1-carboxylic acid tert-butyl ester (2.00 g, 6.74 mmol) in dimethoxyethane (40 mL) was added a solution of aqueous cesium carbonate (2 M, 6.7 mL, 13.47 mmol) and the solution degassed by alternately evacuating and releasing to argon three times. To this heterogeneous mixture was added tetrakis(triphenylphosphine)palladium (389 mg, 0.337 mmol), the reaction mixture was degassed three times and heated to 85° C. with agitation for 2 hours. The mixture was cooled, EtOAc (150 mL) was added, the organic layer washed with water (3×50 mL), and dried over anhydrous sodium sulfate then concentrated. The residue was purified by column chromatography (SiO$_2$, 40 g, 100% to 50% hexane/ethyl acetate) to provide the product as a yellow solid (910 mg, 45%): $^1$H NMR (CDCl$_3$, 300 MHz) δ 9.29 (s, 1H), 8.53 (s, 1H), 8.34 (d, J=8.5 Hz, 1H), 8.27 (d, J=0.7 Hz, 1H), 8.09-8.07 (m, 1H), 7.88-7.85 (m, 2H), 7.71-7.65 (m, 3H), 1.77 (s, 9H); ESI-MS m/z=346 [M+H]$^+$.

Step B: To a solution of product from Step A (910 mg, 2.64 mmol) in anhydrous dichloromethane (40 mL) at 0° C. was added methyl trifluoromethanesulfonate (328 µL, 0.289 mmol). The mixture was stirred at 0° C. for 1 hour, concentrated to dryness and redissolved in methanol (100 mL). To this solution was added sodium cyanoborohydride (1.66 g, 26.3 mmol), the mixture stirred at room temperature for 12 hours and concentrated to dryness. The residue was dissolved in ethyl acetate (250 mL) and the organic layer was washed with sodium hydroxide solution (0.05 M, 50 mL), brine (2×100 mL), dried over anhydrous sodium sulfate and concentrated. The residue was purified by column chromatography (SiO$_2$, 40 g, 100% to 50% hexane/ethyl acetate) to provide the desired tetrahydroisoquinoline as colorless oil (540 mg, 74%): ESI-MS m/z=364 [M+H]$^+$.

Step C: To a solution of the product in Step B (540 mg) in dichloromethane (20 mL) at 0° C. was added TFA (10 mL). The mixture was stirred at room temperature for 2 hours and concentrated. The residue was purified by column chromatography (SiO$_2$, 40 g, 100% to 50% hexane/ethyl acetate then 90% ethyl acetate/methanol+1% concentrated ammonium hydroxide) to provide 4-(1H-indazol-5-yl)-2-methyl-1,2,3,4-tetrahydroisoquinoline as white solid (530 mg, 95%). $^1$H NMR (CD$_3$OD, 300 MHz) δ 7.97 (s, 1H), 7.60 (s, 1H), 7.46 (d, J=8.7 Hz, 1H), 7.16-7.02 (m, 4H), 6.80 (d, J=7.6 Hz, 1H), 4.46-4.41 (m, 1 H), 3.87 (d, J=4.9 Hz, 1H), 3.62 (d, J=4.7 Hz, 1H), 3.18-3.06 (m, 1H), 2.65-2.61 (m, 1H), 2.24 (s, 3H). ESI MS m/z=264 [M+H]$^+$.

Step D: Single enantiomers were obtained through chiral chromatography (Chiralcel OD, 99% heptane/isopropanol with 0.1% diethylamine) of product from Step C. (+)-enantiomer: HPLC>99% ee (Chiralpak AD column. [α]$_D^{25}$ +102.9° (c 0.07, methanol). (−)-enantiomer: HPLC>99% ee (Chiralpak AD column. [α]$_D^{25}$ −54.0° (c 0.1, methanol).

Step E: To an ice-cold solution of the (+)-enantiomer obtained from Step D (38 mg, 0.125 mmol) in DMF (2 mL) was added NaH (60% in mineral oil, 9 mg, 0.190 mmol) and the suspension stirred at 0° C. for 1 hour. To this mixture was added a solution of α-bromo-m-tolunitrile (24.4 mg, 0.124 mmol) in DMF (2 mL) 0° C., and the solution was warmed to room temperature and stirred for 3 hours. The mixture was quenched with water (2 mL), extracted with EtOAc (2×50 mL), and concentrated. The residue was purified by column chromatography (SiO$_2$, 12 g, 50% to 100% ethyl acetate/hexane) to provide (+) 3-[5-(2-methyl-1,2,3,4-tetrahydroisoquinolin-4-yl)indazol-1-ylmethyl]-benzonitrile as a colorless oil (15.4 mg, 33%): $^1$H NMR (CD$_3$OD, 300 MHz) δ 8.06 (s, 1H), 7.64-7.48 (m, 6H), 7.23-7.16 (m, 3H), 7.09-7.05 (m, 1H), 6.84-6.81 (m, 1H), 5.69 (s, 2H), 4.49-4.44 (m, 1H), 3.90-3.85 (d, J=4.9 Hz, 1H), 3.67-3.63 (d, J=4.9 Hz, 1H), 3.18-3.13 (m, 1H), 2.66-2.59 (m, 1H), 2.47 (s, 3H). ESI-MS m/z=379 [M+H]$^+$. [α]$_D^{25}$ +26.2° (c 0.07, Methanol). HPLC>99% ee (Chiralpak AD column).

Step F: To a solution of the product obtained from Step D (14 mg, 0.037 mmol) in methanol (3 mL) was added a solution of maleic acid (4 mg, 0.037 mmol) in methanol (1 mL) at 0° C. The solution was stirred at room temperature overnight, then concentrated, and the solid was washed with ethanol and diethyl ether providing (+)-3-[5-(2-methyl-1,2,3,4-tetrahydroisoquinolin-4-yl)indazol-1-ylmethyl]-benzonitrile, maleate salt as a white powder (13.4 mg, 73%): mp 83-88° C. HPLC>99% AUC. $^1$H NMR (CD$_3$OD, 500 MHz) δ 8.08 (s, 1H), 7.70-7.46 (m, 6H), 7.31-7.19 (m, 4H), 6.92-6.90 (m, 1H), 6.24 (s, 2H), 5.70 (s, 2H), 4.68-4.65 (m, 1H), 4.42 (s, 2H), 3.74-3.70 (m, 1H), 3.42-3.38 (m, 1H), 2.94 (s, 3H). ESI-MS m/z=379 [M+H]$^+$.

Example 129

Preparation of (+)-4-(1H-indazol-6-yl)-2-methyl-1,2,3,4-tetrahydroisoquinoline, fumarate salt and (−) 4-(1H-Indazol-6-yl)-2-methyl-1,2,3,4-tetrahydroisoquinoline, fumarate salt Step A: To a solution of 6-bromoindazole (2.57 g, 13.0 mmol) in acetonitrile (50 mL) was added di-t-butyldicarbonate (4.3 mg, 19.6 mmol), and DMAP (80 mg, 6.52 mmol). The mixture was stirred at room temperature for 26 hours and concentrated to dryness. The residue was purified by column chromatography to provide the pure product (2.09 g, 64%) as a white solid: $^1$H NMR (CDCl$_3$, 300 MHz) δ 8.43 (s, 1H), 8.13 (d, J=0.7 Hz, 1H), 7.60 (d, J=8.4 Hz, 1H), 7.44 (dd, J=8.4 Hz, 1.6 Hz, 1H), 1.73 (s, 9H).

Step B: To a solution of isoquinoline-4-boronic acid (4.36 g, 23.1 mmol) and the product from Step A (4.58 g, 15.4 mmol) in dimethoxyethane (40 mL) was added a aqueous solution of cesium carbonate (2 M, 15 mL, 30.8 mmol) and the solution degassed by alternately evacuating and releasing to argon three times. To this heterogenic mixture was added tetrakis(triphenylphosphine) palladium (890 mg, 0.77 mmol). The reaction mixture was degassed three times and heated to 85° C. with agitation for 4 hours. The cooled reaction mixture was diluted with EtOAc (250 mL), washed with water (3×150 mL), dried (sodium sulfate) and concentrated. The residue was purified by column chromatography (SiO$_2$, 40 g, 100% to 0% hexane/ethyl acetate) provided the product as a yellow solid (4.00 g, 70%): $^1$H NMR (CDCl$_3$, 300 MHz) δ 9.31 (s, 1H), 8.56 (s, 1H), 8.39 (s, 1H), 8.28 (s, 1H), 8.10-8.07 (m, 1H), 7.93-7.87 (m, 2H), 7.71-7.66 (m, 2H), 7.50-7.47 (m, 1H), 1.70 (s, 9H); ESI-MS m/z=345 [M+H]$^+$.

Step C: To a solution of product from Step B (2.00 g, 5.79 mmol) in anhydrous dichloromethane (60 mL) at 0° C. was added methyl trifluoromethanesulfonate (720 μL, 6.37 mmol). The mixture was stirred at 0° C. for 1 hour, concentrated to dryness and dissolved in methanol (60 mL). To this solution was added sodium cyanoborohydride (1.40 g, 23.2 mmol), the mixture stirred at room temperature for 12 hours and concentrated to dryness. The residue was dissolved in ethyl acetate (250 mL) and the organic layer was washed with sodium hydroxide solution (0.05 M, 50 mL), brine (2×100 mL), dried over anhydrous sodium sulfate and concentrated. The residue was purified by column chromatography (SiO$_2$, 40 g, 85% to 0% hexane/ethyl acetate) to provide the tetrahydroisoquinoline as colorless oil (1.56 g, 63%): ESI MS m/z=364 [M+H]$^+$.

Step D: To a solution of the product from Step C (1.56 g) in dichloromethane (20 mL) at 0° C. was added TFA (10 mL). The mixture was stirred at room temperature for 2.5 hours and concentrated. The residue was purified by column chromatography (SiO$_2$, 40 g, 1:0 to 1:1% hexane/ethyl acetate then 90% ethyl acetate/10% methanol+1% ammonium hydroxide) to provide the product as a white solid (970 mg, 95%): $^1$H NMR (CD$_3$OD, 300 MHz) δ 7.99 (d, J=0.6 Hz, 1H), 7.69 (d, J=8.2 Hz, 1H), 7.36 (s, 1H), 7.21-7.15 (m, 2H), 7.10-7.04 (m, 1H), 6.95-6.92 (m, 1H), 6.84-6.82 (d, J=7.6 Hz, 1H), 4.49-4.44 (m, 1H), 3.87 (d, J=15.0 Hz, 1H), 3.64 (d, J=14.9 Hz, 1H), 3.20-3.14 (m, 1H), 2.64 (dd, J=11.6, 9.9 Hz, 1H), 2.45 (s, 3H); ESI-MS m/z=264 [M+H]$^+$.

Step E: Single enantiomers were obtained through chiral chromatography (Chiralcel OD, 95% heptane/5% isopropanol with 0.1% diethylamine) of product from Step D. (+)-enantiomer: [α]$_D^{25}$ +72.0° (c 0.05, methanol); HPLC>99% ee (Chiralpak AD column). (−)-enantiomer: [α]$_D^{25}$ −89.5° (c 0.16, methanol); HPLC>99% ee (Chiralpak AD column).

Step F: To a solution of the single enantiomer obtained from Step E (400 mg, 1.52 mmol) in methanol (40 mL) was added a solution of fumaric acid (352 mg, 3.04 mmol) in methanol (15 mL) at 0° C. The solution was stirred at room temperature for 12 hours then concentrated, and the residue slurried with diethyl ether. The fumarate salt was isolated by filtration as a white powder (650 mg, 87%): $^1$H NMR (CD$_3$OD, 300 MHz) δ 8.04 (s, 1H), 7.79-7.76 (d, J=8.4 Hz, 1H), 7.46 (s, 1H), 7.30-7.20 (m, 3H), 6.99-6.92 (m, 2H), 6.71 (s, 4H), 4.73-4.67 (m, 1H), 4.46 (s, 1H), 3.80-3.74 (m, 1H), 3.53-3.43 (m, 1H), 2.97 (s, 3H); ESI-MS=264 [M+H]$^+$. (+)-enantiomer: mp 114-125° C. HPLC>99% AUC. Anal. Calcd. For C$_{17}$H$_{17}$N$_3$.2C$_4$H$_4$O$_4$.0.5H$_2$O: C, 59.52; H, 5.19; N, 8.33. Found: C, 59.41; H, 5.02; N, 8.34. (−)-enantiomer: mp 110-117° C. HPLC>99% AUC.

Example 130

Preparation of (+)-4-(1H-Indazol-6-yl)-2-ethyl-1,2,3,4-tetrahydroisoquinoline, maleate salt and (−)-4-(1H-Indazol-6-yl)-2-ethyl-1,2,3,4-tetrahydroisoquinoline, maleate salt Racemic 4-(1H-indazol-6-yl)-2-ethyl-1,2,3,4-tetrahydroisoquinoline was prepared from 6-isoquinolin-4-yl-indazole-1-carboxylic acid tert-butyl ester and ethyl trifluoromethanesulfonate by a method similar to the one described in Example 131. This racemic compound (500 mg, 74%) was separated on semi-prep chiral HPLC (Chiralcel OD, 95% heptane/5% isopropanol with 0.1% diethylamine). The resulting free bases were dissolved in methanol and treated with a solution of maleic acid in methanol (5 mL) at 0° C. The solution was stirred at room temperature for 12 hours, then concentrated, and the solid was washed with diethyl ether providing (+)-4-(1H-indazol-6-yl)-2-ethyl-1,2,3,4-tetrahydroisoquinoline, maleate salt [250 mg, 87%, >99% AUC HPLC, 99.6% AUC chiral HPLC (free base)]: $^1$H NMR (CD$_3$OD, 500 MHz) δ 8.03 (d, J=0.86 Hz, 1H), 7.71 (s, 1H), 7.55 (d, J=8.7 Hz, 1H), 7.33-7.19 (m, 4H), 6.91 (d, J=8.7 Hz, 1H), 6.24 (s, 2H), 4.76-4.70 (m, 1H), 4.70-4.50 (m, 2H), 4.57 (s, 3H), 3.84 (dd, J=12.2, 6.1 Hz, 1H), 1.47-1.44 (m, 3H); ESI-MS m/z=278 [M+H]$^+$; $[α]^{25}_D$ +70.0° (c 0.11, MeOH, free base); Anal. Calcd. for C$_{18}$H$_{19}$N$_3$.C$_4$H$_4$O$_4$.0.5 H$_2$O: C, 65.66; H, 6.01; N, 10.44. Found: C, 65.35; H, 5.80; N, 10.27, and (−)-4-(1H-indazol-6-yl)-2-ethyl-1,2,3,4-tetrahydroisoquinoline, maleate salt [280 mg, 97.0% AUC HPLC, 100% AUC chiral HPLC (free base)]: $^1$H NMR (CD$_3$OD, 500 MHz) δ 8.03 (d, J=0.86 Hz, 1H), 7.71 (s, 1H), 7.55 (d, J=8.7 Hz, 1H), 7.33-7.19 (m, 4H), 6.91 (d, J=8.7 Hz, 1H), 6.71 (s, 2H), 4.76-4.70 (m, 1H), 4.70-4.50 (m, 2H), 4.57 (s, 3H), 3.84 (dd, J=12.2, 6.1 Hz, 1H), 1.47-1.44 (m, 3H), ESI-MS m/z=278 [M+H]$^+$; $[α]^{25}_D$ −84.7.0° (c 0.08, MeOH, free base).

Example 131

Preparation of (+/−)-4-benzooxazol-2-yl-2-methyl-1,2,3,4-tetrahydroisoquinoline, maleate salt Step A: Racemic 4-benzooxazol-2-yl-2-methyl-1,2,3,4-tetrahydroisoquinoline was prepared by a method similar to the one described in Example 132, starting from benzooxazole (Steps A to B). The free base (20 mg, 0.076 mmol) was dissolved in methanol (5 mL) was added a solution of maleic acid (8 mg, 0.076 mmol) in methanol (2 mL) at 0° C. The solution was stirred at room temperature for 12 h, concentrated, and the residue was slurried with diethyl ether. Filtration provided the as a 4-benzooxazol-2-yl-2-methyl-1,2,3,4-tetrahydroisoquinoline, maleate salt as a white powder (28 mg, 98%): $^1$H NMR (CD$_3$OD, 500 MHz) δ 7.69 (dd, J=8.3, 6.8 Hz, 2H), 7.62 (dd, J=8.3, 1.3 Hz, 2H), 7.48-7.36 (m, 5H), 7.28 (d, J=2.9 Hz, 1H), 5.42 (s, 2H), 4.98-4.97 (m, 1H), 4.43-4.33 (m, 2H), 4.03 (s, 1H), 3.81-3.77 (m, 1H), 3.04 (s, 3H); ESI-MS m/z=265 [M+H]$^+$; mp 135-140° C.; HPLC 97.5% AUC.

Example 132

Preparation of (+/−)4-benzothiazol-2-yl-2-methyl-1,2,3,4-tetrahydroisoquinoline, maleate salt Step A: To a solution of 4-bromoisoquinoline (2.00 g, 9.61 mmol), benzothiazole (1.08 g, 8.01 mmol), and copper bromide (374 mg, 1.60 mmol) in DMF (50 mL) was added cesium carbonate (3.16 g, 9.70 mmol) and the solution degassed by alternately evacuating and releasing to argon three times. To this heterogeneous mixture was added palladium (II) acetate (540 mg, 0.801 mmol), the reaction mixture was degassed three times and heated to 150° C. with agitation for 3 hours. The mixture was cooled, diethyl ether (150 mL) was added, the organic layer washed with water (3×50 mL), and dried over anhydrous sodium sulfate then concentrated. The residue was purified by column chromatography (SiO$_2$, 40 g, 100% to 0% hexane/ethyl acetate) to provide the product as a yellow solid (646 mg, 31%): ESI-MS m/z=263 [M+H]$^+$.

Step B: To a solution of product from Step A (100 mg, 0.381 mmol) in anhydrous dichloromethane (5 mL) at 0° C. was added methyl trifluoromethanesulfonate (43 μL, 0.381 mmol) dropwise at −40° C. The mixture was stirred at −40° C. for 1 hour, concentrated to dryness and redissolved in methanol (100 mL). To this solution was added sodium cyanoborohydride (1.66 g, 26.3 mmol) at 0° C., the mixture stirred at room temperature for 12 hours and concentrated to dryness. The residue was purified by semi-prep reverse phase HPLC to provide the desired tetrahydroisoquinoline as a white solid (18 mg, 17%). ESI-MS m/z=281 [M+H]$^+$.

Step C: To a solution of product from Step B (18 mg, 0.064 mmol) in methanol (5 mL) was added a solution of maleic acid (7 mg, 0.064 mmol) in methanol (2 mL) at 0° C. The solution was stirred at room temperature for 12 h, concentrated, and the residue was slurried with diethyl ether. Filtration provided (+/−) 4-benzothiazol-2-yl-2-methyl-1,2,3,4-tetrahydroisoquinoline, maleate salt as a white powder (18 mg, 71%): $^1$H NMR (CD$_3$OD, 500 MHz) δ 8.00-7.92 (m, 2H), 7.70-7.29 (m, 6H), 6.26 (s, 4H), 5.11-5.04 (m, 1H), 4.64-4.44 (m, 2H), 4.32-4.19 (bs, 1H), 3.96-3.84 (m, 1H), 3.19-3.10 (m, 3H). ESI MS m/z=281 [M+H]$^+$. mp 165-170° C. HPLC 95.7% AUC.

Example 133

Preparation of (+/−)4-benzothiazol-6-yl-2-methyl-1,2,3,4-tetrahydroisoquinoline, maleate salt Step A: Racemic 4-benzothiazol-6-yl-2-methyl-1,2,3,4-tetrahydroisoquinoline was prepared from 6-bromo-benzothiazole by a method similar to the one described in Example 129 (Steps B to C). The desired tetrahydroisoquinoline (20.5 mg) was dissolved in methanol and treated with a solution of maleic acid in methanol (1 mL) at 0° C. The solution was stirred at room temperature overnight, then concentrated, and the solid was washed with diethyl ether providing (+/−)4-benzothiazol-6-yl-2-methyl-1,2,3,4-tetrahydroisoquinoline, maleate salt (30 mg, 98%, >99% AUC HPLC): $^1$H NMR (CD$_3$OD, 500 MHz) δ 9.28 (d, J=3.9 Hz, 1H), 8.09-8.08 (m, 1H), 8.00-7.99 (m, 1H), 7.44-7.42 (m, 1H), 7.36-7.25 (m, 3H), 6.93-6.92 (m, 1H), 6.26-6.25 (s, 2H), 4.80-4.78 (m, 1H), 4.64-4.56 (m, 2H), 3.93-3.89 (m, 1H), 3.63-3.61 (m, 1H), 3.08 (s, 3H); ESI-MS m/z=281 [M+H]$^+$.

Example 134

Preparation of (−)-4-benzo[d]isothiazol-6-yl-2-methyl, 1,2,3,4-tetrahyrdo-isoquinoline, fumarate salt and (+)-4 Benzo[d]isothiazol-6-yl-2-methyl,1,2,3,4-tetrahyrdo-isoquinoline, fumarate salt Step A: Isoquinoline-4-boronic acid (1.01 g, 6.0 mmol) and 2 M solution of sodium carbonate (5 mL) were added to a solution of 6-bromo-benzo[d]isothiazole (1.12 g, 5.0 mmol) in N,N-dimethylformamide. The mixture was evacuated with argon and stirred vigorously. Tetrakis(triphenylphosphine)palladium (0) (0.6 g, 0.5 mmol) was then added to the reaction mixture which was heated to 85° C. over 4 hours. The reaction mixture was returned to room temperature and water (10 mL) was added to the mixture and extracted with ethyl acetate three times. The organic extract was dried over sodium sulfate, filtered and concentrated to a brown oil. The oil was purified by column chromatography (silica gel, 5:95 to 40:60 ethyl acetate/hexanes as the eluent) to give the desired product (0.76 g, 55%) as a yellow solid: $^1$H NMR (300 MHz, CDCl$_3$) δ 9.33 (s, 1H), 9.03 (s, 1H), 8.56 (s, 1H), 8.22 (d, J=8.2 Hz, 1H), 8.11-8.09 (m, 2H), 7.89-7.87 (m, 1H), 7.72-7.60 (m, 3H).

Step B: The product from Step A (0.74 g, 2.8 mmol) was dissolved in anhydrous methylene chloride (10 mL). The solution was cooled in an ice bath, then methyl trifluormethane sulfonate (0.38 mL) was added dropwise and stirred for 5 minutes. The solution was concentrated to provide (0.78 g, >99%) as a yellow solid. This crude product was used in the next step without further purification.

Step C: The crude product from Step B (0.78 g, 2.8 mmol) was dissolved in methanol (20 mL) and the solution was cooled in an ice bath. Sodium cyanoborohydride (0.35 g, 5.6 mmol) was added portionwise to the reaction mixture and stirred for 2 minutes. The ice bath was removed and the reaction mixture was stirred for an additional 15 minutes. Ethanol was removed and the residue was dissolved in methylene chloride and water. The mixture was extracted with methylene chloride three times. The organic extracts were combined, dried over sodium sulfate, filtered and concentrated. The mixture was purified by column chromatography (silica gel, 2.5% methanol/methylene chloride) to give the desired product (0.55 g, 79%) as a yellow oil: $^1$H NMR (300 MHz, CDCl$_3$) δ 8.86 (d, J=0.6 Hz, 1H), 7.97 (d, J=8.3 Hz, 1H), 7.80 (s, 1H), 7.30 (dd, J=8.3, 1.3 Hz, 1H), 7.18 (t, J=7.3 Hz, 1H), 7.13 (d, J=7.0 Hz, 1H), 7.09 (t, J=7.4 Hz, 1H), 6.87 (d, J=7.7 Hz, 1H), 4.44 (t, J=6.4 Hz, 1H), 3.72 (s, 2H), 3.05 (dd, J=11.5, 5.5 Hz, 1H), 2.71-2.69 (m, 1H), 2.43 (s, 3H). This compound was resolved by preparative chiral HPLC (CHIRALPAK AD column, using 90:10 heptane/isopropanol with 0.1% diethylamine as eluent) to give (+)-enantiomer $[\alpha]^{25}_D$ +67.9° (c 0.36, methanol) and the (−)-enantiomer $[\alpha]^{25}_D$ −72.8° (c 0.36, methanol).

Step D: The (+)-enantiomer from Step C was converted to the fumaric acid salt by dissolving the free-base in a minimal amount of ethanol, adding one equivalent of fumaric acid in enough methanol to completely dissolve the acid, then mixing the two solutions and stirring over 2 hours. The solution was concentrated to a minimal volume, then refrigerated at −30° C. until crystal formation occurred. Filtration yielded the (+)-enantiomer, 4-benzo[d]isothiazol-6-yl-2-methyl-1,2,3,4-tetrahydroisoquinoline, fumarate salt (326 mg, 88%, 96.6% AUC HPLC) as an off-white solid: $^1$H NMR (500 MHz, CD$_3$OD) δ 8.96 (d, J=0.8 Hz, 1H), 8.15 (d, J=8.3 Hz, 1H), 7.98 (s, 1H), 7.33 (dd, J=8.4 Hz, 1H), 7.28-7.25 (m, 2H), 7.21-7.19 (m, 1H), 6.88 (d, J=7.8 Hz, 1H), 6.70 (s, 2H), 4.74-4.71 (m, 1H), 4.30 (d, J=6.9 Hz, 2H), 3.67-3.63 (m, 1H), 3.32-3.27 (m, 1H), 2.85 (s, 3H).

The same procedure was used to transform the (−)-enantiomer to 4-benzo[d]isothiazol-6-yl-2-methyl-1,2,3,4-tetrahydroisoquinoline, fumarate salt (302 mg, 93%, 97.9% AUC HPLC) as an off-white solid: $^1$H NMR (500 MHz, CD$_3$OD) δ 8.96 (s, 1H), 8.14 (d, J=8.3 Hz, 1H), 7.97 (s, 1H), 7.34-7.26 (m, 3H), 7.20-7.19 (m, 1H), 6.88 (d, J=7.8 Hz, 1H), 6.70 (s, 2H), 4.72-4.69 (m, 1H), 4.26 (d, J=8.9 Hz, 2H), 3.62-3.59 (m, 1H), 3.30-3.23 (1H), 2.82 (s, 3H).

Example 135

Preparation of (−)-4-benzo[d]isothiazol-5-yl-2-methyl-1,2,3,4-tetrahydroisoquinoline, maleate salt and (+)-4-benzo[d]isothiazol-5-yl-2-methyl-1,2,3,4-tetrahydroisoquinoline, maleate salt Step A: A solution of 2-bromo-5-fluorobenzaldehyde (8.5 g, 41.9 mmol) was added to a mixture of benzyl mercaptan (5.2 g, 41.9 mmol) and potassium carbonate (7.5 g, 54.4 mmol) in DMF (55 mL). The reaction mixture was heated to 80° C. for 4 hours. After cooling to room temperature, the solvent was evaporated. The residue was diluted with water and extracted with ether three times, washed with brine, dried over sodium sulfate, filtered and concentrated in vacuo. Purification by column chromatography (120 g silica, 90:10 hexane/ethyl acetate) afforded the desired product (6.1 g, 48%) as a light-yellow solid: $^1$H NMR (CDCl$_3$, 500 MHz) δ 10.17 (s, 1H), 7.92 (s, 1H), 7.58 (d, J=8.4 Hz, 1H), 7.32-7.21 (m, 6H), 4.09 (s, 2H).

Step B: Sulfuryl chloride (1.6 mL, 20.3 mmol) was added dropwise to a suspension of product from Step A (6.1 g, 19.9 mmol) in 1,2-dichloroethane (30 mL) at room temperature. The solvent was evaporated. The residue was suspended in THF (30 mL) and treated with ammonia (7 N in methanol, 30 mL) and was stirred at room temperature for 2 hours. After completion, the reaction mixture was diluted with water and the organic layer was separated. The aqueous layer was extracted with ethyl acetate three times. The combined organic extracts were washed with brine, dried over sodium sulfate, filtered and concentrated in vacuo to afford 5-bromo-benzo[d]isothiazole (3.63 g, 84%) as a yellow solid: $^1$H NMR (CDCl$_3$, 500 MHz) δ 8.85 (s, 1H), 8.21 (s, 1H), 7.84 (d, J=7.9 Hz, 1H), 7.62 (d, J=8.5 Hz, 1H).

Step C: A mixture of 5-bromo-benzo[d]isothiazole, obtained from Step B, (1.33 g, 6.21 mmol), isoquinolin-4-boronic acid (1.61 g, 9.32 mmol), and 2N Na$_2$CO$_3$ (9 mL) in ethylene glycol dimethyl ether (19 mL) was degassed with argon. To this mixture was added Pd(Ph$_3$P)$_4$ (0.72 g, 0.62 mmol). The resulting mixture was degassed with argon and then heated to reflux overnight. After cooling to room temperature, the reaction mixture was diluted with water and the organic layer was separated. The aqueous layer was extracted with ethyl acetate three times. The combined organic extracts were washed with brine, dried over sodium sulfate, filtered, and concentrated in vacuo. Purification by column chromatography (80 g silica gel; 60:40 hexanes/ethyl acetate) afforded the product (1.04 g, 64%) as an off-white solid: $^1$H NMR (CDCl$_3$, 500 MHz) δ 9.32 (s, 1H), 9.01 (s, 1H), 8.55 (s, 1H), 8.21 (s, 1H), 8.13-8.08 (m, 2H), 7.70 (d, J=8.5 Hz, 1H), 7.68-7.50 (m, 3H).

Step D: Methyl triflate (0.25 mL, 2.29 mmol) was added dropwise to an ice-cold solution of the product from Step C (0.500 g, 3.81 mmol) in methylene chloride (2.5 mL). The resulting slurry was stirred for 10 minutes at room temperature. The reaction mixture was concentrated in vacuo. The residue (1.05 g, 3.8 mmol) was diluted in methanol (12 mL) and treated with sodium cyanoborohydride (600 mg, 9.5 mmol). The reaction mixture was stirred at room temperature for 20 minutes. The solvent was removed in vacuo and the residue was diluted with ethyl acetate, washed with water three times, dried over sodium sulfate and concentrated in vacuo. Purification by column chromatography (80 g silica; 95:5 methylene chloride/methanol) to afford the product (280 mg, 26%). This material was resolved by chiral HPLC (Chiralpak AD, 95:5 heptane/isopropanol with 0.1% diethylamine). The (−)enantiomer (230 mg, 43%) was obtained as a yellow oil: $[\alpha]^{25}_D$ −58.6° (c 0.10, methanol); $^1$H NMR (500 MHz, CDCl$_3$) δ 8.84 (s, 1H), 7.89-7.86 (m, 2H), 7.40 (d, J=8.4 Hz, 1H), 7.19-7.06 (m, 3H), 6.87 (d, J=7.7 Hz, 1H), 4.43 (t, J=6.5 Hz, 1H), 3.72 (s, 2H), 3.06-3.02 (m, 1H), 2.69-2.66 (m, 1H), 2.43 (s, 3H). The (+)enantiomer (230 mg, 43%) was obtained as a yellow oil: $[\alpha]^{25}_D$ +55.0° (c 0.10, methanol); $^1$H NMR (500 MHz, CDCl$_3$) δ 8.84 (s, 1H), 7.89-7.86 (m, 2H), 7.40 (d, J=8.4 Hz, 1H), 7.19-7.06 (m, 3H), 6.87 (d, J=7.7 Hz, 1H), 4.43 (t, J=6.5 Hz, 1H), 3.72 (s, 2H), 3.06-3.02 (m, 1H), 2.69-2.66 (m, 1H), 2.43 (s, 3H).

Step E: A solution of the (−)enantiomer from Step D (230 mg, 0.820 mmol) and maleic acid (95 mg, 0.820 mmol) in methanol (1 mL) was stirred at room temperature. The solvent was evaporated. The solvent was evaporated.

Lyophilization from acetonitrile (0.5 mL)/water (0.5 mL) yielded (−)-4-benzo[d]isothiazol-5-yl-2-methyl-1,2,3,4-tetrahydroisoquinoline, maleate salt (306 mg, 91%, >99.0% AUC HPLC) as a white solid: mp 127-129° C.; $^1$H NMR (500 MHz, CD$_3$OD) δ 8.95 (s, 1H), 8.11-8.08 (m, 2H), 7.44 (d, J=8.5 Hz, 1H), 7.35-7.24 (m, 3H), 6.92 (d, J=7.7 Hz, 1H), 6.23 (s, 2H), 4.62-4.55 (m, 2H), 3.91-3.87 (m, 1H), 3.61 (t, J=11.7 Hz, 1H), 3.33-3.30 (m, 1H), 3.06 (s, 3H); ESI MS m/z 281 [M+H]$^+$.

Step F: A solution of the (+)-enantiomer from Step D (230 mg, 0.820 mmol) and maleic acid (95 mg, 0.230 mmol) in methanol (1 mL) was stirred at room temperature. The solvent was evaporated. Lyophilization from acetonitrile (0.5 mL)/water (0.5 mL) yielded (+)-4-benzo[d]isothiazol-5-yl-2-methyl-1,2,3,4-tetrahydroisoquinoline, maleate salt (303 mg, 88%, 97.9% AUC HPLC) as a white solid: mp 145-147° C.; $^1$H NMR (500 MHz, CD$_3$OD) δ 8.95 (s, 1H), 8.11-8.08 (m, 2H), 7.44 (d, J=8.5 Hz, 1H), 7.35-7.24 (m, 3H), 6.92 (d, J=7.7 Hz, 1H), 6.23 (s, 2H), 4.62-4.55 (m, 2H), 3.91-3.87 (m, 1H), 3.61 (t, J=11.7 Hz, 1H), 3.33-3.30 (m, 1H), 3.06 (s, 3H); ESI MS m/z 281 [M+H]$^+$.

Example 136

Preparation of (+)-8-methoxy-2-methyl-4-naphthalen-2-yl-1,2,3,4-tetrahydroisoquinolin-7-ol, maleate salt and (−)-8-methoxy-2-methyl-4-naphthalen-2-yl-1,2,3,4-tetrahydroisoquinolin-7-ol, maleate salt Step A: Potassium carbonate (29.2 g, 0.275 mol) was added to a solution of 2,3-dihydroxybenzaldehyde (38.0 g, 0.275 mol) in DMF (500 mL) at 25° C. under nitrogen. The mixture was stirred for 30 minutes and methyl iodide was added dropwise. The mixture was stirred overnight, partitioned with EtOAc (3×200 mL) and water (200 mL). The combined organic extracts were washed with 5% LiCl solution (2×200 mL), dried (Na$_2$SO$_4$) and concentrated under reduced pressure. The crude product was purified by flash column chromatography (eluent hexanes/EtOAc 10:1) to give the methoxy benzaldehyde (24.8 g, 59%) as a yellow solid: $^1$H NMR (CDCl$_3$, 300 MHz) δ 10.27 (s, 1H), 7.38-7.40 (m, 1H), 7.12-7.36 (m, 2H), 5.75 (s, 1H), 3.98 (s, 3H).

Step B: A solution of the methoxy benzaldehyde (7.10 g, 4.67 mmol) from Step A above and methylamine (1.73 g, 56.0 mmol, 40% wt in water) in methanol (150 mL) was stirred for 15 minutes at 25° C. under nitrogen. The mixture was cooled to 0° C. and sodium borohydride (880 mg, 23.3 mmol) was added in portions. The reaction mixture was stirred 2 hours and concentrated under reduced pressure. The residue was partitioned with EtOAc (3×200 mL) and water (200 mL), dried (Na$_2$SO$_4$) and concentrated under reduced pressure to give the methylamino compound (5.0 g, 64%) as a tan solid which was used in the next step without any further purification: $^1$H NMR (CDCl$_3$, 500 MHz) δ 6.88-6.90 (m, 1H), 6.75-6.78 (m, 2H), 4.30 (bs, 1H), 3.81 (s, 3H), 3.77 (s, 1H), 3.74 (s, 2H), 2.48 (s, 3H).

Step C: A solution of the methylamino compound (5.5 g, 32.9 mmol) from Step B above and α-bromo-2'-acetonaphthone (8.2 g, 32.9 mmol) and N,N-diisopropylethylamine (4.25 g, 32.9 mmol) in methylene chloride (150 mL) was stirred for 3 hours at 25° C. under nitrogen. The reaction mixture was partitioned with EtOAc (3×150 mL) and water (200 mL), dried (Na$_2$SO$_4$) and concentrated under reduced pressure to give the desired ketone (10.4 g, 95% crude) as a tan solid which was used in the next step without any further purification: $^1$H NMR (CDCl$_3$, 500 MHz) δ 8.44 (s, 1H), 7.98 (d, J=8.7 Hz, 1H), 7.85-7.91 (m, 3H), 7.54-7.60 (m, 3H), 6.92-7.01 (m, 3H), 3.96 (s, 2H), 3.83 (s, 2H), 3.79 (s, 3H), 2.45 (s, 3H).

Step D: To a solution of the ketone (10.4 g, 31.3 mmol) from Step C above in methanol (150 mL) at 0° C. was added sodium borohydride (1.40 g, 37.6 mmol) in small portions. The reaction solution was stirred at 0° C. for 2 hours, and the solvent was removed under reduced pressure. The residue obtained was partitioned with EtOAc (2×250 mL) and water (200 mL). The organic extracts were dried (Na$_2$SO$_4$) and concentrated under reduced pressure to give the desired alcohol which was used in next step without further purification and characterization. This residue was taken up in methylene chloride (200 mL) and concentrated sulfuric acid (10 mL) was added dropwise. The reaction mixture was stirred 1 h, poured into ice-water, and basicified with concentrated ammonium hydroxide to pH 10 and extracted with EtOAc (3×500 mL), dried (Na$_2$SO$_4$) and concentrated under reduced pressure. The crude product was purified by flash column chromatography (eluent hexanes/EtOAc 7:3) to give the desired tetrahydroisoquinoline (3.90 g, 39%) as a tan foam: $^1$H NMR (CDCl$_3$, 500 MHz) δ 7.74-7.81 (m, 3H), 7.67 (s, 1H), 7.42-7.51 (m, 2H), 7.27-7.28 (m, 1H), 6.70 (d, J=8.4 Hz, 1H), 6.56 (d, J=8.4 Hz, 1H), 5.30 (s, 1H), 4.38 (d, J=8.5 Hz, 6.0 Hz, 1H), 3.91 (d, J=15.3 Hz, 1H), 3.87 (s, 3H), 3.58 (d, J=15.4 Hz, 1H), 3.01 (dd, J=8.5 Hz, 6.0 Hz, 1H), 2.60-2.64 (m, 1H), 2.46 (s, 3H); ESI-MS m/z 320 [M+H]$^+$.

The free base of the ketone (300 mg) was resolved by preparative chiral HPLC (CHIRALPAK AD column, using 85:15:0.1 heptane/EtOH/diethylamine as the eluent) to give the (+)-enantiomer [[α]$^{23}_D$ +80.0° (c 0.08, methanol)] and the (−)-enantiomer [[α]$^{23}_D$ −87.4° (c 0.135, methanol)]. The (+)-enantiomer (56.7 mg, 0.177 mmol) was dissolved in methanol (3 mL) and one equivalent of maleic acid (20.6 mg, 0.177 mmol) was added. The resultant solution was concentrated under reduced pressure to provide (+)-8-methoxy-2-methyl-4-naphthalen-2-yl-1,2,3,4-tetrahydroisoquinolin-7-ol, maleate salt (69.0 mg, 89%, 98.7% AUC HPLC) as a white solid: mp 85-90° C.; $^1$H NMR (CD$_3$OD, 500 MHz) δ 7.82-7.87 (m, 3H), 7.77 (s, 1H), 7.47-7.52 (m, 2H), 7.26 (dd, J=8.5 Hz, 1.4 Hz, 1H), 6.76 (d, J=8.5 Hz, 1H), 6.50 (d, J=8.5 Hz, 1H), 6.24 (s, 2H), 4.63-4.71 (m, 2H), 4.44 (d, J=15.1 Hz, 1H), 3.93 (s, 3H), 3.80-3.85 (m, 1H), 3.54-3.59 (m, 1H), 3.10 (s, 3H); ESI-MS m/z 320 [M+H]$^+$; Anal. Calcd. For C$_{21}$H$_{21}$NO$_2$—C$_4$H$_4$O$_4$-0.90H$_2$O: C, 66.37; H, 5.77; N, 3.10. Found: C, 66.49; H, 5.54; N, 3.08.

The (−)-enantiomer (100 mg, 0.312 mmol) was dissolved in methanol (3 mL) and one equivalent of maleic acid (35.1 mg, 0.312 mmol) was added. The resultant solution was concentrated under reduced pressure and triturated with diethyl ether and to provide (−)-8-methoxy-2-methyl-4-naphthalen-2-yl-1,2,3,4-tetrahydroisoquinolin-7-ol, maleate salt (101.1 mg, 69%, 93.8% AUC HPLC) as a white solid: mp 85-90° C.; $^1$H NMR (CD$_3$OD, 500 MHz) δ 7.82-7.87 (m, 3H), 7.77 (s, 1H), 7.47-7.52 (m, 2H), 7.26 (dd, J=8.5 Hz, 1.4 Hz, 1H), 6.76 (d, J=8.5 Hz, 1H), 6.50 (d, J=8.5 Hz, 1H), 6.24 (s, 2H), 4.63-4.71 (m, 2H), 4.44 (d, J=15.1 Hz, 1H), 3.93 (s, 3H), 3.80-3.85 (m, 1H), 3.54-3.59 (m, 1H), 3.10 (s, 3H); ESI-MS m/z 320 [M+H]$^+$.

Example 137

Preparation of (−)-2-methyl-4-napthalen-2-yl-7-pyridazin-3-yl-1,2,3,4-tetrahydroisoquinoline, maleate salt and (+)-2-methyl-4-napthalen-2-yl-7-pyridazin-3-yl-1,2,3,4-tetrahydroisoquinoline, maleate salt Step A: To a solution of (3-bromo-benzyl)-methyl-amine (2.0 g, 9.99 mmol) in methylene chloride (40 mL) was added diisopropylethylamine (3.5 mL, 20.0 mmol). The reaction mixture was cooled to 0° C. and treated with 2-bromo-2'-acetonapthone (2.49 g, 9.99 mmol) portionwise over a period of 10 minutes. The reaction mixture was warmed to room temperature and stirred for 3 hours. The reaction mixture was washed with water three times, dried over sodium sulfate, filtered, and the solvent was evaporated to afford product (3.57 g, 98%) as a viscous, orange oil: $^1$H NMR (CDCl$_3$, 500 MHz) δ 8.49 (s, 1H), 8.00 (d, J=8.6 Hz, 1H), 7.95 (d, J=8.1 Hz, 1H), 7.87 (t, J=8.2 Hz, 2H), 7.61-7.54 (m, 3H), 7.40 (d, J=7.0 Hz, 1H), 7.31 (d, J=7.6 Hz, 1H), 7.19 (t, J=7.7 Hz, 1H), 3.91 (s, 2H), 3.71 (s, 2H), 2.40 (s, 3H).

Step B: Sodium borohydride (440 mg, 11.6 mmol) was added over a period of 10 minutes to an ice-cooled solution of the product from Step A (3.57 g, 9.69 mmol) in methanol (45 mL). The reaction mixture was allowed to warm to room temperature and continued to stir for an additional 5 hours. The solvent was removed under reduced pressure and the residue was diluted with water and extracted with methylene chloride three times. The combined extracts were dried over sodium sulfate, filtered and concentrated in vacuo to provide the product (2.74 g, 77%) as an orange oil: $^1$H NMR (500 MHz, CDCl$_3$) δ 7.84-7.81 (m, 4H), 7.48-7.40 (m, 5), 7.26 (s, 1H), 7.20 (t, J=7.7 Hz, 1H), 4.92 (dd, J=3.8 Hz, 10.0 Hz, 1H), 3.99 (s, 1H), 3.71 (d, J=13.2 Hz, 1H), 3.52 (d, J=13.2 Hz, 1H), 2.69-2.61 (m, 2H), 2.34 (s, 3H).

Step C: Product from Step B (2.74 g, 7.4 mmol) in 1,2-dichloroethane (45 mL) was added dropwise via addition funnel to methane sulfonic acid (27 mL, 414 mmol) at 40° C. and stirred for an additional 3.5 hours. The cooled reaction mixture was poured over ice and made basic to pH 9 with concentrated ammonium hydroxide. The reaction mixture was extracted with ethyl acetate four times. The combined organic extracts were dried over sodium sulfate, filtered, and concentrated in vacuo. Purification by column chromatography (80 g silica, 99:1 methylene chloride/methanol) provided the product (490 mg, 19%) as a yellow solid: $^1$H NMR (500 MHz, CDCl$_3$) δ 7.81-7.75 (m, 3H), 7.66 (s, 1H), 7.46-7.44 (s, 1H), 7.27 (s, 1H), 7.24-7.23 (m, 2H), 7.16 (d, J=8.3 Hz, 1H), 6.75 (d, J=8.3 Hz, 1H), 4.35 (t, J=6.29 Hz, 1H), 3.75 (d, J=15.1 Hz, 1H), 3.62 (d, J=15.1 Hz, 1H), 3.10-3.06 (m, 1H), 2.66-2.61 (m, 1H), 2.43 (s, 3H).

Step D: A mixture of the product from Step C (490 mg, 1.39 mmol), bis(pinacolato)diboron (389 mg, 1.53 mmol), KOAc (409 mg, 4.17 mmol) was degassed with argon. To this mixture was added PdCl$_2$(dppf) (70 mg, 0.083 mmol). The resulting mixture was degassed with argon and then heated at 80° C. for 6 hours. The cooled mixture was diluted with water and the organic layer was separated. The aqueous layer was extracted with ethyl acetate three times. The combined organic extracts were washed with brine, dried over sodium sulfate, filtered, and concentrated in vacuo to afford a brown oil, which was used in Step E without further purification.

Step E: A mixture of the crude product from Step D (555 mg, 1.39 mmol), 3,6-dichloro-pyridazine (260 mg, 1.74 mmol), and cesium carbonate (1.36 g, 4.17 mmol) in DMF (25 mL) and water (5 mL) was degassed with argon. To this mixture was added PdCl$_2$(dppf) (68 mg, 0.08 mmol). The resulting mixture was degassed with argon and then heated at 80° C. for 4.5 hours. The cooled mixture was filtered through a bed of diatomaceous earth and washed with water three times. The organic layers were separated, dried over sodium sulfate, filtered, and concentrated in vacuo. Purification by column chromatography (40 g silica, 95:5 methylene chloride/methanol) provided the product (470 mg, 88%) as a light-brown solid; $^1$H NMR (500 MHz, CDCl$_3$) δ 7.90 (s, 1H), 7.81-7.77 (m, 4H), 7.71 (s, 1H), 7.67-7.64 (m, 1H), 7.53 (d, J=9.0 Hz, 1H), 7.47-7.45 (m, 3H), 7.05 (d, J=8.0 Hz, 1H), 4.51 (t, J=6.2 Hz, 1H), 3.91 (d, J=15.0 Hz, 1H), 3.75 (d, J=15.0 Hz, 1H), 3.17-3.13 (m, 1H), 2.73-2.69 (m, 1H), 2.47 (s, 3H).

Step F: Hydrazine (2.49 mL, 51.2 mmol) and 10% palladium on carbon (250 mg) was added to a solution of the product from Step E (470 mg, 1.22 mmol) in ethanol (40 mL) and was heated to reflux for 6.5 hours. The cooled mixture was filtered through a bed of diatomaceous earth and flushed with methanol. The solvent was evaporated. Purification by column chromatography (40 g silica, 95:5 methylene chloride/methanol) provided the desired product (150 mg, 35%). This product was resolved by chiral HPLC (Chiralpak AD, 70:30 heptane/isopropanol with 0.1% diethylamine). The (−)-enantiomer (60 mg, 40%) was obtained as a light-orange solid $[α]^{25}_d$ −37.0° (0.1, methanol); $^1$H NMR (500 MHz, CDCl$_3$) δ 9.14 (d, J=4.9 Hz, 1H), 7.96 (s, 1H), 7.95-7.77 (m, 4H), 7.71-7.68 (m, 2H), 7.52-7.46 (m, 3H), 7.30 (d, J=8.4 Hz, 1H), 7.05 (d, J=8.2 Hz, 1H), 4.52 (t, J=6.7 Hz, 1H), 3.92 (d, J=15.0 Hz, 1H), 3.76 (d, J=14.9 Hz, 1H), 3.17-3.14 (m, 1H), 2.73 (m, 1H), 2.49 (s, 3H).

Step G: A solution of the (−)-enantiomer from Step F (60 mg, 0.171 mmol) and maleic acid (20 mg, 0.171 mmol) in methanol (1 mL) was stirred at room temperature. The solvent was evaporated. Lyophilization from acetonitrile (0.5 mL)/water (0.5 mL) yielded (−)-2-methyl-4-napthalen-2-yl-7-pyridazin-3-yl-1,2,3,4-tetrahydroisoquinoline, maleate salt (76 mg, 99%) as an off-white solid: m.p. 91-93° C.; $^1$H NMR (CD$_3$OD, 500 MHz) δ 9.16 (d, J=4.8 Hz, 1H), 8.17 (d, J=8.6 Hz, 1H), 8.07 (s, 1H), 7.90-7.78 (m, 6H), 7.52-7.50 (m, 2H), 7.32 (d, J=8.5 Hz, 1H), 7.12 (d, J=8.2 Hz, 1H), 6.24 (s, 0.8H), 4.81-4.77 (m, 1H), 4.58-4.55 (m, 2H), 3.82-3.78 (m, 1H), 3.54-3.52 (m, 1H), 3.00 (s, 3H); ESI-MS m/z 352 [M+H]$^+$.

Step H: A solution of the (+)-enantiomer from Step F (80 mg, 0.228 mmol) and maleic acid (26 mg, 0.228 mmol) in methanol (1 mL) was stirred at room temperature. The solvent was evaporated. Lyophilization from acetonitrile (0.5 mL)/water (0.5 mL) yielded (+)-2-methyl-4-napthalen-2-yl-7-pyridazin-3-yl-1,2,3,4-tetrahydroisoquinoline, maleate salt (91.6 mg, 78%) as an off-white solid: m.p. 86-88° C.; $^1$H NMR (CD$_3$OD, 500 MHz) δ 9.16 (d, J=4.8 Hz, 1H), 8.17 (d, J=8.6 Hz, 1H), 8.07 (s, 1H), 7.90-7.78 (m, 6H), 7.52-7.50 (m, 2H), 7.32 (d, J=8.5 Hz, 1H), 7.12 (d, J=8.2 Hz, 1H), 6.24 (s, 0.8H), 4.81-4.77 (m, 1H), 4.58-4.55 (m, 2H), 3.82-3.78 (m, 1H), 3.54-3.52 (m, 1H), 3.00 (s, 3H); ESI-MS m/z 352 [M+H]$^+$.

Example 138

Preparation of (+)-4-(1-methoxy-napthalen-2-yl)-2-methyl-7-pyridazin-3-yl-1,2,3,4-tetrahydroisoquinoline, maleate salt and (−)-4-(1-methoxy-napthalen-2-yl)-2-methyl-7-pyridazin-3-yl-1,2,3,4-tetrahydroisoquinoline, maleate salt Step A: Potassium carbonate (5.2 g, 37.6 mmol) and dimethyl sulfate (2.7 mL, 28.2 mmol) were added to a solution of 1'-hydroxy-2'-acetonapthone (3.5 g, 18.8 mmol) in acetone (50 mL) and was heated to reflux for 22.5 hours. The solvent of the cooled reaction mixture was evaporated. The residue was dissolved in methanol (40 mL), treated with sodium hydroxide (5.6 g), and was stirred at room temperature for 1.5 hours. The solvent was evaporated and the residue was diluted with water and extracted with ether three times. The combined organic extracts were washed with brine, dried over sodium sulfate, filtered and concentrated in vacuo. Purification by flash column chromatography (80 g silica gel, 100% hexanes) provided the desired product (3.33 g, 89%) as an off-white solid: $^1$H NMR (CDCl$_3$, 300 MHz) δ 8.24-8.21 (m, 1H), 7.87-7.84 (m, 1H), 7.74 (d, J=8.6 Hz, 1H), 7.64-7.55 (m, 3H), 4.01 (s, 3H), 2.78 (s, 3H).

Step B: Cupric bromide (7.28 g, 32.6 mmol) in ethyl acetate (50 mL) was heated to 78° C. for 15 minutes. Product from Step A (3.33 g, 16.6 mmol) in chloroform (50 mL) was added to the mixture via addition funnel. After addition was complete, the reaction mixture continued to stir at 78° C. for 23 hours. The cooled reaction mixture was filtered through a pad of diatomaceous earth and washed with an excess of ethyl acetate. The solvent was evaporated. Purification by column chromatography (120 g silica gel, 100% hexanes) provided the desired product (1.73 g, 37%) as an off-white solid: NMR (CDCl$_3$, 500 MHz) δ 8.21 (d, J=7.6 Hz, 1H), 7.87 (d, J=7.3 Hz, 1H), 7.74 (d, J=8.6 Hz, 1H), 7.67-7.58 (m, 3H), 4.74 (s, 2H), 4.04 (s, 3H).

Step C: To a solution of (3-bromo-benzyl)-methyl-amine (1.24 g, 6.20 mmol) in methylene chloride (25 mL) was added diisopropylethylamine (2.16 mL, 12.4 mmol). The reaction mixture was cooled to 0° C. and treated with 2-bromo-1-(3-methoxy-napthalen-2-yl)-ethanone obtained in Step B (1.73 g, 6.20 mmol) portionwise over a period of 10 minutes. The reaction mixture was warmed to room temperature and stirred for 3 h. The reaction mixture was washed with water three times, dried over sodium sulfate, filtered, and the solvent was evaporated to afford the desired product (quantitative yield) as a viscous, orange oil: $^1$H NMR (CDCl$_3$, 500 MHz) δ 8.19-8.17 (m, 1H), 7.87-7.84 (m, 1H), 7.64 (s, 2H), 7.60-7.54 (m, 2H), 7.51 (s, 1H), 7.37 (d, J=8.9 Hz, 1H), 7.28-7.25 (m, 1H), 7.15 (t, J=7.7 Hz, 1H), 3.97 (s, 2H), 3.90 (s, 3H), 3.70 (s, 2H), 2.42 (s, 3H).

Step D: Sodium borohydride (281 mg, 7.44 mmol) was added over a period of 10 minutes to an ice-cooled solution of the product from Step C (2.47 g, 6.20 mmol) in methanol (25 mL). The reaction mixture was allowed to warm to room temperature and continued to stir for an additional 5 hours. The solvent was removed under reduced pressure and the residue was diluted with water and extracted with methylene chloride three times. The combined extracts were dried over sodium sulfate, filtered and concentrated in vacuo to provide the desired product (2.37 g, 96%) as an orange oil: $^1$H NMR (500 MHz, CDCl$_3$) δ 8.07 (d, J=8.2 Hz, 1H), 7.83 (d, J=7.7 Hz, 1H), 7.64-7.60 (m, 3H), 7.51-7.47 (m, 4H), 7.27-7.21 (m, 2H), 5.33-5.29 (m, 1H), 3.95 (s, 3H), 3.90 (s, 1H), 3.74 (d, J=13.3 Hz, 1H), 2.66-2.64 (m, 1H), 2.42 (s, 1H), 2.37 (s, 3H).

Step E: Product from Step D (2.37 g, 5.92 mmol) in 1,2-dichloroethane (35 mL) was added dropwise via addition funnel to methane sulfonic acid (22 mL, 331 mmol) at 40° C. and stirred for an additional 19 hours. The cooled reaction mixture was poured over ice and made basic to pH 9 with concentrated ammonium hydroxide. The reaction mixture was extracted with ethyl acetate four times. The combined organic extracts were dried over sodium sulfate, filtered, and concentrated in vacuo. Purification by column chromatography (80 g silica gel, 99:1 methylene chloride/methanol) provided 7-bromo-4-(1-methoxy-napthalen-2-yl)-2-methyl-1,2,3,4-tetrahyrdo-isoquinoline (690 mg, 31%) as an off-white solid; $^1$H NMR (500 MHz, CDCl$_3$) δ 8.13 (d, J=8.4 Hz, 1H), 7.80 (d, J=8.0 Hz, 1H), 7.55-7.46 (m, 3H), 7.13-7.10 (m, 2H), 7.04 (d, J=8.5 Hz, 1H), 6.80 (d, J=8.2 Hz, 1H), 4.92 (t, J=8.5 Hz, 1H), 3.98 (s, 3H), 3.80 (d, J=15.0 Hz, 1H), 3.61 (d, J=15.0 Hz, 1H), 3.11-3.08 (m, 1H), 2.62-2.58 (m, 1H), 2.46 (s, 3H).

Step F: A mixture of the product from Step E (690 mg, 1.80 mmol), bis(pinacolato)diboron (504 mg, 1.99 mmol), and KOAc (530 mg, 5.40 mmol) in DMSO (12 mL) was degassed with argon. To this mixture was added PdCl$_2$(dppf) (88 mg, 0.108 mmol). The resulting mixture was degassed with argon and then heated at 80° C. for 3 hours. After completion (by thin-layer chromatography analysis), the cooled material was diluted with water and the organic layer was separated. The aqueous layer was extracted with ethyl acetate three times. The combined organic extracts were washed with brine, dried over sodium sulfate, filtered, and concentrated in vacuo to afford a brown oil, which was used in Step G without further purification.

Step G: A mixture of the crude product from Step F (773 mg, 1.80 mmol), 3,6-dichloro-pyridazine (335 mg, 2.25 mmol), and cesium carbonate (1.76 g, 5.4 mmol) in DMF (30 mL) and water (6 mL) was degassed with argon. To this mixture was added PdCl$_2$(dppf) (88 mg, 0.108 mmol). The resulting mixture was degassed with argon and then heated at 80° C. for 4 hours. The cooled mixture was filtered through a pad of diatomaceous earth and washed with water three times. The organic layers were separated, dried over sodium sulfate, filtered, and concentrated in vacuo. Purification by column chromatography (80 g silica gel, 98:2 methylene chloride/methanol) provided the desired product (570 mg, 76%) as a light-brown solid; $^1$H NMR (500 MHz, CDCl$_3$) δ 8.15 (d, J=8.2 Hz, 1H), 7.90 (s, 1H), 7.82-7.77 (m, 2H), 7.64 (d, J=7.3 Hz, 1H), 7.55-7.47 (m, 4H), 7.09 (d, J=8.5 Hz, 1H), 6.99 (d, J=8.0 Hz, 1H), 5.07-5.04 (m, 1H), 4.03 (s, 3H), 3.95 (d, J=14.8 Hz, 1H), 3.73 (d, J=15.0 Hz, 1H), 3.18-3.15 (m, 1H), 2.69-2.65 (m, 1H), 2.50 (s, 3H).

Step H: Hydrazine (2.8 mL, 57.5 mmol) and 10% palladium on carbon (280 mg) was added to a solution of the product from Step G (570 mg, 1.37 mmol) in ethanol (45 mL) and the reaction mixture was heated to reflux for 5.5 hours. After completion (by thin-layer chromatography analysis), the cooled material was filtered through a pad of diatomaceous earth and flushed with methanol. The solvent was evaporated. Purification by column chromatography (80 g silica gel, 98:2 methylene chloride/methanol) provided the desired product (320 mg, 61%). This material was resolved by chiral HPLC (Chiralpak AD, 60:40 heptane/isopropanol with 0.1% diethylamine). The (−)-enantiomer (140 mg, 44%) was obtained as a light-orange solid: $[\alpha]^{25}_D$ −191.3° (c 0.11, methanol); $^1$H NMR (500 MHz, CDCl$_3$) δ 9.14 (d, J=6.4 Hz, 1H), 8.16 (d, J=8.1 Hz, 1H), 7.95 (s, 1H), 7.82 (d, J=8.6 Hz, 2H), 7.68 (d, J=8.0 Hz, 1H), 7.56-7.48 (m, 4H), 7.10 (d, J=8.5 Hz, 1H), 6.99 (d, J=8.1 Hz, 1H), 5.07 (t, J=6.9 Hz, 1H), 4.03 (s, 3H), 3.97 (d, J=14.9 Hz, 1H), 3.74 (d, J=15.0 Hz, 1H), 3.19-3.15 (m, 1H), 3.67 (t, J=9.2 Hz, 1H), 2.51 (s, 3H). The (+)-enantiomer (110 mg, 34%) was obtained as a light-yellow solid: $[\alpha]^{25}_D$ +195.3° (c 0.11, methanol); $^1$H NMR (500 MHz, CDCl$_3$) δ 9.14 (d, J=6.4 Hz, 1H), 8.16 (d, J=8.1 Hz, 1H), 7.95 (s, 1H), 7.82 (d, J=8.6 Hz, 2H), 7.68 (d, J=8.0 Hz, 1H), 7.56-7.48 (m, 4H), 7.10 (d, J=8.5 Hz, 1H), 6.99 (d, J=8.1 Hz, 1H), 5.07 (t, J=6.9 Hz, 1H), 4.03 (s, 3H), 3.97 (d, J=14.9 Hz, 1H), 3.74 (d, J=15.0 Hz, 1H), 3.19-3.15 (m, 1H), 3.67 (t, J=9.2 Hz, 1H), 2.51 (s, 3H).

Step I: A solution of the (−)-enantiomer from Step H (140 mg, 0.367 mmol) and maleic acid (42 mg, 0.367 mmol) in methanol (1 mL) was stirred at room temperature. The solvent was evaporated. Lyophilization from acetonitrile (0.5 mL)/water (0.5 mL) yielded (−)-4-(1-methoxy-napthalen-2-yl)-2-methyl-7-pyridzain-3-yl-1,2,3,4-tetrahydroisoquinoline, maleate salt (152.10 mg, 81%, 99% AUC HPLC) as an off-white solid: m.p. 88-90° C.; $^1$H NMR (CD$_3$OD, 500 MHz) δ 9.16 (s, 1H), 8.18-8.12 (m, 3H), 7.96-7.88 (m, 2H), 7.81-7.79 (m, 1H), 7.69 (d, J=8.5 Hz, 1H), 7.60-7.55 (m, 2H), 7.19 (d, J=8.6 Hz, 1H), 7.11 (d, J=8.2 Hz, 1H), 6.25 (s, 1H), 5.27-5.24 (m, 1H), 4.81-4.66 (m, 2H), 3.94-3.90 (m, 4H), 3.78-3.76 (m, 1H), 3.16 (s, 3H); ESI MS m/z 382 [M+H]$^+$.

Step J: A solution of the (+)-enantiomer from Step G (110 mg, 0.228 mmol) and maleic acid (33.5 mg, 0.228 mmol) in methanol (1 mL) was stirred at room temperature. The solvent was evaporated. Lyophylization from acetonitrile (0.5 mL)/water (0.5 mL) yielded (+)-4-(1-methoxy-napthalen-2-yl)-2-methyl-7-pyridzain-3-yl-1,2,3,4-tetrahydroisoquinoline, maleate salt (138.20 mg, 97%, >99.0% AUC HPLC) as an light-yellow solid: m.p. 90-92° C.; $^1$H NMR (CD$_3$OD, 500 MHz) δ 9.16 (d, J=4.8 Hz, 1H), 8.16 (t, J=9.9 Hz, 2H), 8.11 (br s, 1H), 7.92-7.88 (m, 2H), 7.81-7.78 (m, 1H), 7.68 (d, J=8.6 Hz, 1H), 7.61-7.50 (m, 2H), 7.18 (d, J=8.5 Hz, 1H), 7.11 (d, J=8.0 Hz, 1H), 6.24 (s, 1H), 5.27-5.24 (m, 1H), 4.77-4.68 (m, 2H), 3.94 (s, 3H), 3.91-3.87 (m, 1H), 3.72-3.69 (m, 1H), 3.13 (s, 3H); ESI MS m/z 382 [M+H]$^+$.

Example 139

Preparation of (+/−)-2-methyl-4-napthalen-2-yl-7-pyrazin-2-yl-1,2,3,4-tetrahydroisoquinoline, maleate salt Step A: To a solution of (3-bromo-benzyl)-methyl-amine (7.01 g, 35.0 mmol) in methylene chloride (120 mL) was added diisopropylethylamine (12 mL, 70.0 mmol). The reaction mixture was cooled to 0° C. and treated with 2-bromo-2'-acetonapthone (8.73 g, 35.0 mmol) portionwise over a period of 30 minutes. The reaction mixture was warmed to room temperature and stirred for 3 hours. The reaction mixture was washed with water three times, dried over sodium sulfate, filtered, and the solvent was evaporated to afford the desired product (12.54 g, 97%) as a viscous, orange oil: $^1$H NMR (CDCl$_3$, 500 MHz) δ 8.49 (s, 1H), 8.00 (d, J=8.6 Hz, 1H), 7.95 (d, J=8.1 Hz, 1H), 7.87 (t, J=8.2 Hz, 2H), 7.61-7.54 (m, 3H), 7.40 (d, J=7.0 Hz, 1H), 7.31 (d, J=7.6 Hz, 1H), 7.19 (t, J=7.7 Hz, 1H), 3.91 (s, 2H), 3.71 (s, 2H), 2.40 (s, 3H).

Step B: Sodium borohydride (1.55 g, 40.9 mmol) was added over a period of 30 minutes to an ice-cooled solution of the product from Step A (12.54 g, 34.0 mmol) in methanol (140 mL). The reaction mixture was allowed to warm to room temperature and continued to stir for an additional 4 hours. The solvent was removed under reduced pressure and the residue was diluted with water and extracted with methylene chloride three times. The combined extracts were dried over sodium sulfate, filtered and concentrated in vacuo to provide the desired product (11.67 g, 93%) as an orange oil: $^1$H NMR (500 MHz, CDCl$_3$) δ 7.84-7.81 (m, 4H), 7.48-7.40 (m, 5H), 7.24-7.20 (m, 2H), 4.92 (t, J=6.1 Hz, 1H), 3.71 (d, J=13.3 Hz, 1H), 3.52 (d, J=13.3 Hz, 1H), 2.69-2.60 (m, 2H), 2.33 (s, 3H).

Step C: Product from Step B (11.6 g, 31.3 mmol) in 1,2-dichloroethane (170 mL) was added dropwise via addition funnel to methane sulfonic acid (110 mL, 1754 mmol) at 40° C. and stirred for an additional 6.5 hours. The cooled reaction mixture was then stirred at room temperature for 16 hours. The reaction mixture was poured over ice and made basic to pH 9 with concentrated ammonium hydroxide. The reaction mixture was extracted with ethyl acetate four times. The combined organic extracts were dried over sodium sulfate, filtered, and concentrated in vacuo. Purification by column chromatography (330 g silica gel, 90:10 hexane/ethyl acetate) provided 7-bromo-2-methyl-4-napthalen-2-yl-1,2,3,4-tetrahydroisoquinoline (4.24 g, 38%) as an off-white solid; $^1$H NMR (500 MHz, CDCl$_3$) δ 7.81-7.75 (m, 3H), 7.66 (s, 1H), 7.46-7.44 (s, 1H), 7.27 (s, 1H), 7.24-7.23 (m, 2H), 7.16 (d, J=8.3 Hz, 1H), 6.75 (d, J=8.3 Hz, 1H), 4.35 (t, J=6.29 Hz, 1H), 3.75 (d, J=15.1 Hz, 1H), 3.62 (d, J=15.1 Hz, 1H), 3.10-3.06 (m, 1H), 2.66-2.61 (m, 1H), 2.43 (s, 3H).

Step D: A mixture of the product from Step C (1.00 mg, 2.80 mmol), bis(pinacolato)diboron (793 mg, 3.12 mmol), KOAc (830 mg, 8.50 mmol) was degassed with argon. To this mixture was added PdCl$_2$(dppf) (99 mg, 0.122 mmol). The resulting mixture was degassed with argon and then heated at 80° C. for 3 hours. After completion by thin-layer chromatography analysis the cooled material was diluted with water and the organic layer was separated. The aqueous layer was extracted with ethyl acetate three times. The combined organic extracts were washed with brine, dried over sodium sulfate, filtered, and concentrated in vacuo to afford a brown oil, which was used in Step E without further purification.

Step E: A mixture of the crude product from Step D (565 mg, 1.42 mmol), 2-chloropyrazine (200 mg, 1.77 mmol), and cesium carbonate (1.5 g, 4.26 mmol) in DMF (21 mL) and water (3 mL) was degassed with argon. To this mixture was added PdCl$_2$(dppf) (70 mg, 0.085 mmol). The resulting mixture was degassed with argon and then heated at 80° C. for 4 hours. The cooled mixture was filtered through a pad of diatomaceous earth and washed with water three times. The organic layers were separated, dried over sodium sulfate, filtered, and concentrated in vacuo. Purification by column chromatography (80 g silica gel, 100% methylene chloride) provided the product (50 mg, 10%) as a light-red solid; $^1$H NMR (500 MHz, CDCl$_3$) δ 9.00 (s, 1H), 8.61 (s, 1H), 8.48 (s, 1H), 7.82-7.76 (m, 4H), 7.71-7.68 (m, 2H), 7.47-7.44 (m, 2H), 7.29 (d, J=8.4 Hz, 1H), 7.04 (d, J=8.1 Hz, 1H), 4.51 (t, J=6.5 Hz, 1H), 3.91 (d, J=14.9 Hz, 1H), 3.75 (d, J=14.9 Hz, 1H), 3.16-3.13 (m, 1H), 2.73-2.69 (m, 1H), 2.48 (s, 3H).

Step F: A solution of the product from Step E (40 mg, 0.114 mmol) and maleic acid (13 mg, 0.114 mmol) in methanol (1 mL) was stirred at room temperature. The solvent was evaporated. Lyophilization from acetonitrile (0.5 mL)/water (0.5 mL) yielded 2-methyl-4-napthalen-2-yl-7-pyrazin-2-yl-1,2,3,4-tetrahydroisoquinoline, maleate salt (52.2 mg, 98%, >99% AUC HPLC) as a brown solid: m.p. 89-91° C.; H NMR (CD$_3$OD, 500 MHz) δ 9.12 (s, 1H), 8.69-8.68 (m, 1H), 8.56-8.55 (m, 1H), 8.08 (s, 1H), 7.98 (d, J=8.1 Hz, 1H), 7.91-7.85 (m, 4H), 7.54-7.50 (m, 2H), 7.33 (d, J=8.5 Hz, 1H), 7.12 (d, J=8.2 Hz, 1H), 6.24 (s, 1H), 4.72 (br s, 2H), 3.98-3.94 (m, 1H), 3.72 (t, J=11.8 Hz, 1H), 3.30-3.29 (m, 1H), 3.09 (s, 3H); ESI-MS m/z 352 [M+H]$^+$.

Example 140

Preparation of (+)-2-methyl-4-naphthalen-2-yl-7-pyrimidin-2-yl-1,2,3,4-tetrahydroisoquinoline, maleate salt and (−)-2-methyl-4-naphthalen-2-yl-7-pyrimidin-2-yl-1,2,3,4-tetrahydroisoquinoline, maleate salt Step A: To a solution of (3-bromo-benzyl)-methyl-amine (29.4 g, 146.9 mmol) in methylene chloride (300 mL) was added diisopropylethylamine (51 mL, 293.8 mmol). The reaction mixture was cooled to 0° C. and treated with 2-bromo-2'-acetonapthone (36.6 g, 146.9 mmol) portionwise over a period of 40 minutes. The reaction mixture was warmed to room temperature and stirred for 5.5 hours. The reaction mixture was washed with water three times, dried over sodium sulfate, filtered, and the solvent was evaporated to afford the desired product (quantitative yield) as a viscous, orange oil: $^1$H NMR (CDCl$_3$, 500 MHz) δ 8.49 (s, 1H), 8.00 (d, J=8.6 Hz, 1H), 7.95 (d, J=8.1 Hz, 1H), 7.87 (t, J=8.2 Hz, 2H), 7.61-7.54 (m, 3H), 7.40 (d, J=7.0 Hz, 1H), 7.31 (d, J=7.6 Hz, 1H), 7.19 (t, J=7.7 Hz, 1H), 3.91 (s, 2H), 3.71 (s, 2H), 2.40 (s, 3H).

Step B: Sodium borohydride (54.11 g, 155.4 mmol) was added over a period of 45 minutes to an ice-cooled solution of the product from Step A (7.05 g, 186.4 mmol) in methanol (400 mL). The reaction mixture was allowed to warm to room temperature and continued to stir for an additional 21.5 h. The solvent was removed under reduced pressure and the residue was diluted with water and extracted with methylene chloride three times. The combined extracts were dried over sodium sulfate, filtered and concentrated in vacuo to provide the desired product (47.78 g, 83%) as an orange oil: $^1$H NMR (500 MHz, CDCl$_3$) δ 7.84-7.81 (m, 4H), 7.48-7.40 (m, 5H), 7.24-7.20 (m, 2H), 4.92 (t, J=6.1 Hz, 1H), 3.71 (d, J=13.3 Hz, 1H), 3.52 (d, J=13.3 Hz, 1H), 2.69-2.60 (m, 2H), 2.33 (s, 3H).

Step C: Product from Step B (47.78 g, 129.0 mmol) in 1,2-dichloroethane (500 mL) was added dropwise via addition funnel to methane sulfonic acid (469 mL, 7226 mmol) at room temperature and stirred for an additional 6.5 h. The cooled reaction mixture was then stirred at room temperature for 30 minutes. The reaction mixture was poured over ice and made basic to pH 9 with concentrated ammonium hydroxide. The reaction mixture was extracted with ethyl acetate four times. The combined organic extracts were dried over sodium sulfate, filtered, and concentrated in vacuo. Purification by column chromatography (silica gel, 98:2 methylene chloride/methanol) provided 7-bromo-2-methyl-4-napthalen-2-yl-1,2,3,4-tetrahydroisoquinoline (7.12 g, 16%) as an light-brown solid; $^1$H NMR (500 MHz, CDCl$_3$) δ 7.81-7.75 (m, 3H), 7.66 (s, 1H), 7.46-7.44 (s, 1H), 7.27 (s, 1H), 7.24-7.23 (m, 2H), 7.16 (d, J=8.3 Hz, 1H), 6.75 (d, J=8.3 Hz, 1H), 4.35 (t, J=6.29 Hz, 1H), 3.75 (d, J=15.1 Hz, 1H), 3.62 (d, J=15.1 Hz, 1H), 3.10-3.06 (m, 1H), 2.66-2.61 (m, 1H), 2.43 (s, 3H).

Step D: To a mixture of the product from Step C (0.72 g, 2.0 mmol), bis(pinacolato)diboron (571 mg, 2.24 mmol), KOAc (600 mg, 6.12 mmol) was degassed with argon. To this mixture was added PdCl$_2$(dppf) (99 mg, 0.122 mmol). The resulting mixture was degassed with argon and then heated at 80° C. for 3 hours. The cooled mixture was diluted with water and the organic layer was separated. The aqueous layer was extracted with ethyl acetate three times. The combined organic extracts were washed with brine, dried over sodium sulfate, filtered, and concentrated in vacuo to afford a brown oil, which was used in Step E without further purification.

Step E: A mixture of the crude product from Step D (565 mg, 1.42 mmol), 2-chloropyrimidine (395 mg, 1.77 mmol), and cesium carbonate (1.5 g, 4.26 mmol) in DMF (21 mL) and water (3 mL) was degassed with argon. To this mixture was added PdCl$_2$(dppf) (70 mg, 0.085 mmol). The resulting mixture was degassed with argon and then heated at 80° C. for 4 hours. The cooled mixture was filtered through a pad of diatomaceous earth and washed with water three times. The organic layers were separated, dried over sodium sulfate, filtered, and concentrated in vacuo. Purification by column chromatography (80 g silica gel, 98:2 methlyene chloride/methanol) provided 2-methyl-4-naphthalen-2-yl-7-pyrimidin-2-yl-1,2,3,4-tetrahydroisoquinoline (430 mg, 60%). This material was resolved by chiral HPLC (Chiralpak OD, 90:10 heptane/ethanol with 0.1% diethylamine). The (+)-enantiomer (130 mg, 30%) was obtained as a light-yellow solid: $[\alpha]^{24}_D$ +209.47° (c 0.095, methanol); $^1$H NMR (500 MHz, CDCl$_3$) δ 8.78 (s, 2H), 8.22 (s, 1H), 8.12 (d, J=8.1 Hz, 1H), 7.82-7.75 (m, 3H), 7.71 (s, 1H), 7.48-7.42 (m, 2H), 7.29 (d, J=8.4 Hz, 1H), 7.16 (t, J=4.8 Hz, 1H), 7.03 (d, J=8.1 Hz, 1H), 4.51 (t, J=6.4 Hz, 1H), 3.91 (d, J=14.9 Hz, 1H), 3.75 (d, J=14.9 Hz, 1H), 3.75 (d, J=14.9 Hz, 1H), 3.16-3.12 (m, 1H), 2.72-2.66 (m, 1H), 2.48 (s, 3H). The (−)-enantiomer (130 mg, 30%) was obtained as a light-yellow solid $[\alpha]^{24}_D$ −71.66° (c=0.10, methanol); $^1$H NMR (500 MHz, CDCl$_3$) δ 8.78 (s, 2H), 8.22 (s, 1H), 8.12 (d, J=8.1 Hz, 1H), 7.82-7.75 (m, 3H), 7.71 (s, 1H), 7.48-7.42 (m, 2H), 7.29 (d, J=8.4 Hz, 1H), 7.16 (t, J=4.8 Hz, 1H), 7.03 (d, J=8.1 Hz, 1H), 4.51 (t, J=6.4 Hz, 1H), 3.91 (d, J=14.9 Hz, 1H), 3.75 (d, J=14.9 Hz, 1H), 3.16-3.12 (m, 1H), 2.72-2.66 (m, 1H), 2.48 (s, 3H).

Step F: A solution of the (+)-enantiomer from Step E (127.7 mg, 0.363 mmol) and maleic acid (42.2 mg, 0.363 mmol) in methanol (1 mL) was stirred at room temperature. The solvent was evaporated. Lyophilization from acetonitrile (0.5 mL)/water (0.5 mL) yielded (+)-2-methyl-4-naphthalen-2-yl-7-pyrimidin-2-yl-1,2,3,4-tetrahydroisoquinoline, maleate salt (144.40 mg, 79%, 95.2% AUC HPLC) as an off-white solid: m.p. 84-85° C.; $^1$H NMR (500 MHz, CD$_3$OD) δ 8.85 (s, 2H), 8.38 (s, 1H), 8.29 (d, J=8.4 Hz, 1H), 7.92-7.85 (m, 4H), 7.53 (d, J=4.1 Hz, 2H), 7.38 (d, J=9.7 Hz, 1H), 7.33 (d, J=8.5 Hz, 1H), 7.10 (d, J=8.1 Hz, 1H), 6.25 (s, 2.5H), 4.73 (br s, 2H), 3.98-3.94 (m, 1H), 3.75-3.73 (m, 1H), 3.13 (s, 3H); ESI MS m/z 352 [M+H]$^+$; Anal. Calcd. For C$_{24}$H$_{21}$N$_3$-1.25C$_4$H$_4$O$_4$-0.25H$_2$O: C, 69.52; H, 5.33; N, 8.39. Found: C, 69.61; H, 5.24; N, 8.41.

Step G: A solution of the (−)-enantiomer from Step E (130 mg, 0.369 mmol) and maleic acid (42.9 mg, 0.369 mmol) in methanol (1 mL) was stirred at room temperature. The solvent was evaporated. Lyophilization from acetonitrile (0.5 mL)/water (0.5 mL) yielded (−)-2-methyl-4-naphthalen-2-yl-7-pyrimidin-2-yl-1,2,3,4-tetrahydroisoquinoline, maleate salt (140.6 mg, 82%, 95.6% AUC HPLC) as an off-white solid: m.p. 86-88° C.; $^1$H NMR (CD$_3$OD, 500 MHz) δ 8.85 (s, 2H), 8.38 (s, 1H), 8.29 (d, J=8.2 Hz, 1H), 7.91-7.81 (m, 4H), 7.52 (d, J=9.8 Hz, 1H), 7.38 (d, J=9.7 Hz, 1H), 7.33 (d, J=8.5 Hz, 1H), 7.09 (d, J=8.2 Hz, 1H), 6.24 (s, 2H), 4.73 (m, 2H), 3.98-3.94 (m, 1H), 3.75-3.71 (m, 1H), 3.13 (s, 3H); ESI-MS m/z 352 [M+H]$^+$.

Example 141

Preparation of (+)-2-methyl-4-napthalen-2-yl-7-pyrimidin-5-yl-1,2,3,4-tetrahydroisoquinoline, maleate salt and (−)-2-methyl-4-napthalen-2-yl-7-pyrimidin-5-yl-1,2,3,4-tetrahydroisoquinoline, maleate salt Step A: To a solution of (3-bromo-benzyl)-methyl-amine (29.4 g, 146.9 mmol) in methylene chloride (300 mL) was added diisopropylethylamine (51 mL, 293.8 mmol). The reaction mixture was cooled to 0° C. and treated with 2-bromo-2'-acetonapthone (36.6 g, 146.9 mmol) portionwise over a period of 40 minutes. The reaction mixture was warmed to room temperature and stirred for 5.5 hours. The reaction mixture was washed with water three times, dried over sodium sulfate, filtered, and the solvent was evaporated to afford the desired product (quantitative yield) as a viscous, orange oil: ¹H NMR (CDCl₃, 300 MHz) δ 8.49 (s, 1H), 8.00 (d, J=8.6 Hz, 1H), 7.95 (d, J=8.1 Hz, 1H), 7.87 (t, J=8.2 Hz, 2H), 7.61-7.54 (m, 3H), 7.40 (d, J=7.0 Hz, 1H), 7.31 (d, J=7.6 Hz, 1H), 7.19 (t, J=7.7 Hz, 1H), 3.91 (s, 2H), 3.71 (s, 2H), 2.40 (s, 3H).

Step B: Sodium borohydride (54.11 g, 155.4 mmol) was added over a period of 45 minutes to an ice-cooled solution of the product from Step A (7.05 g, 186.4 mmol) in methanol (400 mL). The reaction mixture was allowed to warm to room temperature and continued to stir for an additional 21.5 hours. The solvent was removed under reduced pressure and the residue was diluted with water and extracted with methylene chloride three times. The combined extracts were dried over sodium sulfate, filtered and concentrated in vacuo to provide the desired product (47.78 g, 83%) as an orange oil: ¹H NMR (500 MHz, CDCl₃) δ 7.84-7.81 (m, 4H), 7.48-7.40 (m, 5H), 7.24-7.20 (m, 2H), 4.92 (t, J=6.1 Hz, 1H), 3.71 (d, J=13.3 Hz, 1H), 3.52 (d, J=13.3 Hz, 1H), 2.69-2.60 (m, 2H), 2.33 (s, 3H).

Step C: Product from Step B (47.78 g, 129.0 mmol) in 1,2-dichloroethane (500 mL) was added dropwise via addition funnel to methane sulfonic acid (469 mL, 7226 mmol) at room temperature and stirred for an additional 6.5 hours. The cooled reaction mixture was then stirred at room temperature for 30 minutes. The reaction mixture was poured over ice and made basic to pH 9 with concentrated ammonium hydroxide. The reaction mixture was extracted with ethyl acetate four times. The combined organic extracts were dried over sodium sulfate, filtered, and concentrated in vacuo. Purification by column chromatography (silica gel; 98:2 methylene chloride/methanol) provided 7-bromo-2-methyl-4-napthalen-2-yl-1,2,3,4-tetrahydroisoquinoline (7.12 g, 16%) as an light-brown solid; ¹H NMR (500 MHz, CDCl₃) δ 7.76-7.75 (m, 3H), 7.66 (s, 1H), 7.46-7.44 (s, 1H), 7.27 (s, 1H), 7.24-7.23 (m, 2H), 7.16 (d, J=8.3 Hz, 1H), 6.75 (d, J=8.3 Hz, 1H), 4.35 (t, J=6.29 Hz, 1H), 3.75 (d, J=15.1 Hz, 1H), 3.62 (d, J=15.1 Hz, 1H), 3.10-3.06 (m, 1H), 2.66-2.61 (m, 1H), 2.43 (s, 3H).

Step D: A mixture of the product from Step C (680 mg, 1.93 mmol), bis(pinacolato)diboron (538 mg, 2.12 mmol), KOAc (568 mg, 5.79 mmol) was degassed with argon. To this mixture was added PdCl₂(dppf) (95 mg, 0.116 mmol). The resulting mixture was degassed with argon and then heated at 80° C. for 4.5 hours. After completion (by thin-layer chromatography analysis), the cooled material was diluted with water and the organic layer was separated. The aqueous layer was extracted with ethyl acetate three times. The combined organic extracts were washed with brine, dried over sodium sulfate, filtered, and concentrated in vacuo to afford a brown oil, which was used in Step E without further purification.

Step E: A mixture of the crude product from Step D (771 mg, 1.93 mmol), 5-bromopyrimidine (429 mg, 2.70 mmol), and cesium carbonate (2.04 g, 5.79 mmol) in DMF (21 mL) and water (3 mL) was degassed with argon. To this mixture was added PdCl₂(dppf) (95 mg, 0.116 mmol). The resulting mixture was degassed with argon and then heated at 80° C. for 5 hours. The cooled mixture was filtered through a pad of diatomaceous earth and washed with water three times. The organic layers were separated, dried over sodium sulfate, filtered, and concentrated in vacuo. Purification by column chromatography (80 g silica gel, 98:2 methlyene chloride/methanol) provided 2-methyl-4-napthalen-2-yl-7-pyrimidin-5-yl-1,2,3,4-tetrahydroisoquinoline (370 mg, 55%). This material was resolved by chiral HPLC (Chiralpak AD, 70:30 heptane/IPA with 0.1% diethylamine). The (−)-enantiomer (160 mg, 43%) was obtained as an off-white solid: [α]²⁴_D −73.0° (c 0.14, methanol); ¹H NMR (500 MHz, CDCl₃) δ 9.18 (s, 1H), 8.93 (s, 2H), 7.82-7.77 (m, 3H), 7.72 (s, 1H), 7.49-7.45 (m, 2H), 7.33-7.26 (m, 3H), 7.05 (d, J=7.9 Hz, 1H), 4.51 (t, J=7.6 Hz, 1H), 3.90 (d, J=15.0 Hz, 1H), 3.75 (d, J=14.7 Hz, 1H), 3.19-3.13 (m, 1H), 2.76-2.69 (m, 1H), 2.50 (s, 3H). The (+)-enantiomer (150 mg, 41%) was obtained as a light-red solid: [α]²⁴_D +76.3° (c 0.14, methanol); ¹H NMR (500 MHz, CDCl₃) δ 9.18 (s, 1H), 8.93 (s, 2H), 7.82-7.77 (m, 3H), 7.72 (s, 1H), 7.49-7.45 (m, 2H), 7.33-7.26 (m, 3H), 7.05 (d, J=7.9 Hz, 1H), 4.51 (t, J=7.6 Hz, 1H), 3.90 (d, J=15.0 Hz, 1H), 3.75 (d, J=14.7 Hz, 1H), 3.19-3.13 (m, 1H), 2.76-2.69 (m, 1H), 2.50 (s, 3H).

Step F: The (+)-enantiomer from Step E (160 mg, 0.455 mmol) in methyl ethyl ketone (6 mL) was heated to 60° C. A solution of maleic acid in dioxane (1M, 48 µL) was added and stirred at 60° C. for 1 hours. The reaction mixture was slowly cooled to room temperature and stirred overnight. The solvent was evaporated to yield (+)-2-methyl-4-napthalen-2-yl-7-pyrimidin-5-yl-1,2,3,4-tetrahydroisoquinoline, maleate salt (168.3 mg, 70%, 98% AUC HPLC) as a light-brown solid: m.p. 62-64° C.; ¹H NMR (500 MHz, CD₃OD) δ 9.16 (s, 1H), 9.08 (s, 2H), 7.91-7.85 (m, 4H), 7.71 (s, 1H), 7.64 (d, J=7.9 Hz, 1H), 7.53-7.51 (m, 2H), 7.32 (d, J=8.4 Hz, 1H), 7.13 (d, J=8.1 Hz, 1H), 6.26 (s, 3.0H), 4.73 (s, 2H), 3.99-3.92 (m, 1H), 3.82-3.68 (m, 1H), 3.39-3.30 (m, 1H), 3.11 (s, 3H); ESI MS m/z 352 [M+H]⁺.

Step G: The (−)-enantiomer Step E (140 mg, 0.398 mmol) in methyl ethyl ketone (5 mL) was heated to 60° C. A solution of maleic acid in dioxane (1M, 42 µL) was added and stirred at 60° C. for 1 hour. The reaction mixture was slowly cooled to room temperature and stirred overnight. The solvent was evaporated to yield (−)-2-methyl-4-napthalen-2-yl-7-pyrimidin-5-yl-1,2,3,4-tetrahydroisoquinoline, maleate salt (195.0 mg, 94%, 97% AUC HPLC) as a light-brown solid: m.p. 62-64° C.; ¹H NMR (500 MHz, CD₃OD) δ 9.16 (s, 1H), 9.08 (s, 2H), 7.91-7.85 (m, 4H), 7.71 (s, 1H), 7.64 (d, J=7.9 Hz, 1H), 7.53-7.51 (m, 2H), 7.32 (d, J=8.4 Hz, 1H), 7.13 (d, J=8.1 Hz, 1H), 6.26 (s, 2.4H), 4.73 (s, 2H), 3.99-3.92 (m, 1H), 3.82-3.68 (m, 1H), 3.39-3.30 (m, 1H), 3.11 (s, 3H); ESI MS m/z 352 [M+H]⁺. Anal. Calcd. For C₂₄H₂₁N₃·1.25C₄H₄O₄·1.5H₂O: C, 66.53; H, 5.58; N, 8.03. Found: C, 66.28; H, 5.39; N, 7.66.

Example 142

Preparation of (+/−)-7-(3,5-dimethyl-isoxazol-4-yl)-2-methyl-4-napthalen-2-yl-1,2,3,4-tetrahydroisoquinoline, maleate salt Step A: To a solution of (3-bromo-benzyl)-methyl-amine (7.01 g, 35.0 mmol) in methylene chloride (120 mL) was added diisopropylethylamine (12 mL, 20.0 mmol). The reaction mixture was cooled to 0° C. and treated with 2-bromo-2'-acetonapthone (8.73 g, 35.0 mmol) portionwise over a period of 30 minutes. The reaction mixture was warmed to room temperature and stirred for 3 hours. The reaction mixture was washed with water three times, dried over sodium sulfate, filtered, and the solvent was evaporated to afford the desired product (12.54 g, 97%) as a viscous, orange oil: ¹H NMR (CDCl₃, 500 MHz) δ 8.49 (s, 1H), 8.00 (d, J=8.6 Hz, 1H), 7.95 (d, J=8.1 Hz, 1H), 7.87 (t, J=8.2 Hz, 2H), 7.61-7.54 (m, 3H), 7.40 (d, J=7.0 Hz, 1H), 7.31 (d, J=7.6 Hz, 1H), 7.19 (t, J=7.7 Hz, 1H), 3.91 (s, 2H), 3.71 (s, 2H), 2.40 (s, 3H).

Step B: Sodium borohydride (1.55 g, 40.9 mmol) was added over a period of 30 minutes to an ice-cooled solution of the product from Step A (12.54 g, 34.0 mmol) in methanol (140 mL). The reaction mixture was allowed to warm to room temperature and continued to stir for an additional 4 hours. The solvent was removed under reduced pressure and the residue was diluted with water and extracted with methylene chloride three times. The combined extracts were dried over sodium sulfate, filtered and concentrated in vacuo to provide the desired product (11.67 g, 93%) as an orange oil: $^1$H NMR (500 MHz, CDCl$_3$) δ 7.84-7.81 (m, 4H), 7.48-7.40 (m, 5H), 7.24-7.20 (m, 2H), 4.92 (t, J=6.1 Hz, 1H), 3.71 (d, J=13.3 Hz, 1H), 3.52 (d, J=13.3 Hz, 1H), 2.69-2.60 (m, 2H), 2.33 (s, 3H).

Step C: Product from Step B (11.6 g, 31.3 mmol) in 1,2-dichloroethane (170 mL) was added dropwise via addition funnel to methane sulfonic acid (110 mL, 1754 mmol) at 40° C. and stirred for an additional 6.5 hours. The cooled reaction mixture was then stirred at room temperature for 16 hours. The reaction mixture was poured over ice and made basic to pH 9 with concentrated ammonium hydroxide. The reaction mixture was extracted with ethyl acetate four times. The combined organic extracts were dried over sodium sulfate, filtered, and concentrated in vacuo. Purification by column chromatography (330 g silica gel, 90:10 hexane/ethyl acetate) provided 7-bromo-2-methyl-4-napthalen-2-yl-1,2,3,4-tetrahydroisoquinoline (4.24 g, 38%) as an off-white solid; $^1$H NMR (500 MHz, CDCl$_3$) δ 7.81-7.75 (m, 3H), 7.66 (s, 1H), 7.46-7.44 (s, 1H), 7.27 (s, 1H), 7.24-7.23 (m, 2H), 7.16 (d, J=8.3 Hz, 1H), 6.75 (d, J=8.3 Hz, 1H), 4.35 (t, J=6.29 Hz, 1H), 3.75 (d, J=15.1 Hz, 1H), 3.62 (d, J=15.1 Hz, 1H), 3.10-3.06 (m, 1H), 2.66-2.61 (m, 1H), 2.43 (s, 3H).

Step D: A mixture of the product from Step C (0.50 g, 1.4 mmol), bis(pinacolato)diboron (397 mg, 1.56 mmol), KOAc (415 mg, 4.25 mmol) was degassed with argon. To this mixture was added PdCl$_2$(dppf) (70 mg, 0.085 mmol). The resulting mixture was degassed with argon and then heated to reflux for 3 hours. After completion by thin-layer chromatography analysis the cooled material was diluted with water and the organic layer was separated. The aqueous layer was extracted with ethyl acetate three times. The combined organic extracts were washed with brine, dried over sodium sulfate, filtered, and concentrated in vacuo to afford a brown oil, which was used in Step E without further purification.

Step E: A mixture of the crude product from Step D (565 mg, 1.42 mmol), 3,5-dimethyl-4-iodoisoxazole (395 mg, 1.77 mmol), and cesium carbonate (1.5 g, 4.26 mmol) in DMF (21 mL) and water (3 mL) was degassed with argon. To this mixture was added PdCl$_2$(dppf) (70 mg, 0.085 mmol). The resulting mixture was degassed with argon and then heated at 80° C. for 4 hours. The cooled mixture was filtered through a bed of diatomaceous earth and washed with water three times. The organic layers were separated, dried over sodium sulfate, filtered, and concentrated in vacuo. Purification by column chromatography (80 g silica gel, 98:2 methlyene chloride/methanol) provided the desired product (100 mg, 19%) as a brown solid; $^1$H NMR (500 MHz, CDCl$_3$) δ 7.81-7.79 (m, 3H), 7.77 (s, 1H), 7.48-7.45 (m, 2H), 7.32 (d, J=8.4 Hz, 1H), 6.99 (s, 1H), 6.94-6.93 (m, 2H), 4.47 (t, J=1.95 Hz, 1H), 3.83 (d, J=14.9 Hz, 1H), 3.69 (d, J=14.8 Hz, 1H), 3.16-3.12 (m, 1H), 2.73-2.69 (m, 1H), 2.47 (s, 3H), 2.39 (s, 3H), 2.26 (s, 3H).

Step F: A solution of the product from Step E (98 mg, 0.266 mmol) and maleic acid (31 mg, 0.266 mmol) in methanol (1 mL) was stirred at room temperature. The solvent was evaporated. Lyophilization from acetonitrile (0.5 mL)/water (0.5 mL) yielded 7-(3,5-dimethyl-isoxazol-4-yl)-2-methyl-4-napthalen-2-yl-1,2,3,4-tetrahydroisoquinoline, maleate salt (128.89 mg, 99%, >99% AUC HPLC) as a brown solid: m.p. 88-90° C.; $^1$H NMR (CD$_3$OD, 500 MHz) δ 7.91-7.85 (m, 4H), 7.53-7.50 (m, 2H), 7.33-7.31 (m, 2H), 7.23 (d, J=8.0 Hz, 1H), 7.04 (d, J=8.0 Hz, 1H), 6.23 (s, 1H), 4.81-4.78 (m, 1H), 4.64 (s, 2H), 3.93-3.91 (m, 1H), 3.70-3.67 (m, 1H), 3.09 (s, 3H), 2.40 (s, 3H), 2.24 (s, 3H); ESI MS m/z 369 [M+H]$^+$.

Example 143

Preparation of (+)-2-methyl-7-morpholin-4-yl-4-napthalen-2-yl-1,2,3,4-tetrahydroisoquinoline, maleate salt and (−)-2-Methyl-7-morpholin-4-yl-4-napthalen-2-yl-1,2,3,4-tetrahydroisoquinoline, maleate salt Step A: To a solution of (3-bromo-benzyl)-methyl-amine (2.0 g, 10.0 mmol) in methylene chloride (40 mL) was added diisopropylethylamine (3.5 mL, 20.0 mmol). The reaction mixture was cooled to 0° C. and treated with 2-bromo-2'-acetonapthone (2.49 g, 10.0 mmol) portionwise over a period of 10 minutes. The reaction mixture was warmed to room temperature and stirred for 5.5 hours. The reaction mixture was washed with water three times, dried over sodium sulfate, filtered, and the solvent was evaporated to afford the desired product (3.67 g, 99%) as a viscous, orange oil: $^1$H NMR (CDCl$_3$, 500 MHz) δ 8.49 (s, 1H), 8.00 (d, J=8.6 Hz, 1H), 7.95 (d, J=8.1 Hz, 1H), 7.87 (t, J=8.2 Hz, 2H), 7.61-7.54 (m, 3H), 7.40 (d, J=7.0 Hz, 1H), 7.31 (d, J=7.6 Hz, 1H), 7.19 (t, J=7.7 Hz, 1H), 3.91 (s, 2H), 3.71 (s, 2H), 2.40 (s, 3H).

Step B: Sodium borohydride (453 mg, 12.0 mmol) was added over a period of 10 minutes to an ice-cooled solution of the product from Step A (3.68 g, 10.0 mmol) in methanol (45 mL). The reaction mixture was allowed to warm to room temperature and continued to stir for an additional 2.5 hours. The solvent was removed under reduced pressure and the residue was diluted with water and extracted with methylene chloride three times. The combined extracts were dried over sodium sulfate, filtered and concentrated in vacuo to provide the product (2.99 g, 81%) as an orange oil: $^1$H NMR (500 MHz, CDCl$_3$) δ 7.84-7.81 (m, 4H), 7.48-7.40 (m, 5H), 7.24-7.20 (m, 2H), 4.92 (t, J=6.1 Hz, 1H), 3.71 (d, J=13.3 Hz, 1H), 3.52 (d, J=13.3 Hz, 1H), 2.69-2.60 (m, 2H), 2.33 (s, 3H).

Step C: Product from Step B (2.99 g, 8.07 mmol) in 1,2-dichloroethane (50 mL) was added dropwise via addition funnel to methane sulfonic acid (30 mL, 452 mmol) at 40° C. and stirred for an additional 4 hours. The cooled reaction mixture was poured over ice and made basic to pH 9 with concentrated ammonium hydroxide. The reaction mixture was extracted with ethyl acetate four times. The combined organic extracts were dried over sodium sulfate, filtered, and concentrated in vacuo. Purification by column chromatography (80 g silica, 95:5 hexane/ethyl acetate) provided 7-bromo-2-methyl-4-napthalen-2-yl-1,2,3,4-tetrahydroisoquinoline (790 mg, 28%) as an off-white solid; $^1$H NMR (500 MHz, CDCl$_3$) δ 7.81-7.75 (m, 3H), 7.66 (s, 1H), 7.46-7.44 (s, 1H), 7.27 (s, 1H), 7.24-7.23 (m, 2H), 7.16 (d, J=8.3 Hz, 1H), 6.75 (d, J=8.3 Hz, 1H), 4.35 (t, J=6.29 Hz, 1H), 3.75 (d, J=15.1 Hz, 1H), 3.62 (d, J=15.1 Hz, 1H), 3.10-3.06 (m, 1H), 2.66-2.61 (m, 1H), 2.43 (s, 3H).

Step D: A mixture of product from Step C (790 mg, 2.24 mmol), morpholine (390 mg, 4.48 mmol), cesium carbonate (1.82 g, 5.6 mmol), Xphos (641 mg, 1.34 mmol) in toluene (25 mL) was degassed with argon. To this mixture was added palladium (II) acetate (75 mg, 0.336 mmol). The resulting mixture was degassed with argon and then heated to reflux for 16 hours. After completion (by thin-layer chromatography analysis), the cooled material was filtered through a bed of diatomaceous earth and the solvent was evaporated. Purification by column chromatography (80 g silica gel, 95:5 methlyene chloride/methanol) provided the product (570 mg, 57%) as a yellow solid. This product was resolved by chiral HPLC (Chiralpak AD, 80:20 heptane/isopropanol with 0.1% diethylamine). The (−)enantiomer (150 mg, 35%) was obtained as an off-white solid $[\alpha]^{25}{}_D$ −65.1° (c 0.13, methanol); $^1$H NMR (500 MHz, CDCl$_3$) δ 7.79-7.74 (m, 3H), 7.68 (s, 1H), 7.45-7.42 (m, 2H), 7.29-7.25 (m, 1H), 6.78 (d, J=8.3 Hz, 1H), 6.65 (d, J=9.5 Hz, 2H), 4.38-4.36 (m, 1H), 3.84 (t, J=4.7 Hz, 4H), 3.75 (d, J=14.8 Hz, 1H), 3.62 (d, J=14.7 Hz, 1H), 3.12 (t, J=4.8 Hz, 4H), 3.07-3.06 (m, 1H), 2.65-2.61 (m, 1H), 2.43 (s, 3H). The (+)enantiomer (191 mg, 42%) was obtained as an off-white solid $[\alpha]^{25}{}_D$ +65.1° (c 0.11, methanol); $^1$H NMR (500 MHz, CDCl$_3$) δ 7.79-7.74 (m, 3H), 7.68 (s, 1H), 7.45-7.42 (m, 2H), 7.29-7.25 (m, 1H), 6.78 (d, J=8.3 Hz, 1H), 6.65 (d, J=9.5 Hz, 2H), 4.38-4.36 (m, 1H), 3.84 (t, J=4.7 Hz, 4H), 3.75 (d, J=14.8 Hz, 1H), 3.62 (d, J=14.7 Hz, 1H), 3.12 (t, J=4.8 Hz, 4H), 3.07-3.06 (m, 1H), 2.65-2.61 (m, 1H), 2.43 (s, 3H).

Step E: A solution of the (−)-enantiomer from Step D (150 mg, 0.419 mmol) and maleic acid (48.5 mg, 0.419 mmol) in methanol (1 mL) was stirred at room temperature. The solvent was evaporated. Lyophilization from acetonitrile (0.5 mL)/water (0.5 mL) yielded (−)-2-methyl-7-morpholin-4-yl-4-napthalen-2-yl-1,2,3,4-tetrahydroisoquinoline, maleate salt (197.80 mg, 99%, >99% AUC HPLC) as an off-white solid: m.p. 98-99° C.; $^1$H NMR (CD$_3$OD, 500 MHz) δ 7.87-7.81 (m, 3H), 7.77 (s, 1H), 7.50-7.48 (m, 2H), 7.27 (d, J=8.5 Hz, 1H), 6.87-6.85 (m, 1H), 6.82-6.80 (m, 2H), 6.24 (s, 1H), 4.67-4.63 (m, 1H), 4.53-4.45 (m, 2H), 3.84-3.80 (m, 5H), 3.30-3.26 (m, 1H), 3.16-3.13 (m, 4H), 3.30 (s, 3H); ESI MS m/z 358 [M+H]$^+$.

Step F: A solution of the (+)-enantiomer from Step D (184 mg, 0.513 mmol) and maleic acid (59.6 mg, 0.513 mmol) in methanol (1 mL) was stirred at room temperature. The solvent was evaporated. Lyophilization from acetonitrile (0.5 mL)/water (0.5 mL) yielded (+)-2-methyl-7-morpholin-4-yl-4-napthalen-2-yl-1,2,3,4-tetrahydroisoquinoline, maleate salt (190.9 mg, 77%, >99% AUC HPLC) as an off-white solid: m.p. 94-96° C.; $^1$H NMR (CD$_3$OD, 500 MHz) δ 7.87-7.82 (m, 3H), 7.77 (s, 1H), 7.52-7.48 (m, 2H), 7.27 (d, J=8.5 Hz, 1H), 6.88 (d, J=8.6 Hz, 1H), 6.82-6.80 (m, 2H), 6.24 (s, 1H), 4.68-4.65 (m, 1H), 4.57-4.48 (m, 2H), 3.87-3.80 (m, 5H), 3.60-3.58 (m, 1H), 3.16-3.13 (m, 4H), 3.06 (s, 3H); ESI MS m/z 358 [M+H]$^+$.

Example 144

Preparation of (+/−)-2-methyl-4-napthalen-2-yl-7-piperidin-1-yl-1,2,3,4-tetrahydroisoquinoline, maleate salt Step A: To a solution of (3-bromo-benzyl)-methyl-amine (7.01 g, 35.0 mmol) in methylene chloride (120 mL) was added diisopropylethylamine (12 mL, 20.0 mmol). The reaction mixture was cooled to 0° C. and treated with 2-bromo-2'-acetonapthone (8.73 g, 35.0 mmol) portionwise over a period of 30 minutes. The reaction mixture was warmed to room temperature and stirred for 3 hours. The reaction mixture was washed with water three times, dried over sodium sulfate, filtered, and the solvent was evaporated to afford the desired product (12.54 g, 97%) as a viscous, orange oil: $^1$H NMR (CDCl$_3$, 500 MHz) δ 8.49 (s, 1H), 8.00 (d, J=8.6 Hz, 1H), 7.95 (d, J=8.1 Hz, 1H), 7.87 (t, J=8.2 Hz, 2H), 7.61-7.54 (m, 3H), 7.40 (d, J=7.0 Hz, 1H), 7.31 (d, J=7.6 Hz, 1H), 7.19 (t, J=7.7 Hz, 1H), 3.91 (s, 2H), 3.71 (s, 2H), 2.40 (s, 3H).

Step B: Sodium borohydride (1.55 g, 40.9 mmol) was added over a period of 30 minutes to an ice-cooled solution of the product from Step A (12.54 g, 34.0 mmol) in methanol (140 mL). The reaction mixture was allowed to warm to room temperature and continued to stir for an additional 4 hours. The solvent was removed under reduced pressure and the residue was diluted with water and extracted with methylene chloride three times. The combined extracts were dried over sodium sulfate, filtered and concentrated in vacuo to provide the desired product (11.67 g, 93%) as an orange oil: $^1$H NMR (500 MHz, CDCl$_3$) δ 7.84-7.81 (m, 4H), 7.48-7.40 (m, 5H), 7.24-7.20 (m, 2H), 4.92 (t, J=6.1 Hz, 1H), 3.71 (d, J=13.3 Hz, 1H), 3.52 (d, J=13.3 Hz, 1H), 2.69-2.60 (m, 2H), 2.33 (s, 3H).

Step C: Product from Step B (11.6 g, 31.3 mmol) in 1,2-dichloroethane (170 mL) was added dropwise via addition funnel to methane sulfonic acid (110 mL, 1754 mmol) at 40° C. and stirred for an additional 6.5 hours. The cooled reaction mixture was then stirred at room temperature for 16 hours. The reaction mixture was poured over ice and made basic to pH 9 with concentrated ammonium hydroxide. The reaction mixture was extracted with ethyl acetate four times. The combined organic extracts were dried over sodium sulfate, filtered, and concentrated in vacuo. Purification by column chromatography (330 g silica gel, 90:10 hexanes/ethyl acetate) provided 7-bromo-2-methyl-4-napthalen-2-yl-1,2,3,4-tetrahydroisoquinoline (4.24 g, 38%) as an off-white solid; $^1$H NMR (500 MHz, CDCl$_3$) δ 7.81-7.75 (m, 3H), 7.66 (s, 1H), 7.46-7.44 (s, 1H), 7.27 (s, 1H), 7.24-7.23 (m, 2H), 7.16 (d, J=8.3 Hz, 1H), 6.75 (d, J=8.3 Hz, 1H), 4.35 (t, J=6.29 Hz, 1H), 3.75 (d, J=15.1 Hz, 1H), 3.62 (d, J=15.1 Hz, 1H), 3.10-3.06 (m, 1H), 2.66-2.61 (m, 1H), 2.43 (s, 3H).

Step D: A mixture of product from Step C (260 mg, 0.738 mmol), piperidine (126 mg, 1.48 mmol), cesium carbonate (0.601 g, 1.85 mmol), Xphos (0.211 mg, 0.443 mmol) in toluene (12 mL) was degassed with argon. To this mixture was added palladium (II) acetate (25 mg, 0.111 mmol). The resulting mixture was degassed with argon and then heated to reflux for 17 hours. The cooled mixture was filtered through a bed of diatomaceous earth and the solvent was evaporated. Purification by column chromatography (40 g silica gel, 95:5 methlyene chloride/methanol) provided the desired product (110 mg, 38%) as a light-yellow solid; $^1$H NMR (500 MHz, CDCl$_3$) δ 7.80-7.73 (m, 3H), 7.67 (s, 1H), 7.46-7.40 (m, 2H), 7.29 (d, J=8.4 Hz, 1H), 6.74 (d, J=11.0 Hz, 1H), 6.68-6.66 (m, 2H), 4.36 (t, J=5.9 Hz, 1H), 3.73 (d, J=14.7 Hz, 1H), 3.61 (d, J=14.7 Hz, 1H), 3.11 (t, J=5.4 Hz, 4H), 3.08-3.04 (m, 1H), 2.67-2.55 (m, 1H), 2.42 (s, 3H), 1.71-1.67 (m, 4H) 1.58-1.54 (m, 2H).

Step E: A solution of the product from Step D (110 mg, 0.28 mmol) and maleic acid (32 mg, 0.28 mmol) in methanol (1 mL) was stirred at room temperature. The solvent was evaporated. Lyophilization from acetonitrile (0.5 mL)/water (0.5 mL) yielded (+/−)-2-methyl-4-napthalen-2-yl-7-piperidin-1-yl-1,2,3,4-tetrahydroisoquinoline, maleate salt (131.45 mg, 99%, 94% AUC HPLC) as a light-yellow solid: m.p. 88-90° C.; $^1$H NMR (CD$_3$OD, 500 MHz) δ 7.87-7.81 (m, 3H), 7.77 (s, 1H), 7.51-7.47 (m, 2H), 7.27 (d, J=8.4 Hz, 1H), 6.87 (d, J=8.6 Hz, 1H), 6.81 (s, 1H), 6.77 (d, J=8.7 Hz, 1H), 6.23 (s, 1H), 4.66-4.63 (m, 1H), 4.56 (q, J=15.2 Hz, 2H), 3.84-3.81 (m, 1H), 3.54 (t, J=11.9 Hz, 1H), 3.26-3.15 (m, 4H), 3.04 (s, 3H), 1.69-1.67 (m, 4H), 1.61-1.58 (m, 2H); ESI-MS m/z 357 [M+H]$^+$.

Example 145

Preparation of (+/−)-2-Methyl-4-napthalen-2-yl-7-pyrrolidin-1-yl-1,2,3,4-tetrahydroisoquinoline, maleate salt Step A: To a solution of (3-bromo-benzyl)-methyl-amine (29.40 g, 146.92 mmol) in methylene chloride (300 mL) was added diisopropylethylamine (37.9 mL, 293.85 mmol). The reaction mixture was cooled to 0° C. and treated with 2-bromo-2'-acetonapthone (36.6 g, 146.92 mmol) portionwise over a period of 40 minutes. The reaction mixture was warmed to room temperature and stirred for 5.5 hours. The reaction mixture was washed with water three times, dried over sodium sulfate, filtered, and the solvent was evaporated to afford the desired product (quantitative yield) as a viscous, orange oil: $^1$H NMR (CDCl$_3$, 500 MHz) δ 8.49 (s, 1H), 8.00 (d, J=8.6 Hz, 1H), 7.95 (d, J=8.1 Hz, 1H), 7.87 (t, J=8.2 Hz, 2H), 7.61-7.54 (m, 3H), 7.40 (d, J=7.0 Hz, 1H), 7.31 (d, J=7.6 Hz, 1H), 7.19 (t, J=7.7 Hz, 1H), 3.91 (s, 2H), 3.71 (s, 2H), 2.40 (s, 3H).

Step B: Sodium borohydride (7.05 g, 186.44 mmol) was added over a period of 45 minutes to an ice-cooled solution of the product from Step A (54.11 g, 155.36 mmol) in methanol (400 mL). The reaction mixture was allowed to warm to room temperature and continued to stir for an additional 21.5 hours. The solvent was removed under reduced pressure and the residue was diluted with water and extracted with methylene chloride three times. The combined extracts were dried over sodium sulfate, filtered and concentrated in vacuo to provide the desired product (47.78 g, 83% over two steps) as an orange oil: $^1$H NMR (500 MHz, CDCl$_3$) δ 7.84-7.81 (m, 4H), 7.48-7.40 (m, 5H), 7.24-7.20 (m, 2H), 4.92 (t, J=6.1 Hz, 1H), 3.71 (d, J=13.3 Hz, 1H), 3.52 (d, J=13.3 Hz, 1H), 2.69-2.60 (m, 2H), 2.33 (s, 3H).

Step C: Product from Step B (47.78 g, 129.04 mmol) in 1,2-dichloroethane (500 mL) was added dropwise via addition funnel to methane sulfonic acid (469 mL, 7226 mmol) at room temperature and stirred for an additional 1 hour. The reaction mixture was poured over ice and made basic to pH 9 with concentrated ammonium hydroxide (600 mL). The reaction mixture was extracted with ethyl acetate four times. The combined organic extracts were dried over sodium sulfate, filtered, and concentrated in vacuo. Purification by column chromatography (silica gel, 50:50 hexane/ethyl acetate) provided the 7-bromo-2-methyl-4-napthalen-2-yl-1,2,3,4-tetrahydroisoquinoline (4.72 g, 10%) as an brown solid; $^1$H NMR (500 MHz, CDCl$_3$) δ 7.81-7.75 (m, 3H), 7.66 (s, 1H), 7.46-7.44 (s, 1H), 7.27 (s, 1H), 7.24-7.23 (m, 2H), 7.16 (d, J=8.3 Hz, 1H), 6.75 (d, J=8.3 Hz, 1H), 4.35 (t, J=6.29 Hz, 1H), 3.75 (d, J=15.1 Hz, 1H), 3.62 (d, J=15.1 Hz, 1H), 3.10-3.06 (m, 1H), 2.66-2.61 (m, 1H), 2.43 (s, 3H).

Step D: A mixture of product from Step C (470 mg, 1.33 mmol), pyrollidine (0.22 mL, 1.48 mmol), cesium carbonate (1.08 g, 3.32 mmol), Xphos (0.38 g, 0.798 mmol) in toluene (20 mL) was degassed with argon. To this mixture was added palladium (II) acetate (112 mg, 0.498 mmol). The resulting mixture was degassed with argon and then heated to reflux for 22.5 hours. The cooled mixture was filtered through a bed of diatomaceous earth and the solvent was evaporated. Purification by column chromatography (40 g silica gel, 98:2 methlyene chloride/methanol) provided the desired product (220 mg, 48%) as a light-yellow solid; $^1$H NMR (500 MHz, CDCl$_3$) δ 7.78-7.72 (m, 3H), 7.69 (s, 1H), 7.44-7.42 (m, 2H), 7.30 (d, J=8.4 Hz, 1H), 6.71 (d, J=8.4 Hz, 1H), 6.33-6.29 (m, 2H), 4.36 (t, J=5.9 Hz, 1H), 3.75 (d, J=14.6 Hz, 1H), 3.63 (d, J=14.7 Hz, 1H), 3.25 (t, J=6.5 Hz, 4H), 3.08-3.04 (m, 1H), 2.63-2.59 (m, 1H), 2.43 (s, 3H), 1.99-1.96 (m, 4H).

Step E: A solution of the product from Step D (220 mg, 0.584 mmol) and maleic acid (67.8 mg, 0.584 mmol) in methanol (1 mL) was stirred at room temperature. The solvent was evaporated. Lyophilization from acetonitrile (0.5 mL)/water (0.5 mL) yielded (+/−)-2-methyl-4-naptha-len-2-yl-7-pyrrolidin-1-yl-1,2,3,4-tetrahydroisoquinoline, maleate salt (236.10 mg, 88%, 98.7% AUC HPLC) as a light-yellow solid: m.p. 97-100° C.; $^1$H NMR (CD$_3$OD, 500 MHz) δ 7.86-7.81 (m, 3H), 7.76 (s, 1H), 7.51-7.47 (m, 2H), 7.28 (d, J=8.2 Hz, 1H), 6.72 (d, J=7.5 Hz, 1H), 6.50 (d, J=8.6 Hz, 1H), 6.40 (s, 1H), 6.24 (s, 1H), 4.66-4.63 (m, 1H), 4.57-4.50 (m, 2H), 3.86-3.83 (m, 1H), 3.44-3.43 (m, 1H), 3.30-3.25 (m, 4H), 3.06 (s, 3H), 2.03-2.00 (m, 4H); ESI MS m/z 343 [M+H]$^+$.

Example 146

Preparation of (+/−)-8-methoxy-2-methyl-4-naphthalen-2-yl-7-pyridazin-3-yl-1,2,3,4-tetrahydroisoquinoline, fumarate salt Step A: To a solution of the racemic phenol (2.0 g, 6.26 mmol) from Step D in Example 138 in dichloromethane (30 mL) at 0° C. was added triethylamine (1.30 mL, 9.39 mmol), followed by triflic anhydride (1.26 mL, 7.51 mmol) dropwise. The reaction solution was stirred at 0° C. for 2 hours. The reaction mixture was partitioned with CH$_2$Cl$_2$ (2×100 mL) and water (100 mL), dried (Na$_2$SO$_4$) and concentrated under reduced pressure to give the desired triflate (3.10 g, 100% crude) as an orange tan foam which was used in the next step without any further purification: $^1$H NMR (CDCl$_3$, 500 MHz) δ 7.76-7.83 (m, 3H), 7.68 (s, 1H), 7.46-7.52 (m, 2H), 7.24-7.26 (m, 1H), 6.95 (d, J=8.6 Hz, 1H), 6.70 (d, J=8.9 Hz, 1H), 4.54-4.57 (m, 1H), 3.99 (d, J=15.9 Hz, 1H), 3.94 (s, 3H), 3.69 (d, J=15.9 Hz, 1H), 3.10-3.14 (m, 1H), 2.67-2.70 (m, 1H), 2.53 (s, 3H); ESI-MS m/z 452 [M+H]$^+$.

Step B: To a solution of the triflate (2.10 g, 3.3 mmol) from Step A above in DMSO (25 mL) were added bis (pinacolato)diboron (1.30 g, 5.11 mmol) and potassium acetate (1.37 g, 13.9 mmol). The solution was purged with nitrogen for 10 minutes, and then 1,1'-bis(diphenylphosphino)ferrocenedichloropalladium(II) (190 mg, 0.233 mmol) was added. The reaction solution was heated at 80° C. for 4 hours, and then cooled to room temperature. The resultant reaction solution was diluted with EtOAc (120 mL), washed with water (2×50 mL), dried (Na$_2$SO$_4$) and concentrated under reduced pressure to give the desired product (2.1 g, 100% crude) which was used in next step without further purification: $^1$H NMR (CDCl$_3$, 500 MHz) δ 7.74-7.81 (m, 3H), 7.68 (s, 1H), 7.41-7.51 (m, 2H), 7.26-7.28 (m, 1H), 6.70 (d, J=8.4 Hz, 1H), 6.54 (d, J=8.4 Hz, 1H), 4.43 (dd, J=8.5 Hz, 6.0 Hz, 1H), 3.90 (d, J=15.3 Hz, 1H), 3.87 (s, 3H), 3.60 (d, J=15.4 Hz, 1H), 3.01-3.15 (m, 1H), 2.60-2.64 (m, 1H), 2.46 (s, 3H), 1.35 (s, 12H).

Step C: To a reaction flask with the boronic ester (1.43 g, crude) from Step B above, chloropyridazine (460 mg, 4.01 mmol) and sodium carbonate (1.06 g, 10.0 mmol) were added DMF (15 mL) and water (4.0 mL). The resultant solution was purged with nitrogen for 10 minutes, and then 1,1'-bis(diphenylphosphino)ferrocenedichloropalladium (137 mg, 0.167 mmol) was added. The reaction solution was heated at 100° C. for 5 hours and partitioned with EtOAc (3×150 mL) and water (150 mL), dried (Na$_2$SO$_4$) and concentrated under reduced pressure. The crude product was purified by flash silica gel column chromatography (eluent CHCl$_3$/EtOH 95:5 followed by CH$_2$Cl$_2$/i-PrOH 90:10) to give the desired product (40 mg, 4%) as a tan solid: $^1$H NMR (CDCl$_3$, 500 MHz) δ 9.14 (dd, J=3.2 Hz, 1.7 Hz, 1H), 8.06 (dd, J=6.9 Hz, 1.7 Hz, 1H), 7.77-7.83 (m, 3H), 7.72 (s, 1H), 7.62 (d, J=8.1 Hz, 1H), 7.43-7.52 (m, 3H), 7.29 (dd, J=6.7 Hz, 1.8 Hz, 1H), 6.85 (d, J=8.2 Hz, 1H), 4.50-4.52 (m, 1H), 3.99-4.03 (m, 1H), 3.63 (d, J=15.6 Hz, 1H), 3.54 (s, 3H), 3.11-3.15 (m, 1H), 2.68 (dd, J=8.8 Hz, 2.7 Hz, 1H), 2.52 (s, 3H); ESI-MS m/z 382 [M+H]$^+$.

Step D: To a solution of the 7-pyridazinyl tetrahydroisoquinoline (38.7 mg, 0.101 mmol) from Step C above in methanol (3 mL) was added fumaric acid (12.0 mg, 0.101 mmol). The resultant solution was concentrated under reduced pressure to give (+/−)-8-methoxy-2-methyl-4-naphthalen-2-yl-7-pyridazin-3-yl-1,2,3,4-tetrahydroisoquinoline, fumarate salt (41.0 mg, 82%, AUC HPLC=97.4%) as a tan solid: mp 182-186° C.; $^1$H NMR (CD$_3$OD, 500 MHz) δ 9.17 (dd, J=4.9 Hz, 1.6 Hz, 1H), 8.14 (dd, J=8.6 Hz, 1.6 Hz, 1H), 7.79-7.88 (m, 5H), 7.57 (d, J=8.2 Hz, 1H), 7.48-7.52 (m, 2H), 7.31 (dd, J=8.5 Hz, 1.8 Hz, 1H), 7.31 (d, J=8.5 Hz, 1H), 6.71 (s, 2H), 4.72-4.76 (m, 1H), 4.56 (d, J=15.8 Hz, 1H), 4.22 (d, J=15.6 Hz, 1H), 3.63-3.67 (m, 1H), 3.56 (s, 3H), 3.32-3.35 (m, 1H), 2.91 (s, 3H); ESI-MS m/z 382 [M+H]$^+$.

Example 147

Preparation of (+/−)-4-(quinoxalin-6-yl)-2-methyl-1,2,3,4-tetrahydroisoquinoline, maleate salt Step A: A mixture of 6-bromo-quinoxaline (1.09 g, 5.06 mmol), n-butyl vinyl ether (2.53 g, 25.3 mmol), potassium carbonate (839 mg, 6.07 mmol), dppp (138 mg, 0.334 mmol) and Pd(OAc)$_2$ (34 mg, 0.152 mmol) in DMF (13 mL) and water (1.5 mL) was heated at reflux for 6 hours. The mixture was allowed to cool to room temperature and then 2 N HCl (20 mL) was added. The resulting mixture was stirred at room temperature for 0.5 hour and extracted with ethyl acetate three times. The combined organic extracts were washed with saturated sodium bicarbonate and brine, dried over anhydrous sodium sulfate and concentrated. Purification by column chromatography (silica gel, 20% to 40% ethyl acetate/hexanes) gave the desired product (324 mg, 37%): $^1$H NMR (CDCl$_3$, 500 MHz) δ 8.95 (s, 2H), 8.69 (d, J=1.9 Hz, 1H), 8.36 (dd, J=8.8, 1.9 Hz, 1H), 8.19 (d, J=8.8 Hz, 1H), 2.79 (s, 3H); ESI-MS m/z=229 [M+H]$^+$.

Step B: To a suspension of copper(II) bromide (840 mg, 3.76 mmol) in ethyl acetate (6 mL) was added a solution of the product from Step A (324 mg, 1.88 mmol) in chloroform (5 mL). The reaction mixture was heated at reflux for 4 hours. The mixture was allowed to cool to room temperature. The mixture was diluted with ethyl acetate (20 mL), and saturated ammonium chloride (20 mL) and then filtered through celite. The celite pad was washed with ethyl acetate. The organic layer was separated and washed with brine, dried over anhydrous sodium sulfate and concentrated. Purification by column chromatography (silica gel, 20% to 40% ethyl acetate/hexanes) provided the desired product (174 mg, 43%): $^1$H NMR (CDCl$_3$, 500 MHz) δ 8.97 (s, 2H), 8.74 (d, J=1.9 Hz, 1H), 8.36 (dd, J=8.8, 1.9 Hz, 1H), 8.22 (d, J=8.8 Hz, 1H), 4.61 (s, 2H).

Step C: To a solution of the product from Step B (174 mg, 0.693 mmol) in dichloromethane (5 mL) was added diisopropylethylamine (134 mg, 1.04 mmol) and N-benzylmethylamine (130 mg, 1.04 mmol). The reaction mixture was stirred at room temperature for 4 hours and then diluted with dichloromethane (20 mL). The mixture was washed with water and brine, dried over sodium sulfate and concentrated. Purification by column chromatography (silica gel, 20% to 60% ethyl acetate/hexanes) provided the desired product (103 mg, 51%): $^1$H NMR (CDCl$_3$, 300 MHz) δ 8.94 (d, J=1.7 Hz, 1H), 8.93 (d, J=1.7 Hz, 1H), 8.77 (d, J=1.9 Hz, 1H), 8.32 (dd, J=8.8, 1.9 Hz, 1H), 8.16 (d, J=8.8 Hz, 1H), 7.38-7.26 (m, 5H), 3.94 (s, 2H), 3.74 (s, 2H), 2.42 (s, 3H); ESI-MS m/z=292 [M+H]$^+$.

Step D: To an ice-cooled solution of the product from Step C (103 mg, 0.353 mmol) in methanol (5 mL) was added sodium borohydride (15 mg, 0.4 mmol). The reaction mixture was stirred at 0° C. for 1 hour. The solvent was removed under reduced pressure. The residue was partitioned between dichloromethane and water. The organic extracts were washed with brine, dried over sodium sulfate and concentrated to provide the desired product (100 mg, 97% crude yield): ESI MS m/z=294 [M+H]$^+$. This crude product was used in the next step without further purification.

Step E: To a solution of the product from Step D (100 mg, 0.34 mmol) in 1,2-dichloroethane (10 mL) was added Eaton's reagent (0.9 mL). The reaction mixture was stirred at 90° C. for 24 hours. The mixture was then cooled in an ice-bath and added saturated sodium bicarbonate solution. The organic layer was separated and the aqueous was extracted with dichloromethane. The combined extracts were washed with brine, dried over sodium sulfate and concentrated. Purification by column chromatography (silica gel, 4% to 5% methanol/dichloromethane) provided the desired product (37 mg, 39%): $^1$H NMR (CDCl$_3$, 500 MHz) δ 8.81 (d, J=1.8 Hz, 1H), 8.80 (d, J=1.8 Hz, 1H), 8.01 (d, J=8.7 Hz, 1H), 7.97 (d, J=1.9 Hz, 1H), 7.64 (dd, J=8.7, 1.9 Hz, 1H), 7.19-7.13 (m, 2 H), 7.09-7.06 (m, 1 H), 6.90 (d, J=7.7 Hz, 1H), 4.52 (t, J=6.3 Hz, 1H), 3.76 (d, J=15.0 Hz, 1H), 3.71 (d, J=15.0 Hz, 1H), 3.08 (dd, J=11.5, 5.5 Hz, 1H), 2.78 (dd, J=11.5, 7.2 Hz, 1H), 2.44 (s, 3H); ESI-MS m/z=276 [M+H]$^+$.

Step F: To a solution of the product from Step E (37 mg, 0.134 mmol) in methanol (1 mL) was added maleic acid (15.6 mg, 0.134 mmol). The solvent was removed under reduced pressure to provide (+/−)-4-(quinoxalin-6-yl)-2-methyl-1,2,3,4-tetrahydroisoquinoline, maleate salt as a light brown solid (52 mg, 99%, 96.7% AUC HPLC): $^1$H NMR (CD$_3$OD, 500 MHz) δ 8.91 (s, 2H), 8.13 (d, J=8.7 Hz, 1H), 8.04 (s, 1H), 7.70 (dd, J=8.7, 2.0 Hz, 1H), 7.39-7.33 (m, 2 H), 7.30-7.26 (m, 1H), 6.96 (d, J=7.8 Hz, 1H), 6.24 (s, 1H), 4.95-4.92 (m, 1 H), 4.67 (d, J=15.3 Hz, 1H), 4.61 (d, J=15.3 Hz, 1H), 3.99-3.95 (m, 1H), 3.74-3.69 (m, 1 H), 3.10 (s, 3H); ESI-MS m/z=276 [M+H]$^+$.

Example 148

Preparation of (+)-4-benzo[b]thiophen-6-yl-2-methyl-7-morpholin-4-yl-1,2,3,4-tetrahydroisoquinoline, maleate salt and (−)-4-Benzo[b]thiophen-6-yl-2-methyl-7-morpholin-4-yl-1,2,3,4-tetrahydroisoquinoline, maleate salt Step A: A mixture of 3-methoxy-thiophenol (25.0 g, 175.0 mmol), potassium carbonate (26.6 g, 192.0 mmol), and bromoacetaldehyde-dimethyl-acetal (32.3 mL, 175.0 mmol) was added in acetone (250 mL). The reaction mixture stirred for over 24 hours. Water was added to the reaction and the mixture was extracted with ethyl acetate three times.

The combined organic layer was washed with saturated sodium bicarbonate, then with saturated sodium chloride, and dried over sodium sulfate. The mixture was then filtered and concentrated to give the desired product (48.0 g, 99% crude) as an oil: $^1$HNMR (500 MHz, CDCl$_3$) δ 7.20-7.17 (m, 1H), 6.96-6.92 (m, 2H), 6.73-6.71 (m, 1H), 4.65 (t, J=5.5 Hz, 1H), 3.79 (s, 3H), 3.68 (dd, J=9.3, 7.0 Hz, 2H), 3.55 (dd, J=9.3, 7.0 Hz, 2H), 3.14 (d, J=5.6 Hz, 2H), 1.21 (t, J=7.1 Hz, 6H).

Step B: The product from Step A (15.0 g, 58.5 mmol) was dissolved in methylene chloride (125 mL) and the solution was added to a solution of boron trifluoride diethyl etherate (7.86 mL, 62 mmol) in methylene chloride (900 mL) at room temperature under nitrogen. The reaction mixture was stirred for 30 minutes. Saturated sodium bicarbonate solution was added to the mixture until both phases were clear. The organic layer was extracted with methylene chloride twice. The combined organic layer was dried over sodium sulfate and concentrated to an oil. The oil was purified by column chromatography (100% hexanes) to give the desired 6-methoxy benzothiophene (5.0 g, 52%), as a colorless oil: $^1$H NMR (500 MHz, CDCl$_3$) δ 7.50 (d, J=5.6 Hz, 1H), 7.46 (d, J=8.1 Hz, 1H), 7.3 (d, J=5.6 Hz, 1H), 7.29-7.25 (m, 1H), 6.75 (d, J=7.8 Hz, 1H), 3.96 (s, 3H).

Step C: The product from Step B (9.1 g, 55.0 mmol) was added neat to pyridine hydrochloride (25.6 g, 22 mmol) at 200° C. for over 2.5 hours. The mixture was allowed to cool then added ice water and extracted with methylene chloride twice. The combined extract was dried over sodium sulfate, filtered and concentrated to an oil. The oil solidified on standing, which was then triturated with hexanes to give the desired product (4.42 g, 53.4%): $^1$H NMR (500 MHz, CDCl$_3$) δ 7.67 (d, J=8.6 Hz, 1H), 7.31 (d, J=2.2 Hz, 1H), 7.26-7.22 (m, 2H), 6.91 (dd, J=8.6, 2.3 Hz, 1H), 4.81 (s, 1H).

Step D: The product from Step C (2.9 g, 19.0 mmol) was dissolved in methylene chloride (40 mL) and triethylamine (4.0 mL, 29.0 mmol) was added. The reaction mixture was cooled in an ice bath and added trifluoromethanesulfonic anhydride (3.75 mL, 21.0 mmol) and stirred for 30 minutes. Saturated sodium chloride solution was added to the mixture and extracted with methylene chloride twice. The combined organic extract was dried over sodium sulfate, filtered and concentrated to a yellow solid. (5.4 g, 99%): $^1$H NMR (500 MHz, CDCl$_3$) δ 7.86 (d, J=8.8 Hz, 1H), 7.81 (d, J=2.2 Hz, 1H), 7.56 (d, J=5.4 Hz, 1H), 7.37 (d, J=5.5 Hz, 1H), 7.28 (dd, J=8.7, 2.3 Hz, 1H).

Step E: The product from Step D (5.4 g, 19 mmol), n-butyl vinyl ether (9.84 mL), triethylamine (5.33 mL, 38 mmol) and 1,3-bis(diphenylphosphino)propane (4.73 g, 11 mmol) in N,N-dimethylformamide was degassed with argon and stirred. Palladium(II) acetate was then added to the reaction mixture, which was then heated to 100° C. over 4 hours. The cooled reaction mixture was filtered over a pad of diatomaceous earth and concentrated to a yellow solid. The solid was dissolved in 1 N hydrochloric acid (50.0 mL) and stirred for 1 hour. The mixture was then concentrated and purified by column chromatography (5:95 to 25:75 ethyl acetate/hexanes as the eluent) to give the desired ketone (2.95 g, 87.5%), as a yellow solid: $^1$H NMR (500 MHz, CDCl$_3$) δ 8.52-8.51 (m, 1H), 7.97 (dd, J=8.4, 1.6 Hz, 1H), 7.88 (d, J=8.4 Hz, 1H), 7.67 (d, J=5.5 Hz, 1H), 7.41-7.39 (m, 1H), 2.68 (s, 3H).

Step F: The product from Step E (2.9 g, 16 mmol) was dissolved in ethyl acetate (20 mL) and added to a suspension of copper(II) bromide (7.35 g, 33.0 mmol) in chloroform (40 mL). The reaction mixture was refluxed for 3 hours then allowed to cool to room temperature. The mixture was filtered over a pad of diatomaceous earth and concentrated to a brown solid, then purified by column chromatography (5-10% ethyl acetate/hexanes) to give the desired product (3.71 g, 88.5%): $^1$H NMR (500 MHz, CDCl$_3$) δ 8.56-8.55 (m, 1H), 7.98 (dd, J=8.4, 1.6 Hz, 1H), 7.90 (d, J=8.4 Hz, 1H), 7.72 (d, J=5.5 Hz, 1H), 7.41 (dd, J=5.4, 0.5 Hz, 1H), 4.53 (s, 2H).

Step G: The product from Step F (3.70 g, 14.5 mmol), 4-hydroxy-N-methyl benzylamine (2.37 g, 17.5 mmol) and N,N-diisopropylethylamine (2.8 mL, 16.0 mmol) were suspended in methylene chloride and stirred over 24 hours. Water was added to the reaction mixture and extracted with methylene chloride. The organic layer was washed with 1N HCl, then with saturated sodium chloride solution. The solution was dried over sodium sulfate, filtered, concentrated in vacuo and purified by column chromatography (2-10% methanol/methylene chloride as the eluent) to give the desired product (2.94 g, 65%): $^1$H NMR (500 MHz, CDCl$_3$) δ 8.52 (d, J=0.5 Hz, 1H), 7.95 (dd, J=8.4, 1.5 Hz, 1H), 7.84 (d, J=8.4 Hz, 1H), 7.66 (d, J=5.4 Hz, 1H), 7.38 (d, J=5.4 Hz, 1H), 7.20 (d, J=7.8 Hz, 1H), 6.92-6.90 (m, 2H), 6.77-6.75 (m, 1H), 3.86 (s, 2H), 3.65 (s, 2H), 2.40 (s, 3H).

Step H: The product from Step G (2.94 g, 9.0 mmol) was dissolved in methanol and cooled in an ice bath. Sodium borohydride (0.43 g, 11.0 mmol) was added to the reaction mixture and stirred at room temperature for 1 hour. The methanol was concentrated in vacuo and the solid was redissolved in methylene chloride, washed with water twice and extracted with methylene chloride twice. The combined organic extract was was washed with brine, dried over sodium sulfate, filtered and concentrated to a yellow solid (2.75 g, 93%): $^1$H NMR (500 MHz, CDCl$_3$) δ 7.91 (s, 1H), 7.77 (d, J=8.2 Hz, 1H), 7.41 (d, J=5.4 Hz, 1H), 7.32-7.30 (m, 2H), 7.20 (t, J=7.7 Hz, 1H), 6.87 (d, J=7.6 Hz, 1H), 6.81 (s, 1H), 6.75 (d, J=8.1 Hz, 1H), 4.88 (dd, J=3.6, 10.3 Hz, 1H), 3.71 (d, J=13.1 Hz, 1H), 3.49 (d, J=12.1 Hz, 1H), 2.67-2.56 (m, 2H), 2.34 (s, 3H); ESI MS m/z 314 [M+H]$^+$.

Step I: The product from Step H (2.75 g, 8.8 mmol) was dissolved in methylene chloride (80 mL) and added to a solution of methanesulfonic acid (7.0 mL, 105 mmol) in methylene chloride (400 mL) and stirred for 10 minutes. The reaction mixture was cooled in an ice bath, then quenched with saturated sodium bicarbonate solution and stirred for 1 hour. The organic layer was washed with saturated sodium chloride solution, dried over sodium sulfate, filtered, concentrated and purified by column chromatography (10:90 methanol/methylene chloride) to give the desired 4-benzo[b]thiophen-6-yl-2-methyl-1,2,3,4-tetrahydroisoquinolin-7-ol (0.98 g, 38%): $^1$H NMR (500 MHz, CDCl$_3$) δ 7.72 (t, J=8.2 Hz, 2H), 7.38 (d, J=5.4 Hz, 1H), 7.29 (d, J=5.3 Hz, 1H), 7.18 (d, J=8.1 Hz, 1H), 6.73 (d, J=8.3 Hz, 1H), 6.54 (dd, J=2.6, 8.3 Hz, 1H), 6.49 (s, 1H), 4.33 (t, J=5.9 Hz, 1H), 3.67 (d, J=14.9 Hz, 1H), 3.56 (d, J=7.4 Hz, 1H), 3.09-3.05 (m, 1H), 2.59 (t, J=8.9 Hz, 1H), 2.42 (s, 3H).

Step J: The product from Step I (0.10 g, 0.35 mmol) was converted to the maleic acid salt by dissolving the free base in a minimal amount of ethanol, adding one equivalent of maleic acid in enough methanol to completely dissolve the acid, then combining the two solutions and stirring over 1 hour. The solution was concentrated to a minimal volume, then refrigerated at –30° C. until crystal formation occurred to give 4-benzo[b]thiophen-6-yl-2-methyl-1,2,3,4-tetrahydroisoquinolin-7-ol, maleate salt (0.13 g, 90%, 98.7% AUC HPLC): $^1$H NMR (500 MHz, CD$_3$OD) δ 7.84 (d, J=8.2 Hz, 1H), 7.79 (s, 1H), 7.59 (d, J=5.4 Hz, 1H), 7.37 (d, J=5.4 Hz, 1H), 7.20 (d, J=8.2 Hz, 1H) 6.74-6.6.8 (m, 3H), 6.23 (s, 2H), 4.61-4.59 (M, 1H), 4.52-4.48 (m, 2H), 3.84-3.82 (m, 1H), 3.49-3.47 (m, 1H), 3.05 (s, 3H).

Step K: The product from Step I (0.97 g, 3.3 mmol) was dissolved in methylene chloride (40 mL) and triethylamine (0.69 mL, 4.9 mmol). The reaction mixture was cooled in an ice bath trifluoromethanesulfonic anhydride (0.64 mL, 3.6 mmol) was added and stirred for 30 minutes. Saturated sodium chloride solution was added to the mixture and extracted with methylene chloride twice. The combined organic extract was dried over sodium sulfate, filtered and concentrated to a yellow solid. (1.4 g, 99%): $^1$H NMR (500 MHz, CDCl$_3$) δ 7.82 (d, J=8.2 Hz, 1H), 7.76 (s, 1H), 7.51 (d, J=5.4 Hz, 1H), 7.35 (d, J=5.4 Hz, 1H), 7.14-7.11 (m, 3H), 7.04 (d, J=9.2 Hz, 1H), 5.30-5.02 (m, 1H), 4.70-4.65 (m, 1H), 4.30-4.27 (m, 1H), 3.91-3.79 (m, 1H), 3.26-3.25 (m, 1H), 3.03 (s, 3H).

Step L: The product of Step K (0.54 g, 1.3 mmol), 2-(dicyclohexylphosphino)-2',4',6'-triisopropyl-1,1'biphenyl (0.36 g, 0.76 mmol), morpholine (0.22 mL, 2.5 mmol), cesium carbonate (1.03 g, 3.2 mmol) in toluene was stirred and degassed with argon. Palladium (II) acetate (0.04 g, 1.9 mmol) was added to the reaction mixture and heated to 100° C. for 24 hours. The cooled reaction mixture was filtered over a pad of diatomaceous earth and concentrated to a yellow solid. The solid was purified by column chromatography (5:95 methanol/methylene chloride) to give the desired product (0.23 g, 50%): $^1$H NMR (500 MHz, CDCl$_3$) δ 7.73-7.70 (m, 2H), 7.37 (d, J=5.4 Hz, 1H), 7.29 (d, J=5.4 Hz, 1H), 7.19 (dd, J=1.4 Hz, 8.2 Hz, 1H), 6.79 (d, J=8.5 Hz, 1H), 6.67-6.62 (m, 2H), 4.32 (s, 1H), 3.84 (t, J=4.7 Hz, 4H), 3.71 (d, J=17.4 Hz, 1H), 3.61 (d, J=14.8 Hz, 1H), 3.12 (t, J=4.8 Hz, 4H), 3.04 (dd, J=5.6 Hz, 11.3 Hz, 1H), 2.60 (t, J=8.5 Hz, 1H), 2.42 (s, 3H).

This compound was resolved by preparative chiral HPLC (CHIRALPAK AD column, using 80% heptane/20% isopropanol/0.1% diethylamine) to give the (+)-enantiomer [α]$^{25}_D$ +47.8° (c 0.069, methanol) and the (−)-enantiomer [α]$^{25}_D$ −38.8° (c 0.17, methanol).

Step M: The (+)-enantiomer from Step L (0.10 g, 0.34 mmol) was converted to the maleic acid salt by dissolving the free base in a minimal amount of methanol, adding one equivalent of maleic acid in enough methanol to completely dissolve the acid, then combining the two solutions and stirring over 1 hour. The solution was concentrated to a minimal volume, then refrigerated at −30° C. until crystal formation occurred. Filtration yielded the (+)-4-benzo[b]thiophen-6-yl-2-methyl-7-morpholin-4-yl-1,2,3,4-tetrahydroisoquinoline, maleate salt (86.0 mg, 64%, >99% AUC HPLC) as a brown solid: $^1$H NMR (500 MHz, CD$_3$OD) δ 7.84 (d, J=8.0 Hz, 1H), 7.79 (s, 1H), 7.59 (dd, J=1.4 Hz, 5.4 Hz, 1H), 7.37 (d, J=4.4 Hz, 1H), 7.20 (d, J=8.2 Hz, 1H), 6.90-6.88 (m, 1H), 6.81 (s, 2H), 6.25 (s, 2H), 4.63-4.52 (m, 3H), 3.87-3.80 (m, 5H), 3.59-3.57 (m, 1H), 3.14 (s, 3H), 3.06 (s, 1H).

The same procedure was used to transform the (−)-enantiomer (12 mg, 0.34 mmol) to its maleic salt to give (−)-4-benzo[b]thiophen-6-yl-2-methyl-7-morpholin-4-yl-1,2,3,4-tetrahydroisoquinoline, maleate salt (16.5 mg, >99%, >99% AUC HPLC) as an off-white solid: $^1$H NMR (500 MHz, CD$_3$OD) δ 7.84 (d, J=8.0 Hz, 1H), 7.79 (s, 1H), 7.59 (dd, J=1.4 Hz, 5.4 Hz, 1H), 7.37 (d, J=4.4 Hz, 1H), 7.20 (d, J=8.2 Hz, 1H), 6.90-6.88 (m, 1H), 6.81 (s, 2H), 6.25 (s, 2H), 4.63-4.52 (m, 3H), 3.87-3.80 (m, 5H), 3.59-3.57 (m, 1H), 3.14 (s, 3H), 3.06 (s, 1H).

Example 149

Preparation of (+/−)-4-benzo[b]thiophen-5-yl-2-methyl-8-morpholin-4-yl-1,2,3,4-tetrahydroisoquinoline, fumarate salt Step A: To a solution of 1,3-dibromobenzene (29.2 g, 0.123 mol) in THF (300 mL) at −78° C. was added dropwise lithium diisopropylamide (83 mL, 0.148 mol, 1.8 M in THF) under nitrogen. After 30 minutes at −78° C., N,N-dimethylformamide (10.9 g, 0.148 mol) was added dropwise to the orange suspension. The reaction mixture was stirred for 30 minutes and dilute sulfuric acid (~500 mL) was added dropwise at 0° C. The aqueous layer was extracted with EtOAc (3×350 mL), dried (Na$_2$SO$_4$) and concentrated under reduced pressure to give dibromobenzaldehyde (32.3 g, 99%) as an orange solid which was used directly in the next step without purification. $^1$H NMR (CDCl$_3$, 500 MHz) δ 10.26 (s, 1H), 7.65 (d, J=8.0 Hz, 2H), 7.21-7.24 (m, 1H).

Step B: A solution of the dibromobenzaldehyde (10.00 g, 4.67 mmol) from Step A above and methylamine (1.40 g, 45.4 mmol, 40% wt in water) in methanol (200 mL) was stirred for 15 minutes at 25° C. under nitrogen. The mixture was cooled to 0° C. and sodium borohydride (720 mg, 18.9 mmol) was added in portions. The reaction mixture was stirred 3 hours and concentrated under reduced pressure. The residue was partitioned with EtOAc (3×200 mL) and water (200 mL), dried (Na$_2$SO$_4$) and concentrated under reduced pressure to give the methylamino compound (8.9 g, 84%) as an orange oil which was used in the next step without any further purification: $^1$H NMR (CDCl$_3$, 500 MHz) δ 7.52-7.54 (m, 2H), 6.95-6.98 (m, 1H), 4.09 (s, 2H), 2.46 (s, 3H).

Step C: A suspension of 5-bromobenzo[c]thiophene (4.6 g, 21.6 mmol), 1',1'-bis(diphenylphosphino)ferrocene (2.40 g, 4.31 mmol), thallium(I) acetate (8.50 g, 32.4 mmol) and 1-(tert-butyldimethylsilyloxy)-methoxyethene (4.90 g, 28.1 mmol) in THF (150 mL) was purged with nitrogen for 15 minutes, and then palladium(II) acetate (485 mg, 2.16 mmol) was added. The resultant mixture was refluxed overnight, partitioned with EtOAc (3×200 mL) and water (200 mL), dried (Na$_2$SO$_4$) and concentrated under reduced pressure to give an oily residue. The residue was purified by silica gel column chromatography (eluent hexanes/ethyl acetate 10:1) to give the desired methyl ester (2.63 g, 59%) as a white waxy solid: $^1$H NMR (CDCl$_3$, 500 MHz) δ 7.73 (d, J=8.3 Hz, 1H), 7.64 (s, 1H), 7.34 (d, J=5.4 Hz, 1H), 7.15-7.24 (m, 2H), 3.64 (s, 2H), 3.60 (s, 3H).

Step D: A solution of the methyl ester (2.63 g, 12.8 mmol) from Step C above and lithium hydroxide (763 mg, 31.9 mmol) in THF (60 mL) and water (10 mL) was stirred at ambient temperature overnight. The reaction mixture was concentrated under reduced pressure, partitioned with EtOAc (100 mL) and water (100 mL). The aqueous layer was acidified with 1N HCl (120 mL) and was extracted with EtOAc (3×200 mL). The combined organic extracts were dried (Na$_2$SO$_4$) and concentrated under reduced pressure to give the desired acid (1.90 g, 78%) as a white solid: $^1$H NMR (CD$_3$OD, 500 MHz) δ 7.83 (d, J=8.3 Hz, 1H), 7.77 (s, 1H), 7.54 (d, J=5.4 Hz, 1H), 7.32 (d, J=5.4 Hz, 1H), 7.27 (d, J=8.3 Hz, 1H), 3.72 (s, 2H).

Step E: A solution of the acid (1.40 g, 7.29 mmol) from Step D above, the methylamino compound (2.13 g, 7.65 mmol) from Step B above, EDC (1.82 g, 9.47 mmol), 1-hydroxybenzotriazole (1.28 g, 9.47 mmol) and N,N-diisopropylethylamine (2.82 g, 21.8 mmol) in methylene chloride (50 mL) was stirred overnight at ambient temperature under nitrogen. The mixture was partitioned with CH$_2$Cl$_2$ (3×150 mL) and water (150 mL), dried (Na$_2$SO$_4$) and concentrated under reduced pressure to give an oily residue. The residue was purified by silica gel column chromatography (eluent hexanes/ethyl acetate 5:1) to give the desired amide (1.68 g, 48%) as a yellow solid: $^1$H NMR (CDCl$_3$, 500 MHz) δ 7.82 (d, J=8.2 Hz, 1H), 7.76 (d, J=7.3 Hz, 1H), 7.54-7.59 (m, 2H), 7.42-7.44 (m, 1H), 7.29-7.31 (m, 2H), 7.00-7.03 (m, 1H) 5.05 (s, 1.5H, rotamer), 4.85 (s, 0.5H, rotamer), 4.09 (s, 0.5H, rotamer), 3.88 (s, 1.5H, rotamer), 2.75 (s, 2.2H, rotamer), 2.69 (s, 0.8H, rotamer).

Step F: A solution of the amide (1.68 g, 3.71 mmol) from Step E above in dioxane (8.0 mL) was added dropwise to a nitrogen-degassed solution of potassium tert-butoxide (624 mg, 5.56 mmol), bis(dibenzylideneacetone)palladium(0) (213 mg, 0.371 mmol) and 1,3-bis(diphenylphosphino)ethane (221 mg, 0.556 mmol) in dioxane (10 mL) under nitrogen. The reaction mixture was refluxed for 1 hour, partitioned with EtOAc (3×100 mL) and water (100 mL), dried (Na$_2$SO$_4$) and concentrated under reduced pressure to give an oily residue. The residue was purified by silica gel column chromatography (eluent hexanes/ethyl acetate 5:1) to give the desired lactam (365 mg, 26%) as a yellow foam: $^1$H NMR (CDCl$_3$, 500 MHz) δ 7.79 (d, J=8.3 Hz, 1H), 7.54 (d, J=7.7 Hz, 1H), 7.49-7.51 (m, 1H), 7.41-7.43 (m, 1H), 7.24-7.26 (m, 1H), 7.11-7.17 (m, 3H), 4.98 (s, 1H), 4.58 (s, 2H), 3.15 (s, 3H); ESI-MS m/z 372, 374 [M+H]$^+$.

Step G: Borane dimethyl sulfide complex (5.80 mL, 5.80 mmol, 1.0 M in THF) was added dropwise to a solution of the lactam (362 mg, 0.972 mmol) from Step F above in THF (8.0 mL). The reaction mixture was heated at reflux for 30 minutes under nitrogen. The mixture was concentrated under reduced pressure, and potassium carbonate (1.30 g, 9.72 mmol), dioxane (8.0 mL) and water (4.0 mL) were added to the residue. The mixture was refluxed for 4 h, partitioned with EtOAc (3×40 mL) and water (50 mL), dried (Na$_2$SO$_4$) and concentrated under reduced pressure to give the desired tetrahydroisoquinoline (346 mg, 100% crude) as an oil: $^1$H NMR (CDCl$_3$, 500 MHz) δ 7.78 (d, J=8.3 Hz, 1H), 7.63 (s, 1H), 7.43 (d, J=5.2 Hz, 1H), 7.39 (d, J=7.8 Hz, 1H), 7.26-7.28 (m, 1H), 7.14 (d, J=8.3 Hz, 1H), 6.92-6.95 (m, 1H), 6.85 (d, J=7.7 Hz, 1H), 4.38-4.43 (m, 1H), 3.83 (d, J=15.8 Hz, 1H), 3.56 (d, J=15.9 Hz, 1H), 3.04 (dd, J=14.1 Hz, 6.6 Hz, 1H), 2.64 (dd, J=11.4 Hz, 8.4 Hz, 1H), 2.49 (s, 3H); ESI-MS m/z 358, 360 [M+H]$^+$ Step H: A mixture of the tetrahydroisoquinoline (260 mg, 0.725 mmol) from Step G above, morpholine (126 mg, 1.45 mmol), cesium carbonate (710 mg, 2.18 mmol) and 2-(dicyclohexylphosphino)-2',4',6'-tri-i-propyl-1,1'-biphenyl (104 mg, 0.217 mmol) in m-xylene (10 mL) was degassed with a stream of nitrogen for 10 minutes, and palladium(II) acetate (16 mg, 0.0725 mmol) was added. The reaction mixture was refluxed for 6 hours, and the mixture was filtered over a short pad of Celite washing with methanol. The filtrate was concentrated under reduced pressure to give a brown residue which was purified by silica gel column chromatography (eluent CH$_2$Cl$_2$/MeOH 98:2) to give the target morpholine (30 mg, 11%) as a yellow solid: ESI-MS m/z 365 [M+H]$^+$.

Step I: To a solution of the morpholine target (52 mg, 0.143 mmol) from Step H above in methanol (3 mL) was added fumaric acid (16.5 mg, 0.143 mmol). The solution was concentrated and dried in vacuo overnight to give (+/−)-4-benzo[b]thiophen-5-yl-2-methyl-8-morpholin-4-yl-1,2,3,4-tetrahydroisoquinoline, fumarate salt (AUC HPLC=97.4%) as a yellow solid: mp 148-153° C.; $^1$H NMR (CD$_3$OD, 500 MHz) δ 7.88 (d, J=8.4 Hz, 1H), 7.72 (s, 1H), 7.59 (d, J=5.4 Hz, 1H), 7.33 (d, J=5.4 Hz, 1H), 7.12-7.23 (m, 3H), 6.71 (d, J=7.8 Hz, 1H), 6.95 (s, 2H), 4.66-4.72 (m, 2H), 4.24 (d, J=15.3 Hz, 1H), 3.83-3.93 (m, 4H), 3.70-3.74 (m, 1H), 3.32-3.34 (m, 1H), 3.01-3.06 (m, 2H), 2.97 (s, 3H), 2.81-2.85 (m, 2H); ESI-MS m/z 365 [M+H]$^+$.

Example 150

Preparation of (+/−)-2-(4-Benzo[b]thiophen-5-yl-3,4-dihydro-1H-isoquinolin-2-yl)-ethanol, fumarate salt Step A: A mixture of 4-benzo[b]thiophen-5-yl-1,2,3,4-tetrahydroisoquinoline (40 mg, 0.15 mmol, the preparation of which was described in Example 20), 2-bromoethanol (23 mg, 0.18 mmol), and cesium carbonate (98 mg, 0.30 mmol) in DMF (4 mL) was stirred at room temperature for 12 hours. The mixture was diluted with ethyl acetate, washed with 5% LiOH solution, then brine, and the organic layer dried over magnesium sulfate, and concentrated. The residue was purified by column chromatography (SiO$_2$, 12 g, 85% to 0% hexane/ethyl acetate) to provide the desired tetrahydroisoquinoline (13 mg, 28%). This material was dissolved in methanol and treated with a solution of fumaric acid in methanol (5 mL) at 0° C. The solution was stirred at room temperature for 12 hours, then concentrated, and the solid was washed with diethyl ether providing (+/−)-2-(4-benzo[b]thiophen-5-yl-3,4-dihydro-1H-isoquinolin-2-yl)ethanol, fumarate salt (18 mg, 99%, 96.0% AUC HPLC): $^1$H NMR (CD$_3$OD, 500 MHz) δ 7.92 (d, J=8.4 Hz, 1H), 7.79 (d, J=0.9 Hz, 1H), 7.62 (d, J=5.4 Hz, 1H), 7.36-7.30 (m, 3H), 7.25-7.20 (m, 2H), 6.92 (d, J=7.8 Hz, 1H), 6.74 (s, 2H), 4.77-4.74 (m, 1H), 4.69 (s, 2H), 4.01-3.97 (m, 3H), 3.65-3.58 (m, 1H), 3.48-3.46 (m, 2H), ESI MS m/z=310 [M+H]$^+$.

Example 151

Preparation of (+)-4-benzo[b]thiophen-5-yl-2-methyl-7-pyrimidin-2-yl-1,2,3,4-terahydroisoquinoline A mixture of crude (+)-boronate ester (200 mg, 0.89 mmol) prepared according to Step B of Example 97, 2-chloropyrimidine (100 mg, 0.90 mmol), Cs$_2$CO$_3$ (869 mg, 2.67 mmol), DMF (10 mL) and water (1.5 mL) was flushed with argon via balloon. PdCl$_2$(dppf) (44 mg, 0.05 mmol) was heated added and the mixture heated at 90° C. for 5 h. After cooling the reaction mixture was partitioned between EtOAc (150 mL) and water (150 mL). The organic layer was washed with water (2×100 ml), brine, dried over Na$_2$SO$_4$ and concentrated in vacuo. The residue was purified by silica gel column chromatography using an 40 g ISCO cartridge (eluent: 100:0 to 95:5 EtOAc/MeOH) to afford (+)-4-benzo[b]thiophen-5-yl-2-methyl-7-pyrimidin-2-yl-1,2,3,4-terahydroisoquinoline (52 mg, 16%) as an off-white solid: $^1$H NMR (300 MHz, CDCl$_3$) δ 8.77 (d, J=4.8 Hz, 2H), 8.22 (s, 1H), 8.13 (dd, J=8.2, 1.2 Hz, 1H), 7.80 (d, J=8.3 Hz, 1H), 7.67 (s, 1H), 7.42 (d, J=5.4 Hz, 1H), 7.27 (d, J=5.3 Hz, 1H), 7.13-7.22 (m, 2H), 7.03 (d, J=8.2 Hz, 1H), 4.47 (m, 1H), 3.91 (d, J=15.0 Hz, 1H), 3.74 (d, J=15.0 Hz, 1H), 3.13 (dd, J=11.5, 5.7 Hz, 1H), 2.67 (dd, J=11.4, 8.7 Hz, 1H), 2.47 (s, 3H); ESI-MS m/z 358 [M+H]$^+$.

Example 152

Preparation of (+/−)-4-benzo[b]thiophen-5-yl-2-methyl-7-morpholin-4-yl-1,2,3,4-tetrahydroisoquinoline Step A: To a solution of 4-bromophenyl acetic acid (50 g, 233 mmol) in SOCl$_2$ (170 mL, 2.32 mol) was added DMF (2 mL, 26 mmol). After stirred at this temperature for 1 h, the excess $SOCl_2$ was removed under reduced pressure. The residue was dissolved in $CH_2Cl_2$ (300 mL), and the resulting solution was added to a cooled (0° C.) solution of $CH_3NH_2$ (90 mL, 40 wt % in $H_2O$, 1.03 mol) in THF (200 mL) dropwise. After the addition was complete, the solution was further stirred at 0° C. for 15 min. Water (400 mL) was added to the reaction solution, and organic layer separated. The aqueous layer was extracted with $CH_2Cl_2$ (200 mL). The organic layers were combined, washed with brine (500 mL), dried and concentrated to give 4-bromophenyl-N-methyl acetamide (54 g, quant.) as a white solid: $^1H$ NMR (500 MHz, $CDCl_3$) δ 7.48 (d, J=8.9 Hz, 2H), 7.15 (d, J=8.9 Hz, 2H), 3.51 (s, 2H), 2.77 (s, 3H); ESI-MS m/z 228 $[M+H]^+$.

Step B: 4-Bromophenyl-N-methyl acetamide obtained from Step A (3.8 g, 16.7 mmol), paraformayldehyde (550 mg, 18.4 mmol) and $H_4P_2O_7$ (30 g) were mixed and heated at 150-160° C. for 1 h. The reaction mixture was poured into ice-water (200 mL). The product was extracted with $CH_2Cl_2$ (2×100 mL). The organic layer was washed with $NaHCO_3$ (100 mL), brine (100 mL), dried and concentrated to give the desired product (3.4 g, 85%) as a yellow solid: $^1H$ NMR (500 MHz, $CDCl_3$) δ 7.38 (d, J=8.1 Hz, 1H), 7.32 (s, 1H), 7.03 (d, J=8.1 Hz, 1H), 4.46 (s, 2H), 3.56 (s, 2H), 3.10 (s, 3H); ESI-MS m/z 240 $[M+H]^+$.

Step C: To a solution of 5-bromobenzothiophene (11.6 g, 55.5 mmol) in toluene (150 mL) was added $Pd(OAc)_2$. The mixture was purged with argon; 2,8,9-trisobutyl-2,5,8,9-tetraaza-1-phosphabicyclo[3,3,3]undecane (2.6 g, 7.6 mmol) was added to the mixture. After stirred at room temperature for 2 min, NaOt-Bu (5.4 g, 56 mmol) was added to the mixture followed by the product obtained from Step B (9.0 g, 37.5 mmol). The resulting mixture was heated at 70° C. for 30 min. After cooled to room temperature, the reaction mixture was diluted with $CH_2Cl_2$ (200 mL), washed with saturated aqueous ammonium chloride solution (200 mL) and brine (200 mL), dried and concentrated. The residue was purified by a medium pressure chromatography (eluent: $EtOAc/CH_2Cl_2$ 1:4) to give the desired product (8.84 g, 63%) as a yellow solid: $^1H$ NMR (300 MHz, $CDCl_3$) δ 7.78 (d, J=8.4 Hz, 1H), 7.47-7.41 (m, 4H), 7.23 (d, J=5.6 Hz, 1H), 4.93 (s, 1H), 4.64 (d, J=16.2 Hz, 1H), 4.31 (d, J=16.2 Hz, 1H), 3.09 (s, 3H); ESI-MS m/z 372 $[M+H]^+$.

Step D: To a cooled (0° C.) solution of the product obtained from Step C (3.13 g, 8.4 mmol) in THF (50 mL) was added $BH_3\text{-}Me_2S$ in THF (7.7 mL, 2.0 M, 15.4 mmol) during 15 min period. The resulting solution was stirred at 0° C. to room temperature for 20 min. It was then heated at 50° C. for 20 min. After cooled to room temperature, the solvent was removed. Dioxane (45 mL) and HCl (6 N, 15 mL) were added to the residue. The resulting solution was refluxed for 30 min. After cooled to room temperature, the solution was neutralized with 2 N NaOH. The product was extracted with $CH_2Cl_2$ (2×100 mL). The organic layer was washed with brine (100 mL), dried and concentrated. The residue was purified by a medium pressure chromatography (eluent: MeOH/EtOAc/hexanes 1:9:40) to give the desired product (2.48 g, 82%) as a white foam: $^1H$ NMR (500 MHz, DMSO-$d_6$) δ 7.89 (d, J=8.3 Hz, 1H), 7.72 (d, J=5.4 Hz, 1H), 7.67 (s, 1H), 7.40-7.38 (m, 2H), 7.24-7.19 (m, 2H), 6.76 (d, J=8.3 Hz, 1H), 4.30 (t, J=6.3 Hz, 1H), 3.62 (d, J=15.0 Hz, 1H), 3.58 (d, J=15.0 Hz, 1H), 2.92 (m, 1H), 2.62 (m, 1H), 2.31 (s, 3H); ESI-MS m/z 358 $[M+H]^+$.

Step E: The product obtained from Step D (8.0 g, 22.4 mmol), BINAP (1.4 g, 2.24 mmol), KOt-Bu (5.5 g, 49 mmol), morpholine (7.8 g, 90 mmol) and toluene were mixed, and the mixture was purged with argon. To the mixture was added $Pd(OAc)_2$ (502 mg, 2.24 mmol). The resulting mixture was hearted at reflux for 0.5 h. After cooled to room temperature, the mixture was diluted with $CH_2Cl_2$ (200 mL), washed with saturated aqueous ammonium chloride solution (200 mL), brine (200 ml), dried and concentrated. The residue was purified by a medium pressure chromatography (eluent: MeOH/EtOAc 1:9) to give the desired product (5.2 g, 64%) as a pale foam: $^1H$ NMR (300 MHz, $CDCl_3$) δ 7.78 (d, J=8.3 Hz, 1H), 7.65 (s, 1H), 7.41 (d, J=5.3 Hz, 1H), 7.18 (d, J=8.3 Hz, 1H), 6.79 (d, J=8.4 Hz, 1H), 6.68-6.63 (m, 2H), 4.34-4.30 (m, 1H), 3.86-3.83 (m, 4H), 3.73 (d, J=14.6 Hz, 1H), 3.61 (d, J=14.6 Hz, 1H), 3.14-3.02 (m, 5H), 2.62-2.56 (m, 1H), 2.42 (s, 3H); ESI-MS 365 $[M+H]^+$.

(+/−)-4-Benzo[b]thiophen-5-yl-2-methyl-7-morpholin-4-yl-1,2,3,4-tetrahydroisoquinoline was also prepared using an alternative sequence as described in Step F through Step H below:

Step F: To a solution of the product obtained from Step B (10 g, 41.7 mmol) was added L-proline (1.9 g, 16.7 mmol), morpholine (28.6 g, 336 mmol), CuI (1.57 g, 83.4 mmol) and $K_3PO_4$ (17.5 g, 83.4 mmol). The mixture was heated at 100° C. for 40 h. After cooled to room temperature, the mixture was washed with saturated aqueous ammonium chloride solution (300 mL), brine (300 mL), dried and concentrated. The residue was purified by flash column (eluent: MeOH/EtOAc 1:19) to give the desired product (6.5 g, 63%) as a yellow solid: $^1H$ NMR (300 MHz, $CDCl_3$) δ 7.06 (d, J=8.4 Hz, 1H), 6.84 (d, J=8.4 Hz, 1H), 6.68 (s, 1H), 4.46 (s, 2H), 3.88-3.85 (m, 4H), 3.55 (s, 2H), 3.14-3.10 (m, 7H); ESI-MS m/z 247 $[M+H]^+$.

Step G: The product obtained from Step F (5.5 g, 22 mmol), 5-bromobenzothiophene (4.76 g, 22 mmol) and BINAP (684 mg, 2.2 mmol) were mixed with toluene (50 mL). The mixture was purged with argon. To the mixture was added $Pd(OAc)_2$ (264 mg, 1.1 mmol), followed by NaOt-Bu (3.17 g, 33 mmol). The mixture was then heated at 70° C. for 1.5 h. After cooled to room temperature, the mixture was diluted with $CH_2Cl_2$ (200 mL), and washed with saturated aqueous ammonium chloride solution (200 mL), brine (100 mL), dried and concentrated. The residue was purified by medium pressure chromatography (eluent: EtOAc) to give the desired product (6.5 g, 79%) as a yellow solid: $^1H$ NMR (300 MHz, $CDCl_3$) δ 7.77 (d, J=8.4 Hz, 1H), 7.50 (s, 1H), 7.39 (d, J=5.4 Hz, 1H), 7.23-7.19 (m, 2H), 7.05 (d, J=8.4 Hz, 1H), 6.90-6.85 (m, 1H), 6.77 (s, 1H), 4.91 (s, 1H), 4.64 (d, J=15.9 Hz, 1H), 4.28 (d, J=15.9 Hz, 1H), 3.90-3.87 (m, 4H), 3.20-3.17 (m, 4H), 3.08 (s, 3H); ESI-MS m/z 379 $[M+H]^+$.

Step H: To a solution of the product obtained from Step B (11.5 g, 30.4 mmol) in THF (200 mL) solution heated at reflux was added $BH_3\text{-}Me_2S$ in $CH_2Cl_2$ (61 mL, 1.0 M, 61 mmol) dropwise. The solution was refluxed for 1 h. After cooled to room temperature, the solvent was removed. To the residue was added MeOH (250 mL) and tetramethylethylenediamine (35 mL). The mixture was refluxed for 4.5 h. After cooled to room temperature, the solvent was removed. The residue was purified by a medium pressure chromatography (eluent: MeOH/EtOAc 1:9) to give the desired product (7.0 g, 62%) as a white solid: $^1H$ NMR (500 MHz, $CDCl_3$) δ 7.78 (d, J=8.3 Hz, 1H), 7.65 (s, 1H), 7.41 (d, J=5.3 Hz, 1H), 7.18 (d, J=8.3 Hz, 1H), 6.79 (d, J=8.4 Hz, 1H), 6.68-6.63 (m, 2H), 4.34-4.30 (m, 1H), 3.86-3.83 (m, 4H), 3.73 (d, J=14.6 Hz, 1 H), 3.61 (d, J=14.6 Hz, 1H), 3.14-3.02 (m, 5H), 2.62-2.56 (m, 1H), 2.42 (s, 3H); ESI-MS 365 $[M+H]^+$.

4-Benzo[b]thiophen-5-yl-2-methyl-7-morpholin-4-yl-1,2,3,4-tetrahydroisoquinoline was also prepared using an alternative sequence as described in Step I through Step M below:

Steps I and J: 7-Chloro-2-methyl-1,4-dihydro-2H-isoquinolin-3-one was prepared, using 4-chlorophenylacetic acid (69.22 g, 406.5 mmol) in two steps with an overall yield of 71% as a yellow solid, following a procedure similar to that described in Steps A and B: $^1$H NMR (500 MHz, CDCl$_3$) δ 7.28-7.22 (m, 1H), 7.16 (s, 1H), 7.08 (d, J=8.2 Hz, 1H), 4.46 (s, 2H), 3.57 (s, 2H), 3.10 (s, 3H).

Step K: 4-Benzo[b]thiophen-5-yl-7-chloro-2-methyl-1,4-dihydro-2H-isoquinolin-3-one was prepared, using 7-chloro-2-methyl-1,4-dihydro-2H-isoquinolin-3-one obtained from Step J, with a yield of 63% as a yellow foam, following a procedure similar to that described in Step C: $^1$H NMR (500 MHz, CDCl$_3$) δ 7.78 (d, J=8.4 Hz, 1H), 7.48-7.45 (m, 1H), 7.42 (d, J=5.4 Hz, 1H), 7.30-7.28 (m, 2H), 7.23 (dd, J=0.5, 5.4 Hz, 1H), 7.17 (dd, J=1.7, 8.4 Hz, 1H), 7.09 (d, J=8.8 Hz, 1H), 4.94 (s, 1H), 4.63 (d, J=19.6 Hz, 1H), 4.30 (d, J=16.0 Hz, 1H), 3.09 (s, 3H).

Step L: 4-Benzo[b]thiophen-5-yl-7-chloro-2-methyl-1,2,3,4-tetrahydroisoquinoline was prepared, using 4-benzo[b]thiophen-5-yl-7-chloro-2-methyl-1,4-dihydro-2H-isoquinolin-3-one obtained from Step K, with a yield of 97% as a clear oil, following a procedure similar to that described in Step D: $^1$H NMR (500 MHz, CDCl$_3$) δ 7.78 (d, J=8.4 Hz, 1H), 7.63 (d, J=1.2 Hz, 1H), 7.43 (d, J=5.5 Hz, 1H), 7.27 (d, J=5.4 Hz, 1H), 7.14 (dd, J=8.3, 1.5 Hz, 1H), 7.10 (d, J=1.9 Hz, 1H), 7.02 (dd, J=8.3, 2.1 Hz, 1H), 6.82 (d, J=8.3 Hz, 1H), 4.36-4.31 (m, 1H), 3.73 (d, J=15.1 Hz, 1H), 3.61 (d, J=15.1 Hz, 1H), 3.09-3.02 (m, 1H), 2.61 (dd, J=11.5, 8.5 Hz, 1H), 2.43 (s, 3H).

Step M: (+/−)-4-benzo[b]thiophen-5-yl-2-methyl-7-morpholin-4-yl-1,2,3,4-tetrahydroisoquinoline was prepared, using 4-benzo[b]thiophen-5-yl-7-chloro-2-methyl-1,2,3,4-tetrahydroisoquinoline obtained in Step L, with a yield of 72% as a clear oil, following a procedure similar to that described in Step E: $^1$H NMR (300 MHz, CDCl$_3$) δ 7.78 (d, J=8.3 Hz, 1H), 7.65 (s, 1H), 7.41 (d, J=5.3 Hz, 1H), 7.27-7.25 (m, 1H), 7.18 (d, J=8.3 Hz, 1H), 6.79 (d, J=8.4 Hz, 1H), 6.68-6.63 (m, 2H), 4.34-4.30 (m, 1H), 3.86-3.83 (m, 4H), 3.73 (d, J=14.6 Hz, 1H), 3.61 (d, J=14.6 Hz, 1H), 3.14-3.02 (m, 5H), 2.62-2.56 (m, 1H), 2.42 (s, 3H); ESI-MS m/z 365 [M+H]$^+$.

Example 153

Preparation of (+)-4-Benzo[b]thiophen-5-yl-2-methyl-7-pyridazin-3-yl-1,2,3,4-tetrahydroisoquinoline, (+)-di-p-toluoyl-D-tartaric acid salt (+−)-4-benzo[b]thiophen-5-yl-2-methyl-7-morpholin-4-yl-1,2,3,4-tetrahydroisoquinoline obtained from Example 152 (0.302 g, 8.30 mmol) was dissolved in acetone (5.0 ml, 60 mg/mL) at 50° C. with stirring. After dissolution, (+)-di-p-toluoyl-D-tartaric acid (0.320 g, 1 equiv) was added as a solid. The temperature was held at 50° C. for 10 minutes, during this time the precipitate started to form. The reaction mixture was cooled to room temperature at a rate of 20° C./hr. The reaction mixture was allowed to stir overnight. The solids were filtered off and analyzed by chiral HPLC. The chiral HPLC for the solids showed a % yield of 90.52%. The reaction afforded 0.247 g (39.7%) after drying in vacuo at 55° C. This material was re-crystallized from THF (11 mL) at 60° C. The solids were filtered off, dried in vacuo at 55° C. and analyzed by chiral HPLC. The crystallization afforded 0.158 g of material (25.40% overall recovery from (+−)-4-benzo[b]thiophen-5-yl-2-methyl-7-morpholin-4-yl-1,2,3,4-tetrahydroisoquinoline. The % yield for this material was enhanced to 98.97%.

Example 154

Preparation of (+/−)-4-Benzo[b]thiophen-5-yl-2-methyl-7-pyridazin-3-yl-1,2,3,4-tetrahydroisoquinoline Step A: To a solution of the product obtained from Step D of Example 152 (4.31 g, 12.07 mmol), bis-pinacolatodiboron (4.68 g, 18.42 mmol) and potassium acetate (4.93 g, 50.23 mmol) in DMSO (87 mL) was added PdCl$_2$dppf (1.1 g, 1.34 mmol). The reaction mixture was heated to 70° C. overnight, then cooled to room temperature. The reaction mixture was diluted with EtOAc (500 mL) then, the resulting mixture was washed with water (3×20 mL). The organic phase was dried (Na$_2$SO$_4$) and concentrated to dryness under reduced pressure. The residue was purified using medium pressure chromatography (eluent: EtOAc/hexanes 95:5 to EtOAc 100 to EtOAc/MeOH 99:1) to give the desired crude product as a black oil (~11 g): $^1$H NMR (300 MHz, CDCl$_3$) δ 7.78 (d, J=8.3 Hz, 1H), 7.64 (s, 1H), 7.57 (s, 1H), 7.49 (d, J=7.8 Hz, 1H), 7.41 (d, J=5.4 Hz, 1H), 7.26 (s, 1H), 7.15 (d, J=8.2 Hz, 1H), 6.90 (d, J=7.9 Hz, 1H), 4.42-4.40 (m, 1H), 3.80 (d, J=15.9 Hz, 1H), 3.66 (d, J=15.9 Hz, 1H), 3.10-3.08 (m, 1H), 2.62 (t, J=11.4 Hz, 1H), 2.43 (s, 3H), 1.33 (s, 12H); ESI-MS m/z 406 [M+H]$^+$.

Step B: To a solution of the crude product obtained in Step A, Na$_2$CO$_3$ (4.45 g, 41.99 mmol), 3,6-dichloropyridazine (3.75 g, 25.17 mmol) in a mixture of DMF (210 mL) and H$_2$O (42 mL), was added PdCl$_2$dppf (1.1 g, 1.35 mmol). The reaction mixture was heated to 65° C. overnight. The cooled to room temperature reaction mixture was diluted with H$_2$O (100 mL). The resulting mixture was extracted with CH$_2$Cl$_2$ (3×300 mL). The organic layers were combined, then concentrated to dryness under reduced pressure to afford a brown solid, which was triturated with a mixture of EtOAc/MeOH (9:1). The solid was isolated by filtration, washed sequentially with EtOAc, EtOAc/CH$_2$Cl$_2$ (9:1) and diethyl ether then, dried to afford 4-benzo[b]thiophen-5-yl-7-(6-chloro-pyridazin-3-yl)-2-methyl-1,2,3,4-tetrahydroisoquinoline (2.82 g, 60% over 2 steps) as an off-white solid. The filtrate was concentrated to dryness under reduced pressure and purified using medium pressure chromatography (eluent: EtOAc 100 to EtOAc/MeOH 98:2) to afford a second batch of the desired product (1.20 g, 25% over 2 steps) as a brown solid: $^1$H NMR (500 MHz, DMSO-d$_6$) δ 8.28 (d, J=9.1 Hz, 1H), 7.99 (d, J=9.1 Hz, 1H), 7.96 (s, 1H), 7.91 (d, J=8.3 Hz, 1H), (dd, J=8.8, 1.4 Hz, 1H), 7.74-7.71 (m, 2H), 7.40 (d, J=5.4 Hz, 1H), 7.27 (dd, J=8.4, 1.1 Hz, 1H), 7.00 (d, J=8.2 Hz, 1H), 4.42 (t, J=5.9 Hz, 1H), 3.77 (d, J=15.2 Hz, 1H), 3.72 (d, J=15.2 Hz, 1H), 2.98 (dd, J=11.4, 5.5 Hz, 1H), 2.71-2.65 (m, 1H), 2.36 (s, 3H).

Step C: To a solution of the product obtained in Step B (2.02 g, 5.15 mmol) and hydrazine hydrate (8 mL) in MeOH (100 mL), was added 10% Pd/C (0.25 g). The reaction mixture was heated to reflux 8 h, then, the reaction mixture was filtered through a short pad of celite. The filtrate was concentrated to dryness under reduced pressure. The residue was diluted with CH$_2$Cl$_2$ (60 mL), then, washed with H$_2$O (1×40 mL). The aqueous phase was extracted with additional amount of CH$_2$Cl$_2$ (3×20 mL). The combined organic phases were dried (Na$_2$SO$_4$) and concentrated to dryness under reduced pressure. The residue was purified using medium pressure chromatography (eluent: EtOAc/MeOH 9:1) to afford (+/−)-4-benzo[b]thiophen-5-yl-2-methyl-7-pyridazin-3-yl-1,2,3,4-tetrahydroisoquinoline (1.3 g, 71%, >99% AUC HPLC) as a white solid: $^1$H NMR (500 MHz, CDCl$_3$) δ 9.14 (dd, J=1.6, 4.9 Hz, 1H), 7.94 (d, J=1.5 Hz, 1H), 7.84-7.79 (m, 2H), 7.71-7.67 (m, 2H), 7.51 (dd, J=8.6, 4.9 Hz, 1H), 7.44 (d, J=5.4 Hz, 1H), 7.28-7.26 (m, 1H), 7.20 (dd, J=8.3, 1.6 Hz, 1H), 7.06 (d, J=8.1 Hz, 1H), 4.46 (m, 1H), 3.90 (d, J=14.6 Hz, 1H), 3.76 (d, J=14.6 Hz, 1H), 3.15-3.10 (m, 1H), 2.71-2.65 (m, 1H), 2.48 (s, 3H); ESI-MS m/z 358 [M+H]$^+$.

Example 155

Primary Binding Assay

In order to evaluate the relative affinity of the various compounds at the NE, DA and 5HT transporters, HEK293E cell lines were developed to express each of the three human transporters. cDNAs containing the complete coding regions of each transporter were amplified by PCR from human brain libraries. The cDNAs contained in pCRII vectors were sequenced to verify their identity and then subcloned into an Epstein-Barr virus based expression plasmid (Shen et al., Gene 156:235-239 (1995), which is hereby incorporated by reference in its entirety). This plasmid containing the coding sequence for one of the human transporters was transfected into HEK93E cells. Successful transfection was verified by the ability of known reuptake blockers to inhibit the uptake of tritiated NE, DA or 5HT.

For binding, cells were homogenized, centrifuged, and then resuspended in incubation buffer (5 mM Tris, 120 mM NaCl, 5 mM KCl, pH 7.4). Then, the appropriate radioligand was added. For NET binding, [$^3$H] Nisoxetine (86.0 Ci/mmol, NEN/DuPont) was added to a final concentration of approximately 5 nM. For DAT binding, [$^3$H] WIN 35,428 (84.5 Ci/mmol) at 15 nM was added. For 5HTT binding, [$^3$H] Citolapram (85.0 Ci/mmol) at 1 nM was added. Then, various concentrations ($10^{-5}$ to $10^{-11}$ M) of the compound of interest were temperature for 1 hour in a 96 well plate. Following incubation, the plates were placed on a harvester and washed quickly 4 times with (50 mM tris, 0.9% NaCl, pH 7.4) where the cell membranes containing the bound radioactive label were trapped on Whatman GF/B filters. Scintillation cocktail was added to the filters which were then counted in a Packard TopCount. Binding affinities of the compounds of interest were determined by non-linear curve regression using GraphPad Prism 2.01 software. Non-specific binding was determined by displacement with 10 micromolar mazindol.

Example 156

In Vitro Functional Inhibition of Neurotransmitter Uptake in Rat Synaptosomes

The functional ability of the compounds to inhibit neurotransmitter uptake was established by measuring the inhibition of [$^3$H]-noradrenaline, [$^3$H]-serotonin and [$^3$H]-dopamine uptake into rat brain synaptosomes. A Description of the methods used follows:
[$^3$H] Serotonin Uptake into Rat Brain Synaptosomes
Synaptosome Preparation Frontal cortices were homogenized in ice-cold 0.32 M sucrose (1:20 w/v) using a loose fitting (clearance: 0.5 mm), glass/Teflon, motor driven homogeniser (12 strokes, 800 rpm). Nuclei and cell debris were be removed by centrifugation at 1,500×g for 10 minutes. The resulting supernatant was centrifuged at 18,000×g for 10 minutes. The resulting crude synaptosomal pellet was then resuspended in ice-cold Krebs Henseleit buffer, pH 7.4 at 25° C. (equivalent to 8.3 mg wet weight of tissue/ml). All centrifugations were carried out at 4° C.
Uptake Assay Crude frontal cortical synaptosomes were incubated in a shaking water bath for 15 minutes at 37° C. Aliquots (150 µL; equivalent to 1.25 mg wet weight of tissue/tube) were then added to tubes containing 275 µL of Krebs Henseleit buffer and 50 µL of buffer (total uptake) or 50 µL of drug solution at 10 concentrations ranging from $10^{-11}$-$10^{-4}$ M or 50 µL of zimeldine ($10^{-5}$ M, non-specific uptake). Uptake was initiated by the addition of 25 µL of freshly prepared [$^3$H]5-HT (2 nM), followed by vortexing and was continued for 5 minutes at 37° C. in the shaking water bath.

Uptake was terminated by filtration under vacuum through Skatron 11734 filters using a Skatron cell harvester. Filters were rapidly washed with ice-cold saline (wash setting 9,9,0). Scored filter paper discs were placed into plastic scintillation vials and 25 µl of [$^3$H]5-HT was pipetted into four vials for the accurate determination of the concentration added to each tube. Radioactivity (dpm) was determined by liquid scintillation counting (1 mL Packard MV Gold scintillator).
[$^3$H] Noradrenaline Uptake into Rat Brain Synaptosomes
Synaptosome Preparation Frontal cortices were homogenised in ice-cold 0.32 M sucrose (1:10 w/v) using a loose fitting (clearance: 0.5 mm), glass/Teflon, motor driven homogeniser (12 strokes, 800 rpm). Nuclei and cell debris were removed by centrifugation at 1,500×g for 10 minutes. The supernatant was then centrifuged at 18,000×g for 10 minutes. The resulting crude synaptosomal pellet was resuspended in ice-cold Krebs Physiological buffer, gassed with 95% O$_2$/5% CO$_2$ (equivalent to 16.7 mg wet weight of tissue/ml). All centrifugations were carried out at 4° C.
Uptake Assay Crude frontal cortical synaptosomes were incubated in a shaking water bath for 15 minutes at 37° C. Aliquots (150 µL; equivalent to 2.5 mg wet weight of tissue/tube) were then added to tubes containing 275 µL of Krebs Physiological buffer and 50 µL of buffer (total uptake) or 50 µL of drug solution at 10 concentrations ranging from $10^{-11}$-$10^{-4}$ M or 50 µL of desipramine ($10^{-5}$ M, non-specific uptake). Uptake was initiated by the addition of 25 µL of freshly prepared [$^3$H]noradrenaline (10 nM), followed by vortexing and was continued for 5 minutes at 37° C. in the shaking water bath.

Uptake was terminated by filtration under vacuum through Skatron 11734 filters using a Skatron cell harvester. Filters were rapidly washed with ice-cold saline (wash setting 9,9,0). Scored filter paper discs were placed into plastic scintillation vials and 25 µL of [$^3$H]noradrenaline were pipetted into four vials for the accurate determination of the concentration added to each tube. Radioactivity (dpm) was determined by liquid scintillation counting (1 mL Packard MV Gold scintillator).
[$^3$H] Dopamine uptake into Rat Brain Synaptosomes
Synaptosome Preparation Striata were homogenized in ice-cold 0.32 M sucrose (1:40 w/v) using a loose fitting (clearance: 0.5 mm), glass/Teflon, motor driven homogenizer (12 strokes, 800 rpm). Nuclei and cell debris were removed by centrifugation at 1,500×g for 10 minutes. The resulting supernatant was then centrifuged at 18,000×g for 10 minutes. The resulting crude synaptosomal pellet was then resuspended in ice-cold Krebs Henseleit buffer, pH 7.4 at 25° C. (equivalent to 4.17 mg wet weight of tissue/ml). All centrifugations were carried out at 4° C.

Uptake Assay

Crude striatal synaptosomes were incubated in a shaking water bath for 15 minutes at 37° C. Aliquots (150 µL; equivalent to 0.625 mg wet weight of tissue/tube) were then added to tubes containing 275 µL of Krebs Henseleit buffer and 50 µL of buffer (total uptake) or 50 µL of drug solution at 10 concentrations ranging from $10^{-11}$-$10^{-4}$ M or 50 µL of GBR 12909 ($10^{-5}$ M, non-specific uptake). Uptake was initiated by the addition of 25 µL of freshly prepared [$^3$H]dopamine (2.5 nM), followed by vortexing and was continued for 5 minutes at 37° C. in the shaking water bath.

Uptake was terminated by filtration under vacuum through Skatron 11734 filters using a Skatron cell harvester. Filters were rapidly washed with ice-cold saline (wash setting 9,9,0). Scored filter paper discs were placed into plastic scintillation vials and 25 µL of [$^3$H]-dopamine was pipetted into four vials for the accurate determination of the concentration added to each tube. Radioactivity (dpm) was determined by liquid scintillation counting (1 mL Packard MV Gold scintillator).

Data Analysis

Inhibition Constants ($K_i$ values)

The concentration of compound required to inhibit 50% of specific uptake ($IC_{50}$) was calculated using Prism into which count data (dpm) is entered directly from the Liquid Scintillation Analyser. This program calculates specific uptake in the absence and presence of a range of concentrations of compound and then converts the specific uptake values in the presence and absence of each concentration of compound into percentages of specific uptake in the absence of compound as described for a single concentration.

The percentage specific uptake at each concentration of compound was then plotted against the logarithm$_{10}$ of the concentration of compound. The $IC_{50}$ was calculated using the following formula:

$$\% \text{ Specific uptake} = \frac{(100 - D^P)}{(D^P + IC_{50}^P)}$$

where 100=maximum binding (ie binding in the absence of compound)

P=slope factor which is analogous to the Hill slope

D=concentration of compound (M).

The Hill slope was calculated to detect deviations from simple one-site interactions. A Hill slope approximating to unity indicates displacement from a single site, significantly less than unity indicates displacement from multiple sites and significantly greater than unity indicates positive co-operativity.

The affinity constant ($K_i$) of the compound for the uptake site will then be calculated using the Cheng and Prusoff$^2$ equation:

$$K_i = \frac{IC_{50}}{1 + [L]/K_d}$$

where [L]=the concentration of radioligand (M)

$K_d$=the affinity of the uptake site for the radioligand.

The concentration of radioligand [L] nM $$= \frac{dpm \text{ (total assay radioligand)}}{SA \times (2.22 \times 10^{12})} \times \frac{1}{\text{assay volume}}$$

where SA=specific activity of the radioligand (Ci/mmol).

Example 157

In Vivo Determination of Transporter Occupancy by Rat Ex Vivo Binding

The ex vivo binding model in the rat was used to assess the test compounds ability to reach the target transporters in the rat brain after oral dosing. The protocol for ex vivo binding in the rat was similar to published experimental procedures (Bymaster, et al., *Neuropsychopharmacology*, 25:871-880 (2001), which is hereby incorporated by reference in its entirety) to assess duloxetine's transporter (noradrenaline and serotonin) occupancy in brain tissue. Duloxetine is a known SNRI currently marketed as Cymbalta® for treatment of depression. The ex vivo binding studies in the rat were performed utilizing [$^3$H]-nisoxetine and [$^3$H]-citalopram as the radioligands in the assay. In order to measure dopamine transporter occupancy, an ex vivo binding protocol was established in the rat with the radioligand [$^3$H]-WIN 35428. In addition to proving that test compounds reached desired targets in the rat brain, this experiment provided a surrogate measure of the compounds pharmacokinetic properties, i.e. oral bioavailability and brain penetration.

A description of the methods used follows:

Animals

Male Sprague-Dawley rats (250-300 g) were obtained from Charles River (Margate, Kent) and group-housed at 21±4° C. and 55±20% humidity on a normal 12 hour light/dark cycle (lights on 07.00 h) with free access to standard rodent chow and tap water for at least one week before use.

Drug Treatment

On the day of test, animals (n=5) were dosed orally with vehicle, AMRI compound or duloxetine (positive control). Rats were killed 1 hour after treatment. Whole brains were removed and frontal cortex and *striata* dissected and frozen on dry ice. The tissue was stored at −80° C. until the day of the assay. The frontal cortex from each hemisphere was frozen separately. One was used to determine occupancy of NA transporter sites and the other occupancy of 5-HT transporter sites. Striatum was used to determine occupancy of DA transporter sites. The remaining tissue (excluding the cerebellum) was dissected and analyzed to determine brain concentration of drug.

Membrane Preparation

Frontal cortex from each hemisphere of each animal or striatum was homogenized individually in ice-cold assay buffer using a tight fitting glass/Teflon homogenizer and used immediately in the binding assay.

[$^3$H] Citalopram Binding to 5-HT Transporter Sites in Rat Brain

Frontal cortical membranes (400 µL; equivalent to 1.25 mg wet weight of tissue/tube) were incubated with 50 µL of [$^3$H]citalopram at a single concentration of 1.3 nM and either 50 µL of buffer (total binding) or 50 µl of paroxetine (0.5 µM; non-specific binding) for 1 hour at 27° C. in triplicate.

Membrane bound radioactivity was recovered by filtration under vacuum through Skatron 11734 filters presoaked in 0.5% polyethylenimine (PEI) using a Skatron cell harvester. Filters were rapidly washed with ice-cold 50 mM Tris buffer (wash setting 9,9,0) and radioactivity determined by liquid scintillation counting (1 mL Packard MV Gold scintillator).

[3H] Nisoxetine Binding to Noradrenaline Transporter Sites in Rat Brain

Frontal cortical membranes (400 µL; equivalent to 6.0 mg wet weight of tissue/tube) were incubated with 50 µL of [$^3$H]nisoxetine at a single concentration of 0.6 nM and either 50 µL of buffer (total binding) or 50 µL of mazindol (1 µM; non-specific binding) for 4 hours at 4° C. in triplicate.

Membrane bound radioactivity was recovered by filtration under vacuum through Skatron 11734 filters using a Skatron cell harvester. Filters were rapidly washed with ice-cold 50 mM Tris buffer (wash setting 9,9,0) and radioactivity determined by liquid scintillation counting (1 mL Packard MV Gold scintillator).

[$^3$H]WIN 35428 Binding to DA Transporter Sites in Rat Brain

Striatal membranes (200 µL; equivalent to 2 mg wet weight of tissue/tube) were incubated with 25 µL of [$^3$H] WIN 35428 at a single concentration of 24 nM and either 25 µL of buffer (total binding) or 25 µL of GBR12935 (1 µM; non-specific binding) for 2 hours at 4° C. in triplicate.

Membrane bound radioactivity was recovered by filtration under vacuum through Skatron 11734 filters, presoaked in 0.5% PEI, using a Skatron cell harvester. Filters were rapidly washed with ice-cold phosphate buffer (wash setting 9,9,0) and radioactivity (dpm) was determined by liquid scintillation counting (1 mL Packard MV Gold scintillator).

Data Analysis

A value for specific binding (dpm) was generated by the subtraction of mean non-specific binding (dpm) from mean total binding (dpm) for each animal. Data were presented as mean percentage specific binding of vehicle-treated control and the appropriate statistical analysis applied.

Example 158

Determination of Functional Activity in Mouse Via Biogenic Amine Turnover Experiments Background and Aim of Study—Inhibition of 5-HT Turnover in Mouse Brain 5-Hydroxytryptamine (5-HT) is formed following the action of the enzyme aromatic amino acid decarboxylase on 5-hydroxytryptophan (5-HTP). Measurement of 5-HTP has previously been found to be a useful index of 5-HT turnover (Fuller et al., *Federation Proc.*, 36:2154-2158 (1977), which is hereby incorporated by reference in its entirety). In these studies, the aromatic amino acid decarboxylase inhibitor, m-hydroxybenzylhydrazine (NSD-1015), is used to prevent the decarboxylation of 5-HTP to 5-HT. The accumulation of 5-HTP can then be measured using high performance liquid chromatography with electrochemical detection (HPLC-ECD). The aim of this study is to measure the effects of novel drugs on 5-HTP levels in mouse brain. Compounds inhibiting 5-HT reuptake ex vivo decrease 5-HTP levels. The selective 5-HT reuptake inhibitor, paroxetine, was used as a positive comparator.

Animals

Experiments were conducted in 40 male CD1 mice (20-30 g) obtained from Charles River (Margate, Kent). Animals were group-housed at 21±4° C. and 55±20% humidity on a normal 12 hour light/dark cycle (lights on 07.00 h) with free access to standard rodent chow and tap water. Animals were allowed to acclimatise to the animal house for at least one week before experimentation.

Experimental Procedures

Each experiment contained 5 different treatment groups (vehicle, paroxetine and 3 compound treatment groups (eg one dose of 3 different drugs or three doses of one drug, n=8). On the test day, mice were dosed orally with vehicle, paroxetine or the test compound. Thirty minutes later all mice were given NSD 1015 (100 mg/kg ip) to prevent the metabolism of 5-HTP to 5-HT. After a further 30 minutes (i.e. 60 minutes after drug administration) animals were killed and whole brains minus cerebella removed and frozen using liquid nitrogen. Tissues were prepared for HPLC-ECD analysis using well-established methods. Brain 5-HTP concentrations were determined using peak height, by reference to a standard solution of 5-HTP injected separately.

Drugs and Reagents

All test drugs were provided by AMRI. NSD-1015 was purchased from Sigma-Aldrich (Poole). All drugs were made up fresh each day. Drugs were dissolved in a suitable vehicle and given in a dose volume in the range 1-10 ml/kg. All drug doses are expressed as the free base unless otherwise stated. All reagents for the HPLC-ECD analysis and the 5-HTP standard were obtained from Sigma-Aldrich or a similar commercial supplier.

Data and Statistical Analysis

Results were expressed as means±SEM. Statistical analysis were performed in-house. The exact statistical tests employed depended on the data obtained, however, statistical comparisons between 5-HTP levels of different groups of mice were usually made by analysis of variance followed by suitable T-tests or multiple comparisons test (two-tailed) to compare each treatment group with the vehicle-treated controls. $P<0.05$ are considered to be statistically significant.

Background and Aim of Study—Inhibition of Noradrenaline Turnover in Mouse Brain

Noradrenaline is an important neurotransmitter in the central nervous system. One route of inactivation for noradrenaline consists of conversion firstly to 3,4-dihydroxyphenylglycolaldehyde by monoamine oxidase (MAO) and then to 3,4-dihydroxyphenylglycol (DHPG) by aldehyde reductase. DHPG is subsequently methylated to form 3-methoxy-4-hydroxyphenylglycol (MHPG) by catechol-O-methyltransferase (COMT). As COMT is located extraneuronally it is ideally suited to provide a marker of the release and functional utilisation of noradrenaline. The aim of this study was to investigate the effects of novel compounds on noradrenaline turnover by measuring MHPG levels in mouse brain using high performance liquid chromatography with electrochemical detection (HPLC-ECD). The actions of noradrenaline reuptake inhibitors to increase levels of noradrenaline, at both cell body and terminal regions, results in activation of somatodendritic and terminal $\alpha_2$-adrenergic autoreceptors which attenuate neuronal firing and neurotransmitter release, respectively. Compounds inhibiting noradrenaline reuptake ex vivo would decrease MHPG levels in mouse brain. Desipramine was used as a positive comparator.

Animals

Experiments were conducted in 40 male CD1 mice (20-30 g) obtained from Charles River (Margate, Kent). Animals were group-housed at 21±4° C. and 55±20% humidity on a normal 12 hour light/dark cycle (lights on 07.00 h) with free access to standard rodent chow and tap water. Animals were allowed to acclimatise to the animal house for at least one week before experimentation.

Experimental Procedures

Each experiment contained 5 different treatment groups (vehicle, desipramine and 3 drug treatment groups (eg one dose of 3 different drugs or three doses of one drug, n=8). On the test day, mice were dosed orally with vehicle, desipramine or the test drug. Sixty minutes later, animals were killed and whole brains minus cerebella removed and frozen using liquid nitrogen. Tissues were prepared for HPLC-ECD analysis using well-established methods. Brain MHPG concentrations were determined using peak height, by reference to the ratio of internal standard (iso-MHPG) to MHPG.

Drugs and Reagents

All test drugs were provided by AMRI. Desipramine hydrochloride was purchased from Sigma-Aldrich. All drugs were made up fresh each day. Drugs were dissolved in a suitable vehicle and given in a dose volume in the range 1-10 ml/kg. All drug doses are expressed as the free base unless otherwise stated. All reagents for the HPLC-ECD analysis and MHPG were obtained from Sigma-Aldrich or a similar commercial supplier.

Data and Statistical Analysis

Results are expressed as means±SEM. Statistical analysis was performed in-house. The exact statistical tests employed depended on the data obtained, however, statistical comparisons between MHPG levels of different groups of mice was usually made by analysis of variance followed by suitable t-tests or multiple comparisons test (two-tailed) to compare each treatment group with the vehicle-treated controls. $P<0.05$ is considered to be statistically significant.

Example 159

Microdialysis Study

The aim of this study is to use dual-probe microdialysis to determine the effects of oral administration of compounds on extracellular concentrations of noradrenaline (na) and 5-ht in the prefrontal cortex and dopamine (da) in the striatum of freely-moving Sprague-Dawley rats.

Rats were anaesthetised with isoflurane (5% to induce, 2% to maintain) in an $O_2/N_2O$ (1 litre $min^{-1}$ each) mixture delivered via an anaesthetic unit (St Bernard Medical Services, UK). Concentric microdialysis probes with 2 and 4 mm exposed Hospal membrane tip (CMA) were stereotaxically implanted into the prefrontal cortex and striatum, respectively, using coordinates taken from the stereotaxic atlas of Paxinos and Watson (Paxinos et al., "The Rat Brain in Stereotaxic Coordinates," $2^{nd}$ Edition, London: Academic Press (1986), which is hereby incorporated by reference in its entirety). The upper incisor bar was set at 3.3 mm below the interaural line so that the skull surface between bregma and lambda was horizontal. Additional burr holes were made for skull screws (stainless steel) and the probes were secured using dental cement. Following surgery, animals were individually housed in circular chambers (dimensions 450 mm internal diameter, 320 mm wall height) with the microdialysis probes connected to a liquid swivel and a counterbalanced arm to allow unrestricted movement. Rats were allowed a recovery period of at least 16 hours with food and water available ad libitum. During this time the probes were continuously perfused with an artificial cerebrospinal fluid (aCSF; Harvard Apparatus, UK) at a flow rate of 1.2 µl $min^{-1}$.

The experiment was performed the day following surgery. Dialysate samples were collected every 30 minutes into Eppendorf tubes containing perchloric acid to prevent oxidation. A total of 11 samples were collected for each brain region (3 pre-drug and 8 post-drug). For determination and quantification of 5-HT and NA in the frontal cortex, the microdialysis samples were split and assayed on separate HPLC systems by reverse-phase, ion-pair HPLC coupled with electrochemical detection. In the case of DA in the striatum, microdialysis samples were assayed on a separate HPLC system. The HPLC analysis was conducted over the remainder of the week following experimentation.

Example 160

Behavioral Despair Test in the Rat

The method, also called "forced swim test" or "Porsolt's test", which detects antidepressant activity, follows that described by Porsolt et al (*Eur. J. Pharmacol.*, 47:379-391 (1978), which is hereby incorporated by reference in its entirety). Rats forced to swim in a situation from which they cannot escape rapidly become immobile. Antidepressants decrease the duration of immobility. This study was performed by Porsolt & Partners Pharmacology (Dr. Vincent Castagné, France).

Rats were individually placed in a cylinder (Height=40 cm; Diameter=20 cm) containing 13 cm water (25° C.) for 15 minutes on the first day of the experiment (Session 1) and were then put back in the water 24 hours later for a 5 minute test (Session 2). The duration of immobility during the 5 minute test was measured.

6 rats were studied per group. The test was performed blind.

The test substances were evaluated by administration orally (p.o.) 3 times: 24 hours, 4 hours and 60 minutes before the test (Session 2), and compared with a vehicle control group.

Imipramine (64 mg/kg p.o.), administered under the same experimental conditions, was used as reference substance.

Example 161

Tetrabenazine Assay

In vivo activity for the compounds of this invention in animals was assessed by determining the ability of the compounds to prevent the sedative effects of tetrabenazine (TBZ) (see, e.g., G. Stille, *Arzn. Forsch* 14:534-537 (1964), which is hereby incorporated by reference in its entirety). Randomized and coded doses of test compounds were orally administered to mice, as was then a dose of tetrabenazine. Animals were then evaluated for antagonism of tetrabenazine-induced exploratory loss and ptosis at specified time intervals after drug administration. Exploratory activity is, for example, evaluated by placing the animal in the center of a circle and then evaluating the amount of time it takes for the animal to intersect the circle's perimeter-generally, the longer it takes for the animal to make this intersection, the greater is its loss of exploratory activity. Furthermore, an animal is considered to have ptosis if its eyelids are at least 50% closed. Greater than 95% of the control (vehicle-treated) mice are expected to exhibit exploratory loss and ptosis; compound-related activity is then calculated as the percentage of mice failing to respond to the tetrabenazine challenge dose, with therapeutically more effective compounds expected to better at reducing loss of exploratory behavior and ptosis. Efficacy in the tetrabenazine mouse assay performed as described above provides an indication of the pharmacokinetic properties (oral bioavailability) of the compounds of the present invention and also the compounds ability to penetrate the central nervous system and reach the desired target, the biogenic amine transporters, in the brain. Nomifensine, a CNS agent that exhibited good antidepressant properties in human clinical trials exhibited potent biological activity in this in vivo assay. Ritalin®, the widely used drug for the treatment of attention deficit hyperactivity disorder, also displayed potent activity in this assay.

Male CFI mice (Charles River Breeding Laboratories) weighing 18-25 gm at the time of testing, were housed a minimum of 6 days under carefully controlled environmental conditions (22.2±1.1° C.; 50% average humidity, 12 hour lighting cycle/24 hr). Mice were fasted overnight (16-22 hr) prior to testing. Mice were placed into clear polycarbonated "shoe" boxes (17 cm.times.28.5 cm.times.12 cm). Randomized and coded doses of test compounds were administered p.o. A 45 mg/kg dose of tetrabenazine was administered i.p. 30 minutes prior to score time. All compounds were administered in a volume of 0.1 ml/10 gm body weight. Animals were evaluated for antagonism of tetrabenazine induced exploratory loss and ptosis at specified time intervals after drug administration. At the designated time interval, mice were examined for signs of exploratory activity and ptosis. Exploratory activity was evaluated by placing the animal in the center of a 5 inch circle. Fifteen seconds were allowed for the animal to move and intersect the perimeter. This was considered antagonism of tetrabenazine and given a score of 0. Failure to leave the circle was regarded as exploratory loss and given a score of 4. An animal was considered to have ptosis if its eyelids were at least 50% closed and given a score of 4 if completely closed; no closure was given a score of 0. Greater than 95% of the control (vehicle-treated) mice were expected to exhibit exploratory loss and ptosis. Drug activity was calculated as the percentage of mice failing to respond to the tetrabenazine challenge dose.

Example 162

Statistical Evaluation

Median effective doses ($ED_{50}s$) and 95% confidence limits are determined numerically by the method of Litchfield and Wilcoxon, *Journal of Pharmacology and Experimental Therapeutics*, 96:99-113 (1949), which is hereby incorporated by reference in its entirety.

In the "Background of the Invention", reference is made to known tetrahydroisoquinoline based compounds that possess a heteroaromatic ring substituted at the 4-position of the tetrahydroisoquinoline ring. Table 1, shown below, compares binding affinities (Ki values determined as described in the experimental section above) for compounds with "Monocyclic Heteroaromatic Rings Substituted at the 4-Position" of the 1,2,3,4-tetrahydroisoquinoline with those for compounds of the present invention that possess "Bicyclic Heteroaromatic Rings Substituted at the 4-Position".

TABLE 1

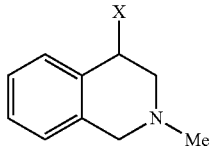

| X | NET Ki (nM) | DAT Ki (nM) | SERT Ki (nM) |
|---|---|---|---|
| Monocyclic Heteroaromatic Rings Substituted at the 4-Position Racemic compounds not claimed in Present Invention | | | |
| 4-(3,5-dimethyl-isoxazol-4-yl) | 41400 | 128000 | 1400 |
| thiophen-2-yl | 3060 | 5990 | 2450 |
| 4-methyl-thiophen-2-yl | 488 | 2250 | 3170 |
| 5-methyl-furan-2-yl | 1640 | 5640 | 7530 |
| 6-methoxy-pyridin-3-yl | 1375 | 2787 | 470 |
| Bicyclic Heteroaromatic Rings Substituted at the 4-Position Representative Compounds of the Present Invention | | | |
| benzothiophen-2-yl (+)-enantiomer Example 21 | 37.9 | 14.3 | 11.5 |
| benzothiophen-5-yl (+)-enantiomer Example 40 | 1.2 | 3.8 | 4.0 |
| benzofuran-2-yl (+)-enantiomer Example 2 | ~20 | 13.5 | 92.3 |
| benzofuran-5-yl (+)-enantiomer racemate Example 19 | 2.0 | 4.5 | 19.2 |

Examination of the binding affinity (Ki values) for the monocyclic heteroaromatic rings, e.g. the thiophen-2-yl, the 4-methyl-thiophen-2-yl, the 5-methyl-furan-2-yl, the 4-(3,5-dimethyl-isoxazol-4-yl, or the 6-methoxy-pyridin-3-yl, shows that these compounds are much less potent towards all three biogenic amine transporters than the compounds of the present invention that possess bicyclic heteroaromatic rings substituted at the 4-position of the 1,2,3,4-tetrahydroisoquinoline. The bicyclic heteroaromatic rings substituted at the 4-position of the 1,2,3,4-tetrahydroisoquinoline is an important structural feature that leads to unexpected improvements in potency and selectivity in compounds of the present invention.

Compounds of the present invention are potent inhibitors of monoamine reuptake by the dopamine, norepinephrine, and serotonin transporters. Compounds of the present invention may be grouped according to the transporter reuptake inhibition profile according to which of the transporters is affected by a particular compound. Due to the varying selectivity profiles it is expected that the compounds claimed in the present invention would have wide utility in the treatment of many disease states where the levels of the neurotransmitters, dopamine, norepinephrine and serotonin have been implicated.

TABLE 2

Inhibition of Radioligand Binding at the Human Biogenic Amine Transporters by Compounds of the Present Invention*

| Example number | Stereoisomer | Ki, nM (% inhibition at 100 nM concentration of test compound) | | |
|---|---|---|---|---|
| | | NET | DAT | SERT |
| 2 | (+)-enantiomer | ~20 | 13.5 | 92.3 |
| 11 | (+)-enantiomer | 22 | >300 | 26.8 |
| 14 | (+)-enantiomer | 2.0 | 4.5 | 19.2 |
| 17 | racemate | 5.2 | 7.5 | 254 |
| 21 | (+)-enantiomer | 28.4 | 128 | 8.8 |

TABLE 2-continued

Inhibition of Radioligand Binding at the Human Biogenic Amine Transporters by Compounds of the Present Invention*

| Example number | Stereoisomer | Ki, nM (% inhibition at 100 nM concentration of test compound) | | |
|---|---|---|---|---|
| | | NET | DAT | SERT |
| 40 | (+)-enantiomer | 1.2 | 3.8 | 4.0 |
| 44 | racemate | 10.3 | 4.5 | 40.3 |
| 49 | racemate | 5.8 | 3.8 | 137 |
| 56 | racemate | 29.3 | 39.5 | 3.4 |
| 70 | (+)-enantiomer | 8.1 | 119 | 2.2 |
| 71 | racemate | (75) | (33) | (91) |
| 73 | racemate | (73) | (39) | (93) |
| 75 | (+)-enantiomer | 21.7 | 284 | 6.7 |
| 76 | (+)-enantiomer | 80.6 | 460 | 30.4 |
| 78 | (+)-enantiomer | 12.6 | 35.4 | 3.3 |
| 82 | (+)-enantiomer | 24.5 | >1000 | 4.3 |
| 84 | (+)-enantiomer | 58.2 | >1000 | 12.9 |
| 97 | (+)-enantiomer | 1.4 | 8.5 | 2.2 |
| 100 | (+)-enantiomer | 7.6 | 53.4 | 7.1 |
| 102 | (+)-enantiomer | <3 | 4.4 | 3.4 |
| 117 | (+)-enantiomer | 2.4 | 41.3 | 4.1 |
| 119 | (+)-enantiomer | 6.7 | 19.8 | 13.9 |
| 122 | (+)-enantiomer | 11.5 | 29.4 | 180 |
| 125 | (+)-enantiomer | 2.6 | 11.5 | 21.3 |
| 129 | (+)-enantiomer | 11.5 | 300 | 22.8 |
| 130 | (+)-enantiomer | 12.7 | 105 | 22.5 |
| 134 | (+)-enantiomer | 4.9 | 36.5 | 205 |
| 135 | (+)-enantiomer | 38.6 | 79.4 | 10.4 |
| 137 | (+)-enantiomer | 4.1 | 59.7 | <3 |
| 142 | (+)-enantiomer | 24.6 | 104 | 5.2 |

*The experimental conditions for the "Primary Binding Assay" are described in Example 155

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A process for preparation of a product compound of Formula (I):

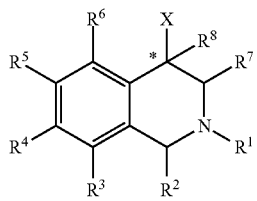

Formula (I)

wherein:

the carbon atom designated * is in the R or S configuration;

X is a fused bicyclic carbocycle or heterocycle selected from the group consisting of benzofuranyl, benzo[b]thiophenyl, benzoisothiazolyl, benzoisoxazolyl, indazolyl, indolyl, isoindolyl, indolizinyl, benzoimidazolyl, benzooxazolyl, benzothiazolyl, benzotriazolyl, imidazo[1,2-a]pyridinyl, pyrazolo[1,5-a]pyridinyl, [1,2,4]triazolo[4,3-a]pyridinyl, thieno[2,3-b]pyridinyl, thieno[3,2-b]pyridinyl, 1H-pyrrolo[2,3-b]pyridinyl, indenyl, indanyl, dihydrobenzocycloheptenyl, tetrahydrobenzocycloheptenyl, dihydrobenzothiophenyl, dihydrobenzofuranyl, indolinyl, naphthyl, tetrahydronaphthyl, quinolinyl, isoquinolinyl, 4H-quinolizinyl, 9aH-quinolizinyl, quinazolinyl, cinnolinyl, phthalazinyl, quinoxalinyl, benzo[1,2,3]triazinyl, benzo[1,2,4]triazinyl, 2H-chromenyl, 4H-chromenyl, and a fused bicyclic carbocycle or fused bicyclic heterocycle optionally substituted with substituents (1 to 4 in number) as defined below in $R^{14}$;

$R^1$ is H, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, each of which is optionally substituted with from 1 to 3 substituents independently selected at each occurrence thereof from the group consisting of: $C_1$-$C_3$ alkyl, halogen, aryl, —CN, —$OR^9$, and —$NR^9R^{10}$;

$R^2$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, or $C_1$-$C_6$ haloalkyl, each of which is optionally substituted with from 1 to 3 substituents independently selected at each occurrence thereof from the group consisting of: $C_1$-$C_3$ alkyl, halogen, aryl, —CN, —$OR^9$, and —$NR^9R^{10}$; or $R^2$ is gem-dimethyl;

$R^3$ is H, halogen, —$OR^{11}$, —$S(O)_nR^{12}$, —CN, —$C(O)R^{12}$, —$C(O)NR^{11}R^{12}$, —$NR^9R^{10}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with from 1 to 3 substituents independently selected at each occurrence thereof from the group consisting of: $C_1$-$C_3$ alkyl, halogen, —CN, —$OR^9$, —$NR^9R^{10}$, and phenyl, which is optionally substituted 1 to 3 times with a substituent selected from the group consisting of: halogen, cyano, $C_1$-$C_4$ alkyl, $C_1$-$C_4$ haloalkyl, $C_1$-$C_4$ alkoxy, —CN, and —$OR^9$;

$R^4$ is H, halogen, —$OR^{11}$, —$S(O)_nR^{12}$, —CN, —$C(O)R^{12}$, —$C(O)NR_{11}R^{12}$, —$NR^9R^{10}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, wherein each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with from 1 to 3 substituents independently selected at each occurrence thereof from the group consisting of: $C_1$-$C_3$ alkyl, halogen, —CN, —$OR^9$, —$NR^9R^{10}$, and phenyl, which is optionally substituted 1 to 3 times with a substituent selected from the group consisting of: halogen, cyano, $C_1$-$C_4$ alkyl, $C_1$-$C_4$ haloalkyl, $C_1$-$C_4$ alkoxy, —CN, and —$OR^9$; or $R^4$ is phenyl, naphthyl, indenyl, pyridyl, pyrimidinyl, pyridazinyl, pyrazinyl, [1,2,4]triazinyl, [1,3,5]triazinyl, triazolyl, furanyl, thiophenyl, pyranyl, indazolyl, benzimidazolyl, quinolinyl, quinazolinyl, quinoxalinyl, phthalazinyl, cinnolinyl, isoquinolinyl, thienyl, imidazolyl, thiazolyl, benzthiazolyl, purinyl, isothiazolyl, indolyl, pyrrolyl, oxazolyl, benzofuranyl, benzothienyl, benzthiazolyl, isoxazolyl, pyrazolyl, oxadiazolyl, thiadiazolyl, 3-oxo-[1,2,4]triazolo[4,3-a]pyridinyl, imidazo[1,2-a]pyridinyl, pyrazolo[1,5-a]pyridinyl, [1,2,4]triazolo[4,3-a]pyridinyl, thieno[2,3-b]pyridinyl, thieno[3,2-b]pyridinyl, 1H-pyrrolo[2,3-b]pyridinyl, or other heterocycles optionally substituted with substituents (1 to 4 in number) as defined below in $R^{14}$;

$R^5$ and $R^6$ are each independently selected from the group consisting of: H, halogen, —$OR^{11}$, —$S(O)_nR^{12}$, —CN, —$C(O)R^{12}$, —$C(O)NR^{11}R^{12}$, —$NR^9R^{10}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and phenyl is optionally substituted with from 1 to 3 substituents independently selected at each occurrence thereof from the group consisting of: $C_1$-$C_3$ alkyl, halogen, —CN, —$OR^9$, —$NR^9R^{10}$, and phenyl, which is optionally substituted 1 to 3 times with a substituent selected from the group consisting of: halogen, $C_1$-$C_4$ alkyl, $C_1$-$C_4$ haloalkyl, $C_1$-$C_4$ alkoxy, —CN, and —$OR^9$;

$R^7$ is H;

$R^8$ is H, halogen, —$OR^9$, —$SR^9$, $C_1$-$C_6$ alkyl, —CN, or —$NR^9R^{10}$;

$R^9$ and $R^{10}$ are each independently selected from the group consisting of: H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —$C(O)R^{13}$, phenyl, and benzyl, where phenyl or benzyl is optionally substituted from 1 to 3 times with a substituent selected independently at each occurrence thereof from the group consisting of: halogen, cyano, $C_1$-$C_4$ alkyl, $C_1$-$C_4$ haloalkyl, and $C_1$-$C_4$ alkoxy; or $R^9$ and $R^{10}$ are taken together with the nitrogen to which they are attached to form a piperidine, pyrrolidine, piperazine, N-methylpiperazine, morpholine, thiomorpholine, [1,2]oxazinane, isoxazolidine, or 2-oxo-2H-pyridine, which is optionally substituted from 1 to 3 times with a substituent selected independently at each occurrence thereof from the group consisting of, halogen, cyano, $C_1$-$C_4$ alkyl, $C_1$-$C_4$ haloalkyl, and $C_1$-$C_4$ alkoxy;

$R^{11}$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —$C(O)R^{13}$, phenyl, or benzyl, where phenyl or benzyl is optionally substituted 1 to 3 times with halogen, cyano, $C_1$-$C_4$ alkyl, $C_1$-$C_4$ haloalkyl, or $C_1$-$C_4$ alkoxy;

$R^{12}$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, phenyl, or benzyl, where phenyl or benzyl is optionally substituted 1 to 3 times with halogen, cyano, $C_1$-$C_4$ alkyl, $C_1$-$C_4$ haloalkyl, or $C_1$-$C_4$ alkoxy; or $R^{11}$ and $R^{12}$ are taken together with the nitrogen to which they are attached to form a piperidine, pyrrolidine, piperazine, N-methylpiperazine, morpholine, or thiomorpholine ring, with the proviso that only one of $R^9$ and $R^{10}$ or $R^{11}$ and $R^{12}$ are taken together with the nitrogen to which they are attached to form a piperidine, pyrrolidine, piperazine, N-methylpiperazine, morpholine, or thiomorpholine ring;

$R^{13}$ is $C_1$-$C_4$ alkyl, $C_1$-$C_4$ haloalkyl, or phenyl;

n is 0, 1, or 2; and $R^{14}$ is independently selected at each occurrence from a substituent selected from the group consisting of: halogen, —$NO_2$, —$OR^{11}$, —$NR^{11}R^{12}$, —$NR^{11}C(O)R^{12}$, —$NR^{11}C(O)_2R^{12}$, —$NR^{11}C(O)NR^{12}R^{13}$, —$S(O)_nR^{12}$, —CN, —$C(O)R^{12}$, —$C(O)NR^{11}R^{12}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl are optionally substituted with 1 to 3 substituents independently selected at each occurrence from the group consisting of: $C_1$-$C_3$ alkyl, halogen, aryl, —CN, —$OR^9$, and —$NR^9R^{10}$;

said process comprising:

treating a second intermediate compound of Formula (VIII):

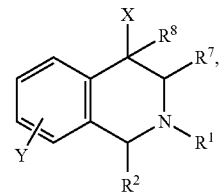

wherein Y is Br, I, or $OSO_2CF_3$, with an aryl or heteroaryl boronic acid or aryl or heteroaryl boronic acid ester, under conditions effective to produce the product compound.

2. The process according to claim 1, wherein treating comprises reacting with an aryl or heteroaryl boronic acid or aryl or heteroaryl boronic acid ester in the presence of a metal catalyst and optionally a base in an inert solvent.

3. The process according to claim 1 further comprising: cyclizing a third intermediate compound of Formula (VII)

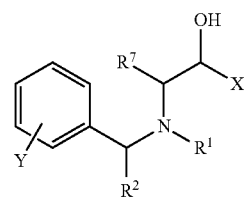

under conditions effective to produce the second intermediate compound of Formula (VIII).

4. The process according to claim 3, wherein cyclizing comprises treating the third intermediate compound of Formula (VII) with a strong acid.

5. The process according to claim 3, further comprising: treating a fourth intermediate compound of Formula (VI):

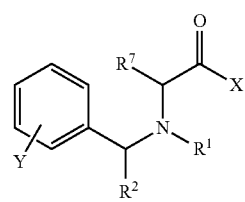

with a reducing agent, under conditions effective to produce the third intermediate compound of Formula (VII).

6. The process according to claim 5, wherein the reducing agent is selected from the group consisting of sodium borohydride, lithium borohydride, borane, diisobutylaluminum hydride, and lithium aluminum hydride.

* * * * *